US009284519B2

(12) United States Patent
Aikens et al.

(10) Patent No.: US 9,284,519 B2
(45) **Date of Patent: *Mar. 15, 2016**

(54) PHOTOBIOREACTOR

(71) Applicant: Proterro, Inc., Ewing, NJ (US)

(72) Inventors: John Aikens, La Grange Park, IL (US); Robert J. Turner, Aurora, IL (US)

(73) Assignee: Proterro, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/272,420

(22) Filed: May 7, 2014

(65) Prior Publication Data

US 2014/0242688 A1 Aug. 28, 2014

Related U.S. Application Data

(60) Continuation of application No. 13/737,201, filed on Jan. 9, 2013, now Pat. No. 8,728,783, which is a division of application No. 12/348,887, filed on Jan. 5, 2009, now Pat. No. 8,367,379.

(60) Provisional application No. 61/085,797, filed on Aug. 1, 2008, provisional application No. 61/018,798, filed on Jan. 3, 2008.

(51) Int. Cl.

| | |
|---|---|
| ***C12M 1/00*** | (2006.01) |
| ***C12M 1/04*** | (2006.01) |
| ***C12M 1/12*** | (2006.01) |
| ***C12N 15/74*** | (2006.01) |
| ***C12N 15/80*** | (2006.01) |
| ***C12P 19/12*** | (2006.01) |
| ***C12P 19/02*** | (2006.01) |

(52) U.S. Cl.

CPC ............... *C12M 21/02* (2013.01); *C12M 23/24* (2013.01); *C12M 23/26* (2013.01); *C12M 25/02* (2013.01); *C12N 15/74* (2013.01); *C12N 15/80* (2013.01); *C12P 19/02* (2013.01); *C12P 19/12* (2013.01)

(58) Field of Classification Search

None

See application file for complete search history.

(56) References Cited

U.S. PATENT DOCUMENTS

| | | | | |
|---|---|---|---|---|
| 4,531,324 | A | 7/1985 | Yang et al. | |
| 4,879,232 | A | 11/1989 | MacDonald et al. | |
| 5,151,347 | A | 9/1992 | Delente et al. | |
| 5,162,051 | A | 11/1992 | Hoeksema | |
| 5,534,417 | A | 7/1996 | Arad et al. | |
| 5,585,266 | A | 12/1996 | Plitt et al. | |
| 5,799,612 | A | 9/1998 | Page | |
| 6,133,034 | A | 10/2000 | Strom et al. | |
| 6,602,703 | B2 | 8/2003 | Dutil | |
| 6,632,602 | B1 | 10/2003 | Sheen et al. | |
| 6,632,661 | B2 | 10/2003 | Wickert | |
| 6,664,095 | B1 | 12/2003 | Suryanarayan et al. | |
| 6,682,918 | B1 | 1/2004 | Haselkorn et al. | |
| 6,699,696 | B2 | 3/2004 | Woods et al. | |
| 6,833,490 | B1 | 12/2004 | Goddijn et al. | |
| 7,247,770 | B2 | 7/2007 | Goddijn et al. | |
| 7,745,201 | B2 | 6/2010 | Melkonian et al. | |
| 7,803,601 | B2 | 9/2010 | Nobles, Jr. et al. | |
| 7,973,214 | B2 | 7/2011 | Lee | |
| 8,367,379 | B2 | 2/2013 | Aikens et al. | |
| 8,507,253 | B2 | 8/2013 | Berzin | |
| 8,691,538 | B1 * | 4/2014 | Moll et al. | 435/139 |
| 8,728,783 | B2 * | 5/2014 | Aikens et al. | 435/162 |
| 2002/0072109 | A1 | 6/2002 | Bayless et al. | |
| 2003/0233675 | A1 | 12/2003 | Cao et al. | |
| 2005/0014239 | A1 | 1/2005 | Melis et al. | |
| 2005/0251882 | A1 | 11/2005 | D'Ordine et al. | |
| 2007/0134790 | A1 | 6/2007 | Gould et al. | |
| 2007/0166266 | A1 | 7/2007 | Dillon et al. | |
| 2007/0166449 | A1 | 7/2007 | Dillon et al. | |
| 2007/0166797 | A1 | 7/2007 | Dillon et al. | |
| 2007/0167396 | A1 | 7/2007 | Dillon et al. | |
| 2007/0167397 | A1 | 7/2007 | Dillon et al. | |
| 2007/0167398 | A1 | 7/2007 | Dillon et al. | |
| 2007/0191303 | A1 | 8/2007 | Dillon et al. | |
| 2008/0044850 | A1 | 2/2008 | Taylor et al. | |
| 2008/0124756 | A1 | 5/2008 | Dillon | |
| 2008/0124767 | A1 | 5/2008 | Nobles et al. | |
| 2008/0153080 | A1 | 6/2008 | Woods et al. | |
| 2008/0274494 | A1 | 11/2008 | Kertz | |

(Continued)

FOREIGN PATENT DOCUMENTS

| | | | |
|---|---|---|---|
| CA | 2232707 | | 3/1997 |
| GB | 2348649 | | 10/2000 |
| JP | 09-501313 | A | 2/1997 |
| JP | 2001-505431 | A | 4/2001 |
| JP | 2006-034128 | A | 2/2006 |
| JP | 2006-075097 | A | 3/2006 |
| JP | 2006230211 | | 9/2006 |
| JP | 2007-020476 | A | 2/2007 |
| SU | 1763484 | | 9/1992 |
| WO | WO 95/01446 | | 1/1995 |

(Continued)

OTHER PUBLICATIONS

ABAD, Alignment, ATZ24631, Jun. 19, 2008, 8 pages.

(Continued)

*Primary Examiner* — Hope Robinson

(74) *Attorney, Agent, or Firm* — Dentons US LLP

(57) ABSTRACT

Provided herein is a transgenic bacteria engineered to accumulate carbohydrates, for example disaccharides. Also provided is a photobioreactor for cultivating photosynthetic microorganisms comprising a non-gelatinous, solid cultivation support suitable for providing nutrients and moisture to photosynthetic microorganisms and a physical barrier covering at least a portion of the surface of the cultivation support. Devices for the large scale and continuous cultivation of photosynthetic microorganisms incorporating photobioreactors and methods of use are disclosed. Also disclosed are methods of producing fermentable sugar from photosynthetic microorganisms using a photobioreactor of the invention.

27 Claims, 11 Drawing Sheets

(56) References Cited

U.S. PATENT DOCUMENTS

| | | | |
|---|---|---|---|
| 2008/0299147 | A1 | 12/2008 | Dillon et al. |
| 2009/0004715 | A1 | 1/2009 | Trimbur et al. |
| 2009/0011480 | A1 | 1/2009 | Trimbur et al. |
| 2009/0023180 | A1 | 1/2009 | Dillon |
| 2009/0035842 | A1 | 2/2009 | Trimbur et al. |
| 2009/0047721 | A1 | 2/2009 | Trimbur et al. |
| 2009/0061493 | A1 | 3/2009 | Trimbur et al. |
| 2009/0069213 | A1 | 3/2009 | Avila et al. |
| 2009/0087890 | A1 | 4/2009 | Pyle et al. |
| 2009/0123977 | A1 | 5/2009 | Mendez et al. |
| 2009/0126260 | A1 | 5/2009 | Aravanis et al. |
| 2009/0148918 | A1 | 6/2009 | Trimbur et al. |
| 2009/0181434 | A1 | 7/2009 | Aikens et al. |
| 2009/0246766 | A1 | 10/2009 | Mayfield et al. |
| 2009/0253169 | A1 | 10/2009 | Mayfield et al. |
| 2009/0269816 | A1 | 10/2009 | Mendez et al. |
| 2009/0274736 | A1 | 11/2009 | Dillon et al. |
| 2009/0280545 | A1 | 11/2009 | Mendez et al. |
| 2009/0285850 | A1 | 11/2009 | Dillon et al. |
| 2009/0291490 | A1 | 11/2009 | Spradling |
| 2009/0305942 | A1 | 12/2009 | Day et al. |
| 2010/0050301 | A1 | 2/2010 | Mendez et al. |
| 2010/0151112 | A1 | 6/2010 | Franklin et al. |
| 2010/0151535 | A1 | 6/2010 | Franklin et al. |
| 2010/0151538 | A1 | 6/2010 | Franklin et al. |
| 2010/0151539 | A1 | 6/2010 | Franklin et al. |
| 2010/0151567 | A1 | 6/2010 | Franklin et al. |
| 2010/0170144 | A1 | 7/2010 | Day et al. |
| 2010/0190235 | A1 | 7/2010 | Schuring et al. |
| 2010/0239712 | A1 | 9/2010 | Brooks et al. |

FOREIGN PATENT DOCUMENTS

| | | |
|---|---|---|
| WO | WO 96/21030 | 7/1996 |
| WO | WO 98/03637 | 1/1998 |
| WO | WO 98/24882 | 6/1998 |
| WO | WO 01/017333 | 3/2001 |
| WO | WO 01/44450 | 6/2001 |
| WO | WO 2004/076356 | 9/2004 |
| WO | WO 2007/035579 | 3/2007 |
| WO | WO 2007/076449 | 7/2007 |
| WO | WO 2007/084477 | 7/2007 |
| WO | WO 2008/042975 | 4/2008 |
| WO | WO 2008/130437 | 10/2008 |
| WO | WO 2009/089185 | 7/2009 |
| WO | WO 2009/111513 | 9/2009 |
| WO | WO 2009/129396 | 10/2009 |
| WO | WO 2010/048525 | 4/2010 |

OTHER PUBLICATIONS

Aichi et al., Role of Ntcb in Activation of Nitrate Assimilation Genes in the Cyanobacterium *Synechocystis* Sp. Strain PCC 6803, J Bacteriol, 2001, pp. 5840-5847, vol. 183, No. 20.

Aoki et al., Circadian Expression of the *dnaK* Gene in the Cyanobacterium *Synechocystis* sp. Strain PCC 6803, J. Bacteriol., 1995, pp. 5606-5611, vol. 177, No. 19.

Australian Examination Report No. 1 dated Jun. 21, 2013 in related Application No. AU 2009204313, 5 pages.

Blumwald et al., Studies of Osmoregulation in Salt Adaption of Cyanobacteria with ESR Spin-Probe Techniques, Proc Natl Acad Sci USA, 1983, pp. 2599-2602, vol. 80.

Chen et al., Lignin modifications improves fementable sugar yields for bio-fuel production, Nature Biotech., 2007, pp. 759-761, vol. 25, No. 7.

Chinese Second Office Action dated Oct. 11, 2013, in English and Chinese, in corresponding Chinese Application No. CN 200980107937.6 filed Jan. 5, 2009, 9 pages.

Chinese Third Office Action dated Jul. 9, 2014, in English and Chinese, in corresponding Chinese Application No. CN 200980107937.6 filed Jan. 5, 2009, 7 pages.

Cumino et al., Sucrose metabolism: Anabaena sucrose-phosphate synthase and sucrose-phosphate phosphatase define minimal functional domains shuffled during evolution, FEBS Letters, 2002, pp. 19-23, vol. 517.

Cumino et al., Carbon Cycling in *Anabaena* sp. PCC 7120. Sucrose Synthesis in the Heterocysts and Possible Role in Nitrogen Fixation, Plant Physiol, 2007, pp. 1385-1397, vol. 143.

Curatti et al., Sucrose is involved in the diazotrophic metabolism of the heterocyst-forming cyanobacterium *Anabaena* sp., FEBS Letters, 2002, pp. 175-178, vol. 513.

Curtis et al., The Transcription Apparatus and the Regulation of Transcription linitiation, in the Molecular Biology of Cyanobacteria, Bryant, D. A. (ed), Kluwer Academic Publishers, 2001, pp. 613-639.

Database, Gen Pept, Accession No, Q5N449, downloaded on Internet at www.ncb.nlm.nih.gov/protein/Q5N499, 2005, 1 page.

Database, GenBank, ABB56840.1, downloaded on Internet at http//www.uniprot.org/uniprot/Q31Q29 accessed Aug. 23, 2011, 4 pages.

Database, GenBank, BAA10782.1, downloaded on Internet at http//www.uniprot.org/uniprot/Q55440 accessed Aug. 23, 2011, 4 pages.

Database, GenBank, AAG31136.1, downloaded on Internet at http//www.uniprot.org/uniprot/P74325 accessed Aug. 23, 2011, 5 pages.

Database, GenBank, AAZ87937.1, downloaded on Internet at http//www.uniprot.org/uniprot/Q3Z2S5 accessed Aug. 23, 2011, 3 pages.

Database, GenBank, BAA18352.1, downloaded on Internet at http//www.uniprot.org/uniprot/P74258 accessed Aug. 23, 2011, 5 pages.

Database, GenBank, AAB41279.1, downloaded on Internet at http//www.uniprot.org/uniprot/Q55034 accessed Aug. 23, 2011, 5 pages.

Database, GenBank, ABU63292.1, downloaded on Internet at http//www.uniprot.org/uniprot/A7TZT2 accessed Aug. 23, 2011, 4 pages.

Database, GenBank, AAK86468.1, downloaded on Internet at http//www.uniprot.org/uniprot/A9CK30 accessed Aug. 23, 2011, 4 pages.

Database, UniProtKB/Swiss-Prot, P72753, 1997, downloaded on Internet at http://www.uniprot.org/uniprot/P72753.txt?version=1 accessed Oct. 30, 2014, 1 page.

Database, UniProtKB/Swiss-Prot, Q31MH4, 2006, downloaded on Internet at http://www.uniprot.org/uniprot/Q31MH4.txt?version=1 accessed Oct. 30, 2014, 1 page.

Dillon et al., RNAi as an Experimental and Therapeutic Tool to Study and Regulate Physiological and Disease Processes, Annual Review of Physiology, 2005, pp. 147-173, vol. 67.

Dwi et al., Utilization of cyanobacterial biomass from water bloom for bioproduction of lactic acid, World Journal of Biotech., 2001, pp. 259-264, vol. 17.

Dykxhoorn and Lieberman, The Silent Revolution: RNA Interference as Basic Biology, Research Tool, and Therapeutic, Annual Review of Medicine, 2005, 56:401-423.

Elhai et al., Conjugal Transfer of DNA to Cyanobacteria, Methods in Enzymology, 1988, pp. 747-754, vol. 167.

EMBL-Bank: U51113.1, Cloning vector pBeloBACl1, downloaded on internet at http//www.ebi.ac.uk/ena/data/view/U51113 accessed Aug. 23, 2011, 2 pages.

EMBL-Bank: CS176720.1, Sequence 24 from Patent W02005093080, downloaded on internet at http//www.ebi.ac.uk/enaldatalviewlCS176720 accessed Aug. 23, 2011, 2 pages.

Eurasian Search Report dated May 13, 2011 issued in related application EA201070788, filed Jan. 5, 2009, in Russian, 2 pages.

Eurasian Search Report dated May 13, 2011 issued in related application EA201070788, filed Jan. 5, 2009, English translation, 2 pages.

Eurasian Office Action dated Nov. 26, 2013 in related Eurasian Patent Application No. 201070788/28 filed on Jan. 5, 2009, in Russian, 3 pages.

Eurasian Office Action dated Nov. 26, 2013 in related Eurasian Patent Application No. 201070788/28 filed on Jan. 5, 2009, in English, 3 pages.

Fanning et al., Gene-expressed RNA as a therapeutic: issues to consider, using ribozymes and small hairpin RNA as specific examples, Handbook Exp Pharmacol., 2006, pp. 289-303, vol. 173.

Ferino et al., A Promoter-Probe Vector-Host System for the Cyanobacterium, *Synechocystis* PCC6803, Gene, 1989, pp. 257-266, vol. 84.

Frey et al., Replication and Copy Number Control of the Broad-Host-Range Plasmid RSF1010, Gene, 1992, pp. 101-106, vol. 113.

(56) References Cited

OTHER PUBLICATIONS

Friedberg, Use of Reporter Genes in Cyanobacteria, Methods in Enzymology, 1988, pp. 736-747, vol. 167.
Furste et al., Molecular Cloning of the Plasmid RP4 Primase Region in a Multi-HostRange tacP Expression Vector, Gene, 1986, pp. 119-131, vol. 48.
Ghadessy et al., Directed Evolution of Polymerase Function by Compartmentalized Self-Replication, Proc Natl Acad Sci USA, 2001, pp. 4552-4557, vol. 98, No. 8.
Golden et al., Optimal Conditions for Genetic Transformation of the Cyanobacterium *Anacystis nidulans* R2, Journal of Bacteriology, 1984, pp. 36-42, vol. 158, No. 1.
Golden et al., Expression of a Family of psbA Genes Encoding a Photosystem II Polypeptide in the Cyanobacterium *Anacystis nidulans* R2, EMBO Journal, 1986, pp. 2789-2798, vol. 5, No. 11.
Golden et al., Genetic Engineering of the Cyanobacterial Chromosome, Methods in Enzymology, 1987, pp. 215-231, vol. 153.
Gorelikova, Fundamentals of Modern Food Biotechnology, 2004, Kemerovo, in Russian, 100 pages.
Gormley et al., Transfer of Plasmid RSF1010 by Conjugation from *Escherichia coli* to *Streptomyces lividans* and *Mycobacterium smegmatis*, J Bacteriology, 1991, pp. 6705-6708, vol. 173, No. 21.
Gutierrez et al., Analysis and DNA sequence of the osmoregulated treA gene encoding the periplasmic trehalase of *Escherichia coli* K12, Mol Gen Genet., 1989, pp. 347-354, vol. 217.
Hagemann et al., Characterization of a glucosylglycerol-phosphate-accumulating, salt-sensitive mutant of the cyanobacterium, *Synechocystis* sp. Strain PCC 6803, Arch. Microbil., 1996, pp. 83-91, vol. 166.
Helene et al., Control of Gene Expression by Triple Helix-Forming Oligonucleotides, Ann. N.Y. Acad. Sci., 1992, pp. 27-36, vol. 660.
Hershkovitz et al., Accumulation of Trehalose and Sucrose in Cyanobacteria Exposed to Matric Water Stress, Appl Environ Microbiol, 1991, pp. 645-648, vol. 57, No. 3.
Ikeuchi et al., *Synechocystis* sp. PCC 680—A Useful Tool in the Study of the Genetics of Cyanobacteria, Photosynthesis Research, 2001, pp. 73-83, vol. 70.
India Office Action dated Jun. 24, 2014 in corresponding Indian Application No. 4728/CHEN/2010 filed Jul. 28, 2010, 3 pages.
International Search Report issued on May 22, 2009, in the related application PCT/US09/30162, 4 pages.
Jahreis et al., Adaptation of Sucrose Metabolism in the *Escherichia coli* Wild-Type Strain EC3132, J. Bacteriol., 2002, pp. 5307-5316, vol. 184, No. 19.
Japanese Office Action dated Oct. 7, 2013, in English and Japanese, in corresponding Japanese Application No. JP 2010-541587 filed Jan. 5, 2009, 8 pages.
Japanese Office Action dated Nov. 10, 2014, in English and Japanese, in corresponding Japanese Application No. JP 2010-541587 filed Jan. 5, 2009, 8 pages.
JP 2006-034128, published Feb. 9, 2006, English Abstract downloaded from PAJ, 1 page.
JP 2006-075097, published Mar. 23, 2006, English Abstract downloaded from PAJ, 1 page.
JP 2007-020476, published Feb. 1, 2007, English Abstract downloaded from PAJ, 1 page.
Kaasen et al., Analysis of the otsBA operon for osmoregulatory trehalose synthesis in *Escherichia coli* and homology of the OtsA and OtsB proteins to the yeast trehalose-6-phosphate synthase/phosphatase complex, Gene, 1994, pp. 9-15, vol. 145.
Kaneko et al., Sequence Analysis of the Genome of the Unicellular Cyanobacterium *Synechocystis* sp. Strain PCC6803. II. Sequence Determination of the Entire Genome and Assignment of Potential Protein-coding Regions, DNA Research, 1996, pp. 109-136, vol. 3.
Koksharova et al., Genetic Tools for cyanobacteria, Appl Microbiol Biotechnol, 2002, pp. 123-137, vol. 58, No. 2.
Koo et al., Regulation of Compatible Solute Accumulation in *Salmonella typhimurium*: Evidence for a Glycine Betaine Efflux System, J Gen Microbial, 1991, pp. 2617-2625, vol. 137.
Kreps et al., Conjugative transfer and autonomous replication of a promiscuous IncQ plasmid in the cyanobacterium Synechocystis PCC 6803, Mol Gen Genet, 1990, pp. 129-133, vol. 221.
Kucho et al., Global Analysis of Circadian Expression in the Cyanobacterium *Synechocystis* sp. Strain PCC 6803, J Bacteriol, 2005, pp. 2190-2199, vol. 187, No. 6.
Labarre et al., Insertional Mutagenesis by Random Cloning of Antibiotic Resistance Genes into the Genome of the Cyanobacterium *Synechocystis* Strain PCC 6803, J Bacteriol, 1989, pp. 3449-3457, vol. 171, No. 6.
Lamark et al., Efflux of choline and glycine betaine from osmoregulating cells of *Escherichia coli*, FEMS Microbiol. Lett, 1992, pp. 149-154, vol. 96.
Lee et al., Aptamer Therapeutics Advance, Curr. Opin. Chem. Biol., 2006, pp. 282-289, vol. 10.
Link et al., Beyond Toothpicks: New Methods for Isolating Mutant Bacteria, Nature Reviews, 2007, pp. 680-688, vol. 5.
Lunn et al., Purification, molecular cloning, and sequence analysis of sucrose-$6^F$-phosphate phosphohydrolase from plants, PNAS 2000, pp. 12914-12919, vol. 97, No. 23.
Lunn, Evolution of Sucrose Synthesis, Plant Physiol, 2002, pp. 1490-1500, vol. 128.
Ma et al., Exogenous expression of the wheat chloroplastic fructose-I ,6-bisphosphatase gene enhances photosynthesis in the transgenic cyanobacterium, Anabaena PCC7120, Journal of Applied Phycology, 2005, pp. 273-280, vol. 17.
Machray et al., Characterisation of a Complementary DNA Encoding a Novel Plant Enzyme with Sucrolytic Activity, FEBS Lett, 1994, pp. 123-127, vol. 354.
Maeda et al., *cis*-Acting Sequences Required for NtcB-Dependent, Nitrite-Responsive Positive Regulation of the Nitrate Assimilation Operon in the Cyanobacterium *Synechococcus* sp. Strain PCC 7942, J. Bacteriol., 1998, pp. 4080-4088, vol. 180, No. 16.
Marin et al., The ggpS Gene from *Synechocystis* sp. Strain PCC 6803 Encoding Glucosyl-Glycerol-Phosphate Synthase is Involved in Osmolyte Syntesis, J of Bacteriology, 1998, pp. 4843-4849, vol. 180, No. 18.
Marraccini et al., A Conjugative Plasmid Vector for Promotor Analysis in Several Cyanobacteria of the Genera *Synechococcus* and *Synechocystis*, Plant Molecular Biology, 1993, pp. 905-909, vol. 23.
Mermet-Bouvier et al., A Conditional Expression Vector for the Cyanobacteria *Synechocystis* sp. Strains PCC6803 and PCC6714 or *Synechococcus* sp. Strains PCC7942 and PCC6301, Current Microbiology, 1994, pp. 145-148, vol. 28.
Mexican Official Office Action dated May 30, 2012 in related Application No. MX/a/2010/007319 filed Jan. 5, 2009, includes English translation, 4 pages.
Miao et al., Sucrose Accumulation in Salt-Stressed Cells of *agp* Gene Deletion-Mutant in Cyanobacterium *Synechocystis* sp. PCC6803, FEMS Microbiol. Lett., 2003, pp. 71-77, vol. 218.
Nitsch et al., Auxin-Dependent Growth of Excised Helianthus Tuberosus Tissues. I., American Journal of Botany, 1956, pp. 839-851, vol. 43.
Pushparaj et al., Short Interfering RNA (siRNA) as a Novel Therapeutic, Clinical and Experimental Pharmacology and Physiology, 2006, pp. 504-510, vol. 33.
Reynolds et al., Rational siRNA Design for RNA Interference, Nature Biotechnology, 2004, pp. 326-330, vol. 22, No. 3.
Richert et al., Characterization of Exopolysaccharides Produced by Cyanobacteria Isolated from Polynesian Microbial Mats, Current Microbiology, 2005, pp. 379-384, vol. 51.
Rose, The Nucleotide Sequence of pACYC177, Nucleic Acids Res, 1988, p. 356, vol. 16.
Sagner et al., Rapid Filter Assay for the Detection of DNA Polymerase Activity: Direct Identification of the Gene for the DNA Polymerase from Thermus Aquaticus, Gene, 1991, pp. 119-123, vol. 97.
Sazuka et al., Sequence Features Surrounding the Translation Initiation Sites Assigned on the Genome Sequence of *Synechocystis* sp. Strain PCC6803 by Amino-Terminal Protein Sequencing, DNA Research, 1996, pp. 225-232, vol. 3.

(56) References Cited

OTHER PUBLICATIONS

Schleyer et al., Transient, Specific and Extremely Rapid Release of Osmolytes from Growing Cells of *Escherichia coli* K-12 Exposed to Hypoosmotic Shock, Arch Microbiol, 1993, pp. 424-443, vol. 160.
Shi et al., Removal of nitrogen and phosphorus from wastewater using microalgae immobilized on twin layers: an experimental study, J App Phyc, 2007, pp. 417-423, vol. 19.
SU1763484 Published Sep. 23, 1992, abstract only in English, 1 page.
Supplementary European Search Report dated Dec. 20, 2010, issued in related EP Application No. 09700920.3.
Studier, Protein Production by Auto-Induction in High-Density Shaking Cultures, Protein Expr Purif, 2005, pp. 207-234, vol. 41.
Torres et al., A metabolic pathway leading to mannoslfructose biosynthesis in Agrobacterium tumefaciens uncovers a family of mannosyltransferases, 2007, PNAS, pp. 14318-14323, vol. 104, No. 36.
Wilson, Preparation of Genomic DNA from Bacteria, *In* Current Protocols in Molecular Biology, John Wiley and Sons, 1997, 2.4.1-2.4.5.
Zang et al., Optimum Conditions for Transformation of *Synechocystis* sp. PCC 6803, Journal of Microbiology, 2007, pp. 241-245, vol. 45.
Zhang et al., Photosynthetic performance of a cyanobacterium in a vertical flat-plate photobioreactor for outdoor microalgal production and fixation of CO2, Biotechnology Letters, 2001, pp. 21-26, vol. 23.
Curatti et al., Sucrose is involved in the diazotrophic metabolism of the heterocyst-forming cyanobacterium Anabaena sp., FEBS Letters, 513, 2-3, 2002, pp. 175-178.
European Search Report dated Sep. 29, 2015 issued in corresponding EP Application No. 15166805.0 (7 pages).
Australia Office action dated Dec. 8, 2015 issued in corresponding AU Application No. 2014250606 filed Jan. 5, 2009 (4 pages).

* cited by examiner

| | |
|---|---|
| Ssp6803_SPS | MSYSSKYILLISVHGLIRGENLELGRDADTGGQTKYVLELARALVKNPQVARVDLTRLI |
| Selo7942_ASF | MAAQNLYILHIQTHGLLRGQNLELGRDADTGGQTKYVLELAQAQAKSPQVQQVDIITRQI |
| Ssp6803_SPP | ------------------------------------------------------------ |

| | |
|---|---|
| Ssp6803_SPS | KDPKVDADYAQPRELIGDRAQIVRIECGPEEYIAKEMLWDYLDNFADHALDYLKEQPELP |
| Selo7942_ASF | TDPRVSVGYSQAIEPFAPKGRIVRLPFGPKRYLRKELLWPHLYTFADAILQYLAQQKRTP |
| Ssp6803_SPP | ------------------------------------------------------------ |

| | |
|---|---|
| Ssp6803_SPS | DVIHSHYADAGYVGTRLSHQLGIPLVHTGHSLGRSKRTRLLLSGIKADEIESRYNMARRI |
| Selo7942_ASF | TWIQAHYADAGQVGSLLSRWLNVPLIFTGHSLGRIKLKKLLEQDWPLEEIEAQFNIQQRI |
| Ssp6803_SPP | ------------------------------------------------------------ |

| | |
|---|---|
| Ssp6803_SPS | NAEEETLGSAARVITSTHQEIAEQYAQYDYYQPDQMLVIPPGTDLEKFYPPKGNEWETPI |
| Selo7942_ASF | DAEEMTLTHADWIVASTQQEVEEQYRVYDRYNPERKLVIPPGVDTDRFRFQPLGDRGVVL |
| Ssp6803_SPP | ------------------------------------------------------------ |

| | |
|---|---|
| Ssp6803_SPS | VQELQRFLRHPRKPIILALSRPDPRKNIHKLIAAYGQSPQLQAQANLVIVAGNRDDITDL |
| Selo7942_ASF | QQELSRFLRDPEKPQILCLCRPAPRKNVPALVRAFGEHPWLRKKANLVLVLGSRQDINQM |
| Ssp6803_SPP | ------------------------------------------------------------ |

| | |
|---|---|
| Ssp6803_SPS | DQGPREVLTDLLLTIDRYDLYGKVAYPKQNQAEDVYALFRLTALSQGVFINPALTEPFGL |
| Selo7942_ASF | DRGSRQVFQEIFHLVDRYDLYGSVAYPKQHQADDVPEFYRLAAHSGGVFVNPALTEPFGL |
| Ssp6803_SPP | ------------------------------------------------------------ |

| | |
|---|---|
| Ssp6803_SPS | TLIEAAACGVPIVATEDGGPVDIIKNCQNGYLINPLDEVDIADKLLKVLNDKQQWQFLSE |
| Selo7942_ASF | TILEAGSCGVPVVATHDGGPQEILKHCDFGTLVDVSRPANIATALATLLSDRDLWQCYHR |
| Ssp6803_SPP | ------------------------------------------------------------ |

DXDXT

| | |
|---|---|
| Ssp6803_SPS | SGLEGVKRHYSWPSHVESYLEAINALTQQTSVLKRSDLKRRRTLYYNGALVT<u>SLDQN</u>LLG |
| Selo7942_ASF | NGIEKVPAHYSWDQHVNTLFERMETVALPRRRAVSFVRSRKRLIDAKRLVVS<u>DIDN</u>TLL- |
| Ssp6803_SPP | ---------------------------------------MRQLLLIS<u>DLDN</u>TWV- |
| |                                              :  :::..*:.. : |

T

| | |
|---|---|
| Ssp6803_SPS | *ALQGGL*PGDRQTLDELLEVLYQHRKNVGFCIA<u>T</u>GRRLDSVLKILREYRIPQPDMLITSMG |
| Selo7942_ASF | -------GDRQGLENLMTYLDQYRDHFAFGIA<u>T</u>GRRLDSAQEVLKEWGVPSPNFWVTSVG |
| Ssp6803_SPP | -------GDQQALEHLQEYLGDRRGNFYLAYA<u>T</u>GRSYHSARELQKQVGLMEPDYWLTAVG |
| |         **:* *:.*   * : * :. : **** .*. :: :: . *: :*::* |

| | |
|---|---|
| Ssp6803_SPS | TEIYSSPDLIPDQSWRNHIDYLWNRNAIVRILGELPGLALQPKEELSAYKISYFYD-AAI |
| Selo7942_ASF | SEIHYGTDAEPDISWEKHINRNWNPQPRIRAVMAQLPFLELQPEEDQTPFKVSFFVR-DRH |
| Ssp6803_SPP | SEIYHP--EGLDQHWADYLSEHWQRDILQAIADGFEALKPQSPLEQNPWKISYHLDPQAC |
| | :**:       *  * .:: .*: :  :   * *. : ..:*:*:. |

K                                        D

| | |
|---|---|
| Ssp6803_SPS | APNLEEIRQLLHKGEQTVNTIISFGQFLDILPIRAS<u>K</u>GYAVRWLSQQWNIPLEHVFTAG<u>G</u> |
| Selo7942_ASF | ETVLREVRQHLRRHRLRLKSIYSHQEFLDILPLAAS<u>K</u>GDAIRHLSLRWRIPLENILVAG<u>D</u> |
| Ssp6803_SPP | PTVIDQLTEMLKETGIPVQVIFSSGKDVDLLPQRSN<u>K</u>GNATQYLQQHLAMEPSQTLVCG<u>D</u> |
| | . : :: : *:.   :: * * : *;**  :,** : * *.  .: ...*. |

D

| | |
|---|---|
| Ssp6803_SPS | SGA<u>D</u>EDMMRGNTLSVVVANRHHEELSNLGEIEP--IYFSEKRYAAGILDGLAHYRFFELL |
| Selo7942_ASF | SGN<u>D</u>EEMLKGHNLGVVVGN-YSPELEPLRSYER--VYFABGHYANGILEALKHYRFFEAI |
| Ssp6803_SPP | SGN<u>D</u>IGLFETSARGVIVRNAQPELLHWYDQWGDSRHYRAQSSHAGAILEAIAHFDFLS-- |
| | ** * ::.   .:* *     *     .    * :: :* .**:.: *: *:. |

| | |
|---|---|
| Ssp6803_SPS | DPV |
| Selo7942_ASF | A-- |
| Ssp6803_SPP | --- |

LEGEND
Ssp6803_SPS    Seq. ID No. 4
Selo7942_ASF   Seq. ID No. 2
Ssp6803_SPP    Seq. ID No. 6

FIG. 5

LEGEND
Nucleotide Seq. ID No. 1
Amino Acid Seq. ID No. 2

A
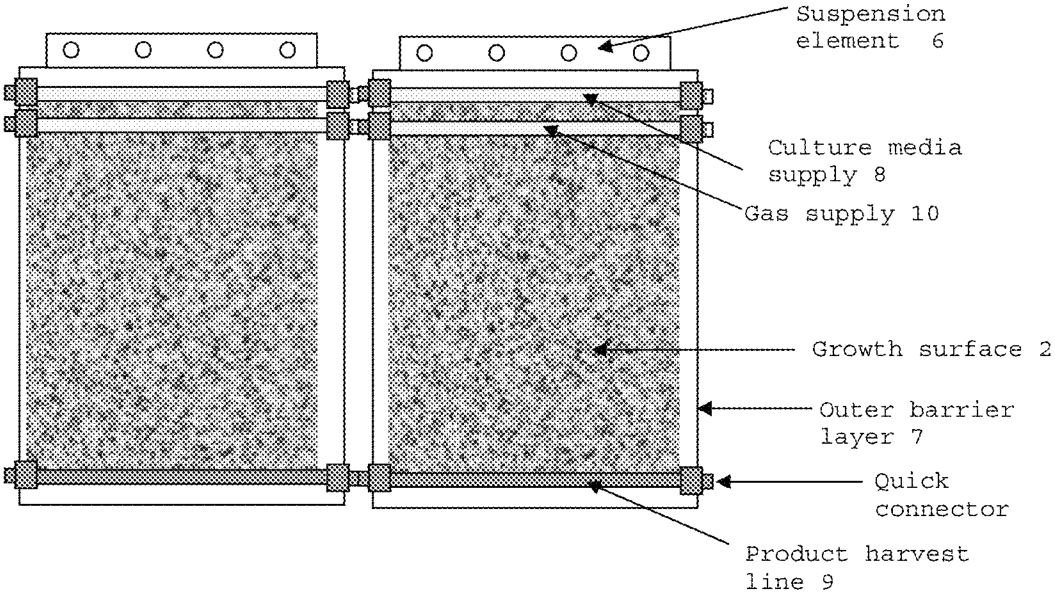
B
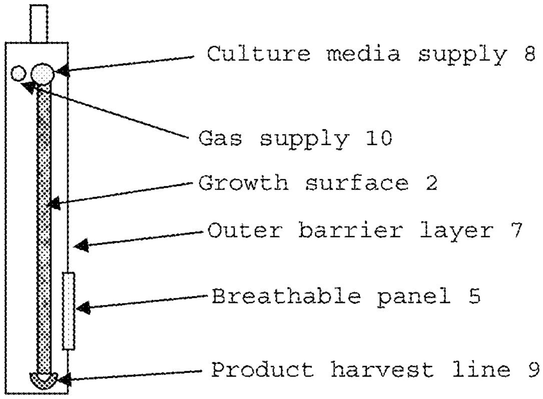
FIG. 12

PHOTOBIOREACTOR

CROSS-REFERENCE TO RELATED APPLICATIONS

The present application is a Continuation of U.S. application Ser. No. 13/737,201 (filed 9 Jan. 2013 now U.S. Pat. No. 8,728,783 issued 20 May 2014), which is a Divisional of U.S. application Ser. No. 12/348,887 (filed 5 Jan. 2009, now U.S. Pat. No. 8,367,379 issued 5 Feb. 2013), which claims priority to U.S. Prov. App. Ser. No. 61/085,797 (filed 1 Aug. 2008) and U.S. Prov. App. Ser. No. 61/018,798 (filed 3 Jan. 2008), each of which is incorporated herein by reference in its entirety.

INCORPORATION-BY-REFERENCE OF MATERIAL SUBMITTED IN COMPUTER READABLE FORM

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

FIELD OF THE INVENTION

The present invention generally relates to transgenic microorganisms and methods and devices for their cultivation.

BACKGROUND

To address the world's increasing energy requirements, efficient and environmentally sound alternatives to the use of fossil fuels are sought after. Alternative fuels, such as ethanol or biodiesel, can be produced from plant biomass. For example, the key ingredient used to produce ethanol from current processes is termed fermentable sugar. Most often, fermentable sugar is in the form of sucrose, glucose, or high-fructose corn syrup. Plants currently grown to produce such biomass include corn, sugarcane, soybeans, canola, jatropha, and so forth. But much of the plant biomass used to produce fermentable sugar requires extensive energy-intensive pre-processing. Further, use of such plant biomass can lead to soil depletion, erosion, and diversion of the food supply.

It is known that some cyanobacteria produce sucrose through the action of sucrose phosphate synthase and sucrose phosphate phosphatase, where it has been studied exclusively as an osmoprotectant. With respect to salt tolerance, cyanobacteria can be divided into three groups. Strains having low tolerance (less than 700 mM) synthesize either sucrose, as is the case with *Synechococcus elongatus* PCC 7942, or another dissaccharide known as trehalose [Blumwald et al., Proc Natl Acd Sci USA (1983) 80:2599-2602 and Reed et al., FEMS Microbiol Rev (1986) 39:51-56]. Glucosylglycerol is produced by strains having moderate halotolerance (0.7-1.8 mM), such as *Synechocystis* sp. PCC 6803. High salt tolerance (up to 2.5 M) results from the accumulation of either glycine betaine or glutamate betaine. Miao et al. [FEMS Microbiol Lett (2003) 218:71-77] determined that when glucosylglycerol biosynthesis is blocked by deletion of the agp gene, however, *Synechocystis* sp. PCC 6803 produces sucrose as its osmoprotectant. Desiccation tolerant cyanobacteria also produce sucrose and trehalose in response to matric water stress [Hershkovitz et al., Appl Environ Microbiol (1991) 57:645-648].

*Synechocystis* spp. PCC 6803 (ATCC 27184) and *Synechococcus elongatus* PCC 7942 (ATCC 33912) are relatively well-studied, have genetic tools available and the sequences of their genomes are known (see e.g., Koksharova, 0. A. and•Wolk, C. P. 2002. Appl Microbiol Biotechnol 58, 123-137; Ikeuchil, M. and Satoshi Tabata, S. 2001. Photosynthesis Research 70, 73-83; Golden, S. S., Brusslan, J. and Haselkorn, R. 1987. Methods in Enzymology 153, 215-231; Friedberg, D. 1988. Methods in Enzymology 167, 736-747; Kaneko, T. et al. 1996. DNA Research 3, 109-136).

The commercial cultivation of photosynthetic microorganisms such as *Spirulina maximum, Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella* sp., *Scenedesmus obliquus, Anabaenopsis, Aulosira, Cylindrospermum, Scenecoccus* sp., *Scenecosystis* sp., and *Tolypothrix* is desirable for numerous applications including the production of fine chemicals, pharmaceuticals, cosmetic pigments, fatty acids, antioxidants, proteins with prophylactic action, growth factors, antibiotics, vitamins and polysaccharides. The algic biomass can also be useful, in a low dose, to replace or decrease the level of antibiotics in animal food or be useful as a source of proteins. Furthermore, the algic biomass provided in a wet form, as opposed to a dried form, can be fermented or liquefied by thermal processes to produce fuel. Thus, there is great interest in the ability to increase the efficiency of cultivating such organisms.

In general, current photosynthetic bioreactors rely on the cultivation of microorganisms in a liquid phase system to produce biomass. These systems are usually open-air pond-type reactors or enclosed tank-type reactors. Enclosed bioreactors, however, typically are considered to be an improvement over pond type reactors in many respects. Importantly, enclosed systems provide a barrier against environmental contamination. In addition, these systems allow for greater control of temperature and gas content of the liquid media.

Still, the uses of enclosed photobioreactors tend to be limited by photosynthetic microorganisms' requirement for light (i.e., actinic radiation provides the energy required by photosynthetic microorganisms to fix carbon dioxide into organic molecules). Thus, sufficient illumination of the photosynthetic microorganisms is an unyielding requirement. Nevertheless, as the cell density in a liquid phase photobioreactor increases, the ability of light to penetrate into the media decreases, which typically limits the cell density that may be achieved. Additionally, some type of agitation of the liquid media is generally required to prevent unwanted sedimentation of the organisms, a process that requires the input of energy.

Numerous attempts have been made to devise a method of bringing light to the organisms in liquid phase systems. For example, some systems involve circulating the liquid culture media through transparent tubes. Other attempts involve placing a light source within the media or introducing reflecting particles into the culture media to adjust the radiation absorbance of the culture. Despite these efforts, a significant increase in the ability to culture organisms in liquid phase systems at higher cell densities has not yet been achieved.

In addition to the aforementioned light requirement, the use of liquid phase photobioreactors has been burdened with providing the photosynthetic microorganisms enough carbon dioxide for photosynthesis. Typically, these systems generally incorporate some type of additional aeration system to increase the concentration of carbon dioxide dissolved in the media. Eliminating the need for aeration would greatly simplify the system thus reducing operating costs.

Liquid phase photobioreactors also tend not to be well suited for conventional methods of continuous production. In general, the transportation of large volumes of liquid is complex and burdensome. Further, because liquid phase systems usually require mechanisms for circulation, agitation, aeration, and the like, it is generally simpler and more cost effective to operate only one or a few large cultivation devices rather than numerous smaller ones. Therefore, currently practiced methods involve processing relatively large batches (i.e., a batch of photosynthetic microorganisms is cultivated and the entire resulting biomass is then harvested).

Thus, there is a great need in the art for advancement in photosynthetic bioreactor design. Providing a new type of photosynthetic bioreactor capable of efficiently cultivating and harvesting relatively high densities of photosynthetic microorganisms without large volumes of water or other liquid media, without the aforementioned extraordinary measures for supplying adequate light and carbon dioxide, and at a reasonable cost would represent a substantial advance in the art, and benefit industry and consumers alike.

SUMMARY OF THE INVENTION

Provided herein is a photobioreactor for cultivating photosynthetic microorganisms comprising a non-gelatinous, solid cultivation support suitable for providing nutrients and moisture to photosynthetic microorganisms and a physical barrier covering at least a portion of the surface of the cultivation support. Devices for the large scale and continuous cultivation of photosynthetic microorganisms incorporating photobioreactors and methods of use are disclosed.

One aspect provides a photobioreactor for cultivating photosynthetic microorganisms. The photobioreactor comprises a non-gelatinous, solid cultivation support suitable for providing nutrients and moisture to photosynthetic microorganisms on at least a portion of a surface thereof, wherein said portion of the surface has a topography that allows photosynthetic microorganisms to adhere thereto when said portion of the surface is oriented non-horizontally; and a physical barrier covering at least said portion of the surface of the cultivation support, wherein the physical barrier is configured so as to allow inoculation of said portion of the surface of the cultivation support, formation and maintenance of an environment suitable for the cultivation of such photosynthetic microorganisms, and harvesting of such cultivated photosynthetic microorganisms.

In some embodiments, the photobioreactor comprises photosynthetic microorganisms on said portion of the surface of the cultivation support. In some embodiments, the photobioreactor further comprises a cell engineered to accumulate a disacharide, as described further below, wherein the cell is adhered to the solid cultivation support. In some embodiments, said portion of the surface of the cultivation support is capable of cultivating photosynthetic microorganisms at a density of at least about 50 grams of dry biomass per liter equivalent.

In some embodiments, the cultivation support is flexible. In some embodiments, the cultivation support comprises one or more rigid materials. In some embodiments, the cultivation support of the photobioreactor comprises at least two layers, a first layer adjacent to a second layer, wherein material of the at least two layers is the same material or different materials. In some embodiments, the first layer comprises a high surface area growth material and the second layer a permeable type material. In some embodiments, the cultivation support of the photobioreactor comprises flexibly connected rigid portions, wherein the rigid portions are comprised of the one or more rigid materials. In some embodiments, the photobioreactor comprises a single cultivation support. In some embodiments, the photobioreactor comprises a plurality of cultivation supports.

In some embodiments, the cultivation support comprises a fabric. In some embodiments, the fabric is comprised of fibers that are natural, modified natural, synthetic, or a combination thereof. In some embodiments, the fabric is a woven fabric, a knitted fabric, a felt, a mesh of cross-linked fiber polymers, or a combination thereof. In some embodiments, the natural fibers are selected from the group consisting of cotton, wool, hemp, tree fiber, other cellulosic fibers, and combinations thereof. In some embodiments, the modified natural fibers are selected from the group consisting of nitrocellulose, cellulose acetate, cellulose sulfonate, crosslinked starches, and combinations thereof. In some embodiments, the synthetic fibers are selected from the group consisting of polyester, polyacrylate, polyamine, polyamide, polysulfone, and combinations thereof.

In some embodiments, the cultivation support is coated with a moisture absorbent polymer. In some embodiments, the fabric, the fiber of the fabric, or both, are coated with a moisture absorbent polymer. In some embodiments, the moisture absorbent polymer is selected from the group consisting of agar, polyacrylate, polyamide, polyamine, polyethylene glycol, modified starches, and combinations thereof.

In some embodiments, the physical barrier of the photobioreactor is at least substantially impermeable to solid particulate and liquid but does not prevent the transport of gas or vapor to and from the space proximate to said portion of the surface of the cultivation support nor actinic irradiation of said portion of the surface of the cultivation support. In some embodiments, the physical barrier is sufficiently impermeable to water vapor so that the cultivation support upon being moistened will retain enough of the moisture so the photosynthetic microorganisms remain adequately hydrated during cultivation. In some embodiments, the barrier is configured to enclose the cultivation support and any photosynthetic microorganisms thereon, and to be releasably sealed during at least a portion of the cultivation of the photosynthetic microorganisms. In some embodiments, the physical barrier is flexible. In some embodiments, the physical barrier further comprises a first portion that is at least substantially impermeable to solid particulate, liquid, gas, and vapor, and a second portion that is permeable to gas and vapor but at least substantially impermeable to solid particulate and liquid. In some embodiments, the second portion of the barrier has a gas or vapor exchange rate that is from at least about 5 Gurley seconds to no greater than about 10,000 Gurley seconds. In some embodiments, the second portion of the barrier comprises a selective membrane comprising olefin fiber or polyethylene fiber material, polytetrafluoroethylene filtration media, cellulosic filter material, fiberglass filter material, polyester filter material, polyacrylate filter material, polysulfone membranes, or nylon membranes. In some embodiments, the first portion is at least substantially transparent to actinic radiation and the second portion is not at least substantially transparent to actinic radiation, and the configuration of the first and second portions relative to each other and at least said portion of the surface of the cultivation support is such that there a sufficient amount of actinic radiation and gas exchange to support photosynthesis by photosynthetic microorganisms.

In some embodiments, the photobioreactor further comprises a source of actinic radiation situated between the cultivation support and the physical barrier. In some embodiments, the physical barrier is between the cultivation support and a source of actinic radiation and is sufficiently transparent to such actinic radiation and sufficiently gas permeable to allow for photosynthesis by the photosynthetic microorganisms during cultivation.

In some embodiments, the photobioreactor further comprises water, nutrients, or a combination thereof on, within, or on and within, the cultivation support. In some embodiments, the photobioreactor further comprises one or more attachment points for attaching the photobioreactor to a structure. In some embodiments, the solid cultivation support further comprises one or more attachment points for attaching the cultivation support. In some embodiments, the photobioreactor further comprises at least one of a fluid supply system, a nutrient supply system, a gas supply system, and a microorgansim supply system.

In some embodiments, the photobioreactor further comprises a conveyance system, wherein the conveyance system moves the solid cultivation support so as to optimize position of the solid cultivation support for receiving light. In some embodiments, the photobioreactor comprises a plurality of solid cultivation supports, wherein the plurality of solid cultivation supports radiate outward from a central point. In some embodiments, one or more solid cultivation supports of the plurality of solid cultivation supports comprises a sheet in which the depth of the solid cultivation support is substantially less than length and width of the solid cultivation support. In some embodiments, the photobioreactor comprises a conveyance system, wherein the conveyance system moves one or more solid cultivation supports of the plurality of solid cultivation supports so as to optimize position thereof for receiving light. In some embodiments, the conveyance system moves the plurality of solid cultivation supports around the central point so as to optimize position of one or more solid cultivation supports for receiving light. In some embodiments, the physical barrier comprises at least a portion sufficiently transparent to actinic radiation for the cultivation of photosynthetic organisms and the position of the transparent portion of the physical barrier is movable to optimize receipt of light by the solid cultivation support. In some embodiments, at least a portion of the solid cultivation support is configured so as to be exposed to an external source of actinic radiation. In some embodiments, the photobioreactor comprises a source of artificial actinic radiation. In some embodiments, the solid cultivation support comprises a material having loops, such as terry cloth.

Another aspect provides a device for cultivating photosynthetic microorganisms. Such device comprises at least one photobioreactor as described above, and a structure to which the at least one photobioreactor is attached that orientates at least one cultivation support of the at least one photobioreactor non-horizontally. In some embodiments, the at least one photobioreactor is suspended from the structure. In some embodiments, the structure is substantially covered by the physical barrier. In some embodiments, the structure comprises a conveyor system or a component thereof such that the at least one cultivation support is capable of being conveyed along the path of the conveyor system. In some embodiments, the device further comprises one, two, or three of the following: an inoculation station such that each cultivation support as it is conveyed along the path of the conveyor system may be inoculated with photosynthetic microorganisms; a cultivating station such that the photosynthetic microorganisms on each inoculated cultivation support are cultivated as each cultivation support is conveyed along the path of the conveyor system; and a harvesting station to which the cultivation support is conveyed so that at least a portion of the cultivated photosynthetic microorganisms may be harvested from each cultivation support. In some embodiments, the inoculation station and the harvesting station are substantially adjacent to each other or are substantially coextensive. In some embodiments, the device further comprises an inducing station for inducing the synthesis of fermentable sugar by photosynthetic microorganisms on each cultivation support. In some embodiments, the device further comprises at least one of a fluid supply system, a nutrient supply system, a gas supply system, or a microorgansim supply system. In some embodiments, the device further comprises a photosynthetic microorganisms adhered on the solid cultivation support. In some embodiments, the device further comprises a cell engineered to accumulate a disacharide, as described further below, wherein the cell is adhered to the solid cultivation support.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 5 is a polypeptide sequence alignment of the *Synechocystis* spp. PCC 6803 (Ssp6803) sucrose phosphate synthase (SPS) and sucrose phosphate phosphatase (SPP) proteins with the *Synechococcus elongatus* PCC 7942 (Selo7942) active SPS/SPP fusion (ASF). Ssp6803 contains separate genes encoding SPS and SPP activities. The SPS protein from *Synechocystis* spp. PCC 6803 bears a presumably inactive SPP domain, as many of the active site residues are not conserved. The canonical HAD hydrolase active site residues are shown above the alignment with conserved amino acids shown underlined and non-conserved residues double underlined. An eight amino acid insertion within the inactive SPP domain of *Synechocystis* spp. PCC 6803 SPS is italicized. Further details regarding methodology are provided in Example 4.

*coli* by cloning cyanobacterial genomic DNA into the MCS. The plasmid library can then be transferred to cyanobacteria by conjugation or direct transformation. Active promoters can then be isolated by selection for resistance to chloramphenicol through expression of the chloramphenicol acetyltransferase gene (cat). The strength of the promoters can be assessed by both assay for chloramphenicol acetyltransferase activity and direct examination of sucrose production. Further details regarding methodology are provided in Example 5.

Figure 7:
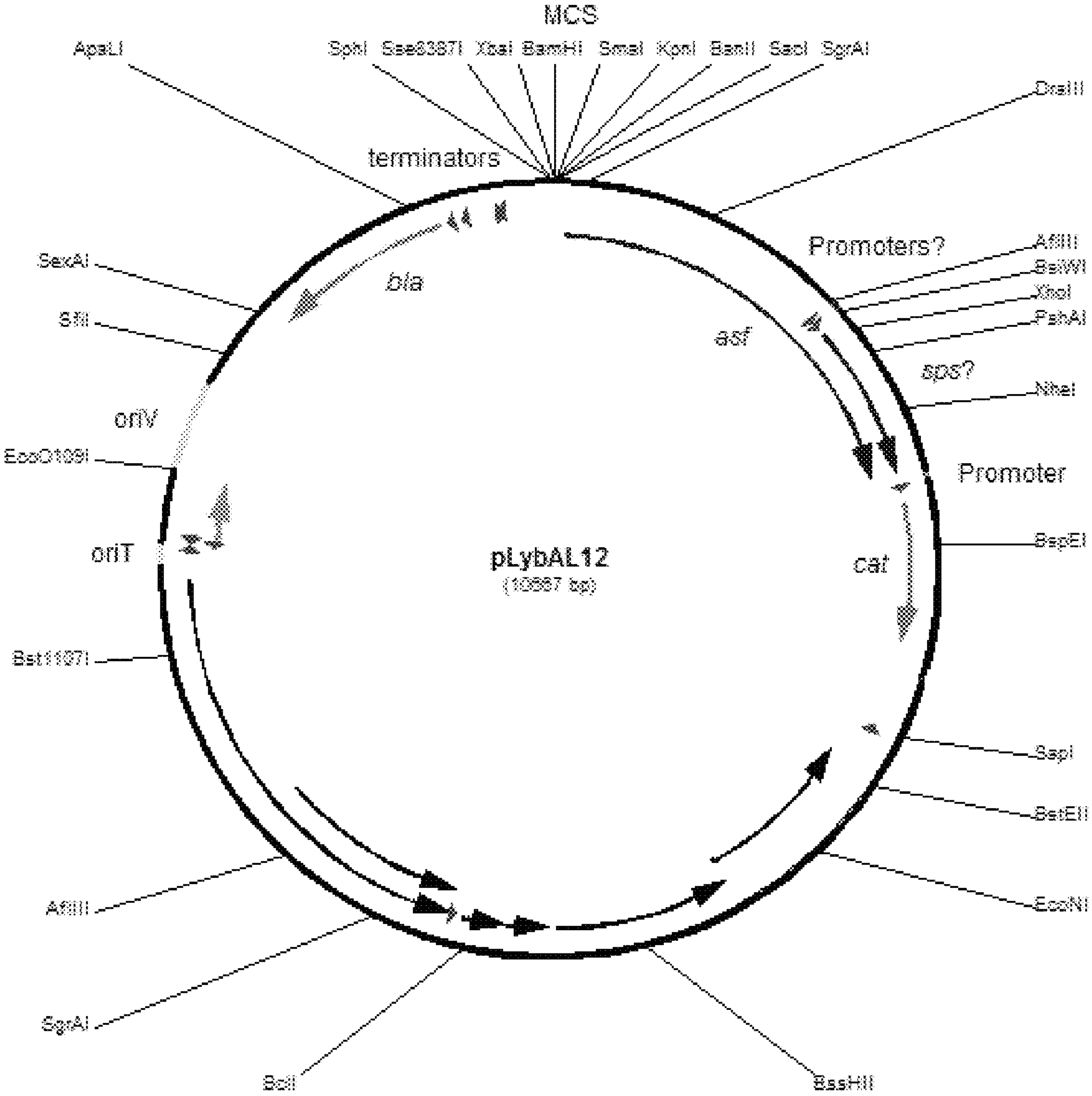

FIG. 7 is schematic depiction of pLybAL12. pLybAL12 allows analysis of the capacity of preselected promoters to drive asf expression. The only difference between pLybAL12 and pLybAL11 is the presence of an active promoter in front of the chloramphenicol acetyltransferase gene (cat). Specific DNA sequences isolated from cyanobacterial chromosomal DNA amplified by PCR can be cloned into the MCS. Both chloramphenicol and ampicillin can be used for selection in *E. coli*. The plasmid library can then be transferred to cyanobacteria by conjugation or direct transformation. Plasmid bearing cyanobacteria can then be isolated by selection for resistance to chloramphenicol through expression of the chloramphenicol acetyltransferase gene (cat). The strength of the promoters can be assessed by both assay for chloramphenicol acetyltransferase activity and direct examination of sucrose production. Further details regarding methodology are provided in Example 5.

Figure 8:
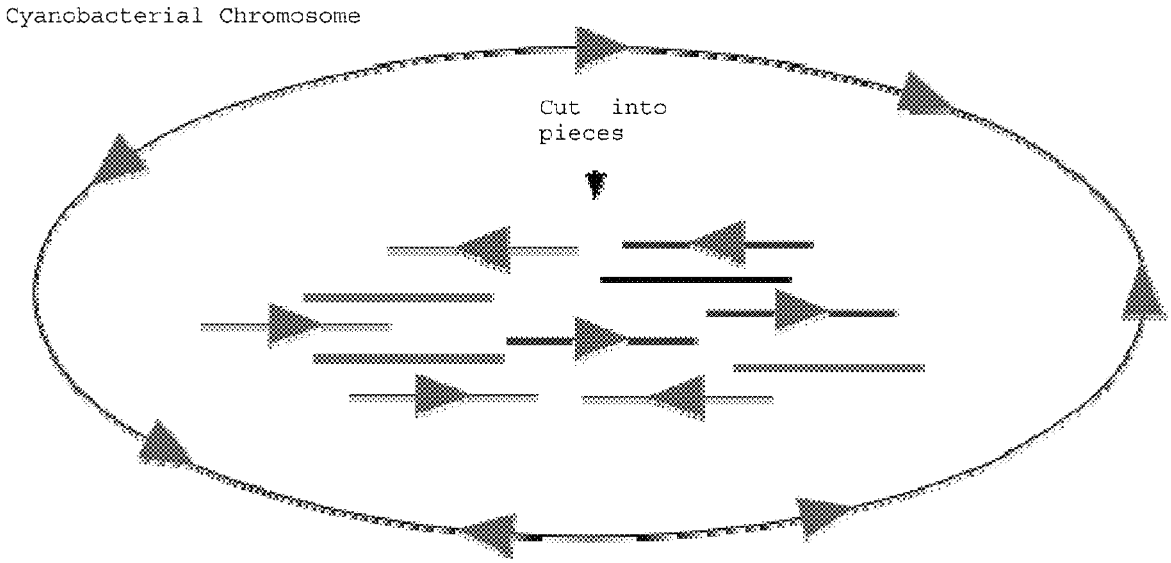

FIG. 8 is a cartoon depicting construction of a cyanobacterial promoter library. Further details regarding methodology are provided in Example 8.

Figure 9:
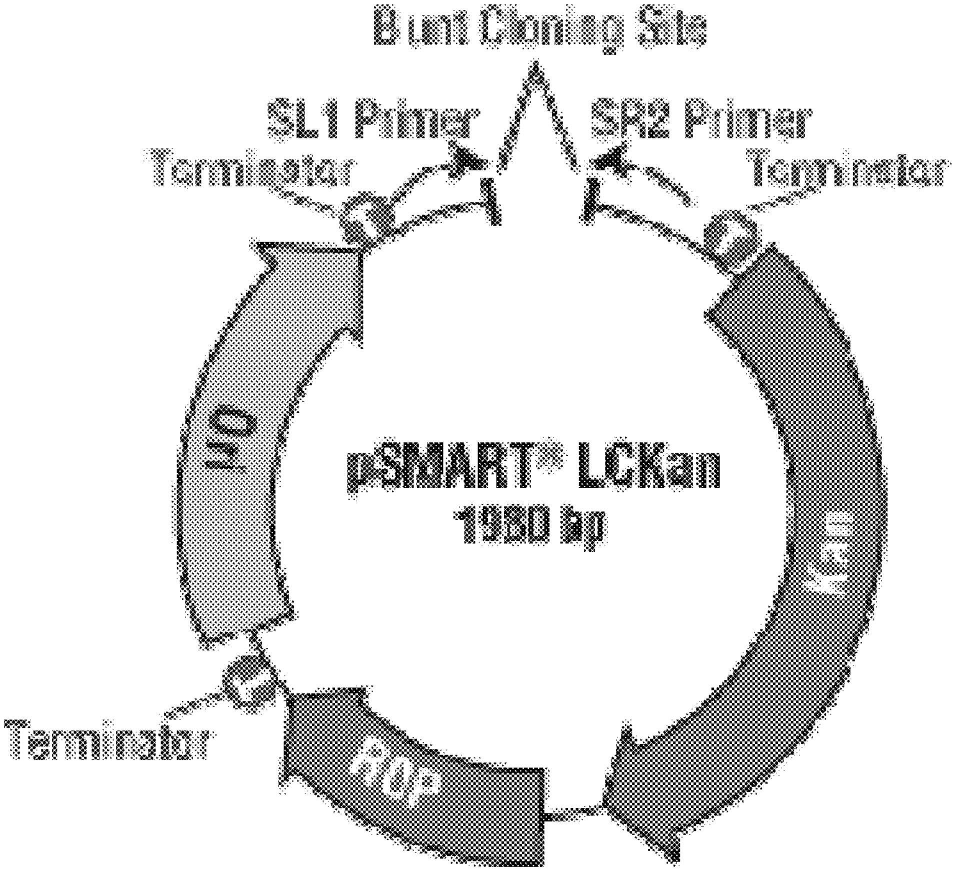

FIG. 9 is a schematic diagram depicting pSMART-LCKan. Further details regarding methodology are provided in Example 8.

Figure 10:
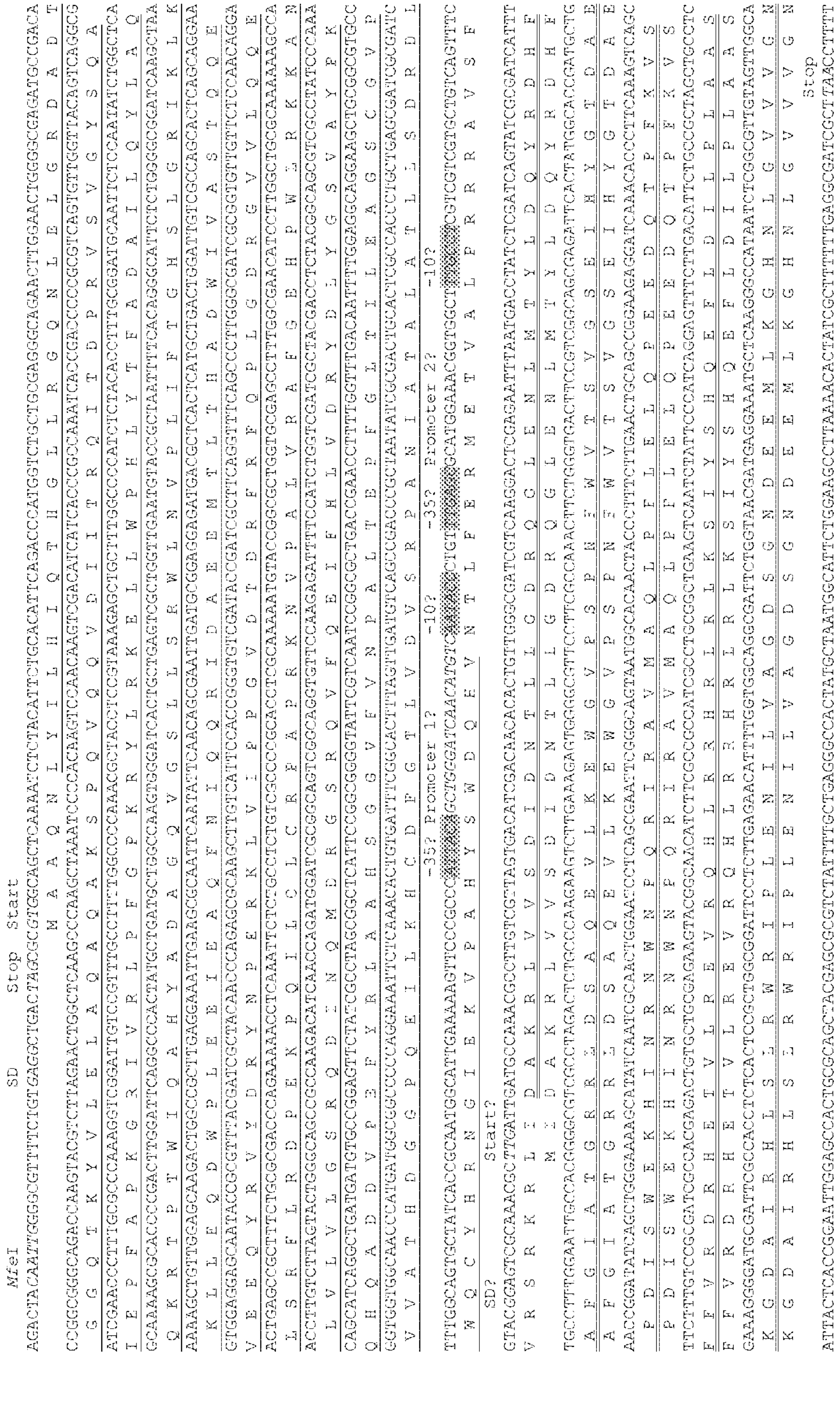

FIG. 10 is a sequence listing showing a possible promoter within *Synechococcus elongatus* PCC 7942 asf. Shown is the amplified PCR product containing the asf gene from *Synechococcus elongatus* PCC 7942 that was cloned upstream of the chloramphenicol resistance marker. The regions of asf encoding the sucrose phosphate synthase and sucrose phosphate phosphatase polypeptide activities are single underlined and double underlined, respectively. All DNA sequence elements are italicized and labeled above. Start and Stop represent the start and stop codons, respectively. SD represents the Shine-Delgarno sequence. The −35 and −10 regions of the putative promoters are highlighted in gray. Further details regarding methodology are provided in Example 8.

Figure 11:
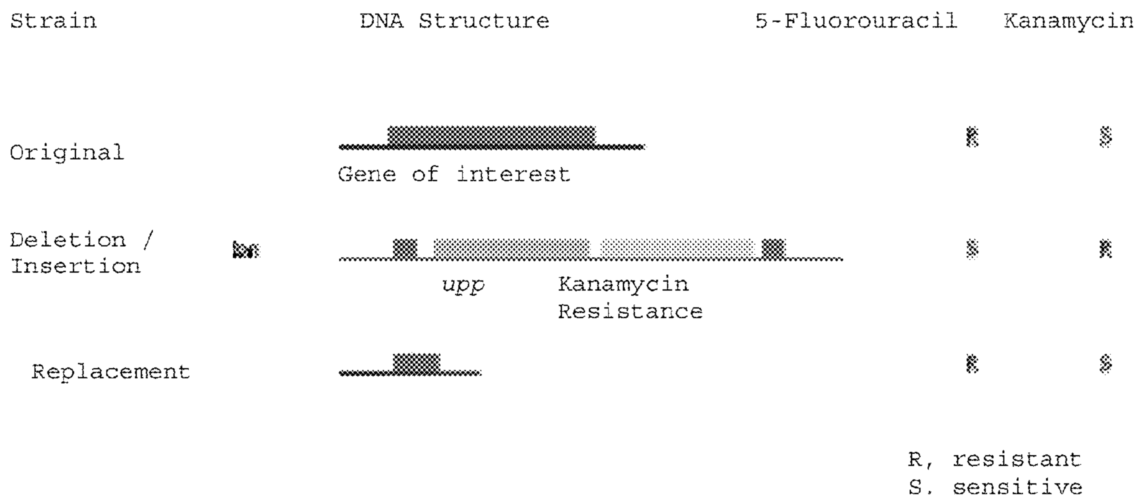

FIG. 11 is a schematic diagram depicting a two-step protocol for markerless deletion of genes in the cyanobacterial genome. This strategy assumes that the cyanobacterial strain being used has had its upp gene deleted. The upp gene will have been deleted during the sucrose biosynthetic insertions. The gene of interest that has been targeted for deletion must be identified. The starting strain is resistant to 5-fluorouracil, but sensitive to kanamycin. The gene is either completely or partially deleted by the insertion of a cassette containing a kanamycin resistance marker and an active upp, making the strain resistant to kanamycin, but sensitive to 5-fluorouracil. The upp and kanamycin resistance markers can then be removed, making the strain once again resistant to 5-fluorouracil, but sensitive to kanamycin. Further details regarding methodology are provided in Example 12.

FIG. 12 is a schematic diagram of a photobioreactor embodiment. FIG. 12A provides a front view while FIG. 12B provides a side view. The photobioreactor includes suspension element (6); culture media supply (8); gas supply (10); growth surface (2); outer barrier layer (7); quick connector; and product harvest line (9).

Figure 13:
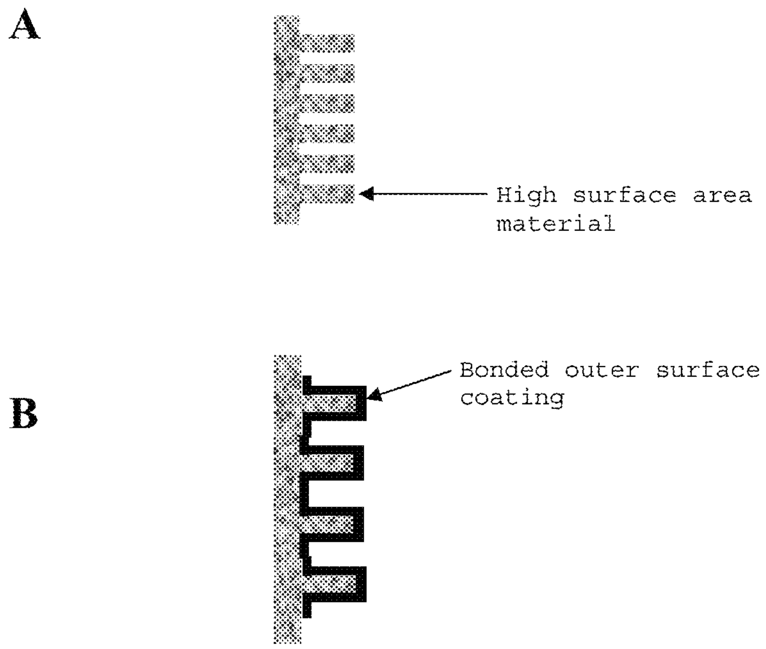

FIG. 13 is a schematic diagram of a growth surface in a single material format (FIG. 13A) and a hybrid material format (FIG. 13B).

DETAILED DESCRIPTION OF THE INVENTION

The present application relates to fermentable sugar accumulating photosynthetic microorganisms, solid-phase photoreactor devices, and methods of using each.

In the fermentable sugar accumulating photosynthetic microorganisms, it may be preferable to produce a dissaccharide sugar not generally utilized by the photosynthetic microorganisms, which therefore can accumulate within the cultivated biomass (e.g., sucrose, trehalose). In some embodiments, photosynthetic microorganisms are genetically engineered to synthesize a dissaccharide sugar normally produced according to osmotic stress pathways (e.g., sucrose or trehalose) such that the sugar is produced in the absence of, or at reduced levels of, osmotic stress. Because of the greater efficiency and lower environmental impact of growing photosynthetic microorganisms compared to higher plants, the method represents important improvements in sustainability over current biofuel production practices. Advantageously, the foregoing method of synthesizing a dissaccharide sugar has been adapted to occur within the photobioreactor(s) of the present invention.

The photobioreactor described herein utilizes a solid cultivation support. Advantageously, the difficulty of providing adequate light exposures is alleviated, at least in part. Utilizing the aforementioned solid cultivation support in a photobioreactor can allow for cultivation and growth of photosynthetic microorganisms at cell densities greater than those of commercial-scale liquid phase bioreactors (e.g., cell densities in excess of 200 grams of dry biomass per liter equivalent). In addition, various embodiments of the photobioreactor described herein can be operated using less energy and more simply than conventional commercial-scale liquid phase photobioreactors.

Embodiments of the photobioreactor described herein provide additional benefits over conventional liquid phase photobioreactors. For example, liquid systems typically require special equipment to deliver adequate concentrations/amount of carbon dioxide to the photosynthetic microorganisms to support their growth and photosynthesis. In contrast, by growing the microorganisms on a solid cultivation support, carbon dioxide can be provided in a relatively simple, less costly manner, such as exposure to surrounding air. If additional carbon dioxide is desired, it can easily be delivered by, for example, adding it to the atmosphere (e.g., air) surrounding or in contact with the cultivation support. Another benefit is ease of transport. Liquid phase photobioreactors can be a pond (completely immobile) or bulky tanks or collections of tubing. In contrast, in various embodiments, the photobioreactor is flat and flexible, which allows for it or a multiplicity of them to be stacked, rolled up, folded, and/or configured in a similar manner for relatively easy transport. In various embodiments, the photobioreactor can be configured in a manner such that it is suspended from a system that allows for easy conveyance of one or more photobioreactors from one location to another. This portability may be utilized on a commercial scale to allow for efficient methods of handling and processing large numbers of photobioreactors in a continuous-type manner.

One aspect of the application is directed to a method of fermentable sugar feedstock production by photosynthetic microorganisms. Preferably, the fermentable sugar is a fermentable disaccharide sugar. Examples of fermentable disaccharide sugars include, but are not limited to sucrose and trehalose. The fermentable sugar can be a disaccharide not generally utilized by photosynthetic microorganisms. For example, trehalose is not generally utilized by cyanobacteria and therefore can accumulate within the cultivated biomass without substantial degradation by endogenous metabolic pathways. The fermentable sugar can be a disaccharide that is generally utilized by photosynthetic microorganisms. For a disaccharide not used as a primary energy source, the disaccharide can often be accumulated to sufficient levels even in the presence of endogenous metabolic pathways. Where endogenous degradation pathways specific for the target fermentable sugar, the photosynthetic microorganism can be engineered to reduce or eliminate such activity. For example, a cyanobacterium engineered to accumulate sucrose can be further engineered to reduce or eliminate sucrose invertase activity. In various embodiments, strains of photosynthetic microorganisms that synthesize fermentable disaccharide sugar in response to osmotic or matric water stress can be used. In other embodiments transgenic strains of photosynthetic microorganisms engineered to accumulate fermentable disaccharide sugar in the absence of, or reduced levels of, osmotic stress. Advantageously, the foregoing methods of synthesizing fermentable disaccharide sugar can be adapted to occur within photobioreactors described herein.

Because of the greater efficiency and lower environmental impact of growing photosynthetic microorganisms compared to higher plants, compositions, devices, and methods described herein represent important improvements in sustainability over current biofuel production practices.

Photosynthetic Microorganism

Provided herein is a photosynthetic microorganism genetically engineered to accumulate a dissaccharide sugar. The photosynthetic microorganism can be, for example, a naturally photosynthetic microorganism, such as a cyanobacterium, or an engineered photosynthetic microorganism, such as an artificially photosynthetic bacterium. Examples of the accumulated dissaccharide sugar include, but are not limited to sucrose, trehalose, gluocosylglycerol, and mannosylfructose. In various embodiments, one or more genes encoding the protein(s) responsible for producing the desired dissaccharide from corresponding phosphorylated monomers is engineered in a host photosynthetic microorganism (e.g., cyanobacterium) so as to result in the accumulation of the desired dissaccharide. In some embodiments, an endogenous pathway of the host photosynthetic microorganism is engineered so as to accumulate a dissaccharide sugar. For example, the osmotic sucrose pathway in cyanobacteria can be engineered to accumulate sucrose in the absence of osmotic stress. In some embodiments, an exogenous dissaccharide pathway is engineered in cyanobacteria so as to accumulate a dissaccharide sugar. For example, the osmotic trehalose pathway from *E. coli* can be engineered to accumulate trehalose in cyanobacteria.

Synthase and Phosphotase

A photosynthetic microorganism can be transformed so as to have a synthase activity and a phosphotase activity for the desired dissaccharide. For example, a cyanobacterium can be engineered to have sucrose phosphate synthase activity and sucrose phosphate phosphatase activity. As another example, a cyanobacterium can be engineered to have trehalose phosphate synthase activity and trehalose phosphate phosphatase activity. As another example, a cyanobacterium can be engineered to have gluocosylglycerol phosphate synthase activity and gluocosylglycerol phosphate phosphatase activity. As another example, a cyanobacterium can be engineered to have mannosylfructose phosphate synthase activity and mannosylfructose phosphate phosphatase activity. It is contemplated these activities can likewise be engineered in other photosynthetic microorganisms.

Synthase activity and phosphotase activity can be engineered into a photosynthetic microorganism by way of the individual genes, one encoding a polypeptide having synthase activity and the other encoding a polypeptide having phosphatase activity; or by one gene encoding both synthase activity and phosphatase activity. For example, synthase activity and phosphatase activity can be present in a fusion polypeptide.

The monomeric sugars of the desired dissaccharide can be endogenous or exogenous to the photosynthetic microorganism. Where monomeric sugars of the desired dissaccharide are endogenous, the photosynthetic microorganism can be engineered to produce increased levels of such monomers. Where monomeric sugars of the desired dissaccharide are exogenous, the photosynthetic microorganism can be engineered to produce such exogenous monomers.

The photosynthetic microorganism can be engineered to synthesize and accumulate the desired dissaccharide continuously, after some developmental state, or upon being induced to do so. Induction of dissaccharide synthesis can be according to the actions of an inducible promoter associated with the encoded synthase or phosphotase and an inducing agent, as discussed in further detail herein.

In some embodiments, transformed cyanobacteria, as described herein, can accumulate at least about 0.1 micrograms of a dissacharide (e.g., sucrose, trehalose, glucosylglycerol, or mannosylfructose) per minute per gram dry biomass. In some embodiments, transformed cyanobacteria can accumulate at least about 0.1 up to about 10 micrograms of a dissaccharide (e.g., sucrose, trehalose, glucosylglycerol, or mannosylfructose) per minute per gram dry biomass. For example, transformed cyanobacteria can accumulate at least about 0.2, at least about 0.3, at least about 0.4, at least about 0.5, at least about 0.6, at least about 0.7, at least about 0.8, or at least about 0.9 micrograms of a dissaccharide (e.g., sucrose, trehalose, glucosylglycerol, or mannosylfructose) per minute per gram dry biomass. In other embodiments, various transformed photosynthetic microorganisms accumulate similar amounts of a dissaccharide.

It is contemplated that that various embodiments will accumulate a disaccharide (e.g., sucrose, trehalose, glucosylglycerol, or mannosylfructose) at defined ranges of the values above. For example, some transformed cyanobacteria can accumulate at least about 0.1 up to about 0.9 micrograms of a disaccharide (e.g., sucrose, trehalose, glucosylglycerol, or mannosylfructose) per minute per gram dry biomass; at least about 0.1 up to about 0.8 micrograms of a disaccharide (e.g., sucrose, trehalose, glucosylglycerol, or mannosylfructose) per minute per gram dry biomass; at least about 0.1 up to about 0.7 micrograms of a disaccharide (e.g., sucrose, trehalose, glucosylglycerol, or mannosylfructose) per minute per gram dry biomass; etc. Similarly, some transformed cyanobacteria can accumulate at least about 0.2 up to about 1.0 micrograms of a disaccharide (e.g., sucrose, trehalose, glucosylglycerol, or mannosylfructose) per minute per gram dry biomass; at least about 0.3 up to about 1.0 micrograms of a disaccharide (e.g., sucrose, trehalose, glucosylglycerol, or mannosylfructose) per minute per gram dry biomass; at least about 0.4 up to about 1.0 micrograms of a disaccharide (e.g., sucrose, trehalose, glucosylglycerol, or mannosylfructose) per minute per gram dry biomass; at least about 0.5 up to about 1.0 micrograms of a disaccharide (e.g., sucrose, trehalose, glucosylglycerol, or mannosylfructose) per minute per gram dry biomass; at least about 0.6 up to about 1.0 micrograms of a disaccharide (e.g., sucrose, trehalose, glucosylglycerol, or mannosylfructose) per minute per gram dry biomass; at least about 0.7 up to about 1.0 micrograms of a disaccharide (e.g., sucrose, trehalose, glucosylglycerol, or mannosylfructose) per minute per gram dry biomass; at least about 0.8 up to about 1.0 micrograms of a disaccharide (e.g., sucrose, trehalose, glucosylglycerol, or mannosylfructose) per minute per gram dry biomass; or at least about 0.9 up to about 1.0 micrograms of a disaccharide (e.g., sucrose, trehalose, glucosylglycerol, or mannosylfructose) per minute per gram dry biomass. Methods for assaying sugar accumulation is host cells are well-known to those of skill in the art (see e.g., Example 10).

Host

The host genetically engineered to accumulate a dissaccharide sugar can be any photosynthetic microorganism. The photosynthetic microorganism can be, for example, a naturally photosynthetic microorganism, such as a cyanobacterium, or an engineered photosynthetic microorganism, such as an artificially photosynthetic bacterium. Exemplary microorgansims that are either naturally photosynthetic or can be engineered to be photosynthetic include, but are not limited to, bacteria; fungi; archaea; protists; microscopic plants, such as a green algae; and animals such as plankton, planarian, and amoeba. Examples of naturally occurring photosynthetic microorganisms include, but are not limited to, *Spirulina maximum, Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella* sp., *Scenedesmus obliquus, Anabaenopsis, Aulosira, Cylindrospermum, Synechoccus* sp., *Synechocystis* sp., and/or *Tolypothrix*.

Preferably, the host photosynthetic microorganism is a cyanobacterium. Cyanobacteria, also known as blue-green algae, are a broad range of oxygengenic photoautotophs. The host cyanobacterium can be any photosynthetic microorganism from the phylum Cyanophyta. The host cyanobacterium can have a unicellular or colonial (e.g., filaments, sheets, or balls) morphology. Preferably, the host cyanobacterium is a unicellular cyanobacterium. Examples of cyanobacteria that can be engineered to accumulate a disaccharide sugar include, but are not limited to, the genus *Synechocystis, Synechococcus, Thermosynechococcus, Nostoc, Prochlorococcu, Microcystis, Anabaena, Spirulina*, and *Gloeobacter*. Preferably the host cyanobacterium is a *Synechocystis* spp. or *Synechococcus* spp. More preferably, the host cyanobacterium is *Synechococcus elongatus* PCC 7942 (ATCC 33912) and/or *Synechocystis* spp. PCC 6803 (ATCC 27184).

Sucrose

Figure 4:
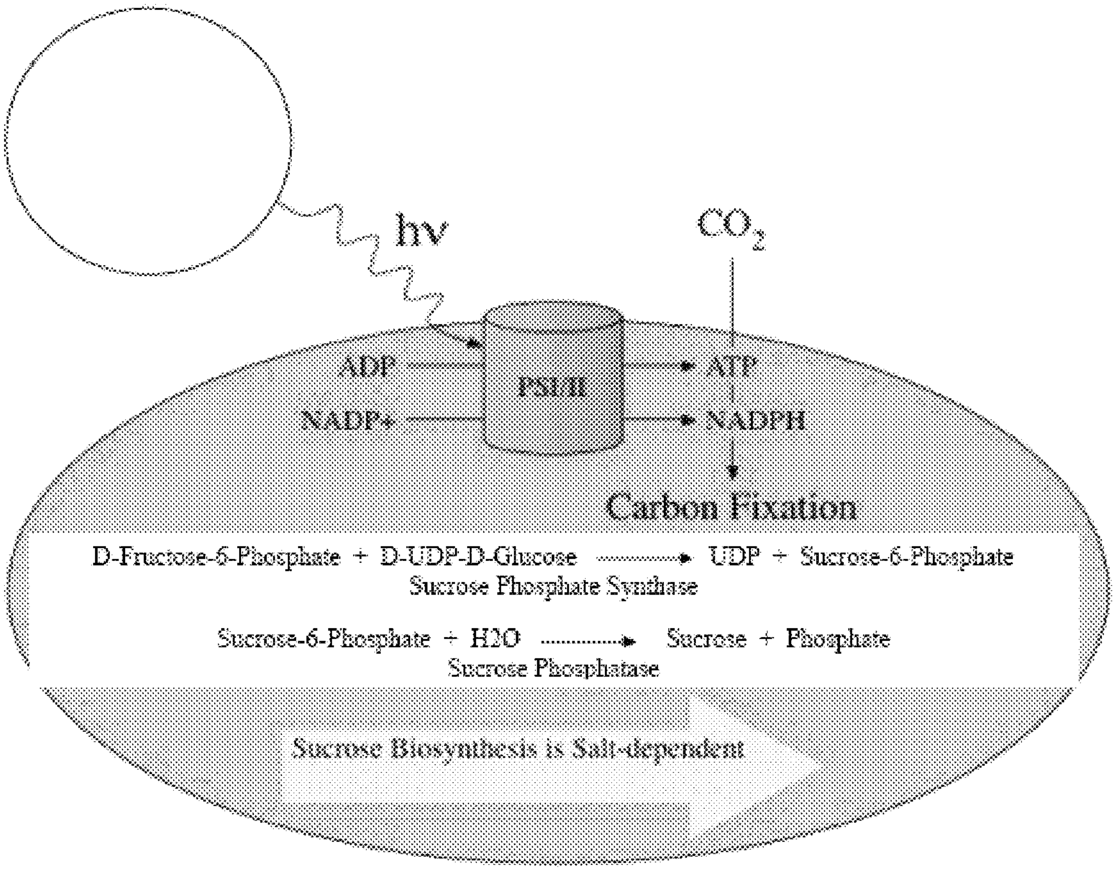
FIG. 4 is a cartoon depicting photosynthetic production of sucrose in cyanobacteria.

Biosynthesis of sucrose in a photosynthetic microorganism, such as cyanobacteria, can be accomplished through the catalytic action of two enzyme activities, sucrose phosphate synthase (sps) and sucrose phosphate phosphatase (spp), functioning in sequence (see e.g., FIG. 4). Such activities are present in some cyanobacteria for acclimation to osmotic and matric water stress (see e.g., Lunn, J. E. 2002. Plant Physiol 128, 1490-1500). Either or both of these activities can be engineered in a cyanobacterium so as to result in accumulation of sucrose.

A gene of particular interest for engineering a photosynthetic microorganism to accumulate sucrose is the active sps/spp fusion (asf) gene from *Synechococcus elongatus* PCC 7942. Asf has both sps and spp biosynthetic functions (see e.g., Example 4). In some embodiments, an ASF-encoding nucleotide sequence is cloned from its native source (e.g., *Synechococcus elongatus* PCC 7942) and inserted into a host cyanobacterium (see e.g., Examples 4-9). In some embodiments, a transformed host photosynthetic microorganism comprises an asf polynucleotide of SEQ ID NO: 1. In some embodiments, a photosynthetic microorganism is transformed with a nucleotide sequence encoding ASF polypeptide of SEQ ID NO: 2. In further embodiments, a transformed host photosynthetic microorganism comprises a nucleotide sequence having at least about 80% sequence identity to SEQ ID NO: 1 or a nucleotide sequence encoding a polypeptide having sps and spp activity and at least about 80% sequence identity to SEQ ID NO: 2. As an example, a transformed host photosynthetic microorganism, such as a cyanobacterium, can comprise a nucleotide sequence having at least about 85%, at least about 90%, at least about 95%, or at least about 99% sequence identity to SEQ ID NO: 1, wherein the transformed host exhibits ASF, SPS, and/or SPP activity and/or accumulation of sucrose. As an example, a transformed host photosynthetic microorganism can comprise a nucleotide sequence encoding a polypeptide having at least about 85%, at least about 90%, at least about 95%, or at least about 99% sequence identity to SEQ ID NO: 2, wherein the transformed host exhibits ASF, SPS, and/or SPP activity and/or accumulation of sucrose. As another example, a transformed host photosynthetic microorganism can comprise a nucleotide sequence that hybridizes under stringent conditions to SEQ ID NO: 1 over the entire length of SEQ ID NO: 1, and which encodes an active SPS/SPP fusion (ASF) polypeptide. As a further example, a transformed host photosynthetic microorganism can comprise the complement to any of the above sequences.

In some embodiments, a sucrose phosphate synthase (sps) (see e.g., SEQ ID NO: 3 encoding sps gene and SEQ ID NO: 4 encoding SPS polypeptide), or homologue thereof, is engineered to be expressed or overexpressed in a transformed photosynthetic microorganism. For example, a photosynthetic microorganism can be transformed with a nucleotide having a sequence of SEQ ID NO: 3 so as to express sucrose phosphate synthase. As another example, a photosynthetic microorganism can be transformed with a nucleotide having at least about 80%, at least about 85%, at least about 90%, at least about 95%, or at least about 99% percent identity to SEQ ID NO: 3 encoding a polypeptide having sucrose phosphate synthase. As another example, a transformed host photosynthetic microorganism can comprise a nucleotide sequence encoding a polypeptide having at least about 85%, at least about 90%, at least about 95%, or at least about 99% sequence identity to SEQ ID NO: 4, wherein the transformed host exhibits SPS activity and/or accumulation of sucrose.

In some embodiments, sucrose phosphate phosphatase (spp) (see e.g., SEQ ID NO: 5 encoding spp gene and SEQ ID NO: 6 encoding SPP polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 5 so as to express sucrose phosphate phosphatase. As another example, a photosynthetic microorganism can be transformed with a nucleotide having at least about 80%, at least about 85%, at least about 90%, at least about 95%, or at least about 99% percent identity to SEQ ID NO: 5 encoding a polypeptide having sucrose phosphate phosphatase activity. As another example, a transformed host photosynthetic microorganism can comprise a nucleotide sequence encoding a polypeptide having at least about 85%, at least about 90%, at least about 95%, or at least about 99% sequence identity to SEQ ID NO: 6, wherein the transformed host exhibits SPP activity and/or accumulation of sucrose.

In some embodiments, a photosynthetic microorganism is engineered to express one or more of ASF, SPS, and/or SPP. For example, a photosynthetic microorganism, such as a cyanobacterium, can be engineered to express ASF and SPS; ASF and SPP; SPS and SPP; or ASF, SPS, and SPP.

Trehalose

Biosynthesis of trehalose can be accomplished through the catalytic action of two enzyme activities, trehalose phosphate synthase (tps) and trehalose phosphate phosphatase (tpp), functioning in sequence. Either or both of these activities can be engineered in a photosynthetic microorganism so as to result in accumulation of trehalose. Biosynthesis of trehalose does not naturally occur in some photosynthetic microorganisms, such as cyanobacteria.

In some embodiments, a trehalose phosphate synthase (tps) (see e.g., SEQ ID NO: 76 encoding tps gene and SEQ ID NO: 77 encoding TPS polypeptide), or homologue thereof, is engineered to be expressed or overexpressed in a transformed photosynthetic microorganism. For example, a photosynthetic microorganism, such as cyanobacterium, can be transformed with a nucleotide having a sequence of SEQ ID NO: 76 so as to express trehalose phosphate synthase. As another example, a photosynthetic microorganism can be transformed with a nucleotide having at least about 80%, at least about 85%, at least about 90%, at least about 95%, or at least about 99% percent identity to SEQ ID NO: 76 encoding a polypeptide having trehalose phosphate synthase. As another example, a transformed host photosynthetic microorganism can comprise a nucleotide sequence encoding a polypeptide having at least about 85%, at least about 90%, at least about 95%, or at least about 99% sequence identity to SEQ ID NO: 77, wherein the transformed host exhibits TPS activity and/or accumulation of trehalose.

In some embodiments, trehalose phosphate phosphatase (op) (see e.g., SEQ ID NO: 78 encoding tpp gene and SEQ ID NO: 79 encoding TPP polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 78 so as to express trehalose phosphate phosphatase. As another example, a photosynthetic microorganism can be transformed with a nucleotide having at least about 80%, at least about 85%, at least about 90%, at least about 95%, or at least about 99% percent identity to SEQ ID NO: 78 encoding a polypeptide having trehalose phosphate phosphatase activity. As another example, a transformed host photosynthetic microorganism can comprise a nucleotide sequence encoding a polypeptide having at least about 85%, at least about 90%, at least about 95%, or at least about 99% sequence identity to SEQ ID NO: 79, wherein the transformed host exhibits TPP activity and/or accumulation of trehalose.

Glucosylglycerol

In some embodiments, a glucosylglycerolphosphate synthase (gps) (see e.g., SEQ ID NO: 80 encoding gps gene and SEQ ID NO: 81 encoding GPS polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 80 so as to express glucosylglycerolphosphate synthase. As another example, a photosynthetic microorganism can be transformed with a nucleotide having at least about 80%, at least about 85%, at least about 90%, at least about 95%, or at least about 99% percent identity to SEQ ID NO: 80 encoding a polypeptide having glucosylglycerolphosphate synthase. As another example, a transformed host photosynthetic microorganism can comprise a nucleotide sequence encoding a polypeptide having at least about 85%, at least about 90%, at least about 95%, or at least about 99% sequence identity to SEQ ID NO: 81, wherein the transformed host exhibits GPS activity and/or accumulation of glucosylgycerol.

In some embodiments, glucosylglycerolphosphate phosphatase (gpp) (see e.g., SEQ ID NO: 82 encoding gpp gene and SEQ ID NO: 83 encoding GPP polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 82 so as to express glucosylglycerolphosphate phosphatase. As another example, a photosynthetic microorganism can be transformed with a nucleotide having at least about 80%, at least about 85%, at least about 90%, at least about 95%, or at least about 99% percent identity to SEQ ID NO: 82 encoding a polypeptide having glucosylglycerolphosphate phosphatase activity. As another example, a transformed host photosynthetic microorganism can comprise a nucleotide sequence encoding a polypeptide having at least about 85%, at least about 90%, at least about 95%, or at least about 99% sequence identity to SEQ ID NO: 83, wherein the transformed host exhibits GPP activity and/or accumulation of glucosylgycerol.

Mannosylfructose

In some embodiments, a mannosylfructose phosphate synthase (mps) (see e.g., SEQ ID NO: 84 encoding mps gene and SEQ ID NO: 85 encoding MPS polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 84 so as to express mannosylfructose phosphate synthase. As another example, a photosynthetic microorganism can be transformed with a nucleotide having at least about 80%, at least about 85%, at least about 90%, at least about 95%, or at least about 99% percent identity to SEQ ID NO: 84 encoding a polypeptide having mannosylfructose phosphate synthase. As another example, a transformed host photosynthetic microorganism can comprise a nucleotide sequence encoding a polypeptide having at least about 85%, at least about 90%, at least about 95%, or at least about 99% sequence identity to SEQ ID NO: 85, wherein the transformed host exhibits MPS activity and/or accumulation of mannosylfructose.

In some embodiments, mannosylfructose phosphate phosphatase (mpp) (see e.g., SEQ ID NO: 86 encoding mpp gene and SEQ ID NO: 87 encoding MPP polypeptide), or homologue thereof, is engineered to be expressed or overexpressed in a transformed photosynthetic microorganism. For example, a photosynthetic microorganism, such as a cyanobacterium, can be transformed with a nucleotide having a sequence of SEQ ID NO: 86 so as to express mannosylfructose phosphate phosphatase. As another example, a photosynthetic microorganism can be transformed with a nucleotide having at least about 80%, at least about 85%, at least about 90%, at least about 95%, or at least about 99% percent identity to SEQ ID NO: 86 encoding a polypeptide having mannosylfructose phosphate phosphatase activity. As another example, a transformed host photosynthetic microorganism can comprise a nucleotide sequence encoding a polypeptide having at least about 85%, at least about 90%, at least about 95%, or at least about 99% sequence identity to SEQ ID NO: 87, wherein the transformed host exhibits MPP activity and/or accumulation of mannosylfructose.

Molecular Engineering

Design, generation, and testing of the variant nucleotides, and their encoded polypeptides, having the above required percent identities to an asf sequence and retaining a required activity of the expressed protein and/or sugar accumulation phenotype is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide (e.g., asf, sps, spp, tps, Op, gps, gpp, mps, or mpp) and/or polypeptide (e.g., ASF, SPS, SPP, TPS, TPP, GPS, GPP, MPS, or MPP) variants having, for example, at least 95-99% identity to the reference sequence described herein and screen such for phenotypes including disaccharide accumulation according to methods routine in the art. Generally, conservative substitutions can be made at any position so long as the required activity is retained.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$ [$Na^+$])+0.41 (fraction G/C content)−0.63(% formamide)−(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Promoter

One or more of the nucleotide sequences discussed above (e.g., asf, sps, spp, Os, tpp, mps, mpp, gps, gpp) can be operably linked to a promoter that can function in the host photosynthetic microorganism. Where the host is cyanobacteria, preferably, the promoter can function efficiently in both cyanobacteria and a bacteria, such as *E. coli*. Promoter selection can allow expression of a desired gene product under a variety of conditions.

Promoters can be selected for optimal function in a photosynthetic microorganism host cell, such as a cyanobacterium, into which the vector construct will be inserted. Promoters can also be selected on the basis of their regulatory features. Examples of such features include enhancement of transcriptional activity and inducibility.

The promoter can be an inducible promoter. For example, the promoter can be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters will be known to one of skill in the art.

In some embodiments, the promoter is a temperature inducible promoter. For example, the Lambda promoter is a temperature inducible promoter that can function in cyanobacteria. Surprisingly, the Lambda promoter functions at a temperature different than when utilized in *E. coli*. In *E. coli*, the Lambda promoter is most active at 42° C., a temperature above the normal viability range for cyanobacteria. Generally, in *E. coli*, the Lambda promoter has about a 5% to 10% increased expression from about 30° C. to 35° C. and at about 37° C. has about a 20% increased expression; but from about 37° C. to 42° C. provides about 100% increased expression. In cyanobacteria, the Lambda promoter is most active at around 30° C. to 35° C., an ideal growth temperature range for cyanobacteria and a range much lower than optimal expression of the Lambda promoter in *E. coli*. So, the Lambda promoter provides for effective expression of disaccharide biotsynthetic activity in cyanabcteria.

Examples of promoters that can be inserted into the plasmid include, but are not limited to, carB, nirA, psbAII, dnaK, kaiA, and $\lambda_{PR}$ (see e.g., Example 6). In some embodiments, the promoter can function efficiently in both cyanobacteria and *E. coli*. In some embodiments, the asf coding region comprises a promoter with said coding region (see e.g., Example 8). For example, the asf coding region can comprise a promoter in front of the SPP domain of asf (see e.g., FIG. 10). Such an internal promoter can occur with or without a promoter at the start of the asf coding region.

The term "chimeric" is understood to refer to the product of the fusion of portions of two or more different polynucleotide molecules. "Chimeric promoter" is understood to refer to a promoter produced through the manipulation of known promoters or other polynucleotide molecules. Such chimeric promoters can combine enhancer domains that can confer or modulate gene expression from one or more promoters or regulatory elements, for example, by fusing a heterologous enhancer domain from a first promoter to a second promoter with its own partial or complete regulatory elements. Thus, the design, construction, and use of chimeric promoters according to the methods disclosed herein for modulating the expression of operably linked polynucleotide sequences are encompassed by the present invention.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter.

Constructs

Any of the transcribable polynucleotide molecule sequences described above can be provided in a construct. Constructs of the present invention generally include a promoter functional in the host photosynthetic microorganism, such as cyanobacteria, operably linked to a transcribable polynucleotide molecule for disaccharide biosynthesis (e.g., asf, sps, spp, tps, tpp, mps, mpp, gps, gpp), such as provided in SEQ ID NO: 1, 3, 5, 76, 78, 80, 82, 84, and 86, and variants thereof as discussed above.

Exemplary promoters are discussed above. One or more additional promoters may also be provided in the recombinant construct. These promoters can be operably linked to any of the transcribable polynucleotide molecule sequences described above.

The term "construct" is understood to refer to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. The term "vector" or "vector construct" is understood to refer to any recombinant polynucleotide construct that may be used for the purpose of transformation, i.e., the introduction of heterologous DNA into a host photosynthetic microorganism, such as a cyanobacterium.

In addition, constructs may include, but are not limited to, additional polynucleotide molecules from an untranslated region of the gene of interest. These additional polynucleotide molecules can be derived from a source that is native or heterologous with respect to the other elements present in the construct.

Plasmid

In some embodiments, a host photosynthetic microorgansim, such as a cyanobacterium, is transformed with a plasmid-based expression system (see e.g., Example 5). Preferably the plasmid encoding the gene of interest comprises a promoter, such as one or more of those discussed above. For plasmid based transformation, preferred is a broad host range plasmid that enables function in both *E. coli* and cyanobacteria, which provides the advantage of working in a convenient fast growing well understood system (*E. coli*) that can be efficiently transferred to the final host (cyanobacteria). In some embodiments, plasmid based transformation and chromosomal integration are used in conjunction, where the plasmid protocol is used for design and testing of gene variants followed by chromosomal integration of identified variants.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Provided herein are nucleotide sequences for plasmid constructs encoding sps, spp, and/or asf. Examples of plasmid constructs encoding sps, spp, and/or asf include, but are not limited to, pLybAL11 (SEQ ID NO: 19) (see e.g., FIG. 6) and pLybAL12 (SEQ ID NO: 20) (see e.g., FIG. 7). Also provided herein are nucleotide sequences for plasmid constructs encoding tps and tpp. Examples of plasmid constructs encoding tps and tpp include, but are not limited to, pLybAL23 (SEQ ID NO: 118). A skilled artisan will understand that similar constructs can be generated for biosynthetic genes necessary for accumulation of other disaccharides, such as glucosylglycerol and mannosylfructose.

In some embodiments, the transformed host photosynthetic microorganism comprises pLybAL11 (SEQ ID NO: 19) or pLybAL12 (SEQ ID NO: 20). In some embodiments, the transformed host photosynthetic microorganism comprises pLybAL23 (SEQ ID NO: 118). For example, a transformed cyanobacterium can comprise pLybAL11 (SEQ ID NO: 19), pLybAL12 (SEQ ID NO: 20), or pLybAL23 (SEQ ID NO: 118).

A plasmid construct comprising a disaccharide biosynthetic gene(s) can also include a promoter. Examples of plasmid constructs comprising sps, spp, and/or asf and a promoter include, but are not limited to, pLybAL7f (SEQ ID NO: 65); pLybAL8f, including kanamycin resistance (SEQ ID NO: 69); pLybAL13f (SEQ ID NO: 51), pLyAL13r (SEQ ID NO: 52), pLybAL14f (SEQ ID NO: 53), pLybAL14r (SEQ ID NO: 54), pLybAL15 (SEQ ID NO: 44), pLybAL16 (SEQ ID NO: 45), pLybAL17 (SEQ ID NO: 46), pLybAL18 (SEQ ID NO: 47), pLybAL19 (SEQ ID NO: 48), pLybAL21 (SEQ ID NO: 49), and pLybAL22 (SEQ ID NO: 50). Examples of plasmid constructs comprising tps and tpp and a promoter include, but are not limited to, pLybAL23 (SEQ ID NO: 118), pLybAL28 (SEQ ID NO: 121), pLybAL29 (SEQ ID NO: 122), and pLybAL30 (SEQ ID NO: 123). A skilled artisan will understand that similar promoter containing constructs can be generated for biosynthetic genes necessary for accumulation of other disaccharides, such as glucosylglycerol and mannosylfructose.

In some embodiments, the transformed host cyanobacterium comprises pLybAL7f (SEQ ID NO: 65); pLybAL8f (SEQ ID NO: 69); pLybAL13f (SEQ ID NO: 51), pLyAL13r (SEQ ID NO: 52), pLybAL14f (SEQ ID NO: 53), pLybAL14r (SEQ ID NO: 54), pLybAL15 (SEQ ID NO: 44), pLybAL16 (SEQ ID NO: 45), pLybAL17 (SEQ ID NO: 46), pLybAL18 (SEQ ID NO: 47), pLybAL19 (SEQ ID NO: 48), pLybAL21 (SEQ ID NO: 49), and pLybAL22 (SEQ ID NO: 50). In some embodiments, the transformed host cyanobacterium comprises pLybAL28 (SEQ ID NO: 121), pLybAL29 (SEQ ID NO: 122), pLybAL30 (SEQ ID NO: 123), and pLybAL23 (SEQ ID NO: 118).

Sugar Secretion

In various embodiments, a transformed disaccharide-accumulating photosynthetic microorganism can secrete the accumulated disaccharide from within the cell into its growth environment. Secretion of the disaccharide can be an inherent effect of transforming the photosynthetic microorganism to accumulate a disaccharide or the photosynthetic microorganism can be further engineered to secrete the disaccharide. For example, some cyanobacteria transformed to accumulate trehalose inherently secrete trehalose from the cell (see e.g., Examples 19-20). As another example, a cyanobacterium transformed to accumulate sucrose can be further engineered to secrete sucrose from the cell (see e.g., Example 16).

A host photosynthetic microorganism, such as a cyanobacterium, can be further engineered to secrete a disaccharide. In some embodiment, a transformed host photosynthetic microorganism is engineered to express a porin specific for the accumulated disaccharide. For example, a cyanobacterium engineered to accumulate sucrose can be further engineered to express a sucrose porin (see e.g., Example 16). In one embodiment, the transformed disaccharide-accumulating cyanobacterium comprises an scrY nucleic acid, such as SEQ ID NO: 94. In one embodiment, the transformed disaccharide-accumulating cyanobacterium comprises a nucleic acid encoding a scrY polypeptide, such as SEQ ID NO: 95. In one embodiment, the transformed disaccharide-accumulating cyanobacterium comprises a plasmid containing scrY, such as pLybAL32 (SEQ ID NO: 91). It is contemplated that a similar approach can be applied to other photosynthetic microorganisms or other target disaccharides.

Modulation of Sugar Degradation

In some embodiments, a host photosynthetic microorganism, such as a cyanobacterium, is further engineered to improve disaccharide production by modulation of degradation activity (see e.g., Example 14). In some embodiments, an invertase homologue can be down-regulated or eliminated in a transformed photosynthetic microorgansim. For example an invertase homologue from *Synechocystis* spp. PCC 6803 (nucleotide sequence SEQ ID NO: 70; polypeptide sequence SEQ ID NO: 71) can be down-regulated or eliminated in a transformed cyanobacterium. As another example, an invertase homologue from *Synechococcus elongatus* PCC 7942 (nucleotide sequence SEQ ID NO: 72; polypeptide sequence SEQ ID NO: 73) can be down-regulated or eliminated in a transformed cyanobacterium. In some embodiments, a sucraseferredoxin-like protein is down-regulated or eliminated in a transformed cyanobacteriuma. For example, a sucraseferredoxin-like protein from *Synechocystis* spp. PCC 6803 (nucleotide sequence SEQ ID NO: 74; polypeptide sequence SEQ ID NO: 75) (Machray G. C. et al. 1994. FEBS Lett 354, 123-127) can be down-regulated or eliminated in a transformed cyanobacterium. These genes can be deleted using the markerless deletion protocol described in, for example, FIG. 11 (see e.g., Examples 12-13) A similar approach can be taken for other disaccharides engineered to be accumulated in a cyanobacterium.

Other methods of down-regulation or silencing the above genes are known in the art. For example, disaccharide degradative activity can be down-regulated or eliminated using antisense oligonucleotides, protein aptamers, nucelotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, Mo.; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

In some embodiments, a host photosynthetic microorganism can be further engineered to promote disaccharide secretion from the cells. For example, a cyanobacterium can be further engineered to promote sucrose secretion from the cells (see e.g., Example 15-16). When in a low osmotic environment, the sucrose can be automatically expunged from the cells, as done with osomoprotectants by some organisms when transitioning from high to low salt environments (Schleyer, M., Schmidt, R. and Bakker, E. P. 1993. Arch Microbiol 160, 424-43; Koo, S. P., Higgins, C. F. and Booth, I. R. 1991. J Gen Microbiol 137, 2617-2625; Lamark, T., Styrvold, O. B. and Strgim, A. R. 1992. FEMS Microbiol. Lett 96, 149-154). Sucrose porins can be engineered to be expressed in a transformed cyanobacterium (see e.g., Example 16). These genes can be cloned and transformed into cyanobacteria according to techniques described above. Such approaches can be adapted to other photosynthetic microorganisms.

In some embodiments, a host photosynthetic microorganism is transformed by stable integration into a chromosome of the host. For example, a host cyanobacterium can be transformed by stable integration into a chromosome of the host (see e.g., Examples 11-13). Chromosomal integration can insure that the target gene(s) is installed into the organism without risk of expulsion as sometimes occurs with plasmid-based gene expression. Chromosomal integration can also reduce or eliminate the need for antibiotics to maintain target genes.

Preferably, the strategy for chromosomal integration targets gene insertion into what is termed the upp locus on the chromosome (see e.g., Example 11-13). This site codes for the enzyme uracil phosphoribosyltransferase (UPRTase) which is a scavenger enzyme in pyrimidine biosynthesis. Using this strategy allows candidate selection by 5-fluorouracil (5-FU), which can eliminate non-integrated organisms. Segregation methods are generally used in cyanobacterial systems because these organisms contain multiple copies of their chromosomes (e.g., up to 12 for *Synechocystis* spp. PCC 6803 and 16 for *Synechococcus elongatus* PCC 7942). This strategy is particularly attractive for cyanobacteria, because this approach can avoid the use of traditional segregation techniques that rely on selective pressure and statistical integration for successful segregation. Using 5-FU as a screening agent can be more efficient because it can prevent growth for any organism that contains even a single active upp gene. In this manner, fully integrated candidates can be selected rapidly over fewer generation cycles compared to the processes required of traditional techniques.

Solid Phase Photosynthetic Bioreactor

Provided herein is a photobioreactor for culturing photosynthetic microorganisms comprising a solid phase cultivation support for the growth of photosynthetic microorganisms. A solid phase cultivation support, or solid cultivation support, or solid support, or the like, is generally understood to mean a cultivation support that is neither a liquid nor a gas. Although the support itself is a solid, the support structure may be selected so that it absorbs a liquid (e.g., growth media), a gas, or both. In certain preferred embodiments, as described more fully below, the solid support can absorb moisture for use by the microorganisms during cultivation.

Various embodiments of the photobioreactor(s) described herein can support the growth a photosynthetic microorganism. The photosynthetic microorganism grown in the photobioreactor can be, for example, a naturally photosynthetic microorganism, such as a cyanobacterium, or an engineered photosynthetic microorganism, such as an artificially photosynthetic bacterium. Exemplary microorganisms that are either naturally photosynthetic or can be engineered to be photosynthetic include, but are not limited to, bacteria; fungi; archaea; protists; microscopic plants, such as a green algae; and animals such as plankton, planarian, and amoeba. Examples of naturally occurring photosynthetic microorganisms include, but are not limited to, *Spirulina maximum, Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella* sp., *Scenedesmus obliquus, Anabaenopsis, Aulosira, Cylindrospermum, Synechoccus* sp., *Synechocystis* sp., and/or *Tolypothrix.*

Preferably, the bioreactor is configured to support innoculation, growth, and/or harvesting of cyanobacteria transformed to accumulate a disaccharide, as described above.

The photobioreactor can be an open or a closed system, as described more fully below. In various embodiments, the photobioreactor includes a solid phase cultivation support, a protective barrier layer, and a suspension element. Some embodiments of the photobioreactor can contain a system for delivery and/or removal of gas, fluids, nutrients, and/or photosynthetic microorganisms. Delivery systems can be, for example, standard plumbing fixtures. Any of the various lines can include quick-connect plumbing fixtures. The photobioreactor can have a gas delivery line, which can deliver, for example, delivering carbon dioxide or normal atmospheric air. The photobioreactor can have a fluid delivery line. Preferably, the fluid delivery line connects to a trickle or drip system which conveys a fluid (e.g., water) to the solid phase cultivation support. The photobioreactor can have a nutrient delivery line. Formulation of a nutrient composition for the growth and maintenance of a photosynthetic microorganism is within the ordinary skill of the art. In some embodiments, the nutrient and fluid delivery lines can be combined, for example to supply a fluid-based nutrient mixture. In some embodiments, the fluid delivery line or the nutrient delivery line can be a spray device for distributing a liquid medium over the growth surface. In such spray devices, the photobioreactor is large enough to accommodate, for example, a spray device between an outer layer, such as a barrier layer, and the solid phase cultivation support. Usually, nutrients are supplied in a water-based composition. It can be advantageous to provide for different water delivery line(s) and nutrient delivery line(s) so as to provide for independent control of moisture and nutrient levels. The photobioreactor can have a product harvest line so as to provide for collection of photosynthetic microorganisms and/or liquid suspended/soluble products. The photobioreactor can have an inoculation line so as to provide for inoculation of photosynthetic microorganisms. In some embodiments, the fluid, nutrient, and/or inoculation lines can be combined.

Figure 1:
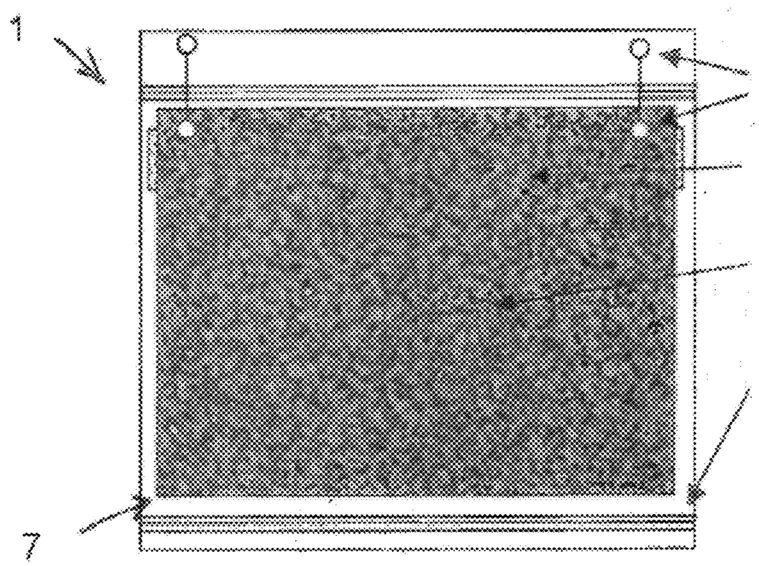
FIG. 1 illustrates a front view of the photobioreactor of the invention including a solid cultivation support, an outer protective transparent barrier layer, a selective panel, resealable closures, and support elements for suspending the device.
Figure 2:
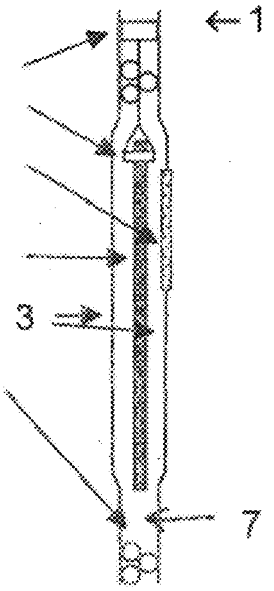
FIG. 2 illustrates a side view of the photobioreactor of the invention including a solid cultivation support, an outer protective transparent barrier layer, a selective panel, resealable closures, and support elements for suspending the device.

One embodiment of a solid-phase photobioreactor is depicted in FIG. 1 (front view) and FIG. 2 (side view). In these embodiments, a solid phase cultivation support 2 is enclosed by protective barrier 7. FIG. 2 shows that the solid cultivation support is between protective barrier layers 3 that comprise the protective barrier 7. The solid cultivation support 2 provides the surface upon which photosynthetic microorganisms are cultivated. The protective barrier layers 3 that make up the protective barrier 7 are transparent to allow actinic radiation to reach the surface of the solid cultivation support 2 to support the growth of photosynthetic microorganisms. Resealable closures 4 allow for a protective barrier 7 that is releasably sealed. Exchange of gases and vapor occurs through a selective panel 5 of material that is incorporated into the protective barrier 7. The photobioreactor 1 can be suspended by support elements 6 to allow for a vertical or non-horizontal orientation.

Another embodiment of a solid-phase photobioreactor is depicted in FIG. 12A (front view) and FIG. 12B (side view). The reactor 1 can be designed in a segmented format, which can aid in servicing and minimizes potential contamination of the surface and/or plumbing. Each segment can be connected to the reactor through plumbing (e.g., quick connect type plumbing) of the various supply and product harvest lines. The reactor can be supported by a suspension element 6 from, for example, rails, which allows the reactor 1 to hang in space and aid in rapid servicing of each segment. The outer protective barrier 7 can be a transparent material that enables light penetration facilitating photosynthesis on the growth surface 2, while preventing environmental contamination and moisture loss from evaporation. The growth surface 2 can be composed of a material that retains moisture, supplies nutrients, removes products, and/or enables high density growth of photosynthetic microorganisms. The growth surface 2 can be serviced by plumbing that provides continuous feeding/product harvest from the surface by liquid culture media. The media tubing 8 can be a porous hose that seeps liquid to the surface 2, which can percolate through the growth surface 2 by gravity. The liquid can be harvested at the bottom of the reactor by a harvesting tube 9, which collects products and excess liquid media for transport from the reactor 1. Gases, such as carbon dioxide and air, can be supplied to the reactor by a gas dispersion tube 10. The gas supply tube 10 can provide a positive pressure environment and is expected to supply gases necessary for growth in a controlled, efficient manner. The gas supply line 10 can also assist in minimizing moisture loss by humidifying incoming gas streams. Excess gas from the reactor can be vented by a breathable panel 5 (on the reverse side, not shown) that is a porous material that allows for gas passage but minimizes or eliminates environmental contamination. Contamination is expected to be minimized by the positive pressure configuration of the reactor 1 through filtration of the incoming gas delivered by the supply line 10. Positive pressure can also prevent contamination from the environment by providing an inside out pathway for gas flow.

In the embodiment depicted in FIG. 12B, features of the reactor 1 are depicted in an orientation relative to the growth surface. The breathable panel 5 allowing for excess gas to escape the reactor 1 can be located toward the bottom of the device to provide a path for gas to migrate across the growth surface 2. Location of the breathable panel 5 on the bottom of the barrier surface 7 also minimizes or prevents the possibility of carbon dioxide segregation and build up resulting from its higher density relative to air. The dimensions of the breathable panel 5 can be determined based on gas flow rate requirements for optimal growth on the cultivation surface 2.

Solid Phase Cultivation Support

The solid phase cultivation support of a photobioreactor as described herein provides a surface on and/or in which a photosynthetic microorganism can grow. Preferably, the solid phase cultivation support comprises a material that provides or facilitates the provision and/or retention of moisture and/or nutrients to the organisms, so as to promote and sustain growth. Embodiments of the invention are not limited to the type or strain of photosynthetic microorganisms that can be cultivated. One of ordinary skill in the art will recognize that the amount of moisture and the amount and composition of nutrients desirable for cell growth will vary with the type or strain of photosynthetic microorganism and the application for which it is to be grown. Materials (or the substances contained within or on those materials) that may have a deleterious effect on the growth of photosynthetic microorganisms are generally avoided.

A single photobioreactor can be used to cultivate a single type or multiple types or strains of photosynthetic microorganisms. Further, the solid cultivation support can comprise material(s) such that it is suitable for a single cultivation cycle or multiple cycles of cultivation, with or without sterilization between cultivation cycles. Still further, a photobioreactor can be configured to cultivate a single type or strain of microorganism or multiple types or strains of microorganisms on a single or multiple solid supports. In some embodiments, instead of an axenic culture, a community of different photosynthetic microorganisms, or a community of photosynthetic and non-photosynthetic microorganisms, can be grown together simultaneously on one cultivation support. A single photobioreactor can also comprise multiple cultivation supports. Thus in another embodiment, multiple cultivation supports within a single protective barrier can cultivate one or more types or strains of photosynthetic microorganisms simultaneously.

The solid cultivation support preferably comprises a relatively porous material. A relatively porous material generally has increased surface area and can retain and/or absorb more moisture than a relatively non-porous material. Also preferred is a solid cultivation support that has a textured or topographical surface(s). A textured or topographical surface can enhance cell density compared to a relatively non-textured or smooth surface. Although the choice of support material and surface topography are typically selected to enhance the adhesion of microorganisms to the support, it generally is desirable that the organisms not so tightly adhere so as to impede their removal or harvest. In some embodiments, the solid cultivation support comprises a material suitable for adhesion and growth of microorganisms. In some embodiments, the solid cultivation support comprises a material that reduces or eliminates biofilm formation.

The solid-phase supports of the photobioreactors described herein are believed to be different from solid supports that have been utilized in the art (e.g., the most commonly used solid phase support for the growth of microorganisms is agar). Agar is generally cast into rigid forms, such as a petri dish, and used while therein to maintain its physical integrity because agar tends to break or tear when subjected to minimal levels of stress, strain, or both. In contrast, various embodiments of the cultivation support is sufficiently strong and durable that it can be used in a photobioreactor while maintaining its physical integrity without the need of a stronger, more durable "frame". Or stated another way, the prior art involved a sufficient portion of the weak agar support in contact with a substantially stronger, more durable material (e.g., a petri dish) such that a composite is formed. Thus, the solid-phase supports of various embodiments of the photobioreactor are suitable in themselves for the cultivation of microorganisms and are sufficiently strong and durable.

Other desirable physical characteristics and/or operation parameters of the solid-phase support are described below. For example, the support can be relatively flat and rigid (like a plate) or it may consist of a multiplicity of flat and rigid sections flexibly connected by, e.g., hinges, springs, wires, threads, etc. Suitable rigid materials include, but are not limited to, various metals, polymers, ceramics, and composites thereof. The rigid materials preferably have surface topographies that enhance the adherence of the photosynthetic microorganisms thereto. Further, the rigid materials may be formed with a desired level of porosity to enhance the ability to deliver moisture and/or nutrients to the photosynthetic microorganisms. Still further, the rigid materials may be coated with absorbent or super absorbent polymer formulations (see below). Alternatively, the support may consist essentially of flexible material, such as a fabric. Fabrics for use in a solid-phase support include, but are not limited to, cotton, polyester, and/or cotton polyester blends, optionally coated with absorbent or super absorbent polymer formulations. Flexibility of the cultivation support can be greatly advantageous because it allows for the cultivation support to be folded, twisted, draped, or rolled for storage, transport, or handling.

In addition, the solid-phase cultivation support is preferably structurally stable at elevated temperatures (e.g., about 120° C. and above), such as would be typically encountered during autoclave sterilization, and will not melt like agar. Thus, in one embodiment, the cultivation support may be sterilized by autoclaving and then placed within the protective barrier of the invention. In another embodiment, the cultivation support can be placed within the protective barrier, and the entire photobioreactor may then be autoclaved. Although autoclaving is one method for sterilization, one of skill in the art will recognize that any other appropriate method of sterilization may be utilized.

The solid cultivation support of the present invention can comprise or be made of any material appropriate for supporting the growth of photosynthetic microorganisms. For example, the support may be composed of natural materials, modified natural materials, synthetic materials, or any combination thereof. Natural materials can include, but are not limited to cotton, wool, processed woven plant fibers, and natural polysaccharides (e.g., agar, starches, cellulosics). Modified natural materials can include, but are not limited to, chemically modified plant fibers such as nitrocellulose or cellulose esters, in addition to natural fibers co-woven or blended with polyester or polyamide fibers. Synthetic materials can include, but are not limited to, fibers composed of nylon, fiberglass, polysiloxanes, polyester, polyolefins, polyamide, copolyester polyethylene, polyacrylates, or polysulfonates. Further examples of solid cultivation support materials include wire mesh, polyurethane foams, polyethylene foams, vitreous carbon foams, polyester/polyethylene foams, polyimide foams, polyisocyanate foams, polystyrene foams, and polyether foams, or combinations thereof.

In various embodiments, the solid cultivation support is a fabric. The fabric can be formed by methods such as, but not limited to, weaving, knitting, felting, and the bonding or cross-linking of fibers or polymers together. The construction of the fabric can be loose or open. Alternatively, the fabric can be tightly constructed. That said, fabrics that have a significant texture, surface area, topographical variability, and/or roughness may provide more mechanical bonding or adherence of the photosynthetic microorganisms to the cultivation support and thus may be preferable, especially in embodiments wherein the photobioreactor is handled, transported, or otherwise moved during the process for inoculating the support with, and/or growing and/or harvesting the organisms.

Preferably, in most applications the adherence of the organisms to the substrate should not be so great as to unduly hinder their removal during a harvesting operation. Still further, the ability of a fabric to retain moisture and/or nutrients for use by the organisms can be controlled by selecting fibers that are generally hydrophobic, hydrophilic, or a mixture of such fibers. These properties allow for moisture and/or nutrients dissolved therein to be retained and/or transported by the solid support so that they are available to the microorganisms growing on the surface.

The properties of the cultivation support, especially moisture and/or nutrient retention, can be enhanced by coating the support with a material selected to enhance photosynthetic microorganism growth. For example, the cultivation support can be coated with agar or a super absorbent polymer such as modified cellulose ester, acrylate or acrylate/polyamine copolymer blends. These coating materials are typically able to absorb and retain greater than 10 to 100 times their dry weight in water. In some embodiments, these materials are formulated such that they would retain their superabsorbent properties in the presence of ionic culture media components. The coating material can coat the surface of the cultivation support, or the fibers of a fabric if used, or both. In one embodiment, a swatch of terrycloth serving as the cultivation support is coated in agar. When a solid cultivation support is coated as such, the "surface" of the cultivation support includes the surface of the coating if photosynthetic microorganisms attach to such. To keep the cultivation support thin, pliable, and light, the coating is preferably thin, for example, no greater than about 100 microns. However, thicker coatings can also be used depending on the application desired, or on the combination of solid cultivation support and coating material selected.

The solid-phase cultivation support can be a composite, layered structure. The solid-phase cultivation support can comprise at least two layers arranged so as to be adjacent. Multiple layers of the solid-phase cultivation support can be coupled, such as by bonding, stitching, adhesive, compression, or any other suitable means. The various layers can each independently be selected from among the several materials discussed above. For example, the solid-phase cultivation support can comprise a first material layer of fabric bonded to a second material layer of synthetic foam. An another example, the solid-phase cultivation support can comprise a first material layer of synthetic foam bonded to a second material layer of synthetic foam of the same or different density. Preferably, the solid-phase cultivation support is a composite, layered structure comprising at least a first layer, which is composed of a high surface area growth material, and a second layer, which is composed of a permeable type material.

In addition to supplying moisture, nutrients, and a surface for attachment, the cultivation support can provide a surface for capturing actinic radiation. Thus, in some embodiments, the dimensions of the solid cultivation support are sheet-like. That is, the depth of the support is small relative to the length and width of the support. In one embodiment, the cultivation support is a sheet-like layer between film-like layers of a protective barrier. Such a flat bioreactor can be suspended like a flat panel. In another embodiment, just the cultivation support is suspended like a curtain enclosed by the outer barrier of the photobioreactor. A thin sheet of a traditional solid phase support such as agar would easily rip apart, and would likely not be able to be suspended as such. Therefore, it is preferable that the solid cultivation support alone be able to maintain its integrity when suspended, even when saturated with liquid.

As shown herein, a fabric with a terrycloth-type weave can provide a suitable solid support (see e.g., Example 1). One of skill in the art will understand that other natural, modified-natural, and synthetic materials may also be acceptable. Terrycloth provides many of the attributes believed to be desirable in a solid support of the present invention. For example, it is flexible, and not prone to tearing, ripping, breaking, or cracking when handled in accordance with non-destructive techniques (e.g., bending, folding, twisting, or rolling) under conventional conditions (e.g., temperature). Likewise, terrycloth is typically not prone to tearing, ripping, or breaking when modestly stretched (even when saturated with liquid). Additionally, terrycloth tends to be highly textured because it is composed of the many loops of fibers. This provides a large amount of surface area for the attachment of microorganisms thereby increasing the amount of microorganisms that can be grown on a support of any given size. Further, a cotton terrycloth typically absorbs at least about three times its own weight, which allows for moisture and any nutrients dissolved therein to be retained by the fabric support so that they are available to the microorganisms growing on the surface of the support. Thus, various embodiments provide for a solid cultivation support that is thin or sheet-like in dimension, able to support its own wet weight while suspended, flexible, pliable, absorbent, highly textured, or any combination thereof.

The above-described supports can be, and in many applications preferably are, used repeatedly and more preferably for so long as they are structurally sound and provide a surface adequate to support the growth of the microorganisms disposed of after a single use thereby reducing operational costs and waste. That said, there can be certain applications in which single-use supports would be desirable, such as cultivation of recombinant photosynthetic microorganisms useful in producing pharmaceutical products such as small organic molecules or therapeutic proteins and peptides. To reduce the costs of such single-use supports and in view of the fact that that they will not be reused, such supports need not be as durable and therefore can be made or constructed using methods and/or materials that are less costly and less durable. For example, supports comprised of paper fibers similar to that of paper towels may be appropriate.

Several embodiments of a solid phase cultivation support are depicted in FIG. 13. The solid phase cultivation support material depicted in FIG. 13A is a single material that can provide sustainable surface for organism growth, access to moisture and nutrients, point of organism attachment, and/or removal of cultivation products. The material can allow for liquid percolation and equilibrium diffusion to exchange nutrients, moisture, and products between the surface and organisms. The rendering of the structure configuration is an example of a high surface area material, which can be optimized for dimension and shape. The solid phase cultivation support material depicted in FIG. 13B is a hybrid material that is composed of multiple layers of materials, each having specific functions for the growth surface. The base layer can be a porous material that efficiently allows for supply of nutrients and moisture as well as removal of products that are percolated through the material. The base material can also provide physical support for the growth surface. The outer layer(s) is expected to be attached to the base layer and can be optimized to provide point of attachment for the organisms. The surface layer can achieve more control of the surface growth environment in terms of surface area and compatibility with the cultivated organism.

Protective Barrier

A photobioreactor as described herein can comprise a barrier that protects the solid cultivation support and growth surface from contamination and/or moisture loss. At the same time, the photobioreactor provides for actinic radiation, either sunlight or artificial light, and carbon dioxide reaching the photosynthetic microorganisms. In various embodiments, the photobioreactor comprises at least one solid support and a protective barrier for the cultivation of photosynthetic microorganisms.

Protection from Physical Handling and/or Contamination

To prevent contamination, a protective physical barrier can at least partially cover the solid cultivation support. In certain embodiments, the physical barrier can enclose the cultivation support. The protective barrier can also control, at least in part, the loss of the moisture from the support and/or the atmosphere within the photobioreactor to the atmosphere outside the photobioreactor. One of skill in the art will recognize that the protective barrier can be constructed from any of numerous types of materials depending on the embodiment of the invention desired.

The protective barrier can completely enclose the cultivation support. If the protective barrier is permanently sealed, the barrier must be breached, cut, torn, or the like to access the cultivation support within. Thus, in some embodiments, access is provided through the protective barrier to the cultivation support and the surface on which the microorganisms are grown.

In preferred embodiments, the protective barrier is releasably sealed. The releasable seal can be any of a number of closure types including, but not limited to zipper-type closures such as found in Ziploc® storage bags (SC Johnson Company), hook-and-loop type fasteners (e.g., Velcro USA, Inc.), twist ties, zipties, snaps, clips, pressure sensitive adhesive backed surfaces, and all art recognized equivalents thereto. A complete seal, however, is not necessarily required; and it may be more efficient not to completely seal the outer barrier to allow for easier access to the cultivation support.

The photobioreactor can comprise a single cultivation support or multiple cultivation supports within a protective barrier. In some embodiments, a single cultivation support is enclosed within a single protective barrier. For example, a plastic bag may form a protective barrier within which a single solid cultivation support is enclosed (see e.g., FIG. 1). In other embodiments, a single protective barrier may enclose multiple solid cultivation supports. For example, a greenhouse-type structure may form a protective barrier within which multiple solid cultivation supports are enclosed.

Transmission of Actinic Radiation

The photobioreactor can provide for transmission of actinic radiation, either sunlight or artificial light, to the photosynthetic microorganisms. But the protective barrier of the invention need not necessarily be transparent to light. Some embodiments can comprise a cultivation support enclosed within a non-transparent protective barrier if a sufficient light source for the growth of photosynthetic microorganisms is provided within. It may be desirable, simpler, more economical, and the like to provide a transparent barrier to utilize sunlight, for instance, as a light source.

Preferred embodiments provide for a transparent barrier comprising a material such as, but not limited, glass or any type of transparent or generally visible light transmitting polymer such as polyethylene, acrylic polymers, polyethylene terephthalate, polystyrene, polytetrafluoroethylene, or co-polymers thereof, or combinations thereof. The transparent barrier can be selected from materials that are durable and not prone to ripping, tearing, cracking, fraying, shredding, or other such physical damage. The transparent barrier material can be selected for its ability to withstand autoclave sterilization or other exposure to temperature extremes. Further, the transparent barrier materials can be selected to withstand prolonged exposure to sunlight or other radiation without discoloring or deteriorating. One of skill in the art will recognize that certain coatings or formulations that resist photooxidation can be particularly useful. In addition, infrared reflecting or absorbing coatings can be selected to reduce and/or otherwise regulate the buildup of temperature within the photobioreactor of the invention.

One of skill in the art will recognize that the thickness of the transparent barrier material will vary depending on mechanical properties of scale. For example, the transparent barrier material may be of an industrial/marine type plastic about 10 mil thick or it may be of the type used in a household plastic bag, i.e., around 2 mil thick. In one embodiment, the transparent barrier material is thin and flexible. For example, the transparent barrier material can be less than about 10 mil.

In some embodiments, the barrier forms a protective layer or film covering the two sides of a thin, flexible, solid cultivation support. The assembled photobioreactor of this embodiment would be flexible, and could be bent, rolled, folded, twisted, or the like for storage, transport, conveying, or handling. In another embodiment, the transparent barrier material is rigid. For example, the barrier can be a glass greenhouse. Most likely, the thickness of the greenhouse glass would preferably be consistent with building practices but it is possible that it could be altered. The photobioreactor of such an embodiment would be for practical purposes immovable, but multiple solid supports could be handled, transported, conveyed and the like within the confines of one protective, transparent barrier.

Although a protective barrier can be selected to provide sufficient light for the growth of photosynthetic microorganisms, it is not necessary that the entire barrier be transparent. Thus, in some embodiments, portions of the barrier, such as one or more edges, are made from a non-transparent material. The non-transparent material can be composed of materials including, but not limited to polyethylene fiber material (Tyvek®), polytetrafluoroethylene filtration media, cellulosic filter material, fiberglass filter material, polyester filter material and polyacrylate filter material, and combinations thereof. The non-transparent material can be selected for durability. In such an embodiment, a transparent portion of the barrier would be further protected from tearing, ripping, fraying, shredding, and the like by a durable, non-transparent portion. In one embodiment, a non-transparent portion provides or comprises an attachment structure and/or reinforcement for suspending the photobioreactor by further comprising mounting or attachment points (e.g., holes, loops, hooks, grommets, or other art equivalent device, opening or, recess) and/or or a mechanism for securing the photobioreactor to a structure. Although it is not required that any such mounting points, etc., be located in or on the non-transparent portion, they can be contained within or on a non-transparent portion of the barrier, within or on a transparent portion of the barrier, or within or on a non-transparent and a transparent portion of the barrier. The attaching structure may also be contained within or on, or pass through, the solid cultivation support.

In some embodiments, the device has a discernable front side and back side. The front side of this device is meant to face a light source, and thus the portion of the barrier on the front side is preferably transparent, while the portion of the protective barrier on the side facing away from the light source is not necessarily transparent.

Provision of Gas Exchange

During photosynthesis, photosynthetic microorganisms consume carbon dioxide and release oxygen. A photobioreactor as described herein can provide carbon dioxide sufficient for a desired amount of photosynthesis to occur. One way to supply carbon dioxide to the inside of the photobioreactor is to allow direct gas exchange between the air inside and the air surrounding the photobioreactor. For example, holes, vents, windows, or other such openings can be provided in the protective barrier so that the system is open to the surrounding atmosphere.

But such an open configuration may not be desirable when contamination of the photosynthetic microorganisms is a concern. To address this concern, the protective barrier can completely seal off the solid support or supports enclosed within from the outside air. In such an embodiment, the desired concentration of carbon dioxide can be maintained by introducing it into the enclosure. For example, one of skill in the art would recognize that plumbing or tubing from a tank of compressed carbon dioxide would allow for carbon dioxide to be mixed into the air enclosed within the photobioreactor. In addition, it is known that the emissions from factories, industrial plants, power plants, or the like can be harnessed as a source of carbon dioxide for photosynthetic microorganisms, thus reducing carbon emissions. In one embodiment, a gas supply line can provide carbon dioxide to the growth surface local area.

It may be desirable, simpler, more economical, and the like to provide a selective barrier that is gas permeable to utilize atmospheric carbon dioxide. Thus, some photobioreactor embodiments provide for a selective barrier that allows gas and vapor exchange between the environment enclosed within the protective barrier and the surrounding air, while still providing a sealed physical barrier against contamination. Such barrier can be at least partially gas/vapor permeable (e.g., much less permeable than conventional textile fabrics, higher than that of plastic films, and/or similar to that of coated papers), thus allowing the exchange of gases such as carbon dioxide and oxygen but is additionally at least partially and preferably considered to be impermeable to solids and liquids. In some embodiments, the photobioreactor can contain a semi-permeable barrier layer and a gas supply line to maintain an elevated carbon dioxide concentration in the area around or near the growth surface.

In some embodiments, a selective barrier can have an average pore size or diameter of no greater than about 10 micrometers and a gas exchange rate that is at least about 5 and no greater than about 10,000 Gurley seconds (a Gurley second or Gurley is a unit describing the number of seconds required for 100 cubic centimeters of gas to pass through 1.0 square inch of a given material at a given pressure differential) . Therefore, in addition to allowing gas exchange, the selective barrier can prevent loss of moisture from the enclosed system.

The selective barrier portion of the protective barrier can be composed of any appropriate polymer-based material, such as spunbonded olefin barriers. Spunbonded olefin barriers (very fine polyethylene fibers) with various properties are readily available from DuPont under the brand name Tyvek®. Such materials are particularly advantageous because of their combination of physical properties, i.e., they tend to resist the transmission of liquids such as water yet they have a sufficiently high degree of gas/vapor permeability; they are relatively strong, absorb little or no moisture, are rip-resistant, have a significant degree of elasticity, and are highly flexible. Spunbonded olefin can exceed 20,000 cycles when tested on an MIT flex tester (TAPPI method T-423). In addition, they are inert to most acids, bases and salts although a prolonged exposure to oxidizing substances, such as concentrated nitric acid or sodium persulfate, will cause some loss of strength. Spunbonded olefin barriers have good dimensional stability in that sheet dimensions tend to change less than 0.01% between 0 and 100% relative humidity at constant temperature. Certain products meet the requirements of Title 21 of the United States Code of Federal Regulations (21 CFR 177.1520) for direct food contact applications. They also have excellent mold and mildew resistance; and are of a neutral pH. Unfortunately, however, their UV resistance is not exceptional. That said, at least one to three months of useful outdoor life can usually be expected. Additionally, their UV resistance can be improved with opaque coatings or by including UV inhibitors in the polymer fibers. Additionally, because the spunbonded oelefins produced to date are opaque, the portion of the protective barrier that would comprise such material is preferably not situated and/or so extensive as to compromise the cultivation of the photosynthetic microorganisms.

In particular, spunbonded olefin can be produced in "hard" and "soft" structure types. Type 10, a "hard," area-bonded product, is a smooth, stiff non-directional paper-like form. Types 14 and 16 are "soft," point-bonded products with an embossed pattern, providing a fabric-like flexible substrate. Type 14 styles (or the equivalent thereof) can be used, for example, where barrier, durability, and breathability are required. Type 16 styles are pin perforated with 5-20 mil (0.13-0.51 mm) holes, giving them much higher air and moisture permeability, additional softness, and greater flexibility and drape than Type 14 styles, but at the expense of lower tear strength and barrier properties. Thus, the particular properties of the selective barrier can be customized by selecting one or more types of spunbonded olefin products.

Other examples of selective polymer barriers include, but are not limited to nylon, polysulfone, polytetrafluoroethylene, cellulosic, fiberglass, polyester and polyacrylate membranes and filter material, and combinations thereof.

The entirety of the protective barrier need not be gas permeable to provide for a barrier that is sufficiently selective for the growth of photosynthetic microorganisms. Only a portion of the protective barrier sufficient to allow for adequate gas exchange need be gas permeable. In one embodiment, the selective portion is a panel of the protective barrier (see e.g., FIG. 1). The size and placement of the selective panel in relation to the area of the support surface can be altered to achieve a desired amount of gas exchange for a particular application without unduly hindering the cultivation of the microorganisms. One of skill in the art will recognize that the percentage of the area of the outer barrier composed of the gas permeable selective material will depend on the gas permeability rate of the material. In fact, because the gas permeable portion will still allow the transport of water vapor across it, in various embodiments, the size of the gas permeable portion of the protective barrier is selected so as to allow for sufficient transport of oxygen and carbon dioxide while minimizing the loss of moisture.

Suspension and Conveyance System

Figure 3:
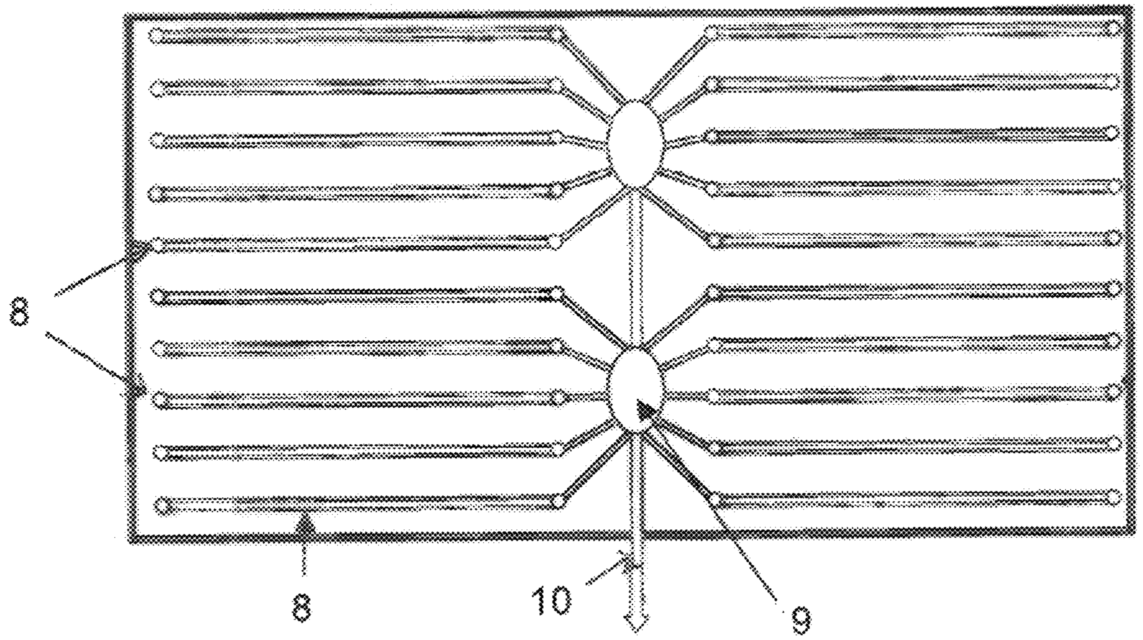
FIG. 3 illustrates an arrangement of multiple photobioreactors or cultivation supports of the invention along multiple closed loop conveyor systems radiating out from common inoculation and harvesting centers to comprise a photobioreactor farm.

Photobioreactors described herein can be configured for large scale production and/or harvesting through, for example, integration into a handling and conveyance system. FIG. 3 shows an above view of an exemplary design of a photobioreactor farm for handling large numbers of photobioreactors in a continuous process. The photobioreactors or cultivation panels (not individually shown) are attached to conveyor systems 8. The conveyor systems 8 move the cultivation panels along their paths. Multiple conveyor systems converge at centrally located inoculation and harvesting centers 9. Thus, the cultivation panels are moved into the inoculation and harvesting centers 9 where they can be processed (e.g., harvested and/or inoculated) and then the panels are moved away from the centers following inoculation and during the period of cultivation of the biomass. The panels are then moved back towards the centers during the latter period of cultivation prior to harvesting, eventually arriving back at the centers with mature biomass for harvest. The cycle is then repeated. Harvested biomass can be transported through a pipeline 10 for further processing. The capacity of the photobioreactor farm can be increased by adding additional conveyor systems or additional inoculation and harvest centers to form large arrays dedicated to biomass production.

Suspension of Photobioreactor

To supply light to photosynthetic microorganisms, a favored embodiment of the photobioreactor is one in which the cultivation support is thin and sheet-like. When oriented horizontally, the efficient utilization of floor space tends to decrease, therefore in certain embodiments of the invention the cultivation support is oriented non-horizontally, preferably substantially vertically, or more preferably vertically. Nevertheless, the cultivation support may be oriented in essentially any manner so long as a sufficient amount of actinic radiation can reach the microorganisms. Thus, when the photobioreactor is of the type where the protective barrier forms a closely associated film or layer around the solid support, a preferred orientation of the entire photobioreactor is vertical, but any orientation is acceptable. To be clear, the aforementioned orientations (e.g., vertical, horizontal, substantially vertical, non-horizontal, etc.) are relative to the floor or ground beneath the cultivation support, assuming that the floor or ground is horizontal.

Various structures, scaffolding, stands, racks, etc. may be used to hold or suspend a cultivation support or an entire photobioreactor in a desired orientation. In particular, the cultivation support and/or the protective barrier can be suspended from, or attached to. a rope, line, hook, cable, track, rail, chain, shelf, pole, tube, scaffold, stand, beam or any other such structure capable of suspending the solid cultivation support and/or photobioreactor. Multiple cultivation supports and/or photobioreactors may be suspended from a common structure, like sheets hanging from a clothes line. The cultivation support(s) and/or photobioreactor(s) may be suspended statically, or in a manner that allows for their movement. The position of the holes, loops, hooks, or the like will preferably distribute the weight of the cultivation support and/or photobioreactor substantially evenly.

Suspension of the photobioreactor or cultivation support, especially in a vertical orientation, is space efficient and may provide advantages in handling. However, the bioreactor or cultivation support of the invention need not be suspended. For example, in certain embodiments of the present invention, the cultivation support is sufficiently rigid that if oriented non-horizontally, vertically, or substantially vertically (e.g., by securing or placing its base to/on a surface, in an embodiment in which the support is like a rigid plate, panel, grid, etc.) it can support its own weight and will remain so oriented. In another embodiment, the protective barrier is free standing, such as a greenhouse, and multiple cultivation supports are suspended and/or free-standing within.

Suspension of the photobioreactor and/or cultivation support, especially in a vertical orientation, is space efficient and may provide advantages in handling. However, the bioreactor or cultivation support of the invention need not be suspended. For example, in certain embodiments of the present invention, the cultivation support is sufficiently rigid that if oriented non-horizontally, vertically, or substantially vertically (e.g., by securing or placing its base to/on a surface, in an embodiment in which the support is like a rigid plate, panel, grid, etc.) it can support its own weight and will remain so oriented. In another embodiment, the protective barrier is free standing, such as a greenhouse, and multiple cultivation supports are suspended and/or free-standing within.

Conveyance

Also described herein is a system for conveying photobioreactors, cultivation supports within the protective barrier of a photobioreactor, or some combination thereof from one location to another. The ability to transport a photobioreactor and/or cultivation support can be advantageous for a variety of reasons. For example, it may allow for optimizing their position(s) for receiving light, and for maintaining a desired temperature or gas content. The transportability can be particularly advantageous when multiple photobioreactors or cultivation supports are to be subject to discrete steps, such as inoculating, cultivating, inducing, and/or harvesting, because it is likely to be more efficient to move the photobioreactors or cultivation supports to several assigned locations in a continuous-type process instead of transporting the necessary materials and equipment to stationary photobioreactors or cultivation supports.

Thus, the growing surface, whether the cultivation support alone, or the cultivation support enclosed in a protective barrier, can be conveyed, even after inoculation. One of skill in the art will be familiar with numerous types of conveyor systems frequently used in industrial applications. The conveyance system is not limited to any particular type so long as it is capable of moving one or more photobioreactors or cultivation supports. One skilled in the art will recognize that the type of attachment between the photobioreactor or cultivation support and the conveyor system will vary with the type of conveyance system employed and will be selected to work cooperatively with any mounting points that are part of the cultivation support and/or the protective barrier. Although it is envisioned that the cultivation support(s) or photobioreactor(s) will be conveyed in a mechanized manner powered by one or more motors (e.g., through the action of a chain and gears), it is also possible for them to be conveyed with human effort (e.g., by simply pushing suspended bioreactors that are attached to a rail by a bearing mechanism that slides along the rail).

A conveyor system that suspends photobioreactor(s) and/or cultivation support(s), especially in a vertical orientation, is space efficient and may provide advantages in handling. But the conveyor system need not rely on suspending photobioreactor(s) or cultivation support(s). For example, a photobioreactor may move along on top of the conveyor system, such as by sliding over a roller conveyor. In one embodiment, the conveyor system may move photobioreactors comprising a cultivation support enclosed in a protective barrier. Alternatively, the protective barrier of a photobioreactor may be a large enclosure protecting one or more conveyor systems moving multiple cultivation supports.

Photobioreactor Farm

For large scale applications, it may be impractical to construct a single cultivation support of sufficient size. Thus is provided use of two or several or tens or hundreds or thousands or more cultivation supports to cultivate photosynthetic microorganisms in a photobioreactor "farm." These cultivation supports can all reside within a single protective barrier, thus comprising a single photobioreactor, or multiple cultivation supports may be part of multiple photobioreactors. In either case, it can be beneficial to organize the multiple photobioreactors or cultivation supports within a photobioreactor farm for ease and efficiency of handling and processing. It can also be beneficial to organize their arrangement to maximize the amount of energy captured from a light source such as the sun. Such organization can consist of arranging numerous photobioreactors or cultivation supports in an orderly fashion such as, but not limited to, rows, columns, concentric circles, in grids, radiating outward from a central point, and so forth.

In various embodiments, the farm comprises multiple photobioreactors or cultivation supports suspended from a common structure such as a track, rail, chain, line, or the like. In further embodiments, the structure is part of a conveyor system and the photobioreactors or cultivation supports move along the path of the conveyor system from one location to another.

A photobioreactor farm can comprise one or an arrangement of multiple conveyor systems handling numerous photobioreactors or cultivation supports. Such an arrangement could be scaled up to comprise two or several or tens or hundreds or thousands or more conveyor systems together handling two or several or tens or hundreds or thousands or more photobioreactors or cultivation supports. In addition to the conveyor system(s), a photobioreactor farm can include defined areas, stations, or centers for performing steps such as inoculating, cultivating, inducing, and/or harvesting photosynthetic microorganisms. Such centers can be the location of specialized equipment for performing certain steps. The paths of the conveyor systems can bring the photobioreactors or cultivation supports to such centers where a particular step is performed. The photobioreactor or cultivation support can then be moved along to the next area or center in the sequence. Different photobioreactors or cultivation supports along the conveyor system can reside at different centers along the path and thus be subject to different steps simultaneously. In one embodiment, the path of the conveyor system is a loop. Once a photobioreactor or cultivation support completes one round of steps in the cultivation process, it can repeat the process. Allowing for some units to be damaged or otherwise eventually needing replacement, essentially the same set of photobioreactors or solid cultivation supports can be used repeatedly.

In a further embodiment, cultivation and harvest can occur at the same or nearly the same location. This location is termed an inoculation and harvest center (see e.g., FIG. 3). Inoculation of the photobioreactors and/or solid cultivation supports occurs at the inoculation and harvest center. The conveyor system forms a loop that then transports the photobioreactors or cultivation supports away from the inoculation and harvest center. The photobioreactors or cultivation supports then travel along the path of the conveyor system for an amount of time sufficient for the desired amount of cell growth. The conveyor system then returns the photobioreactors or cultivation supports back to the inoculation and harvest center for harvest. Multiple conveyor systems can share a common inoculation and harvest center from which they radiate out from. If even more capacity is needed, a photobioreactor farm can comprise multiple inoculation and harvest centers handling the photobioreactors or cultivation supports from multiple conveyor systems. Although increased efficiencies may be realized, it is not necessary that the location of inoculation and of harvest be the same or nearly the same location.

Methods of Using a Photobioreactor

Cultivation of Photosynthetic Microorganisms

A solid phase photobioreactor, as described herein, can be used for cultivating photosynthetic microorganisms. Photosynthetic microorganisms that can be grown in the solid phase photobioreactor include, but are not limited to, a naturally photosynthetic microorganism, such as a cyanobacterium, or an engineered photosynthetic microorganism, such as an artificially photosynthetic bacterium. Exemplary microorgansims that are either naturally photosynthetic or can be engineered to be photosynthetic include, but are not limited to, bacteria; fungi; archaea; protists; microscopic plants, such as a green algae; and animals such as plankton, planarian, and amoeba. Examples of naturally occurring photosynthetic microorganisms that can be grown in the bioreactor include, but are not limited to, *Spirulina maximum, Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella* sp., *Scenedesmus obliquus, Anabaenopsis, Aulosira, Cylindrospermum, Synechoccus* sp., *Synechocystis* sp., and/or *Tolypothrix.*

Preferably, the photosynthetic microorganisms grown in the solid phase photobioreactor comprise cyanobacteria. The cyanobacterium grown in the bioreactor can be any photosynthetic microorganism from the phylum Cyanophyta. The cyanobacterium grown in the bioreactor can have a unicellular or colonial (e.g., filaments, sheets, or balls) morphology. Preferably, the cyanobacterium grown in the bioreactor is a unicellular cyanobacterium. Examples of cyanobacteria that can be grown in the bioreactor include, but are not limited to, the genus *Synechocystis, Synechococcus, Thermosynechococcus, Nostoc, Prochlorococcu, Microcystis, Anabaena, Spirulina*, and *Gloeobacter*. Preferably the cyanobacterium grown in the bioreactor is a *Synechocystis* spp. or *Synechococcus* spp. (e.g., *Synechococcus elongatus* PCC 7942 (ATCC 33912) and/or *Synechocystis* spp. PCC 6803 (ATCC 27184)). More preferably, the photosynthetic microorganism grown in the bioreactor is a transgenic photosynthetic microorganism engineered to accumulate a disaccharide, as disclosed herein.

A solid cultivation support of a photobioreactor can be inoculated with a photosynthetic microorganism, along with addition of moisture and other components including, but not limited to, nutrients, salts, buffers, metals, nitrogen, phosphate, sulfur, etc. The photobioreactor can then be releasably sealed with the cultivation support within the protective barrier. The sealed photobioreactor can be placed, for example by suspending it, in a location and manner to allow for control of illumination and temperature. The placement can be static, or the photobioreactor can be moved, such as to ensure maximum exposure to the sun's radiation over the course of a day. The photosynthetic microorganisms can be cultivated for a desired amount of time. One of skill in the art will recognize that the length of time will vary according to the type of microorganism and the density of cell growth desired. For example, for certain strains of cyanobacteria, a cultivation period that is within the range of about four to about seven days can provide a yield of cells that is within the range of about 50 to about 250 grams of dry biomass per liter equivalent. Following a period for cultivation, the releasable seal can be opened and the photosynthetic microorganisms can be harvested.

As used herein, "grams of dry biomass per liter equivalent" is a unit determined by calculating the average depth of the biomass layer (e.g., about 150 microns) growing on the cultivation surface and multiplying that value by the length and the width of the cultivation surface. This calculation provides a volume. The weight of the collected biomass from the cultivation surface can then be correlated to the volume and expressed as "grams of dry biomass per liter equivalent."

Method of Continuous Cultivation

Greater efficiencies can be realized if the process of cultivating photosynthetic microorganisms were to be made continuous, for example, like an assembly line. Instead of requiring the equipment and capacity to handle a large amount of biomass all at once that then sits idle in between batches, a continuous system would require less total capacity, but would utilize that capacity more efficiently through continuous operation. By dividing cultivation into smaller but more numerous components, the components can be organized in a spatially continuous arrangement. Different discrete steps of the overall production process can then occur simultaneously. After a cultivation component is subjected to a process step, the component moves forward in the process while another component replaces it in that step. Therefore, production of the end product would not be limited to the maturation of a large batch, but can occur regularly as individual components complete the assembly line-like process. Further, following the completion of one round of the process, the components can immediately start the process over and do so repeatedly.

More specifically, continuous cultivation relates to methods of using conveyable photobioreactors or cultivation supports for cultivating photosynthetic microorganisms in a continuous manner. Continuous or continuous process is understood as the spatial relationship that can allow the photobioreactors or solid cultivation supports to progress from one step of the cultivation process to another. Alternatively, it is possible for a single large structural support to be utilized in a continuous process. Specifically, the support can be a loop of material (e.g., terry cloth fabric) that is made to travel along a circuit (e.g., like a conveyor belt that is arranged preferably vertically). The end result is that biomass production can be achieved regularly as multiple photobioreactors or solid cultivation supports finish the process sequentially and repeatedly. This type of process presents opportunities in large scale applications for increased efficiencies over producing biomass in large, but infrequent batches.

In a preferred embodiment, the continuous spatial relationship is along the path of a conveyor system. The manner of operation is analogous to an assembly line. Such a conveyor system can operate in a number of ways. For example, the conveyor system can operate without interruption while moving the photobioreactors or cultivation supports from one location to another. In such an embodiment, inoculation, harvesting, and the like occur while the photobioreactors or cultivation supports are in motion. Alternatively, the conveyor system can stop to allow for steps to be performed, and then resume to move the photobioreactors or cultivation supports to the location of the next step. Further, the conveyor system can operate without interruption, and the photobioreactors or cultivation supports can be detached from the movement of the conveyor system for processing, and then reattached to re-enter into the stream of conveyance. One skilled in the art will realize that other permutations of this general theme are also possible.

In one embodiment of a method of continuous cultivation, multiple photobioreactors are inoculated at one location along the conveyor system. The conveyor system then moves the photobioreactors to an area where cultivation of the photosynthetic microorganisms occurs. During this portion of conveyance, the photobioreactors can be positioned to allow for optimal illumination to promote growth and photosynthesis. Next, the photobioreactors would arrive at a location where the photosynthetic microorganisms can be harvested. The photobioreactors can then return along the path of the conveyor system to the point of inoculation to begin the process again. To improve efficiency, the time between when the photobioreactors leave the location of inoculation and arrive at the location of harvest can be made to coincide with the time it takes for the desired amount of growth of the photosynthetic microorganisms to occur. The steps of the process are not limited to inoculation, cultivation, and harvest; additional steps can include inducement of the cells to synthesize a desired product or sterilization. Although the above embodiment describes a system of conveyable photobioreactors, it will be appreciated that the same type of continuous cultivation can be practiced within a single protective barrier to convey and process multiple solid cultivation supports.

Method of Producing Fermentable Sugars

One technology that can benefit from the ability to more efficiently grow photosynthetic microorganisms is the production of biomass for alternative fuels such as ethanol or biodiesel. Relative to plants currently grown to produce biomass such as corn, sugarcane, soybeans, canola, jatropha, and so forth, photosynthetic microorganisms, such as cyanobacteria, produce biomass at a much faster rate, which may lead to much greater productivity. In addition, direct production of disaccharides by microorganisms avoids much of the extensive energy-intensive pre-processing of using plant biomass to produce fermentable sugar. Further, the use of phototrophic microorganisms instead of plants can lead to higher yields of fermentable sugars without soil depletion, erosion, and diversion of the food supply. Relative to other microorganisms, preference is given to phototrophic microorganisms because their sources of carbon ($CO_2$) and energy (light) can be supplied from the environment, making them far less expensive to cultivate. In addition, phototrophic microorganisms can be utilized to consume carbon emissions from industrial processes, thus providing further benefits to the environment.

One obstacle to producing high quantities of fermentable sugars from photosynthetic microorganisms is that they generally consume produced carbohydrates rather than accumulating them. While some sugars, such as sucrose or trehalose, are not utilized as a primary carbon source by photosynthetic microorganisms, there are mechanisms for slow assimilation. In spite of reprocessing mechanisms, such material can accumulate without being metabolized. If the organism is engineered appropriately, the assimilation mechanism can be inactivated, which enables high yields of sugars to be produced.

Provided herein is a method for producing fermentable sugars, especially disaccharide sugars, by photosynthetic microorganisms. Examples of fermentable sugars include, but are not limited to, sucrose, trehalose, glucosylgycerol, and mannosylfructose. Preferably, the fermentable sugar is sucrose or trehalose. The method can be adapted to occur in a continuous manner to improve the cost effectiveness of production.

Various embodiments of this method can be practiced using a photosynthetic microorganism capable of synthesizing fermentable sugars. Some embodiments harness and control the natural phenomena of osmo- and matric water protection for the generation of fermentation feedstocks. In one embodiment, synthesis of fermentable sugars is inducible. In another embodiment, synthesis of fermentable sugars can be modified by genetic manipulation to be produced constitutively.

Fermentable sugar-producing photosynthetic microorganisms are preferably cyanobacteria. In some embodiments, a cyanobacterium accumulates a disaccharide according to inducible endogenous pathways. In some embodiments, a transgenic cyanobacterium accumulates a disaccharide according to engineered exogenous pathways. Both endogenous and exogenous pathways are discussed in further detail above.

Preferably, the transgenic photosynthetic microorganisms are one or more of those discussed above.

Two non-limiting examples of strains of cyanobacteria capable of accumulating a disaccharide are *Synechococcus elongatus* PCC 7942 and *Synechocystis* sp. PCC 6803. Naturally occurring *Synechococcus elongatus* PCC 7942 synthesizes sucrose upon exposure to salt concentrations of up to about 700 mM, its tolerance limit. When glucosylglycerol biosynthesis is blocked by deletion of the agp gene, *Synechocystis* sp. PCC 6803 produces sucrose as its osmoprotectant upon exposure to salt concentrations up to its tolerance limit which may approach 900 mM. In some embodiments, salt induction can be accomplished by introducing aerosolized saline solution applied directly to the cultivation surface. One advantage of this process is application can be controllably introduced along the growing surface depending on growth time of the cultivar thereby balancing accumulation of biomass and production of a disaccharide such as sucrose.

For producing fermentable sugars, the photosynthetic microorganisms can be cultured and grown on a solid medium or in a liquid or gel medium. Culture and growth of photosynthetic microorganisms are well known in the art. Except as otherwise noted herein, therefore, culture and growth of photosynthetic microorganisms can be carried out in accordance with such known processes. For example, a transgenic cyanobacteria engineered to accumulate a disaccharide can be cultured and grown in a liquid medium. The accumulated sugar can be isolated from such liquid medium if excreted from the cell. The accumulated sugar can be isolated from photosynthetic microorganisms harvested from the liquid medium. In one embodiment, a transgenic cyanobacteria engineered to accumulate trehalose, as discussed above, is cultured and grown in a liquid medium. Trehalose secreted from the transgenic cyanobacteria can be isolated directly from the liquid medium. In one embodiment, a transgenic cyanobacteria engineered to accumulate sucrose, as discussed above, is cultured and grown in a liquid medium. Sucrose can be isolated directly from engineered cyanobactria harvested from the liquid medium. In one embodiment, a transgenic cyanobacteria engineered to accumulate and secrete sucrose, as discussed above, is cultured and grown in a liquid medium. Sucrose secreted from the transgenic cyanobacteria can be isolated directly from the liquid medium.

Preferably, photosynthetic microorganisms are cultivated to a relatively high cell density of at least about 50 grams of dry biomass per liter equivalent prior to induction. Such relatively high cell densities can be achieved using a solid phase photobioreactor, as described herein. Disaccharide (e.g., sucrose) production can then be initiated/induced by treating the accumulated biomass with defined concentrations of suitable salt compounds effective at altering the activity of water in the culture media as measured by solution conductivity. In a further preferred embodiment, sodium chloride is the salt used. Following an appropriate response time period (e.g., at least about 1 hour to no greater than about 48 hours), the sucrose laden cells can be harvested and processed to isolate and recover the sucrose produced. Typically, an appropriate response period is within the range of at least about 5 hours to no greater than about 24 hours. More typically, the appropriate response period is within the range of at least about 10 hours to no greater than about 20 hours.

In one embodiment, the majority of disaccharide (e.g., sucrose, trehalose, glucosylglycerol, mannosylfructose) synthesized accumulates within the cells. In another embodiment, the disaccharide is secreted by the cells which can then be recovered from the photobioreactor. Regardless of whether the disaccharide is within the cells or secreted, the disaccharide can be obtained using any appropriate harvesting process including, but not limited to, an aqueous spray wash applied to the cultivation surface. The wash comprising cells and/or disaccharide can be collected and processed to isolate and recover the disaccharide.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Solid Phase Photobioreactor

A static prototype device was constructed composed of a 2 mil polyethylene barrier layer with a Ziploc® resealable closure. A 60 sq. cm breathable panel was incorporated into one surface, and a 225 sq. cm woven cotton fabric cultivation support surface was placed inside. The device was sterilized by treatment with 70% volume aqueous ethanol followed by drying of the device at 50° C. with a stream of sterile filtered air. 30 ml of sterile BG-11 culture media was absorbed onto the cultivation support followed by inoculation of the growing surface with a pre-culture of *Synechococcus* elongates PCC 7942. using an aerosol applicator. The preculture was grown in BG-11 media at 26° C. for 2 days prior to inoculation. The photobioreactor was placed in an incubation chamber maintained at 33° C. and illuminated at 300 microeinsteins with cool white fluorescent lamps. After 2 days, the reactor displayed active growth of organisms and was allowed to continue growth for an additional 2 days whereupon the reactor was removed from the incubator and the growth surface washed with deionized water. The water was removed by evaporation to afford 254 mg dry weight biomass.

Example 2

Production of Sucrose by Photosynthetic Microorganisms

The following is a prophetic example to illustrate a method for production of sucrose by photosynthetic microorganism in combination with a photobioreactor. At least one photobioreactor, for example a photobioreactor of the current invention such as described in Example 1 or Example 3, may be run for approximately 4-7 days with either *Synechocystis* sp. PCC6803. or engineered *Synechocystis* sp. at a temperature range of between about 15 and 40° C., under illumination of between about 60 and 300 microeinsteins, and carbon dioxide concentration of between about 0.2 and 15 volume %. Following the initial cultivation period the growth surface may be treated with an aqueous salt solution in the concentration range of between about 0.01 and 1.5 M, more preferably between about 0.2 and 0.9 M, using an aerosol spray. The cultivation may be allowed to continue for approximately an additional one to two days to allow sucrose production. The growth surface may then be harvested by washing the surface with deionized water. In a further embodiment the wash water is sterile fresh cultivation media and the washing stringency is such that between about 70 and 90% of the cell mass is collected. The biomass remaining on the cultivation support may then be allowed to continue growth as a subsequent cycle. It is anticipated that the yield for these cultivations should be between about 200 and 600 mg dry biomass depending on the growth surface material and organism employed.

Example 3

Solid Cultivation Support Coated with an Absorbent Polymer

The growth surface of a static photobioreactor of the type described in Example 1 was prepared by dip coating the sterile dry surface of the material with a heated solution of sterile 1.5 weight percent agar dispersed in BG-11 culture media. The coated growth surface was allowed to cool and harden upon which the surface was inserted into a sterilized protective barrier to form a photobioreactor device and inoculated with *Synechococcus* sp. grown in preculture as described in Example 1. Cultivation and harvesting were performed essentially as described in Example 1.

Example 4

ASF Gene Target

Biosynthesis of sucrose in cyanobacteria was explored through modulation of sucrose phosphate synthase (sps) and sucrose phosphate phosphatase (spp) activities. Such activities are already present in many cyanobacteria for acclimation to osmotic and matric water stress (see e.g., Lunn, J. E. 2002. Plant Physiol 128, 1490-1500).

Lunn, J. E. (2002. Plant Physiol 128, 1490-1500) analyzed the genomic organization of the sps and spp genes of several organisms, including *Synechocystis* spp. PCC 6803 and *Synechococcus elongatus* PCC 7942. Lunn proposed that the sucrose phosphate synthase (SPS) of *Synechocystis* spp. PCC 6803 (SEQ ID NO: 3) has an inactive sucrose phosphate phosphatase (SPP-like) domain and a distinct SPP activity. The SPP-like domain has a high level of identity with the spp, but is missing many of the conserved active site residues of the haloacid dehalogenase (HAD) superfamily. While no work has yet been done on *Synechococcus elongatus* PCC 7942, Lunn proposed that both activities are contained within a single enzyme. An alignment of these enzymes is shown in FIG. 5.

Searches of the *Synechococcus elongatus* PCC 7942 genome did not reveal a distinct sps gene elsewhere on the chromosome. The *Synechococcus elongatus* PCC 7942 enzyme (SEQ ID NO: 2) was utilized so as to avoid the necessity of multiple gene expression. While the gene from PCC 7942 has been termed sps, because it is a single enzyme fusion bearing both SPS and SPP activities, it was termed asf for active SPS/SPP fusion (SEQ ID NO: 1) (see below for further information on the possible expression of a distinct SPP enzyme.)

There are two approaches to expressing the *Synechococcus elongatus* PCC 7942 asf gene product (SEQ ID NO: 2).

The first approach is a plasmid-based expression system built upon the broad host range vector pMMB67EH (Furste, J. P., Pansegrau, W., Frank, R., Blocker, H., Scholz, P., Bagdasarian, M. and Lanka, E. 1986. Gene 48, 119-131). Plasmid pMMB67EH is a derivative of RSF1010, which replicates in most Gram-negative and even some Gram-positive organisms, thus allowing for plasmid-based analysis of sucrose production in *E. coli, Synechocystis* spp. PCC 6803*, Synechococcus elongatus* PCC 7942 and a variety of other cyanobacteria (Kreps, S., Ferino, F., Mosrin, C., Gerits, J., Mergeay, M. and Thuriaux, P. 1990. Mol Gen Genet 221, 129-133; Marraccini, P., Bulteau, S., Cassier-Chauvat, C., Mermet-Bouvier, P. and Chauvat, F. 1993. Plant Molecular Biology 23, 905-909; Gormley, E. P. and Davies, J. 1991. J Bacteriology 173, 6705-8).

The second approach is stable integration into the chromosome of *Synechocystis* spp. PCC 6803 and *Synechococcus elongatus* PCC 7942 at the upp (uracil phosphoribosyltransferase) locus. The upp locus was chosen for reasons described below.

Example 5

Plasmid-Based Expression

Figure 6:
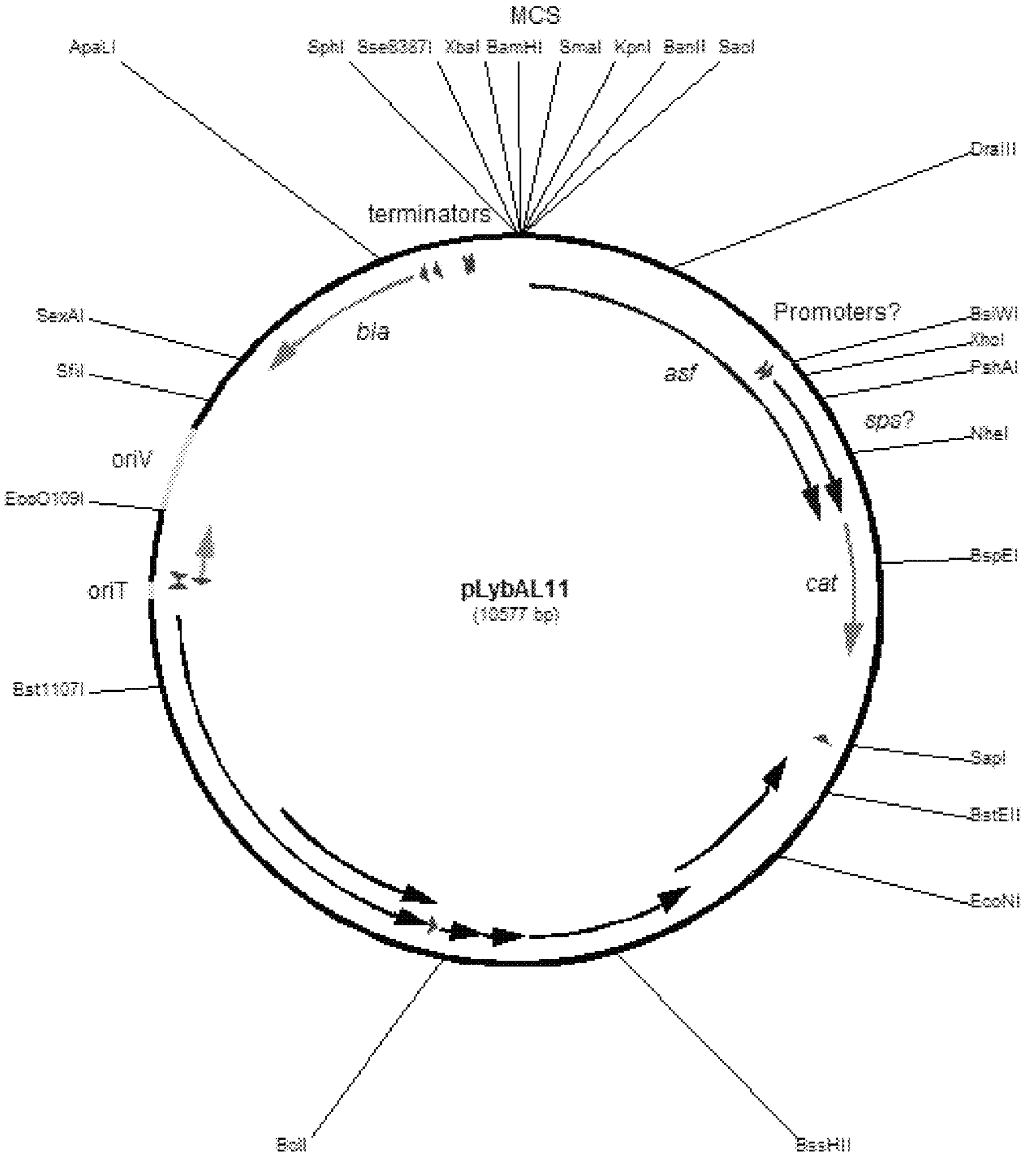
FIG. 6 is schematic depiction of pLybAL11. pLybAL11 allows construction of libraries of cyanobacterial DNA and selection for promoter sequences. The promoterless asf gene is behind bidirectional terminators, separated by a multiple cloning site (MCS). oriV allows for plasmid replication in most Gram-negative organisms. oriT allows for conjugal transfer of the plasmid from *E. coli* to a chosen cyanobacterium (or other organism) with the assistance of the pRK2013 helper plasmid. The β-lactamase gene (bla) is present for selection in *E. coli*. DNA libraries can be constructed in *E.*

Two plasmids were designed for plasmid-based expression of the asf gene product, pLybAL11 (see e.g., FIG. 6; SEQ ID NO: 19) and pLybAL12 (see e.g., FIG. 7; SEQ ID NO: 20). Plasmid pLybAL12 was constructed for expression from predetermined promoters and pLybAL11 was constructed for expression from promoters selected at random.

Both plasmids were constructed as follows. The asf gene from *Synechococcus elongatus* PCC 7942 was amplified by PCR with the oligonucleotides 5'-AGACTACAATTGGGGCGTTTTCTGTGAG-3' (the MfeI restriction endonuclease site is nucleotide positions 7-12) (SEQ ID NO: 7) and 5'-CTTACGTGCCGATCAACGTCTCATTCTGAAAAGGTTAAGCGATCGCCTC-3' (SEQ ID NO: 8) using whole cells as the template, yielding the product of SEQ ID NO: 1.

The gene encoding for chloramphenicol acetytransferase (cat), both with and without the upstream promoter, was amplified from pBeloBAC11 (GenBank Accession U51113).

The cat gene lacking the promoter was amplified from pBeloBAC11 by PCR with the oligonucleotides 5'-TTATCGCGATCGTCAGGAGCTAAGGAAGCTAAAATGGAG-3' (SEQ ID NO: 9) and 5'-CGACCAATTCACGTGTTTGACAGCTTATC-3' (SEQ ID NO: 10) (the PvuI and PmlI restriction endonuclease sites are at nucleotide positions 4-9 and 10-15, respectively) to yield the product of SEQ ID NO: 11.

The cat gene bearing the promoter was amplified from pBeloBAC11 by PCR with the oligonucleotides 5'-TTTTGGCGATCGTGAGACGTTGATCGGCACGTAAG-3' (SEQ ID NO: 12) and 5'-CGACCAATTCACGTGTTTGACAGCTTATC-3' (SEQ ID NO: 13) (the PvuI and PmlI restriction endonuclease sites are at nucleotide positions 7-12 and 10-15, respectively) to yield the product of SEQ ID NO: 14.

The PCR products bearing the cat gene were digested with PvuI and the ends blunted with T4 DNA polymerase. They were then individually ligated to the asf PCR product. The resultant products were purified by agarose gel electrophoresis, digested with MfeI and PmlI and then ligated with T4 DNA ligase to the 6.6 Kbp product of pMMB67EH digested with EcoRI and HpaI. The ligation products were transformed into chemically competent NEB5α (New England Biolabs; Ipswich, Mass.) and selected for at 37° C. on LB agar supplemented with 100 μg/ml ampicillin. Selected candidates were grown at 37° C. in LB supplemented with 100 n/ml ampicillin for miniprep, analyzed by restriction endonuclease digest and then verified by sequence analysis with the oligonucleotides 5'-GCTTCTGCGTTCTGATTTAATCTGTAT-CAG-3' (SEQ ID NO: 15), 5'-TATCACTTATTCAGGCG-TAGCAACCAG-3' (SEQ ID NO: 16), 5'-GTCGTTAGTGACATCGACAACACACTG-3' (SEQ ID NO: 17), and 5'-GATCGCGATACTGATCGAGATAGGTC-3' (SEQ ID NO: 18). Candidate number 5 of pLybAL11 (pLybAL11-5) (SEQ ID NO: 19) and Candidate number 1 of pLybAL12 (pLybAL12-1) (SEQ ID NO: 20) were chosen for further study.

Based upon plasmid yield during minipreps, it appears that the copy number of these plasmids is greatly reduced when propagated in the *E. coli* strain NEB Turbo (New England Biolabs; Ipswich, Mass.), suggesting the importance in choice of host strain for these plasmids.

Example 6

Promoter Insertion

Six promoters were chosen for insertion into pLybAL12-5. The presumed promoter for *Synechocystis* spp. PCC 6803 carB encoding carbamoyl phosphate synthase, which is likely to be immediately upstream of the gene pyrR where they would be co-transcribed as an operon, was chosen because it is likely to be strong due to its role in both pyrimidine and arginine biosynthesis. The nitrate reductase (nirA) promoters from both *Synechocystis* spp. PCC 6803 (Aichi, M., Takatani, N. and Omata, T. 2001. J Bacteriol. 183, 5840-5847) and *Synechococcus elongatus* PCC 7942 (Maeda, S-I. et al. 1998. J Bacteriol 180, 4080-4088) were chosen for their ability to be regulated by the source of nitrogen. The strong light-phase promoter for the photosystem II D1 protein (psbAII) from *Synechococcus elongatus* PCC 7942 (Golden, S. S., Brusslan, J. and Haselkorn, R. 1986. EMBO Journal 5, 2789-2798) and two dark-phase promoters from *Synechocystis* spp. PCC 6803 [dnaK (Aoki, S., Kondo, T. and Ishiura M. 1995. J Bacteriol 177, 5606-11) and kaiA (Kucho, K-I. et al. 2005. J Bacteriol 187, 2190-2199)] were also selected as regulated cyanobacterial derived promoters. Lastly, the $\lambda_{PR}$ temperature-regulated promoter, which has been shown to be active in cyanobacteria, was chosen (Ferino, F. and Chauvat, F. 1989. Gene 84, 257-66; Mermet-Bouvier, P. and Chauvat, F. 1994. Current Microbiology 28, 145-148).

The following oligonucleotides were used to amplify the promoters by PCR using whole cells as the template, yielding the products shown. The restriction endonuclease sites incorporated for cloning are provided in the sequence.

*Synechocystis* spp. PCC 6803 pyrR (SphI/KpnI) (SEQ ID NO: 23) was amplified from whole cells by PCR with the oligonucleotides 5'-CGGTGT GCATGCCGTTATTGATGGAATG-3' (SEQ ID NO: 21) and 5'-TCACTAGGTACCTAAATTACCTGGGAAGCCAG-3' (SEQ ID NO: 22), having restriction endonuclease sites at nucleotide positions 7-12 for both.

*Synechocystis* spp. PCC 6803 nirA (SphI/KpnI) (SEQ ID NO: 26) was amplified from whole cells by PCR with the oligonucleotides 5'-CCCAAGGCATGCAGGAAA ACAAGCTCAGAATGCTG-3' (SEQ ID NO: 24) and 5'-TT-TATTGGTACCAACGCTTCAAGCCAGATAACAGTAG AGATC-3' (SEQ ID NO: 25), having restriction endonuclease sites at nucleotide positions 7-12 for both.

*Synechococcus elongatus* PCC 7942 psbAII (SphI/KpnI) (SEQ ID NO: 29) was amplified from whole cells by PCR with the oligonucleotides 5'-ATCTTTGCGTTCCGTGACG-GCTACTG-3' (SEQ ID NO: 27) and 5'-GCAGAT GGTACCGGTCAGCAGAGTG-3' (having restriction endonuclease sites at nucleotide positions 7-12) (SEQ ID NO: 28).

*Synechococcus elongatus* PCC 7942 nirA (SphI/KpnI) (SEQ ID NO: 32) was amplified from whole cells by PCR with the oligonucleotides 5'-CAGCCA GCATGCATAAATTTCTGTTTTGACCAAACCATCC-3' (SEQ ID NO: 30) and 5'-GTGGCT GGTACCATGGATTCATCTGCCTACAAAG-3' (SEQ ID NO: 31), having restriction endonuclease sites at nucleotide positions 7-12 for both.

$\lambda_{PR}$ (XbaI/KpnI) (SEQ ID NO: 35) was amplified from whole cells by PCR with the oligonucleotides 5'-GTGCAT TCTAGATGGCTACGAGGGCAGACAGTAAG-3' (SEQ ID NO: 33) and 5'-TTCTGTGGTACCATATGGATCCTC-CTTCTTAAGATGCAACCATTATCACC-3' (SEQ ID NO: 34), having restriction endonuclease sites at nucleotide positions 7-12 for both.

*Synechocystis* spp. PCC 6803 dnaK (SphI/KpnI) (SEQ ID NO: 38) was amplified from whole cells by PCR with the oligonucleotides 5'-GCCCCA GCATGCACCAGTAAACATAAATCTC-3' (SEQ ID NO: 36) and 5'-ATTGGT GGTACCGAGGTCAATCCCAACAAC-3' (SEQ ID NO: 37), having restriction endonuclease sites at nucleotide positions 7-12 for both.

*Synechocystis* spp. PCC 6803 kiaA (SphI/KpnI) (SEQ ID NO: 41) was amplified from whole cells by PCR with the oligonucleotides 5'-GCCAGA GCATGCAAAGCTCACTAACTGG-3' (SEQ ID NO: 39) and 5'-GGAAAA GGTACCTGAGTCTATGGGCAACGTG-3' (SEQ ID NO: 40), having restriction endonuclease sites at nucleotide positions 7-12 for both.

After amplification, the PCR products were digested with the restriction endonucleases shown above, gel purified, and ligated into similarly digested pLybAL12-1 to yield plasmids pLybAL15 (SEQ ID NO: 44), pLybAL16 (SEQ ID NO: 45), pLybAL17 (SEQ ID NO: 46), pLybAL18 (SEQ ID NO: 47), pLybAL19 (SEQ ID NO: 48), pLybAL21 (SEQ ID NO: 49), and pLybAL21 (SEQ ID NO: 50), respectively. The ligation products were transformed into electrocompetent NEB5α (New England Biolabs; Ipswich, Mass.) and selected for at 30° C. on LB agar supplemented with 100 μg/ml ampicillin, 34 μg/ml chloramphenicol, and 5% sucrose. Selected candidates were grown at 30° C. in LB supplemented with 100 μg/ml ampicillin, 34 μg/ml chloramphenicol and 5% sucrose for miniprep, analyzed by restriction endonuclease digest, and then verified by sequence analysis with the oligonucleotides 5'-GCTTCTGCGTTCTGATTTAATCTGTATCAG-3' (SEQ ID NO: 42) and 5'-ATGGGTCTGAATGTGCAGAAT-GTAGAG-3' (SEQ ID NO: 43). Candidates 6 and 7 (pLybAL15-6 and pLybAL15-7), 2 (pLybAL16-2), 4 and 5 (pLybAL17-4 and pLybAL17-5), 1 and 2 (pLybAL18-1 and pLybAL18-2), 1 and 2 (pLybAL19-1 and pLybAL19-2), 3 and 5 (pLybAL21-3 and pLybAL21-5) and 4 and 8 (pLybAL22-4 and pLybAL22-8) were chosen for plasmids pLybAL15 (SEQ ID NO: 44), pLybAL16 (SEQ ID NO: 45), pLybAL17 (SEQ ID NO: 46), pLybAL18 (SEQ ID NO: 47), pLybAL19 (SEQ ID NO: 48), pLybAL21 (SEQ ID NO: 49), and pLybAL21 (SEQ ID NO: 50), respectively.

Selection and growth of these plasmids on LB supplemented with sucrose and both antibiotics was essential to obtaining clones. Selection was originally conducted on LB supplemented with ampicillin alone, but plasmids containing a promoter could not be isolated. Isolates were either religation of the vector alone or of varying size and lacking the ability to be propagated in the presence chloramphenicol. It is thought that internal sucrose was being produced, creating an osmotic shock for the cells that leads to deletions preventing sucrose production. Subsequent experiments indicated that, once isolated, the plasmids may be stable in the absence of sucrose, possibly through the eventual induction of osmotic stress machinery and/or sucrose consumption enzymes.

Example 7

Transformation of *Synechocystis* and *Synechococcus*

The promoter-containing plasmids, pLybAL15 (SEQ ID NO: 44), pLybAL16 (SEQ ID NO: 45), pLybAL17 (SEQ ID NO: 46), pLybAL18 (SEQ ID NO: 47), pLybAL19 (SEQ ID NO: 48), pLybAL21 (SEQ ID NO: 49), and pLybAL21 (SEQ ID NO: 50), as well as the promoterless pLybAL12-1 vector (SEQ ID NO: 20) (see Examples 5-6), were placed into both *Synechocystis* spp. PCC 6803 and *Synechococcus elongatus* PCC 7942 by triparental conjugation, performed consistent with Elhai, J. and Wolk, C. P. 1988. Methods in Enzymology 167, 747-754, unless indicated otherewise.

Overnight cultures of the cargo strains (NEB5α bearing the plasmids to be transferred), as well as an overnight culture of HB101 bearing the helper plasmid pRK2013 (ATCC 37159) grown at 30° C. were pelleted by centrifugation, washed twice with LB and then resuspended in LB in one-tenth the original volume. Each cyanobacterium was grown at 30° C. in BG11-A, which is the same as BG11 except the trace elements have been replaced with Nitsch's trace elements (Nitsch, J. P. and Nitsch, C. 1956. American Journal of Botany 43, 839-851) under constant illumination to an $OD_{730}$ of approximately 0.5. The cells were pelleted by centrifugation, washed twice with BG11-A, and resuspended in BG11-A with a 7.5-fold increase in concentration. A series of 10-fold dilutions of the cyanobacteria in BG11-A were prepared down to $10^{-5}$. At each dilution, 100 μl of the cyanobacterium was combined with 50 μl each of the cargo and helper strains of *E. coli*. 150 μl of each mixture was then plated onto BG11-A agar (1.5%) plates supplemented with 5% LB. The plates were incubated at 26-28° C. under constant illumination for 16 to 24 hours. The agar (app. 30 ml) on each plate was lifted and 300 μl of a 100× chloramphenicol solution was added. The final concentration of chloramphenicol was 25 μg/ml for *Synechocystis* spp. PCC 6803 and 7.5 μg/ml for *Synechococcus elongatus* PCC 7942. Incubation continued for 8-12 days. Individual colonies of transconjugants were purified away from contaminating *E. coli* by restreaking onto BG11-A supplemented with the appropriate amount of chloramphenicol to, again, obtain isolated colonies.

Example 8

Promoter Library in pLybAL11-5

The following example describes construction of a library of cyanobacterial DNA for promoter selection using pLybAL11-5 (SEQ ID NO: 19) (see Example 5). A modified, scaled up version of the chromosomal DNA isolation protocol of Wilson, K. (1997. Preparation of Genomic DNA from Bacteria. In Current Protocols in Molecular Biology. John Wiley and Sons Vol. 1, pp. 2.4.1-2.4.5) was employed, where the primary differences were much longer incubation times and the replacement of SDS with Sarkosyl. The DNA isolated was of sufficient quality for partial Sau3AI digest for insertion into the BamHI site of pLybAL11-5. As shown in FIG. 8, some of the fragments would have promoters and others would not.

During the process of library construction, a possible promoter within the asf gene was discovered. To function as a promoter cloning vector, plasmid pLybAL11-5 (SEQ ID NO: 19) is supposed to only be resistant to chloramphenicol when a promoter has been inserted in front of the asf gene, as the marker lacks its normal promoter and the promoter upstream of asf was not included. Once constructed, however, the chloramphenicol resistance conferred by this plasmid was examined in *E. coli*. When NEB5α bearing pLybAL11-5 was cultured on LB agar (1.5%) supplemented with 34 μg/ml chloramphenicol at 37° C., growth was observed. When cultured in liquid LB medium supplemented with 34 μg/ml chloramphenicol, however, little-to-no growth was observed. NEB5α bearing pLybAL12-1 (SEQ ID NO: 20) grows in the presence of chloramphenicol on both solid and in liquid LB medium.

To verify there was no missed promoter upstream of the asf gene but downstream of the transcription terminators, the insert placed into pMMB67EH to make pLybAL11 was cloned into Lucigen Corp.'s (Middleton, Wis.) pSMART-LCKan blunt-end cloning vector using Lucigen's CloneSmart kit with the Lucigen strain of *E. coli* (*E. cloni* 10G) competent cells (see e.g., FIG. 9). Because it was blunt-ended cloning, the inserts could ligate to the plasmid in either direction to create pLybAL13f (SEQ ID NO: 51) and pLyAL13r (SEQ ID NO: 52). This vector is specifically designed to eliminate transcription read through from the vector by surrounding the cloning site with terminators. As a control, the insert used to construct pLybAL12 was also placed into this vector, creating pLybAL14f (SEQ ID NO: 53) and pLybAL14r (SEQ ID NO: 54). The plasmids looked to be the appropriate size on an agarose gel but inserts were not verified by DNA sequencing to confirm the integrity of the clones. Similar results, however, were seen for *E. cloni* 10G bearing pLybAL13 and pLybAL14 (with the cloned DNA ligated in either direction f or r) as were seen for NEB5α bearing pLybAL11 (SEQ ID NO: 19) and pLybAL12 (SEQ ID NO: 20), respectively. This indicates that the activity of this promoter is weak in *E. coli*.

Many *E. coli* promoters do not function in cyanobacteria, and vice versa. It is possible that this promoter activity would not be observed in *Synechocystis* spp. PCC 6803 or *Synechococcus elongatus* PCC 7942. To check this, pLybAL11-5 (SEQ ID NO: 19) was inserted into both organisms by conjugation, as described above. On BG11-A agar (1.5%) supplemented with chloramphenicol (25 μg/ml and 7.5 μg/ml for *Synechocystis* spp. PCC 6803 and *Synechococcus elongatus* PCC 7942, respectively), growth was observed.

Growth of these organisms bearing pLybAL11-5 (SEQ ID NO: 19) on liquid BG11-A supplemented with chloramphenicol was examined. It is possible that this activity is very weak and is only observable when present on a multiple-copy plasmid. This may be the case with *E. coli*, but is not likely with the cyanobacteria. RSF1010 is a relatively low-copy plasmid, having only 12 copies in *E. coli* (Frey, J., Bagdasarian, M. M. and Bagdasarian, M. 1992). *Gene* 113, 101-106). *E. coli* undergoing rapid division has at most 2 copies of its chromosome, thus at least a 6-fold increase in copy number.

A comparable copy number in cyanobacteria for this plasmid is likely. The chromosomal copy numbers of *Synechocystis* spp. PCC 6803 and *Synechococcus elongatus* PCC 7942 of 10-12 and 16, respectively, are similar (Labarre, J., Chauvat, F. and Thuriaux, P. 1989. J Bacteriol 171, 3449-57). The results above suggest the presence of a promoter within the asf gene of cyanobacteria.

FIG. 10 shows a possible location of a promoter (or promoters) within the asf gene. Transcription initiation elements have been described by Curtis, S. E. [1994. The transcription apparatus and the regulation of transcription initiation. In The Molecular Biology of Cyanobacteria. Bryant, D. A. (ed). Kluwer Academic Publishers pp. 613-699]. Translation initiation elements have been defined by Sazuka, T. and Ohara, O. (1996. DNA Research 3, 225-232).

Based upon alignment to known SPS enzymes and the presence of a stop codon only two codons upstream, the translation initiation of the asf gene is predicted to start at a GTG start codon. While ATG start codons are the most common, GTG and TTG are less common, but not rare. A typical *E. coli*-like Shine-Delgarno sequence (GGAG or GAGG) complementary the 3'-end of the 16S rRNA for which the adenine nucleotide is optimally 9-12 bp away from the first nucleotide of the start codon is also present, except with somewhat longer spacing. This sequence is found in about half the genes studied by Sazuka and Ohara. Less optimal spacing is not uncommon, but often leads to reduced levels of expression. There is too little sequence upstream of the Shine-Delgarno sequence but downstream of the MfeI site to incorporate a promoter. It is possible that a partial promoter may be incorporated, but the rest of the promoter would have to produced by the vector sequence of all three plasmids (pLybAL11-5 (SEQ ID NO: 19); pLybAL13f (SEQ ID NO: 51); and pLybAL13r (SEQ ID NO: 52)), which is improbable.

Thus it likely that the promoter activity is located within the asf gene. If the promoter is within the asf gene, one potential position is in front of the SPP domain of asf. This would give the sucrose biosynthetic enzymes of *Synechococcus elongatus* PCC 7942 a similar quaternary structure to those from *Synechocystis* spp. PCC 6803. Each organism would have two proteins, an SPS domain with a translationally fused SPP or SPP-like domain and a distinct SPP that may (or may not) interact with each other.

First, it was determined whether the SPP domain of asf could even be translated separately. As can be seen in FIG. 10 and Table 1, there is a TTG start codon immediately upstream of the SPP domain that is preceded by a Shine-Delgarno sequence.

The region surrounding the start codon matches the consensus determined by Sazuka and Ohara for 72 cyanobacterial genes almost as well as the native start codon. While determining cyanobacterial promoters based upon rules established for *E. coli* promoters, the typical −35 and −10 elements were searched for since the promoter does appear to be active in *E. coli*. Two possible promoters were identified, as seen in FIG. 10. There remains the possibility of an additional promoter(s) elsewhere in asf.

Example 9

Transfer of Plasmids from *E. coli* to Cyanobacteria

Conjugation was used for transfer of the pMMB67EH-based plasmids into cyanobacteria. Protocols exist for the transformation of these organisms (Zang, X., Liu, B., Liu, S., Arunakumara, K. K. I. U. and Zhang, X. 2007. Journal of Microbiology 45, 241-245; Golden, S. S. and Sherman, L. A. 1984. Journal of Bacteriology 158, 36-42), but such approaches were unsuccessful for placing these plasmids into *Synechocystis* spp. PCC 6803 and *Synechococcus elongatus* PCC 7942 using natural transformation.

The presence of the plasmids in the cyanobacteria was verified. Transconjugants were analyzed for the presence of plasmid by PCR of the asf/cat gene combination with the oligonucleotides 5'-AGACTACAATTGGGGCGTTTTCTGTGAG-3' (SEQ ID NO: 7) and 5'-GGTGGTTGTGTTTGACAGCTTATC-3' (SEQ ID NO: 55), yielding a 3.1 kb product. In addition, plasmids were isolated and analyzed. Cultures of cells grown in BG11-A supplemented with chloramphenicol (at the concentrations described above) are pelleted by centrifugation, resuspended in TE, heat-treated and miniprepped by the Promega Wizard SV Plus miniprep kit. But with poor yield, direct plasmid analysis is difficult. As such, the isolated DNA is transformed into *E. coli* NEB5α, re-isolated using the Promega Wizard SV Plus miniprep kit, and then subjected to restriction endonuclease analysis.

Example 10

Sucrose Production Assay and Analysis

*Synechococcus* transformed with pLybAL19 or pLybAL17 (see Example 7) was assayed for sucrose accumulation. Sucrose is measured with BioVision, Inc.'s (Mountain View, Calif.) sucrose assay kit. Assays were run following a 4 hour induction period (increased light to 180 microeinsteins from 50 microeinsteins for pLybAL17 (SEQ ID NO: 46) and increased temperature from 26 to 39° C. for pLybAL19 (SEQ ID NO: 48)). Data was corrected for background glucose present in the cells.

TABLE 1

Nucleotides immediately surrounding the proposed spp start codon. The nucleotides immediately surrounding the proposed spp start codon are compared to the consensus of 72 cyanobacterial genes.

| NT# | −10 | −9 | −8 | −7 | −6 | −5 | −4 | −3 | −2 | −1 | 123 | 4 | 5 6 |
|---|---|---|---|---|---|---|---|---|---|---|---|---|---|
| Consensus | A/G | A/G | A/T | A/T | A/T | A/T | A/T | A/T | C/T | T/C | ATG | A/G | C C/T |
| Selo7942 asf | T | *G* | *A* | C | *T* | *A* | G | C | G | *C* | GTG | G | C A |
| Selo7942 spp | T | C | G | C | *A* | *A* | *A* | C | G | *C* | TTG | A | T *T* |

Nucleotides matching the consensus are italicized, whereas nucleotides that do not match the consensus are underlined. Nucleotide numbers are relative to the first nucleotide of the start codon.

Results showed *Synechococcus* transformed with pLybAL19 (SEQ ID NO: 48) accumulated 0.78 nanomoles of sucrose per mg of dry biomass. Results also showed that *Synechococcus* transformed with pLybAL17 (SEQ ID NO: 46) accumulated 0.95 nanomoles of sucrose per mg of dry biomass.

Further analysis for plasmid-based sucrose production in *E. coli, Synechocystis* spp. PCC 6803, and *Synechococcus elongatus* PCC 7942 was performed. Because bacteria can consume sucrose, detection may be difficult. As such, cells are grown under suppressing conditions and then assayed shortly after induction. The pyrR promoter may be suppressed by growth with uracil and induced by transfer medium lacking uracil. The nirA promoters can be suppressed by growth with ammonium ions as the nitrogen source and induced by transfer to medium with nitrate as the nitrogen source. The psbAII promoter can be shifted from low light to high light. The dark phase promoters can be shifted from light to dark. And, the $\lambda_{PR}$ promoter can be shifted from low (25° C.) to high (39° C.) temperature.

Example 11

Expression Through Stable Chromosomal Integration

Insertion of sucrose biosynthetic genes can cause a negative impact on cell growth, leading to difficulties in obtaining complete segregation of the 10-16 chromosomes. With normal selection for an antibiotic resistance marker, having additional copies of the marker does not dramatically impact the cells ability to survive in the presence of antibiotic. Therefore, complete chromosomal segregation can be difficult to achieve using antibiotic selection when faced with a negative phenotype.

Deletion of the upp gene (encoding for uracil phosphoribosyltransferase) in most organisms leads to resistance to the otherwise toxic 5-fluorouracil. To obtain complete resistance, all copies of the upp gene must be deleted. Thus integrating into the upp locus of *Synechocystis* spp. PCC 6803 (SEQ ID NO: 56) and *Synechococcus elongatus* PCC 7942 (SEQ ID NO: 58) will lead to 5-fluorouracil resistance and allow for positive selection of complete segregation, even in the presence of a negative phenotype.

Example 12

The Upp/Kanamycin Resistance Cassette

A general strategy for genomic manipulation using a upp/kanamycin resistance cassette is outlined in FIG. 11. Deletion of a gene is depicted, but the strategy can easily be modified at the "replacement" step for insertions and mutations.

An upp/kanamycin resistance cassette was constructed. The cassette was constructed in Epicentre Biotechnologies CopyControl cloning kit with blunt-end cloning vector pCC1 and *E. coli* strain EPI300 according to manufacturer protocols. The upp gene from *Bacillus subtilis* 168 was amplified from whole cells using the oligonucleotides 5"-AAGAAGCAAGACAGCGTGTAGCTGCTCTGACTG-3" (SEQ ID NO: 60) and 5"-TCCCGGGATTTGGTACCTTATTTTGTTCCAAACATGCGGTCACCCGCATC-3" (having restriction endonuclease sites at nucleotide positions 2-7 and 12-17) (SEQ ID NO: 61), yielding the product of SEQ ID NO: 62.

The PCR product was cloned into pCC1 and those bearing the insert were selected for on LB supplemented with chloramphenicol as described in Epicentre Biotechnologies' protocol. The forward orientation, relative to lacZ, was screened for by restriction endonuclease digest, yielding pLybAL7f (SEQ ID NO: 65). The exact sequence of the insert was verified by DNA sequencing with the oligonucleotides 5 GTAATACGACTCACTATAGGGC-3 (SEQ ID NO: 63) and 5'-CACACAGGAAACAGCTATGACCAT-3'(SEQ ID NO: 64) for candidates 3 and 8 (pLybAL7-3 and pLybAL7-8).

The kanamycin resistance marker from the Lybradyn vector pLybAA1 [originally derived from pACYC177 (Rose, R. E. 1988. Nucleic Acids Res. 16, 356] was amplified with the oligonucleotides 5'-GTCAGTGCACTGCTCTGCCAGTGTTACAACC-3' (having ApaLI restriction endonuclease sites at nucleotide positions 5-10) (SEQ ID NO: 66) and 5'-CTCAGTGGCGCCAAAACTCACGTTAAGGGATTTTGGTC-3' (SEQ ID NO: 67) (having NarI restriction endonuclease sites at nucleotide positions 7-12), yielding the product of SEQ ID NO: 68.

The PCR product was digested with ApaLI and NarI and ligated into similarly digested pLybAL7f, creating pLybAL8f (SEQ ID NO: 69). The proper plasmid was selected for on LB supplemented with 50 μg/ml neomycin and examined by restriction endonuclease digestion.

Example 13

UPP Deletion

One strategy to force segregation of chromosomal inserts for the expression of sugars, including sucrose, trehalose, glucosylglycerol, and mannosylfructose, utilizes deletion of upp from the chromosome leading to resistance to 5-fluorouracil. While this has been established in many organisms (such as *E. coli* and *B. subtilis*), it has not previously been established for cyanobacteria, such as *Synechocystis* spp. PCC 6803 and *Synechococcus elongatus* PCC 7942.

Testing showed that growth of each of these organisms was completely inhibited by 1 μg/ml, 5-fluorouracil. Growth of *Synechocystis* spp. PCC 6803 is completely inhibited by 0.5 μg/ml, 5-fluorouracil and is sensitive to as little as little as 0.1 μg/ml, 5-fluorouracil.

The upp gene and surrounding sequences of both *Synechocystis* spp. PCC 6803 was amplified with the oligonucleotides Sspupp-F (SEQ ID NO: 96) and Sspupp-R (SEQ ID NO: 97). The upp gene and surrounding sequences of *Synechococcus elongatus* PCC 7942 was amplified with the oligonucleotides Seloupp-F (SEQ ID NO: 98) and Seloupp-R (SEQ ID NO: 99). The PCR products (upp of *Synechocystis* spp. PCC 6803, SEQ ID NO: 100; upp of *Synechococcus elongatus* PCC 7942, SEQ ID NO: 101) were then cloned into the Epicentre Biotechnologies' (Madison, Wis.) blunt cloning vector pCC1, as per the manufacturer's instructions.

While the PCR product (SEQ ID NO: 100 or SEQ ID NO: 101) can ligate into pCC1 in either direction, the forward orientation relative to the lac promoter was chosen, generating pLybAL3f (SEQ ID NO: 102) (containing upp of *Synechocystis* spp. PCC 6803) and pLybAL5f (SEQ ID NO: 103) (containing upp of *Synechococcus elongatus* PCC 7942), respectively. The inserts were sequenced using oligonucleotides T7long (SEQ ID NO: 104) and M13rev (SEQ ID NO: 105). The nucleotide sequence of upp of *Synechocystis* spp. PCC 6803 is represented by SEQ ID NO: 111 and the polypeptide sequence by SEQ ID NO: 112. The nucleotide sequence of upp of *Synechococcus elongatus* PCC 7942 is represented by SEQ ID NO: 113 and the polypeptide sequence by SEQ ID NO: 114.

Plasmid pLybAL4f (SEQ ID NO: 106) was created from pLybAL3f (SEQ ID NO: 102) by removal of the BlpI and ApaLI fragment, blunt ending with T4 DNA polymerase and then recircularizing with T4 DNA ligase. Part of the *Synechocystis* spp. PCC 6803 upp gene was then deleted by digesting pLybAL4f with AvrII and SgfI, blunt ending with T4 DNA polymerase and then recircularizing with T4 DNA ligase, creating pLybAL9f (SEQ ID NO: 107). The SacI/SphI fragment (SEQ ID NO: 108) bearing the cyanobacterial DNA was excised from pLybAL9f (SEQ ID NO: 107) and ligated into similarly digested pARO180 (sequence not completely known; Parke, D. 1990. Construction of mobilizable vectors derived from plasmids RP4, pUC18 and pUC19. Gene 93:135-137; ATCC 77123), creating pLybAL25. Plasmid pLybAL6fb (SEQ ID NO: 109) was created from pLybAL5f by removal of the SapI and ApaLI fragment, blunt ending with T4 DNA polymerase and then recircularizing with T4 DNA ligase. Part of the *Synechococcus elongatus* PCC 7942 upp gene was then deleted by digesting pLybAL6fb with BssHII and BsaI, blunt ending with T4 DNA polymerase and then recircularizing with T4 DNA ligase, creating pLybAL10fb (SEQ ID NO: 110). The SacI/SphI fragment (SEQ ID NO: 138) bearing the cyanobacterial DNA was excised from pLybAL10fb and ligated into similarly digested pARO180, creating pLybAL26.

Plasmids pLybAL25 and pLybAL26 were placed in *E. coli* 517-1 (ATCC 47055). Plasmids pLybAL25 and pLybAL26 are to be transferred to *Synechocystis* spp. PCC 6803 and *Synechococcus elongatus* PCC 7942 by biparental conjugation. Since these plasmids do not replicate in cyanobacteria, they should function as suicide vectors and cross over into the chromosome, deleting upp on one of the copies of the chromosome. An optimized protocol will enable speeding of segregation without killing the cells by premature exposure to too much 5-fluorouracil.

Example 14

Modification of Sucrose Degradation Enzymes

Cyanobacteria transformed with asf are further engineered to improve sucrose production by modulation of sucrose degradation activity.

The inventors have identified genes encoding invertase homologues in both *Synechocystis* spp. PCC 6803 (nucleotide sequence SEQ ID NO: 70; polypeptide sequence SEQ ID NO: 71) and *Synechococcus elongatus* PCC 7942 (nucleotide sequence SEQ ID NO: 72; polypeptide sequence SEQ ID NO: 73). *Synechocystis* spp. PCC 6803 also encodes a sucraseferredoxin-like protein (nucleotide sequence SEQ ID NO: 74; polypeptide sequence SEQ ID NO: 75) (Machray G. C. et al. 1994. FEBS Lett 354, 123-127).

These genes are deleted using the markerless deletion protocol described in FIG. 11.

Example 15

Modification of Sucrose Degradation Enzymes

Cyanobacteria transformed with asf are further engineered to promote sucrose secretion from the cells.

When in a low osmotic environment, the sucrose may be automatically expunged from the cells, as done with osomoprotectants by some organisms when transitioning from high to low salt environments (Schleyer, M., Schmidt, R. and Bakker, E. P. 1993. Arch Microbiol 160, 424-43; Koo, S. P., Higgins, C. F. and Booth, I. R. 1991. J Gen Microbiol 137, 2617-2625; Lamark, T., Styrvold, O. B. and Strgim, A. R. 1992. FEMS Microbiol. Lett 96, 149-154). Engineering of cyanobacteria can promote such a process.

Cyanobacteria transformed with asf are further engineered to express sucrose permease, such as those used by *E. coli* and *Salmonella* or in the transport of sucrose to nitrogen-fixing cysts of certain cyanobacteria (Jahreis K. et al. 2002. J Bacteriol 184, 5307-5316; Cumino, A. C. 2007. Plant Physiol 143, 1385-97). These genes are cloned and transformed into cyanobacteria according to techniques described above.

Example 16

Sucrose Secretion by Cyanobacteria Transformed with Porin

Sucrose secretion from *Synechocystis* spp. PCC 6803 and *Synechococcus elongatus* PCC 7942 can be facilitated by transformation with sucrose porin.

The gene encoding sucrose porin (scrY) from *Enterobacter sakazakii* ATCC BAA-894 was cloned for expression in *Synechocystis* spp. PCC 6803 and *Synechococcus elongatus* PCC 7942. The function of this gene has been inferred from its sequence and those of its neighbors. *Enterobacter sakazakii* scrY was amplified from chromosomal DNA by PCR with the oligonucleotides EsscrYBamHI-F (SEQ ID NO: 88) and EsscrYSacI-R (SEQ ID NO: 89). The PCR product (SEQ ID NO: 90) was digested with BamHI and SacI and ligated into similarly digested pLybAL19 and cloned into NEB5$\alpha$, creating pLybAL32 (SEQ ID NO: 91). The scrY gene (nucleic acid SEQ ID NO: 94; polypeptide sequence, SEQ ID NO: 95) was then sequenced with the oligonucleotides EsscrYmidseq-F (SEQ ID NO: 92) and EsscrYmidseq-R (SEQ ID NO: 93). When introduced into the host, this construct allows for the co-expression of the genes scrY and asf under the control of the temperature-inducible promoter. This plasmid was transferred by tri-parental conjugation (as described above) into *Synechocystis* spp. PCC 6803. The transformed *Synechocystis* spp. PCC 6803 is tested for efficacy in the secretion of sucrose. Similar transformation and testing of *Synechococcus elongatus* PCC 7942 follows.

Example 17

Generation of Trehalose Accumulating Cyanobacteria

The trehalose biosynthetic genes encoding trehalose phosphate synthase and trehalose phosphate phosphatase (otsA and otsB, respectively) from *E. coli* are found in a two gene operon, otsBA (SEQ ID NO: 115). The operon was cloned by PCR amplification of *E. coli* K12 genomic DNA with the oligonucleotides EcotsBA-F (SEQ ID NO: 116) and EcotsBA-R (SEQ ID NO: 117). The PCR product was digested with AflII and NheI and was cloned into pLybAL19 (SEQ ID NO: 48), replacing most of the asf gene. The new plasmid, pLybAL23 (SEQ ID NO: 118), places the trehalose biosynthetic genes under the control of the temperature-inducible $\lambda_{PR}$ promoter. The genes were sequenced to verify their integrity with the oligonucleotides EcotsBAmidseq-F (SEQ ID NO: 119) and EcotsBAmidseq-R (SEQ ID NO: 120). Expression of the otsBA operon was then placed under control of the pyrR, psbAII, dnaK and kiaA promoters (as described above) by ligating the AflII (blunt-ended with T4 DNA polymerase)/NheI fragment of pLybAL23 bearing the otsBA operon, into pLybAL15, pLybAL17, pLybAL21 and pLybAL22 digested with SacI (blunt-ended with T4 DNA polymerase) and NheI, creating pLybAL28 (SEQ ID NO: 121), pLybAL29 (SEQ ID NO: 122), pLybAL30 (SEQ ID NO: 123), and pLybAL31 (SEQ ID NO: 124), respectively.

Each of plasmids pLybAL28 (SEQ ID NO: 121), pLybAL29 (SEQ ID NO: 122), pLybAL30 (SEQ ID NO: 123), and pLybAL31 (SEQ ID NO: 124) were moved into *Synechocystis* spp. PCC 6803 by tri-parental conjugation (as described above).

Expression of the otsBA operon from pLybAL23 was placed under the control of the *Synechocystis* spp. PCC 6803 and *Synechococcus elongatus* PCC 7942 nirA promoters (as described above) in pLybAL16 and pLybAL18 in the same way as just described for the other promoters, creating pLybAL36 (SEQ ID NO: 125) and pLybAL37 (SEQ ID NO: 126), respectively.

Example 18

Trehalose Assay

Biomass was separated from the culture broth as necessary by centrifugation and residual biomass was removed from the clarified culture broth by filtration through 0.2 micron filter. The culture broth was concentrated to a residue by evaporation under reduced pressure. The concentrated culture broth was dissolved in 1 ml of de-ionized water and then 10 microliters of solution was sampled in a trehalose assay. The biomass collected by centrifugation was transferred to a weigh dish and heated to 100° C. to remove residual moisture. The dry biomass was weighed and then a 100 mg sample was dissolved in 1 ml of de-ionized water. The mixture was then ground and the solids were removed by centrifugation. A 10 microliter sample of the clarified supernatant was diluted 100 fold with de-ionized water and 10 microliters of the diluted sample were tested for trehalose.

The assay for trehalose used a modified procedure of a commercially supplied sucrose assay kit available through Biovision, Inc. The modification to the standard protocol was the substitution of trehalase for the kit supplied invertase enzyme solution. The kit involves the hydrolysis of trehalose with trehalase to release glucose. The glucose is oxidized by glucose oxidase to produce hydrogen peroxide which is detected by the action of peroxidase in the presence of a colored indicator. The colored indicator is quantitatively measured by its characteristic absorbance at 570 nm to afford the concentration of glucose originally present in the sample.

Trehalase (treA nucleic acid SEQ ID NO: 134 encoding trehalase polypeptide SEQ ID NO: 135) was prepared from the recombinant *E. coli* treA gene which has been engineered into a plasmid and transformed into an *E. coli* host by a similar method as described by Gutierrez C, Ardourel M, Bremer E, Middendorf A, Boos W, Ehmann U. Mol Gen Genet. 1989 June; 217(2-3):347-54. Periplasmic trehalase was cloned from *E. coli* K12, encoded by treA. The treA PCR product (SEQ ID NO: 127) was digested with AflII/XbaI and then ligated into similarly digested pLybCB6, a proprietary plasmid with a constitutive version of the strong *E. coli* trp promoter, creating pLybAL24 (SEQ ID NO: 130). The integrity of the insert was analyzed by sequencing with the oligonucleotides EctreAmidseq-F and EctreAmidseq-R.

A C-terminal $His_6$-tagged version of the trehalase was constructed. The gene was amplified by PCR with the oligonucleotides EctreA-F2 (SEQ ID NO: 131) and EctreA-R2 (SEQ ID NO: 132). The PCR product (SEQ ID NO: 136) was then digested with AflII/XbaI and then ligated into similarly digested pLybAL24, creating pLybAL33 (SEQ ID NO: 133).

Strong constitutive expression of the periplasmic trehalase is detrimental to the cells, causing a strong growth defect at 37° C. This can be significantly alleviated by growing the cells at 30° C.

The protein was expressed in *E. coli* BW25113 on a plasmid pLYBAL24 (SEQ ID NO: 130) which was grown in 2×YT media containing kanamycin. The protein was produced constitutively using the Trp promoter and contains a signal peptide which allows the protein to be transported to the periplasm. Following fermentation and harvesting of the biomass, the enzyme was purified by selective periplasmic release by treatment of the washed and resuspended cell pellet with 2% v/v dichloromethane in 50 mM Tris buffer pH 8. The lysate was separated from cell debris by centrifugation and further processed by concentration using an Amicon ultrafilter fitted with a 10,000 Dalton membrane. The concentrated lysate may be used in assays directly or the enzyme can be further purified by metal ion affinity chromatography using the engineered 6× poly histidine tag on the C-terminus of the enzyme (SEQ ID NO: 137).

Example 19

Solid Phase Trehalose Production

A solid composite fabric covered hydrophilic foam composed of a substrate foam used as a media/moisture reservoir (Foamex Aquazone) was bound to a fabric layer (DuPont Sontara) used as a growth surface measuring 15 cm by 15 cm. The composite material was sterilized by soaking in 70% ethanol in water and then hung in a vertical bioreactor plumbed to deliver solutions to the top of the composite material. The solutions were allowed to percolate through the growing composite surface by gravity. Residual ethanol was removed from the sterilized growing surface by passage of 1 liter of sterile de-ionized water flowing at 0.2 ml/min. The growing surface was equilibrated with culture media by flowing 0.5 liters of BG11A growth medium containing 10 micrograms/ml chloramphenicol through the composite material at 0.2 ml/min.

The equilibrated, sterile growth surface was inoculated by flooding the surface with 10 ml of a 4 day pre-culture of *Synechocystis* spp. PCC 6803 transformed by plasmid pLYBAL23. Following 30 minute incubation the reactor was turned to a vertical position and the fermentation was begun. The reactor was illuminated with 80 microeisteins of light from a white LED array. Temperature was maintained at 28° C., by a resistive heating device attached to the bioreactor. The reactor was continuously purged with 0.2 micron filtered air at 0.2 L/min and fresh culture media was supplied by pump and gravity percolation through the foam layer of the growth composite at a rate of 0.2 ml/min for 30 minutes every 6 hours. The reactor was run continuously for 4-7 days during which the growth surface of the composite was overspread with a dense lawn of cyanobacteria. Following the initial cultivation period the temperature of the bioreactor was increased to 40° C. and maintained at this temperature for an additional 24 hours. During the elevated temperature period spent culture broth was collected and processed for trehalose determination. At the completion of the fermentation run the biomass was collected by rinsing the growth surface with de-ionized water which can be processed for trehalose assay.

The amount of trehalose produced and retained in the biomass grown on the solid surface was up to 2.5 wt % of the total dry weight biomass recovered from the bioreactor following temperature induction. 0.8 wt % of the dry biomass equivalent weight of trehalose was recovered from the culture medium following temperature induction.

Example 20

Trehalose Production Liquid Phase 1 liter of sterile BG11A media was prepared in a Bioflow reactor to which chloramphenicol was added to a concentration of 10 micrograms/ml. The reactor was then inoculated with a 5% by volume, 4 day pre-culture of *Synechocystis* spp. PCC 6803 transformed with plasmid pLYBAL23. The reactor was run at 28° C., 300 RPM, 0.2 L/min 0.2 micron filtered air purge and illuminated at 80 microeinsteins of light using a fluorescent bulb array. The cultivation was maintained for 4-7 days following which a 200 ml sample was removed for processing and trehalose assay. The temperature of the fermentation was then elevated to 40° C. for 24 hours. A 200 ml sample was then removed from the bioreactor for processing and trehalose assay.

Following temperature induction the dried biomass produced up to 3 wt % trehalose while the spent culture broth contained 0.3 wt % trehalose equivalent relative to biomass.

REFERENCES

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A photobioreactor comprising:

a solid cultivation support, wherein the solid cultivation support comprises a non-gelatinous, textured surface suitable for culturing photosynthetic microorganisms;

a physical barrier; and a volume of air;

wherein, the physical barrier is disposed over at least a portion of the solid cultivation support; and the volume of air is between the physical barrier and the solid cultivation support.

2. The photobioreactor of claim 1, wherein the photobioreactor comprises a plurality of cultivation supports.

3. The photobioreactor of claim 1, wherein the solid cultivation support is suitable for adherence of a photosynthetic microorganism.

4. The photobioreactor of claim 1, wherein the solid cultivation support is suitable for culturing photosynthetic microorganisms at a density of at least about 50 grams of dry biomass per liter equivalent.

5. The photobioreactor of claim 1, further comprising a spray device for distributing a liquid medium over the solid cultivation support.

6. The photobioreactor of claim 1, wherein the solid cultivation support has a sheet shape and depth of the solid cultivation support that is substantially less than length and width of the solid cultivation support.

7. The photobioreactor of claim 1, wherein the solid cultivation support comprises:

(i) a fabric comprising a natural, modified natural, or synthetic fiber, or a combination thereof;

(ii) a fabric comprising a woven fabric, a knitted fabric, a felt, a mesh of cross-linked fiber polymers, or a combination thereof;

(iii) a fabric comprising natural fibers selected from the group consisting of cotton, wool, hemp, tree fiber, other cellulosic fibers, and combinations thereof;

(iv) a fabric comprising modified natural fibers selected from the group consisting of nitrocellulose, cellulose acetate, cellulose sulfonate, crosslinked starches, and combinations thereof;

(v) a fabric comprising synthetic fibers selected from the group consisting of polyester, polyacrylate, polyamine, polyamide, polysulfone, and combinations thereof;

(vi) a material having loops;

(vii) a material having loops, the material being terry cloth; or (viii) a combination thereof.

8. The photobioreactor of claim 1, wherein the solid cultivation support further comprises a coating of a moisture absorbent polymer selected from the group consisting of agar, polyacrylate, polyamide, polyamine, polyethylene glycol, modified starches, and combinations thereof.

9. The photobioreactor of claim 1, further comprising water, nutrients, or a combination thereof on or within the solid cultivation support.

10. The photobioreactor of claim 1, wherein the solid cultivation support comprises: (i) a flexible material, (ii) a rigid material, or (iii) flexibly connected rigid portions, wherein the rigid portions are comprised of a rigid material.

11. The photobioreactor of claim 1, wherein the cultivation support comprises at least two layers, a first layer adjacent to a second layer, wherein material of the at least two layers is the same material or different materials; and optionally, the first layer comprises a high surface area growth material and the second layer comprises a fluid permeable type material.

12. The photobioreactor of claim 1, further comprising a suspension element, wherein the solid cultivation support is suspended from the suspension element.

13. The photobioreactor of claim 12, wherein the solid cultivation support is suspended non-horizontally from the suspension element.

14. The photobioreactor of claim 12, wherein the solid cultivation support is suspended substantially vertically from the suspension element.

15. The photobioreactor of claim 12, wherein the suspension element comprises one or more attachment points for attaching the photobioreactor to a structure.

16. The photobioreactor of claim 1, wherein the physical barrier is releasably sealed so as to enclose the solid cultivation support.

17. The photobioreactor of claim 1, wherein the physical barrier, or a portion thereof, is a flexible physical barrier.

18. The photobioreactor of claim 1, wherein the physical barrier, or a portion thereof, is (i) substantially impermeable to solid particulate or liquid and (ii) partially or substantially permeable to gas or vapor.

19. The photobioreactor of claim 1, wherein the physical barrier, or a portion thereof, is substantially transparent to actinic irradiation.

20. The photobioreactor of claim 1, wherein the physical barrier comprises a first barrier portion and a second barrier portion, wherein the first barrier portion and the second barrier portion are different with respect to one or more of liquid permeability, gas permeability, or transparency to actinic radiation.

21. The photobioreactor of claim 1, further comprising a source of actinic radiation that is (i) external to the physical barrier and the physical barrier is substantially transparent to actinic radiation or (ii) between the solid cultivation support and the physical barrier.

22. The photobioreactor of claim 1, further comprising at least one of a fluid supply system, nutrient supply system, gas supply system, or microorganism supply system.

23. The photobioreactor of claim 1, further comprising photosynthetic microorganisms in or on the solid cultivation support.

24. The photobioreactor of claim 23, wherein the photosynthetic microorganisms comprise a transgenic photosynthetic microorganism cell, the cell comprising an artificial DNA construct comprising, as operably associated components in the 5' to 3' direction of transcription, a promoter functional in the photosynthetic microorganism cell, a polynucleotide comprising a nucleotide sequence encoding a polypeptide having a disaccharide biosynthetic activity selected from the group consisting of a disaccharide phosphate synthase and a disaccharide phosphate phosphatase, and a transcriptional termination sequence;

wherein, the transgenic photosynthetic microorganism cell accumulates increased levels of the disaccharide compared to a photosynthetic microorganism cell not comprising the DNA construct, and the cell is adhered to said portion of the surface of the cultivation support.

25. A device for cultivating photosynthetic microorganisms, comprising:

the photobioreactor of claim 1; and a structure;

wherein the photobioreactor is attached to the structure; and the solid cultivation support is oriented non-horizontally.

26. The device of claim 1, further comprising:

at least one of a fluid supply system, nutrient supply system, gas supply system, or microorganism supply system;

wherein the fluid supply system, nutrient supply system, gas supply system, or microorganism supply system is operably connected to the photobioreactor.

27. The device of claim 1, wherein the photobioreactor is suspended from the structure and the structure is substantially covered by the physical barrier.

* * * * *

SEQUENCE LISTING

```
<160> NUMBER OF SEQ ID NOS: 138

<210> SEQ ID NO 1
<211> LENGTH: 2204
<212> TYPE: DNA
<213> ORGANISM: Synechococcus PCC7942

<400> SEQUENCE: 1

agactacaat tggggcgttt tctgtgaggc tgactagcgc gtggcagctc aaaatctcta     60

cattctgcac attcagaccc atggtctgct gcgagggcag aacttggaac tggggcgaga    120

tgccgacacc ggcgggcaga ccaagtacgt cttagaactg gctcaagccc aagctaaatc    180

cccacaagtc caacaagtcg acatcatcac ccgccaaatc accgaccccc gcgtcagtgt    240

tggttacagt caggcgatcg aaccctttgc gcccaaaggt cggattgtcc gtttgccttt    300

tggccccaaa cgctacctcc gtaaagagct gctttggccc catctctaca cctttgcgga    360

tgcaattctc caatatctgg ctcagcaaaa gcgcaccccg acttggattc aggcccacta    420

tgctgatgct ggccaagtgg gatcactgct gagtcgctgg ttgaatgtac cgctaatttt    480

cacagggcat tctctggggc ggatcaagct aaaaaagctg ttggagcaag actggccgct    540

tgaggaaatt gaagcgcaat tcaatattca acagcgaatt gatgcggagg agatgacgct    600

cactcatgct gactggattg tcgccagcac tcagcaggaa gtggaggagc aataccgcgt    660

ttacgatcgc tacaacccag agcgcaagct tgtcattcca ccgggtgtcg ataccgatcg    720

cttcaggttt cagcccttgg gcgatcgcgg tgttgttctc caacaggaac tgagccgctt    780

tctgcgcgac ccagaaaaac ctcaaattct ctgcctctgt cgccccgcac ctcgcaaaaa    840

tgtaccggcg ctggtgcgag cctttggcga acatccttgg ctgcgcaaaa aagccaacct    900

tgtcttagta ctgggcagcc gccaagacat caaccagatg gatcgcggca gtcggcaggt    960

gttccaagag attttccatc tggtcgatcg ctacgacctc tacggcagcg tcgcctatcc   1020

caaacagcat caggctgatg atgtgccgga gttctatcgc ctagcggctc attccggcgg   1080

ggtattcgtc aatccggcgc tgaccgaacc ttttggtttg acaattttgg aggcaggaag   1140

ctgcggcgtg ccggtggtgg caacccatga tggcggcccc caggaaattc tcaaacactg   1200

tgatttcggc actttagttg atgtcagccg acccgctaat atcgcgactg cactcgccac   1260

cctgctgagc gatcgcgatc tttggcagtg ctatcaccgc aatggcattg aaaaagttcc   1320

cgcccattac agctgggatc aacatgtcaa taccctgttt gagcgcatgg aaacggtggc   1380

tttgcctcgt cgtcgtgctg tcagtttcgt acggagtcgc aaacgcttga ttgatgccaa   1440
```

-continued

```
acgccttgtc gttagtgaca tcgacaacac actgttgggc gatcgtcaag gactcgagaa   1500

tttaatgacc tatctcgatc agtatcgcga tcattttgcc tttggaattg ccacggggcg   1560

tcgcctagac tctgcccaag aagtcttgaa agagtggggc gttccttcgc caaacttctg   1620

ggtgacttcc gtcggcagcg agattcacta tggcaccgat gctgaaccgg atatcagctg   1680

ggaaaagcat atcaatcgca actggaatcc tcagcgaatt cgggcagtaa tggcacaact   1740

accctttctt gaactgcagc cggaagagga tcaaacaccc ttcaaagtca gcttctttgt   1800

ccgcgatcgc cacgagactg tgctgcgaga agtacggcaa catcttcgcc gccatcgcct   1860

gcggctgaag tcaatctatt cccatcagga gtttcttgac attctgccgc tagctgcctc   1920

gaaaggggat gcgattcgcc acctctcact ccgctggcgg attcctcttg agaacatttt   1980

ggtggcaggc gattctggta acgatgagga aatgctcaag ggccataatc tcggcgttgt   2040

agttggcaat tactcaccgg aattggagcc actgcgcagc tacgagcgcg tctattttgc   2100

tgagggccac tatgctaatg gcattctgga agccttaaaa cactatcgct tttttgaggc   2160

gatcgcttaa cctttttcaga atgagacgtt gatcggcacg taag                   2204
```

<210> SEQ ID NO 2
<211> LENGTH: 709
<212> TYPE: PRT
<213> ORGANISM: Synechococcus PCC7942

<400> SEQUENCE: 2

```
Met Ala Ala Gln Asn Leu Tyr Ile Leu His Ile Gln Thr His Gly Leu
1               5                   10                  15

Leu Arg Gly Gln Asn Leu Glu Leu Gly Arg Asp Ala Asp Thr Gly Gly
            20                  25                  30

Gln Thr Lys Tyr Val Leu Glu Leu Ala Gln Ala Gln Ala Lys Ser Pro
        35                  40                  45

Gln Val Gln Gln Val Asp Ile Ile Thr Arg Gln Ile Thr Asp Pro Arg
    50                  55                  60

Val Ser Val Gly Tyr Ser Gln Ala Ile Glu Pro Phe Ala Pro Lys Gly
65                  70                  75                  80

Arg Ile Val Arg Leu Pro Phe Gly Pro Lys Arg Tyr Leu Arg Lys Glu
                85                  90                  95

Leu Leu Trp Pro His Leu Tyr Thr Phe Ala Asp Ala Ile Leu Gln Tyr
            100                 105                 110

Leu Ala Gln Gln Lys Arg Thr Pro Thr Trp Ile Gln Ala His Tyr Ala
        115                 120                 125

Asp Ala Gly Gln Val Gly Ser Leu Leu Ser Arg Trp Leu Asn Val Pro
    130                 135                 140

Leu Ile Phe Thr Gly His Ser Leu Gly Arg Ile Lys Leu Lys Lys Leu
145                 150                 155                 160

Leu Glu Gln Asp Trp Pro Leu Glu Glu Ile Glu Ala Gln Phe Asn Ile
                165                 170                 175

Gln Gln Arg Ile Asp Ala Glu Glu Met Thr Leu Thr His Ala Asp Trp
            180                 185                 190

Ile Val Ala Ser Thr Gln Gln Glu Val Glu Glu Gln Tyr Arg Val Tyr
        195                 200                 205

Asp Arg Tyr Asn Pro Glu Arg Lys Leu Val Ile Pro Pro Gly Val Asp
    210                 215                 220

Thr Asp Arg Phe Arg Phe Gln Pro Leu Gly Asp Arg Gly Val Val Leu
225                 230                 235                 240
```

-continued

```
Gln Gln Glu Leu Ser Arg Phe Leu Arg Asp Pro Glu Lys Pro Gln Ile
                245                 250                 255

Leu Cys Leu Cys Arg Pro Ala Pro Arg Lys Asn Val Pro Ala Leu Val
            260                 265                 270

Arg Ala Phe Gly Glu His Pro Trp Leu Arg Lys Lys Ala Asn Leu Val
        275                 280                 285

Leu Val Leu Gly Ser Arg Gln Asp Ile Asn Gln Met Asp Arg Gly Ser
    290                 295                 300

Arg Gln Val Phe Gln Glu Ile Phe His Leu Val Asp Arg Tyr Asp Leu
305                 310                 315                 320

Tyr Gly Ser Val Ala Tyr Pro Lys Gln His Gln Ala Asp Asp Val Pro
                325                 330                 335

Glu Phe Tyr Arg Leu Ala Ala His Ser Gly Gly Val Phe Val Asn Pro
            340                 345                 350

Ala Leu Thr Glu Pro Phe Gly Leu Thr Ile Leu Glu Ala Gly Ser Cys
        355                 360                 365

Gly Val Pro Val Val Ala Thr His Asp Gly Gly Pro Gln Glu Ile Leu
    370                 375                 380

Lys His Cys Asp Phe Gly Thr Leu Val Asp Val Ser Arg Pro Ala Asn
385                 390                 395                 400

Ile Ala Thr Ala Leu Ala Thr Leu Leu Ser Asp Arg Asp Leu Trp Gln
                405                 410                 415

Cys Tyr His Arg Asn Gly Ile Glu Lys Val Pro Ala His Tyr Ser Trp
            420                 425                 430

Asp Gln His Val Asn Thr Leu Phe Glu Arg Met Glu Thr Val Ala Leu
        435                 440                 445

Pro Arg Arg Arg Ala Val Ser Phe Val Arg Ser Arg Lys Arg Leu Ile
    450                 455                 460

Asp Ala Lys Arg Leu Val Val Ser Asp Ile Asp Asn Thr Leu Leu Gly
465                 470                 475                 480

Asp Arg Gln Gly Leu Glu Asn Leu Met Thr Tyr Leu Asp Gln Tyr Arg
                485                 490                 495

Asp His Phe Ala Phe Gly Ile Ala Thr Gly Arg Arg Leu Asp Ser Ala
            500                 505                 510

Gln Glu Val Leu Lys Glu Trp Gly Val Pro Ser Pro Asn Phe Trp Val
        515                 520                 525

Thr Ser Val Gly Ser Glu Ile His Tyr Gly Thr Asp Ala Glu Pro Asp
    530                 535                 540

Ile Ser Trp Glu Lys His Ile Asn Arg Asn Trp Asn Pro Gln Arg Ile
545                 550                 555                 560

Arg Ala Val Met Ala Gln Leu Pro Phe Leu Glu Leu Gln Pro Glu Glu
                565                 570                 575

Asp Gln Thr Pro Phe Lys Val Ser Phe Phe Val Arg Asp Arg His Glu
            580                 585                 590

Thr Val Leu Arg Glu Val Arg Gln His Leu Arg Arg His Arg Leu Arg
        595                 600                 605

Leu Lys Ser Ile Tyr Ser His Gln Glu Phe Leu Asp Ile Leu Pro Leu
    610                 615                 620

Ala Ala Ser Lys Gly Asp Ala Ile Arg His Leu Ser Leu Arg Trp Arg
625                 630                 635                 640

Ile Pro Leu Glu Asn Ile Leu Val Ala Gly Asp Ser Gly Asn Asp Glu
                645                 650                 655

Glu Met Leu Lys Gly His Asn Leu Gly Val Val Val Gly Asn Tyr Ser
```

-continued

```
            660                 665                 670

Pro Glu Leu Glu Pro Leu Arg Ser Tyr Glu Arg Val Tyr Phe Ala Glu
        675                 680                 685

Gly His Tyr Ala Asn Gly Ile Leu Glu Ala Leu Lys His Tyr Arg Phe
    690                 695                 700

Phe Glu Ala Ile Ala
705


<210> SEQ ID NO 3
<211> LENGTH: 2163
<212> TYPE: DNA
<213> ORGANISM: Synechocystis PCC6803

<400> SEQUENCE: 3

atgagctatt catcaaaata cattttacta attagtgtcc atggtttaat tcggggagaa     60

aaccttgagt tgggcagaga tgccgacacc ggcgggcaaa ccaaatatgt gctggaactg    120

gcccgggcct tggtaaaaaa tccccaggtg gccagggtgg atttgctgac ccgtttaatt    180

aaagatccca aagtagatgc agattatgcc cagcctagag aacttattgg cgatcgggcc    240

cagattgttc gcattgagtg cggcccggag gaatatattg ccaaggaaat gctctgggac    300

tatttggata attttgctga ccatgccctg gactatctca aagaacagcc cgaactgccc    360

gatgtcatcc atagccatta cgccgatgcg ggttacgtgg gcaccagact ttctcaccaa    420

ttgggtattc ctttggtgca caccggacat tccctgggtc gtagtaagcg cacccgtctc    480

ctgctcagtg ggattaaagc cgacgaaatt gaaagccgtt acaatatggc ccgccggatt    540

aacgcggagg aagaaaccct aggatcagcg gcgagggtga ttaccagtac ccatcaggaa    600

atcgcagaac agtacgccca atacgactat taccagccag accagatgtt ggttattccc    660

cccggcactg atttagaaaa gttttatccc cccaaaggga acgagtggga aacgcccatt    720

gttcaagagt tgcaacgatt tctacggcat ccccgtaagc ctattatcct cgctttgtcc    780

cgaccggatc cccgcaaaaa tatccataaa ttaattgcag cctatggcca gtccccgcag    840

ttacaggccc aggccaattt ggtcattgtg gcgggcaatc gggatgacat cacggatcta    900

gaccaggggc cgagggaagt actgacggat ttactgttga ccattgaccg ttacgatctc    960

tacggcaaag tggcttaccc caaacagaat caggcggagg atgtgtatgc tttgtttcgc   1020

ctcactgctt tatcccaggg agtatttatc aatccggctt tgacggaacc ctttggttta   1080

actttgattg aagcggcggc ctgtggtgtg cccattgtgg ccacggagga tgggggcccg   1140

gtggatatta tcaaaaattg tcagaatggc tatctaatta atcccctcga tgaagtggat   1200

attgcggata aattgctcaa agtactaaac gacaaacaac aatggcaatt cctttctgaa   1260

agtggtctag agggagttaa gcgccattat tcttggcctt cccacgttga aagttattta   1320

gaagccatca acgctctgac ccaacagact tcagtgctga aacgtagtga tttaaagcgg   1380

cggcggactt tgtactataa cggtgccctg gttactagtt tggaccaaaa tttactgggg   1440

gcattacagg ggggattacc gggcgatcgc cagacgttgg acgaattact ggaagtgctg   1500

tatcaacatc gaaaaaatgt cggcttttgc attgccactg ggagaagatt ggattcggtg   1560

ctgaaaattt tgcgggagta tcgcattccc caaccggata tgttgatcac cagcatgggc   1620

acggaaattt attcttcccc ggatttgatc cccgaccaga gttggcgcaa tcacattgat   1680

tatttgtgga accgtaacgc cattgtgcgt attttggggg aattacccgg tttagccctc   1740

caacccaagg aagaactgag cgcctataaa attagctatt tctacgatgc ggcgatcgcc   1800
```

-continued

```
cctaacctag aagaaattcg gcaactgttg cataaagggg aacaaaccgt aaataccatc   1860

atttcctttg gtcaattttt ggatattctg cccatccgag cttccaaagg ctatgctgtg   1920

cgttggttga gccaacagtg gaatattccc ctggagcacg ttttcaccgc cggaggatcg   1980

ggagccgacg aagatatgat gcggggtaac accctttccg tcgtcgtggc taaccgtcac   2040

catgaggaac tttctaatct aggggagatc gaaccgattt atttttccga aaaacgttac   2100

gccgccggta ttctggacgg tctggcccat taccgcttct ttgagttgtt agaccccgtt   2160

taa                                                                 2163
```

```
<210> SEQ ID NO 4
<211> LENGTH: 720
<212> TYPE: PRT
<213> ORGANISM: Synechocystis PCC6803

<400> SEQUENCE: 4

Met Ser Tyr Ser Ser Lys Tyr Ile Leu Leu Ile Ser Val His Gly Leu
1               5                   10                  15

Ile Arg Gly Glu Asn Leu Glu Leu Gly Arg Asp Ala Asp Thr Gly Gly
            20                  25                  30

Gln Thr Lys Tyr Val Leu Glu Leu Ala Arg Ala Leu Val Lys Asn Pro
        35                  40                  45

Gln Val Ala Arg Val Asp Leu Leu Thr Arg Leu Ile Lys Asp Pro Lys
    50                  55                  60

Val Asp Ala Asp Tyr Ala Gln Pro Arg Glu Leu Ile Gly Asp Arg Ala
65                  70                  75                  80

Gln Ile Val Arg Ile Glu Cys Gly Pro Glu Glu Tyr Ile Ala Lys Glu
                85                  90                  95

Met Leu Trp Asp Tyr Leu Asp Asn Phe Ala Asp His Ala Leu Asp Tyr
            100                 105                 110

Leu Lys Glu Gln Pro Glu Leu Pro Asp Val Ile His Ser His Tyr Ala
        115                 120                 125

Asp Ala Gly Tyr Val Gly Thr Arg Leu Ser His Gln Leu Gly Ile Pro
    130                 135                 140

Leu Val His Thr Gly His Ser Leu Gly Arg Ser Lys Arg Thr Arg Leu
145                 150                 155                 160

Leu Leu Ser Gly Ile Lys Ala Asp Glu Ile Glu Ser Arg Tyr Asn Met
                165                 170                 175

Ala Arg Arg Ile Asn Ala Glu Glu Glu Thr Leu Gly Ser Ala Ala Arg
            180                 185                 190

Val Ile Thr Ser Thr His Gln Glu Ile Ala Glu Gln Tyr Ala Gln Tyr
        195                 200                 205

Asp Tyr Tyr Gln Pro Asp Gln Met Leu Val Ile Pro Pro Gly Thr Asp
    210                 215                 220

Leu Glu Lys Phe Tyr Pro Pro Lys Gly Asn Glu Trp Glu Thr Pro Ile
225                 230                 235                 240

Val Gln Glu Leu Gln Arg Phe Leu Arg His Pro Arg Lys Pro Ile Ile
                245                 250                 255

Leu Ala Leu Ser Arg Pro Asp Pro Arg Lys Asn Ile His Lys Leu Ile
            260                 265                 270

Ala Ala Tyr Gly Gln Ser Pro Gln Leu Gln Ala Gln Ala Asn Leu Val
        275                 280                 285

Ile Val Ala Gly Asn Arg Asp Asp Ile Thr Asp Leu Asp Gln Gly Pro
    290                 295                 300
```

-continued

```
Arg Glu Val Leu Thr Asp Leu Leu Leu Thr Ile Asp Arg Tyr Asp Leu
305                 310                 315                 320

Tyr Gly Lys Val Ala Tyr Pro Lys Gln Asn Gln Ala Glu Asp Val Tyr
                325                 330                 335

Ala Leu Phe Arg Leu Thr Ala Leu Ser Gln Gly Val Phe Ile Asn Pro
            340                 345                 350

Ala Leu Thr Glu Pro Phe Gly Leu Thr Leu Ile Glu Ala Ala Ala Cys
        355                 360                 365

Gly Val Pro Ile Val Ala Thr Glu Asp Gly Gly Pro Val Asp Ile Ile
    370                 375                 380

Lys Asn Cys Gln Asn Gly Tyr Leu Ile Asn Pro Leu Asp Glu Val Asp
385                 390                 395                 400

Ile Ala Asp Lys Leu Leu Lys Val Leu Asn Asp Lys Gln Gln Trp Gln
                405                 410                 415

Phe Leu Ser Glu Ser Gly Leu Glu Gly Val Lys Arg His Tyr Ser Trp
            420                 425                 430

Pro Ser His Val Glu Ser Tyr Leu Glu Ala Ile Asn Ala Leu Thr Gln
        435                 440                 445

Gln Thr Ser Val Leu Lys Arg Ser Asp Leu Lys Arg Arg Arg Thr Leu
    450                 455                 460

Tyr Tyr Asn Gly Ala Leu Val Thr Ser Leu Asp Gln Asn Leu Leu Gly
465                 470                 475                 480

Ala Leu Gln Gly Gly Leu Pro Gly Asp Arg Gln Thr Leu Asp Glu Leu
                485                 490                 495

Leu Glu Val Leu Tyr Gln His Arg Lys Asn Val Gly Phe Cys Ile Ala
            500                 505                 510

Thr Gly Arg Arg Leu Asp Ser Val Leu Lys Ile Leu Arg Glu Tyr Arg
        515                 520                 525

Ile Pro Gln Pro Asp Met Leu Ile Thr Ser Met Gly Thr Glu Ile Tyr
    530                 535                 540

Ser Ser Pro Asp Leu Ile Pro Asp Gln Ser Trp Arg Asn His Ile Asp
545                 550                 555                 560

Tyr Leu Trp Asn Arg Asn Ala Ile Val Arg Ile Leu Gly Glu Leu Pro
                565                 570                 575

Gly Leu Ala Leu Gln Pro Lys Glu Glu Leu Ser Ala Tyr Lys Ile Ser
            580                 585                 590

Tyr Phe Tyr Asp Ala Ala Ile Ala Pro Asn Leu Glu Glu Ile Arg Gln
        595                 600                 605

Leu Leu His Lys Gly Glu Gln Thr Val Asn Thr Ile Ile Ser Phe Gly
    610                 615                 620

Gln Phe Leu Asp Ile Leu Pro Ile Arg Ala Ser Lys Gly Tyr Ala Val
625                 630                 635                 640

Arg Trp Leu Ser Gln Gln Trp Asn Ile Pro Leu Glu His Val Phe Thr
                645                 650                 655

Ala Gly Gly Ser Gly Ala Asp Glu Asp Met Met Arg Gly Asn Thr Leu
            660                 665                 670

Ser Val Val Val Ala Asn Arg His His Glu Glu Leu Ser Asn Leu Gly
        675                 680                 685

Glu Ile Glu Pro Ile Tyr Phe Ser Glu Lys Arg Tyr Ala Ala Gly Ile
    690                 695                 700

Leu Asp Gly Leu Ala His Tyr Arg Phe Phe Glu Leu Leu Asp Pro Val
705                 710                 715                 720
```

-continued

<210> SEQ ID NO 5
<211> LENGTH: 735
<212> TYPE: DNA
<213> ORGANISM: Synechocystis PCC6803

<400> SEQUENCE: 5

```
atgcgacagt tattgctaat ttctgacctg gacaatacct gggtcggaga tcaacaagcc     60

ctggaacatt tgcaagaata tctaggcgat cgccggggaa atttttattt ggcctatgcc    120

acggggcgtt cctaccattc cgcgagggag ttgcaaaaac aggtgggact catggaaccg    180

gactattggc tcaccgcggt ggggagtgaa atttaccatc cagaaggcct ggaccaacat    240

tgggctgatt acctctctga gcattggcaa cgggatatcc tccaggcgat cgccgatggt    300

tttgaggcct taaaacccca atctcccttg gaacaaaacc catggaaaat tagctatcat    360

ctcgatcccc aggcttgccc caccgtcatc gaccaattaa cggagatgtt gaaggaaacc    420

ggcatcccgg tgcaggtgat tttcagcagt ggcaaagatg tggatttatt gccccaacgg    480

agtaacaaag gtaacgccac ccaatatctg caacaacatt tagccatgga gccgtctcaa    540

accctggtgt gtggggactc cggcaatgat attggcttat ttgaaacttc cgctcggggt    600

gtcattgtcc gtaatgccca gccggaatta ttgcactggt atgaccaatg gggggattct    660

cgtcattatc gggcccaatc gagccatgct ggcgctatcc tagaggcgat cgcccatttc    720

gatttttga gctga                                                      735
```

<210> SEQ ID NO 6
<211> LENGTH: 244
<212> TYPE: PRT
<213> ORGANISM: Synechocystis PCC6803

<400> SEQUENCE: 6

```
Met Arg Gln Leu Leu Leu Ile Ser Asp Leu Asp Asn Thr Trp Val Gly
1               5                   10                  15

Asp Gln Gln Ala Leu Glu His Leu Gln Glu Tyr Leu Gly Asp Arg Arg
            20                  25                  30

Gly Asn Phe Tyr Leu Ala Tyr Ala Thr Gly Arg Ser Tyr His Ser Ala
        35                  40                  45

Arg Glu Leu Gln Lys Gln Val Gly Leu Met Glu Pro Asp Tyr Trp Leu
    50                  55                  60

Thr Ala Val Gly Ser Glu Ile Tyr His Pro Glu Gly Leu Asp Gln His
65                  70                  75                  80

Trp Ala Asp Tyr Leu Ser Glu His Trp Gln Arg Asp Ile Leu Gln Ala
                85                  90                  95

Ile Ala Asp Gly Phe Glu Ala Leu Lys Pro Gln Ser Pro Leu Glu Gln
            100                 105                 110

Asn Pro Trp Lys Ile Ser Tyr His Leu Asp Pro Gln Ala Cys Pro Thr
        115                 120                 125

Val Ile Asp Gln Leu Thr Glu Met Leu Lys Glu Thr Gly Ile Pro Val
    130                 135                 140

Gln Val Ile Phe Ser Ser Gly Lys Asp Val Asp Leu Leu Pro Gln Arg
145                 150                 155                 160

Ser Asn Lys Gly Asn Ala Thr Gln Tyr Leu Gln Gln His Leu Ala Met
                165                 170                 175

Glu Pro Ser Gln Thr Leu Val Cys Gly Asp Ser Gly Asn Asp Ile Gly
            180                 185                 190

Leu Phe Glu Thr Ser Ala Arg Gly Val Ile Val Arg Asn Ala Gln Pro
        195                 200                 205
```

```
Glu Leu Leu His Trp Tyr Asp Gln Trp Gly Asp Ser Arg His Tyr Arg
    210                 215                 220

Ala Gln Ser Ser His Ala Gly Ala Ile Leu Glu Ala Ile Ala His Phe
225                 230                 235                 240

Asp Phe Leu Ser


<210> SEQ ID NO 7
<211> LENGTH: 28
<212> TYPE: DNA
<213> ORGANISM: Artificial
<220> FEATURE:
<223> OTHER INFORMATION: primer for amplificaiton of asf

<400> SEQUENCE: 7

agactacaat tggggcgttt tctgtgag                                        28


<210> SEQ ID NO 8
<211> LENGTH: 49
<212> TYPE: DNA
<213> ORGANISM: Artificial
<220> FEATURE:
<223> OTHER INFORMATION: primer for amplificaiton of asf

<400> SEQUENCE: 8

cttacgtgcc gatcaacgtc tcattctgaa aaggttaagc gatcgcctc                 49


<210> SEQ ID NO 9
<211> LENGTH: 39
<212> TYPE: DNA
<213> ORGANISM: Artificial
<220> FEATURE:
<223> OTHER INFORMATION: Primer for amplifying cat gene from pBeloBAC11

<400> SEQUENCE: 9

ttatcgcgat cgtcaggagc taaggaagct aaaatggag                            39


<210> SEQ ID NO 10
<211> LENGTH: 29
<212> TYPE: DNA
<213> ORGANISM: Artificial
<220> FEATURE:
<223> OTHER INFORMATION: primer for amplificaiton of cat

<400> SEQUENCE: 10

cgaccaattc acgtgtttga cagcttatc                                       29


<210> SEQ ID NO 11
<211> LENGTH: 811
<212> TYPE: DNA
<213> ORGANISM: Artificial
<220> FEATURE:
<223> OTHER INFORMATION: cat gene amplified from pBeloBAC11

<400> SEQUENCE: 11

ttatcgcgat cgtcaggagc taaggaagct aaaatggaga aaaaaatcac tggatatacc     60

accgttgata tatcccaatg gcatcgtaaa gaacattttg aggcatttca gtcagttgct    120

caatgtacct ataaccagac cgttcagctg gatattacgg cctttttaaa gaccgtaaag    180

aaaaataagc acaagtttta tccggccttt attcacattc ttgcccgcct gatgaatgct    240

catccggaat tccgtatggc aatgaaagac ggtgagctgg tgatatggga tagtgttcac    300

ccttgttaca ccgttttcca tgagcaaact gaaacgtttt catcgctctg gagtgaatac    360
```

-continued

```
cacgacgatt tccggcagtt tctacacata tattcgcaag atgtggcgtg ttacggtgaa    420

aacctggcct atttccctaa agggtttatt gagaatatgt ttttcgtctc agccaatccc    480

tgggtgagtt tcaccagttt tgatttaaac gtggccaata tggacaactt cttcgccccc    540

gttttcacca tgggcaaata ttatacgcaa ggcgacaagg tgctgatgcc gctggcgatt    600

caggttcatc atgccgtttg tgatggcttc catgtcggca gaatgcttaa tgaattacaa    660

cagtactgcg atgagtggca gggcggggcg taattttttt aaggcagtta ttggtgccct    720

taaacgcctg gttgctacgc ctgaataagt gataataagc ggatgaatgg cagaaattcg    780

atgataagct gtcaaacacg tgaattggtc g                                    811
```

<210> SEQ ID NO 12
<211> LENGTH: 35
<212> TYPE: DNA
<213> ORGANISM: Artificial
<220> FEATURE:
<223> OTHER INFORMATION: primer for amplifying cat gene bearing the promoter from pBeloBAC11

<400> SEQUENCE: 12

```
ttttggcgat cgtgagacgt tgatcggcac gtaag                                 35
```

<210> SEQ ID NO 13
<211> LENGTH: 29
<212> TYPE: DNA
<213> ORGANISM: Artificial
<220> FEATURE:
<223> OTHER INFORMATION: primer for amplifying cat gene bearing the promoter from pBeloBAC11

<400> SEQUENCE: 13

```
cgaccaattc acgtgtttga cagcttatc                                        29
```

<210> SEQ ID NO 14
<211> LENGTH: 901
<212> TYPE: DNA
<213> ORGANISM: Artificial
<220> FEATURE:
<223> OTHER INFORMATION: cat gene bearing the promoter amplified from pBeloBAC11

<400> SEQUENCE: 14

```
ttttggcgat cgtgagacgt tgatcggcac gtaagaggtt ccaactttca ccataatgaa     60

ataagatcac taccgggcgt atttttttgag ttatcgagat tttcaggagc taaggaagct    120

aaaatggaga aaaaaatcac tggatatacc accgttgata tatcccaatg gcatcgtaaa    180

gaacattttg aggcatttca gtcagttgct caatgtacct ataaccagac cgttcagctg    240

gatattacgg cctttttaaa gaccgtaaag aaaaataagc acaagtttta tccggccttt    300

attcacattc ttgcccgcct gatgaatgct catccggaat tccgtatggc aatgaaagac    360

ggtgagctgg tgatatggga tagtgttcac ccttgttaca ccgttttcca tgagcaaact    420

gaaacgtttt catcgctctg gagtgaatac cacgacgatt tccggcagtt tctacacata    480

tattcgcaag atgtggcgtg ttacggtgaa aacctggcct atttccctaa agggtttatt    540

gagaatatgt ttttcgtctc agccaatccc tgggtgagtt tcaccagttt tgatttaaac    600

gtggccaata tggacaactt cttcgccccc gttttcacca tgggcaaata ttatacgcaa    660

ggcgacaagg tgctgatgcc gctggcgatt caggttcatc atgccgtttg tgatggcttc    720

catgtcggca gaatgcttaa tgaattacaa cagtactgcg atgagtggca gggcggggcg    780
```

taattttttt aaggcagtta ttggtgccct taaacgcctg gttgctacgc ctgaataagt 840
gataataagc ggatgaatgg cagaaattcg atgataagct gtcaaacacg tgaattggtc 900
g 901

<210> SEQ ID NO 15
<211> LENGTH: 30
<212> TYPE: DNA
<213> ORGANISM: Artificial
<220> FEATURE:
<223> OTHER INFORMATION: primer for sequence verification of cat/asf

<400> SEQUENCE: 15
gcttctgcgt tctgatttaa tctgtatcag 30

<210> SEQ ID NO 16
<211> LENGTH: 27
<212> TYPE: DNA
<213> ORGANISM: Artificial
<220> FEATURE:
<223> OTHER INFORMATION: primer for sequence verification of cat/asf

<400> SEQUENCE: 16
tatcacttat tcaggcgtag caaccag 27

<210> SEQ ID NO 17
<211> LENGTH: 27
<212> TYPE: DNA
<213> ORGANISM: Artificial
<220> FEATURE:
<223> OTHER INFORMATION: primer for sequence verification of cat/asf

<400> SEQUENCE: 17
gtcgttagtg acatcgacaa cacactg 27

<210> SEQ ID NO 18
<211> LENGTH: 26
<212> TYPE: DNA
<213> ORGANISM: Artificial
<220> FEATURE:
<223> OTHER INFORMATION: primer for sequence verification of cat/asf

<400> SEQUENCE: 18
gatcgcgata ctgatcgaga taggtc 26

<210> SEQ ID NO 19
<211> LENGTH: 10577
<212> TYPE: DNA
<213> ORGANISM: Artificial
<220> FEATURE:
<223> OTHER INFORMATION: Plasmid pLybAL11 containing ASF gene from
Synechococcus elongatus PCC 7942

<400> SEQUENCE: 19
tgcatgcctg caggtcgact ctagaggatc cccgggtacc gagctcgaat tggggcgttt 60
tctgtgaggc tgactagcgc gtggcagctc aaaatctcta cattctgcac attcagaccc 120
atggtctgct gcgagggcag aacttggaac tggggcgaga tgccgacacc ggcgggcaga 180
ccaagtacgt cttagaactg gctcaagccc aagctaaatc cccacaagtc caacaagtcg 240
acatcatcac ccgccaaatc accgaccccc gcgtcagtgt tggttacagt caggcgatcg 300
aaccctttgc gcccaaaggt cggattgtcc gtttgccttt tggccccaaa cgctacctcc 360
gtaaagagct gctttggccc catctctaca cctttgcgga tgcaattctc caatatctgg 420

-continued

```
ctcagcaaaa gcgcaccccg acttggattc aggcccacta tgctgatgct ggccaagtgg    480
gatcactgct gagtcgctgg ttgaatgtac cgctaatttt cacagggcat tctctggggc    540
ggatcaagct aaaaaagctg ttggagcaag actggccgct tgaggaaatt gaagcgcaat    600
tcaatattca acagcgaatt gatgcggagg agatgacgct cactcatgct gactggattg    660
tcgccagcac tcagcaggaa gtggaggagc aataccgcgt ttacgatcgc tacaacccag    720
agcgcaagct tgtcattcca ccgggtgtcg ataccgatcg cttcaggttt cagcccttgg    780
gcgatcgcgg tgttgttctc caacaggaac tgagccgctt tctgcgcgac ccagaaaaac    840
ctcaaattct ctgcctctgt cgccccgcac ctcgcaaaaa tgtaccggcg ctggtgcgag    900
cctttggcga acatccttgg ctgcgcaaaa aagccaacct tgtcttagta ctgggcagcc    960
gccaagacat caaccagatg gatcgcggca gtcggcaggt gttccaagag attttccatc   1020
tggtcgatcg ctacgacctc tacggcagcg tcgcctatcc caaacagcat caggctgatg   1080
atgtgccgga gttctatcgc ctagcggctc attccggcgg ggtattcgtc aatccggcgc   1140
tgaccgaacc ttttggtttg acaattttgg aggcaggaag ctgcggcgtg ccggtggtgg   1200
caacccatga tggcggcccc caggaaattc tcaaacactg tgatttcggc actttagttg   1260
atgtcagccg acccgctaat atcgcgactg cactcgccac cctgctgagc gatcgcgatc   1320
tttggcagtg ctatcaccgc aatggcattg aaaaagttcc cgcccattac agctgggatc   1380
aacatgtcaa taccctgttt gagcgcatgg aaacggtggc tttgcctcgt cgtcgtgctg   1440
tcagtttcgt acggagtcgc aaacgcttga ttgatgccaa acgccttgtc gttagtgaca   1500
tcgacaacac actgttgggc gatcgtcaag gactcgagaa tttaatgacc tatctcgatc   1560
agtatcgcga tcattttgcc tttggaattg ccacggggcg tcgcctagac tctgcccaag   1620
aagtcttgaa agagtggggc gttccttcgc caaacttctg ggtgacttcc gtcggcagcg   1680
agattcacta tggcaccgat gctgaaccgg atatcagctg ggaaaagcat atcaatcgca   1740
actggaatcc tcagcgaatt cgggcagtaa tggcacaact acccttttctt gaactgcagc   1800
cggaagagga tcaaacaccc ttcaaagtca gcttctttgt ccgcgatcgc cacgagactg   1860
tgctgcgaga agtacggcaa catcttcgcc gccatcgcct gcggctgaag tcaatctatt   1920
cccatcagga gtttcttgac attctgccgc tagctgcctc gaaaggggat gcgattcgcc   1980
acctctcact ccgctggcgg attcctcttg agaacatttt ggtggcaggc gattctggta   2040
acgatgagga aatgctcaag ggccataatc tcggcgttgt agttggcaat tactcaccgg   2100
aattggagcc actgcgcagc tacgagcgcg tctattttgc tgagggccac tatgctaatg   2160
gcattctgga agccttaaaa cactatcgct tttttgaggc gatcgcttaa ccttttcaga   2220
atgagacgtt gatcggcacg taagcgtcag gagctaagga agctaaaatg gagaaaaaaa   2280
tcactggata taccaccgtt gatatatccc aatggcatcg taaagaacat tttgaggcat   2340
ttcagtcagt tgctcaatgt acctataacc agaccgttca gctggatatt acggcctttt   2400
taaagaccgt aaagaaaaat aagcacaagt tttatccggc ctttattcac attcttgccc   2460
gcctgatgaa tgctcatccg gaattccgta tggcaatgaa agacggtgag ctggtgatat   2520
gggatagtgt tcacccttgt tacaccgttt tccatgagca aactgaaacg ttttcatcgc   2580
tctggagtga ataccacgac gatttccggc agtttctaca catatattcg caagatgtgg   2640
cgtgttacgg tgaaaacctg gcctatttcc ctaaagggtt tattgagaat atgtttttcg   2700
tctcagccaa tccctgggtg agtttcacca gttttgattt aaacgtggcc aatatggaca   2760
acttcttcgc ccccgttttc accatgggca aatattatac gcaaggcgac aaggtgctga   2820
```

-continued

```
tgccgctggc gattcaggtt catcatgccg tttgtgatgg cttccatgtc ggcagaatgc   2880
ttaatgaatt acaacagtac tgcgatgagt ggcagggcgg ggcgtaattt ttttaaggca   2940
gttattggtg cccttaaacg cctggttgct acgcctgaat aagtgataat aagcggatga   3000
atggcagaaa ttcgatgata agctgtcaaa cacaaccacc atcaaacagg attttcgcct   3060
gctggggcaa accagcgtgg accgcttgct gcaactctct cagggccagg cggtgaaggg   3120
caatcagctg ttgcccgtct cactggtgaa aagaaaaacc accctggcgc ccaatacgca   3180
aaccgcctct ccccgcgcgt tggccgattc attaatgcag ctggcacgac aggtttcccg   3240
actggaaagc gggcagtgag cgcaacgcaa ttaatgtaag ttagcgcgaa ttgcaagctg   3300
gccgacgcgc tgggctacgt cttgctggcg ttcgggagca gaagagcata catctggaag   3360
caaagccagg aaagcggcct atggagctgt gcggcagcgc tcagtaggca atttttcaaa   3420
atattgttaa gccttttctg agcatggtat ttttcatggt attaccaatt agcaggaaaa   3480
taagccattg aatataaaag ataaaaatgt cttgtttaca atagagtggg gggggtcagc   3540
ctgccgcctt gggccgggtg atgtcgtact tgcccgccgc gaactcggtt accgtccagc   3600
ccagcgcgac cagctccggc aacgcctcgc gcacccgctt gcggcgcttg cgcatggtcg   3660
aaccactggc ctctgacggc cagacatagc cgcacaaggt atctatggaa gccttgccgg   3720
ttttgccggg gtcgatccag ccacacagcc gctggtgcag caggcgggcg gtttcgctgt   3780
ccagcgcccg cacctcgtcc atgctgatgc gcacatgctg gccgccaccc atgacggcct   3840
gcgcgatcaa ggggttcagg gccacgtaca ggcgcccgtc cgcctcgtcg ctggcgtact   3900
ccgacagcag ccgaaacccc tgccgcttgc ggccattctg ggcgatgatg gataccttcc   3960
aaaggcgctc gatgcagtcc tgtatgtgct tgagcgcccc accactatcg acctctgccc   4020
cgatttcctt tgccagcgcc cgatagctac ctttgaccac atggcattca gcggtgacgg   4080
cctcccactt gggttccagg aacagccgga gctgccgtcc gccttcggtc ttgggttccg   4140
ggccaagcac taggccatta ggcccagcca tggccaccag cccttgcagg atgcgcagat   4200
catcagcgcc cagcggctcc gggccgctga actcgatccg cttgccgtcg ccgtagtcat   4260
acgtcacgtc cagcttgctg cgcttgcgct cgccccgctt gagggcacgg aacaggccgg   4320
gggccagaca gtgcgccggg tcgtgccgga cgtggctgag gctgtgcttg ttcttaggct   4380
tcaccacggg gcaccccctt gctcttgcgc tgcctctcca gcacggcggg cttgagcacc   4440
ccgccgtcat gccgcctgaa ccaccgatca gcgaacggtg cgccatagtt ggccttgctc   4500
acaccgaagc ggacgaagaa ccggcgctgg tcgtcgtcca caccccattc ctcggcctcg   4560
gcgctggtca tgctcgacag gtaggactgc cagcggatgt tatcgaccag taccgagctg   4620
ccccggctgg cctgctgctg gtcgcctgcg cccatcatgg ccgcgccctt gctggcatgg   4680
tgcaggaaca cgatagagca cccggtatcg gcggcgatgg cctccatgcg accgatgacc   4740
tgggccatgg ggccgctggc gttttcttcc tcgatgtgga accggcgcag cgtgtccagc   4800
accatcaggc ggcggccctc ggcggcgcgc ttgaggccgt cgaaccactc cggggccatg   4860
atgttgggca ggctgccgat cagcggctgg atcagcaggc cgtcagccac ggcttgccgt   4920
tcctcggcgc tgaggtgcgc cccaagggcg tgcaggcggt gatgaatggc ggtgggcggg   4980
tcttcggcgg gcaggtagat caccgggccg gtgggcagtt cgcccacctc cagcagatcc   5040
ggcccgcctg caatctgtgc ggccagttgc agggccagca tggatttacc ggcaccaccg   5100
ggcgacacca gcgccccgac cgtaccggcc accatgttgg gcaaaacgta gtccagcggt   5160
```

-continued

```
ggcggcgctg ctgcgaacgc ctccagaata ttgataggct tatgggtagc cattgattgc   5220
ctcctttgca ggcagttggt ggttaggcgc tggcggggtc actacccccg ccctgcgccg   5280
ctctgagttc ttccaggcac tcgcgcagcg cctcgtattc gtcgtcggtc agccagaact   5340
tgcgctgacg catccctttg gccttcatgc gctcggcata tcgcgcttgg cgtacagcgt   5400
cagggctggc cagcaggtcg ccggtctgct tgtccttttg gtctttcata tcagtcaccg   5460
agaaacttgc cggggccgaa aggcttgtct tcgcggaaca aggacaaggt gcagccgtca   5520
aggttaaggc tggccatatc agcgactgaa aagcggccag cctcggcctt gtttgacgta   5580
taaccaaagc caccgggcaa ccaatagccc ttgtcacttt tgatcaggta gaccgaccct   5640
gaagcgcttt tttcgtattc cataaaaccc ccttctgtgc gtgagtactc atagtataac   5700
aggcgtgagt accaacgcaa gcactacatg ctgaaatctg gcccgcccct gtccatgcct   5760
cgctggcggg gtgccggtgc ccgtgccagc tcggcccgcg caagctggac gctgggcaga   5820
cccatgacct tgctgacggt gcgctcgatg taatccgctt cgtggccggg cttgcgctct   5880
gccagcgctg ggctggcctc ggccatggcc ttgccgattt cctcggcact gcggccccgg   5940
ctggccagct tctgcgcggc gataaagtcg cacttgctga ggtcatgacc gaagcgcttg   6000
accagcccgg ccatctcgct gcggtactcg tccagcgccg tgcgccggtg gcggctaagc   6060
tgccgctcgg gcagttcgag gctggccagc ctgcgggcct tctcctgctg ccgctgggcc   6120
tgctcgatct gctggccagc ctgctgcacc agcgccgggc cagcggtggc ggtcttgccc   6180
ttggattcac gcagcagcac ccacggctga taaccggcgc gggtggtgtg cttgtccttg   6240
cggttggtga agcccgccaa gcggccatag tggcggctgt cggcgctggc cgggtcggcg   6300
tcgtactcgc tggccagcgt ccgggcaatc tgcccccgaa gttcaccgcc tgcggcgtcg   6360
gccaccttga cccatgcctg atagttcttc gggctggttt ccactaccag ggcaggctcc   6420
cggccctcgg ctttcatgtc atccaggtca aactcgctga ggtcgtccac cagcaccaga   6480
ccatgccgct cctgctcggc gggcctgata tacacgtcat tgccctgggc attcatccgc   6540
ttgagccatg gcgtgttctg gagcacttcg gcggctgacc attcccggtt catcatctgg   6600
ccggtgggtg cgtccctgac gccgatatcg aagcgctcac agcccatggc cttgagctgt   6660
cggcctatgg cctgcaaagt cctgtcgttc ttcatcgggc caccaagcgc agccagatcg   6720
agccgtcctc ggttgtcagt ggcgtcaggt cgagcaagag caacgatgcg atcagcagca   6780
ccaccgtagg catcatggaa gccagcatca cggttagcca tagcttccag tgccaccccc   6840
gcgacgcgct ccgggcgctc tgcgcggcgc tgctcacctc ggcggctacc tcccgcaact   6900
ctttggccag ctccacccat gccgcccctg tctggcgctg ggctttcagc cactccgccg   6960
cctgcgcctc gctggcctgc ttggtctggc tcatgacctg ccgggcttcg tcggccagtg   7020
tcgccatgct ctgggccagc ggttcgatct gctccgctaa ctcgttgatg cctctggatt   7080
tcttcactct gtcgattgcg ttcatggtct attgcctccc ggtattcctg taagtcgatg   7140
atctgggcgt tggcggtgtc gatgttcagg gccacgtctg cccggtcggt gcggatgccc   7200
cggccttcca tctccaccac gttcggcccc aggtgaacac cgggcaggcg ctcgatgccc   7260
tgcgcctcaa gtgttctgtg gtcaatgcgg gcgtcgtggc cagcccgctc taatgcccgg   7320
ttggcatggt cggcccatgc ctcgcgggtc tgctcaagcc atgccttggg cttgagcgct   7380
tcggtcttct gtgccccgcc cttctccggg gtcttgccgt tgtaccgctt gaaccactga   7440
gcggcgggcc gctcgatgcc gtcattgatc cgctcggaga tcatcaggtg gcagtgcggg   7500
ttctcgccgc caccggcatg gatggccagc gtatacggca ggcgctcggc accggtcagg   7560
```

-continued tgctgggcga actcggacgc cagcgccttc tgctggtcga gggtcagctc gaccggcagg 7620
gcaaattcga cctccttgaa cagccgccca ttggcgcgtt catacaggtc ggcagcatcc 7680
cagtagtcgg cgggccgctc gacgaactcc ggcatgtgcc cggattcggc gtgcaagact 7740
tcatccatgt cgcgggcata cttgccttcg cgctggatgt agtcggcctt ggccctggcc 7800
gattggccgc ccgacctgct gccggttttc gccgtaaggt gataaatcgc catgctgcct 7860
cgctgttgct tttgcttttc ggctccatgc aatggccctc ggagagcgca ccgcccgaag 7920
ggtggccgtt aggccagttt ctcgaagaga aaccggtaag tgcgccctcc cctacaaagt 7980
agggtcggga ttgccgccgc tgtgcctcca tgatagccta cgagacagca cattaacaat 8040
ggggtgtcaa gatggttaag gggagcaaca aggcggcgga tcggctggcc aagctcgaag 8100
aacaacgagc gcgaatcaat gccgaaattc agcgggagcg ggcaagggaa cagcagcaag 8160
agcgcaagaa cgaaacaagg cgcaaggtgc tggtgggggc catgattttg gccaaggtga 8220
acagcagcga gtggccggag gatcggctca tggcggcaat ggatgcgtac cttgaacgcg 8280
accacgaccg cgccttgttc ggtctgccgc cacgccagaa ggatgagccg ggctgaatga 8340
tcgaccgaga caggccctgc ggggctgcac acgcgccccc acccttcggg taggggggaa 8400
ggccgctaaa gcggctaaaa gcgctccagc gtatttctgc ggggtttggt gtggggttta 8460
gcgggctttg cccgcctttc cccctgccgc gcagcggtgg ggcggtgtgt agcctagcgc 8520
agcgaataga ccagctatcc ggcctctggc cgggcatatt gggcaagggc agcagcgccc 8580
cacaagggcg ctgataaccg cgcctagtgg attattctta gataatcatg gatggatttt 8640
tccaacaccc cgccagcccc cgcccctgct gggtttgcag gtttgggggc gtgacagtta 8700
ttgcaggggt tcgtgacagt tattgcaggg gggcgtgaca gttattgcag gggttcgtga 8760
cagttagtac gggagtgacg ggcactggct ggcaatgtct agcaacggca ggcatttcgg 8820
ctgagggtaa aagaactttc cgctaagcga tagactgtat gtaaacacag tattgcaagg 8880
acgcggaaca tgcctcatgt ggcggccagg acggccagcc gggatcggga tactggtcgt 8940
taccagagcc accgacccga gcaaaccctt ctctatcaga tcgttgacga gtattacccg 9000
gcattcgctg cgcttatggc agagcaggga aaggaattgc cgggctatgt gcaacgggaa 9060
tttgaagaat ttctccaatg cgggcggctg gagcatggct ttctacgggt tcgctgcgag 9120
tcttgccacg ccgagcacct ggtcgctttc agaaatcaat ctaaagtata tatgagtaaa 9180
cttggtctga cagttaccaa tgcttaatca gtgaggcacc tatctcagcg atctgtctat 9240
ttcgttcatc catagttgcc tgactccccg tcgtgtagat aactacgata cgggagggct 9300
taccatctgg ccccagtgct gcaatgatac cgcgagaccc acgctcaccg gctccagatt 9360
tatcagcaat aaaccagcca gccggaaggg ccgagcgcag aagtggtcct gcaactttat 9420
ccgcctccat ccagtctatt aattgttgcc gggaagctag agtaagtagt tcgccagtta 9480
atagtttgcg caacgttgtt gccattgcta caggcatcgt ggtgtcacgc tcgtcgtttg 9540
gtatggcttc attcagctcc ggttcccaac gatcaaggcg agttacatga tcccccatgt 9600
tgtgcaaaaa agcggttagc tccttcggtc ctccgatcgt tgtcagaagt aagttggccg 9660
cagtgttatc actcatggtt atggcagcac tgcataattc tcttactgtc atgccatccg 9720
taagatgctt ttctgtgact ggtgagtact caaccaagtc attctgagaa tagtgtatgc 9780
ggcgaccgag ttgctcttgc ccggcgtcaa cacgggataa taccgcgcca catagcagaa 9840
ctttaaaagt gctcatcatt ggaaaacgtt cttcggggcg aaaactctca aggatcttac 9900

```
cgctgttgag atccagttcg atgtaaccca ctcgtgcacc caactgatct tcagcatctt   9960

ttactttcac cagcgtttct gggtgagcaa aaacaggaag gcaaaatgcc gcaaaaaagg  10020

gaataagggc gacacggaaa tgttgaatac tcatactctt cctttttcaa tattattgaa  10080

gcatttatca gggttattgt ctcatgagcg gatacatatt tgaatgtatt tagaaaaata  10140

aacaaaagag tttgtagaaa cgcaaaaagg ccatccgtca ggatggcctt ctgcttaatt  10200

tgatgcctgg cagtttatgg cgggcgtcct gcccgccacc ctccgggccg ttgcttcgca  10260

acgttcaaat ccgctcccgg cggatttgtc ctactcagga gagcgttcac cgacaaacaa  10320

cagataaaac gaaaggccca gtctttcgac tgagcctttc gttttatttg atgcctggca  10380

gttccctact ctcgcatggg gagaccccac actaccatcg gcgctacggc gtttcacttc  10440

tgagttcggc atggggtcag gtgggaccac cgcgctactg ccgccaggca aattctgttt  10500

tatcagaccg cttctgcgtt ctgatttaat ctgtatcagg ctgaaaatct tctctcatcc  10560

gccaaaacag ccaagct                                                  10577
```

```
<210> SEQ ID NO 20
<211> LENGTH: 10667
<212> TYPE: DNA
<213> ORGANISM: Artificial
<220> FEATURE:
<223> OTHER INFORMATION: Plasmid pLybAL12 containing asf gene from
      Synechococcus elongatus PCC 7942

<400> SEQUENCE: 20
```

```
tgcatgcctg caggtcgact ctagaggatc cccgggtacc gagctcgaat tggggcgttt     60

tctgtgaggc tgactagcgc gtggcagctc aaaatctcta cattctgcac attcagaccc    120

atggtctgct gcgagggcag aacttggaac tggggcgaga tgccgacacc ggcgggcaga    180

ccaagtacgt cttagaactg gctcaagccc aagctaaatc cccacaagtc caacaagtcg    240

acatcatcac ccgccaaatc accgaccccc gcgtcagtgt tggttacagt caggcgatcg    300

aaccctttgc gcccaaaggt cggattgtcc gtttgccttt tggccccaaa cgctacctcc    360

gtaaagagct gctttggccc catctctaca cctttgcgga tgcaattctc caatatctgg    420

ctcagcaaaa gcgcaccccg acttggattc aggcccacta tgctgatgct ggccaagtgg    480

gatcactgct gagtcgctgg ttgaatgtac cgctaatttt cacagggcat tctctggggc    540

ggatcaagct aaaaaagctg ttggagcaag actggccgct tgaggaaatt gaagcgcaat    600

tcaatattca acagcgaatt gatgcggagg agatgacgct cactcatgct gactggattg    660

tcgccagcac tcagcaggaa gtggaggagc aataccgcgt ttacgatcgc tacaacccag    720

agcgcaagct tgtcattcca ccgggtgtcg ataccgatcg cttcaggttt cagcccttgg    780

gcgatcgcgg tgttgttctc caacaggaac tgagccgctt tctgcgcgac ccagaaaaac    840

ctcaaattct ctgcctctgt cgccccgcac ctcgcaaaaa tgtaccggcg ctggtgcgag    900

cctttggcga acatccttgg ctgcgcaaaa aagccaacct tgtcttagta ctgggcagcc    960

gccaagacat caaccagatg gatcgcggca gtcggcaggt gttccaagag attttccatc   1020

tggtcgatcg ctacgacctc tacggcagcg tcgcctatcc caaacagcat caggctgatg   1080

atgtgccgga gttctatcgc ctagcggctc attccggcgg ggtattcgtc aatccggcgc   1140

tgaccgaacc ttttggtttg acaattttgg aggcaggaag ctgcggcgtg ccggtggtgg   1200

caacccatga tggcggcccc caggaaattc tcaaacactg tgatttcggc actttagttg   1260

atgtcagccg acccgctaat atcgcgactg cactcgccac cctgctgagc gatcgcgatc   1320
```

-continued

```
tttggcagtg ctatcaccgc aatggcattg aaaaagttcc cgcccattac agctgggatc   1380
aacatgtcaa taccctgttt gagcgcatgg aaacggtggc tttgcctcgt cgtcgtgctg   1440
tcagtttcgt acggagtcgc aaacgcttga ttgatgccaa acgccttgtc gttagtgaca   1500
tcgacaacac actgttgggc gatcgtcaag gactcgagaa tttaatgacc tatctcgatc   1560
agtatcgcga tcattttgcc tttggaattg ccacggggcg tcgcctagac tctgcccaag   1620
aagtcttgaa agagtggggc gttccttcgc caaacttctg ggtgacttcc gtcggcagcg   1680
agattcacta tggcaccgat gctgaaccgg atatcagctg ggaaaagcat atcaatcgca   1740
actggaatcc tcagcgaatt cgggcagtaa tggcacaact accctttctt gaactgcagc   1800
cggaagagga tcaaacaccc ttcaaagtca gcttctttgt ccgcgatcgc cacgagactg   1860
tgctgcgaga agtacggcaa catcttcgcc gccatcgcct gcggctgaag tcaatctatt   1920
cccatcagga gtttcttgac attctgccgc tagctgcctc gaaaggggat gcgattcgcc   1980
acctctcact ccgctggcgg attcctcttg agaacatttt ggtggcaggc gattctggta   2040
acgatgagga aatgctcaag ggccataatc tcggcgttgt agttggcaat tactcaccgg   2100
aattggagcc actgcgcagc tacgagcgcg tctattttgc tgagggccac tatgctaatg   2160
gcattctgga agccttaaaa cactatcgct tttttgaggc gatcgcttaa ccttttcaga   2220
atgagacgtt gatcggcacg taagcgtgag acgttgatcg gcacgtaaga ggttccaact   2280
ttcaccataa tgaaataaga tcactaccgg gcgtattttt tgagttatcg agattttcag   2340
gagctaagga agctaaaatg gagaaaaaaa tcactggata taccaccgtt gatatatccc   2400
aatggcatcg taaagaacat tttgaggcat ttcagtcagt tgctcaatgt acctataacc   2460
agaccgttca gctggatatt acggcctttt taaagaccgt aaagaaaaat aagcacaagt   2520
tttatccggc ctttattcac attcttgccc gcctgatgaa tgctcatccg gaattccgta   2580
tggcaatgaa agacggtgag ctggtgatat gggatagtgt tcacccttgt tacaccgttt   2640
tccatgagca aactgaaacg ttttcatcgc tctggagtga ataccacgac gatttccggc   2700
agtttctaca catatattcg caagatgtgg cgtgttacgg tgaaaacctg gcctatttcc   2760
ctaaagggtt tattgagaat atgtttttcg tctcagccaa tccctgggtg agtttcacca   2820
gttttgattt aaacgtggcc aatatggaca acttcttcgc ccccgttttc accatgggca   2880
aatattatac gcaaggcgac aaggtgctga tgccgctggc gattcaggtt catcatgccg   2940
tttgtgatgg cttccatgtc ggcagaatgc ttaatgaatt acaacagtac tgcgatgagt   3000
ggcagggcgg ggcgtaattt ttttaaggca gttattggtg cccttaaacg cctggttgct   3060
acgcctgaat aagtgataat aagcggatga atggcagaaa ttcgatgata agctgtcaaa   3120
cacaaccacc atcaaacagg attttcgcct gctggggcaa accagcgtgg accgcttgct   3180
gcaactctct cagggccagg cggtgaaggg caatcagctg ttgcccgtct cactggtgaa   3240
aagaaaaacc accctggcgc ccaatacgca aaccgcctct ccccgcgcgt tggccgattc   3300
attaatgcag ctggcacgac aggtttcccg actggaaagc gggcagtgag cgcaacgcaa   3360
ttaatgtaag ttagcgcgaa ttgcaagctg gccgacgcgc tgggctacgt cttgctggcg   3420
ttcgggagca gaagagcata catctggaag caaagccagg aaagcggcct atggagctgt   3480
gcggcagcgc tcagtaggca atttttcaaa atattgttaa gccttttctg agcatggtat   3540
ttttcatggt attaccaatt agcaggaaaa taagccattg aatataaaag ataaaaatgt   3600
cttgtttaca atagagtggg gggggtcagc ctgccgcctt gggccgggtg atgtcgtact   3660
tgcccgccgc gaactcggtt accgtccagc ccagcgcgac cagctccggc aacgcctcgc   3720
```

-continued

```
gcacccgctt gcggcgcttg cgcatggtcg aaccactggc ctctgacggc cagacatagc   3780
cgcacaaggt atctatggaa gccttgccgg ttttgccggg gtcgatccag ccacacagcc   3840
gctggtgcag caggcgggcg gtttcgctgt ccagcgcccg cacctcgtcc atgctgatgc   3900
gcacatgctg gccgccaccc atgacggcct gcgcgatcaa ggggttcagg gccacgtaca   3960
ggcgcccgtc cgcctcgtcg ctggcgtact ccgacagcag ccgaaacccc tgccgcttgc   4020
ggccattctg ggcgatgatg gataccttcc aaaggcgctc gatgcagtcc tgtatgtgct   4080
tgagcgcccc accactatcg acctctgccc cgatttcctt tgccagcgcc cgatagctac   4140
ctttgaccac atggcattca gcggtgacgg cctcccactt gggttccagg aacagccgga   4200
gctgccgtcc gccttcggtc ttgggttccg ggccaagcac taggccatta ggcccagcca   4260
tggccaccag cccttgcagg atgcgcagat catcagcgcc cagcggctcc gggccgctga   4320
actcgatccg cttgccgtcg ccgtagtcat acgtcacgtc cagcttgctg cgcttgcgct   4380
cgccccgctt gagggcacgg aacaggccgg gggccagaca gtgcgccggg tcgtgccgga   4440
cgtggctgag gctgtgcttg ttcttaggct tcaccacggg gcaccccctt gctcttgcgc   4500
tgcctctcca gcacggcggg cttgagcacc ccgccgtcat gccgcctgaa ccaccgatca   4560
gcgaacggtg cgccatagtt ggccttgctc acaccgaagc ggacgaagaa ccggcgctgg   4620
tcgtcgtcca caccccattc ctcggcctcg gcgctggtca tgctcgacag gtaggactgc   4680
cagcggatgt tatcgaccag taccgagctg ccccggctgg cctgctgctg gtcgcctgcg   4740
cccatcatgg ccgcgccctt gctggcatgg tgcaggaaca cgatagagca cccggtatcg   4800
gcggcgatgg cctccatgcg accgatgacc tgggccatgg ggccgctggc gttttcttcc   4860
tcgatgtgga accggcgcag cgtgtccagc accatcaggc ggcggccctc ggcggcgcgc   4920
ttgaggccgt cgaaccactc cggggccatg atgttgggca ggctgccgat cagcggctgg   4980
atcagcaggc cgtcagccac ggcttgccgt tcctcggcgc tgaggtgcgc cccaagggcg   5040
tgcaggcggt gatgaatggc ggtgggcggg tcttcggcgg gcaggtagat caccgggccg   5100
gtgggcagtt cgcccacctc cagcagatcc ggcccgcctg caatctgtgc ggccagttgc   5160
agggccagca tggatttacc ggcaccaccg ggcgacacca gcgccccgac cgtaccggcc   5220
accatgttgg gcaaaacgta gtccagcggt ggcggcgctg ctgcgaacgc ctccagaata   5280
ttgataggct tatgggtagc cattgattgc ctcctttgca ggcagttggt ggttaggcgc   5340
tggcggggtc actacccccg ccctgcgccg ctctgagttc ttccaggcac tcgcgcagcg   5400
cctcgtattc gtcgtcggtc agccagaact tgcgctgacg catccctttg gccttcatgc   5460
gctcggcata tcgcgcttgg cgtacagcgt cagggctggc cagcaggtcg ccggtctgct   5520
tgtccttttg gtctttcata tcagtcaccg agaaacttgc cggggccgaa aggcttgtct   5580
tcgcggaaca aggacaaggt gcagccgtca aggttaaggc tggccatatc agcgactgaa   5640
aagcggccag cctcggcctt gtttgacgta taaccaaagc caccgggcaa ccaatagccc   5700
ttgtcacttt tgatcaggta gaccgaccct gaagcgcttt tttcgtattc cataaaaccc   5760
ccttctgtgc gtgagtactc atagtataac aggcgtgagt accaacgcaa gcactacatg   5820
ctgaaatctg gcccgcccct gtccatgcct cgctggcggg gtgccggtgc ccgtgccagc   5880
tcggcccgcg caagctggac gctgggcaga cccatgacct tgctgacggt gcgctcgatg   5940
taatccgctt cgtggccggg cttgcgctct gccagcgctg ggctggcctc ggccatggcc   6000
ttgccgattt cctcggcact gcggccccgg ctggccagct tctgcgcggc gataaagtcg   6060
```

-continued

```
cacttgctga ggtcatgacc gaagcgcttg accagcccgg ccatctcgct gcggtactcg   6120
tccagcgccg tgcgccggtg gcggctaagc tgccgctcgg gcagttcgag gctggccagc   6180
ctgcgggcct tctcctgctg ccgctgggcc tgctcgatct gctggccagc ctgctgcacc   6240
agcgccgggc cagcggtggc ggtcttgccc ttggattcac gcagcagcac ccacggctga   6300
taaccggcgc gggtggtgtg cttgtccttg cggttggtga agcccgccaa gcggccatag   6360
tggcggctgt cggcgctggc cgggtcggcg tcgtactcgc tggccagcgt ccgggcaatc   6420
tgcccccgaa gttcaccgcc tgcggcgtcg gccaccttga cccatgcctg atagttcttc   6480
gggctggttt ccactaccag ggcaggctcc cggccctcgg ctttcatgtc atccaggtca   6540
aactcgctga ggtcgtccac cagcaccaga ccatgccgct cctgctcggc gggcctgata   6600
tacacgtcat tgccctgggc attcatccgc ttgagccatg gcgtgttctg gagcacttcg   6660
gcggctgacc attcccggtt catcatctgg ccggtgggtg cgtccctgac gccgatatcg   6720
aagcgctcac agcccatggc cttgagctgt cggcctatgg cctgcaaagt cctgtcgttc   6780
ttcatcgggc caccaagcgc agccagatcg agccgtcctc ggttgtcagt ggcgtcaggt   6840
cgagcaagag caacgatgcg atcagcagca ccaccgtagg catcatggaa gccagcatca   6900
cggttagcca tagcttccag tgccaccccc gcgacgcgct ccgggcgctc tgcgcggcgc   6960
tgctcacctc ggcggctacc tcccgcaact ctttggccag ctccacccat gccgcccctg   7020
tctggcgctg ggctttcagc cactccgccg cctgcgcctc gctggcctgc ttggtctggc   7080
tcatgacctg ccgggcttcg tcggccagtg tcgccatgct ctgggccagc ggttcgatct   7140
gctccgctaa ctcgttgatg cctctggatt tcttcactct gtcgattgcg ttcatggtct   7200
attgcctccc ggtattcctg taagtcgatg atctgggcgt tggcggtgtc gatgttcagg   7260
gccacgtctg cccggtcggt gcggatgccc cggccttcca tctccaccac gttcggcccc   7320
aggtgaacac cgggcaggcg ctcgatgccc tgcgcctcaa gtgttctgtg gtcaatgcgg   7380
gcgtcgtggc cagcccgctc taatgcccgg ttggcatggt cggcccatgc ctcgcgggtc   7440
tgctcaagcc atgccttggg cttgagcgct tcggtcttct gtgccccgcc cttctccggg   7500
gtcttgccgt tgtaccgctt gaaccactga gcggcgggcc gctcgatgcc gtcattgatc   7560
cgctcggaga tcatcaggtg gcagtgcggg ttctcgccgc caccggcatg gatggccagc   7620
gtatacggca ggcgctcggc accggtcagg tgctgggcga actcggacgc cagcgccttc   7680
tgctggtcga gggtcagctc gaccggcagg gcaaattcga cctccttgaa cagccgccca   7740
ttggcgcgtt catacaggtc ggcagcatcc cagtagtcgg cgggccgctc gacgaactcc   7800
ggcatgtgcc cggattcggc gtgcaagact tcatccatgt cgcgggcata cttgccttcg   7860
cgctggatgt agtcggcctt ggccctggcc gattggccgc ccgacctgct gccggttttc   7920
gccgtaaggt gataaatcgc catgctgcct cgctgttgct tttgcttttc ggctccatgc   7980
aatggccctc ggagagcgca ccgcccgaag ggtggccgtt aggccagttt ctcgaagaga   8040
aaccggtaag tgcgccctcc cctacaaagt agggtcggga ttgccgccgc tgtgcctcca   8100
tgatagccta cgagacagca cattaacaat ggggtgtcaa gatggttaag gggagcaaca   8160
aggcggcgga tcggctggcc aagctcgaag aacaacgagc gcgaatcaat gccgaaattc   8220
agcgggagcg ggcaagggaa cagcagcaag agcgcaagaa cgaaacaagg cgcaaggtgc   8280
tggtgggggc catgattttg gccaaggtga acagcagcga gtggccggag gatcggctca   8340
tggcggcaat ggatgcgtac cttgaacgcg accacgaccg cgccttgttc ggtctgccgc   8400
cacgccagaa ggatgagccg ggctgaatga tcgaccgaga caggccctgc ggggctgcac   8460
```

-continued acgcgccccc acccttcggg tagggggaaa ggccgctaaa gcggctaaaa gcgctccagc 8520
gtatttctgc ggggtttggt gtggggttta gcgggctttg cccgcctttc cccctgccgc 8580
gcagcggtgg ggcggtgtgt agcctagcgc agcgaataga ccagctatcc ggcctctggc 8640
cgggcatatt gggcaagggc agcagcgccc cacaagggcg ctgataaccg cgcctagtgg 8700
attattctta gataatcatg gatggatttt tccaacaccc cgccagcccc cgcccctgct 8760
gggtttgcag gtttgggggc gtgacagtta ttgcaggggt tcgtgacagt tattgcaggg 8820
gggcgtgaca gttattgcag gggttcgtga cagttagtac gggagtgacg ggcactggct 8880
ggcaatgtct agcaacggca ggcatttcgg ctgagggtaa aagaactttc cgctaagcga 8940
tagactgtat gtaaacacag tattgcaagg acgcggaaca tgcctcatgt ggcggccagg 9000
acggccagcc gggatcggga tactggtcgt taccagagcc accgacccga gcaaaccctt 9060
ctctatcaga tcgttgacga gtattacccg gcattcgctg cgcttatggc agagcaggga 9120
aaggaattgc cgggctatgt gcaacgggaa tttgaagaat ttctccaatg cgggcggctg 9180
gagcatggct ttctacgggt tcgctgcgag tcttgccacg ccgagcacct ggtcgctttc 9240
agaaatcaat ctaaagtata tatgagtaaa cttggtctga cagttaccaa tgcttaatca 9300
gtgaggcacc tatctcagcg atctgtctat ttcgttcatc catagttgcc tgactccccg 9360
tcgtgtagat aactacgata cgggagggct taccatctgg ccccagtgct gcaatgatac 9420
cgcgagaccc acgctcaccg gctccagatt tatcagcaat aaaccagcca gccggaaggg 9480
ccgagcgcag aagtggtcct gcaactttat ccgcctccat ccagtctatt aattgttgcc 9540
gggaagctag agtaagtagt tcgccagtta atagtttgcg caacgttgtt gccattgcta 9600
caggcatcgt ggtgtcacgc tcgtcgtttg gtatggcttc attcagctcc ggttcccaac 9660
gatcaaggcg agttacatga tcccccatgt tgtgcaaaaa agcggttagc tccttcggtc 9720
ctccgatcgt tgtcagaagt aagttggccg cagtgttatc actcatggtt atggcagcac 9780
tgcataattc tcttactgtc atgccatccg taagatgctt ttctgtgact ggtgagtact 9840
caaccaagtc attctgagaa tagtgtatgc ggcgaccgag ttgctcttgc ccggcgtcaa 9900
cacgggataa taccgcgcca catagcagaa ctttaaaagt gctcatcatt ggaaaacgtt 9960
cttcggggcg aaaactctca aggatcttac cgctgttgag atccagttcg atgtaaccca 10020
ctcgtgcacc caactgatct tcagcatctt ttactttcac cagcgtttct gggtgagcaa 10080
aaacaggaag gcaaaatgcc gcaaaaaagg gaataagggc gacacggaaa tgttgaatac 10140
tcatactctt cctttttcaa tattattgaa gcatttatca gggttattgt ctcatgagcg 10200
gatacatatt tgaatgtatt tagaaaaata aacaaaagag tttgtagaaa cgcaaaaagg 10260
ccatccgtca ggatggcctt ctgcttaatt tgatgcctgg cagtttatgg cgggcgtcct 10320
gcccgccacc ctccgggccg ttgcttcgca acgttcaaat ccgctcccgg cggatttgtc 10380
ctactcagga gagcgttcac cgacaaacaa cagataaaac gaaaggccca gtctttcgac 10440
tgagcctttc gttttatttg atgcctggca gttccctact ctcgcatggg gagaccccac 10500
actaccatcg gcgctacggc gtttcacttc tgagttcggc atggggtcag gtgggaccac 10560
cgcgctactg ccgccaggca aattctgttt tatcagaccg cttctgcgtt ctgatttaat 10620
ctgtatcagg ctgaaaatct tctctcatcc gccaaaacag ccaagct 10667

<210> SEQ ID NO 21
<211> LENGTH: 28
<212> TYPE: DNA

<213> ORGANISM: Artificial
<220> FEATURE:
<223> OTHER INFORMATION: primer for amplifying Synechocystis spp. PCC
      6803 pyrR (SphI/KpnI)

<400> SEQUENCE: 21
cggtgtgcat gccgttattg atggaatg 28

<210> SEQ ID NO 22
<211> LENGTH: 32
<212> TYPE: DNA
<213> ORGANISM: Artificial
<220> FEATURE:
<223> OTHER INFORMATION: primer for amplifying Synechocystis spp. PCC
      6803 pyrR (SphI/KpnI)

<400> SEQUENCE: 22
tcactaggta cctaaattac ctgggaagcc ag 32

<210> SEQ ID NO 23
<211> LENGTH: 474
<212> TYPE: DNA
<213> ORGANISM: Synechocystis PCC6803

<400> SEQUENCE: 23
cggtgtgcat gccgttattg atggaatggg aagaagcaat ggtcacaata aactggaggt 60
tatgggtatg ttttttagcc ctaatgctcc aatcgccttg attgtatcga atgatgcagt 120
ctctaaaatt gtatccgtaa aagacctctg caccgccgac gggtctggat tatgggcaat 180
aatcacagtc gagccagact acccctggag gtaaactccg gggctggagc cataaagatt 240
aggaattcat taagaaatgt aacaatcgac gttctagatc ataccacgcc cccactgtcc 300
ggcagggtga acagaggaga ctttcccctg ttacagtgtc agtgacaaaa caactttttg 360
gcatcggtgc aggtggtgag ccatggcggc ccagatcatt gaaattcttt ccccggagga 420
aatccgacgt acccttaccc gtctggcttc ccaggtaatt taggtaccta gtga 474

<210> SEQ ID NO 24
<211> LENGTH: 35
<212> TYPE: DNA
<213> ORGANISM: Artificial
<220> FEATURE:
<223> OTHER INFORMATION: primer for amplifying Synechocystis spp. PCC
      6803 nirA (SphI/KpnI)

<400> SEQUENCE: 24
cccaaggcat gcaggaaaac aagctcagaa tgctg 35

<210> SEQ ID NO 25
<211> LENGTH: 42
<212> TYPE: DNA
<213> ORGANISM: Artificial
<220> FEATURE:
<223> OTHER INFORMATION: primer for amplifying Synechocystis spp. PCC
      6803 nirA (SphI/KpnI)

<400> SEQUENCE: 25
tttattggta ccaacgcttc aagccagata acagtagaga tc 42

<210> SEQ ID NO 26
<211> LENGTH: 384
<212> TYPE: DNA
<213> ORGANISM: Synechocystis PCC6803

<400> SEQUENCE: 26

```
cccaaggcat gcaggaaaac aagctcagaa tgctgcgggg agaagggcaa ctccccacca     60

gccccaaatt tttgctggcg ataaatattt ttcggtttaa ttgttcacaa agctttttga    120

atttgagttt atagaaattt attggctggt aatgcttttt tgcccccctg caggacttca    180

ttgatccttg cctataccat caatatcatt ggtcaataat gatgatgatt gactaaaaca    240

tgtttaacaa aatttaacgc atatgctaaa tgcgtaaact gcatatgcct tggctgagtg    300

taatttacgt tacaaatttt aacgaaacgg gaaccctata ttgatctcta ctgttatctg    360

gcttgaagcg ttggtaccaa taaa                                            384


<210> SEQ ID NO 27
<211> LENGTH: 26
<212> TYPE: DNA
<213> ORGANISM: Artificial
<220> FEATURE:
<223> OTHER INFORMATION: primer for amplifying Synechococcus elongatus
      PCC 7942 psbAII (SphI/KpnI)

<400> SEQUENCE: 27

atctttgcgt tccgtgacgg ctactg                                          26


<210> SEQ ID NO 28
<211> LENGTH: 25
<212> TYPE: DNA
<213> ORGANISM: Artificial
<220> FEATURE:
<223> OTHER INFORMATION: primer for amplifying Synechococcus elongatus
      PCC 7942 psbAII (SphI/KpnI)

<400> SEQUENCE: 28

gcagatggta ccggtcagca gagtg                                           25


<210> SEQ ID NO 29
<211> LENGTH: 676
<212> TYPE: DNA
<213> ORGANISM: Synechococcus PCC7942

<400> SEQUENCE: 29

atctttgcgt tccgtgacgg ctactgccag catgccgagc ctgatgtgtg acacctaaga     60

tcactccagt tctctttgga aactggctga tgagtgaaga caccatcttt ggcaagatca    120

tccggcgcga gattccagca gacattgttt atgaagatga tctctgtctg gcttttcgag    180

atgtggcacc ccaagcgccg gttcacattc tggtgattcc caagcaacca attgccaacc    240

ttttggaagc gacagcagaa catcaagcgc tgctgggtca tttgttgctg actgtaaagg    300

cgatcgcggc ccaagaagga ctcaccgagg gctaccgcac cgtgattaac acgggccctg    360

cgggtgggca aaccgtttac cacctgcata ttcacttact gggcgggcga tcgctggctt    420

ggccgcccgg ctgagaaaag tctgaaagtt ctttacaaaa ctcaatctgc ttgttagatt    480

ttactcacga ggctattaag tctcgtaaat agttcaacta aggactcatc gcaaaatgac    540

gactgcattg cagcggcgcg agagcgccag cctgtggcag cagttctgcg agtgggtaac    600

cagcaccgac aaccgcctct atgtgggttg gttcggcgtg ctgatgatcc ccactctgct    660

gaccggtacc atctgc                                                     676


<210> SEQ ID NO 30
<211> LENGTH: 40
<212> TYPE: DNA
<213> ORGANISM: Artificial
<220> FEATURE:
```

-continued

<223> OTHER INFORMATION: primer for amplifying Synechococcus elongatus
      PCC 7942 nirA

<400> SEQUENCE: 30
cagccagcat gcataaattt ctgttttgac caaaccatcc 40

<210> SEQ ID NO 31
<211> LENGTH: 34
<212> TYPE: DNA
<213> ORGANISM: Artificial
<220> FEATURE:
<223> OTHER INFORMATION: primer for amplifying Synechococcus elongatus
      PCC 7942 nirA

<400> SEQUENCE: 31
gtggctggta ccatggattc atctgcctac aaag 34

<210> SEQ ID NO 32
<211> LENGTH: 579
<212> TYPE: DNA
<213> ORGANISM: Synechococcus PCC7942

<400> SEQUENCE: 32
cagccagcat gcataaattt ctgttttgac caaaccatcc cgacataact cggtcagggc 60
ttgcaaaaca gcggggatgc gatcgtgctg ccagagactg caaaggtgag ccaataacca 120
ctgcgtctgc cagtcatcag gtatcgcttg gcagcgctgc aacccagctt cgaggacgcg 180
aacatcaact gttttggcca gttgctgaac ctgtcgccaa caatgttcaa aatcaccgct 240
tggccagccg tcactctctg caaacgctgc atcagtcatg tgcaatcaat acaggttaaa 300
aaccatgcta atggctccac ctaagcgggc ttcagagtca aggcttgtag caattgctac 360
taaaaactgc gatcgctgct gaaatgagct ggaattctgt ccctctcagc tcaaaaagta 420
tcaatgatta cttaatgttt gttctgcgca aacttcttgc agaacatgca tgatttacaa 480
aaagttgtag tttctgttac caattgcgaa tcgagaactg cctaatctgc cgagtatgca 540
agctgctttg taggcagatg aatccatggt accagccac 579

<210> SEQ ID NO 33
<211> LENGTH: 35
<212> TYPE: DNA
<213> ORGANISM: Artificial
<220> FEATURE:
<223> OTHER INFORMATION: primer for amplifying gammaPR (XbaI/KpnI)

<400> SEQUENCE: 33
gtgcattcta gatggctacg agggcagaca gtaag 35

<210> SEQ ID NO 34
<211> LENGTH: 50
<212> TYPE: DNA
<213> ORGANISM: Artificial
<220> FEATURE:
<223> OTHER INFORMATION: primer for amplifying gammaPR (XbaI/KpnI)

<400> SEQUENCE: 34
ttctgtggta ccatatggat cctccttctt aagatgcaac cattatcacc 50

<210> SEQ ID NO 35
<211> LENGTH: 1186
<212> TYPE: DNA
<213> ORGANISM: Artificial
<220> FEATURE:
<223> OTHER INFORMATION: gammaPR (XbaI/KpnI) promoter

<400> SEQUENCE: 35

```
gtgcattcta gatggctacg agggcagaca gtaagtggat ttaccataat cccttaattg    60
tacgcaccgc taaaacgcgt tcagcgcgat cacggcagca gacaggtaaa aatggcaaca   120
aaccacccta aaaactgcgc gatcgcgcct gataaatttt aaccgtatga ataccTatgc   180
aaccagaggg tacaggccac attaccccca cttaatccac tgaagctgcc attttTcatg   240
gtttcaccat cccagcgaag ggccatgcat gcatcgaaat taatacgacg aaattaatac   300
gactcactat agggcaattg ttatcagcta tgcgccgacc agaacacctt gccgatcagc   360
caaacgtctc ttcaggccac tgactagcga taactttccc cacaacggaa caactctcac   420
tgcatgggat cattgggtac tgtgggttta gtggttgtaa aaacacctga ccgctatccc   480
tgatcagttt cttgaaggta aactcatcac ccccaagtct ggctatgcag aaatcacctg   540
gctcaacagc ctgctcaggg tcaacgagaa ttaacattcc gtcaggaaag cttggcttgg   600
agcctgttgg tgcggtcatg gaattacctt caacctcaag ccagaatgca gaatcactgg   660
cttTcttggt tgtgcttacc catctctccg catcaccttt ggtaaaggtt ctaagcttag   720
gtgagaacat ccctgcctga acatgagaaa aaacagggta ctcatactca cttctaagtg   780
acggctgcat actaaccgct tcatacatct cgtagatttc tctggcgatt gaagggctaa   840
attcttcaac gctaactttg agaattttTg taagcaatgc ggcgttataa gcatttaatg   900
cattgatgcc attaaataaa gcaccaacgc ctgactgccc catccccatc ttgtctgcga   960
cagattcctg ggataagcca agttcatttt tctttttttc ataaattgct ttaaggcgac  1020
gtgcgtcctc aagctgctct tgtgttaatg gtttcttttt tgtgctcata cgttaaatct  1080
atcaccgcaa gggataaata tctaacaccg tgcgtgttga ctatTttacc tctggcggtg  1140
ataatggttg catcttaaga aggaggatcc atatggtacc acagaa               1186
```

<210> SEQ ID NO 36
<211> LENGTH: 31
<212> TYPE: DNA
<213> ORGANISM: Artificial
<220> FEATURE:
<223> OTHER INFORMATION: primer for amplifying Synechocystis spp. PCC 6803 dnaK (SphI/KpnI)

<400> SEQUENCE: 36

```
gccccagcat gcaccagtaa acataaatct c                                   31
```

<210> SEQ ID NO 37
<211> LENGTH: 30
<212> TYPE: DNA
<213> ORGANISM: Artificial
<220> FEATURE:
<223> OTHER INFORMATION: primer for amplifying Synechocystis spp. PCC 6803 dnaK (SphI/KpnI)

<400> SEQUENCE: 37

```
attggtggta ccgaggtcaa tcccaacaac                                     30
```

<210> SEQ ID NO 38
<211> LENGTH: 895
<212> TYPE: DNA
<213> ORGANISM: Synechocystis PCC6803

<400> SEQUENCE: 38

```
gccccagcat gcaccagtaa acataaatct ccccggcgac gcaaaaaacg ggtgaccatc    60
```

-continued

```
aagccggtgc gcttcggcat ttttctgctt tgcctagcag gcattgtggg gggggcaact    120

gccctaatta tcaatcgtac tggcgatccc ctaggtgggt tgctagaaga ccccctagat    180

gttttcctgg accaaccttc agaatttatc cccgatgaag ccacgagccg gaatttgatt    240

ctcagtcaac ccaacttcaa tcagcaagtg ggtcagatgg tagtacaagg ctggcttgat    300

agtaaaaagt tagcctttgg ccaaaactac gatgtcgggg cattgcagag tgttttagcc    360

cccaatctcc ttgcccaaca acggggtcgg gcccaacggg atcaagccca aaaggtctat    420

caccaatacg aacacaagtt gcagatttta gcctatcaag ttaacccccca agaccccaac    480

cgagccaccg ttactgcccg ggtagaagaa attagccagc cctttaccct aggtaatcaa    540

cagcagaagg gctccgccac caaagatgac ttgactgtgc gctatcagct agtacgacac    600

caaggggttt ggaaaattga ccaaatacaa gtggtaaatg gcccccgtta gtgcgtggcg    660

ttaactcccc ttttgaccaa tggcatacgg ctagatgccc ccataggtac ggaaacctgc    720

acttccgaga actaagcccc taccgtcact ataagagtgt gaacgtgtcg gccccaggca    780

atggattgga accatggctt ttcggcccat cgttgtgtct tatattctta cttgttaacg    840

ggagttaatt aaaattatgg gaaaagttgt tgggattgac ctcggtacca ccaat         895
```

<210> SEQ ID NO 39
<211> LENGTH: 28
<212> TYPE: DNA
<213> ORGANISM: Artificial
<220> FEATURE:
<223> OTHER INFORMATION: primer for amplifying Synechocystis spp. PCC 6803 kiaA (SphI/KpnI)

<400> SEQUENCE: 39

```
gccagagcat gcaaagctca ctaactgg                                        28
```

<210> SEQ ID NO 40
<211> LENGTH: 31
<212> TYPE: DNA
<213> ORGANISM: Artificial
<220> FEATURE:
<223> OTHER INFORMATION: primer for amplifying Synechocystis spp. PCC 6803 kiaA (SphI/KpnI)

<400> SEQUENCE: 40

```
ggaaaaggta cctgagtcta tgggcaacgt g                                    31
```

<210> SEQ ID NO 41
<211> LENGTH: 603
<212> TYPE: DNA
<213> ORGANISM: Synechocystis PCC6803

<400> SEQUENCE: 41

```
gccagagcat gcaaagctca ctaactgggc gggattttcc gggtccggtt gctgacggta     60

atagtcgtct aaaagtttgg ccacatccaa aaggctgtcg gcggggggat gctggccggc    120

gaggggatta attctgcttg tcatatacaa aaattgtaaa aaatggaggg cggcgatcag    180

gggcttagac acccaaatcc tagccaaaaa gggttaacta gccaagggct atccatgggc    240

aaagagataa aagaaaaagt ctccaaatcc ctggtcatag agaaaaaatt gccaaagtta    300

ccccaggcca tacacggccc agcgccaaga tggggagcac aaattcaaac tttgtaaaca    360

ggccggaagc tatccggcca aggagcactc agattgtgtt aacgttcagg ggagttgctt    420

aacacaattt tccaattaat agtattaata ttttcttaac ttgcaccgta ccatggtgag    480

aaagcctatc tgagccctta tttgattaac cttcgactga ttattgatcc cctgtgcagt    540
```

```
ctcccctctc cctctgtctt tttgctcccg aacacgttgc ccatagactc aggtaccttt    600

tcc                                                                  603
```

<210> SEQ ID NO 42
<211> LENGTH: 30
<212> TYPE: DNA
<213> ORGANISM: Artificial
<220> FEATURE:
<223> OTHER INFORMATION: primer for sequence analysis of pLybAL

<400> SEQUENCE: 42

```
gcttctgcgt tctgatttaa tctgtatcag                                      30
```

<210> SEQ ID NO 43
<211> LENGTH: 27
<212> TYPE: DNA
<213> ORGANISM: Artificial
<220> FEATURE:
<223> OTHER INFORMATION: primer for sequence analysis of pLybAL

<400> SEQUENCE: 43

```
atgggtctga atgtgcagaa tgtagag                                         27
```

<210> SEQ ID NO 44
<211> LENGTH: 11090
<212> TYPE: DNA
<213> ORGANISM: Artificial
<220> FEATURE:
<223> OTHER INFORMATION: plasmid pLybAL15

<400> SEQUENCE: 44

```
tgcatgccgt tattgatgga atgggaagaa gcaatggtca caataaactg gaggttatgg     60

gtatgttttt tagccctaat gctccaatcg ccttgattgt atcgaatgat gcagtctcta    120

aaattgtatc cgtaaaagac ctctgcaccg ccgacgggtc tggattatgg gcaataatca    180

cagtcgagcc agactacccc tggaggtaaa ctccggggct ggagccataa agattaggaa    240

ttcattaaga aatgtaacaa tcgacgttct agatcatacc acgcccccac tgtccggcag    300

ggtgaacaga ggagactttc ccctgttaca gtgtcagtga caaaacaact tttggcatc    360

ggtgcaggtg gtgagccatg gcggcccaga tcattgaaat tctttccccg gaggaaatcc    420

gacgtaccct tacccgtctg gcttcccagg taatttaggt accgagctcg aattggggcg    480

ttttctgtga ggctgactag cgcgtggcag ctcaaaatct ctacattctg cacattcaga    540

cccatggtct gctgcgaggg cagaacttgg aactggggcg agatgccgac accggcgggc    600

agaccaagta cgtcttagaa ctggctcaag cccaagctaa atccccacaa gtccaacaag    660

tcgacatcat cacccgccaa atcaccgacc cccgcgtcag tgttggttac agtcaggcga    720

tcgaaccctt tgcgcccaaa ggtcggattg tccgtttgcc ttttggcccc aaacgctacc    780

tccgtaaaga gctgctttgg ccccatctct acacctttgc ggatgcaatt ctccaatatc    840

tggctcagca aaagcgcacc ccgacttgga ttcaggccca ctatgctgat gctggccaag    900

tgggatcact gctgagtcgc tggttgaatg taccgctaat tttcacaggg cattctctgg    960

ggcggatcaa gctaaaaaag ctgttggagc aagactggcc gcttgaggaa attgaagcgc   1020

aattcaatat tcaacagcga attgatgcgg aggagatgac gctcactcat gctgactgga   1080

ttgtcgccag cactcagcag gaagtggagg agcaataccg cgtttacgat cgctacaacc   1140

cagagcgcaa gcttgtcatt ccaccgggtg tcgataccga tcgcttcagg tttcagccct   1200
```

-continued

```
tgggcgatcg cggtgttgtt ctccaacagg aactgagccg ctttctgcgc gacccagaaa   1260
aacctcaaat tctctgcctc tgtcgccccg cacctcgcaa aaatgtaccg gcgctggtgc   1320
gagcctttgg cgaacatcct tggctgcgca aaaaagccaa ccttgtctta gtactgggca   1380
gccgccaaga catcaaccag atggatcgcg gcagtcggca ggtgttccaa gagattttcc   1440
atctggtcga tcgctacgac ctctacggca gcgtcgccta tcccaaacag catcaggctg   1500
atgatgtgcc ggagttctat cgcctagcgg ctcattccgg cggggtattc gtcaatccgg   1560
cgctgaccga accttttggt ttgacaattt tggaggcagg aagctgcggc gtgccggtgg   1620
tggcaaccca tgatggcggc ccccaggaaa ttctcaaaca ctgtgatttc ggcactttag   1680
ttgatgtcag ccgacccgct aatatcgcga ctgcactcgc caccctgctg agcgatcgcg   1740
atctttggca gtgctatcac cgcaatggca ttgaaaaagt tcccgcccat tacagctggg   1800
atcaacatgt caataccctg tttgagcgca tggaaacggt ggctttgcct cgtcgtcgtg   1860
ctgtcagttt cgtacggagt cgcaaacgct tgattgatgc caaacgcctt gtcgttagtg   1920
acatcgacaa cacactgttg ggcgatcgtc aaggactcga gaatttaatg acctatctcg   1980
atcagtatcg cgatcatttt gcctttggaa ttgccacggg gcgtcgccta gactctgccc   2040
aagaagtctt gaaagagtgg ggcgttcctt cgccaaactt ctgggtgact tccgtcggca   2100
gcgagattca ctatggcacc gatgctgaac cggatatcag ctgggaaaag catatcaatc   2160
gcaactggaa tcctcagcga attcgggcag taatggcaca actacccttt cttgaactgc   2220
agccggaaga ggatcaaaca cccttcaaag tcagcttctt tgtccgcgat cgccacgaga   2280
ctgtgctgcg agaagtacgg caacatcttc gccgccatcg cctgcggctg aagtcaatct   2340
attcccatca ggagtttctt gacattctgc cgctagctgc ctcgaaaggg gatgcgattc   2400
gccacctctc actccgctgg cggattcctc ttgagaacat tttggtggca ggcgattctg   2460
gtaacgatga ggaaatgctc aagggccata atctcggcgt tgtagttggc aattactcac   2520
cggaattgga gccactgcgc agctacgagc gcgtctattt tgctgagggc cactatgcta   2580
atggcattct ggaagcctta aaacactatc gctttttttga ggcgatcgct taaccttttc   2640
agaatgagac gttgatcggc acgtaagcgt gagacgttga tcggcacgta agaggttcca   2700
actttcacca taatgaaata agatcactac cgggcgtatt ttttgagtta tcgagatttt   2760
caggagctaa ggaagctaaa atggagaaaa aaatcactgg atataccacc gttgatatat   2820
cccaatggca tcgtaaagaa cattttgagg catttcagtc agttgctcaa tgtacctata   2880
accagaccgt tcagctggat attacggcct ttttaaagac cgtaaagaaa aataagcaca   2940
agttttatcc ggcctttatt cacattcttg cccgcctgat gaatgctcat ccggaattcc   3000
gtatggcaat gaaagacggt gagctggtga tatgggatag tgttcaccct tgttacaccg   3060
ttttccatga gcaaactgaa acgttttcat cgctctggag tgaataccac gacgatttcc   3120
ggcagtttct acacatatat tcgcaagatg tggcgtgtta cggtgaaaac ctggcctatt   3180
tccctaaagg gtttattgag aatatgtttt tcgtctcagc caatccctgg gtgagtttca   3240
ccagttttga tttaaacgtg gccaatatgg acaacttctt cgcccccgtt ttcaccatgg   3300
gcaaatatta tacgcaaggc gacaaggtgc tgatgccgct ggcgattcag gttcatcatg   3360
ccgtttgtga tggcttccat gtcggcagaa tgcttaatga attacaacag tactgcgatg   3420
agtggcaggg cggggcgtaa tttttttaag gcagttattg gtgcccttaa acgcctggtt   3480
gctacgcctg aataagtgat aataagcgga tgaatggcag aaattcgatg ataagctgtc   3540
aaacacaacc accatcaaac aggattttcg cctgctgggg caaaccagcg tggaccgctt   3600
```

-continued

```
gctgcaactc tctcagggcc aggcggtgaa gggcaatcag ctgttgcccg tctcactggt   3660
gaaaagaaaa accaccctgg cgcccaatac gcaaaccgcc tctccccgcg cgttggccga   3720
ttcattaatg cagctggcac gacaggtttc ccgactggaa agcgggcagt gagcgcaacg   3780
caattaatgt aagttagcgc gaattgcaag ctggccgacg cgctgggcta cgtcttgctg   3840
gcgttcggga gcagaagagc atacatctgg aagcaaagcc aggaaagcgg cctatggagc   3900
tgtgcggcag cgctcagtag gcaatttttc aaaatattgt taagcctttt ctgagcatgg   3960
tatttttcat ggtattacca attagcagga aaataagcca ttgaatataa aagataaaaa   4020
tgtcttgttt acaatagagt ggggggggtc agcctgccgc cttgggccgg gtgatgtcgt   4080
acttgcccgc cgcgaactcg gttaccgtcc agcccagcgc gaccagctcc ggcaacgcct   4140
cgcgcacccg cttgcggcgc ttgcgcatgg tcgaaccact ggcctctgac ggccagacat   4200
agccgcacaa ggtatctatg gaagccttgc cggttttgcc ggggtcgatc cagccacaca   4260
gccgctggtg cagcaggcgg gcggtttcgc tgtccagcgc ccgcacctcg tccatgctga   4320
tgcgcacatg ctggccgcca cccatgacgg cctgcgcgat caaggggttc agggccacgt   4380
acaggcgccc gtccgcctcg tcgctggcgt actccgacag cagccgaaac ccctgccgct   4440
tgcggccatt ctgggcgatg atggatacct tccaaaggcg ctcgatgcag tcctgtatgt   4500
gcttgagcgc cccaccacta tcgacctctg ccccgatttc ctttgccagc gcccgatagc   4560
tacctttgac cacatggcat tcagcggtga cggcctccca cttgggttcc aggaacagcc   4620
ggagctgccg tccgccttcg gtcttgggtt ccgggccaag cactaggcca ttaggcccag   4680
ccatggccac cagcccttgc aggatgcgca gatcatcagc gcccagcggc tccgggccgc   4740
tgaactcgat ccgcttgccg tcgccgtagt catacgtcac gtccagcttg ctgcgcttgc   4800
gctcgccccg cttgagggca cggaacaggc cgggggccag acagtgcgcc gggtcgtgcc   4860
ggacgtggct gaggctgtgc ttgttcttag gcttcaccac ggggcacccc cttgctcttg   4920
cgctgcctct ccagcacggc gggcttgagc accccgccgt catgccgcct gaaccaccga   4980
tcagcgaacg gtgcgccata gttggccttg ctcacaccga agcggacgaa gaaccggcgc   5040
tggtcgtcgt ccacacccca ttcctcggcc tcggcgctgg tcatgctcga caggtaggac   5100
tgccagcgga tgttatcgac cagtaccgag ctgccccggc tggcctgctg ctggtcgcct   5160
gcgcccatca tggccgcgcc cttgctggca tggtgcagga acacgataga gcacccggta   5220
tcggcggcga tggcctccat gcgaccgatg acctgggcca tggggccgct ggcgttttct   5280
tcctcgatgt ggaaccggcg cagcgtgtcc agcaccatca ggcggcggcc ctcggcggcg   5340
cgcttgaggc cgtcgaacca ctccggggcc atgatgttgg gcaggctgcc gatcagcggc   5400
tggatcagca ggccgtcagc cacggcttgc cgttcctcgg cgctgaggtg cgccccaagg   5460
gcgtgcaggc ggtgatgaat ggcggtgggc gggtcttcgg cgggcaggta gatcaccggg   5520
ccggtgggca gttcgcccac ctccagcaga tccggcccgc ctgcaatctg tgcggccagt   5580
tgcagggcca gcatggattt accggcacca ccgggcgaca ccagcgcccc gaccgtaccg   5640
gccaccatgt tgggcaaaac gtagtccagc ggtggcggcg ctgctgcgaa cgcctccaga   5700
atattgatag gcttatgggt agccattgat tgcctccttt gcaggcagtt ggtggttagg   5760
cgctggcggg gtcactaccc ccgccctgcg ccgctctgag ttcttccagg cactcgcgca   5820
gcgcctcgta ttcgtcgtcg gtcagccaga acttgcgctg acgcatccct ttggccttca   5880
tgcgctcggc atatcgcgct tggcgtacag cgtcagggct ggccagcagg tcgccggtct   5940
```

gcttgtcctt ttggtctttc atatcagtca ccgagaaact tgccggggcc gaaaggcttg 6000
tcttcgcgga acaaggacaa ggtgcagccg tcaaggttaa ggctggccat atcagcgact 6060
gaaaagcggc cagcctcggc cttgtttgac gtataaccaa agccaccggg caaccaatag 6120
cccttgtcac ttttgatcag gtagaccgac cctgaagcgc ttttttcgta ttccataaaa 6180 ccccccttctg tgcgtgagta ctcatagtat aacaggcgtg agtaccaacg caagcactac 6240
atgctgaaat ctggcccgcc cctgtccatg cctcgctggc ggggtgccgg tgcccgtgcc 6300
agctcggccc gcgcaagctg gacgctgggc agacccatga ccttgctgac ggtgcgctcg 6360
atgtaatccg cttcgtggcc gggcttgcgc tctgccagcg ctgggctggc ctcggccatg 6420
gccttgccga tttcctcggc actgcggccc cggctggcca gcttctgcgc ggcgataaag 6480
tcgcacttgc tgaggtcatg accgaagcgc ttgaccagcc cggccatctc gctgcggtac 6540
tcgtccagcg ccgtgcgccg gtggcggcta agctgccgct cgggcagttc gaggctggcc 6600
agcctgcggg ccttctcctg ctgccgctgg gcctgctcga tctgctggcc agcctgctgc 6660
accagcgccg ggccagcggt ggcggtcttg cccttggatt cacgcagcag cacccacggc 6720
tgataaccgg cgcgggtggt gtgcttgtcc ttgcggttgg tgaagcccgc caagcggcca 6780
tagtggcggc tgtcggcgct ggccgggtcg gcgtcgtact cgctggccag cgtccgggca 6840
atctgccccc gaagttcacc gcctgcggcg tcggccacct tgacccatgc ctgatagttc 6900
ttcgggctgg tttccactac cagggcaggc tcccggccct cggctttcat gtcatccagg 6960
tcaaactcgc tgaggtcgtc caccagcacc agaccatgcc gctcctgctc ggcgggcctg 7020
atatacacgt cattgccctg ggcattcatc cgcttgagcc atggcgtgtt ctggagcact 7080
tcggcggctg accattcccg gttcatcatc tggccggtgg gtgcgtccct gacgccgata 7140
tcgaagcgct cacagcccat ggccttgagc tgtcggccta tggcctgcaa agtcctgtcg 7200
ttcttcatcg ggccaccaag cgcagccaga tcgagccgtc ctcggttgtc agtggcgtca 7260
ggtcgagcaa gagcaacgat gcgatcagca gcaccaccgt aggcatcatg gaagccagca 7320
tcacggttag ccatagcttc cagtgccacc cccgcgacgc gctccgggcg ctctgcgcgg 7380
cgctgctcac ctcggcggct acctcccgca actctttggc cagctccacc catgccgccc 7440
ctgtctggcg ctgggctttc agccactccg ccgcctgcgc ctcgctggcc tgcttggtct 7500
ggctcatgac ctgccgggct tcgtcggcca gtgtcgccat gctctgggcc agcggttcga 7560
tctgctccgc taactcgttg atgcctctgg atttcttcac tctgtcgatt gcgttcatgg 7620
tctattgcct cccggtattc ctgtaagtcg atgatctggg cgttggcggt gtcgatgttc 7680
agggccacgt ctgcccggtc ggtgcggatg ccccggcctt ccatctccac cacgttcggc 7740
cccaggtgaa caccgggcag gcgctcgatg ccctgcgcct caagtgttct gtggtcaatg 7800
cgggcgtcgt ggccagcccg ctctaatgcc cggttggcat ggtcggccca tgcctcgcgg 7860
gtctgctcaa gccatgcctt gggcttgagc gcttcggtct tctgtgcccc gcccttctcc 7920
ggggtcttgc cgttgtaccg cttgaaccac tgagcggcgg gccgctcgat gccgtcattg 7980
atccgctcgg agatcatcag gtggcagtgc gggttctcgc cgccaccggc atggatggcc 8040
agcgtatacg gcaggcgctc ggcaccggtc aggtgctggg cgaactcgga cgccagcgcc 8100
ttctgctggt cgagggtcag ctcgaccggc agggcaaatt cgacctcctt gaacagccgc 8160
ccattggcgc gttcatacag gtcggcagca tcccagtagt cggcgggccg ctcgacgaac 8220
tccggcatgt gcccggattc ggcgtgcaag acttcatcca tgtcgcgggc atacttgcct 8280
tcgcgctgga tgtagtcggc cttggccctg gccgattggc cgcccgacct gctgccggtt 8340

-continued ttcgccgtaa ggtgataaat cgccatgctg cctcgctgtt gcttttgctt ttcggctcca 8400
tgcaatggcc ctcggagagc gcaccgcccg aagggtggcc gttaggccag tttctcgaag 8460
agaaaccggt aagtgcgccc tcccctacaa agtagggtcg ggattgccgc cgctgtgcct 8520
ccatgatagc ctacgagaca gcacattaac aatggggtgt caagatggtt aaggggagca 8580
acaaggcggc ggatcggctg gccaagctcg aagaacaacg agcgcgaatc aatgccgaaa 8640
ttcagcggga gcgggcaagg gaacagcagc aagagcgcaa gaacgaaaca aggcgcaagg 8700
tgctggtggg ggccatgatt ttggccaagg tgaacagcag cgagtggccg gaggatcggc 8760
tcatggcggc aatggatgcg taccttgaac gcgaccacga ccgcgccttg ttcggtctgc 8820
cgccacgcca gaaggatgag ccgggctgaa tgatcgaccg agacaggccc tgcggggctg 8880
cacacgcgcc cccacccttc gggtaggggg aaaggccgct aaagcggcta aaagcgctcc 8940
agcgtatttc tgcggggttt ggtgtggggt ttagcgggct ttgcccgcct ttccccctgc 9000
cgcgcagcgg tggggcggtg tgtagcctag cgcagcgaat agaccagcta tccggcctct 9060
ggccgggcat attgggcaag ggcagcagcg ccccacaagg gcgctgataa ccgcgcctag 9120
tggattattc ttagataatc atggatggat ttttccaaca ccccgccagc cccgcccct 9180
gctgggtttg caggtttggg ggcgtgacag ttattgcagg ggttcgtgac agttattgca 9240
ggggggcgtg acagttattg caggggttcg tgacagttag tacgggagtg acgggcactg 9300
gctggcaatg tctagcaacg gcaggcattt cggctgaggg taaaagaact ttccgctaag 9360
cgatagactg tatgtaaaca cagtattgca aggacgcgga acatgcctca tgtggcggcc 9420
aggacggcca gccgggatcg ggatactggt cgttaccaga gccaccgacc cgagcaaacc 9480
cttctctatc agatcgttga cgagtattac ccggcattcg ctgcgcttat ggcagagcag 9540
ggaaaggaat tgccgggcta tgtgcaacgg gaatttgaag aatttctcca atgcgggcgg 9600
ctggagcatg gctttctacg ggttcgctgc gagtcttgcc acgccgagca cctggtcgct 9660
ttcagaaatc aatctaaagt atatatgagt aaacttggtc tgacagttac caatgcttaa 9720
tcagtgaggc acctatctca gcgatctgtc tatttcgttc atccatagtt gcctgactcc 9780
ccgtcgtgta gataactacg atacgggagg gcttaccatc tggccccagt gctgcaatga 9840
taccgcgaga cccacgctca ccggctccag atttatcagc aataaaccag ccagccggaa 9900
gggccgagcg cagaagtggt cctgcaactt tatccgcctc catccagtct attaattgtt 9960
gccgggaagc tagagtaagt agttcgccag ttaatagttt gcgcaacgtt gttgccattg 10020
ctacaggcat cgtggtgtca cgctcgtcgt ttggtatggc ttcattcagc tccggttccc 10080
aacgatcaag gcgagttaca tgatccccca tgttgtgcaa aaaagcggtt agctccttcg 10140
gtcctccgat cgttgtcaga agtaagttgg ccgcagtgtt atcactcatg gttatggcag 10200
cactgcataa ttctcttact gtcatgccat ccgtaagatg cttttctgtg actggtgagt 10260
actcaaccaa gtcattctga gaatagtgta tgcggcgacc gagttgctct tgcccggcgt 10320
caacacggga taataccgcg ccacatagca gaactttaaa agtgctcatc attggaaaac 10380
gttcttcggg gcgaaaactc tcaaggatct taccgctgtt gagatccagt tcgatgtaac 10440
ccactcgtgc acccaactga tcttcagcat cttttacttt caccagcgtt tctgggtgag 10500
caaaaacagg aaggcaaaat gccgcaaaaa agggaataag ggcgacacgg aaatgttgaa 10560
tactcatact cttccttttt caatattatt gaagcattta tcagggttat tgtctcatga 10620
gcggatacat atttgaatgt atttagaaaa ataaacaaaa gagtttgtag aaacgcaaaa 10680
aggccatccg tcaggatggc cttctgctta atttgatgcc tggcagttta tggcgggcgt 10740
cctgcccgcc accctccggg ccgttgcttc gcaacgttca aatccgctcc cggcggattt 10800
gtcctactca ggagagcgtt caccgacaaa caacagataa aacgaaaggc ccagtctttc 10860
gactgagcct ttcgttttat ttgatgcctg gcagttccct actctcgcat ggggagaccc 10920
cacactacca tcggcgctac ggcgtttcac ttctgagttc ggcatggggt caggtgggac 10980
caccgcgcta ctgccgccag gcaaattctg ttttatcaga ccgcttctgc gttctgattt 11040
aatctgtatc aggctgaaaa tcttctctca tccgccaaaa cagccaagct 11090

<210> SEQ ID NO 45
<211> LENGTH: 11000
<212> TYPE: DNA
<213> ORGANISM: Artificial
<220> FEATURE:
<223> OTHER INFORMATION: plasmid pLybAL16

<400> SEQUENCE: 45
tgcatgcagg aaaacaagct cagaatgctg cggggagaag ggcaactccc caccagcccc 60
aaatttttgc tggcgataaa tatttttcgg tttaattgtt cacaaagctt tttgaatttg 120
agtttataga aatttattgg ctggtaatgc ttttttgccc ccctgcagga cttcattgat 180
ccttgcctat accatcaata tcattggtca ataatgatga tgattgacta aaacatgttt 240
aacaaaattt aacgcatatg ctaaatgcgt aaactgcata tgccttggct gagtgtaatt 300
tacgttacaa attttaacga aacgggaacc ctatattgat ctctactgtt atctggcttg 360
aagcgttggt accgagctcg aattggggcg ttttctgtga ggctgactag cgcgtggcag 420
ctcaaaatct ctacattctg cacattcaga cccatggtct gctgcgaggg cagaacttgg 480
aactggggcg agatgccgac accggcgggc agaccaagta cgtcttagaa ctggctcaag 540
cccaagctaa atccccacaa gtccaacaag tcgacatcat cacccgccaa atcaccgacc 600
cccgcgtcag tgttggttac agtcaggcga tcgaaccctt tgcgcccaaa ggtcggattg 660
tccgtttgcc ttttggcccc aaacgctacc tccgtaaaga gctgctttgg ccccatctct 720
acacctttgc ggatgcaatt ctccaatatc tggctcagca aaagcgcacc ccgacttgga 780
ttcaggccca ctatgctgat gctggccaag tgggatcact gctgagtcgc tggttgaatg 840
taccgctaat tttcacaggg cattctctgg ggcggatcaa gctaaaaaag ctgttggagc 900
aagactggcc gcttgaggaa attgaagcgc aattcaatat tcaacagcga attgatgcgg 960
aggagatgac gctcactcat gctgactgga ttgtcgccag cactcagcag gaagtggagg 1020
agcaataccg cgtttacgat cgctacaacc cagagcgcaa gcttgtcatt ccaccgggtg 1080
tcgataccga tcgcttcagg tttcagccct tgggcgatcg cggtgttgtt ctccaacagg 1140
aactgagccg ctttctgcgc gacccagaaa aacctcaaat tctctgcctc tgtcgccccg 1200
cacctcgcaa aaatgtaccg gcgctggtgc gagcctttgg cgaacatcct tggctgcgca 1260
aaaaagccaa ccttgtctta gtactgggca gccgccaaga catcaaccag atggatcgcg 1320
gcagtcggca ggtgttccaa gagattttcc atctggtcga tcgctacgac ctctacggca 1380
gcgtcgccta tcccaaacag catcaggctg atgatgtgcc ggagttctat cgcctagcgg 1440
ctcattccgg cggggtattc gtcaatccgg cgctgaccga acctttttggt ttgacaattt 1500 tggaggcagg aagctgcggc gtgccggtgg tggcaaccca tgatggcggc ccccaggaaa 1560
ttctcaaaca ctgtgatttc ggcactttag ttgatgtcag ccgacccgct aatatcgcga 1620
ctgcactcgc caccctgctg agcgatcgcg atctttggca gtgctatcac cgcaatggca 1680

```
ttgaaaaagt tcccgcccat tacagctggg atcaacatgt caataccctg tttgagcgca    1740
tggaaacggt ggctttgcct cgtcgtcgtg ctgtcagttt cgtacggagt cgcaaacgct    1800
tgattgatgc caaacgcctt gtcgttagtg acatcgacaa cacactgttg ggcgatcgtc    1860
aaggactcga gaatttaatg acctatctcg atcagtatcg cgatcatttt gcctttggaa    1920
ttgccacggg gcgtcgccta gactctgccc aagaagtctt gaaagagtgg ggcgttcctt    1980
cgccaaactt ctgggtgact tccgtcggca gcgagattca ctatggcacc gatgctgaac    2040
cggatatcag ctgggaaaag catatcaatc gcaactggaa tcctcagcga attcgggcag    2100
taatggcaca actacccttt cttgaactgc agccggaaga ggatcaaaca cccttcaaag    2160
tcagcttctt tgtccgcgat cgccacgaga ctgtgctgcg agaagtacgg caacatcttc    2220
gccgccatcg cctgcggctg aagtcaatct attcccatca ggagtttctt gacattctgc    2280
cgctagctgc ctcgaaaggg gatgcgattc gccacctctc actccgctgg cggattcctc    2340
ttgagaacat tttggtggca ggcgattctg gtaacgatga ggaaatgctc aagggccata    2400
atctcggcgt tgtagttggc aattactcac cggaattgga gccactgcgc agctacgagc    2460
gcgtctattt tgctgagggc cactatgcta atggcattct ggaagcctta aaacactatc    2520
gcttttttga ggcgatcgct taaccttttc agaatgagac gttgatcggc acgtaagcgt    2580
gagacgttga tcggcacgta agaggttcca actttcacca taatgaaata agatcactac    2640
cgggcgtatt ttttgagtta tcgagatttt caggagctaa ggaagctaaa atggagaaaa    2700
aaatcactgg atataccacc gttgatatat cccaatggca tcgtaaagaa cattttgagg    2760
catttcagtc agttgctcaa tgtacctata accagaccgt tcagctggat attacggcct    2820
ttttaaagac cgtaaagaaa aataagcaca agttttatcc ggcctttatt cacattcttg    2880
cccgcctgat gaatgctcat ccggaattcc gtatggcaat gaaagacggt gagctggtga    2940
tatgggatag tgttcaccct tgttacaccg ttttccatga gcaaactgaa acgttttcat    3000
cgctctggag tgaataccac gacgatttcc ggcagtttct acacatatat tcgcaagatg    3060
tggcgtgtta cggtgaaaac ctggcctatt tccctaaagg gtttattgag aatatgtttt    3120
tcgtctcagc caatccctgg gtgagtttca ccagttttga tttaaacgtg gccaatatgg    3180
acaacttctt cgcccccgtt ttcaccatgg gcaaatatta tacgcaaggc gacaaggtgc    3240
tgatgccgct ggcgattcag gttcatcatg ccgtttgtga tggcttccat gtcggcagaa    3300
tgcttaatga attacaacag tactgcgatg agtggcaggg cggggcgtaa ttttttttaag    3360
gcagttattg gtgcccttaa acgcctggtt gctacgcctg aataagtgat aataagcgga    3420
tgaatggcag aaattcgatg ataagctgtc aaacacaacc accatcaaac aggattttcg    3480
cctgctgggg caaaccagcg tggaccgctt gctgcaactc tctcagggcc aggcggtgaa    3540
gggcaatcag ctgttgcccg tctcactggt gaaaagaaaa accaccctgg cgcccaatac    3600
gcaaaccgcc tctccccgcg cgttggccga ttcattaatg cagctggcac gacaggtttc    3660
ccgactggaa agcgggcagt gagcgcaacg caattaatgt aagttagcgc gaattgcaag    3720
ctggccgacg cgctgggcta cgtcttgctg gcgttcggga gcagaagagc atacatctgg    3780
aagcaaagcc aggaaagcgg cctatggagc tgtgcggcag cgctcagtag gcaatttttc    3840
aaaatattgt taagcctttt ctgagcatgg tatttttcat ggtattacca attagcagga    3900
aaataagcca ttgaatataa aagataaaaa tgtcttgttt acaatagagt gggggggtc     3960
agcctgccgc cttgggccgg gtgatgtcgt acttgcccgc cgcgaactcg gttaccgtcc    4020
```

-continued agcccagcgc gaccagctcc ggcaacgcct cgcgcacccg cttgcggcgc ttgcgcatgg 4080
tcgaaccact ggcctctgac ggccagacat agccgcacaa ggtatctatg gaagccttgc 4140
cggttttgcc ggggtcgatc cagccacaca gccgctggtg cagcaggcgg gcggtttcgc 4200
tgtccagcgc ccgcacctcg tccatgctga tgcgcacatg ctggccgcca cccatgacgg 4260
cctgcgcgat caaggggttc agggccacgt acaggcgccc gtccgcctcg tcgctggcgt 4320
actccgacag cagccgaaac ccctgccgct tgcggccatt ctgggcgatg atggatacct 4380
tccaaaggcg ctcgatgcag tcctgtatgt gcttgagcgc cccaccacta tcgacctctg 4440
ccccgatttc ctttgccagc gcccgatagc tacctttgac cacatggcat tcagcggtga 4500
cggcctccca cttgggttcc aggaacagcc ggagctgccg tccgccttcg gtcttgggtt 4560
ccgggccaag cactaggcca ttaggcccag ccatggccac cagcccttgc aggatgcgca 4620
gatcatcagc gcccagcggc tccgggccgc tgaactcgat ccgcttgccg tcgccgtagt 4680
catacgtcac gtccagcttg ctgcgcttgc gctcgccccg cttgagggca cggaacaggc 4740
cgggggccag acagtgcgcc gggtcgtgcc ggacgtggct gaggctgtgc ttgttcttag 4800
gcttcaccac ggggcacccc cttgctcttg cgctgcctct ccagcacggc gggcttgagc 4860
accccgccgt catgccgcct gaaccaccga tcagcgaacg gtgcgccata gttggccttg 4920
ctcacaccga agcggacgaa gaaccggcgc tggtcgtcgt ccacacccca ttcctcggcc 4980
tcggcgctgg tcatgctcga caggtaggac tgccagcgga tgttatcgac cagtaccgag 5040
ctgccccggc tggcctgctg ctggtcgcct gcgcccatca tggccgcgcc cttgctggca 5100
tggtgcagga acacgataga gcacccggta tcggcggcga tggcctccat gcgaccgatg 5160
acctgggcca tggggccgct ggcgttttct tcctcgatgt ggaaccggcg cagcgtgtcc 5220
agcaccatca ggcggcggcc ctcggcggcg cgcttgaggc cgtcgaacca ctccggggcc 5280
atgatgttgg gcaggctgcc gatcagcggc tggatcagca ggccgtcagc cacggcttgc 5340
cgttcctcgg cgctgaggtg cgccccaagg gcgtgcaggc ggtgatgaat ggcggtgggc 5400
gggtcttcgg cgggcaggta gatcaccggg ccggtgggca gttcgcccac ctccagcaga 5460
tccggcccgc ctgcaatctg tgcggccagt tgcagggcca gcatggattt accggcacca 5520
ccgggcgaca ccagcgcccc gaccgtaccg gccaccatgt tgggcaaaac gtagtccagc 5580
ggtggcggcg ctgctgcgaa cgcctccaga atattgatag gcttatgggt agccattgat 5640
tgcctccttt gcaggcagtt ggtggttagg cgctggcggg gtcactaccc ccgccctgcg 5700
ccgctctgag ttcttccagg cactcgcgca gcgcctcgta ttcgtcgtcg gtcagccaga 5760
acttgcgctg acgcatccct ttggccttca tgcgctcggc atatcgcgct tggcgtacag 5820
cgtcagggct ggccagcagg tcgccggtct gcttgtcctt ttggtctttc atatcagtca 5880
ccgagaaact tgccggggcc gaaaggcttg tcttcgcgga acaaggacaa ggtgcagccg 5940
tcaaggttaa ggctggccat atcagcgact gaaaagcggc cagcctcggc cttgtttgac 6000
gtataaccaa agccaccggg caaccaatag cccttgtcac ttttgatcag gtagaccgac 6060
cctgaagcgc ttttttcgta ttccataaaa ccccccttctg tgcgtgagta ctcatagtat 6120
aacaggcgtg agtaccaacg caagcactac atgctgaaat ctggcccgcc cctgtccatg 6180
cctcgctggc ggggtgccgg tgcccgtgcc agctcggccc gcgcaagctg gacgctgggc 6240
agacccatga ccttgctgac ggtgcgctcg atgtaatccg cttcgtggcc gggcttgcgc 6300
tctgccagcg ctgggctggc ctcggccatg gccttgccga tttcctcggc actgcggccc 6360
cggctggcca gcttctgcgc ggcgataaag tcgcacttgc tgaggtcatg accgaagcgc 6420

-continued

```
ttgaccagcc cggccatctc gctgcggtac tcgtccagcg ccgtgcgccg gtggcggcta   6480
agctgccgct cgggcagttc gaggctggcc agcctgcggg ccttctcctg ctgccgctgg   6540
gcctgctcga tctgctggcc agcctgctgc accagcgccg ggccagcggt ggcggtcttg   6600
cccttggatt cacgcagcag cacccacggc tgataaccgg cgcgggtggt gtgcttgtcc   6660
ttgcggttgg tgaagcccgc caagcggcca tagtggcggc tgtcggcgct ggccgggtcg   6720
gcgtcgtact cgctggccag cgtccgggca atctgccccc gaagttcacc gcctgcggcg   6780
tcggccacct tgacccatgc ctgatagttc ttcgggctgg tttccactac cagggcaggc   6840
tcccggccct cggctttcat gtcatccagg tcaaactcgc tgaggtcgtc caccagcacc   6900
agaccatgcc gctcctgctc ggcgggcctg atatacacgt cattgccctg ggcattcatc   6960
cgcttgagcc atggcgtgtt ctggagcact tcggcggctg accattcccg gttcatcatc   7020
tggccggtgg gtgcgtccct gacgccgata tcgaagcgct cacagcccat ggccttgagc   7080
tgtcggccta tggcctgcaa agtcctgtcg ttcttcatcg ggccaccaag cgcagccaga   7140
tcgagccgtc ctcggttgtc agtggcgtca ggtcgagcaa gagcaacgat gcgatcagca   7200
gcaccaccgt aggcatcatg gaagccagca tcacggttag ccatagcttc cagtgccacc   7260
cccgcgacgc gctccgggcg ctctgcgcgg cgctgctcac ctcggcggct acctcccgca   7320
actctttggc cagctccacc catgccgccc ctgtctggcg ctgggctttc agccactccg   7380
ccgcctgcgc ctcgctggcc tgcttggtct ggctcatgac ctgccgggct tcgtcggcca   7440
gtgtcgccat gctctgggcc agcggttcga tctgctccgc taactcgttg atgcctctgg   7500
atttcttcac tctgtcgatt gcgttcatgg tctattgcct cccggtattc ctgtaagtcg   7560
atgatctggg cgttggcggt gtcgatgttc agggccacgt ctgcccggtc ggtgcggatg   7620
ccccggcctt ccatctccac cacgttcggc cccaggtgaa caccgggcag gcgctcgatg   7680
ccctgcgcct caagtgttct gtggtcaatg cgggcgtcgt ggccagcccg ctctaatgcc   7740
cggttggcat ggtcggccca tgcctcgcgg gtctgctcaa gccatgcctt gggcttgagc   7800
gcttcggtct tctgtgcccc gcccttctcc ggggtcttgc cgttgtaccg cttgaaccac   7860
tgagcggcgg gccgctcgat gccgtcattg atccgctcgg agatcatcag gtggcagtgc   7920
gggttctcgc cgccaccggc atggatggcc agcgtatacg gcaggcgctc ggcaccggtc   7980
aggtgctggg cgaactcgga cgccagcgcc ttctgctggt cgagggtcag ctcgaccggc   8040
agggcaaatt cgacctcctt gaacagccgc ccattggcgc gttcatacag gtcggcagca   8100
tcccagtagt cggcgggccg ctcgacgaac tccggcatgt gcccggattc ggcgtgcaag   8160
acttcatcca tgtcgcgggc atacttgcct tcgcgctgga tgtagtcggc cttggccctg   8220
gccgattggc cgcccgacct gctgccggtt ttcgccgtaa ggtgataaat cgccatgctg   8280
cctcgctgtt gcttttgctt ttcggctcca tgcaatggcc ctcggagagc gcaccgcccg   8340
aagggtggcc gttaggccag tttctcgaag agaaaccggt aagtgcgccc tcccctacaa   8400
agtagggtcg ggattgccgc cgctgtgcct ccatgatagc ctacgagaca gcacattaac   8460
aatggggtgt caagatggtt aaggggagca acaaggcggc ggatcggctg gccaagctcg   8520
aagaacaacg agcgcgaatc aatgccgaaa ttcagcggga gcgggcaagg gaacagcagc   8580
aagagcgcaa gaacgaaaca aggcgcaagg tgctggtggg ggccatgatt ttggccaagg   8640
tgaacagcag cgagtggccg gaggatcggc tcatggcggc aatggatgcg taccttgaac   8700
gcgaccacga ccgcgccttg ttcggtctgc cgccacgcca gaaggatgag ccgggctgaa   8760
```

-continued tgatcgaccg agacaggccc tgcggggctg cacacgcgcc cccacccttc gggtaggggg 8820
aaaggccgct aaagcggcta aaagcgctcc agcgtatttc tgcggggttt ggtgtggggt 8880
ttagcgggct ttgcccgcct ttcccccctgc cgcgcagcgg tggggcggtg tgtagcctag 8940
cgcagcgaat agaccagcta tccggcctct ggccgggcat attgggcaag ggcagcagcg 9000
ccccacaagg gcgctgataa ccgcgcctag tggattattc ttagataatc atggatggat 9060
ttttccaaca ccccgccagc ccccgcccct gctgggtttg caggtttggg ggcgtgacag 9120
ttattgcagg ggttcgtgac agttattgca ggggggcgtg acagttattg caggggttcg 9180
tgacagttag tacgggagtg acgggcactg gctggcaatg tctagcaacg gcaggcattt 9240
cggctgaggg taaaagaact ttccgctaag cgatagactg tatgtaaaca cagtattgca 9300
aggacgcgga acatgcctca tgtggcggcc aggacggcca gccgggatcg ggatactggt 9360
cgttaccaga gccaccgacc cgagcaaacc cttctctatc agatcgttga cgagtattac 9420
ccggcattcg ctgcgcttat ggcagagcag ggaaaggaat tgccgggcta tgtgcaacgg 9480
gaatttgaag aatttctcca atgcgggcgg ctggagcatg gctttctacg ggttcgctgc 9540
gagtcttgcc acgccgagca cctggtcgct ttcagaaatc aatctaaagt atatatgagt 9600
aaacttggtc tgacagttac caatgcttaa tcagtgaggc acctatctca gcgatctgtc 9660
tatttcgttc atccatagtt gcctgactcc ccgtcgtgta gataactacg atacgggagg 9720
gcttaccatc tggccccagt gctgcaatga taccgcgaga cccacgctca ccggctccag 9780
atttatcagc aataaaccag ccagccggaa gggccgagcg cagaagtggt cctgcaactt 9840
tatccgcctc catccagtct attaattgtt gccgggaagc tagagtaagt agttcgccag 9900
ttaatagttt gcgcaacgtt gttgccattg ctacaggcat cgtggtgtca cgctcgtcgt 9960
ttggtatggc ttcattcagc tccggttccc aacgatcaag gcgagttaca tgatccccca 10020
tgttgtgcaa aaaagcggtt agctccttcg gtcctccgat cgttgtcaga agtaagttgg 10080
ccgcagtgtt atcactcatg gttatggcag cactgcataa ttctcttact gtcatgccat 10140
ccgtaagatg cttttctgtg actggtgagt actcaaccaa gtcattctga gaatagtgta 10200
tgcggcgacc gagttgctct tgcccggcgt caacacggga taataccgcg ccacatagca 10260
gaactttaaa agtgctcatc attggaaaac gttcttcggg gcgaaaactc tcaaggatct 10320
taccgctgtt gagatccagt tcgatgtaac ccactcgtgc acccaactga tcttcagcat 10380
cttttacttt caccagcgtt tctgggtgag caaaaacagg aaggcaaaat gccgcaaaaa 10440
agggaataag ggcgacacgg aaatgttgaa tactcatact cttccttttt caatattatt 10500
gaagcattta tcagggttat tgtctcatga gcggatacat atttgaatgt atttagaaaa 10560
ataaacaaaa gagtttgtag aaacgcaaaa aggccatccg tcaggatggc cttctgctta 10620
atttgatgcc tggcagttta tggcgggcgt cctgcccgcc accctccggg ccgttgcttc 10680
gcaacgttca aatccgctcc cggcggattt gtcctactca ggagagcgtt caccgacaaa 10740
caacagataa aacgaaaggc ccagtctttc gactgagcct ttcgttttat ttgatgcctg 10800
gcagttccct actctcgcat ggggagaccc cacactacca tcggcgctac ggcgtttcac 10860
ttctgagttc ggcatggggt caggtgggac caccgcgcta ctgccgccag gcaaattctg 10920
ttttatcaga ccgcttctgc gttctgattt aatctgtatc aggctgaaaa tcttctctca 10980
tccgccaaaa cagccaagct 11000

<210> SEQ ID NO 46
<211> LENGTH: 11269

<212> TYPE: DNA
<213> ORGANISM: Artificial
<220> FEATURE:
<223> OTHER INFORMATION: plasmid pLybAL17

<400> SEQUENCE: 46

```
tgcatgccga gcctgatgtg tgacacctaa gatcactcca gttctctttg gaaactggct      60
gatgagtgaa gacaccatct ttggcaagat catccggcgc gagattccag cagacattgt     120
ttatgaagat gatctctgtc tggcttttcg agatgtggca ccccaagcgc cggttcacat     180
tctggtgatt cccaagcaac caattgccaa ccttttggaa gcgacagcag aacatcaagc     240
gctgctgggt catttgttgc tgactgtaaa ggcgatcgcg gcccaagaag gactcaccga     300
gggctaccgc accgtgatta acacgggccc tgcgggtggg caaaccgttt accacctgca     360
tattcactta ctgggcgggc gatcgctggc ttggccgccc ggctgagaaa agtctgaaag     420
ttctttacaa aactcaatct gcttgttaga ttttactcac gaggctatta agtctcgtaa     480
atagttcaac taaggactca tcgcaaaatg acgactgcat tgcagcggcg cgagagcgcc     540
agcctgtggc agcagttctg cgagtgggta accagcaccg acaaccgcct ctatgtgggt     600
tggttcggcg tgctgatgat ccccactctg ctgaccggta ccgagctcga attggggcgt     660
tttctgtgag gctgactagc gcgtggcagc tcaaaatctc tacattctgc acattcagac     720
ccatggtctg ctgcgagggc agaacttgga actggggcga gatgccgaca ccggcgggca     780
gaccaagtac gtcttagaac tggctcaagc ccaagctaaa tccccacaag tccaacaagt     840
cgacatcatc acccgccaaa tcaccgaccc ccgcgtcagt gttggttaca gtcaggcgat     900
cgaacccttt gcgcccaaag gtcggattgt ccgtttgcct tttggcccca aacgctacct     960
ccgtaaagag ctgctttggc cccatctcta cacctttgcg gatgcaattc tccaatatct    1020
ggctcagcaa aagcgcaccc cgacttggat tcaggcccac tatgctgatg ctggccaagt    1080
gggatcactg ctgagtcgct ggttgaatgt accgctaatt ttcacagggc attctctggg    1140
gcggatcaag ctaaaaaagc tgttggagca agactggccg cttgaggaaa ttgaagcgca    1200
attcaatatt caacagcgaa ttgatgcgga ggagatgacg ctcactcatg ctgactggat    1260
tgtcgccagc actcagcagg aagtggagga gcaataccgc gtttacgatc gctacaaccc    1320
agagcgcaag cttgtcattc caccgggtgt cgataccgat cgcttcaggt ttcagccctt    1380
gggcgatcgc ggtgttgttc tccaacagga actgagccgc tttctgcgcg acccagaaaa    1440
acctcaaatt ctctgcctct gtcgccccgc acctcgcaaa aatgtaccgg cgctggtgcg    1500
agcctttggc gaacatcctt ggctgcgcaa aaaagccaac cttgtcttag tactgggcag    1560
ccgccaagac atcaaccaga tggatcgcgg cagtcggcag gtgttccaag agattttcca    1620
tctggtcgat cgctacgacc tctacggcag cgtcgcctat cccaaacagc atcaggctga    1680
tgatgtgccg gagttctatc gcctagcggc tcattccggc ggggtattcg tcaatccggc    1740
gctgaccgaa ccttttggtt tgacaatttt ggaggcagga agctgcggcg tgccggtggt    1800
ggcaacccat gatggcggcc cccaggaaat tctcaaacac tgtgatttcg gcactttagt    1860
tgatgtcagc cgacccgcta atatcgcgac tgcactcgcc accctgctga gcgatcgcga    1920
tctttggcag tgctatcacc gcaatggcat tgaaaaagtt cccgcccatt acagctggga    1980
tcaacatgtc aataccctgt ttgagcgcat ggaaacggtg gctttgcctc gtcgtcgtgc    2040
tgtcagtttc gtacggagtc gcaaacgctt gattgatgcc aaacgccttg tcgttagtga    2100
catcgacaac acactgttgg gcgatcgtca aggactcgag aatttaatga cctatctcga    2160
```

-continued tcagtatcgc gatcattttg cctttggaat tgccacgggg cgtcgcctag actctgccca 2220
agaagtcttg aaagagtggg gcgttccttc gccaaacttc tgggtgactt ccgtcggcag 2280
cgagattcac tatggcaccg atgctgaacc ggatatcagc tgggaaaagc atatcaatcg 2340
caactggaat cctcagcgaa ttcgggcagt aatggcacaa ctaccctttc ttgaactgca 2400
gccggaagag gatcaaacac ccttcaaagt cagcttcttt gtccgcgatc gccacgagac 2460
tgtgctgcga gaagtacggc aacatcttcg ccgccatcgc ctgcggctga agtcaatcta 2520
ttcccatcag gagtttcttg acattctgcc gctagctgcc tcgaaagggg atgcgattcg 2580
ccacctctca ctccgctggc ggattcctct tgagaacatt ttggtggcag gcgattctgg 2640
taacgatgag gaaatgctca agggccataa tctcggcgtt gtagttggca attactcacc 2700
ggaattggag ccactgcgca gctacgagcg cgtctatttt gctgagggcc actatgctaa 2760
tggcattctg gaagccttaa aacactatcg ctttttgag gcgatcgctt aacctttca 2820 gaatgagacg ttgatcggca cgtaagcgtg agacgttgat cggcacgtaa gaggttccaa 2880
ctttcaccat aatgaaataa gatcactacc gggcgtattt tttgagttat cgagattttc 2940
aggagctaag gaagctaaaa tggagaaaaa aatcactgga tataccaccg ttgatatatc 3000
ccaatggcat cgtaaagaac attttgaggc atttcagtca gttgctcaat gtacctataa 3060
ccagaccgtt cagctggata ttacggcctt tttaaagacc gtaaagaaaa ataagcacaa 3120
gttttatccg gcctttattc acattcttgc ccgcctgatg aatgctcatc cggaattccg 3180
tatggcaatg aaagacggtg agctggtgat atgggatagt gttcaccctt gttacaccgt 3240
tttccatgag caaactgaaa cgttttcatc gctctggagt gaataccacg acgatttccg 3300
gcagtttcta cacatatatt cgcaagatgt ggcgtgttac ggtgaaaacc tggcctattt 3360
ccctaaaggg tttattgaga atatgttttt cgtctcagcc aatccctggg tgagtttcac 3420
cagttttgat ttaaacgtgg ccaatatgga caacttcttc gcccccgttt tcaccatggg 3480
caaatattat acgcaaggcg acaaggtgct gatgccgctg gcgattcagg ttcatcatgc 3540
cgtttgtgat ggcttccatg tcggcagaat gcttaatgaa ttacaacagt actgcgatga 3600
gtggcagggc ggggcgtaat ttttttaagg cagttattgg tgcccttaaa cgcctggttg 3660
ctacgcctga ataagtgata ataagcggat gaatggcaga aattcgatga taagctgtca 3720
aacacaacca ccatcaaaca ggattttcgc ctgctggggc aaaccagcgt ggaccgcttg 3780
ctgcaactct ctcagggcca ggcggtgaag ggcaatcagc tgttgcccgt ctcactggtg 3840
aaaagaaaaa ccaccctggc gcccaatacg caaaccgcct ctccccgcgc gttggccgat 3900
tcattaatgc agctggcacg acaggtttcc cgactggaaa gcgggcagtg agcgcaacgc 3960
aattaatgta agttagcgcg aattgcaagc tggccgacgc gctgggctac gtcttgctgg 4020
cgttcgggag cagaagagca tacatctgga agcaaagcca ggaaagcggc ctatggagct 4080
gtgcggcagc gctcagtagg caatttttca aaatattgtt aagccttttc tgagcatggt 4140
atttttcatg gtattaccaa ttagcaggaa aataagccat tgaatataaa agataaaaat 4200
gtcttgttta caatagagtg gggggggtca gcctgccgcc ttgggccggg tgatgtcgta 4260
cttgcccgcc gcgaactcgg ttaccgtcca gcccagcgcg accagctccg gcaacgcctc 4320
gcgcacccgc ttgcggcgct tgcgcatggt cgaaccactg gcctctgacg gccagacata 4380
gccgcacaag gtatctatgg aagccttgcc ggttttgccg gggtcgatcc agccacacag 4440
ccgctggtgc agcaggcggg cggtttcgct gtccagcgcc cgcacctcgt ccatgctgat 4500
gcgcacatgc tggccgccac ccatgacggc ctgcgcgatc aaggggttca gggccacgta 4560
caggcgcccg tccgcctcgt cgctggcgta ctccgacagc agccgaaacc cctgccgctt 4620
gcggccattc tgggcgatga tggatacctt ccaaaggcgc tcgatgcagt cctgtatgtg 4680
cttgagcgcc ccaccactat cgacctctgc cccgatttcc tttgccagcg cccgatagct 4740
acctttgacc acatggcatt cagcggtgac ggcctcccac ttgggttcca ggaacagccg 4800
gagctgccgt ccgccttcgg tcttgggttc cgggccaagc actaggccat taggcccagc 4860
catggccacc agcccttgca ggatgcgcag atcatcagcg cccagcggct ccgggccgct 4920
gaactcgatc cgcttgccgt cgccgtagtc atacgtcacg tccagcttgc tgcgcttgcg 4980
ctcgccccgc ttgagggcac ggaacaggcc gggggccaga cagtgcgccg ggtcgtgccg 5040
gacgtggctg aggctgtgct tgttcttagg cttcaccacg gggcaccccc ttgctcttgc 5100
gctgcctctc cagcacggcg ggcttgagca ccccgccgtc atgccgcctg aaccaccgat 5160
cagcgaacgg tgcgccatag ttggccttgc tcacaccgaa gcggacgaag aaccggcgct 5220
ggtcgtcgtc cacaccccat tcctcggcct cggcgctggt catgctcgac aggtaggact 5280
gccagcggat gttatcgacc agtaccgagc tgccccggct ggcctgctgc tggtcgcctg 5340
cgcccatcat ggccgcgccc ttgctggcat ggtgcaggaa cacgatagag cacccggtat 5400
cggcggcgat ggcctccatg cgaccgatga cctgggccat ggggccgctg gcgttttctt 5460
cctcgatgtg gaaccggcgc agcgtgtcca gcaccatcag gcggcggccc tcggcggcgc 5520
gcttgaggcc gtcgaaccac tccggggcca tgatgttggg caggctgccg atcagcggct 5580
ggatcagcag gccgtcagcc acggcttgcc gttcctcggc gctgaggtgc gccccaaggg 5640
cgtgcaggcg gtgatgaatg gcggtgggcg ggtcttcggc gggcaggtag atcaccgggc 5700
cggtgggcag ttcgcccacc tccagcagat ccggcccgcc tgcaatctgt gcggccagtt 5760
gcagggccag catggattta ccggcaccac cgggcgacac cagcgccccg accgtaccgg 5820
ccaccatgtt gggcaaaacg tagtccagcg gtggcggcgc tgctgcgaac gcctccagaa 5880
tattgatagg cttatgggta gccattgatt gcctcctttg caggcagttg gtggttaggc 5940
gctggcgggg tcactacccc cgccctgcgc cgctctgagt tcttccaggc actcgcgcag 6000
cgcctcgtat tcgtcgtcgg tcagccagaa cttgcgctga cgcatccctt tggccttcat 6060
gcgctcggca tatcgcgctt ggcgtacagc gtcagggctg gccagcaggt cgccggtctg 6120
cttgtccttt tggtctttca tatcagtcac cgagaaactt gccggggccg aaaggcttgt 6180
cttcgcggaa caaggacaag gtgcagccgt caaggttaag gctggccata tcagcgactg 6240
aaaagcggcc agcctcggcc ttgtttgacg tataaccaaa gccaccgggc aaccaatagc 6300
ccttgtcact tttgatcagg tagaccgacc ctgaagcgct tttttcgtat tccataaaac 6360
ccccttctgt gcgtgagtac tcatagtata acaggcgtga gtaccaacgc aagcactaca 6420
tgctgaaatc tggcccgccc ctgtccatgc ctcgctggcg gggtgccggt gcccgtgcca 6480
gctcggcccg cgcaagctgg acgctgggca gacccatgac cttgctgacg gtgcgctcga 6540
tgtaatccgc ttcgtggccg ggcttgcgct ctgccagcgc tgggctggcc tcggccatgg 6600
ccttgccgat ttcctcggca ctgcggcccc ggctggccag cttctgcgcg gcgataaagt 6660
cgcacttgct gaggtcatga ccgaagcgct tgaccagccc ggccatctcg ctgcggtact 6720
cgtccagcgc cgtgcgccgg tggcggctaa gctgccgctc gggcagttcg aggctggcca 6780
gcctgcgggc cttctcctgc tgccgctggg cctgctcgat ctgctggcca gcctgctgca 6840
ccagcgccgg gccagcggtg gcggtcttgc ccttggattc acgcagcagc acccacggct 6900

-continued gataaccggc gcgggtggtg tgcttgtcct tgcggttggt gaagcccgcc aagcggccat 6960
agtggcggct gtcggcgctg gccgggtcgg cgtcgtactc gctggccagc gtccgggcaa 7020
tctgcccccg aagttcaccg cctgcggcgt cggccacctt gacccatgcc tgatagttct 7080
tcgggctggt ttccactacc agggcaggct cccggccctc ggctttcatg tcatccaggt 7140
caaactcgct gaggtcgtcc accagcacca gaccatgccg ctcctgctcg gcgggcctga 7200
tatacacgtc attgccctgg gcattcatcc gcttgagcca tggcgtgttc tggagcactt 7260
cggcggctga ccattcccgg ttcatcatct ggccggtggg tgcgtccctg acgccgatat 7320
cgaagcgctc acagcccatg gccttgagct gtcggcctat ggcctgcaaa gtcctgtcgt 7380
tcttcatcgg gccaccaagc gcagccagat cgagccgtcc tcggttgtca gtggcgtcag 7440
gtcgagcaag agcaacgatg cgatcagcag caccaccgta ggcatcatgg aagccagcat 7500
cacggttagc catagcttcc agtgccaccc ccgcgacgcg ctccgggcgc tctgcgcggc 7560
gctgctcacc tcggcggcta cctcccgcaa ctctttggcc agctccaccc atgccgcccc 7620
tgtctggcgc tgggctttca gccactccgc cgcctgcgcc tcgctggcct gcttggtctg 7680
gctcatgacc tgccgggctt cgtcggccag tgtcgccatg ctctgggcca gcggttcgat 7740
ctgctccgct aactcgttga tgcctctgga tttcttcact ctgtcgattg cgttcatggt 7800
ctattgcctc ccggtattcc tgtaagtcga tgatctgggc gttggcggtg tcgatgttca 7860
gggccacgtc tgcccggtcg gtgcggatgc cccggccttc catctccacc acgttcggcc 7920
ccaggtgaac accgggcagg cgctcgatgc cctgcgcctc aagtgttctg tggtcaatgc 7980
gggcgtcgtg gccagcccgc tctaatgccc ggttggcatg gtcggcccat gcctcgcggg 8040
tctgctcaag ccatgccttg ggcttgagcg cttcggtctt ctgtgccccg cccttctccg 8100
gggtcttgcc gttgtaccgc ttgaaccact gagcggcggg ccgctcgatg ccgtcattga 8160
tccgctcgga gatcatcagg tggcagtgcg ggttctcgcc gccaccggca tggatggcca 8220
gcgtatacgg caggcgctcg gcaccggtca ggtgctgggc gaactcggac gccagcgcct 8280
tctgctggtc gagggtcagc tcgaccggca gggcaaattc gacctccttg aacagccgcc 8340
cattggcgcg ttcatacagg tcggcagcat cccagtagtc ggcgggccgc tcgacgaact 8400
ccggcatgtg cccggattcg gcgtgcaaga cttcatccat gtcgcgggca tacttgcctt 8460
cgcgctggat gtagtcggcc ttggccctgg ccgattggcc gcccgacctg ctgccggttt 8520
tcgccgtaag gtgataaatc gccatgctgc ctcgctgttg cttttgcttt tcggctccat 8580
gcaatggccc tcggagagcg caccgcccga agggtggccg ttaggccagt ttctcgaaga 8640
gaaaccggta agtgcgccct cccctacaaa gtagggtcgg gattgccgcc gctgtgcctc 8700
catgatagcc tacgagacag cacattaaca atggggtgtc aagatggtta aggggagcaa 8760
caaggcggcg gatcggctgg ccaagctcga agaacaacga gcgcgaatca atgccgaaat 8820
tcagcgggag cgggcaaggg aacagcagca agagcgcaag aacgaaacaa ggcgcaaggt 8880
gctggtgggg gccatgattt tggccaaggt gaacagcagc gagtggccgg aggatcggct 8940
catggcggca atggatgcgt accttgaacg cgaccacgac cgcgccttgt tcggtctgcc 9000
gccacgccag aaggatgagc cgggctgaat gatcgaccga gacaggccct gcggggctgc 9060
acacgcgccc ccaccccttcg ggtaggggga aaggccgcta aagcggctaa aagcgctcca 9120
gcgtatttct gcggggtttg gtgtggggtt tagcgggctt tgcccgcctt tccccctgcc 9180
gcgcagcggt ggggcggtgt gtagcctagc gcagcgaata gaccagctat ccggcctctg 9240
gccgggcata ttgggcaagg gcagcagcgc cccacaaggg cgctgataac cgcgcctagt 9300
ggattattct tagataatca tggatggatt tttccaacac cccgccagcc cccgcccctg 9360
ctgggtttgc aggtttgggg gcgtgacagt tattgcaggg gttcgtgaca gttattgcag 9420
gggggcgtga cagttattgc aggggttcgt gacagttagt acgggagtga cgggcactgg 9480
ctggcaatgt ctagcaacgg caggcatttc ggctgagggt aaaagaactt tccgctaagc 9540
gatagactgt atgtaaacac agtattgcaa ggacgcggaa catgcctcat gtggcggcca 9600
ggacggccag ccgggatcgg gatactggtc gttaccagag ccaccgaccc gagcaaaccc 9660
ttctctatca gatcgttgac gagtattacc cggcattcgc tgcgcttatg gcagagcagg 9720
gaaaggaatt gccgggctat gtgcaacggg aatttgaaga atttctccaa tgcgggcggc 9780
tggagcatgg ctttctacgg gttcgctgcg agtcttgcca cgccgagcac ctggtcgctt 9840
tcagaaatca atctaaagta tatatgagta aacttggtct gacagttacc aatgcttaat 9900
cagtgaggca cctatctcag cgatctgtct atttcgttca tccatagttg cctgactccc 9960
cgtcgtgtag ataactacga tacgggaggg cttaccatct ggccccagtg ctgcaatgat 10020
accgcgagac ccacgctcac cggctccaga tttatcagca ataaaccagc cagccggaag 10080
ggccgagcgc agaagtggtc ctgcaacttt atccgcctcc atccagtcta ttaattgttg 10140
ccgggaagct agagtaagta gttcgccagt taatagtttg cgcaacgttg ttgccattgc 10200
tacaggcatc gtggtgtcac gctcgtcgtt tggtatggct tcattcagct ccggttccca 10260
acgatcaagg cgagttacat gatcccccat gttgtgcaaa aaagcggtta gctccttcgg 10320
tcctccgatc gttgtcagaa gtaagttggc cgcagtgtta tcactcatgg ttatggcagc 10380
actgcataat tctcttactg tcatgccatc cgtaagatgc ttttctgtga ctggtgagta 10440
ctcaaccaag tcattctgag aatagtgtat gcggcgaccg agttgctctt gcccggcgtc 10500
aacacgggat aataccgcgc cacatagcag aactttaaaa gtgctcatca ttggaaaacg 10560
ttcttcgggg cgaaaactct caaggatctt accgctgttg agatccagtt cgatgtaacc 10620
cactcgtgca cccaactgat cttcagcatc ttttactttc accagcgttt ctgggtgagc 10680
aaaaacagga aggcaaaatg ccgcaaaaaa gggaataagg gcgacacgga aatgttgaat 10740
actcatactc ttcctttttc aatattattg aagcatttat cagggttatt gtctcatgag 10800
cggatacata tttgaatgta tttagaaaaa taaacaaaag agtttgtaga aacgcaaaaa 10860
ggccatccgt caggatggcc ttctgcttaa tttgatgcct ggcagtttat ggcgggcgtc 10920
ctgcccgcca ccctccgggc cgttgcttcg caacgttcaa atccgctccc ggcggatttg 10980
tcctactcag gagagcgttc accgacaaac aacagataaa acgaaaggcc cagtctttcg 11040
actgagcctt tcgttttatt tgatgcctgg cagttcccta ctctcgcatg gggagacccc 11100
acactaccat cggcgctacg gcgtttcact tctgagttcg gcatggggtc aggtgggacc 11160
accgcgctac tgccgccagg caaattctgt tttatcagac cgcttctgcg ttctgattta 11220
atctgtatca ggctgaaaat cttctctcat ccgccaaaac agccaagct 11269

<210> SEQ ID NO 47
<211> LENGTH: 11195
<212> TYPE: DNA
<213> ORGANISM: Artificial
<220> FEATURE:
<223> OTHER INFORMATION: plasmid pLybAL18

<400> SEQUENCE: 47
tgcatgcata aatttctgtt ttgaccaaac catcccgaca taactcggtc agggcttgca 60

-continued

```
aaacagcggg gatgcgatcg tgctgccaga gactgcaaag gtgagccaat aaccactgcg    120
tctgccagtc atcaggtatc gcttggcagc gctgcaaccc agcttcgagg acgcgaacat    180
caactgtttt ggccagttgc tgaacctgtc gccaacaatg ttcaaaatca ccgcttggcc    240
agccgtcact ctctgcaaac gctgcatcag tcatgtgcaa tcaatacagg ttaaaaacca    300
tgctaatggc tccacctaag cgggcttcag agtcaaggct tgtagcaatt gctactaaaa    360
actgcgatcg ctgctgaaat gagctggaat tctgtccctc tcagctcaaa aagtatcaat    420
gattacttaa tgtttgttct gcgcaaactt cttgcagaac atgcatgatt tacaaaaagt    480
tgtagtttct gttaccaatt gcgaatcgag aactgcctaa tctgccgagt atgcaagctg    540
ctttgtaggc agatgaatcc atggtaccga gctcgaattg gggcgttttc tgtgaggctg    600
actagcgcgt ggcagctcaa aatctctaca ttctgcacat tcagacccat ggtctgctgc    660
gagggcagaa cttggaactg gggcgagatg ccgacaccgg cgggcagacc aagtacgtct    720
tagaactggc tcaagcccaa gctaaatccc cacaagtcca acaagtcgac atcatcaccc    780
gccaaatcac cgacccccgc gtcagtgttg gttacagtca ggcgatcgaa ccctttgcgc    840
ccaaaggtcg gattgtccgt ttgccttttg gccccaaacg ctacctccgt aaagagctgc    900
tttggcccca tctctacacc tttgcggatg caattctcca atatctggct cagcaaaagc    960
gcaccccgac ttggattcag gcccactatg ctgatgctgg ccaagtggga tcactgctga   1020
gtcgctggtt gaatgtaccg ctaattttca cagggcattc tctggggcgg atcaagctaa   1080
aaaagctgtt ggagcaagac tggccgcttg aggaaattga agcgcaattc aatattcaac   1140
agcgaattga tgcggaggag atgacgctca ctcatgctga ctggattgtc gccagcactc   1200
agcaggaagt ggaggagcaa taccgcgttt acgatcgcta caacccagag cgcaagcttg   1260
tcattccacc gggtgtcgat accgatcgct tcaggtttca gcccttgggc gatcgcggtg   1320
ttgttctcca acaggaactg agccgctttc tgcgcgaccc agaaaaacct caaattctct   1380
gcctctgtcg ccccgcacct cgcaaaaatg taccggcgct ggtgcgagcc tttggcgaac   1440
atccttggct gcgcaaaaaa gccaaccttg tcttagtact gggcagccgc caagacatca   1500
accagatgga tcgcggcagt cggcaggtgt tccaagagat tttccatctg gtcgatcgct   1560
acgacctcta cggcagcgtc gcctatccca aacagcatca ggctgatgat gtgccggagt   1620
tctatcgcct agcggctcat tccggcgggg tattcgtcaa tccggcgctg accgaacctt   1680
ttggtttgac aattttggag gcaggaagct gcggcgtgcc ggtggtggca acccatgatg   1740
gcggccccca ggaaattctc aaacactgtg atttcggcac tttagttgat gtcagccgac   1800
ccgctaatat cgcgactgca ctcgccaccc tgctgagcga tcgcgatctt tggcagtgct   1860
atcaccgcaa tggcattgaa aaagttcccg cccattacag ctgggatcaa catgtcaata   1920
ccctgtttga gcgcatggaa acggtggctt tgcctcgtcg tcgtgctgtc agtttcgtac   1980
ggagtcgcaa acgcttgatt gatgccaaac gccttgtcgt tagtgacatc gacaacacac   2040
tgttgggcga tcgtcaagga ctcgagaatt taatgaccta tctcgatcag tatcgcgatc   2100
attttgcctt tggaattgcc acggggcgtc gcctagactc tgcccaagaa gtcttgaaag   2160
agtggggcgt tccttcgcca aacttctggg tgacttccgt cggcagcgag attcactatg   2220
gcaccgatgc tgaaccggat atcagctggg aaaagcatat caatcgcaac tggaatcctc   2280
agcgaattcg ggcagtaatg gcacaactac cctttcttga actgcagccg gaagaggatc   2340
aaacaccctt caaagtcagc ttctttgtcc gcgatcgcca cgagactgtg ctgcgagaag   2400
tacggcaaca tcttcgccgc catcgcctgc ggctgaagtc aatctattcc catcaggagt   2460
```

-continued ttcttgacat tctgccgcta gctgcctcga aaggggatgc gattcgccac ctctcactcc 2520
gctggcggat tcctcttgag aacattttgg tggcaggcga ttctggtaac gatgaggaaa 2580
tgctcaaggg ccataatctc ggcgttgtag ttggcaatta ctcaccggaa ttggagccac 2640
tgcgcagcta cgagcgcgtc tattttgctg agggccacta tgctaatggc attctggaag 2700
ccttaaaaca ctatcgcttt tttgaggcga tcgcttaacc ttttcagaat gagacgttga 2760
tcggcacgta agcgtgagac gttgatcggc acgtaagagg ttccaacttt caccataatg 2820
aaataagatc actaccgggc gtattttttg agttatcgag attttcagga gctaaggaag 2880
ctaaaatgga gaaaaaaatc actggatata ccaccgttga tatatcccaa tggcatcgta 2940
aagaacattt tgaggcattt cagtcagttg ctcaatgtac ctataaccag accgttcagc 3000
tggatattac ggccttttta aagaccgtaa agaaaaataa gcacaagttt tatccggcct 3060
ttattcacat tcttgcccgc ctgatgaatg ctcatccgga attccgtatg gcaatgaaag 3120
acggtgagct ggtgatatgg gatagtgttc acccttgtta caccgttttc catgagcaaa 3180
ctgaaacgtt ttcatcgctc tggagtgaat accacgacga tttccggcag tttctacaca 3240
tatattcgca agatgtggcg tgttacggtg aaaacctggc ctatttccct aaagggttta 3300
ttgagaatat gtttttcgtc tcagccaatc cctgggtgag tttcaccagt tttgatttaa 3360
acgtggccaa tatggacaac ttcttcgccc ccgttttcac catgggcaaa tattatacgc 3420
aaggcgacaa ggtgctgatg ccgctggcga ttcaggttca tcatgccgtt tgtgatggct 3480
tccatgtcgg cagaatgctt aatgaattac aacagtactg cgatgagtgg cagggcgggg 3540
cgtaattttt ttaaggcagt tattggtgcc cttaaacgcc tggttgctac gcctgaataa 3600
gtgataataa gcggatgaat ggcagaaatt cgatgataag ctgtcaaaca caaccaccat 3660
caaacaggat tttcgcctgc tggggcaaac cagcgtggac cgcttgctgc aactctctca 3720
gggccaggcg gtgaagggca atcagctgtt gcccgtctca ctggtgaaaa gaaaaaccac 3780
cctggcgccc aatacgcaaa ccgcctctcc ccgcgcgttg gccgattcat taatgcagct 3840
ggcacgacag gtttcccgac tggaaagcgg gcagtgagcg caacgcaatt aatgtaagtt 3900
agcgcgaatt gcaagctggc cgacgcgctg ggctacgtct tgctggcgtt cgggagcaga 3960
agagcataca tctggaagca aagccaggaa agcggcctat ggagctgtgc ggcagcgctc 4020
agtaggcaat ttttcaaaat attgttaagc cttttctgag catggtattt ttcatggtat 4080
taccaattag caggaaaata agccattgaa tataaaagat aaaaatgtct tgtttacaat 4140
agagtggggg gggtcagcct gccgccttgg gccgggtgat gtcgtacttg cccgccgcga 4200
actcggttac cgtccagccc agcgcgacca gctccggcaa cgcctcgcgc acccgcttgc 4260
ggcgcttgcg catggtcgaa ccactggcct ctgacggcca gacatagccg cacaaggtat 4320
ctatggaagc cttgccggtt ttgccggggt cgatccagcc acacagccgc tggtgcagca 4380
ggcgggcggt ttcgctgtcc agcgcccgca cctcgtccat gctgatgcgc acatgctggc 4440
cgccacccat gacggcctgc gcgatcaagg ggttcagggc cacgtacagg cgcccgtccg 4500
cctcgtcgct ggcgtactcc gacagcagcc gaaacccctg ccgcttgcgg ccattctggg 4560
cgatgatgga taccttccaa aggcgctcga tgcagtcctg tatgtgcttg agcgccccac 4620
cactatcgac ctctgccccg atttcctttg ccagcgcccg atagctacct ttgaccacat 4680
ggcattcagc ggtgacggcc tcccacttgg gttccaggaa cagccggagc tgccgtccgc 4740
cttcggtctt gggttccggg ccaagcacta ggccattagg cccagccatg gccaccagcc 4800

-continued

```
cttgcaggat gcgcagatca tcagcgccca gcggctccgg gccgctgaac tcgatccgct   4860
tgccgtcgcc gtagtcatac gtcacgtcca gcttgctgcg cttgcgctcg ccccgcttga   4920
gggcacggaa caggccgggg gccagacagt gcgccgggtc gtgccggacg tggctgaggc   4980
tgtgcttgtt cttaggcttc accacggggc accccccttgc tcttgcgctg cctctccagc   5040
acggcgggct tgagcacccc gccgtcatgc cgcctgaacc accgatcagc gaacggtgcg   5100
ccatagttgg ccttgctcac accgaagcgg acgaagaacc ggcgctggtc gtcgtccaca   5160
ccccattcct cggcctcggc gctggtcatg ctcgacaggt aggactgcca gcggatgtta   5220
tcgaccagta ccgagctgcc ccggctggcc tgctgctggt cgcctgcgcc catcatggcc   5280
gcgcccttgc tggcatggtg caggaacacg atagagcacc cggtatcggc ggcgatggcc   5340
tccatgcgac cgatgacctg ggccatgggg ccgctggcgt tttcttcctc gatgtggaac   5400
cggcgcagcg tgtccagcac catcaggcgg cggccctcgg cggcgcgctt gaggccgtcg   5460
aaccactccg gggccatgat gttgggcagg ctgccgatca gcggctggat cagcaggccg   5520
tcagccacgg cttgccgttc ctcggcgctg aggtgcgccc caagggcgtg caggcggtga   5580
tgaatggcgg tgggcgggtc ttcggcgggc aggtagatca ccgggccggt gggcagttcg   5640
cccacctcca gcagatccgg cccgcctgca atctgtgcgg ccagttgcag ggccagcatg   5700
gatttaccgg caccaccggg cgacaccagc gccccgaccg taccggccac catgttgggc   5760
aaaacgtagt ccagcggtgg cggcgctgct gcgaacgcct ccagaatatt gataggctta   5820
tgggtagcca ttgattgcct cctttgcagg cagttggtgg ttaggcgctg gcggggtcac   5880
taccccgcc ctgcgccgct ctgagttctt ccaggcactc gcgcagcgcc tcgtattcgt   5940
cgtcggtcag ccagaacttg cgctgacgca tccctttggc cttcatgcgc tcggcatatc   6000
gcgcttggcg tacagcgtca gggctggcca gcaggtcgcc ggtctgcttg tccttttggt   6060
ctttcatatc agtcaccgag aaacttgccg gggccgaaag gcttgtcttc gcggaacaag   6120
gacaaggtgc agccgtcaag gttaaggctg gccatatcag cgactgaaaa gcggccagcc   6180
tcggccttgt ttgacgtata accaaagcca ccgggcaacc aatagccctt gtcacttttg   6240
atcaggtaga ccgaccctga agcgcttttt tcgtattcca taaaaccccc ttctgtgcgt   6300
gagtactcat agtataacag gcgtgagtac caacgcaagc actacatgct gaaatctggc   6360
ccgcccctgt ccatgcctcg ctggcggggt gccggtgccc gtgccagctc ggcccgcgca   6420
agctggacgc tgggcagacc catgaccttg ctgacggtgc gctcgatgta atccgcttcg   6480
tggccgggct tgcgctctgc cagcgctggg ctggcctcgg ccatggcctt gccgatttcc   6540
tcggcactgc ggccccggct ggccagcttc tgcgcggcga taaagtcgca cttgctgagg   6600
tcatgaccga agcgcttgac cagcccggcc atctcgctgc ggtactcgtc cagcgccgtg   6660
cgccggtggc ggctaagctg ccgctcgggc agttcgaggc tggccagcct gcgggccttc   6720
tcctgctgcc gctgggcctg ctcgatctgc tggccagcct gctgcaccag cgccgggcca   6780
gcggtggcgg tcttgccctt ggattcacgc agcagcaccc acggctgata accggcgcgg   6840
gtggtgtgct tgtccttgcg gttggtgaag cccgccaagc ggccatagtg gcggctgtcg   6900
gcgctggccg ggtcggcgtc gtactcgctg gccagcgtcc gggcaatctg cccccgaagt   6960
tcaccgcctg cggcgtcggc caccttgacc catgcctgat agttcttcgg gctggtttcc   7020
actaccaggg caggctcccg gccctcggct ttcatgtcat ccaggtcaaa ctcgctgagg   7080
tcgtccacca gcaccagacc atgccgctcc tgctcggcgg gcctgatata cacgtcattg   7140
ccctgggcat tcatccgctt gagccatggc gtgttctgga gcacttcggc ggctgaccat   7200
```

-continued

```
tcccggttca tcatctggcc ggtgggtgcg tccctgacgc cgatatcgaa gcgctcacag   7260
cccatggcct tgagctgtcg gcctatggcc tgcaaagtcc tgtcgttctt catcgggcca   7320
ccaagcgcag ccagatcgag ccgtcctcgg ttgtcagtgg cgtcaggtcg agcaagagca   7380
acgatgcgat cagcagcacc accgtaggca tcatggaagc cagcatcacg gttagccata   7440
gcttccagtg ccacccccgc gacgcgctcc gggcgctctg cgcggcgctg ctcacctcgg   7500
cggctacctc ccgcaactct ttggccagct ccacccatgc cgcccctgtc tggcgctggg   7560
ctttcagcca ctccgccgcc tgcgcctcgc tggcctgctt ggtctggctc atgacctgcc   7620
gggcttcgtc ggccagtgtc gccatgctct gggccagcgg ttcgatctgc tccgctaact   7680
cgttgatgcc tctggatttc ttcactctgt cgattgcgtt catggtctat tgcctcccgg   7740
tattcctgta agtcgatgat ctgggcgttg gcggtgtcga tgttcagggc cacgtctgcc   7800
cggtcggtgc ggatgccccg gccttccatc tccaccacgt tcggccccag gtgaacaccg   7860
ggcaggcgct cgatgccctg cgcctcaagt gttctgtggt caatgcgggc gtcgtggcca   7920
gcccgctcta atgcccggtt ggcatggtcg gcccatgcct cgcgggtctg ctcaagccat   7980
gccttgggct tgagcgcttc ggtcttctgt gccccgccct tctccggggt cttgccgttg   8040
taccgcttga accactgagc ggcgggccgc tcgatgccgt cattgatccg ctcggagatc   8100
atcaggtggc agtgcgggtt ctcgccgcca ccggcatgga tggccagcgt atacggcagg   8160
cgctcggcac cggtcaggtg ctgggcgaac tcggacgcca gcgccttctg ctggtcgagg   8220
gtcagctcga ccggcagggc aaattcgacc tccttgaaca gccgcccatt ggcgcgttca   8280
tacaggtcgg cagcatccca gtagtcggcg ggccgctcga cgaactccgg catgtgcccg   8340
gattcggcgt gcaagacttc atccatgtcg cgggcatact tgccttcgcg ctggatgtag   8400
tcggccttgg ccctggccga ttggccgccc gacctgctgc cggttttcgc cgtaaggtga   8460
taaatcgcca tgctgcctcg ctgttgcttt tgcttttcgg ctccatgcaa tggccctcgg   8520
agagcgcacc gcccgaaggg tggccgttag gccagtttct cgaagagaaa ccggtaagtg   8580
cgccctcccc tacaaagtag ggtcgggatt gccgccgctg tgcctccatg atagcctacg   8640
agacagcaca ttaacaatgg ggtgtcaaga tggttaaggg gagcaacaag gcggcggatc   8700
ggctggccaa gctcgaagaa caacgagcgc gaatcaatgc cgaaattcag cgggagcggg   8760
caagggaaca gcagcaagag cgcaagaacg aaacaaggcg caaggtgctg gtgggggcca   8820
tgattttggc caaggtgaac agcagcgagt ggccggagga tcggctcatg gcggcaatgg   8880
atgcgtacct tgaacgcgac cacgaccgcg ccttgttcgg tctgccgcca cgccagaagg   8940
atgagccggg ctgaatgatc gaccgagaca ggccctgcgg ggctgcacac gcgcccccac   9000
ccttcgggta gggggaaagg ccgctaaagc ggctaaaagc gctccagcgt atttctgcgg   9060
ggtttggtgt ggggtttagc gggctttgcc cgcctttccc cctgccgcgc agcggtgggg   9120
cggtgtgtag cctagcgcag cgaatagacc agctatccgg cctctggccg ggcatattgg   9180
gcaagggcag cagcgcccca caagggcgct gataaccgcg cctagtggat tattcttaga   9240
taatcatgga tggatttttc caacaccccg ccagcccccg cccctgctgg gtttgcaggt   9300
ttgggggcgt gacagttatt gcaggggttc gtgacagtta ttgcaggggg gcgtgacagt   9360
tattgcaggg gttcgtgaca gttagtacgg gagtgacggg cactggctgg caatgtctag   9420
caacggcagg catttcggct gagggtaaaa gaactttccg ctaagcgata gactgtatgt   9480
aaacacagta ttgcaaggac gcggaacatg cctcatgtgg cggccaggac ggccagccgg   9540
```

gatcgggata ctggtcgtta ccagagccac cgacccgagc aaacccttct ctatcagatc 9600
gttgacgagt attacccggc attcgctgcg cttatggcag agcagggaaa ggaattgccg 9660
ggctatgtgc aacgggaatt tgaagaattt ctccaatgcg ggcggctgga gcatggcttt 9720
ctacgggttc gctgcgagtc ttgccacgcc gagcacctgg tcgctttcag aaatcaatct 9780
aaagtatata tgagtaaact tggtctgaca gttaccaatg cttaatcagt gaggcaccta 9840
tctcagcgat ctgtctattt cgttcatcca tagttgcctg actccccgtc gtgtagataa 9900
ctacgatacg ggagggctta ccatctggcc ccagtgctgc aatgataccg cgagacccac 9960
gctcaccggc tccagattta tcagcaataa accagccagc cggaagggcc gagcgcagaa 10020
gtggtcctgc aactttatcc gcctccatcc agtctattaa ttgttgccgg gaagctagag 10080
taagtagttc gccagttaat agtttgcgca acgttgttgc cattgctaca ggcatcgtgg 10140
tgtcacgctc gtcgtttggt atggcttcat tcagctccgg ttcccaacga tcaaggcgag 10200
ttacatgatc ccccatgttg tgcaaaaaag cggttagctc cttcggtcct ccgatcgttg 10260
tcagaagtaa gttggccgca gtgttatcac tcatggttat ggcagcactg cataattctc 10320
ttactgtcat gccatccgta agatgctttt ctgtgactgg tgagtactca accaagtcat 10380
tctgagaata gtgtatgcgg cgaccgagtt gctcttgccc ggcgtcaaca cgggataata 10440
ccgcgccaca tagcagaact ttaaaagtgc tcatcattgg aaaacgttct tcggggcgaa 10500
aactctcaag gatcttaccg ctgttgagat ccagttcgat gtaacccact cgtgcaccca 10560
actgatcttc agcatctttt actttcacca gcgtttctgg gtgagcaaaa acaggaaggc 10620
aaaatgccgc aaaaaaggga ataagggcga cacggaaatg ttgaatactc atactcttcc 10680
tttttcaata ttattgaagc atttatcagg gttattgtct catgagcgga tacatatttg 10740
aatgtattta gaaaaataaa caaaagagtt tgtagaaacg caaaaaggcc atccgtcagg 10800
atggccttct gcttaatttg atgcctggca gtttatggcg ggcgtcctgc ccgccaccct 10860
ccgggccgtt gcttcgcaac gttcaaatcc gctcccggcg gatttgtcct actcaggaga 10920
gcgttcaccg acaaacaaca gataaaacga aaggcccagt ctttcgactg agcctttcgt 10980
tttatttgat gcctggcagt tccctactct cgcatgggga gaccccacac taccatcggc 11040
gctacggcgt ttcacttctg agttcggcat ggggtcaggt gggaccaccg cgctactgcc 11100
gccaggcaaa ttctgtttta tcagaccgct tctgcgttct gatttaatct gtatcaggct 11160
gaaaatcttc tctcatccgc caaaacagcc aagct 11195

<210> SEQ ID NO 48
<211> LENGTH: 11820
<212> TYPE: DNA
<213> ORGANISM: Artificial
<220> FEATURE:
<223> OTHER INFORMATION: plasmid pLybAL19

<400> SEQUENCE: 48
tgcatgcctg caggtcgact ctagatggct acgagggcag acagtaagtg gatttaccat 60
aatcccttaa ttgtacgcac cgctaaaacg cgttcagcgc gatcacggca gcagacaggt 120
aaaaatggca acaaaccacc ctaaaaactg cgcgatcgcg cctgataaat tttaaccgta 180
tgaataccta tgcaaccaga gggtacaggc cacattaccc ccacttaatc cactgaagct 240
gccatttttc atggtttcac catcccagcg aagggccatg catgcatcga aattaatacg 300
acgaaattaa tacgactcac tatagggcaa ttgttatcag ctatgcgccg accagaacac 360
cttgccgatc agccaaacgt ctcttcaggc cactgactag cgataacttt ccccacaacg 420

-continued

```
gaacaactct cactgcatgg gatcattggg tactgtgggt ttagtggttg taaaaacacc    480
tgaccgctat ccctgatcag tttcttgaag gtaaactcat cacccccaag tctggctatg    540
cagaaatcac ctggctcaac agcctgctca gggtcaacga gaattaacat tccgtcagga    600
aagcttggct tggagcctgt tggtgcggtc atggaattac cttcaacctc aagccagaat    660
gcagaatcac tggctttctt ggttgtgctt acccatctct ccgcatcacc tttggtaaag    720
gttctaagct taggtgagaa catccctgcc tgaacatgag aaaaaacagg gtactcatac    780
tcacttctaa gtgacggctg catactaacc gcttcataca tctcgtagat ttctctggcg    840
attgaagggc taaattcttc aacgctaact ttgagaattt ttgtaagcaa tgcggcgtta    900
taagcattta atgcattgat gccattaaat aaagcaccaa cgcctgactg ccccatcccc    960
atcttgtctg cgacagattc ctgggataag ccaagttcat ttttcttttt ttcataaatt   1020
gctttaaggc gacgtgcgtc ctcaagctgc tcttgtgtta atggtttctt ttttgtgctc   1080
atacgttaaa tctatcaccg caagggataa atatctaaca ccgtgcgtgt tgactatttt   1140
acctctggcg gtgataatgg ttgcatctta agaaggagga tccatatggt accgagctcg   1200
aattggggcg ttttctgtga ggctgactag cgcgtggcag ctcaaaatct ctacattctg   1260
cacattcaga cccatggtct gctgcgaggg cagaacttgg aactggggcg agatgccgac   1320
accggcgggc agaccaagta cgtcttagaa ctggctcaag cccaagctaa atccccacaa   1380
gtccaacaag tcgacatcat cacccgccaa atcaccgacc cccgcgtcag tgttggttac   1440
agtcaggcga tcgaaccctt tgcgcccaaa ggtcggattg tccgtttgcc ttttggcccc   1500
aaacgctacc tccgtaaaga gctgctttgg ccccatctct acacctttgc ggatgcaatt   1560
ctccaatatc tggctcagca aaagcgcacc ccgacttgga ttcaggccca ctatgctgat   1620
gctggccaag tgggatcact gctgagtcgc tggttgaatg taccgctaat tttcacaggg   1680
cattctctgg ggcggatcaa gctaaaaaag ctgttggagc aagactggcc gcttgaggaa   1740
attgaagcgc aattcaatat tcaacagcga attgatgcgg aggagatgac gctcactcat   1800
gctgactgga ttgtcgccag cactcagcag gaagtggagg agcaataccg cgtttacgat   1860
cgctacaacc cagagcgcaa gcttgtcatt ccaccgggtg tcgataccga tcgcttcagg   1920
tttcagccct tgggcgatcg cggtgttgtt ctccaacagg aactgagccg ctttctgcgc   1980
gacccagaaa aacctcaaat tctctgcctc tgtcgccccg cacctcgcaa aaatgtaccg   2040
gcgctggtgc gagcctttgg cgaacatcct tggctgcgca aaaaagccaa ccttgtctta   2100
gtactgggca gccgccaaga catcaaccag atggatcgcg gcagtcggca ggtgttccaa   2160
gagattttcc atctggtcga tcgctacgac ctctacggca gcgtcgccta tcccaaacag   2220
catcaggctg atgatgtgcc ggagttctat cgcctagcgg ctcattccgg cggggtattc   2280
gtcaatccgg cgctgaccga accttttggt ttgacaattt tggaggcagg aagctgcggc   2340
gtgccggtgg tggcaaccca tgatggcggc ccccaggaaa ttctcaaaca ctgtgatttc   2400
ggcactttag ttgatgtcag ccgacccgct aatatcgcga ctgcactcgc caccctgctg   2460
agcgatcgcg atctttggca gtgctatcac cgcaatggca ttgaaaaagt tcccgcccat   2520
tacagctggg atcaacatgt caataccctg tttgagcgca tggaaacggt ggctttgcct   2580
cgtcgtcgtg ctgtcagttt cgtacggagt cgcaaacgct tgattgatgc caaacgcctt   2640
gtcgttagtg acatcgacaa cacactgttg ggcgatcgtc aaggactcga gaatttaatg   2700
acctatctcg atcagtatcg cgatcatttt gcctttggaa ttgccacggg gcgtcgccta   2760
```

-continued

```
gactctgccc aagaagtctt gaaagagtgg ggcgttcctt cgccaaactt ctgggtgact   2820
tccgtcggca gcgagattca ctatggcacc gatgctgaac cggatatcag ctgggaaaag   2880
catatcaatc gcaactggaa tcctcagcga attcgggcag taatggcaca actacccttt   2940
cttgaactgc agccggaaga ggatcaaaca cccttcaaag tcagcttctt tgtccgcgat   3000
cgccacgaga ctgtgctgcg agaagtacgg caacatcttc gccgccatcg cctgcggctg   3060
aagtcaatct attcccatca ggagtttctt gacattctgc cgctagctgc ctcgaaaggg   3120
gatgcgattc gccacctctc actccgctgg cggattcctc ttgagaacat tttggtggca   3180
ggcgattctg gtaacgatga ggaaatgctc aagggccata atctcggcgt tgtagttggc   3240
aattactcac cggaattgga gccactgcgc agctacgagc gcgtctattt tgctgagggc   3300
cactatgcta atggcattct ggaagcctta aaacactatc gctttttga ggcgatcgct    3360
taacctttc agaatgagac gttgatcggc acgtaagcgt gagacgttga tcggcacgta    3420
agaggttcca actttcacca taatgaaata agatcactac cgggcgtatt ttttgagtta   3480
tcgagatttt caggagctaa ggaagctaaa atggagaaaa aaatcactgg atataccacc   3540
gttgatatat cccaatggca tcgtaaagaa cattttgagg catttcagtc agttgctcaa   3600
tgtacctata accagaccgt tcagctggat attacggcct ttttaaagac cgtaaagaaa   3660
aataagcaca agttttatcc ggcctttatt cacattcttg cccgcctgat gaatgctcat   3720
ccggaattcc gtatggcaat gaaagacggt gagctggtga tatgggatag tgttcaccct   3780
tgttacaccg ttttccatga gcaaactgaa acgttttcat cgctctggag tgaataccac   3840
gacgatttcc ggcagtttct acacatatat tcgcaagatg tggcgtgtta cggtgaaaac   3900
ctggcctatt tccctaaagg gtttattgag aatatgtttt tcgtctcagc caatccctgg   3960
gtgagtttca ccagttttga tttaaacgtg gccaatatgg acaacttctt cgcccccgtt   4020
ttcaccatgg gcaaatatta tacgcaaggc gacaaggtgc tgatgccgct ggcgattcag   4080
gttcatcatg ccgtttgtga tggcttccat gtcggcagaa tgcttaatga attacaacag   4140
tactgcgatg agtggcaggg cggggcgtaa tttttttaag gcagttattg gtgcccttaa   4200
acgcctggtt gctacgcctg aataagtgat aataagcgga tgaatggcag aaattcgatg   4260
ataagctgtc aaacacaacc accatcaaac aggattttcg cctgctgggg caaaccagcg   4320
tggaccgctt gctgcaactc tctcagggcc aggcggtgaa gggcaatcag ctgttgcccg   4380
tctcactggt gaaaagaaaa accaccctgg cgcccaatac gcaaaccgcc tctccccgcg   4440
cgttggccga ttcattaatg cagctggcac gacaggtttc ccgactggaa agcgggcagt   4500
gagcgcaacg caattaatgt aagttagcgc gaattgcaag ctggccgacg cgctgggcta   4560
cgtcttgctg gcgttcggga gcagaagagc atacatctgg aagcaaagcc aggaaagcgg   4620
cctatggagc tgtgcggcag cgctcagtag gcaatttttc aaaatattgt taagcctttt   4680
ctgagcatgg tatttttcat ggtattacca attagcagga aaataagcca ttgaatataa   4740
aagataaaaa tgtcttgttt acaatagagt ggggggggtc agcctgccgc cttgggccgg   4800
gtgatgtcgt acttgcccgc cgcgaactcg gttaccgtcc agcccagcgc gaccagctcc   4860
ggcaacgcct cgcgcacccg cttgcggcgc ttgcgcatgg tcgaaccact ggcctctgac   4920
ggccagacat agccgcacaa ggtatctatg gaagccttgc cggttttgcc ggggtcgatc   4980
cagccacaca gccgctggtg cagcaggcgg gcggtttcgc tgtccagcgc ccgcacctcg   5040
tccatgctga tgcgcacatg ctggccgcca cccatgacgg cctgcgcgat caaggggttc   5100
agggccacgt acaggcgccc gtccgcctcg tcgctggcgt actccgacag cagccgaaac   5160
```

-continued

```
ccctgccgct tgcggccatt ctgggcgatg atggatacct tccaaaggcg ctcgatgcag   5220
tcctgtatgt gcttgagcgc cccaccacta tcgacctctg ccccgatttc ctttgccagc   5280
gcccgatagc tacctttgac cacatggcat tcagcggtga cggcctccca cttgggttcc   5340
aggaacagcc ggagctgccg tccgccttcg gtcttgggtt ccgggccaag cactaggcca   5400
ttaggcccag ccatggccac cagcccttgc aggatgcgca gatcatcagc gcccagcggc   5460
tccgggccgc tgaactcgat ccgcttgccg tcgccgtagt catacgtcac gtccagcttg   5520
ctgcgcttgc gctcgccccg cttgagggca cggaacaggc cgggggccag acagtgcgcc   5580
gggtcgtgcc ggacgtggct gaggctgtgc ttgttcttag gcttcaccac ggggcacccc   5640
cttgctcttg cgctgcctct ccagcacggc gggcttgagc accccgccgt catgccgcct   5700
gaaccaccga tcagcgaacg gtgcgccata gttggccttg ctcacaccga agcggacgaa   5760
gaaccggcgc tggtcgtcgt ccacacccca ttcctcggcc tcggcgctgg tcatgctcga   5820
caggtaggac tgccagcgga tgttatcgac cagtaccgag ctgccccggc tggcctgctg   5880
ctggtcgcct gcgcccatca tggccgcgcc cttgctggca tggtgcagga acacgataga   5940
gcacccggta tcggcggcga tggcctccat gcgaccgatg acctgggcca tggggccgct   6000
ggcgttttct tcctcgatgt ggaaccggcg cagcgtgtcc agcaccatca ggcggcggcc   6060
ctcggcggcg cgcttgaggc cgtcgaacca ctccggggcc atgatgttgg gcaggctgcc   6120
gatcagcggc tggatcagca ggccgtcagc cacggcttgc cgttcctcgg cgctgaggtg   6180
cgccccaagg gcgtgcaggc ggtgatgaat ggcggtgggc gggtcttcgg cgggcaggta   6240
gatcaccggg ccggtgggca gttcgcccac ctccagcaga tccggcccgc ctgcaatctg   6300
tgcggccagt tgcagggcca gcatggattt accggcacca ccgggcgaca ccagcgcccc   6360
gaccgtaccg gccaccatgt tggcaaaac gtagtccagc ggtggcggcg ctgctgcgaa   6420
cgcctccaga atattgatag gcttatgggt agccattgat tgcctccttt gcaggcagtt   6480
ggtggttagg cgctggcggg gtcactaccc ccgccctgcg ccgctctgag ttcttccagg   6540
cactcgcgca gcgcctcgta ttcgtcgtcg gtcagccaga acttgcgctg acgcatccct   6600
ttggccttca tgcgctcggc atatcgcgct tggcgtacag cgtcagggct ggccagcagg   6660
tcgccggtct gcttgtcctt ttggtctttc atatcagtca ccgagaaact tgccggggcc   6720
gaaaggcttg tcttcgcgga acaaggacaa ggtgcagccg tcaaggttaa ggctggccat   6780
atcagcgact gaaaagcggc cagcctcggc cttgtttgac gtataaccaa agccaccggg   6840
caaccaatag cccttgtcac ttttgatcag gtagaccgac cctgaagcgc ttttttcgta   6900
ttccataaaa ccccccttctg tgcgtgagta ctcatagtat aacaggcgtg agtaccaacg   6960
caagcactac atgctgaaat ctggcccgcc cctgtccatg cctcgctggc ggggtgccgg   7020
tgcccgtgcc agctcggccc gcgcaagctg gacgctgggc agacccatga ccttgctgac   7080
ggtgcgctcg atgtaatccg cttcgtggcc gggcttgcgc tctgccagcg ctgggctggc   7140
ctcggccatg gccttgccga tttcctcggc actgcggccc cggctggcca gcttctgcgc   7200
ggcgataaag tcgcacttgc tgaggtcatg accgaagcgc ttgaccagcc cggccatctc   7260
gctgcggtac tcgtccagcg ccgtgcgccg gtggcggcta agctgccgct cgggcagttc   7320
gaggctggcc agcctgcggg ccttctcctg ctgccgctgg gcctgctcga tctgctggcc   7380
agcctgctgc accagcgccg ggccagcggt ggcggtcttg cccttggatt cacgcagcag   7440
cacccacggc tgataaccgg cgcgggtggt gtgcttgtcc ttgcggttgg tgaagcccgc   7500
```

-continued

```
caagcggcca tagtggcggc tgtcggcgct ggccgggtcg gcgtcgtact cgctggccag   7560
cgtccgggca atctgccccc gaagttcacc gcctgcggcg tcggccacct tgacccatgc   7620
ctgatagttc ttcgggctgg tttccactac cagggcaggc tcccggccct cggctttcat   7680
gtcatccagg tcaaactcgc tgaggtcgtc caccagcacc agaccatgcc gctcctgctc   7740
ggcgggcctg atatacacgt cattgccctg ggcattcatc cgcttgagcc atggcgtgtt   7800
ctggagcact tcggcggctg accattcccg gttcatcatc tggccggtgg gtgcgtccct   7860
gacgccgata tcgaagcgct cacagcccat ggccttgagc tgtcggccta tggcctgcaa   7920
agtcctgtcg ttcttcatcg ggccaccaag cgcagccaga tcgagccgtc ctcggttgtc   7980
agtggcgtca ggtcgagcaa gagcaacgat gcgatcagca gcaccaccgt aggcatcatg   8040
gaagccagca tcacggttag ccatagcttc cagtgccacc cccgcgacgc gctccgggcg   8100
ctctgcgcgg cgctgctcac ctcggcggct acctcccgca actctttggc cagctccacc   8160
catgccgccc ctgtctggcg ctgggctttc agccactccg ccgcctgcgc ctcgctggcc   8220
tgcttggtct ggctcatgac ctgccgggct tcgtcggcca gtgtcgccat gctctgggcc   8280
agcggttcga tctgctccgc taactcgttg atgcctctgg atttcttcac tctgtcgatt   8340
gcgttcatgg tctattgcct cccggtattc ctgtaagtcg atgatctggg cgttggcggt   8400
gtcgatgttc agggccacgt ctgcccggtc ggtgcggatg ccccggcctt ccatctccac   8460
cacgttcggc cccaggtgaa caccgggcag gcgctcgatg ccctgcgcct caagtgttct   8520
gtggtcaatg cgggcgtcgt ggccagcccg ctctaatgcc cggttggcat ggtcggccca   8580
tgcctcgcgg gtctgctcaa gccatgcctt gggcttgagc gcttcggtct tctgtgcccc   8640
gcccttctcc ggggtcttgc cgttgtaccg cttgaaccac tgagcggcgg gccgctcgat   8700
gccgtcattg atccgctcgg agatcatcag gtggcagtgc gggttctcgc cgccaccggc   8760
atggatggcc agcgtatacg gcaggcgctc ggcaccggtc aggtgctggg cgaactcgga   8820
cgccagcgcc ttctgctggt cgagggtcag ctcgaccggc agggcaaatt cgacctcctt   8880
gaacagccgc ccattggcgc gttcatacag gtcggcagca tcccagtagt cggcgggccg   8940
ctcgacgaac tccggcatgt gcccggattc ggcgtgcaag acttcatcca tgtcgcgggc   9000
atacttgcct tcgcgctgga tgtagtcggc cttggccctg gccgattggc cgcccgacct   9060
gctgccggtt ttcgccgtaa ggtgataaat cgccatgctg cctcgctgtt gcttttgctt   9120
ttcggctcca tgcaatggcc ctcggagagc gcaccgcccg aagggtggcc gttaggccag   9180
tttctcgaag agaaaccggt aagtgcgccc tcccctacaa agtagggtcg ggattgccgc   9240
cgctgtgcct ccatgatagc ctacgagaca gcacattaac aatggggtgt caagatggtt   9300
aaggggagca acaaggcggc ggatcggctg gccaagctcg aagaacaacg agcgcgaatc   9360
aatgccgaaa ttcagcggga gcgggcaagg gaacagcagc aagagcgcaa gaacgaaaca   9420
aggcgcaagg tgctggtggg ggccatgatt ttggccaagg tgaacagcag cgagtggccg   9480
gaggatcggc tcatggcggc aatggatgcg taccttgaac gcgaccacga ccgcgccttg   9540
ttcggtctgc cgccacgcca gaaggatgag ccgggctgaa tgatcgaccg agacaggccc   9600
tgcggggctg cacacgcgcc cccacccttc gggtaggggg aaaggccgct aaagcggcta   9660
aaagcgctcc agcgtatttc tgcggggttt ggtgtggggt ttagcgggct ttgcccgcct   9720
ttcccccctgc cgcgcagcgg tggggcggtg tgtagcctag cgcagcgaat agaccagcta   9780
tccggcctct ggccgggcat attgggcaag ggcagcagcg ccccacaagg gcgctgataa   9840
ccgcgcctag tggattattc ttagataatc atggatggat ttttccaaca ccccgccagc   9900
```

```
ccccgcccct gctgggtttg caggtttggg ggcgtgacag ttattgcagg ggttcgtgac   9960
agttattgca ggggggcgtg acagttattg caggggttcg tgacagttag tacgggagtg  10020
acgggcactg gctggcaatg tctagcaacg gcaggcattt cggctgaggg taaaagaact  10080
ttccgctaag cgatagactg tatgtaaaca cagtattgca aggacgcgga acatgcctca  10140
tgtggcggcc aggacggcca gccgggatcg ggatactggt cgttaccaga gccaccgacc  10200
cgagcaaacc cttctctatc agatcgttga cgagtattac ccggcattcg ctgcgcttat  10260
ggcagagcag ggaaaggaat tgccgggcta tgtgcaacgg gaatttgaag aatttctcca  10320
atgcgggcgg ctggagcatg gctttctacg ggttcgctgc gagtcttgcc acgccgagca  10380
cctggtcgct ttcagaaatc aatctaaagt atatatgagt aaacttggtc tgacagttac  10440
caatgcttaa tcagtgaggc acctatctca gcgatctgtc tatttcgttc atccatagtt  10500
gcctgactcc ccgtcgtgta gataactacg atacgggagg gcttaccatc tggccccagt  10560
gctgcaatga taccgcgaga cccacgctca ccggctccag atttatcagc aataaaccag  10620
ccagccggaa gggccgagcg cagaagtggt cctgcaactt tatccgcctc catccagtct  10680
attaattgtt gccgggaagc tagagtaagt agttcgccag ttaatagttt gcgcaacgtt  10740
gttgccattg ctacaggcat cgtggtgtca cgctcgtcgt ttggtatggc ttcattcagc  10800
tccggttccc aacgatcaag gcgagttaca tgatccccca tgttgtgcaa aaaagcggtt  10860
agctccttcg gtcctccgat cgttgtcaga agtaagttgg ccgcagtgtt atcactcatg  10920
gttatggcag cactgcataa ttctcttact gtcatgccat ccgtaagatg cttttctgtg  10980
actggtgagt actcaaccaa gtcattctga gaatagtgta tgcggcgacc gagttgctct  11040
tgcccggcgt caacacggga taataccgcg ccacatagca gaactttaaa agtgctcatc  11100
attggaaaac gttcttcggg gcgaaaactc tcaaggatct taccgctgtt gagatccagt  11160
tcgatgtaac ccactcgtgc acccaactga tcttcagcat cttttacttt caccagcgtt  11220
tctgggtgag caaaaacagg aaggcaaaat gccgcaaaaa agggaataag ggcgacacgg  11280
aaatgttgaa tactcatact cttccttttt caatattatt gaagcattta tcagggttat  11340
tgtctcatga gcggatacat atttgaatgt atttagaaaa ataaacaaaa gagtttgtag  11400
aaacgcaaaa aggccatccg tcaggatggc cttctgctta atttgatgcc tggcagttta  11460
tggcgggcgt cctgcccgcc accctccggg ccgttgcttc gcaacgttca aatccgctcc  11520
cggcggattt gtcctactca ggagagcgtt caccgacaaa caacagataa aacgaaaggc  11580
ccagtctttc gactgagcct ttcgttttat ttgatgcctg gcagttccct actctcgcat  11640
ggggagaccc cacactacca tcggcgctac ggcgtttcac ttctgagttc ggcatggggt  11700
caggtgggac caccgcgcta ctgccgccag gcaaattctg ttttatcaga ccgcttctgc  11760
gttctgattt aatctgtatc aggctgaaaa tcttctctca tccgccaaaa cagccaagct  11820
```

<210> SEQ ID NO 49
<211> LENGTH: 11511
<212> TYPE: DNA
<213> ORGANISM: Artificial
<220> FEATURE:
<223> OTHER INFORMATION: plasmid pLybAL21

<400> SEQUENCE: 49

```
tgcatgcacc agtaaacata aatctccccg gcgacgcaaa aaacgggtga ccatcaagcc     60
ggtgcgcttc ggcatttttc tgctttgcct agcaggcatt gtgggggggg caactgccct    120
```

```
aattatcaat cgtactggcg atcccctagg tgggttgcta gaagaccccc tagatgtttt    180
cctggaccaa ccttcagaat ttatccccga tgaagccacg agccggaatt tgattctcag    240
tcaacccaac ttcaatcagc aagtgggtca gatggtagta caaggctggc ttgatagtaa    300
aaagttagcc tttggccaaa actacgatgt cggggcattg cagagtgttt tagcccccaa    360
tctccttgcc caacaacggg gtcgggccca acgggatcaa gcccaaaagg tctatcacca    420
atacgaacac aagttgcaga ttttagccta tcaagttaac ccccaagacc ccaaccgagc    480
caccgttact gcccgggtag aagaaattag ccagcccttt accctaggta atcaacagca    540
gaagggctcc gccaccaaag atgacttgac tgtgcgctat cagctagtac gacaccaagg    600
ggtttggaaa attgaccaaa tacaagtggt aaatggcccc cgttagtgcg tggcgttaac    660
tcccctttg accaatggca tacggctaga tgcccccata ggtacggaaa cctgcacttc    720
cgagaactaa gcccctaccg tcactataag agtgtgaacg tgtcggcccc aggcaatgga    780
ttggaaccat ggcttttcgg cccatcgttg tgtcttatat tcttacttgt taacgggagt    840
taattaaaat tatgggaaaa gttgttggga ttgacctcgg taccgagctc gaattggggc    900
gttttctgtg aggctgacta gcgcgtggca gctcaaaatc tctacattct gcacattcag    960
acccatggtc tgctgcgagg gcagaacttg gaactggggc gagatgccga caccggcggg   1020
cagaccaagt acgtcttaga actggctcaa gcccaagcta aatccccaca agtccaacaa   1080
gtcgacatca tcacccgcca aatcaccgac ccccgcgtca gtgttggtta cagtcaggcg   1140
atcgaaccct ttgcgcccaa aggtcggatt gtccgtttgc cttttggccc caaacgctac   1200
ctccgtaaag agctgctttg gccccatctc tacacctttg cggatgcaat tctccaatat   1260
ctggctcagc aaaagcgcac cccgacttgg attcaggccc actatgctga tgctggccaa   1320
gtgggatcac tgctgagtcg ctggttgaat gtaccgctaa ttttcacagg gcattctctg   1380
gggcggatca agctaaaaaa gctgttggag caagactggc cgcttgagga aattgaagcg   1440
caattcaata ttcaacagcg aattgatgcg gaggagatga cgctcactca tgctgactgg   1500
attgtcgcca gcactcagca ggaagtggag gagcaatacc gcgtttacga tcgctacaac   1560
ccagagcgca agcttgtcat tccaccgggt gtcgataccg atcgcttcag gtttcagccc   1620
ttgggcgatc gcggtgttgt tctccaacag gaactgagcc gctttctgcg cgacccagaa   1680
aaacctcaaa ttctctgcct ctgtcgcccc gcacctcgca aaaatgtacc ggcgctggtg   1740
cgagcctttg gcgaacatcc ttggctgcgc aaaaaagcca accttgtctt agtactgggc   1800
agccgccaag acatcaacca gatggatcgc ggcagtcggc aggtgttcca agagattttc   1860
catctggtcg atcgctacga cctctacggc agcgtcgcct atcccaaaca gcatcaggct   1920
gatgatgtgc cggagttcta tcgcctagcg gctcattccg gcggggtatt cgtcaatccg   1980
gcgctgaccg aaccttttgg tttgacaatt ttggaggcag gaagctgcgg cgtgccggtg   2040
gtggcaaccc atgatggcgg cccccaggaa attctcaaac actgtgattt cggcacttta   2100
gttgatgtca gccgacccgc taatatcgcg actgcactcg ccaccctgct gagcgatcgc   2160
gatctttggc agtgctatca ccgcaatggc attgaaaaag ttcccgccca ttacagctgg   2220
gatcaacatg tcaataccct gtttgagcgc atggaaacgg tggctttgcc tcgtcgtcgt   2280
gctgtcagtt tcgtacggag tcgcaaacgc ttgattgatg ccaaacgcct tgtcgttagt   2340
gacatcgaca acacactgtt gggcgatcgt caaggactcg agaatttaat gacctatctc   2400
gatcagtatc gcgatcattt tgcctttgga attgccacgg ggcgtcgcct agactctgcc   2460
caagaagtct tgaaagagtg gggcgttcct tcgccaaact tctgggtgac ttccgtcggc   2520
```

```
agcgagattc actatggcac cgatgctgaa ccggatatca gctgggaaaa gcatatcaat   2580
cgcaactgga atcctcagcg aattcgggca gtaatggcac aactaccctt tcttgaactg   2640
cagccggaag aggatcaaac acccttcaaa gtcagcttct ttgtccgcga tcgccacgag   2700
actgtgctgc gagaagtacg gcaacatctt cgccgccatc gcctgcggct gaagtcaatc   2760
tattcccatc aggagtttct tgacattctg ccgctagctg cctcgaaagg ggatgcgatt   2820
cgccacctct cactccgctg gcggattcct cttgagaaca ttttggtggc aggcgattct   2880
ggtaacgatg aggaaatgct caagggccat aatctcggcg ttgtagttgg caattactca   2940
ccggaattgg agccactgcg cagctacgag cgcgtctatt ttgctgaggg ccactatgct   3000
aatggcattc tggaagcctt aaaacactat cgcttttttg aggcgatcgc ttaacctttt   3060
cagaatgaga cgttgatcgg cacgtaagcg tgagacgttg atcggcacgt aagaggttcc   3120
aactttcacc ataatgaaat aagatcacta ccgggcgtat tttttgagtt atcgagattt   3180
tcaggagcta aggaagctaa aatggagaaa aaaatcactg gatataccac cgttgatata   3240
tcccaatggc atcgtaaaga acattttgag gcatttcagt cagttgctca atgtacctat   3300
aaccagaccg ttcagctgga tattacggcc tttttaaaga ccgtaaagaa aaataagcac   3360
aagttttatc cggcctttat tcacattctt gcccgcctga tgaatgctca tccggaattc   3420
cgtatggcaa tgaaagacgg tgagctggtg atatgggata gtgttcaccc ttgttacacc   3480
gttttccatg agcaaactga aacgttttca tcgctctgga gtgaatacca cgacgatttc   3540
cggcagtttc tacacatata ttcgcaagat gtggcgtgtt acggtgaaaa cctggcctat   3600
ttccctaaag ggtttattga gaatatgttt ttcgtctcag ccaatccctg ggtgagtttc   3660
accagttttg atttaaacgt ggccaatatg gacaacttct tcgcccccgt tttcaccatg   3720
ggcaaatatt atacgcaagg cgacaaggtg ctgatgccgc tggcgattca ggttcatcat   3780
gccgtttgtg atggcttcca tgtcggcaga atgcttaatg aattacaaca gtactgcgat   3840
gagtggcagg gcggggcgta atttttttaa ggcagttatt ggtgccctta aacgcctggt   3900
tgctacgcct gaataagtga taataagcgg atgaatggca gaaattcgat gataagctgt   3960
caaacacaac caccatcaaa caggattttc gcctgctggg gcaaaccagc gtggaccgct   4020
tgctgcaact ctctcagggc caggcggtga agggcaatca gctgttgccc gtctcactgg   4080
tgaaaagaaa aaccaccctg gcgcccaata cgcaaaccgc ctctccccgc gcgttggccg   4140
attcattaat gcagctggca cgacaggttt cccgactgga aagcgggcag tgagcgcaac   4200
gcaattaatg taagttagcg cgaattgcaa gctggccgac gcgctgggct acgtcttgct   4260
ggcgttcggg agcagaagag catacatctg gaagcaaagc caggaaagcg gcctatggag   4320
ctgtgcggca gcgctcagta ggcaattttt caaaatattg ttaagccttt tctgagcatg   4380
gtatttttca tggtattacc aattagcagg aaaataagcc attgaatata aaagataaaa   4440
atgtcttgtt tacaatagag tgggggggt cagcctgccg ccttgggccg ggtgatgtcg   4500
tacttgcccg ccgcgaactc ggttaccgtc cagcccagcg cgaccagctc cggcaacgcc   4560
tcgcgcaccc gcttgcggcg cttgcgcatg gtcgaaccac tggcctctga cggccagaca   4620
tagccgcaca aggtatctat ggaagccttg ccggttttgc cggggtcgat ccagccacac   4680
agccgctggt gcagcaggcg ggcggtttcg ctgtccagcg cccgcacctc gtccatgctg   4740
atgcgcacat gctggccgcc acccatgacg gcctgcgcga tcaaggggtt cagggccacg   4800
tacaggcgcc cgtccgcctc gtcgctggcg tactccgaca gcagccgaaa cccctgccgc   4860
```

-continued ttgcggccat tctgggcgat gatggatacc ttccaaaggc gctcgatgca gtcctgtatg 4920
tgcttgagcg ccccaccact atcgacctct gccccgattt cctttgccag cgcccgatag 4980
ctacctttga ccacatggca ttcagcggtg acggcctccc acttgggttc caggaacagc 5040
cggagctgcc gtccgccttc ggtcttgggt tccgggccaa gcactaggcc attaggccca 5100
gccatggcca ccagcccttg caggatgcgc agatcatcag cgcccagcgg ctccgggccg 5160
ctgaactcga tccgcttgcc gtcgccgtag tcatacgtca cgtccagctt gctgcgcttg 5220
cgctcgcccc gcttgagggc acggaacagg ccgggggcca gacagtgcgc cgggtcgtgc 5280
cggacgtggc tgaggctgtg cttgttctta ggcttcacca cggggcaccc ccttgctctt 5340
gcgctgcctc tccagcacgg cgggcttgag caccccgccg tcatgccgcc tgaaccaccg 5400
atcagcgaac ggtgcgccat agttggcctt gctcacaccg aagcggacga agaaccggcg 5460
ctggtcgtcg tccacacccc attcctcggc ctcggcgctg gtcatgctcg acaggtagga 5520
ctgccagcgg atgttatcga ccagtaccga gctgccccgg ctggcctgct gctggtcgcc 5580
tgcgcccatc atggccgcgc ccttgctggc atggtgcagg aacacgatag agcacccggt 5640
atcggcggcg atggcctcca tgcgaccgat gacctgggcc atggggccgc tggcgttttc 5700
ttcctcgatg tggaaccggc gcagcgtgtc cagcaccatc aggcggcggc cctcggcggc 5760
gcgcttgagg ccgtcgaacc actccggggc catgatgttg ggcaggctgc cgatcagcgg 5820
ctggatcagc aggccgtcag ccacggcttg ccgttcctcg gcgctgaggt gcgccccaag 5880
ggcgtgcagg cggtgatgaa tggcggtggg cgggtcttcg gcgggcaggt agatcaccgg 5940
gccggtgggc agttcgccca cctccagcag atccggcccg cctgcaatct gtgcggccag 6000
ttgcagggcc agcatggatt taccggcacc accgggcgac accagcgccc cgaccgtacc 6060
ggccaccatg ttgggcaaaa cgtagtccag cggtggcggc gctgctgcga acgcctccag 6120
aatattgata ggcttatggg tagccattga ttgcctcctt tgcaggcagt tggtggttag 6180
gcgctggcgg ggtcactacc cccgccctgc gccgctctga gttcttccag gcactcgcgc 6240
agcgcctcgt attcgtcgtc ggtcagccag aacttgcgct gacgcatccc tttggccttc 6300
atgcgctcgg catatcgcgc ttggcgtaca gcgtcagggc tggccagcag gtcgccggtc 6360
tgcttgtcct tttggtcttt catatcagtc accgagaaac ttgccggggc cgaaaggctt 6420
gtcttcgcgg aacaaggaca aggtgcagcc gtcaaggtta aggctggcca tatcagcgac 6480
tgaaaagcgg ccagcctcgg ccttgtttga cgtataacca aagccaccgg gcaaccaata 6540
gcccttgtca cttttgatca ggtagaccga ccctgaagcg ctttttttcgt attccataaa 6600
accccccttct gtgcgtgagt actcatagta taacaggcgt gagtaccaac gcaagcacta 6660
catgctgaaa tctggcccgc ccctgtccat gcctcgctgg cggggtgccg gtgcccgtgc 6720
cagctcggcc cgcgcaagct ggacgctggg cagacccatg accttgctga cggtgcgctc 6780
gatgtaatcc gcttcgtggc cgggcttgcg ctctgccagc gctgggctgg cctcggccat 6840
ggccttgccg atttcctcgg cactgcggcc ccggctggcc agcttctgcg cggcgataaa 6900
gtcgcacttg ctgaggtcat gaccgaagcg cttgaccagc ccggccatct cgctgcggta 6960
ctcgtccagc gccgtgcgcc ggtggcggct aagctgccgc tcgggcagtt cgaggctggc 7020
cagcctgcgg gccttctcct gctgccgctg ggcctgctcg atctgctggc cagcctgctg 7080
caccagcgcc gggccagcgg tggcggtctt gcccttggat tcacgcagca gcacccacgg 7140
ctgataaccg gcgcgggtgg tgtgcttgtc cttgcggttg gtgaagcccg ccaagcggcc 7200
atagtggcgg ctgtcggcgc tggccgggtc ggcgtcgtac tcgctggcca gcgtccgggc 7260
aatctgcccc cgaagttcac cgcctgcggc gtcggccacc ttgacccatg cctgatagtt 7320
cttcgggctg gtttccacta ccagggcagg ctcccggccc tcggctttca tgtcatccag 7380
gtcaaactcg ctgaggtcgt ccaccagcac cagaccatgc cgctcctgct cggcgggcct 7440
gatatacacg tcattgccct gggcattcat ccgcttgagc catggcgtgt tctggagcac 7500
ttcggcggct gaccattccc ggttcatcat ctggccggtg ggtgcgtccc tgacgccgat 7560
atcgaagcgc tcacagccca tggccttgag ctgtcggcct atggcctgca aagtcctgtc 7620
gttcttcatc gggccaccaa gcgcagccag atcgagccgt cctcggttgt cagtggcgtc 7680
aggtcgagca agagcaacga tgcgatcagc agcaccaccg taggcatcat ggaagccagc 7740
atcacggtta gccatagctt ccagtgccac ccccgcgacg cgctccgggc gctctgcgcg 7800
gcgctgctca cctcggcggc tacctcccgc aactctttgg ccagctccac ccatgccgcc 7860
cctgtctggc gctgggcttt cagccactcc gccgcctgcg cctcgctggc ctgcttggtc 7920
tggctcatga cctgccgggc ttcgtcggcc agtgtcgcca tgctctgggc cagcggttcg 7980
atctgctccg ctaactcgtt gatgcctctg gatttcttca ctctgtcgat tgcgttcatg 8040
gtctattgcc tcccggtatt cctgtaagtc gatgatctgg gcgttggcgg tgtcgatgtt 8100
cagggccacg tctgcccggt cggtgcggat gccccggcct tccatctcca ccacgttcgg 8160
ccccaggtga acaccgggca ggcgctcgat gccctgcgcc tcaagtgttc tgtggtcaat 8220
gcgggcgtcg tggccagccc gctctaatgc ccggttggca tggtcggccc atgcctcgcg 8280
ggtctgctca agccatgcct tgggcttgag cgcttcggtc ttctgtgccc cgcccttctc 8340
cggggtcttg ccgttgtacc gcttgaacca ctgagcggcg ggccgctcga tgccgtcatt 8400
gatccgctcg gagatcatca ggtggcagtg cgggttctcg ccgccaccgg catggatggc 8460
cagcgtatac ggcaggcgct cggcaccggt caggtgctgg gcgaactcgg acgccagcgc 8520
cttctgctgg tcgagggtca gctcgaccgg cagggcaaat tcgacctcct tgaacagccg 8580
cccattggcg cgttcataca ggtcggcagc atcccagtag tcggcgggcc gctcgacgaa 8640
ctccggcatg tgcccggatt cggcgtgcaa gacttcatcc atgtcgcggg catacttgcc 8700
ttcgcgctgg atgtagtcgg ccttggccct ggccgattgg ccgcccgacc tgctgccggt 8760
tttcgccgta aggtgataaa tcgccatgct gcctcgctgt tgcttttgct tttcggctcc 8820
atgcaatggc cctcggagag cgcaccgccc gaagggtggc cgttaggcca gtttctcgaa 8880
gagaaaccgg taagtgcgcc ctcccctaca aagtagggtc gggattgccg ccgctgtgcc 8940
tccatgatag cctacgagac agcacattaa caatggggtg tcaagatggt taaggggagc 9000
aacaaggcgg cggatcggct ggccaagctc gaagaacaac gagcgcgaat caatgccgaa 9060
attcagcggg agcgggcaag ggaacagcag caagagcgca agaacgaaac aaggcgcaag 9120
gtgctggtgg gggccatgat tttggccaag gtgaacagca gcgagtggcc ggaggatcgg 9180
ctcatggcgg caatggatgc gtaccttgaa cgcgaccacg accgcgcctt gttcggtctg 9240
ccgccacgcc agaaggatga gccgggctga atgatcgacc gagacaggcc ctgcggggct 9300
gcacacgcgc cccccaccctt cgggtagggg gaaaggccgc taaagcggct aaaagcgctc 9360
cagcgtattt ctgcggggtt tggtgtgggg tttagcgggc tttgcccgcc tttcccccctg 9420 ccgcgcagcg gtggggcggt gtgtagccta gcgcagcgaa tagaccagct atccggcctc 9480
tggccgggca tattgggcaa gggcagcagc gccccacaag ggcgctgata accgcgccta 9540
gtggattatt cttagataat catggatgga tttttccaac accccgccag cccccgcccc 9600

```
tgctgggttt gcaggtttgg gggcgtgaca gttattgcag gggttcgtga cagttattgc   9660

aggggggcgt gacagttatt gcaggggttc gtgacagtta gtacgggagt gacgggcact   9720

ggctggcaat gtctagcaac ggcaggcatt tcggctgagg gtaaaagaac tttccgctaa   9780

gcgatagact gtatgtaaac acagtattgc aaggacgcgg aacatgcctc atgtggcggc   9840

caggacggcc agccgggatc gggatactgg tcgttaccag agccaccgac ccgagcaaac   9900

ccttctctat cagatcgttg acgagtatta cccggcattc gctgcgctta tggcagagca   9960

gggaaaggaa ttgccgggct atgtgcaacg ggaatttgaa gaatttctcc aatgcgggcg  10020

gctggagcat ggctttctac gggttcgctg cgagtcttgc cacgccgagc acctggtcgc  10080

tttcagaaat caatctaaag tatatatgag taaacttggt ctgacagtta ccaatgctta  10140

atcagtgagg cacctatctc agcgatctgt ctatttcgtt catccatagt tgcctgactc  10200

cccgtcgtgt agataactac gatacgggag ggcttaccat ctggccccag tgctgcaatg  10260

ataccgcgag acccacgctc accggctcca gatttatcag caataaacca gccagccgga  10320

agggccgagc gcagaagtgg tcctgcaact ttatccgcct ccatccagtc tattaattgt  10380

tgccgggaag ctagagtaag tagttcgcca gttaatagtt tgcgcaacgt tgttgccatt  10440

gctacaggca tcgtggtgtc acgctcgtcg tttggtatgg cttcattcag ctccggttcc  10500

caacgatcaa ggcgagttac atgatccccc atgttgtgca aaaaagcggt tagctccttc  10560

ggtcctccga tcgttgtcag aagtaagttg gccgcagtgt tatcactcat ggttatggca  10620

gcactgcata attctcttac tgtcatgcca tccgtaagat gcttttctgt gactggtgag  10680

tactcaacca agtcattctg agaatagtgt atgcggcgac cgagttgctc ttgcccggcg  10740

tcaacacggg ataataccgc gccacatagc agaactttaa aagtgctcat cattggaaaa  10800

cgttcttcgg ggcgaaaact ctcaaggatc ttaccgctgt tgagatccag ttcgatgtaa  10860

cccactcgtg cacccaactg atcttcagca tcttttactt tcaccagcgt ttctgggtga  10920

gcaaaaacag gaaggcaaaa tgccgcaaaa aagggaataa gggcgacacg gaaatgttga  10980

atactcatac tcttcctttt tcaatattat tgaagcattt atcagggtta ttgtctcatg  11040

agcggataca tatttgaatg tatttagaaa aataaacaaa agagtttgta gaaacgcaaa  11100

aaggccatcc gtcaggatgg ccttctgctt aatttgatgc ctggcagttt atggcgggcg  11160

tcctgcccgc caccctccgg gccgttgctt cgcaacgttc aaatccgctc ccggcggatt  11220

tgtcctactc aggagagcgt tcaccgacaa acaacagata aaacgaaagg cccagtcttt  11280

cgactgagcc tttcgtttta tttgatgcct ggcagttccc tactctcgca tggggagacc  11340

ccacactacc atcggcgcta cggcgtttca cttctgagtt cggcatgggg tcaggtggga  11400

ccaccgcgct actgccgcca ggcaaattct gttttatcag accgcttctg cgttctgatt  11460

taatctgtat caggctgaaa atcttctctc atccgccaaa acagccaagc t           11511
```

<210> SEQ ID NO 50
<211> LENGTH: 11219
<212> TYPE: DNA
<213> ORGANISM: Artificial
<220> FEATURE:
<223> OTHER INFORMATION: plasmid pLybAL22

<400> SEQUENCE: 50

```
tgcatgcaaa gctcactaac tgggcgggat tttccgggtc cggttgctga cggtaatagt     60

cgtctaaaag tttggccaca tccaaaaggc tgtcggcggg gggatgctgg ccggcgaggg    120

gattaattct gcttgtcata tacaaaaatt gtaaaaaatg gagggcggcg atcaggggct    180
```

-continued

```
tagacaccca aatcctagcc aaaaagggtt aactagccaa gggctatcca tgggcaaaga    240
gataaaagaa aaagtctcca aatccctggt catagagaaa aaattgccaa agttacccca    300
ggccatacac ggcccagcgc caagatgggg agcacaaatt caaactttgt aaacaggccg    360
gaagctatcc ggccaaggag cactcagatt gtgttaacgt tcaggggagt tgcttaacac    420
aattttccaa ttaatagtat taatattttc ttaacttgca ccgtaccatg gtgagaaagc    480
ctatctgagc ccttatttga ttaaccttcg actgattatt gatcccctgt gcagtctccc    540
ctctccctct gtctttttgc tcccgaacac gttgcccata gactcaggta ccgagctcga    600
attggggcgt tttctgtgag gctgactagc gcgtggcagc tcaaaatctc tacattctgc    660
acattcagac ccatggtctg ctgcgagggc agaacttgga actggggcga gatgccgaca    720
ccggcgggca gaccaagtac gtcttagaac tggctcaagc ccaagctaaa tccccacaag    780
tccaacaagt cgacatcatc acccgccaaa tcaccgaccc ccgcgtcagt gttggttaca    840
gtcaggcgat cgaacccttt gcgcccaaag gtcggattgt ccgtttgcct tttggcccca    900
aacgctacct ccgtaaagag ctgctttggc cccatctcta cacctttgcg gatgcaattc    960
tccaatatct ggctcagcaa aagcgcaccc cgacttggat tcaggcccac tatgctgatg   1020
ctggccaagt gggatcactg ctgagtcgct ggttgaatgt accgctaatt ttcacagggc   1080
attctctggg gcggatcaag ctaaaaaagc tgttggagca agactggccg cttgaggaaa   1140
ttgaagcgca attcaatatt caacagcgaa ttgatgcgga ggagatgacg ctcactcatg   1200
ctgactggat tgtcgccagc actcagcagg aagtggagga gcaataccgc gtttacgatc   1260
gctacaaccc agagcgcaag cttgtcattc caccgggtgt cgataccgat cgcttcaggt   1320
ttcagccctt gggcgatcgc ggtgttgttc tccaacagga actgagccgc tttctgcgcg   1380
acccagaaaa acctcaaatt ctctgcctct gtcgccccgc acctcgcaaa aatgtaccgg   1440
cgctggtgcg agcctttggc gaacatcctt ggctgcgcaa aaaagccaac cttgtcttag   1500
tactgggcag ccgccaagac atcaaccaga tggatcgcgg cagtcggcag gtgttccaag   1560
agattttcca tctggtcgat cgctacgacc tctacggcag cgtcgcctat cccaaacagc   1620
atcaggctga tgatgtgccg gagttctatc gcctagcggc tcattccggc ggggtattcg   1680
tcaatccggc gctgaccgaa ccttttggtt tgacaatttt ggaggcagga agctgcggcg   1740
tgccggtggt ggcaacccat gatggcggcc cccaggaaat tctcaaacac tgtgatttcg   1800
gcactttagt tgatgtcagc cgacccgcta atatcgcgac tgcactcgcc accctgctga   1860
gcgatcgcga tctttggcag tgctatcacc gcaatggcat tgaaaaagtt cccgcccatt   1920
acagctggga tcaacatgtc aataccctgt ttgagcgcat ggaaacggtg gctttgcctc   1980
gtcgtcgtgc tgtcagtttc gtacggagtc gcaaacgctt gattgatgcc aaacgccttg   2040
tcgttagtga catcgacaac acactgttgg gcgatcgtca aggactcgag aatttaatga   2100
cctatctcga tcagtatcgc gatcattttg cctttggaat tgccacgggg cgtcgcctag   2160
actctgccca agaagtcttg aaagagtggg gcgttccttc gccaaacttc tgggtgactt   2220
ccgtcggcag cgagattcac tatggcaccg atgctgaacc ggatatcagc tgggaaaagc   2280
atatcaatcg caactggaat cctcagcgaa ttcgggcagt aatggcacaa ctaccctttc   2340
ttgaactgca gccggaagag gatcaaacac ccttcaaagt cagcttcttt gtccgcgatc   2400
gccacgagac tgtgctgcga gaagtacggc aacatcttcg ccgccatcgc ctgcggctga   2460
agtcaatcta ttcccatcag gagtttcttg acattctgcc gctagctgcc tcgaaagggg   2520
```

-continued

```
atgcgattcg ccacctctca ctccgctggc ggattcctct tgagaacatt ttggtggcag   2580
gcgattctgg taacgatgag gaaatgctca agggccataa tctcggcgtt gtagttggca   2640
attactcacc ggaattggag ccactgcgca gctacgagcg cgtctatttt gctgagggcc   2700
actatgctaa tggcattctg gaagccttaa aacactatcg ctttttgag gcgatcgctt    2760
aacctttca gaatgagacg ttgatcggca cgtaagcgtg agacgttgat cggcacgtaa    2820
gaggttccaa ctttcaccat aatgaaataa gatcactacc gggcgtattt tttgagttat   2880
cgagattttc aggagctaag gaagctaaaa tggagaaaaa aatcactgga tataccaccg   2940
ttgatatatc ccaatggcat cgtaaagaac attttgaggc atttcagtca gttgctcaat   3000
gtacctataa ccagaccgtt cagctggata ttacggcctt tttaaagacc gtaaagaaaa   3060
ataagcacaa gttttatccg gcctttattc acattcttgc ccgcctgatg aatgctcatc   3120
cggaattccg tatggcaatg aaagacggtg agctggtgat atgggatagt gttcaccctt   3180
gttacaccgt tttccatgag caaactgaaa cgttttcatc gctctggagt gaataccacg   3240
acgatttccg gcagtttcta cacatatatt cgcaagatgt ggcgtgttac ggtgaaaacc   3300
tggcctattt ccctaaaggg tttattgaga atatgttttt cgtctcagcc aatccctggg   3360
tgagtttcac cagttttgat ttaaacgtgg ccaatatgga caacttcttc gcccccgttt   3420
tcaccatggg caaatattat acgcaaggcg acaaggtgct gatgccgctg gcgattcagg   3480
ttcatcatgc cgtttgtgat ggcttccatg tcggcagaat gcttaatgaa ttacaacagt   3540
actgcgatga gtggcagggc ggggcgtaat ttttttaagg cagttattgg tgcccttaaa   3600
cgcctggttg ctacgcctga ataagtgata ataagcggat gaatggcaga aattcgatga   3660
taagctgtca aacacaacca ccatcaaaca ggattttcgc ctgctggggc aaaccagcgt   3720
ggaccgcttg ctgcaactct ctcagggcca ggcggtgaag ggcaatcagc tgttgcccgt   3780
ctcactggtg aaaagaaaaa ccaccctggc gcccaatacg caaaccgcct ctccccgcgc   3840
gttggccgat tcattaatgc agctggcacg acaggtttcc cgactggaaa gcgggcagtg   3900
agcgcaacgc aattaatgta agttagcgcg aattgcaagc tggccgacgc gctgggctac   3960
gtcttgctgg cgttcgggag cagaagagca tacatctgga agcaaagcca ggaaagcggc   4020
ctatggagct gtgcggcagc gctcagtagg caatttttca aaatattgtt aagcctttc    4080
tgagcatggt atttttcatg gtattaccaa ttagcaggaa aataagccat tgaatataaa   4140
agataaaaat gtcttgttta caatagagtg gggggggtca gcctgccgcc ttgggccggg   4200
tgatgtcgta cttgcccgcc gcgaactcgg ttaccgtcca gcccagcgcg accagctccg   4260
gcaacgcctc gcgcacccgc ttgcggcgct tgcgcatggt cgaaccactg gcctctgacg   4320
gccagacata gccgcacaag gtatctatgg aagccttgcc ggttttgccg gggtcgatcc   4380
agccacacag ccgctggtgc agcaggcggg cggtttcgct gtccagcgcc cgcacctcgt   4440
ccatgctgat gcgcacatgc tggccgccac ccatgacggc ctgcgcgatc aaggggttca   4500
gggccacgta caggcgcccg tccgcctcgt cgctggcgta ctccgacagc agccgaaacc   4560
cctgccgctt gcggccattc tgggcgatga tggatacctt ccaaaggcgc tcgatgcagt   4620
cctgtatgtg cttgagcgcc ccaccactat cgacctctgc cccgatttcc tttgccagcg   4680
cccgatagct acctttgacc acatggcatt cagcggtgac ggcctcccac ttgggttcca   4740
ggaacagccg gagctgccgt ccgccttcgg tcttgggttc cgggccaagc actaggccat   4800
taggcccagc catggccacc agcccttgca ggatgcgcag atcatcagcg cccagcggct   4860
ccgggccgct gaactcgatc cgcttgccgt cgccgtagtc atacgtcacg tccagcttgc   4920
```

-continued

```
tgcgcttgcg ctcgccccgc ttgagggcac ggaacaggcc gggggccaga cagtgcgccg   4980
ggtcgtgccg gacgtggctg aggctgtgct tgttcttagg cttcaccacg ggcacccccc   5040
ttgctcttgc gctgcctctc cagcacggcg ggcttgagca ccccgccgtc atgccgcctg   5100
aaccaccgat cagcgaacgg tgcgccatag ttggccttgc tcacaccgaa gcggacgaag   5160
aaccggcgct ggtcgtcgtc cacaccccat tcctcggcct cggcgctggt catgctcgac   5220
aggtaggact gccagcggat gttatcgacc agtaccgagc tgccccggct ggcctgctgc   5280
tggtcgcctg cgcccatcat ggccgcgccc ttgctggcat ggtgcaggaa cacgatagag   5340
cacccggtat cggcggcgat ggcctccatg cgaccgatga cctgggccat ggggccgctg   5400
gcgttttctt cctcgatgtg gaaccggcgc agcgtgtcca gcaccatcag gcggcggccc   5460
tcggcggcgc gcttgaggcc gtcgaaccac tccggggcca tgatgttggg caggctgccg   5520
atcagcggct ggatcagcag gccgtcagcc acggcttgcc gttcctcggc gctgaggtgc   5580
gccccaaggg cgtgcaggcg gtgatgaatg gcggtgggcg ggtcttcggc gggcaggtag   5640
atcaccgggc cggtgggcag ttcgcccacc tccagcagat ccggcccgcc tgcaatctgt   5700
gcggccagtt gcagggccag catggattta ccggcaccac cgggcgacac cagcgccccg   5760
accgtaccgg ccaccatgtt gggcaaaacg tagtccagcg gtggcggcgc tgctgcgaac   5820
gcctccagaa tattgatagg cttatgggta gccattgatt gcctcctttg caggcagttg   5880
gtggttaggc gctggcgggg tcactacccc cgccctgcgc cgctctgagt tcttccaggc   5940
actcgcgcag cgcctcgtat tcgtcgtcgg tcagccagaa cttgcgctga cgcatcccct   6000
tggccttcat gcgctcggca tatcgcgctt ggcgtacagc gtcagggctg gccagcaggt   6060
cgccggtctg cttgtccttt tggtctttca tatcagtcac cgagaaactt gccggggccg   6120
aaaggcttgt cttcgcggaa caaggacaag gtgcagccgt caaggttaag gctggccata   6180
tcagcgactg aaaagcggcc agcctcggcc ttgtttgacg tataaccaaa gccaccgggc   6240
aaccaatagc ccttgtcact tttgatcagg tagaccgacc ctgaagcgct tttttcgtat   6300
tccataaaac ccccttctgt gcgtgagtac tcatagtata acaggcgtga gtaccaacgc   6360
aagcactaca tgctgaaatc tggcccgccc ctgtccatgc ctcgctggcg gggtgccggt   6420
gcccgtgcca gctcggcccg cgcaagctgg acgctgggca gacccatgac cttgctgacg   6480
gtgcgctcga tgtaatccgc ttcgtggccg ggcttgcgct ctgccagcgc tgggctggcc   6540
tcggccatgg ccttgccgat ttcctcggca ctgcggcccc ggctggccag cttctgcgcg   6600
gcgataaagt cgcacttgct gaggtcatga ccgaagcgct tgaccagccc ggccatctcg   6660
ctgcggtact cgtccagcgc cgtgcgccgg tggcggctaa gctgccgctc gggcagttcg   6720
aggctggcca gcctgcgggc cttctcctgc tgccgctggg cctgctcgat ctgctggcca   6780
gcctgctgca ccagcgccgg gccagcggtg gcggtcttgc ccttggattc acgcagcagc   6840
acccacggct gataaccggc gcgggtggtg tgcttgtcct tgcggttggt gaagcccgcc   6900
aagcggccat agtggcggct gtcggcgctg gccgggtcgg cgtcgtactc gctggccagc   6960
gtccgggcaa tctgccccccg aagttcaccg cctgcggcgt cggccacctt gacccatgcc   7020
tgatagttct tcgggctggt ttccactacc agggcaggct cccggccctc ggctttcatg   7080
tcatccaggt caaactcgct gaggtcgtcc accagcacca gaccatgccg ctcctgctcg   7140
gcgggcctga tatacacgtc attgccctgg gcattcatcc gcttgagcca tggcgtgttc   7200
tggagcactt cggcggctga ccattcccgg ttcatcatct ggccggtggg tgcgtccctg   7260
```

-continued

```
acgccgatat cgaagcgctc acagcccatg gccttgagct gtcggcctat ggcctgcaaa   7320
gtcctgtcgt tcttcatcgg gccaccaagc gcagccagat cgagccgtcc tcggttgtca   7380
gtggcgtcag gtcgagcaag agcaacgatg cgatcagcag caccaccgta ggcatcatgg   7440
aagccagcat cacggttagc catagcttcc agtgccaccc ccgcgacgcg ctccgggcgc   7500
tctgcgcggc gctgctcacc tcggcggcta cctcccgcaa ctctttggcc agctccaccc   7560
atgccgcccc tgtctggcgc tgggctttca gccactccgc cgcctgcgcc tcgctggcct   7620
gcttggtctg gctcatgacc tgccgggctt cgtcggccag tgtcgccatg ctctgggcca   7680
gcggttcgat ctgctccgct aactcgttga tgcctctgga tttcttcact ctgtcgattg   7740
cgttcatggt ctattgcctc ccggtattcc tgtaagtcga tgatctgggc gttggcggtg   7800
tcgatgttca gggccacgtc tgcccggtcg gtgcggatgc cccggccttc catctccacc   7860
acgttcggcc ccaggtgaac accgggcagg cgctcgatgc cctgcgcctc aagtgttctg   7920
tggtcaatgc gggcgtcgtg gccagcccgc tctaatgccc ggttggcatg gtcggcccat   7980
gcctcgcggg tctgctcaag ccatgccttg ggcttgagcg cttcggtctt ctgtgccccg   8040
cccttctccg ggtcttgccc gttgtaccgc ttgaaccact gagcggcggg ccgctcgatg   8100
ccgtcattga tccgctcgga gatcatcagg tggcagtgcg ggttctcgcc gccaccggca   8160
tggatggcca gcgtatacgg caggcgctcg gcaccggtca ggtgctgggc gaactcggac   8220
gccagcgcct tctgctggtc gagggtcagc tcgaccggca gggcaaattc gacctccttg   8280
aacagccgcc cattggcgcg ttcatacagg tcggcagcat cccagtagtc ggcgggccgc   8340
tcgacgaact ccggcatgtg cccggattcg gcgtgcaaga cttcatccat gtcgcgggca   8400
tacttgcctt cgcgctggat gtagtcggcc ttggccctgg ccgattggcc gcccgacctg   8460
ctgccggttt tcgccgtaag gtgataaatc gccatgctgc ctcgctgttg cttttgcttt   8520
tcggctccat gcaatggccc tcggagagcg caccgcccga agggtggccg ttaggccagt   8580
ttctcgaaga gaaaccggta agtgcgccct cccctacaaa gtagggtcgg gattgccgcc   8640
gctgtgcctc catgatagcc tacgagacag cacattaaca atggggtgtc aagatggtta   8700
aggggagcaa caaggcggcg gatcggctgg ccaagctcga agaacaacga gcgcgaatca   8760
atgccgaaat tcagcgggag cgggcaaggg aacagcagca agagcgcaag aacgaaacaa   8820
ggcgcaaggt gctggtgggg gccatgattt tggccaaggt gaacagcagc gagtggccgg   8880
aggatcggct catggcggca atggatgcgt accttgaacg cgaccacgac cgcgccttgt   8940
tcggtctgcc gccacgccag aaggatgagc cgggctgaat gatcgaccga gacaggccct   9000
gcggggctgc acacgcgccc ccacccttcg ggtaggggga aaggccgcta aagcggctaa   9060
aagcgctcca gcgtatttct gcggggtttg gtgtggggtt tagcgggctt tgcccgcctt   9120
tccccctgcc gcgcagcggt ggggcggtgt gtagcctagc gcagcgaata gaccagctat   9180
ccggcctctg gccgggcata ttgggcaagg gcagcagcgc cccacaaggg cgctgataac   9240
cgcgcctagt ggattattct tagataatca tggatggatt tttccaacac cccgccagcc   9300
cccgcccctg ctgggtttgc aggtttgggg gcgtgacagt tattgcaggg gttcgtgaca   9360
gttattgcag gggggcgtga cagttattgc aggggttcgt gacagttagt acgggagtga   9420
cgggcactgg ctggcaatgt ctagcaacgg caggcatttc ggctgagggt aaaagaactt   9480
tccgctaagc gatagactgt atgtaaacac agtattgcaa ggacgcggaa catgcctcat   9540
gtggcggcca ggacggccag ccgggatcgg gatactggtc gttaccagag ccaccgaccc   9600
gagcaaaccc ttctctatca gatcgttgac gagtattacc cggcattcgc tgcgcttatg   9660
```

```
gcagagcagg gaaaggaatt gccgggctat gtgcaacggg aatttgaaga atttctccaa   9720
tgcgggcggc tggagcatgg ctttctacgg gttcgctgcg agtcttgcca cgccgagcac   9780
ctggtcgctt tcagaaatca atctaaagta tatatgagta aacttggtct gacagttacc   9840
aatgcttaat cagtgaggca cctatctcag cgatctgtct atttcgttca tccatagttg   9900
cctgactccc cgtcgtgtag ataactacga tacgggaggg cttaccatct ggccccagtg   9960
ctgcaatgat accgcgagac ccacgctcac cggctccaga tttatcagca ataaaccagc  10020
cagccggaag ggccgagcgc agaagtggtc ctgcaacttt atccgcctcc atccagtcta  10080
ttaattgttg ccgggaagct agagtaagta gttcgccagt taatagtttg cgcaacgttg  10140
ttgccattgc tacaggcatc gtggtgtcac gctcgtcgtt tggtatggct tcattcagct  10200
ccggttccca acgatcaagg cgagttacat gatcccccat gttgtgcaaa aaagcggtta  10260
gctccttcgg tcctccgatc gttgtcagaa gtaagttggc cgcagtgtta tcactcatgg  10320
ttatggcagc actgcataat tctcttactg tcatgccatc cgtaagatgc ttttctgtga  10380
ctggtgagta ctcaaccaag tcattctgag aatagtgtat gcggcgaccg agttgctctt  10440
gcccggcgtc aacacgggat aataccgcgc cacatagcag aactttaaaa gtgctcatca  10500
ttggaaaacg ttcttcgggg cgaaaactct caaggatctt accgctgttg agatccagtt  10560
cgatgtaacc cactcgtgca cccaactgat cttcagcatc ttttactttc accagcgttt  10620
ctgggtgagc aaaaacagga aggcaaaatg ccgcaaaaaa gggaataagg gcgacacgga  10680
aatgttgaat actcatactc ttcctttttc aatattattg aagcatttat cagggttatt  10740
gtctcatgag cggatacata tttgaatgta tttagaaaaa taaacaaaag agtttgtaga  10800
aacgcaaaaa ggccatccgt caggatggcc ttctgcttaa tttgatgcct ggcagtttat  10860
ggcgggcgtc ctgcccgcca ccctccgggc cgttgcttcg caacgttcaa atccgctccc  10920
ggcggatttg tcctactcag gagagcgttc accgacaaac aacagataaa acgaaaggcc  10980
cagtctttcg actgagcctt tcgttttatt tgatgcctgg cagttcccta ctctcgcatg  11040
gggagacccc acactaccat cggcgctacg gcgtttcact tctgagttcg gcatggggtc  11100
aggtgggacc accgcgctac tgccgccagg caaattctgt tttatcagac cgcttctgcg  11160
ttctgattta atctgtatca ggctgaaaat cttctctcat ccgccaaaac agccaagct   11219
```

<210> SEQ ID NO 51
<211> LENGTH: 4962
<212> TYPE: DNA
<213> ORGANISM: Artificial
<220> FEATURE:
<223> OTHER INFORMATION: plasmid pLybAL13f

<400> SEQUENCE: 51

```
cgaccaattc acgtgtttga cagcttatca tcgaatttct gccattcatc cgcttattat     60
cacttattca ggcgtagcaa ccaggcgttt aagggcacca ataactgcct taaaaaaatt    120
acgccccgcc ctgccactca tcgcagtact gttgtaattc attaagcatt ctgccgacat    180
ggaagccatc acaaacggca tgatgaacct gaatcgccag cggcatcagc accttgtcgc    240
cttgcgtata atatttgccc atggtgaaaa cgggggcgaa gaagttgtcc atattggcca    300
cgtttaaatc aaaactggtg aaactcaccc agggattggc tgagacgaaa aacatattct    360
caataaaccc tttagggaaa taggccaggt tttcaccgta acacgccaca tcttgcgaat    420
atatgtgtag aaactgccgg aaatcgtcgt ggtattcact ccagagcgat gaaaacgttt    480
```

-continued

```
cagtttgctc atggaaaacg gtgtaacaag ggtgaacact atcccatatc accagctcac    540
cgtctttcat tgccatacgg aattccggat gagcattcat caggcgggca agaatgtgaa    600
taaaggccgg ataaaacttg tgcttatttt tctttacggt ctttaaaaag gccgtaatat    660
ccagctgaac ggtctggtta taggtacatt gagcaactga ctgaaatgcc tcaaaatgtt    720
ctttacgatg ccattgggat atatcaacgg tggtatatcc agtgattttt ttctccattt    780
tagcttcctt agctcctgac gttctgaaaa ggttaagcga tcgcctcaaa aaagcgatag    840
tgttttaagg cttccagaat gccattagca tagtggccct cagcaaaata gacgcgctcg    900
tagctgcgca gtggctccaa ttccggtgag taattgccaa ctacaacgcc gagattatgg    960
cccttgagca tttcctcatc gttaccagaa tcgcctgcca ccaaaatgtt ctcaagagga   1020
atccgccagc ggagtgagag gtggcgaatc gcatcccctt tcgaggcagc tagcggcaga   1080
atgtcaagaa actcctgatg ggaatagatt gacttcagcc gcaggcgatg gcggcgaaga   1140
tgttgccgta cttctcgcag cacagtctcg tggcgatcgc ggacaaagaa gctgactttg   1200
aagggtgttt gatcctcttc cggctgcagt tcaagaaagg gtagttgtgc cattactgcc   1260
cgaattcgct gaggattcca gttgcgattg atatgctttt cccagctgat atccggttca   1320
gcatcggtgc catagtgaat ctcgctgccg acggaagtca cccagaagtt tggcgaagga   1380
acgccccact ctttcaagac ttcttgggca gagtctaggc gacgccccgt ggcaattcca   1440
aaggcaaaat gatcgcgata ctgatcgaga taggtcatta aattctcgag tccttgacga   1500
tcgcccaaca gtgtgttgtc gatgtcacta acgacaaggc gtttggcatc aatcaagcgt   1560
ttgcgactcc gtacgaaact gacagcacga cgacgaggca aagccaccgt ttccatgcgc   1620
tcaaacaggg tattgacatg ttgatcccag ctgtaatggg cgggaacttt ttcaatgcca   1680
ttgcggtgat agcactgcca aagatcgcga tcgctcagca gggtggcgag tgcagtcgcg   1740
atattagcgg gtcggctgac atcaactaaa gtgccgaaat cacagtgttt gagaatttcc   1800
tgggggccgc catcatgggt tgccaccacc ggcacgccgc agcttcctgc ctccaaaatt   1860
gtcaaaccaa aaggttcggt cagcgccgga ttgacgaata ccccgccgga atgagccgct   1920
aggcgataga actccggcac atcatcagcc tgatgctgtt tgggataggc gacgctgccg   1980
tagaggtcgt agcgatcgac cagatggaaa atctcttgga acacctgccg actgccgcga   2040
tccatctggt tgatgtcttg gcggctgccc agtactaaga caaggttggc tttttttgcgc   2100
agccaaggat gttcgccaaa ggctcgcacc agcgccggta catttttgcg aggtgcgggg   2160
cgacagaggc agagaatttg aggtttttct gggtcgcgca gaaagcggct cagttcctgt   2220
tggagaacaa caccgcgatc gcccaagggc tgaaacctga agcgatcggt atcgacaccc   2280
ggtggaatga caagcttgcg ctctgggttg tagcgatcgt aaacgcggta ttgctcctcc   2340
acttcctgct gagtgctggc gacaatccag tcagcatgag tgagcgtcat ctcctccgca   2400
tcaattcgct gttgaatatt gaattgcgct tcaatttcct caagcggcca gtcttgctcc   2460
aacagctttt ttagcttgat ccgccccaga gaatgccctg tgaaaattag cggtacattc   2520
aaccagcgac tcagcagtga tcccacttgg ccagcatcag catagtgggc ctgaatccaa   2580
gtcggggtgc gcttttgctg agccagatat tggagaattg catccgcaaa ggtgtagaga   2640
tggggccaaa gcagctcttt acggaggtag cgtttggggc caaaaggcaa acggacaatc   2700
cgacctttgg gcgcaaaggg ttcgatcgcc tgactgtaac caacactgac gcgggggtcg   2760
gtgatttggc gggtgatgat gtcgacttgt tggacttgtg gggatttagc ttgggcttga   2820
gccagttcta agacgtactt ggtctgcccg ccggtgtcgg catctcgccc cagttccaag   2880
```

-continued

```
ttctgccctc gcagcagacc atgggtctga atgtgcagaa tgtagagatt ttgagctgcc   2940
acgcgctagt cagcctcaca gaaaacgccc caattgtagt ctaacgaatt caagcttgat   3000
atcattcagg acgagcctca gactccagcg taactggact gcaatcaact cactggctca   3060
ccttcacggg tgggcctttc ttcggtagaa aatcaaagga tcttcttgag atcctttttt   3120
tctgcgcgta atctgctgct tgcaaacaaa aaaaccaccg ctaccagcgg tggtttgttt   3180
gccggatcaa gagctaccaa ctctttttcc gaggtaactg gcttcagcag agcgcagata   3240
ccaaatactg ttcttctagt gtagccgtag ttaggccacc acttcaagaa ctctgtagca   3300
ccgcctacat acctcgctct gctaatcctg ttaccagtgg ctgctgccag tggcgataag   3360
tcgtgtctta ccgggttgga ctcaagacga tagttaccgg ataaggcgca gcggtcgggc   3420
tgaacggggg gttcgtgcac acagcccagc ttggagcgaa cgacctacac cgaactgaga   3480
tacctacagc gtgagctatg agaaagcgcc acgcttcccg aagggagaaa ggcggacagg   3540
tatccggtaa gcggcagggt cggaacagga gagcgcacga gggagcttcc agggggaaac   3600
gcctggtatc tttatagtcc tgtcgggttt cgccacctct gacttgagca tcgatttttg   3660
tgatgctcgt caggggggcg gagcctatgg aaaaacgcca gcaacgcaga aaggcccacc   3720
cgaaggtgag ccaggtgatt acatttgggc cctcatcaga ggttttcacc gtcatcaccg   3780
aaacgcgcga ggcagctgcg gtaaagctca tcagcgtggt cgtgaagcga ttcacagatg   3840
tctgcctgtt catccgcgtc cagctcgttg agtttctcca gaagcgttaa tgtctggctt   3900
ctgataaagc gggccatgtt aagggcggtt ttttcctgtt tggtcattta gaaaaactca   3960
tcgagcatca agtgaaactg caatttattc atatcaggat tatcaatacc atatttttga   4020
aaaagccgtt tctgtaatga aggagaaaac tcaccgaggc agttccatag gatggcaaga   4080
tcctggtatc ggtctgcgat tccgactcgt ccaacatcaa tacaacctat taatttcccc   4140
tcgtcaaaaa taaggttatc aagtgagaaa tcaccatgag tgacgactga atccggtgag   4200
aatggcaaaa gcttatgcat ttctttccag acttgttcaa caggccagcc attacgctcg   4260
tcatcaaaat cactcgcacc aaccaaaccg ttattcattc gtgattgcgc ctgagcgaga   4320
cgaaatacgc gatcgccgtt aaaaggacaa ttacaaacag gaatcgaatg caaccggcgc   4380
aggaacactg ccagcgcatc aacaatattt tcacctgaat caggatattc ttctaatacc   4440
tggaatgctg ttttccctgg gatcgcagtg gtgagtaacc atgcatcatc aggagtacgg   4500
ataaaatgct tgatggtcgg aagaggcata aattccgtca gccagtttag cctgaccatc   4560
tcatctgtaa catcattggc aacgctacct ttgccatgtt tcagaaacaa ctctggcgca   4620
tcgggcttcc catacaatcg atagattgtc gcacctgatt gcccgacatt atcgcgagcc   4680
catttatacc catataaatc agcatccatg ttggaattta atcgcggcct cgagcaagac   4740
gtttcccgtt gaatatggct cattttagct tccttagctc ctgaaaatct cgataactca   4800
aaaaatacgc ccggtagtga tcttatttca ttatggtgaa agttggaacc tcttacgtgc   4860
cgatcaagtc aaaagcctcc ggtcggaggc ttttgacttt ctgctatgga ggtcaggtat   4920
gatttaaatg gtcagtattg agcgatatct agagaattcg tc                       4962
```

<210> SEQ ID NO 52
<211> LENGTH: 4962
<212> TYPE: DNA
<213> ORGANISM: Artificial
<220> FEATURE:
<223> OTHER INFORMATION: plasmid pLybAL13r -continued

<400> SEQUENCE: 52

```
agactacaat tggggcgttt tctgtgaggc tgactagcgc gtggcagctc aaaatctcta     60
cattctgcac attcagaccc atggtctgct gcgagggcag aacttggaac tggggcgaga    120
tgccgacacc ggcgggcaga ccaagtacgt cttagaactg gctcaagccc aagctaaatc    180
cccacaagtc caacaagtcg acatcatcac ccgccaaatc accgaccccc gcgtcagtgt    240
tggttacagt caggcgatcg aacccctttgc gcccaaaggt cggattgtcc gtttgccttt   300
tggccccaaa cgctacctcc gtaaagagct gctttggccc catctctaca cctttgcgga    360
tgcaattctc caatatctgg ctcagcaaaa gcgcaccccg acttggattc aggcccacta    420
tgctgatgct ggccaagtgg gatcactgct gagtcgctgg ttgaatgtac cgctaatttt    480
cacagggcat tctctggggc ggatcaagct aaaaaagctg ttggagcaag actggccgct    540
tgaggaaatt gaagcgcaat tcaatattca acagcgaatt gatgcggagg agatgacgct    600
cactcatgct gactggattg tcgccagcac tcagcaggaa gtggaggagc aataccgcgt    660
ttacgatcgc tacaacccag agcgcaagct tgtcattcca ccgggtgtcg ataccgatcg    720
cttcaggttt cagcccttgg gcgatcgcgg tgttgttctc caacaggaac tgagccgctt    780
tctgcgcgac ccagaaaaac ctcaaattct ctgcctctgt cgccccgcac ctcgcaaaaa    840
tgtaccggcg ctggtgcgag cctttggcga acatccttgg ctgcgcaaaa aagccaacct    900
tgtcttagta ctgggcagcc gccaagacat caaccagatg gatcgcggca gtcggcaggt    960
gttccaagag attttccatc tggtcgatcg ctacgacctc tacggcagcg tcgcctatcc   1020
caaacagcat caggctgatg atgtgccgga gttctatcgc ctagcggctc attccggcgg   1080
ggtattcgtc aatccggcgc tgaccgaacc ttttggtttg acaattttgg aggcaggaag   1140
ctgcggcgtg ccggtggtgg caacccatga tggcggcccc caggaaattc tcaaacactg   1200
tgatttcggc actttagttg atgtcagccg acccgctaat atcgcgactg cactcgccac   1260
cctgctgagc gatcgcgatc tttggcagtg ctatcaccgc aatggcattg aaaaagttcc   1320
cgcccattac agctgggatc aacatgtcaa taccctgttt gagcgcatgg aaacggtggc   1380
tttgcctcgt cgtcgtgctg tcagtttcgt acggagtcgc aaacgcttga ttgatgccaa   1440
acgccttgtc gttagtgaca tcgacaacac actgttgggc gatcgtcaag gactcgagaa   1500
tttaatgacc tatctcgatc agtatcgcga tcattttgcc tttggaattg ccacggggcg   1560
tcgcctagac tctgcccaag aagtcttgaa agagtggggc gttccttcgc caaacttctg   1620
ggtgacttcc gtcggcagcg agattcacta tggcaccgat gctgaaccgg atatcagctg   1680
ggaaaagcat atcaatcgca actggaatcc tcagcgaatt cgggcagtaa tggcacaact   1740
accctttctt gaactgcagc cggaagagga tcaaacaccc ttcaaagtca gcttctttgt   1800
ccgcgatcgc cacgagactg tgctgcgaga agtacggcaa catcttcgcc gccatcgcct   1860
gcggctgaag tcaatctatt cccatcagga gtttcttgac attctgccgc tagctgcctc   1920
gaaaggggat gcgattcgcc acctctcact ccgctggcgg attcctcttg agaacatttt   1980
ggtggcaggc gattctggta acgatgagga aatgctcaag ggccataatc tcggcgttgt   2040
agttggcaat tactcaccgg aattggagcc actgcgcagc tacgagcgcg tctattttgc   2100
tgagggccac tatgctaatg gcattctgga agccttaaaa cactatcgct tttttgaggc   2160
gatcgcttaa ccttttcaga acgtcaggag ctaaggaagc taaaatggag aaaaaaatca   2220
ctggatatac caccgttgat atatcccaat ggcatcgtaa agaacatttt gaggcatttc   2280
agtcagttgc tcaatgtacc tataaccaga ccgttcagct ggatattacg gcctttttaa   2340
```

-continued

```
agaccgtaaa gaaaaataag cacaagtttt atccggcctt tattcacatt cttgcccgcc   2400
tgatgaatgc tcatccggaa ttccgtatgg caatgaaaga cggtgagctg gtgatatggg   2460
atagtgttca cccttgttac accgttttcc atgagcaaac tgaaacgttt tcatcgctct   2520
ggagtgaata ccacgacgat ttccggcagt ttctacacat atattcgcaa gatgtggcgt   2580
gttacggtga aaacctggcc tatttcccta aagggtttat tgagaatatg tttttcgtct   2640
cagccaatcc ctgggtgagt ttcaccagtt ttgatttaaa cgtggccaat atggacaact   2700
tcttcgcccc cgttttcacc atgggcaaat attatacgca aggcgacaag gtgctgatgc   2760
cgctggcgat tcaggttcat catgccgttt gtgatggctt ccatgtcggc agaatgctta   2820
atgaattaca acagtactgc gatgagtggc agggcggggc gtaatttttt taaggcagtt   2880
attggtgccc ttaaacgcct ggttgctacg cctgaataag tgataataag cggatgaatg   2940
gcagaaattc gatgataagc tgtcaaacac gtgaattggt cgaacgaatt caagcttgat   3000
atcattcagg acgagcctca gactccagcg taactggact gcaatcaact cactggctca   3060
ccttcacggg tgggcctttc ttcggtagaa aatcaaagga tcttcttgag atcctttttt   3120
tctgcgcgta atctgctgct tgcaaacaaa aaaaccaccg ctaccagcgg tggtttgttt   3180
gccggatcaa gagctaccaa ctctttttcc gaggtaactg gcttcagcag agcgcagata   3240
ccaaatactg ttcttctagt gtagccgtag ttaggccacc acttcaagaa ctctgtagca   3300
ccgcctacat acctcgctct gctaatcctg ttaccagtgg ctgctgccag tggcgataag   3360
tcgtgtctta ccgggttgga ctcaagacga tagttaccgg ataaggcgca gcggtcgggc   3420
tgaacggggg gttcgtgcac acagcccagc ttggagcgaa cgacctacac cgaactgaga   3480
tacctacagc gtgagctatg agaaagcgcc acgcttcccg aagggagaaa ggcggacagg   3540
tatccggtaa gcggcagggt cggaacagga gagcgcacga gggagcttcc agggggaaac   3600
gcctggtatc tttatagtcc tgtcgggttt cgccacctct gacttgagca tcgatttttg   3660
tgatgctcgt caggggggcg gagcctatgg aaaaacgcca gcaacgcaga aaggcccacc   3720
cgaaggtgag ccaggtgatt acatttgggc cctcatcaga ggttttcacc gtcatcaccg   3780
aaacgcgcga ggcagctgcg gtaaagctca tcagcgtggt cgtgaagcga ttcacagatg   3840
tctgcctgtt catccgcgtc cagctcgttg agtttctcca gaagcgttaa tgtctggctt   3900
ctgataaagc gggccatgtt aagggcggtt ttttcctgtt tggtcattta gaaaaactca   3960
tcgagcatca agtgaaactg caatttattc atatcaggat tatcaatacc atatttttga   4020
aaaagccgtt tctgtaatga aggagaaaac tcaccgaggc agttccatag gatggcaaga   4080
tcctggtatc ggtctgcgat tccgactcgt ccaacatcaa tacaacctat taatttcccc   4140
tcgtcaaaaa taaggttatc aagtgagaaa tcaccatgag tgacgactga atccggtgag   4200
aatggcaaaa gcttatgcat ttctttccag acttgttcaa caggccagcc attacgctcg   4260
tcatcaaaat cactcgcacc aaccaaaccg ttattcattc gtgattgcgc ctgagcgaga   4320
cgaaatacgc gatcgccgtt aaaaggacaa ttacaaacag gaatcgaatg caaccggcgc   4380
aggaacactg ccagcgcatc aacaatattt tcacctgaat caggatattc ttctaatacc   4440
tggaatgctg ttttccctgg gatcgcagtg gtgagtaacc atgcatcatc aggagtacgg   4500
ataaaatgct tgatggtcgg aagaggcata aattccgtca gccagtttag cctgaccatc   4560
tcatctgtaa catcattggc aacgctacct ttgccatgtt tcagaaacaa ctctggcgca   4620
tcgggcttcc catacaatcg atagattgtc gcacctgatt gcccgacatt atcgcgagcc   4680
```

-continued catttatacc catataaatc agcatccatg ttggaattta atcgcggcct cgagcaagac 4740
gtttcccgtt gaatatggct cattttagct tccttagctc ctgaaaatct cgataactca 4800
aaaaatacgc ccggtagtga tcttatttca ttatggtgaa agttggaacc tcttacgtgc 4860
cgatcaagtc aaaagcctcc ggtcggaggc ttttgacttt ctgctatgga ggtcaggtat 4920
gatttaaatg gtcagtattg agcgatatct agagaattcg tc 4962

<210> SEQ ID NO 53
<211> LENGTH: 5052
<212> TYPE: DNA
<213> ORGANISM: Artificial
<220> FEATURE:
<223> OTHER INFORMATION: plasmid pLybAL14f

<400> SEQUENCE: 53
cgaccaattc acgtgtttga cagcttatca tcgaatttct gccattcatc cgcttattat 60
cacttattca ggcgtagcaa ccaggcgttt aagggcacca ataactgcct taaaaaaatt 120
acgccccgcc ctgccactca tcgcagtact gttgtaattc attaagcatt ctgccgacat 180
ggaagccatc acaaacggca tgatgaacct gaatcgccag cggcatcagc accttgtcgc 240
cttgcgtata atatttgccc atggtgaaaa cgggggcgaa gaagttgtcc atattggcca 300
cgtttaaatc aaaactggtg aaactcaccc agggattggc tgagacgaaa aacatattct 360
caataaaccc tttagggaaa taggccaggt tttcaccgta acacgccaca tcttgcgaat 420
atatgtgtag aaactgccgg aaatcgtcgt ggtattcact ccagagcgat gaaaacgttt 480
cagtttgctc atggaaaacg gtgtaacaag ggtgaacact atcccatatc accagctcac 540
cgtctttcat tgccatacgg aattccggat gagcattcat caggcgggca agaatgtgaa 600
taaaggccgg ataaaacttg tgcttatttt tctttacggt ctttaaaaag gccgtaatat 660
ccagctgaac ggtctggtta taggtacatt gagcaactga ctgaaatgcc tcaaaatgtt 720
ctttacgatg ccattgggat atatcaacgg tggtatatcc agtgattttt ttctccattt 780
tagcttcctt agctcctgaa aatctcgata actcaaaaaa tacgcccggt agtgatctta 840
tttcattatg gtgaaagttg gaacctctta cgtgccgatc aacgtctcac gttctgaaaa 900
ggttaagcga tcgcctcaaa aaagcgatag tgttttaagg cttccagaat gccattagca 960
tagtggccct cagcaaaata gacgcgctcg tagctgcgca gtggctccaa ttccggtgag 1020
taattgccaa ctacaacgcc gagattatgg cccttgagca tttcctcatc gttaccagaa 1080
tcgcctgcca ccaaaatgtt ctcaagagga atccgccagc ggagtgagag gtggcgaatc 1140
gcatcccctt tcgaggcagc tagcggcaga atgtcaagaa actcctgatg ggaatagatt 1200
gacttcagcc gcaggcgatg gcggcgaaga tgttgccgta cttctcgcag cacagtctcg 1260
tggcgatcgc ggacaaagaa gctgactttg aagggtgttt gatcctcttc cggctgcagt 1320
tcaagaaagg gtagttgtgc cattactgcc cgaattcgct gaggattcca gttgcgattg 1380
atatgctttt cccagctgat atccggttca gcatcggtgc catagtgaat ctcgctgccg 1440
acggaagtca cccagaagtt tggcgaagga acgccccact ctttcaagac ttcttgggca 1500
gagtctaggc gacgccccgt ggcaattcca aaggcaaaat gatcgcgata ctgatcgaga 1560
taggtcatta aattctcgag tccttgacga tcgcccaaca gtgtgttgtc gatgtcacta 1620
acgacaaggc gtttggcatc aatcaagcgt ttgcgactcc gtacgaaact gacagcacga 1680
cgacgaggca aagccaccgt ttccatgcgc tcaaacaggg tattgacatg ttgatcccag 1740
ctgtaatggg cgggaacttt ttcaatgcca ttgcggtgat agcactgcca aagatcgcga 1800

-continued

```
tcgctcagca gggtggcgag tgcagtcgcg atattagcgg gtcggctgac atcaactaaa   1860
gtgccgaaat cacagtgttt gagaatttcc tgggggccgc catcatgggt tgccaccacc   1920
ggcacgccgc agcttcctgc ctccaaaatt gtcaaaccaa aaggttcggt cagcgccgga   1980
ttgacgaata ccccgccgga atgagccgct aggcgataga actccggcac atcatcagcc   2040
tgatgctgtt tgggataggc gacgctgccg tagaggtcgt agcgatcgac cagatggaaa   2100
atctcttgga acacctgccg actgccgcga tccatctggt tgatgtcttg gcggctgccc   2160
agtactaaga caaggttggc ttttttgcgc agccaaggat gttcgccaaa ggctcgcacc   2220
agcgccggta catttttgcg aggtgcgggg cgacagaggc agagaatttg aggtttttct   2280
gggtcgcgca gaaagcggct cagttcctgt tggagaacaa caccgcgatc gcccaagggc   2340
tgaaacctga agcgatcggt atcgacaccc ggtggaatga caagcttgcg ctctgggttg   2400
tagcgatcgt aaacgcggta ttgctcctcc acttcctgct gagtgctggc gacaatccag   2460
tcagcatgag tgagcgtcat ctcctccgca tcaattcgct gttgaatatt gaattgcgct   2520
tcaatttcct caagcggcca gtcttgctcc aacagctttt ttagcttgat ccgccccaga   2580
gaatgccctg tgaaaattag cggtacattc aaccagcgac tcagcagtga tcccacttgg   2640
ccagcatcag catagtgggc ctgaatccaa gtcggggtgc gcttttgctg agccagatat   2700
tggagaattg catccgcaaa ggtgtagaga tggggccaaa gcagctcttt acggaggtag   2760
cgtttggggc caaaaggcaa acggacaatc cgacctttgg gcgcaaaggg ttcgatcgcc   2820
tgactgtaac caacactgac gcgggggtcg gtgatttggc gggtgatgat gtcgacttgt   2880
tggacttgtg ggatttagc ttgggcttga gccagttcta agacgtactt ggtctgcccg   2940
ccggtgtcgg catctcgccc cagttccaag ttctgccctc gcagcagacc atgggtctga   3000
atgtgcagaa tgtagagatt ttgagctgcc acgcgctagt cagcctcaca gaaaacgccc   3060
caattgtagt ctaacgaatt caagcttgat atcattcagg acgagcctca gactccagcg   3120
taactggact gcaatcaact cactggctca ccttcacggg tgggcctttc ttcggtagaa   3180
aatcaaagga tcttcttgag atcctttttt tctgcgcgta atctgctgct tgcaaacaaa   3240
aaaaccaccg ctaccagcgg tggtttgttt gccggatcaa gagctaccaa ctcttttcc    3300
gaggtaactg gcttcagcag agcgcagata ccaaatactg ttcttctagt gtagccgtag   3360
ttaggccacc acttcaagaa ctctgtagca ccgcctacat acctcgctct gctaatcctg   3420
ttaccagtgg ctgctgccag tggcgataag tcgtgtctta ccgggttgga ctcaagacga   3480
tagttaccgg ataaggcgca gcggtcgggc tgaacggggg gttcgtgcac acagcccagc   3540
ttggagcgaa cgacctacac cgaactgaga tacctacagc gtgagctatg agaaagcgcc   3600
acgcttcccg aagggagaaa ggcggacagg tatccggtaa gcggcagggt cggaacagga   3660
gagcgcacga gggagcttcc agggggaaac gcctggtatc tttatagtcc tgtcgggttt   3720
cgccacctct gacttgagca tcgatttttg tgatgctcgt caggggggcg gagcctatgg   3780
aaaaacgcca gcaacgcaga aaggcccacc cgaaggtgag ccaggtgatt acatttgggc   3840
cctcatcaga ggttttcacc gtcatcaccg aaacgcgcga ggcagctgcg gtaaagctca   3900
tcagcgtggt cgtgaagcga ttcacagatg tctgcctgtt catccgcgtc cagctcgttg   3960
agtttctcca gaagcgttaa tgtctggctt ctgataaagc gggccatgtt aagggcggtt   4020
ttttcctgtt tggtcattta gaaaaactca tcgagcatca agtgaaactg caatttattc   4080
atatcaggat tatcaatacc atatttttga aaaagccgtt tctgtaatga aggagaaaac   4140
```

-continued tcaccgaggc agttccatag gatggcaaga tcctggtatc ggtctgcgat tccgactcgt 4200
ccaacatcaa tacaacctat taatttcccc tcgtcaaaaa taaggttatc aagtgagaaa 4260
tcaccatgag tgacgactga atccggtgag aatggcaaaa gcttatgcat ttctttccag 4320
acttgttcaa caggccagcc attacgctcg tcatcaaaat cactcgcacc aaccaaaccg 4380
ttattcattc gtgattgcgc ctgagcgaga cgaaatacgc gatcgccgtt aaaaggacaa 4440
ttacaaacag gaatcgaatg caaccggcgc aggaacactg ccagcgcatc aacaatattt 4500
tcacctgaat caggatattc ttctaatacc tggaatgctg ttttccctgg gatcgcagtg 4560
gtgagtaacc atgcatcatc aggagtacgg ataaaatgct tgatggtcgg aagaggcata 4620
aattccgtca gccagtttag cctgaccatc tcatctgtaa catcattggc aacgctacct 4680
ttgccatgtt tcagaaacaa ctctggcgca tcgggcttcc catacaatcg atagattgtc 4740
gcacctgatt gcccgacatt atcgcgagcc catttatacc catataaatc agcatccatg 4800
ttggaattta atcgcggcct cgagcaagac gtttcccgtt gaatatggct cattttagct 4860
tccttagctc ctgaaaatct cgataactca aaaaatacgc ccggtagtga tcttatttca 4920
ttatggtgaa agttggaacc tcttacgtgc cgatcaagtc aaaagcctcc ggtcggaggc 4980
ttttgacttt ctgctatgga ggtcaggtat gatttaaatg gtcagtattg agcgatatct 5040
agagaattcg tc 5052

<210> SEQ ID NO 54
<211> LENGTH: 5052
<212> TYPE: DNA
<213> ORGANISM: Artificial
<220> FEATURE:
<223> OTHER INFORMATION: plasmid pLybAL14r

<400> SEQUENCE: 54
agactacaat tggggcgttt tctgtgaggc tgactagcgc gtggcagctc aaaatctcta 60
cattctgcac attcagaccc atggtctgct gcgagggcag aacttggaac tggggcgaga 120
tgccgacacc ggcgggcaga ccaagtacgt cttagaactg gctcaagccc aagctaaatc 180
cccacaagtc caacaagtcg acatcatcac ccgccaaatc accgaccccc gcgtcagtgt 240
tggttacagt caggcgatcg aaccctttgc gcccaaaggt cggattgtcc gtttgccttt 300
tggccccaaa cgctacctcc gtaaagagct gctttggccc catctctaca cctttgcgga 360
tgcaattctc caatatctgg ctcagcaaaa gcgcaccccg acttggattc aggcccacta 420
tgctgatgct ggccaagtgg gatcactgct gagtcgctgg ttgaatgtac cgctaatttt 480
cacagggcat tctctggggc ggatcaagct aaaaaagctg ttggagcaag actggccgct 540
tgaggaaatt gaagcgcaat tcaatattca acagcgaatt gatgcggagg agatgacgct 600
cactcatgct gactggattg tcgccagcac tcagcaggaa gtggaggagc aataccgcgt 660
ttacgatcgc tacaacccag agcgcaagct tgtcattcca ccgggtgtcg ataccgatcg 720
cttcaggttt cagcccttgg gcgatcgcgg tgttgttctc caacaggaac tgagccgctt 780
tctgcgcgac ccagaaaaac ctcaaattct ctgcctctgt cgccccgcac ctcgcaaaaa 840
tgtaccggcg ctggtgcgag cctttggcga acatccttgg ctgcgcaaaa aagccaacct 900
tgtcttagta ctgggcagcc gccaagacat caaccagatg gatcgcggca gtcggcaggt 960
gttccaagag attttccatc tggtcgatcg ctacgacctc tacggcagcg tcgcctatcc 1020
caaacagcat caggctgatg atgtgccgga gttctatcgc ctagcggctc attccggcgg 1080
ggtattcgtc aatccggcgc tgaccgaacc ttttggtttg acaattttgg aggcaggaag 1140

-continued

```
ctgcggcgtg ccggtggtgg caacccatga tggcggcccc caggaaattc tcaaacactg   1200
tgatttcggc actttagttg atgtcagccg acccgctaat atcgcgactg cactcgccac   1260
cctgctgagc gatcgcgatc tttggcagtg ctatcaccgc aatggcattg aaaaagttcc   1320
cgcccattac agctgggatc aacatgtcaa taccctgttt gagcgcatgg aaacggtggc   1380
tttgcctcgt cgtcgtgctg tcagtttcgt acggagtcgc aaacgcttga ttgatgccaa   1440
acgccttgtc gttagtgaca tcgacaacac actgttgggc gatcgtcaag gactcgagaa   1500
tttaatgacc tatctcgatc agtatcgcga tcattttgcc tttggaattg ccacggggcg   1560
tcgcctagac tctgcccaag aagtcttgaa agagtggggc gttccttcgc caaacttctg   1620
ggtgacttcc gtcggcagcg agattcacta tggcaccgat gctgaaccgg atatcagctg   1680
ggaaaagcat atcaatcgca actggaatcc tcagcgaatt cggcagtaa tggcacaact   1740
accctttctt gaactgcagc cggaagagga tcaaacaccc ttcaaagtca gcttctttgt   1800
ccgcgatcgc cacgagactg tgctgcgaga agtacggcaa catcttcgcc gccatcgcct   1860
gcggctgaag tcaatctatt cccatcagga gtttcttgac attctgccgc tagctgcctc   1920
gaaaggggat gcgattcgcc acctctcact ccgctggcgg attcctcttg agaacatttt   1980
ggtggcaggc gattctggta acgatgagga aatgctcaag ggccataatc tcggcgttgt   2040
agttggcaat tactcaccgg aattggagcc actgcgcagc tacgagcgcg tctattttgc   2100
tgagggccac tatgctaatg gcattctgga agccttaaaa cactatcgct tttttgaggc   2160
gatcgcttaa ccttttcaga acgtgagacg ttgatcggca cgtaagaggt tccaactttc   2220
accataatga aataagatca ctaccgggcg tatttttga gttatcgaga ttttcaggag   2280
ctaaggaagc taaaatggag aaaaaaatca ctggatatac caccgttgat atatcccaat   2340
ggcatcgtaa agaacatttt gaggcatttc agtcagttgc tcaatgtacc tataaccaga   2400
ccgttcagct ggatattacg gcctttttaa agaccgtaaa gaaaaataag cacaagtttt   2460
atccggcctt tattcacatt cttgcccgcc tgatgaatgc tcatccggaa ttccgtatgg   2520
caatgaaaga cggtgagctg gtgatatggg atagtgttca cccttgttac accgttttcc   2580
atgagcaaac tgaaacgttt tcatcgctct ggagtgaata ccacgacgat ttccggcagt   2640
ttctacacat atattcgcaa gatgtggcgt gttacggtga aaacctggcc tatttcccta   2700
aagggtttat tgagaatatg tttttcgtct cagccaatcc ctgggtgagt ttcaccagtt   2760
ttgatttaaa cgtggccaat atggacaact tcttcgcccc cgttttcacc atgggcaaat   2820
attatacgca aggcgacaag gtgctgatgc cgctggcgat tcaggttcat catgccgttt   2880
gtgatggctt ccatgtcggc agaatgctta atgaattaca acagtactgc gatgagtggc   2940
agggcggggc gtaatttttt taaggcagtt attggtgccc ttaaacgcct ggttgctacg   3000
cctgaataag tgataataag cggatgaatg gcagaaattc gatgataagc tgtcaaacac   3060
gtgaattggt cgaacgaatt caagcttgat atcattcagg acgagcctca gactccagcg   3120
taactggact gcaatcaact cactggctca ccttcacggg tgggcctttc ttcggtagaa   3180
aatcaaagga tcttcttgag atcctttttt tctgcgcgta atctgctgct tgcaaacaaa   3240
aaaaccaccg ctaccagcgg tggtttgttt gccggatcaa gagctaccaa ctctttttcc   3300
gaggtaactg gcttcagcag agcgcagata ccaaatactg ttcttctagt gtagccgtag   3360
ttaggccacc acttcaagaa ctctgtagca ccgcctacat acctcgctct gctaatcctg   3420
ttaccagtgg ctgctgccag tggcgataag tcgtgtctta ccgggttgga ctcaagacga   3480
```

tagttaccgg ataaggcgca gcggtcgggc tgaacggggg gttcgtgcac acagcccagc 3540
ttggagcgaa cgacctacac cgaactgaga tacctacagc gtgagctatg agaaagcgcc 3600
acgcttcccg aagggagaaa ggcggacagg tatccggtaa gcggcagggt cggaacagga 3660
gagcgcacga gggagcttcc agggggaaac gcctggtatc tttatagtcc tgtcgggttt 3720
cgccacctct gacttgagca tcgatttttg tgatgctcgt caggggggcg gagcctatgg 3780
aaaaacgcca gcaacgcaga aaggcccacc cgaaggtgag ccaggtgatt acatttgggc 3840
cctcatcaga ggttttcacc gtcatcaccg aaacgcgcga ggcagctgcg gtaaagctca 3900
tcagcgtggt cgtgaagcga ttcacagatg tctgcctgtt catccgcgtc cagctcgttg 3960
agtttctcca gaagcgttaa tgtctggctt ctgataaagc gggccatgtt aagggcggtt 4020
ttttcctgtt tggtcattta gaaaaactca tcgagcatca agtgaaactg caatttattc 4080
atatcaggat tatcaatacc atatttttga aaaagccgtt tctgtaatga aggagaaaac 4140
tcaccgaggc agttccatag gatggcaaga tcctggtatc ggtctgcgat tccgactcgt 4200
ccaacatcaa tacaacctat taatttcccc tcgtcaaaaa taaggttatc aagtgagaaa 4260
tcaccatgag tgacgactga atccggtgag aatggcaaaa gcttatgcat ttctttccag 4320
acttgttcaa caggccagcc attacgctcg tcatcaaaat cactcgcacc aaccaaaccg 4380
ttattcattc gtgattgcgc ctgagcgaga cgaaatacgc gatcgccgtt aaaaggacaa 4440
ttacaaacag gaatcgaatg caaccggcgc aggaacactg ccagcgcatc aacaatattt 4500
tcacctgaat caggatattc ttctaatacc tggaatgctg ttttccctgg gatcgcagtg 4560
gtgagtaacc atgcatcatc aggagtacgg ataaaatgct tgatggtcgg aagaggcata 4620
aattccgtca gccagtttag cctgaccatc tcatctgtaa catcattggc aacgctacct 4680
ttgccatgtt tcagaaacaa ctctggcgca tcgggcttcc catacaatcg atagattgtc 4740
gcacctgatt gcccgacatt atcgcgagcc catttatacc catataaatc agcatccatg 4800
ttggaattta atcgcggcct cgagcaagac gtttcccgtt gaatatggct cattttagct 4860
tccttagctc ctgaaaatct cgataactca aaaaatacgc ccggtagtga tcttatttca 4920
ttatggtgaa agttggaacc tcttacgtgc cgatcaagtc aaaagcctcc ggtcggaggc 4980
ttttgacttt ctgctatgga ggtcaggtat gatttaaatg gtcagtattg agcgatatct 5040
agagaattcg tc 5052

<210> SEQ ID NO 55
<211> LENGTH: 24
<212> TYPE: DNA
<213> ORGANISM: Artificial
<220> FEATURE:
<223> OTHER INFORMATION: primer for detection of plasmid in cyanobacteria

<400> SEQUENCE: 55
ggtggttgtg tttgacagct tatc 24

<210> SEQ ID NO 56
<211> LENGTH: 651
<212> TYPE: DNA
<213> ORGANISM: Synechocystis PCC6803

<400> SEQUENCE: 56
atggcttctc aattacgtgt ttatgtgccg gagcatcctc taattaagca ttggttgggg 60
gtagctaggg atgaaaacac gccgccggtt ttgtttaaaa ctgccatggg ggaattggga 120

-continued

```
cgttggttga cctatgaggc cgctcgttat tggttgccga cggtggatac ggaagtgaaa    180

actcccctgg cgatcgccaa ggccagtctt attgaccccc aaacgcccctt tgtcattgtg    240

cccattttgc gggcggggtt ggctctggtg gaaggggccc aggggttgtt gcccctggca    300

aaaatttacc atctgggttt agtgcgcaat gaaactaccc tggaacctag tctgtatctg    360

aacaagttgc cggagcggtt tgcccccggt acccatcttt tgttgctaga tcccatgttg    420

gctacgggta ataccatcat ggctgctttg gatttgctga tggcccggga cattgatgcc    480

aatttaatcc gtttggtctc cgtggtggcc gcccccactg ccctgcaaaa attaagtaat    540

gcccatccca atttgaccat ctacaccgcc atgattgacg aacaactcaa tgaccggggt    600

tacattgtgc ccggcctagg ggatgcaggc gatcgttgct ttggtacttg a             651


<210> SEQ ID NO 57
<211> LENGTH: 216
<212> TYPE: PRT
<213> ORGANISM: Synechocystis PCC6803

<400> SEQUENCE: 57

Met Ala Ser Gln Leu Arg Val Tyr Val Pro Glu His Pro Leu Ile Lys
1               5                   10                  15

His Trp Leu Gly Val Ala Arg Asp Glu Asn Thr Pro Pro Val Leu Phe
            20                  25                  30

Lys Thr Ala Met Gly Glu Leu Gly Arg Trp Leu Thr Tyr Glu Ala Ala
        35                  40                  45

Arg Tyr Trp Leu Pro Thr Val Asp Thr Glu Val Lys Thr Pro Leu Ala
    50                  55                  60

Ile Ala Lys Ala Ser Leu Ile Asp Pro Gln Thr Pro Phe Val Ile Val
65                  70                  75                  80

Pro Ile Leu Arg Ala Gly Leu Ala Leu Val Glu Gly Ala Gln Gly Leu
                85                  90                  95

Leu Pro Leu Ala Lys Ile Tyr His Leu Gly Leu Val Arg Asn Glu Thr
            100                 105                 110

Thr Leu Glu Pro Ser Leu Tyr Leu Asn Lys Leu Pro Glu Arg Phe Ala
        115                 120                 125

Pro Gly Thr His Leu Leu Leu Leu Asp Pro Met Leu Ala Thr Gly Asn
    130                 135                 140

Thr Ile Met Ala Ala Leu Asp Leu Leu Met Ala Arg Asp Ile Asp Ala
145                 150                 155                 160

Asn Leu Ile Arg Leu Val Ser Val Val Ala Ala Pro Thr Ala Leu Gln
                165                 170                 175

Lys Leu Ser Asn Ala His Pro Asn Leu Thr Ile Tyr Thr Ala Met Ile
            180                 185                 190

Asp Glu Gln Leu Asn Asp Arg Gly Tyr Ile Val Pro Gly Leu Gly Asp
        195                 200                 205

Ala Gly Asp Arg Cys Phe Gly Thr
    210                 215


<210> SEQ ID NO 58
<211> LENGTH: 654
<212> TYPE: DNA
<213> ORGANISM: Synechococcus PCC7942

<400> SEQUENCE: 58

atggctcctc aactgcgtat cttcgtgccg ccccatccct taattcggca ctggctgggc     60

attgcccgcg atcgccagac gccgacgcct ctgtttcgca ccgcgatcgc agagctgggc    120
```

```
cgctggctcg cctatgaggc tgtgcgggaa tggctaccaa cgattccagc ggcggtgcaa    180

actcctcttg cagaaacccc agcggagttc gtcgattttt cgcaaccctt ggcgatcgtg    240

ccgattctgc gcgcaggtct gggtttagtg gagtctgtcc aacaggtttt gccgactgcc    300

cgcatttttc acgtgggtct caagcgggat gaagtcagtc ttgaaccgcg ctgctacctc    360

aatcacctgc cagagcaact tgaagtgaac agtcgcgttc tggttctcga cccgatgctg    420

gcgacaggtg gctcgctgct ctataccctt gatttgctgc gcgatcgcgg tgtctctgct    480

gagcaagtgc gggtgctttc aattgtggct gccccgccag cgctacaaaa actcagtcaa    540

gcctacccgg cgttgacgat ttacagcgcc atcattgatg agcagctgaa cgacaaaggc    600

tttatcgtgc cggggctggg ggatgctggc gatcgcctgt ttggtactcc ttga          654
```

<210> SEQ ID NO 59
<211> LENGTH: 217
<212> TYPE: PRT
<213> ORGANISM: Synechococcus PCC7942

<400> SEQUENCE: 59

```
Met Ala Pro Gln Leu Arg Ile Phe Val Pro Pro His Pro Leu Ile Arg
1               5                   10                  15

His Trp Leu Gly Ile Ala Arg Asp Arg Gln Thr Pro Thr Pro Leu Phe
            20                  25                  30

Arg Thr Ala Ile Ala Glu Leu Gly Arg Trp Leu Ala Tyr Glu Ala Val
        35                  40                  45

Arg Glu Trp Leu Pro Thr Ile Pro Ala Ala Val Gln Thr Pro Leu Ala
    50                  55                  60

Glu Thr Pro Ala Glu Phe Val Asp Phe Ser Gln Pro Leu Ala Ile Val
65                  70                  75                  80

Pro Ile Leu Arg Ala Gly Leu Gly Leu Val Glu Ser Val Gln Gln Val
                85                  90                  95

Leu Pro Thr Ala Arg Ile Phe His Val Gly Leu Lys Arg Asp Glu Val
            100                 105                 110

Ser Leu Glu Pro Arg Cys Tyr Leu Asn His Leu Pro Glu Gln Leu Glu
        115                 120                 125

Val Asn Ser Arg Val Leu Val Leu Asp Pro Met Leu Ala Thr Gly Gly
    130                 135                 140

Ser Leu Leu Tyr Thr Leu Asp Leu Leu Arg Asp Arg Gly Val Ser Ala
145                 150                 155                 160

Glu Gln Val Arg Val Leu Ser Ile Val Ala Ala Pro Pro Ala Leu Gln
                165                 170                 175

Lys Leu Ser Gln Ala Tyr Pro Ala Leu Thr Ile Tyr Ser Ala Ile Ile
            180                 185                 190

Asp Glu Gln Leu Asn Asp Lys Gly Phe Ile Val Pro Gly Leu Gly Asp
        195                 200                 205

Ala Gly Asp Arg Leu Phe Gly Thr Pro
    210                 215
```

<210> SEQ ID NO 60
<211> LENGTH: 33
<212> TYPE: DNA
<213> ORGANISM: Artificial
<220> FEATURE:
<223> OTHER INFORMATION: primer for amplifying upp gene from Bacillus
subtilis 168

<400> SEQUENCE: 60
aagaagcaag acagcgtgta gctgctctga ctg 33

<210> SEQ ID NO 61
<211> LENGTH: 50
<212> TYPE: DNA
<213> ORGANISM: Artificial
<220> FEATURE:
<223> OTHER INFORMATION: primer for amplifying upp gene from Bacillus subtilis 168

<400> SEQUENCE: 61
tcccgggatt tggtacctta ttttgttcca aacatgcggt cacccgcatc 50

<210> SEQ ID NO 62
<211> LENGTH: 849
<212> TYPE: DNA
<213> ORGANISM: Bacillus subtilis

<400> SEQUENCE: 62
aagaagcaag acagcgtgta gctgctctga ctgataaatt tcctttatat aaagaattag 60
attattaaga tcctaaaacc cgcttgggct tatgcccggc gggttttttg acgatgttct 120
tgaaactcaa tgtctttttt tgtagaatca atagaagtgt gtaattgttg atgggacaat 180
aaaaaaggag ctgaaacaca gtatgggaaa ggtttatgta tttgatcatc ctttaattca 240
gcacaagctg acatatatac ggaatgaaaa tacaggtacg aaggatttta gagagttagt 300
agatgaagtg gctacactca tggcatttga aattacccgc gatcttcctc tggaagaagt 360
ggatatcaat acaccggttc aggctgcgaa atcgaaagtc atctcaggga aaaaactcgg 420
agtggttcct atcctcagag caggattggg aatggttgac ggcattttaa agctgattcc 480
tgcggcaaaa gtgggacatg tcggccttta ccgtgatcca gaaaccttaa aacccgtgga 540
atactatgtc aagcttcctt ctgatgtgga agagcgtgaa ttcatcgtgg ttgacccgat 600
gctcgctaca ggcggttccg cagttgaagc cattcacagc cttaaaaaac gcggtgcgaa 660
aaatatccgt ttcatgtgtc ttgtagcagc gccggagggt gtggaagaat tgcagaagca 720
tcattcggac gttgatattt acattgcggc gctagatgaa aaattaaatg aaaaaggata 780
tattgttcca ggtctcggag atgcgggtga ccgcatgttt ggaacaaaat aaggtaccaa 840
atcccggga 849

<210> SEQ ID NO 63
<211> LENGTH: 22
<212> TYPE: DNA
<213> ORGANISM: Artificial
<220> FEATURE:
<223> OTHER INFORMATION: primer for sequence verification of pLybAL7f

<400> SEQUENCE: 63
gtaatacgac tcactatagg gc 22

<210> SEQ ID NO 64
<211> LENGTH: 24
<212> TYPE: DNA
<213> ORGANISM: Artificial
<220> FEATURE:
<223> OTHER INFORMATION: primer for sequence verification of pLybAL7f

<400> SEQUENCE: 64
cacacaggaa acagctatga ccat 24

<210> SEQ ID NO 65
<211> LENGTH: 8988
<212> TYPE: DNA
<213> ORGANISM: Artificial
<220> FEATURE:
<223> OTHER INFORMATION: plasmid pLybAL7f

<400> SEQUENCE: 65
gcggccgcaa ggggttcgcg tcagcgggtg ttggcgggtg tcggggctgg cttaactatg 60
cggcatcaga gcagattgta ctgagagtgc accatatgcg gtgtgaaata ccgcacagat 120
gcgtaaggag aaaataccgc atcaggcgcc attcgccatt cagctgcgca actgttggga 180
agggcgatcg gtgcgggcct cttcgctatt acgccagctg gcgaaagggg gatgtgctgc 240
aaggcgatta agttgggtaa cgccagggtt ttcccagtca cgacgttgta aaacgacggc 300
cagtgaattg taatacgact cactataggg cgaattcgag ctcggtaccc ggggatccca 360
ctcccgggat ttggtacctt attttgttcc aaacatgcgg tcacccgcat ctccgagacc 420
tggaacaata tatccttttt catttaattt ttcatctagc gccgcaatgt aaatatcaac 480
gtccgaatga tgcttctgca attcttccac accctccggc gctgctacaa gacacatgaa 540
acggatattt ttcgcaccgc gtttttaag gctgtgaatg gcttcaactg cggaaccgcc 600
tgtagcgagc atcgggtcaa ccacgatgaa ttcacgctct tccacatcag aaggaagctt 660
gacatagtat tccacgggtt ttaaggtttc tggatcacgg taaaggccga catgtcccac 720
ttttgccgca ggaatcagct ttaaaatgcc gtcaaccatt cccaatcctg ctctgaggat 780
aggaaccact ccgagttttt tccctgagat gactttcgat ttcgcagcct gaaccggtgt 840
attgatatcc acttcttcca gaggaagatc gcgggtaatt tcaaatgcca tgagtgtagc 900
cacttcatct actaactctc taaaatcctt cgtacctgta ttttcattcc gtatatatgt 960
cagcttgtgc tgaattaaag gatgatcaaa tacataaacc tttcccatac tgtgtttcag 1020
ctcctttttt attgtcccat caacaattac acacttctat tgattctaca aaaaaagaca 1080
ttgagtttca agaacatcgt caaaaaaccc gccgggcata agcccaagcg ggttttagga 1140
tcttaataat ctaattcttt atataaagga aatttatcag tcagagcagc tacacgctgt 1200
cttgcttctt gtgggatcct ctagagtcga cctgcaggca tgcaagcttg agtattctat 1260
agtctcacct aaatagcttg gcgtaatcat ggtcatagct gtttcctgtg tgaaattgtt 1320
atccgctcac aattccacac aacatacgag ccggaagcat aaagtgtaaa gcctggggtg 1380
cctaatgagt gagctaactc acattaattg cgttgcgctc actgcccgct ttccagtcgg 1440
gaaacctgtc gtgccagctg cattaatgaa tcggccaacg cgaacccctt gcggccgccc 1500
gggccgtcga ccaattctca tgtttgacag cttatcatcg aatttctgcc attcatccgc 1560
ttattatcac ttattcaggc gtagcaacca ggcgtttaag ggcaccaata actgccttaa 1620
aaaaattacg ccccgccctg ccactcatcg cagtactgtt gtaattcatt aagcattctg 1680
ccgacatgga agccatcaca aacggcatga tgaacctgaa tcgccagcgg catcagcacc 1740
ttgtcgcctt gcgtataata tttgcccatg gtgaaaacgg gggcgaagaa gttgtccata 1800
ttggccacgt ttaaatcaaa actggtgaaa ctcacccagg gattggctga gacgaaaaac 1860
atattctcaa taaacccttt agggaaatag gccaggtttt caccgtaaca cgccacatct 1920
tgcgaatata tgtgtagaaa ctgccggaaa tcgtcgtggt attcactcca gagcgatgaa 1980
aacgtttcag tttgctcatg gaaaacggtg taacaagggt gaacactatc ccatatcacc 2040
agctcaccgt ctttcattgc catacgaaat tccggatgag cattcatcag gcgggcaaga 2100

-continued

```
atgtgaataa aggccggata aaacttgtgc ttatttttct ttacggtctt taaaaaggcc   2160
gtaatatcca gctgaacggt ctggttatag gtacattgag caactgactg aaatgcctca   2220
aaatgttctt tacgatgcca ttgggatata tcaacggtgg tatatccagt gatttttttc   2280
tccattttag cttccttagc tcctgaaaat ctcgataact caaaaaatac gcccggtagt   2340
gatcttattt cattatggtg aaagttggaa cctcttacgt gccgatcaac gtctcatttt   2400
cgccaaaagt tggcccaggg cttcccggta tcaacaggga caccaggatt tatttattct   2460
gcgaagtgat cttccgtcac aggtatttat tcgcgataag ctcatggagc ggcgtaaccg   2520
tcgcacagga aggacagaga aagcgcggat ctgggaagtg acggacagaa cggtcaggac   2580
ctggattggg gaggcggttg ccgccgctgc tgctgacggt gtgacgttct ctgttccggt   2640
cacaccacat acgttccgcc attcctatgc gatgcacatg ctgtatgccg gtataccgct   2700
gaaagttctg caaagcctga tgggacataa gtccatcagt tcaacggaag tctacacgaa   2760
ggtttttgcg ctggatgtgg ctgcccggca ccgggtgcag tttgcgatgc cggagtctga   2820
tgcggttgcg atgctgaaac aattatcctg agaataaatg ccttggcctt tatatggaaa   2880
tgtggaactg agtggatatg ctgtttttgt ctgttaaaca gagaagctgg ctgttatcca   2940
ctgagaagcg aacgaaacag tcgggaaaat ctcccattat cgtagagatc cgcattatta   3000
atctcaggag cctgtgtagc gtttatagga agtagtgttc tgtcatgatg cctgcaagcg   3060
gtaacgaaaa cgatttgaat atgccttcag gaacaataga aatcttcgtg cggtgttacg   3120
ttgaagtgga gcggattatg tcagcaatgg acagaacaac ctaatgaaca cagaaccatg   3180
atgtggtctg tccttttaca gccagtagtg ctcgccgcag tcgagcgaca gggcgaagcc   3240
ctcggctggt tgccctcgcc gctgggctgg cggccgtcta tggccctgca aacgcgccag   3300
aaacgccgtc gaagccgtgt gcgagacacc gcggccggcc gccggcgttg tggatacctc   3360
gcggaaaact tggccctcac tgacagatga ggggcggacg ttgacacttg aggggccgac   3420
tcacccggcg cggcgttgac agatgagggg caggctcgat ttcggccggc gacgtggagc   3480
tggccagcct cgcaaatcgg cgaaaacgcc tgattttacg cgagtttccc acagatgatg   3540
tggacaagcc tggggataag tgccctgcgg tattgacact tgaggggcgc gactactgac   3600
agatgagggg cgcgatcctt gacacttgag gggcagagtg ctgacagatg aggggcgcac   3660
ctattgacat ttgaggggct gtccacaggc agaaaatcca gcatttgcaa gggtttccgc   3720
ccgtttttcg gccaccgcta acctgtcttt taacctgctt ttaaaccaat atttataaac   3780
cttgttttta accagggctg cgccctgtgc gcgtgaccgc gcacgccgaa ggggggtgcc   3840
ccccttctc gaaccctccc ggtcgagtga gcgaggaagc accagggaac agcacttata   3900
tattctgctt acacacgatg cctgaaaaaa cttcccttgg ggttatccac ttatccacgg   3960
ggatattttt ataattattt tttttatagt ttttagatct tctttttag agcgccttgt   4020
aggcctttat ccatgctggt tctagagaag gtgttgtgac aaattgccct ttcagtgtga   4080
caaatcaccc tcaaatgaca gtcctgtctg tgacaaattg cccttaaccc tgtgacaaat   4140
tgccctcaga agaagctgtt ttttcacaaa gttatccctg cttattgact cttttttatt   4200
tagtgtgaca atctaaaaac ttgtcacact tcacatggat ctgtcatggc ggaaacagcg   4260
gttatcaatc acaagaaacg taaaaatagc ccgcgaatcg tccagtcaaa cgacctcact   4320
gaggcggcat atagtctctc ccgggatcaa aaacgtatgc tgtatctgtt cgttgaccag   4380
atcagaaaat ctgatggcac cctacaggaa catgacggta tctgcgagat ccatgttgct   4440
aaatatgctg aaatattcgg attgacctct gcggaagcca gtaaggatat acggcaggca   4500
```

-continued

```
ttgaagagtt tcgcggggaa ggaagtggtt ttttatcgcc ctgaagagga tgccggcgat   4560

gaaaaaggct atgaatcttt tccttggttt atcaaacgtg cgcacagtcc atccagaggg   4620

ctttacagtg tacatatcaa cccatatctc attcccttct ttatcgggtt acagaaccgg   4680

tttacgcagt ttcggcttag tgaaacaaaa gaaatcacca atccgtatgc catgcgttta   4740

tacgaatccc tgtgtcagta tcgtaagccg gatggctcag gcatcgtctc tctgaaaatc   4800

gactggatca tagagcgtta ccagctgcct caaagttacc agcgtatgcc tgacttccgc   4860

cgccgcttcc tgcaggtctg tgttaatgag atcaacagca gaactccaat gcgcctctca   4920

tacattgaga aaaagaaagg ccgccagacg actcatatcg tattttcctt ccgcgatatc   4980

acttccatga cgacaggata gtctgagggt tatctgtcac agatttgagg gtggttcgtc   5040

acatttgttc tgacctactg agggtaattt gtcacagttt tgctgtttcc ttcagcctgc   5100

atggattttc tcatactttt tgaactgtaa tttttaagga agccaaattt gagggcagtt   5160

tgtcacagtt gatttccttc tctttccctt cgtcatgtga cctgatatcg gggggttagtt   5220

cgtcatcatt gatgagggtt gattatcaca gtttattact ctgaattggc tatccgcgtg   5280

tgtacctcta cctggagttt ttcccacggt ggatatttct tcttgcgctg agcgtaagag   5340

ctatctgaca gaacagttct tctttgcttc ctcgccagtt cgctcgctat gctcggttac   5400

acggctgcgg cgagcgctag tgataataag tgactgaggt atgtgctctt cttatctcct   5460

tttgtagtgt tgctcttatt ttaaacaact ttgcggtttt ttgatgactt tgcgattttg   5520

ttgttgcttt gcagtaaatt gcaagattta ataaaaaaac gcaaagcaat gattaaagga   5580

tgttcagaat gaaactcatg gaaacactta accagtgcat aaacgctggt catgaaatga   5640

cgaaggctat cgccattgca cagtttaatg atgacagccc ggaagcgagg aaaataaccc   5700

ggcgctggag aataggtgaa gcagcggatt tagttggggt ttcttctcag gctatcagag   5760

atgccgagaa agcagggcga ctaccgcacc cggatatgga aattcgagga cgggttgagc   5820

aacgtgttgg ttatacaatt gaacaaatta atcatatgcg tgatgtgttt ggtacgcgat   5880

tgcgacgtgc tgaagacgta tttccaccgg tgatcggggt tgctgcccat aaaggtggcg   5940

tttacaaaac ctcagtttct gttcatcttg ctcaggatct ggctctgaag gggctacgtg   6000

ttttgctcgt ggaaggtaac gacccccagg gaacagcctc aatgtatcac ggatgggtac   6060

cagatcttca tattcatgca gaagacactc tcctgccttt ctatcttggg gaaaaggacg   6120

atgtcactta tgcaataaag cccacttgct ggccggggct tgacattatt ccttcctgtc   6180

tggctctgca ccgtattgaa actgagttaa tgggcaaatt tgatgaaggt aaactgccca   6240

ccgatccaca cctgatgctc cgactggcca ttgaaactgt tgctcatgac tatgatgtca   6300

tagttattga cagcgcgcct aacctgggta tcggcacgat taatgtcgta tgtgctgctg   6360

atgtgctgat tgttcccacg cctgctgagt tgtttgacta cacctccgca ctgcagtttt   6420

tcgatatgct tcgtgatctg ctcaagaacg ttgatcttaa agggttcgag cctgatgtac   6480

gtattttgct taccaaatac agcaatagta atggctctca gtccccgtgg atggaggagc   6540

aaattcggga tgcctgggga agcatggttc taaaaaatgt tgtacgtgaa acggatgaag   6600

ttggtaaagg tcagatccgg atgagaactg tttttgaaca ggccattgat caacgctctt   6660

caactggtgc ctggagaaat gctctttcta tttgggaacc tgtctgcaat gaaattttcg   6720

atcgtctgat taaaccacgc tgggagatta gataatgaag cgtgcgcctg ttattccaaa   6780

acatacgctc aatactcaac cggttgaaga tacttcgtta tcgacaccag ctgccccgat   6840
```

-continued

```
ggtggattcg ttaattgcgc gcgtaggagt aatggctcgc ggtaatgcca ttactttgcc   6900
tgtatgtggt cgggatgtga agtttactct tgaagtgctc cggggtgata gtgttgagaa   6960
gacctctcgg gtatggtcag gtaatgaacg tgaccaggag ctgcttactg aggacgcact   7020
ggatgatctc atcccttctt ttctactgac tggtcaacag acaccggcgt tcggtcgaag   7080
agtatctggt gtcatagaaa ttgccgatgg gagtcgccgt cgtaaagctg ctgcacttac   7140
cgaaagtgat tatcgtgttc tggttggcga gctggatgat gagcagatgg ctgcattatc   7200
cagattgggt aacgattatc gcccaacaag tgcttatgaa cgtggtcagc gttatgcaag   7260
ccgattgcag aatgaatttg ctggaaatat ttctgcgctg gctgatgcgg aaaatatttc   7320
acgtaagatt attacccgct gtatcaacac cgccaaattg cctaaatcag ttgttgctct   7380
tttttctcac cccggtgaac tatctgcccg gtcaggtgat gcacttcaaa aagcctttac   7440
agataaagag gaattactta agcagcaggc atctaacctt catgagcaga aaaaagctgg   7500
ggtgatattt gaagctgaag aagttatcac tcttttaact tctgtgctta aaacgtcatc   7560
tgcatcaaga actagtttaa gctcacgaca tcagtttgct cctggagcga cagtattgta   7620
taagggcgat aaaatggtgc ttaacctgga caggtctcgt gttccaactg agtgtataga   7680
gaaaattgag gccattctta aggaacttga aaagccagca ccctgatgcg accacgtttt   7740
agtctacgtt tatctgtctt tacttaatgt cctttgttac aggccagaaa gcataactgg   7800
cctgaatatt ctctctgggc ccactgttcc acttgtatcg tcggtctgat aatcagactg   7860
ggaccacggt cccactcgta tcgtcggtct gattattagt ctgggaccac ggtcccactc   7920
gtatcgtcgg tctgattatt agtctgggac cacggtccca ctcgtatcgt cggtctgata   7980
atcagactgg gaccacggtc ccactcgtat cgtcggtctg attattagtc tgggaccatg   8040
gtcccactcg tatcgtcggt ctgattatta gtctgggacc acggtcccac tcgtatcgtc   8100
ggtctgatta ttagtctgga accacggtcc cactcgtatc gtcggtctga ttattagtct   8160
gggaccacgg tcccactcgt atcgtcggtc tgattattag tctgggacca cgatcccact   8220
cgtgttgtcg gtctgattat cggtctggga ccacggtccc acttgtattg tcgatcagac   8280
tatcagcgtg agactacgat tccatcaatg cctgtcaagg gcaagtattg acatgtcgtc   8340
gtaacctgta gaacggagta acctcggtgt gcggttgtat gcctgctgtg gattgctgct   8400
gtgtcctgct tatccacaac attttgcgca cggttatgtg gacaaaatac ctggttaccc   8460
aggccgtgcc ggcacgttaa ccgggctgca tccgatgcaa gtgtgtcgct gtcgacgagc   8520
tcgcgagctc ggacatgagg ttgccccgta ttcagtgtcg ctgatttgta ttgtctgaag   8580
ttgtttttac gttaagttga tgcagatcaa ttaatacgat acctgcgtca taattgatta   8640
tttgacgtgg tttgatggcc tccacgcacg ttgtgatatg tagatgataa tcattatcac   8700
tttacgggtc ctttccggtg atccgacagg ttacggggcg gcgacctcgc gggttttcgc   8760
tatttatgaa aattttccgg tttaaggcgt ttccgttctt cttcgtcata acttaatgtt   8820
tttatttaaa ataccctctg aaaagaaagg aaacgacagg tgctgaaagc gagctttttg   8880
gcctctgtcg tttcctttct ctgtttttgt ccgtggaatg aacaatggaa gtccgagctc   8940
atcgctaata acttcgtata gcatacatta tacgaagtta tattcgat               8988
```

<210> SEQ ID NO 66
<211> LENGTH: 31
<212> TYPE: DNA
<213> ORGANISM: Artificial
<220> FEATURE:
<223> OTHER INFORMATION: primer for amplifying kanamycin resistance marker vector pLybAA1

<400> SEQUENCE: 66
gtcagtgcac tgctctgcca gtgttacaac c 31

<210> SEQ ID NO 67
<211> LENGTH: 38
<212> TYPE: DNA
<213> ORGANISM: Artificial
<220> FEATURE:
<223> OTHER INFORMATION: primer for amplifying kanamycin resistance marker vector pLybAA1

<400> SEQUENCE: 67
ctcagtggcg ccaaaactca cgttaaggga ttttggtc 38

<210> SEQ ID NO 68
<211> LENGTH: 950
<212> TYPE: DNA
<213> ORGANISM: Artificial
<220> FEATURE:
<223> OTHER INFORMATION: kanamycin resistance marker from vector pLybAA1, originally derived from pACYC177

<400> SEQUENCE: 68
gtcagtgcac tgctctgcca gtgttacaac caattaacca attctgatta gaaaaactca 60
tcgagcatca aatgaaactg caatttattc atatcaggat tatcaatacc atatttttga 120
aaaagccgtt tctgtaatga aggagaaaac tcaccgaggc agttccatag gatggcaaga 180
tcctggtatc ggtctgcgat tccgactcgt ccaacatcaa tacaacctat taatttcccc 240
tcgtcaaaaa taaggttatc aagtgagaaa tcaccatgag tgacgactga atccggtgag 300
aatggcaaaa gcttatgcat ttctttccag acttgttcaa caggccagcc attacgctcg 360
tcatcaaaat cactcgcatc aaccaaaccg ttattcattc gtgattgcgc ctgagcgaga 420
cgaaatacgc gatcgctgtt aaaaggacaa ttacaaacag gaatcgaatg caaccggcgc 480
aggaacactg ccagcgcatc aacaatattt tcacctgaat caggatattc ttctaatacc 540
tggaatgctg ttttcccggg gatcgcagtg gtgagtaacc atgcatcatc aggagtacgg 600
ataaaatgct tgatggtcgg aagaggcata aattccgtca gccagtttag tctgaccatc 660
tcatctgtaa catcattggc aacgctacct ttgccatgtt tcagaaacaa ctctggcgca 720
tcgggcttcc catacaatcg atagattgtc gcacctgatt gcccgacatt atcgcgagcc 780
catttatacc catataaatc agcatccatg ttggaattta atcgcggcct cgagcaagac 840
gtttcccgtt gaatatggct cataacaccc cttgtattac tgtttatgta agcagacagt 900
tttattgttc atgaccaaaa tcccttaacg tgagttttgg cgccactgag 950

<210> SEQ ID NO 69
<211> LENGTH: 9864
<212> TYPE: DNA
<213> ORGANISM: Artificial
<220> FEATURE:
<223> OTHER INFORMATION: plasmid pLybAL8f (kanamycin resistance marker plus pLybAL7f)

<400> SEQUENCE: 69
gcggccgcaa ggggttcgcg tcagcgggtg ttggcgggtg tcggggctgg cttaactatg 60
cggcatcaga gcagattgta ctgagagtgc actgctctgc cagtgttaca accaattaac 120
caattctgat tagaaaaact catcgagcat caaatgaaac tgcaatttat tcatatcagg 180

-continued

```
attatcaata ccatattttt gaaaaagccg tttctgtaat gaaggagaaa actcaccgag    240

gcagttccat aggatggcaa gatcctggta tcggtctgcg attccgactc gtccaacatc    300

aatacaacct attaatttcc cctcgtcaaa aataaggtta tcaagtgaga aatcaccatg    360

agtgacgact gaatccggtg agaatggcaa aagcttatgc atttctttcc agacttgttc    420

aacaggccag ccattacgct cgtcatcaaa atcactcgca tcaaccaaac cgttattcat    480

tcgtgattgc gcctgagcga gacgaaatac gcgatcgctg ttaaaaggac aattacaaac    540

aggaatcgaa tgcaaccggc gcaggaacac tgccagcgca tcaacaatat tttcacctga    600

atcaggatat tcttctaata cctggaatgc tgttttcccg gggatcgcag tggtgagtaa    660

ccatgcatca tcaggagtac ggataaaatg cttgatggtc ggaagaggca taaattccgt    720

cagccagttt agtctgacca tctcatctgt aacatcattg gcaacgctac ctttgccatg    780

tttcagaaac aactctggcg catcgggctt cccatacaat cgatagattg tcgcacctga    840

ttgcccgaca ttatcgcgag cccatttata cccatataaa tcagcatcca tgttggaatt    900

taatcgcggc ctcgagcaag acgtttcccg ttgaatatgg ctcataacac cccttgtatt    960

actgtttatg taagcagaca gttttattgt tcatgaccaa aatcccttaa cgtgagtttt   1020

ggcgccattc gccattcagc tgcgcaactg ttgggaaggg cgatcggtgc gggcctcttc   1080

gctattacgc cagctggcga aagggggatg tgctgcaagg cgattaagtt gggtaacgcc   1140

agggttttcc cagtcacgac gttgtaaaac gacggccagt gaattgtaat acgactcact   1200

atagggcgaa ttcgagctcg gtacccgggg atcccactcc cgggatttgg taccttattt   1260

tgttccaaac atgcggtcac ccgcatctcc gagacctgga acaatatatc ctttttcatt   1320

taatttttca tctagcgccg caatgtaaat atcaacgtcc gaatgatgct tctgcaattc   1380

ttccacaccc tccggcgctg ctacaagaca catgaaacgg atatttttcg caccgcgttt   1440

tttaaggctg tgaatggctt caactgcgga accgcctgta gcgagcatcg ggtcaaccac   1500

gatgaattca cgctcttcca catcagaagg aagcttgaca tagtattcca cgggttttaa   1560

ggtttctgga tcacggtaaa ggccgacatg tcccactttt gccgcaggaa tcagctttaa   1620

aatgccgtca accattccca atcctgctct gaggatagga accactccga gtttttttccc   1680

tgagatgact ttcgatttcg cagcctgaac cggtgtattg atatccactt cttccagagg   1740

aagatcgcgg gtaatttcaa atgccatgag tgtagccact tcatctacta actctctaaa   1800

atccttcgta cctgtatttt cattccgtat atatgtcagc ttgtgctgaa ttaaaggatg   1860

atcaaataca taaacctttc ccatactgtg tttcagctcc ttttttattg tcccatcaac   1920

aattacacac ttctattgat tctacaaaaa aagacattga gtttcaagaa catcgtcaaa   1980

aaacccgccg ggcataagcc caagcgggtt ttaggatctt aataatctaa ttctttatat   2040

aaaggaaatt tatcagtcag agcagctaca cgctgtcttg cttcttgtgg gatcctctag   2100

agtcgacctg caggcatgca agcttgagta ttctatagtc tcacctaaat agcttggcgt   2160

aatcatggtc atagctgttt cctgtgtgaa attgttatcc gctcacaatt ccacacaaca   2220

tacgagccgg aagcataaag tgtaaagcct ggggtgccta atgagtgagc taactcacat   2280

taattgcgtt gcgctcactg cccgctttcc agtcgggaaa cctgtcgtgc cagctgcatt   2340

aatgaatcgg ccaacgcgaa ccccttgcgg ccgcccgggc cgtcgaccaa ttctcatgtt   2400

tgacagctta tcatcgaatt tctgccattc atccgcttat tatcacttat tcaggcgtag   2460

caaccaggcg tttaagggca ccaataactg ccttaaaaaa attacgcccc gccctgccac   2520

tcatcgcagt actgttgtaa ttcattaagc attctgccga catggaagcc atcacaaacg   2580
```

-continued gcatgatgaa cctgaatcgc cagcggcatc agcaccttgt cgccttgcgt ataatatttg 2640
cccatggtga aaacgggggc gaagaagttg tccatattgg ccacgtttaa atcaaaactg 2700
gtgaaactca cccagggatt ggctgagacg aaaaacatat tctcaataaa ccctttaggg 2760
aaataggcca ggttttcacc gtaacacgcc acatcttgcg aatatatgtg tagaaactgc 2820
cggaaatcgt cgtggtattc actccagagc gatgaaaacg tttcagtttg ctcatggaaa 2880
acggtgtaac aagggtgaac actatcccat atcaccagct caccgtcttt cattgccata 2940
cgaaattccg gatgagcatt catcaggcgg gcaagaatgt gaataaaggc cggataaaac 3000
ttgtgcttat ttttctttac ggtctttaaa aaggccgtaa tatccagctg aacggtctgg 3060
ttataggtac attgagcaac tgactgaaat gcctcaaaat gttctttacg atgccattgg 3120
gatatatcaa cggtggtata tccagtgatt tttttctcca ttttagcttc cttagctcct 3180
gaaaatctcg ataactcaaa aaatacgccc ggtagtgatc ttatttcatt atggtgaaag 3240
ttggaacctc ttacgtgccg atcaacgtct cattttcgcc aaaagttggc ccagggcttc 3300
ccggtatcaa cagggacacc aggatttatt tattctgcga agtgatcttc cgtcacaggt 3360
atttattcgc gataagctca tggagcggcg taaccgtcgc acaggaagga cagagaaagc 3420
gcggatctgg gaagtgacgg acagaacggt caggacctgg attggggagg cggttgccgc 3480
cgctgctgct gacggtgtga cgttctctgt tccggtcaca ccacatacgt tccgccattc 3540
ctatgcgatg cacatgctgt atgccggtat accgctgaaa gttctgcaaa gcctgatggg 3600
acataagtcc atcagttcaa cggaagtcta cacgaaggtt tttgcgctgg atgtggctgc 3660
ccggcaccgg gtgcagtttg cgatgccgga gtctgatgcg gttgcgatgc tgaaacaatt 3720
atcctgagaa taaatgcctt ggcctttata tggaaatgtg gaactgagtg gatatgctgt 3780
ttttgtctgt taaacagaga agctggctgt tatccactga gaagcgaacg aaacagtcgg 3840
gaaaatctcc cattatcgta gagatccgca ttattaatct caggagcctg tgtagcgttt 3900
ataggaagta gtgttctgtc atgatgcctg caagcggtaa cgaaaacgat ttgaatatgc 3960
cttcaggaac aatagaaatc ttcgtgcggt gttacgttga agtggagcgg attatgtcag 4020
caatggacag aacaacctaa tgaacacaga accatgatgt ggtctgtcct tttacagcca 4080
gtagtgctcg ccgcagtcga gcgacagggc gaagccctcg gctggttgcc ctcgccgctg 4140
ggctggcggc cgtctatggc cctgcaaacg cgccagaaac gccgtcgaag ccgtgtgcga 4200
gacaccgcgg ccggccgccg gcgttgtgga tacctcgcgg aaaacttggc cctcactgac 4260
agatgagggg cggacgttga cacttgaggg gccgactcac ccggcgcggc gttgacagat 4320
gaggggcagg ctcgatttcg gccggcgacg tggagctggc cagcctcgca aatcggcgaa 4380
aacgcctgat tttacgcgag tttcccacag atgatgtgga caagcctggg gataagtgcc 4440
ctgcggtatt gacacttgag gggcgcgact actgacagat gaggggcgcg atccttgaca 4500
cttgaggggc agagtgctga cagatgaggg gcgcacctat tgacatttga ggggctgtcc 4560
acaggcagaa aatccagcat ttgcaagggt ttccgcccgt ttttcggcca ccgctaacct 4620
gtcttttaac ctgcttttaa accaatattt ataaaccttg tttttaacca gggctgcgcc 4680
ctgtgcgcgt gaccgcgcac gccgaagggg ggtgcccccc cttctcgaac cctcccggtc 4740
gagtgagcga ggaagcacca gggaacagca cttatatatt ctgcttacac acgatgcctg 4800
aaaaaacttc ccttggggtt atccacttat ccacggggat atttttataa ttatttttttt 4860
tatagttttt agatcttctt ttttagagcg ccttgtaggc ctttatccat gctggttcta 4920

-continued gagaaggtgt tgtgacaaat tgccctttca gtgtgacaaa tcaccctcaa atgacagtcc 4980
tgtctgtgac aaattgccct taaccctgtg acaaattgcc ctcagaagaa gctgtttttt 5040
cacaaagtta tccctgctta ttgactcttt tttatttagt gtgacaatct aaaaacttgt 5100
cacacttcac atggatctgt catggcggaa acagcggtta tcaatcacaa gaaacgtaaa 5160
aatagcccgc gaatcgtcca gtcaaacgac ctcactgagg cggcatatag tctctcccgg 5220
gatcaaaaac gtatgctgta tctgttcgtt gaccagatca gaaaatctga tggcacccta 5280
caggaacatg acggtatctg cgagatccat gttgctaaat atgctgaaat attcggattg 5340
acctctgcgg aagccagtaa ggatatacgg caggcattga agagtttcgc ggggaaggaa 5400
gtggtttttt atcgccctga agaggatgcc ggcgatgaaa aaggctatga atcttttcct 5460
tggtttatca aacgtgcgca cagtccatcc agagggcttt acagtgtaca tatcaaccca 5520
tatctcattc ccttctttat cgggttacag aaccggttta cgcagtttcg gcttagtgaa 5580
acaaaagaaa tcaccaatcc gtatgccatg cgtttatacg aatccctgtg tcagtatcgt 5640
aagccggatg gctcaggcat cgtctctctg aaaatcgact ggatcataga gcgttaccag 5700
ctgcctcaaa gttaccagcg tatgcctgac ttccgccgcc gcttcctgca ggtctgtgtt 5760
aatgagatca acagcagaac tccaatgcgc ctctcataca ttgagaaaaa gaaaggccgc 5820
cagacgactc atatcgtatt ttccttccgc gatatcactt ccatgacgac aggatagtct 5880
gagggttatc tgtcacagat ttgagggtgg ttcgtcacat ttgttctgac ctactgaggg 5940
taatttgtca cagttttgct gtttccttca gcctgcatgg attttctcat actttttgaa 6000
ctgtaatttt taaggaagcc aaatttgagg gcagtttgtc acagttgatt tccttctctt 6060
tcccttcgtc atgtgacctg atatcggggg ttagttcgtc atcattgatg agggttgatt 6120
atcacagttt attactctga attggctatc cgcgtgtgta cctctacctg gagtttttcc 6180
cacggtggat atttcttctt gcgctgagcg taagagctat ctgacagaac agttcttctt 6240
tgcttcctcg ccagttcgct cgctatgctc ggttacacgg ctgcggcgag cgctagtgat 6300
aataagtgac tgaggtatgt gctcttctta tctccttttg tagtgttgct cttattttaa 6360
acaactttgc ggtttttga tgactttgcg attttgttgt tgctttgcag taaattgcaa 6420
gatttaataa aaaaacgcaa agcaatgatt aaaggatgtt cagaatgaaa ctcatggaaa 6480
cacttaacca gtgcataaac gctggtcatg aaatgacgaa ggctatcgcc attgcacagt 6540
ttaatgatga cagcccggaa gcgaggaaaa taacccggcg ctggagaata ggtgaagcag 6600
cggatttagt tggggtttct tctcaggcta tcagagatgc cgagaaagca gggcgactac 6660
cgcacccgga tatggaaatt cgaggacggg ttgagcaacg tgttggttat acaattgaac 6720
aaattaatca tatgcgtgat gtgtttggta cgcgattgcg acgtgctgaa gacgtatttc 6780
caccggtgat cggggttgct gcccataaag gtggcgttta caaaacctca gtttctgttc 6840
atcttgctca ggatctggct ctgaaggggc tacgtgtttt gctcgtggaa ggtaacgacc 6900
cccagggaac agcctcaatg tatcacggat gggtaccaga tcttcatatt catgcagaag 6960
acactctcct gcctttctat cttggggaaa aggacgatgt cacttatgca ataaagccca 7020
cttgctggcc ggggcttgac attattcctt cctgtctggc tctgcaccgt attgaaactg 7080
agttaatggg caaatttgat gaaggtaaac tgcccaccga tccacacctg atgctccgac 7140
tggccattga aactgttgct catgactatg atgtcatagt tattgacagc gcgcctaacc 7200
tgggtatcgg cacgattaat gtcgtatgtg ctgctgatgt gctgattgtt cccacgcctg 7260
ctgagttgtt tgactacacc tccgcactgc agtttttcga tatgcttcgt gatctgctca 7320
agaacgttga tcttaaaggg ttcgagcctg atgtacgtat tttgcttacc aaatacagca 7380
atagtaatgg ctctcagtcc ccgtggatgg aggagcaaat tcgggatgcc tggggaagca 7440
tggttctaaa aaatgttgta cgtgaaacgg atgaagttgg taaaggtcag atccggatga 7500
gaactgtttt tgaacaggcc attgatcaac gctcttcaac tggtgcctgg agaaatgctc 7560
tttctatttg ggaacctgtc tgcaatgaaa ttttcgatcg tctgattaaa ccacgctggg 7620
agattagata atgaagcgtg cgcctgttat tccaaaacat acgctcaata ctcaaccggt 7680
tgaagatact tcgttatcga caccagctgc cccgatggtg gattcgttaa ttgcgcgcgt 7740
aggagtaatg gctcgcggta atgccattac tttgcctgta tgtggtcggg atgtgaagtt 7800
tactcttgaa gtgctccggg gtgatagtgt tgagaagacc tctcgggtat ggtcaggtaa 7860
tgaacgtgac caggagctgc ttactgagga cgcactggat gatctcatcc cttcttttct 7920
actgactggt caacagacac cggcgttcgg tcgaagagta tctggtgtca tagaaattgc 7980
cgatgggagt cgccgtcgta aagctgctgc acttaccgaa agtgattatc gtgttctggt 8040
tggcgagctg gatgatgagc agatggctgc attatccaga ttgggtaacg attatcgccc 8100
aacaagtgct tatgaacgtg gtcagcgtta tgcaagccga ttgcagaatg aatttgctgg 8160
aaatatttct gcgctggctg atgcggaaaa tatttcacgt aagattatta cccgctgtat 8220
caacaccgcc aaattgccta aatcagttgt tgctcttttt tctcaccccg gtgaactatc 8280
tgcccggtca ggtgatgcac ttcaaaaagc ctttacagat aaagaggaat tacttaagca 8340
gcaggcatct aaccttcatg agcagaaaaa agctggggtg atatttgaag ctgaagaagt 8400
tatcactctt ttaacttctg tgcttaaaac gtcatctgca tcaagaacta gtttaagctc 8460
acgacatcag tttgctcctg gagcgacagt attgtataag ggcgataaaa tggtgcttaa 8520
cctggacagg tctcgtgttc caactgagtg tatagagaaa attgaggcca ttcttaagga 8580
acttgaaaag ccagcaccct gatgcgacca cgttttagtc tacgtttatc tgtctttact 8640
taatgtcctt tgttacaggc cagaaagcat aactggcctg aatattctct ctgggcccac 8700
tgttccactt gtatcgtcgg tctgataatc agactgggac cacggtccca ctcgtatcgt 8760
cggtctgatt attagtctgg gaccacggtc ccactcgtat cgtcggtctg attattagtc 8820
tgggaccacg gtcccactcg tatcgtcggt ctgataatca gactgggacc acggtcccac 8880
tcgtatcgtc ggtctgatta ttagtctggg accatggtcc cactcgtatc gtcggtctga 8940
ttattagtct gggaccacgg tcccactcgt atcgtcggtc tgattattag tctggaacca 9000
cggtcccact cgtatcgtcg gtctgattat tagtctggga ccacggtccc actcgtatcg 9060
tcggtctgat tattagtctg ggaccacgat cccactcgtg ttgtcggtct gattatcggt 9120
ctgggaccac ggtcccactt gtattgtcga tcagactatc agcgtgagac tacgattcca 9180
tcaatgcctg tcaagggcaa gtattgacat gtcgtcgtaa cctgtagaac ggagtaacct 9240
cggtgtgcgg ttgtatgcct gctgtggatt gctgctgtgt cctgcttatc cacaacattt 9300
tgcgcacggt tatgtggaca aaatacctgg ttacccaggc cgtgccggca cgttaaccgg 9360
gctgcatccg atgcaagtgt gtcgctgtcg acgagctcgc gagctcggac atgaggttgc 9420
cccgtattca gtgtcgctga tttgtattgt ctgaagttgt ttttacgtta agttgatgca 9480
gatcaattaa tacgatacct gcgtcataat tgattatttg acgtggtttg atggcctcca 9540
cgcacgttgt gatatgtaga tgataatcat tatcacttta cgggtccttt ccggtgatcc 9600
gacaggttac ggggcggcga cctcgcgggt tttcgctatt tatgaaaatt ttccggttta 9660

-continued aggcgtttcc gttcttcttc gtcataactt aatgttttta tttaaaatac cctctgaaaa 9720
gaaaggaaac gacaggtgct gaaagcgagc tttttggcct ctgtcgtttc ctttctctgt 9780
ttttgtccgt ggaatgaaca atggaagtcc gagctcatcg ctaataactt cgtatagcat 9840
acattatacg aagttatatt cgat 9864

<210> SEQ ID NO 70
<211> LENGTH: 1470
<212> TYPE: DNA
<213> ORGANISM: Synechocystis PCC6803

<400> SEQUENCE: 70
atgaaatccc cccaggctca acaaatccta gaccaggccc gccgtttgct ctacgaaaaa 60
gccatggtca aaatcaatgg gcaatacgtg ggacggtgg cggccattcc ccaatcggat 120
caccatgatt tgaactatac ggaagttttc attcgggaca atgtgccggt gatgatcttc 180
ttgttactgc aaaatgaaac ggaaattgtc caaaactttt tggaaatttg cctcaccctc 240
caaagtaagg gctttcccac ctacggcatt tttcccacta gttttgtgga aacggaaaac 300
catgaactca aggcagacta tggccaacgg gcgatcggtc gagtttgctc ggtggatgcg 360
tccctctggt ggcctatttt ggcctattac tacgtgcaaa gaaccggcaa tgaagcctgg 420
gctagacaaa cccatgtgca attggggcta caaaagtttt taaacctcat tctccatcca 480
gtctttcggg atgcacccac tttgtttgtg cccgacgggg cctttatgat tgaccgcccc 540
atggatgtgt ggggagcgcc gttggaaatc caaaccctgc tctacggagc cctgaaaagt 600
gcggcggggt tactgttaat cgacctcaag gcgaagggtt attgcagcaa taaagaccat 660
ccttttgaca gcttcacgat ggagcagagt catcaattta acctgagtgt ggattggctc 720
aaaaaactcc gcacctatct gctcaagcat tattggatta attgcaatat tgtccaagct 780
ctccgccgcc gtcccacgga acagtacggt gaagaagcca gcaacgaaca taatgtccac 840
acagaaacca ttcccaactg gctccaggat tggctcggcg atcggggagg ctatttaatc 900
ggcaatatcc gcacgggtcg ccccgatttt cgctttttct ccctgggtaa ttgcttgggg 960
gcaattttcg atgtcactag cttggcccag caacgttcct tttccgtttt ggtattaaat 1020
aatcagcggg agttatgtgc ccaaatgccc ctgaggattt gccatccccc cctcaaagat 1080
gacgattggc gcagtaaaac cggctttgac cgcaaaaatt taccctggtg ctaccacaac 1140
gccggccatt ggccctgttt attttggttt ctggtggtgg cggtgctccg ccatagctgc 1200
cattccaact acggcacggt ggagtatgcg gaaatgggga acctaattcg caataactat 1260
gaggtgcttt tgcgccgttt gcccaagcat aaatgggctg aatattttga tggccccacg 1320
ggcttttggg tcgggcaaca atcccgttcc taccaaacct ggaccattgt gggcctattg 1380
ctagtacacc atttcacaga agttaacccc gacgatgctt tgatgttcga tttgcctagt 1440
ttgaaaagtt tgcatcaagc gctgcattaa 1470

<210> SEQ ID NO 71
<211> LENGTH: 489
<212> TYPE: PRT
<213> ORGANISM: Synechocystis PCC6803

<400> SEQUENCE: 71

Met Lys Ser Pro Gln Ala Gln Gln Ile Leu Asp Gln Ala Arg Arg Leu
1 5 10 15

Leu Tyr Glu Lys Ala Met Val Lys Ile Asn Gly Gln Tyr Val Gly Thr
20 25 30

-continued

```
Val Ala Ala Ile Pro Gln Ser Asp His His Asp Leu Asn Tyr Thr Glu
        35                  40                  45

Val Phe Ile Arg Asp Asn Val Pro Val Met Ile Phe Leu Leu Leu Gln
    50                  55                  60

Asn Glu Thr Glu Ile Val Gln Asn Phe Leu Glu Ile Cys Leu Thr Leu
65                  70                  75                  80

Gln Ser Lys Gly Phe Pro Thr Tyr Gly Ile Phe Pro Thr Ser Phe Val
                85                  90                  95

Glu Thr Glu Asn His Glu Leu Lys Ala Asp Tyr Gly Gln Arg Ala Ile
            100                 105                 110

Gly Arg Val Cys Ser Val Asp Ala Ser Leu Trp Trp Pro Ile Leu Ala
        115                 120                 125

Tyr Tyr Tyr Val Gln Arg Thr Gly Asn Glu Ala Trp Ala Arg Gln Thr
    130                 135                 140

His Val Gln Leu Gly Leu Gln Lys Phe Leu Asn Leu Ile Leu His Pro
145                 150                 155                 160

Val Phe Arg Asp Ala Pro Thr Leu Phe Val Pro Asp Gly Ala Phe Met
                165                 170                 175

Ile Asp Arg Pro Met Asp Val Trp Gly Ala Pro Leu Glu Ile Gln Thr
            180                 185                 190

Leu Leu Tyr Gly Ala Leu Lys Ser Ala Ala Gly Leu Leu Leu Ile Asp
        195                 200                 205

Leu Lys Ala Lys Gly Tyr Cys Ser Asn Lys Asp His Pro Phe Asp Ser
    210                 215                 220

Phe Thr Met Glu Gln Ser His Gln Phe Asn Leu Ser Val Asp Trp Leu
225                 230                 235                 240

Lys Lys Leu Arg Thr Tyr Leu Leu Lys His Tyr Trp Ile Asn Cys Asn
                245                 250                 255

Ile Val Gln Ala Leu Arg Arg Arg Pro Thr Glu Gln Tyr Gly Glu Glu
            260                 265                 270

Ala Ser Asn Glu His Asn Val His Thr Glu Thr Ile Pro Asn Trp Leu
        275                 280                 285

Gln Asp Trp Leu Gly Asp Arg Gly Gly Tyr Leu Ile Gly Asn Ile Arg
    290                 295                 300

Thr Gly Arg Pro Asp Phe Arg Phe Phe Ser Leu Gly Asn Cys Leu Gly
305                 310                 315                 320

Ala Ile Phe Asp Val Thr Ser Leu Ala Gln Gln Arg Ser Phe Phe Arg
                325                 330                 335

Leu Val Leu Asn Asn Gln Arg Glu Leu Cys Ala Gln Met Pro Leu Arg
            340                 345                 350

Ile Cys His Pro Pro Leu Lys Asp Asp Asp Trp Arg Ser Lys Thr Gly
        355                 360                 365

Phe Asp Arg Lys Asn Leu Pro Trp Cys Tyr His Asn Ala Gly His Trp
    370                 375                 380

Pro Cys Leu Phe Trp Phe Leu Val Val Ala Val Leu Arg His Ser Cys
385                 390                 395                 400

His Ser Asn Tyr Gly Thr Val Glu Tyr Ala Glu Met Gly Asn Leu Ile
                405                 410                 415

Arg Asn Asn Tyr Glu Val Leu Leu Arg Arg Leu Pro Lys His Lys Trp
            420                 425                 430

Ala Glu Tyr Phe Asp Gly Pro Thr Gly Phe Trp Val Gly Gln Gln Ser
        435                 440                 445
```

Arg Ser Tyr Gln Thr Trp Thr Ile Val Gly Leu Leu Leu Val His His
    450                 455                 460

Phe Thr Glu Val Asn Pro Asp Asp Ala Leu Met Phe Asp Leu Pro Ser
465                 470                 475                 480

Leu Lys Ser Leu His Gln Ala Leu His
                485

<210> SEQ ID NO 72
<211> LENGTH: 1392
<212> TYPE: DNA
<213> ORGANISM: Synechococcus PCC7942

<400> SEQUENCE: 72
atgcccgatt ctgttgtgct gcccgctacg ctgcagaccg cgctgcaaac agcggagcag 60
ttactttggg atcgggcctt ggttcgctat cacgatcagt gggcgggggc gatcgcggca 120
ctgcctgaag atcaggagtt ggcggcagcg aactaccgcg aaatctttat tcgcgacaac 180
gtgccggtga tgctctacct gctgttgcag ggcaaaactg acgttgtccg cgacttcttg 240
caactgtcgc tttctctcca gagccaggca ctgcaaacct atggcattct gccgaccagt 300
ttcgtctgtg aggaaaccca ctgcgttgct gactatggtc agcgggcgat cgggcgggtg 360
gtttctgctg accctagcct ttggtggccg gtgctgctac aggcctatcg gcgggcctcc 420
catgatgatg cctttgtcca cagtccgact gttcagcagg ggttacagcg gttgctggct 480
ttcctgctgc gtccggtttt caaccaaaac ccactgctcg aggtgcccga tggggccttc 540
atggtcgatc gtcccttgga tgtggcgggc gcacctttag aaattcaagt cctgctctac 600
ggggcactgc gggcttgtgg gcagttgctg caatacaccg aagcggccaa tgctgcccat 660
gtgcaagccc gtcgcctgcg gcagtatctc tgctggcact actgggtgac gcccgatcgc 720
ctgcgacgct ggcagcagtg gcccaccgaa gaatttggcg atcgcagcca taacccctac 780
aacattcagc cgatcgccat ccctgactgg gttgaacctt ggctgggtga gtcgggtggc 840
tacttcctag ggaacatacg ggcaggacgt cctgacttcc gctttttag ccttggcaat 900 ttgctggcga tcgttttcga tgtgcttccg ctcaatcagc agggtgcgat tctgcgcttg 960
attttgcaga acgaagccca gattttgggc caagtgccgt tgcggctctg ctatcccgct 1020
ttaaccggat cggcgtggaa aatcctgacg ggttgcgatc ctaaaaatca gccttggtcc 1080
tatcacaacg gtggtagttg gccatccctg ctttggtatc tcagtgcggc ggtcttgcac 1140
taccaacagc ggggaggcga tcgcaatctc tgtcaggtct ggctgaataa gcttcagcac 1200
taccacactc agcagtgcga gcaactccct ggcgatgagt ggccagagta ctacgagggt 1260
caggactcgg tccagattgc tactcgcgcc tgccgttatc agacttggac gtttacggga 1320
ttgctgctga atcacgcact gctctcgcag ccccagggca ttcaactgct gagtctgcgg 1380
ggcttaccct aa 1392

<210> SEQ ID NO 73
<211> LENGTH: 463
<212> TYPE: PRT
<213> ORGANISM: Synechococcus PCC7942

<400> SEQUENCE: 73

Met Pro Asp Ser Val Val Leu Pro Ala Thr Leu Gln Thr Ala Leu Gln
1               5                   10                  15

Thr Ala Glu Gln Leu Leu Trp Asp Arg Ala Leu Val Arg Tyr His Asp
            20                  25                  30

```
Gln Trp Ala Gly Ala Ile Ala Ala Leu Pro Glu Asp Gln Glu Leu Ala
        35                  40                  45

Ala Ala Asn Tyr Arg Glu Ile Phe Ile Arg Asp Asn Val Pro Val Met
    50                  55                  60

Leu Tyr Leu Leu Leu Gln Gly Lys Thr Asp Val Val Arg Asp Phe Leu
65                  70                  75                  80

Gln Leu Ser Leu Ser Leu Gln Ser Gln Ala Leu Gln Thr Tyr Gly Ile
                85                  90                  95

Leu Pro Thr Ser Phe Val Cys Glu Glu Thr His Cys Val Ala Asp Tyr
            100                 105                 110

Gly Gln Arg Ala Ile Gly Arg Val Val Ser Ala Asp Pro Ser Leu Trp
        115                 120                 125

Trp Pro Val Leu Leu Gln Ala Tyr Arg Arg Ala Ser His Asp Asp Ala
    130                 135                 140

Phe Val His Ser Pro Thr Val Gln Gln Gly Leu Gln Arg Leu Leu Ala
145                 150                 155                 160

Phe Leu Leu Arg Pro Val Phe Asn Gln Asn Pro Leu Leu Glu Val Pro
                165                 170                 175

Asp Gly Ala Phe Met Val Asp Arg Pro Leu Asp Val Ala Gly Ala Pro
            180                 185                 190

Leu Glu Ile Gln Val Leu Leu Tyr Gly Ala Leu Arg Ala Cys Gly Gln
        195                 200                 205

Leu Leu Gln Tyr Thr Glu Ala Ala Asn Ala Ala His Val Gln Ala Arg
    210                 215                 220

Arg Leu Arg Gln Tyr Leu Cys Trp His Tyr Trp Val Thr Pro Asp Arg
225                 230                 235                 240

Leu Arg Arg Trp Gln Gln Trp Pro Thr Glu Glu Phe Gly Asp Arg Ser
                245                 250                 255

His Asn Pro Tyr Asn Ile Gln Pro Ile Ala Ile Pro Asp Trp Val Glu
            260                 265                 270

Pro Trp Leu Gly Glu Ser Gly Gly Tyr Phe Leu Gly Asn Ile Arg Ala
        275                 280                 285

Gly Arg Pro Asp Phe Arg Phe Phe Ser Leu Gly Asn Leu Leu Ala Ile
    290                 295                 300

Val Phe Asp Val Leu Pro Leu Asn Gln Gln Gly Ala Ile Leu Arg Leu
305                 310                 315                 320

Ile Leu Gln Asn Glu Ala Gln Ile Leu Gly Gln Val Pro Leu Arg Leu
                325                 330                 335

Cys Tyr Pro Ala Leu Thr Gly Ser Ala Trp Lys Ile Leu Thr Gly Cys
            340                 345                 350

Asp Pro Lys Asn Gln Pro Trp Ser Tyr His Asn Gly Gly Ser Trp Pro
        355                 360                 365

Ser Leu Leu Trp Tyr Leu Ser Ala Ala Val Leu His Tyr Gln Gln Arg
    370                 375                 380

Gly Gly Asp Arg Asn Leu Cys Gln Val Trp Leu Asn Lys Leu Gln His
385                 390                 395                 400

Tyr His Thr Gln Gln Cys Glu Gln Leu Pro Gly Asp Glu Trp Pro Glu
                405                 410                 415

Tyr Tyr Glu Gly Gln Asp Ser Val Gln Ile Ala Thr Arg Ala Cys Arg
            420                 425                 430

Tyr Gln Thr Trp Thr Phe Thr Gly Leu Leu Leu Asn His Ala Leu Leu
        435                 440                 445

Ser Gln Pro Gln Gly Ile Gln Leu Leu Ser Leu Arg Gly Leu Pro
```

```
    450                 455                 460

<210> SEQ ID NO 74
<211> LENGTH: 966
<212> TYPE: DNA
<213> ORGANISM: Synechocystis PCC6803

<400> SEQUENCE: 74

atgattaatt gtcaattttg ttccgttatt tccaaatcta acggggaaga tcctatcggc      60

acagcaaatt caagtgatcg ttggttaatt atggaattac cccaaccttg gacagaggaa     120

cgctttcatc atgaccccat tcttaaacca attcatgatc tttttcatca actttctgat     180

caaggagtta aagtatctcc aatggcgatc gcctcagatc acgagtattc tcaatcagga     240

tttagtcgta ttattcacta ccaaaagttt aatttgctct tttccagttt tataaaagaa     300

gaatatttag ttcctgatga tcaaaggtgg gatcttatca aaaatttatg ttatcaatct     360

ccagagttag aaaattttcg taactataaa ctgtcagatg ttgttgatcg agatatgatg     420

gtatgtactc atggaaacat tgatgtggct tgttcgagat ttggttatcc tatttataaa     480

caattacgac aaaaatatgc atcaaaaaat ttaagaatat ggcgctgctc tcattttggg     540

ggacatcagt ttgctccgac tttaattgat tttccaaatg ggcaagtttg ggacatcttt     600

gagtctgaag ttttagataa tctggtaagg caagaaggtc aagttaaaca actttataaa     660

ttttatcgag gttgggtagg cgtaacaaaa tttgcccaga ttgttgagcg tgaaatttgg     720

actcaacgag gttggcaatg gttaaattat caaaaatcag ctcaaatatt gaacatggat     780

gataatcagc atgatcccaa ttgggtagag gttcaatttg attttatttc tcccgataaa     840

gttaaaggag cttattttgc aagagttgaa gtcaatgggt cagtgatgac tgctagaaat     900

tcaggagatg aacttatttc tgtcaagcag tatagtgtca gctacttaaa agaaattgat     960

aaataa                                                                966

<210> SEQ ID NO 75
<211> LENGTH: 321
<212> TYPE: PRT
<213> ORGANISM: Synechocystis PCC6803

<400> SEQUENCE: 75

Met Ile Asn Cys Gln Phe Cys Ser Val Ile Ser Lys Ser Asn Gly Glu
1               5                   10                  15

Asp Pro Ile Gly Thr Ala Asn Ser Ser Asp Arg Trp Leu Ile Met Glu
            20                  25                  30

Leu Pro Gln Pro Trp Thr Glu Glu Arg Phe His His Asp Pro Ile Leu
        35                  40                  45

Lys Pro Ile His Asp Leu Phe His Gln Leu Ser Asp Gln Gly Val Lys
    50                  55                  60

Val Ser Pro Met Ala Ile Ala Ser Asp His Glu Tyr Ser Gln Ser Gly
65                  70                  75                  80

Phe Ser Arg Ile Ile His Tyr Gln Lys Phe Asn Leu Leu Phe Ser Ser
                85                  90                  95

Phe Ile Lys Glu Glu Tyr Leu Val Pro Asp Asp Gln Arg Trp Asp Leu
            100                 105                 110

Ile Lys Asn Leu Cys Tyr Gln Ser Pro Glu Leu Glu Asn Phe Arg Asn
        115                 120                 125

Tyr Lys Leu Ser Asp Val Val Asp Arg Asp Met Met Val Cys Thr His
    130                 135                 140
```

```
Gly Asn Ile Asp Val Ala Cys Ser Arg Phe Gly Tyr Pro Ile Tyr Lys
145                 150                 155                 160

Gln Leu Arg Gln Lys Tyr Ala Ser Lys Asn Leu Arg Ile Trp Arg Cys
                165                 170                 175

Ser His Phe Gly Gly His Gln Phe Ala Pro Thr Leu Ile Asp Phe Pro
            180                 185                 190

Asn Gly Gln Val Trp Gly His Leu Glu Ser Glu Val Leu Asp Asn Leu
        195                 200                 205

Val Arg Gln Glu Gly Gln Val Lys Gln Leu Tyr Lys Phe Tyr Arg Gly
    210                 215                 220

Trp Val Gly Val Thr Lys Phe Ala Gln Ile Val Glu Arg Glu Ile Trp
225                 230                 235                 240

Thr Gln Arg Gly Trp Gln Trp Leu Asn Tyr Gln Lys Ser Ala Gln Ile
                245                 250                 255

Leu Asn Met Asp Asp Asn Gln His Asp Pro Asn Trp Val Glu Val Gln
            260                 265                 270

Phe Asp Phe Ile Ser Pro Asp Lys Val Lys Gly Ala Tyr Phe Ala Arg
        275                 280                 285

Val Glu Val Asn Gly Ser Val Met Thr Ala Arg Asn Ser Gly Asp Glu
    290                 295                 300

Leu Ile Ser Val Lys Gln Tyr Ser Val Ser Tyr Leu Lys Glu Ile Asp
305                 310                 315                 320

Lys


<210> SEQ ID NO 76
<211> LENGTH: 1425
<212> TYPE: DNA
<213> ORGANISM: Escherichia coli

<400> SEQUENCE: 76

atgagtcgtt tagtcgtagt atctaaccgg attgcaccac cagacgagca cgccgccagt      60

gccggtggcc ttgccgttgg catactgggg gcactgaaag ccgcaggcgg actgtggttt     120

ggctggagtg gtgaaacagg gaatgaggat cagccgctaa aaaaggtgaa aaaaggtaac     180

attacgtggg cctcttttaa cctcagcgaa caggaccttg acgaatacta caaccaattc     240

tccaatgccg ttctctggcc cgcttttcat tatcggctcg atctggtgca atttcagcgt     300

cctgcctggg acggctatct acgcgtaaat gcgttgctgg cagataaatt actgccgctg     360

ttgcaagacg atgacattat ctggatccac gattatcacc tgttgccatt tgcgcatgaa     420

ttacgcaaac ggggagtgaa taatcgcatt ggtttctttc tgcatattcc tttcccgaca     480

ccggaaatct tcaacgcgct gccgacatat gacaccttgc ttgaacagct ttgtgattat     540

gatttgctgg gtttccagac agaaaacgat cgtctggcgt tcctggattg tctttctaac     600

ctgacccgcg tcacgacacg tagcgcaaaa agccatacag cctggggcaa agcatttcga     660

acagaagtct acccgatcgg cattgaaccg aaagaaatag ccaaacaggc tgccgggcca     720

ctgccgccaa aactggcgca acttaaagcg gaactgaaaa acgtacaaaa tatcttttct     780

gtcgaacggc tggattattc caaaggtttg ccagagcgtt ttctcgccta tgaagcgttg     840

ctggaaaaat atccgcagca tcatggtaaa attcgttata cccagattgc accaacgtcg     900

cgtggtgatg tgcaagccta tcaggatatt cgtcatcagc tcgaaaatga agctggacga     960

attaatggta aatacgggca attaggctgg acgccgcttt attatttgaa tcagcatttt    1020

gaccgtaaat tactgatgaa aatattccgc tactctgacg tgggcttagt gacgccactg    1080
```

-continued

```
cgtgacggga tgaacctggt agcaaaagag tatgttgctg ctcaggaccc agccaatccg   1140

ggcgttcttg ttctttcgca atttgcggga gcggcaaacg agttaacgtc ggcgttaatt   1200

gttaacccct acgatcgtga cgaagttgca gctgcgctgg atcgtgcatt gactatgtcg   1260

ctggcggaac gtatttcccg tcatgcagaa atgctggacg ttatcgtgaa aaacgatatt   1320

aaccactggc aggagtgctt cattagcgac ctaaagcaga tagttccgcg aagcgcggaa   1380

agccagcagc gcgataaagt tgctaccttt ccaaagcttg cgtag                   1425
```

<210> SEQ ID NO 77
<211> LENGTH: 474
<212> TYPE: PRT
<213> ORGANISM: Escherichia coli

<400> SEQUENCE: 77

```
Met Ser Arg Leu Val Val Val Ser Asn Arg Ile Ala Pro Pro Asp Glu
1               5                   10                  15

His Ala Ala Ser Ala Gly Gly Leu Ala Val Gly Ile Leu Gly Ala Leu
            20                  25                  30

Lys Ala Ala Gly Gly Leu Trp Phe Gly Trp Ser Gly Glu Thr Gly Asn
        35                  40                  45

Glu Asp Gln Pro Leu Lys Lys Val Lys Lys Gly Asn Ile Thr Trp Ala
    50                  55                  60

Ser Phe Asn Leu Ser Glu Gln Asp Leu Asp Glu Tyr Tyr Asn Gln Phe
65                  70                  75                  80

Ser Asn Ala Val Leu Trp Pro Ala Phe His Tyr Arg Leu Asp Leu Val
                85                  90                  95

Gln Phe Gln Arg Pro Ala Trp Asp Gly Tyr Leu Arg Val Asn Ala Leu
            100                 105                 110

Leu Ala Asp Lys Leu Leu Pro Leu Leu Gln Asp Asp Asp Ile Ile Trp
        115                 120                 125

Ile His Asp Tyr His Leu Leu Pro Phe Ala His Glu Leu Arg Lys Arg
    130                 135                 140

Gly Val Asn Asn Arg Ile Gly Phe Phe Leu His Ile Pro Phe Pro Thr
145                 150                 155                 160

Pro Glu Ile Phe Asn Ala Leu Pro Thr Tyr Asp Thr Leu Leu Glu Gln
                165                 170                 175

Leu Cys Asp Tyr Asp Leu Leu Gly Phe Gln Thr Glu Asn Asp Arg Leu
            180                 185                 190

Ala Phe Leu Asp Cys Leu Ser Asn Leu Thr Arg Val Thr Thr Arg Ser
        195                 200                 205

Ala Lys Ser His Thr Ala Trp Gly Lys Ala Phe Arg Thr Glu Val Tyr
    210                 215                 220

Pro Ile Gly Ile Glu Pro Lys Glu Ile Ala Lys Gln Ala Ala Gly Pro
225                 230                 235                 240

Leu Pro Pro Lys Leu Ala Gln Leu Lys Ala Glu Leu Lys Asn Val Gln
                245                 250                 255

Asn Ile Phe Ser Val Glu Arg Leu Asp Tyr Ser Lys Gly Leu Pro Glu
            260                 265                 270

Arg Phe Leu Ala Tyr Glu Ala Leu Leu Glu Lys Tyr Pro Gln His His
        275                 280                 285

Gly Lys Ile Arg Tyr Thr Gln Ile Ala Pro Thr Ser Arg Gly Asp Val
    290                 295                 300

Gln Ala Tyr Gln Asp Ile Arg His Gln Leu Glu Asn Glu Ala Gly Arg
305                 310                 315                 320
```

Ile Asn Gly Lys Tyr Gly Gln Leu Gly Trp Thr Pro Leu Tyr Tyr Leu
325 330 335

Asn Gln His Phe Asp Arg Lys Leu Leu Met Lys Ile Phe Arg Tyr Ser
340 345 350

Asp Val Gly Leu Val Thr Pro Leu Arg Asp Gly Met Asn Leu Val Ala
355 360 365

Lys Glu Tyr Val Ala Ala Gln Asp Pro Ala Asn Pro Gly Val Leu Val
370 375 380

Leu Ser Gln Phe Ala Gly Ala Ala Asn Glu Leu Thr Ser Ala Leu Ile
385 390 395 400

Val Asn Pro Tyr Asp Arg Asp Glu Val Ala Ala Ala Leu Asp Arg Ala
405 410 415

Leu Thr Met Ser Leu Ala Glu Arg Ile Ser Arg His Ala Glu Met Leu
420 425 430

Asp Val Ile Val Lys Asn Asp Ile Asn His Trp Gln Glu Cys Phe Ile
435 440 445

Ser Asp Leu Lys Gln Ile Val Pro Arg Ser Ala Glu Ser Gln Gln Arg
450 455 460

Asp Lys Val Ala Thr Phe Pro Lys Leu Ala
465 470

<210> SEQ ID NO 78
<211> LENGTH: 746
<212> TYPE: DNA
<213> ORGANISM: Escherichia coli

<400> SEQUENCE: 78
atgatcttga tggaacgctg gcggaaatca aaccgcatcc cgatcaggtc gtcgtgcctg 60
acaatattct gcaaggacta cagctactgg caaccgcaag tgatggtgca ttggcattga 120
tatcagggcg ctcaatggtg gagcttgacg cactggcaaa accttatcgc ttcccgttag 180
cgggcgtgca tggggcggag cgccgtgaca tcaatggtaa aacacatatc gttcatctgc 240
cggatgcgat tgcgcgtgat attagcgtgc aactgcatac agtcatcgct cagtatcccg 300
gcgcggagct ggaggcgaaa gggatggctt ttgcgctgca ttatcgtcag gctccgcagc 360
atgaagacgc attaatgaca ttagcgcaac gtattactca gatctggcca caaatggcgt 420
tacagcaggg aaagtgtgtt gtcgagatca aaccgagagg taccagtaaa ggtgaggcaa 480
ttgcagcttt tatgcaggaa gctcccttta tcgggcgaac gcccgtattt ctgggcgatg 540
atttaaccga tgaatctggc ttcgcagtcg ttaaccgact gggcggaatg tcagtaaaaa 600
ttggcacagg tgcaactcag gcatcatggc gactggcggg tgtgccggat gtctggagct 660
ggcttgaaat gataaccacc gcattacaac aaaaaagaga aaataacagg agtgatgact 720
atgagtcgtt tagtcgtagt atctaa 746

<210> SEQ ID NO 79
<211> LENGTH: 266
<212> TYPE: PRT
<213> ORGANISM: Escherichia coli

<400> SEQUENCE: 79

Met Thr Glu Pro Leu Thr Glu Thr Pro Glu Leu Ser Ala Lys Tyr Ala
1 5 10 15

Trp Phe Phe Asp Leu Asp Gly Thr Leu Ala Glu Ile Lys Pro His Pro
20 25 30

```
Asp Gln Val Val Val Pro Asp Asn Ile Leu Gln Gly Leu Gln Leu Leu
        35                  40                  45

Ala Thr Ala Ser Asp Gly Ala Leu Ala Leu Ile Ser Gly Arg Ser Met
    50                  55                  60

Val Glu Leu Asp Ala Leu Ala Lys Pro Tyr Arg Phe Pro Leu Ala Gly
65                  70                  75                  80

Val His Gly Ala Glu Arg Arg Asp Ile Asn Gly Lys Thr His Ile Val
                85                  90                  95

His Leu Pro Asp Ala Ile Ala Arg Asp Ile Ser Val Gln Leu His Thr
            100                 105                 110

Val Ile Ala Gln Tyr Pro Gly Ala Glu Leu Glu Ala Lys Gly Met Ala
        115                 120                 125

Phe Ala Leu His Tyr Arg Gln Ala Pro Gln His Glu Asp Ala Leu Met
    130                 135                 140

Thr Leu Ala Gln Arg Ile Thr Gln Ile Trp Pro Gln Met Ala Leu Gln
145                 150                 155                 160

Gln Gly Lys Cys Val Val Glu Ile Lys Pro Arg Gly Thr Ser Lys Gly
                165                 170                 175

Glu Ala Ile Ala Ala Phe Met Gln Glu Ala Pro Phe Ile Gly Arg Thr
            180                 185                 190

Pro Val Phe Leu Gly Asp Asp Leu Thr Asp Glu Ser Gly Phe Ala Val
        195                 200                 205

Val Asn Arg Leu Gly Gly Met Ser Val Lys Ile Gly Thr Gly Ala Thr
    210                 215                 220

Gln Ala Ser Trp Arg Leu Ala Gly Val Pro Asp Val Trp Ser Trp Leu
225                 230                 235                 240

Glu Met Ile Thr Thr Ala Leu Gln Gln Lys Arg Glu Asn Asn Arg Ser
                245                 250                 255

Asp Asp Tyr Glu Ser Phe Ser Arg Ser Ile
            260                 265
```

<210> SEQ ID NO 80
<211> LENGTH: 1500
<212> TYPE: DNA
<213> ORGANISM: Synechocystis PCC6803

<400> SEQUENCE: 80

```
atgaattcat cccttgtgat cctttaccac cgtgagccct acgacgaagt tagggaaaat      60

ggcaaaacgg tgtatcgaga gaaaaagagt cccaacggga ttttgcccac cctcaaaagt     120

ttttttgccg atgcggaaca gagcacctgg gtcgcatgga aacaggtttc gccgaagcaa     180

aaggatgatt ttcaggcgga tatgtccatt gaaggccttg gcgatcgttg tacggtgcgc     240

cgggtgcccc tgacggcgga gcaggtaaaa aacttctatc acatcacttc caaggaagcc     300

ttttggccca ttctccactc tttcccctgg cagttcacct acgattcttc tgattgggat     360

aattttcagc acattaaccg cttatttgcc gaggcggcct gtgccgatgc cgatgacaat     420

gcattgtttt gggtccacga ctataacctc tggttagcgc ccctttacat tcgtcagctc     480

aagcccaacg ccaagattgc ctttttccac cacacccccct tccccagcgt tgatattttc     540

aatattttgc cctggcggga ggcgatcgta gaaagcttgc tggcctgtga tctctgtggt     600

tttcatattc cccgctacgt agaaaatttt gtcgccgtgg cccgtagtct caagccggtg     660

gaaatcacca gacgggttgt ggtagaccaa gcctttaccc cctacggtac ggccctggcg     720

gaaccggaac tcaccaccca gttgcgttat ggcgatcgcc tcattaacct cgatgcgttt     780
```

```
cccgtgggca ccaatccggc aaatatccgg gcgatcgtgg ccaaagaaag tgtgcaacaa    840

aaagttgctg aaattaaaca agatttaggc ggtaagaggc taattgtttc cgctgggcgg    900

gtggattacg tgaagggcac caaggaaatg ttgatgtgct atgaacgtct actggagcgt    960

cgccccgaat tgcaggggga aattagcctg gtagtccccg tagccaaggc cgctgaggga   1020

atgcgtattt atcgcaacgc ccaaaacgaa attgaacgac tggcagggaa aattaacggt   1080

cgctttgcca aactgtcctg gacaccagtg atgctgttca cctctccttt agcctatgag   1140

gagctcattg ccctgttctg tgccgccgac attgcctgga tcactcccct gcgggatggg   1200

ctaaacctgg tggctaagga gtatgtggtg gctaaaaatg gcgaagaagg agttctgatc   1260

ctctcggaat ttgccggttg tgcggtggaa ctacccgatg cggtgttgac taacccctac   1320

gcttccagcc gtatggacga atccattgac caggccctgg ccatggacaa agacgaacag   1380

aaaaaacgca tggggagaat gtacgccgcc attaagcgtt acgacgttca acaatgggcc   1440

aatcacctac tgcgggaagc ctacgccgat gtggtactgg gagagccccc ccaaatgtag   1500
```

```
<210> SEQ ID NO 81
<211> LENGTH: 499
<212> TYPE: PRT
<213> ORGANISM: Synechocystis PCC6803

<400> SEQUENCE: 81

Met Asn Ser Ser Leu Val Ile Leu Tyr His Arg Glu Pro Tyr Asp Glu
1               5                   10                  15

Val Arg Glu Asn Gly Lys Thr Val Tyr Arg Glu Lys Lys Ser Pro Asn
            20                  25                  30

Gly Ile Leu Pro Thr Leu Lys Ser Phe Phe Ala Asp Ala Glu Gln Ser
        35                  40                  45

Thr Trp Val Ala Trp Lys Gln Val Ser Pro Lys Gln Lys Asp Asp Phe
    50                  55                  60

Gln Ala Asp Met Ser Ile Glu Gly Leu Gly Asp Arg Cys Thr Val Arg
65                  70                  75                  80

Arg Val Pro Leu Thr Ala Glu Gln Val Lys Asn Phe Tyr His Ile Thr
                85                  90                  95

Ser Lys Glu Ala Phe Trp Pro Ile Leu His Ser Phe Pro Trp Gln Phe
            100                 105                 110

Thr Tyr Asp Ser Ser Asp Trp Asp Asn Phe Gln His Ile Asn Arg Leu
        115                 120                 125

Phe Ala Glu Ala Ala Cys Ala Asp Ala Asp Asp Asn Ala Leu Phe Trp
    130                 135                 140

Val His Asp Tyr Asn Leu Trp Leu Ala Pro Leu Tyr Ile Arg Gln Leu
145                 150                 155                 160

Lys Pro Asn Ala Lys Ile Ala Phe Phe His His Thr Pro Phe Pro Ser
                165                 170                 175

Val Asp Ile Phe Asn Ile Leu Pro Trp Arg Glu Ala Ile Val Glu Ser
            180                 185                 190

Leu Leu Ala Cys Asp Leu Cys Gly Phe His Ile Pro Arg Tyr Val Glu
        195                 200                 205

Asn Phe Val Ala Val Ala Arg Ser Leu Lys Pro Val Glu Ile Thr Arg
    210                 215                 220

Arg Val Val Val Asp Gln Ala Phe Thr Pro Tyr Gly Thr Ala Leu Ala
225                 230                 235                 240

Glu Pro Glu Leu Thr Thr Gln Leu Arg Tyr Gly Asp Arg Leu Ile Asn
                245                 250                 255
```

```
Leu Asp Ala Phe Pro Val Gly Thr Asn Pro Ala Asn Ile Arg Ala Ile
            260                 265                 270

Val Ala Lys Glu Ser Val Gln Gln Lys Val Ala Glu Ile Lys Gln Asp
        275                 280                 285

Leu Gly Gly Lys Arg Leu Ile Val Ser Ala Gly Arg Val Asp Tyr Val
    290                 295                 300

Lys Gly Thr Lys Glu Met Leu Met Cys Tyr Glu Arg Leu Leu Glu Arg
305                 310                 315                 320

Arg Pro Glu Leu Gln Gly Glu Ile Ser Leu Val Val Pro Val Ala Lys
                325                 330                 335

Ala Ala Glu Gly Met Arg Ile Tyr Arg Asn Ala Gln Asn Glu Ile Glu
            340                 345                 350

Arg Leu Ala Gly Lys Ile Asn Gly Arg Phe Ala Lys Leu Ser Trp Thr
        355                 360                 365

Pro Val Met Leu Phe Thr Ser Pro Leu Ala Tyr Glu Glu Leu Ile Ala
    370                 375                 380

Leu Phe Cys Ala Ala Asp Ile Ala Trp Ile Thr Pro Leu Arg Asp Gly
385                 390                 395                 400

Leu Asn Leu Val Ala Lys Glu Tyr Val Val Ala Lys Asn Gly Glu Glu
                405                 410                 415

Gly Val Leu Ile Leu Ser Glu Phe Ala Gly Cys Ala Val Glu Leu Pro
            420                 425                 430

Asp Ala Val Leu Thr Asn Pro Tyr Ala Ser Ser Arg Met Asp Glu Ser
        435                 440                 445

Ile Asp Gln Ala Leu Ala Met Asp Lys Asp Glu Gln Lys Lys Arg Met
    450                 455                 460

Gly Arg Met Tyr Ala Ala Ile Lys Arg Tyr Asp Val Gln Gln Trp Ala
465                 470                 475                 480

Asn His Leu Leu Arg Glu Ala Tyr Ala Asp Val Val Leu Gly Glu Pro
                485                 490                 495

Pro Gln Met


<210> SEQ ID NO 82
<211> LENGTH: 1269
<212> TYPE: DNA
<213> ORGANISM: Synechocystis PCC6803

<400> SEQUENCE: 82

atggtattac accaacaacg tttctccctc gaccatggag ctttttgtca aaccttagcc      60

caaactgaaa atttactcat tgtccaagac ttggatgggg tctgcatgga attagtgcaa     120

gatcccctca gtcgccgcct ggatgccgat tatgtccggg ccaccaccct gtttgctgaa     180

catttttacg tgttgaccaa tggggagcac gtgggaaaaa gaggagtaca gggcattgtg     240

gaacaatcct ttggggatgc ttcctttgtg caacaggaag gcctatattt gcccggtttg     300

gcggccgggg gagtgcagtg gcaggatcgc catggcaaag taagtcatcc tggagtgggg     360

caaacggagc tggagttttt agcggcggtg cccgaaaaaa tcactaattg tttaaaaacc     420

ttttttggcg atcgccccca ttccctatcc ccagagcaat tacaaacggg cattgaagct     480

tcggttttag ataatgtggc ttcccccacc gccaatttaa ataccttggc caatctgtta     540

caagactttc cgcaaattta ccgagatttg caggaaacca tggctcaatt attggatcag     600

ttgatggcgg aagccgttgc ccagggtttg gggaatagtt tttttgtcca ctatgctccc     660

aatttaggta gggatgaacg aggtaaggaa attattcgtt gggccaaagc tggggattcc     720
```

-continued

```
ggcaccaccg attttcaatt tatgttgcgg ggtggggtca aagaagccgg ggttttggct    780

ttgctaaatc gttactatca caatcggaca gggcaatatc ctctgggaga aagttttagt    840

gctcgccaag cgcccccatc ccaccaggac ttgttgcatt tggtgaaagc gcaatttgat    900

ccggccttga tgccgctgat cattggagtt ggggatacgg tcaccagtca ggtggatgaa    960

gctaccgggg aaattcgacg tggcgggagc gatcgccaat tttgcaatt aatccaagat   1020

ttgggggatt ggggaaatca cggtaactta gtggtgtatg tggacagttc ccagggggag   1080

gtgaaaaatc gccaacctct acaactagaa accgtggcgg ggcaaaccca agtggtggct   1140

ggccctgggg atatgcggga cagggaagag ccattgaaga tcaatgtggc ttttcctggt   1200

ggccatgacc aatatgtagc ggcgtttaag caggcggccc agcgccgaag agtccatttt   1260

tcccagtag                                                           1269
```

<210> SEQ ID NO 83
<211> LENGTH: 422
<212> TYPE: PRT
<213> ORGANISM: Synechocystis PCC6803

<400> SEQUENCE: 83

```
Met Val Leu His Gln Gln Arg Phe Ser Leu Asp His Gly Ala Phe Cys
1               5                   10                  15

Gln Thr Leu Ala Gln Thr Glu Asn Leu Leu Ile Val Gln Asp Leu Asp
            20                  25                  30

Gly Val Cys Met Glu Leu Val Gln Asp Pro Leu Ser Arg Arg Leu Asp
        35                  40                  45

Ala Asp Tyr Val Arg Ala Thr Thr Leu Phe Ala Glu His Phe Tyr Val
    50                  55                  60

Leu Thr Asn Gly Glu His Val Gly Lys Arg Gly Val Gln Gly Ile Val
65                  70                  75                  80

Glu Gln Ser Phe Gly Asp Ala Ser Phe Val Gln Gln Glu Gly Leu Tyr
                85                  90                  95

Leu Pro Gly Leu Ala Ala Gly Gly Val Gln Trp Gln Asp Arg His Gly
            100                 105                 110

Lys Val Ser His Pro Gly Val Gly Gln Thr Glu Leu Glu Phe Leu Ala
        115                 120                 125

Ala Val Pro Glu Lys Ile Thr Asn Cys Leu Lys Thr Phe Phe Gly Asp
    130                 135                 140

Arg Pro His Ser Leu Ser Pro Glu Gln Leu Gln Thr Gly Ile Glu Ala
145                 150                 155                 160

Ser Val Leu Asp Asn Val Ala Ser Pro Thr Ala Asn Leu Asn Thr Leu
                165                 170                 175

Ala Asn Leu Leu Gln Asp Phe Pro Gln Ile Tyr Arg Asp Leu Gln Glu
            180                 185                 190

Thr Met Ala Gln Leu Leu Asp Gln Leu Met Ala Glu Ala Val Ala Gln
        195                 200                 205

Gly Leu Gly Asn Ser Phe Phe Val His Tyr Ala Pro Asn Leu Gly Arg
    210                 215                 220

Asp Glu Arg Gly Lys Glu Ile Ile Arg Trp Ala Lys Ala Gly Asp Ser
225                 230                 235                 240

Gly Thr Thr Asp Phe Gln Phe Met Leu Arg Gly Gly Val Lys Glu Ala
                245                 250                 255

Gly Val Leu Ala Leu Leu Asn Arg Tyr Tyr His Asn Arg Thr Gly Gln
            260                 265                 270
```

Tyr Pro Leu Gly Glu Ser Phe Ser Ala Arg Gln Ala Pro Pro Ser His
275 280 285

Gln Asp Leu Leu His Leu Val Lys Ala Gln Phe Asp Pro Ala Leu Met
290 295 300

Pro Leu Ile Ile Gly Val Gly Asp Thr Val Thr Ser Gln Val Asp Glu
305 310 315 320

Ala Thr Gly Glu Ile Arg Arg Gly Gly Ser Asp Arg Gln Phe Leu Gln
325 330 335

Leu Ile Gln Asp Leu Gly Asp Trp Gly Asn His Gly Asn Leu Val Val
340 345 350

Tyr Val Asp Ser Ser Gln Gly Glu Val Lys Asn Arg Gln Pro Leu Gln
355 360 365

Leu Glu Thr Val Ala Gly Gln Thr Gln Val Val Ala Gly Pro Gly Asp
370 375 380

Met Arg Asp Arg Glu Glu Pro Leu Lys Ile Asn Val Ala Phe Pro Gly
385 390 395 400

Gly His Asp Gln Tyr Val Ala Ala Phe Lys Gln Ala Ala Gln Arg Arg
405 410 415

Arg Val His Phe Ser Gln
420

<210> SEQ ID NO 84
<211> LENGTH: 1365
<212> TYPE: DNA
<213> ORGANISM: Agrobacterium tumefaciens

<400> SEQUENCE: 84
ttggaaaaat ttaccaagat gggacccatg acaaccacga gcgaaactga acgctatccg 60
cggatagctc tcatatcgac gcatggctat gtcgccgcac acccgcccct gggcgctgcc 120
gataccgggg ggcaggtggt ttatgtgctt gagcttgcac gaaaactcgg ccaactcggt 180
tataccgtcg atctttacac ccgacgcttc gaagaccagc cggaattcga cgaggtcgat 240
gagcgcgtcc gtgtggtgcg cattccctgc ggcgggcgcg atttcattcc caaggaatat 300
ctgcaccggc acctgatgga atggtgcgag aacgcgctac gcttcatcaa aaaaaacgac 360
ctcaattact ccttcatcaa cagccactac tgggatgccg gcgtggccgg gcagcggctc 420
tccgaagcac tgaaaatccc ccatctgcac acgccgcact cgctcggcat ctggaagaag 480
cgccagatgg agaccgatta tccggaaaag gccgatacgt tcgagcttga gttcaacttc 540
aaggagcgca tccagcacga gctgatcatc tatcgcagct gcgacatggt gatcgccacc 600
acgccggtgc agctggacgt gctgatcgaa gattatggcc tgaagcgcaa acatatccac 660
atgatcccgc cgggttatga cgacaaccgc ttcttccccg tctcggatgc gacgcgtcag 720
atgatccggc agcgtttcgg ttttgaaggc aaagtggtgc tggcactcgg tcggctcgcc 780
accaacaagg gctacgacct gctgatcgac ggcttttccg tgcttgccga gcgcgagccg 840
gaagcccgcc tgcatctggc cgtcggcggc gagaatatgg acgagcagga aaccaccatt 900
ctcaaccagc tgaaggagcg ggtgaaatcg ctcgggctgg aagacaaggt ggctttctct 960
ggttatgtcg cggacgagga tttgccggat atctatcggg ctgccgatct cttcgtgctt 1020
tccagccgct acgagccctt cggcatgacc gccatcgagg ccatggcgag cggcacgccg 1080
accgtcgtca ccatccatgg cgggctgttc cgcgccatca gctatgggcg acatgcgctg 1140
tttgccgatc ctttcgacaa ggaagatctc ggcattacca tgatgaagcc gttcaagcat 1200
gaacggctct acgggcggct ttcgcgcatg ggagcccaca aggcacgcag cctgttcaca 1260
tggaccggaa ttgcccagca acttctcgcg ctcgtggaag gcaggaccat gatgccggtt 1320
ctggaagaag ccgactgggc cgaaccatgg aatgacggcg attga 1365

<210> SEQ ID NO 85
<211> LENGTH: 454
<212> TYPE: PRT
<213> ORGANISM: Agrobacterium tumefaciens

<400> SEQUENCE: 85

Met Glu Lys Phe Thr Lys Met Gly Pro Met Thr Thr Thr Ser Glu Thr
1 5 10 15

Glu Arg Tyr Pro Arg Ile Ala Leu Ile Ser Thr His Gly Tyr Val Ala
20 25 30

Ala His Pro Pro Leu Gly Ala Ala Asp Thr Gly Gly Gln Val Val Tyr
35 40 45

Val Leu Glu Leu Ala Arg Lys Leu Gly Gln Leu Gly Tyr Thr Val Asp
50 55 60

Leu Tyr Thr Arg Arg Phe Glu Asp Gln Pro Glu Phe Asp Glu Val Asp
65 70 75 80

Glu Arg Val Arg Val Val Arg Ile Pro Cys Gly Gly Arg Asp Phe Ile
85 90 95

Pro Lys Glu Tyr Leu His Arg His Leu Met Glu Trp Cys Glu Asn Ala
100 105 110

Leu Arg Phe Ile Lys Lys Asn Asp Leu Asn Tyr Ser Phe Ile Asn Ser
115 120 125

His Tyr Trp Asp Ala Gly Val Ala Gly Gln Arg Leu Ser Glu Ala Leu
130 135 140

Lys Ile Pro His Leu His Thr Pro His Ser Leu Gly Ile Trp Lys Lys
145 150 155 160

Arg Gln Met Glu Thr Asp Tyr Pro Glu Lys Ala Asp Thr Phe Glu Leu
165 170 175

Glu Phe Asn Phe Lys Glu Arg Ile Gln His Glu Leu Ile Ile Tyr Arg
180 185 190

Ser Cys Asp Met Val Ile Ala Thr Thr Pro Val Gln Leu Asp Val Leu
195 200 205

Ile Glu Asp Tyr Gly Leu Lys Arg Lys His Ile His Met Ile Pro Pro
210 215 220

Gly Tyr Asp Asp Asn Arg Phe Phe Pro Val Ser Asp Ala Thr Arg Gln
225 230 235 240

Met Ile Arg Gln Arg Phe Gly Phe Glu Gly Lys Val Val Leu Ala Leu
245 250 255

Gly Arg Leu Ala Thr Asn Lys Gly Tyr Asp Leu Leu Ile Asp Gly Phe
260 265 270

Ser Val Leu Ala Glu Arg Glu Pro Glu Ala Arg Leu His Leu Ala Val
275 280 285

Gly Gly Glu Asn Met Asp Glu Gln Glu Thr Thr Ile Leu Asn Gln Leu
290 295 300

Lys Glu Arg Val Lys Ser Leu Gly Leu Glu Asp Lys Val Ala Phe Ser
305 310 315 320

Gly Tyr Val Ala Asp Glu Asp Leu Pro Asp Ile Tyr Arg Ala Ala Asp
325 330 335

Leu Phe Val Leu Ser Ser Arg Tyr Glu Pro Phe Gly Met Thr Ala Ile
340 345 350

```
Glu Ala Met Ala Ser Gly Thr Pro Thr Val Val Thr Ile His Gly Gly
        355                 360                 365

Leu Phe Arg Ala Ile Ser Tyr Gly Arg His Ala Leu Phe Ala Asp Pro
    370                 375                 380

Phe Asp Lys Glu Asp Leu Gly Ile Thr Met Met Lys Pro Phe Lys His
385                 390                 395                 400

Glu Arg Leu Tyr Gly Arg Leu Ser Arg Met Gly Ala His Lys Ala Arg
                405                 410                 415

Ser Leu Phe Thr Trp Thr Gly Ile Ala Gln Gln Leu Leu Ala Leu Val
            420                 425                 430

Glu Gly Arg Thr Met Met Pro Val Leu Glu Glu Ala Asp Trp Ala Glu
        435                 440                 445

Pro Trp Asn Asp Gly Asp
    450


<210> SEQ ID NO 86
<211> LENGTH: 747
<212> TYPE: DNA
<213> ORGANISM: Agrobacterium tumefaciens

<400> SEQUENCE: 86

ttgaaaccgc ttcgtcttct ttccaccgat cttgacggaa ccgtcgtcgg cgataatgac      60

gccacgcggc ggttccgcga tttctggcac gcactgccgg atgatcttcg cccggttctg     120

gtcttcaaca gcggccggtt gatcgacgat cagcttgccc ttttggaaga ggtgccgctg     180

ccgcagccgg actacatcat cggcggtgtc ggcaccatgc tgcatgcaaa aaaacgcagc     240

gaactggaaa ccgcctatac acagtcgctc ggcaccggtt ttgacccgcg gaagattgcc     300

gatgtcatga accgcattgc gggcgtgacg atgcaggagg agcgttatca gcacggcctg     360

aaatcgagct ggttcctgca tgacgccgat gccgccgcgc tcggcgagat cgaggccgcg     420

cttctggccg ccgatattga cgctcgtatc gtttattcca gcgatcgcga cctcgacata     480

ttgccgaagg ccgccgacaa aggcgcggca cttgcatggt tgtgtggaca attgcgcatc     540

ggcctcgacg aatcagtggt ctcgggtgat actggcaatg accgtgcgat gtttgagttg     600

aagactatcc gcggcgtgat cgtgggcaat gccctgcctg agcttgtctc gctggcgcat     660

caggacaatc gctttttttca ctcgaccgcg aaagaagcgg atggcgtgat cgaaggcctg     720

cggcactggg gactgaaccc ccgctaa                                         747


<210> SEQ ID NO 87
<211> LENGTH: 248
<212> TYPE: PRT
<213> ORGANISM: Agrobacterium tumefaciens

<400> SEQUENCE: 87

Met Lys Pro Leu Arg Leu Leu Ser Thr Asp Leu Asp Gly Thr Val Val
1               5                   10                  15

Gly Asp Asn Asp Ala Thr Arg Arg Phe Arg Asp Phe Trp His Ala Leu
            20                  25                  30

Pro Asp Asp Leu Arg Pro Val Leu Val Phe Asn Ser Gly Arg Leu Ile
        35                  40                  45

Asp Asp Gln Leu Ala Leu Leu Glu Glu Val Pro Leu Pro Gln Pro Asp
    50                  55                  60

Tyr Ile Ile Gly Gly Val Gly Thr Met Leu His Ala Lys Lys Arg Ser
65                  70                  75                  80
```

```
Glu Leu Glu Thr Ala Tyr Thr Gln Ser Leu Gly Thr Gly Phe Asp Pro
                85                  90                  95

Arg Lys Ile Ala Asp Val Met Asn Arg Ile Ala Gly Val Thr Met Gln
            100                 105                 110

Glu Glu Arg Tyr Gln His Gly Leu Lys Ser Ser Trp Phe Leu His Asp
        115                 120                 125

Ala Asp Ala Ala Ala Leu Gly Glu Ile Glu Ala Ala Leu Leu Ala Ala
    130                 135                 140

Asp Ile Asp Ala Arg Ile Val Tyr Ser Ser Asp Arg Asp Leu Asp Ile
145                 150                 155                 160

Leu Pro Lys Ala Ala Asp Lys Gly Ala Ala Leu Ala Trp Leu Cys Gly
                165                 170                 175

Gln Leu Arg Ile Gly Leu Asp Glu Ser Val Val Ser Gly Asp Thr Gly
            180                 185                 190

Asn Asp Arg Ala Met Phe Glu Leu Lys Thr Ile Arg Gly Val Ile Val
        195                 200                 205

Gly Asn Ala Leu Pro Glu Leu Val Ser Leu Ala His Gln Asp Asn Arg
    210                 215                 220

Phe Phe His Ser Thr Ala Lys Glu Ala Asp Gly Val Ile Glu Gly Leu
225                 230                 235                 240

Arg His Trp Gly Leu Asn Pro Arg
                245
```

<210> SEQ ID NO 88
<211> LENGTH: 35
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: BamHI restriction site

<400> SEQUENCE: 88
tctcagggat cccataccat gattaaaaaa agtac 35

<210> SEQ ID NO 89
<211> LENGTH: 26
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: SacI restriction site

<400> SEQUENCE: 89
ggccgtgagc tcagaaccag gtttcc 26

<210> SEQ ID NO 90
<211> LENGTH: 1546
<212> TYPE: DNA
<213> ORGANISM: Artificial Sequence
<220> FEATURE:
<223> OTHER INFORMATION: PCR product
<220> FEATURE:
<221> NAME/KEY: misc_feature
<222> LOCATION: (7)..(12)
<223> OTHER INFORMATION: BamHI restriction site
<220> FEATURE:
<221> NAME/KEY: misc_feature
<222> LOCATION: (1535)..(1540)

-continued

<223> OTHER INFORMATION: SacI restriction site

<400> SEQUENCE: 90

```
tctcagggat cccataccat gattaaaaaa agtacgcttg cccttaccct tggcttaatg     60
gccggtactc ccgccgcctt tgccgacagc aatatgtcca gcattgaggc gcgtctcgcc    120
gcgctggaac aacgtcttca ggcggctgaa cagcgcgcca gcgcggcgga aacccgcgct    180
gaagccgcag agcgtcaggc acaggcgctt gccgcgcaac aaaaagcgca gccgccggtt    240
cagcctgtcg ccgcgcaacc tgcgccgcag cccgccacgc aaacggcgga taacagcggg    300
tttgaattcc acggctacgc ccgctcgggc ctgctgatga acgattccgc cgcgaaaacg    360
cagggcggcc cgtccttcac gccagcgggt gaaaccggcg gtcacgtcgg gcgtctcggc    420
aatgagccgg acacttacct tgaaatgaac ctagagcaca aacagacgct cgcgaacggc    480
gccaccacgc gctttaaagt gatggtcgct gacggtcagc gcagctataa cgactggacg    540
gcctccacca gcgatctcaa cgtgcgccag gcgtttaccg aactcggcca cctgccgacc    600
ttcatcggcg cgtttaaaga tgccaccgtc tgggccggta aacgcttcga tcgtgataac    660
ttcgatatcc actggattga ctccgacgtg gtgttcctcg ccggtacggg tgcgggtatc    720
tacgacatgc gctggagcga taacgcccgc agtaacttct cgctgtatgg ccgcaccttc    780
ggcgatatcg aaaacagcga aaacaccgcc cagaactata tccttacgct taataactac    840
gtcgggccgg tacagctgat ggtgagcggg atgcgcgcca aagataacga agaccgcgtg    900
gatatcgagg gtaaccgcgt gaaaaaagac gcggcggaag atggcgtgca tgcgctgctc    960
ggcctgcata acgacagctt ctacggtctg agcgacggct cctcgaaaac cgcactgctg   1020
tatggacatg gcctgggcgc ggaagtgaaa tccatcggct ccgatggcgc gctgctgccg   1080
caggccgata cctggcgtct cgcgacctac ggcatgacac cgctcggcgg cggctggcat   1140
atcgcaccgg cggtgctggc gcagagcagt aaagatcgct acgtcaaagg cgacagctac   1200
cagtgggcga ccgccaacct gcgcctcatt caggagatta accagaactt tgagctgcag   1260
tatgagggca gctatcagta catggatctg cgcccgaaag gttacaacga ccgcaacgcg   1320
gtcagcggca acttctataa gctgaccttt gcgccgacgc tgaaagcggg cgacgtgggc   1380
gaattcctca agcgtcctga actgcgcctg ttcgccacct ggatggactg ggatcatcgc   1440
ctggataact acgccagcaa tgatgccttt ggcagcaccg gctttaccgc cggcggtgaa   1500
tggaacttcg gcgtacagat ggaaacctgg ttctgagctc acggcc                  1546
```

<210> SEQ ID NO 91
<211> LENGTH: 13332
<212> TYPE: DNA
<213> ORGANISM: Artificial Sequence
<220> FEATURE:
<223> OTHER INFORMATION: artifical plasmid pLybAL32 containing scrY

<400> SEQUENCE: 91

```
aggcccagtc tttcgactga gcctttcgtt ttatttgatg cctggcagtt ccctactctc     60
gcatggggag accccacact accatcggcg ctacggcgtt tcacttctga gttcggcatg    120
gggtcaggtg ggaccaccgc gctactgccg ccaggcaaat tctgttttat cagaccgctt    180
ctgcgttctg atttaatctg tatcaggctg aaaatcttct ctcatccgcc aaaacagcca    240
agcttgcatg cctgcaggtc gactctagat ggctacgagg gcagacagta agtggattta    300
ccataatccc ttaattgtac gcaccgctaa aacgcgttca gcgcgatcac ggcagcagac    360
aggtaaaaat ggcaacaaac caccctaaaa actgcgcgat cgcgcctgat aaattttaac    420
```

cgtatgaata cctatgcaac cagagggtac aggccacatt acccccactt aatccactga 480
agctgccatt tttcatggtt tcaccatccc agcgaagggc catgcatgca tcgaaattaa 540
tacgacgaaa ttaatacgac tcactatagg gcaattgtta tcagctatgc gccgaccaga 600
acaccttgcc gatcagccaa acgtctcttc aggccactga ctagcgataa ctttccccac 660
aacggaacaa ctctcactgc atgggatcat tgggtactgt gggtttagtg gttgtaaaaa 720
cacctgaccg ctatccctga tcagtttctt gaaggtaaac tcatcacccc caagtctggc 780
tatgcagaaa tcacctggct caacagcctg ctcagggtca acgagaatta acattccgtc 840
aggaaagctt ggcttggagc ctgttggtgc ggtcatggaa ttaccttcaa cctcaagcca 900
gaatgcagaa tcactggctt tcttggttgt gcttacccat ctctccgcat cacctttggt 960
aaaggttcta agcttaggtg agaacatccc tgcctgaaca tgagaaaaaa cagggtactc 1020
atactcactt ctaagtgacg gctgcatact aaccgcttca tacatctcgt agatttctct 1080
ggcgattgaa gggctaaatt cttcaacgct aactttgaga atttttgtaa gcaatgcggc 1140
gttataagca tttaatgcat tgatgccatt aaataaagca ccaacgcctg actgccccat 1200
ccccatcttg tctgcgacag attcctggga taagccaagt tcatttttct tttttcata 1260
aattgcttta aggcgacgtg cgtcctcaag ctgctcttgt gttaatggtt tctttttgt 1320
gctcatacgt taaatctatc accgcaaggg ataaatatct aacaccgtgc gtgttgacta 1380
ttttacctct ggcggtgata atggttgcat cttaagaagg aggatcccat accatgatta 1440
aaaaaagtac gcttgccctt acccttggct taatggccgg tactcccgcc gcctttgccg 1500
acagcaatat gtccagcatt gaggcgcgtc tcgccgcgct ggaacaacgt cttcaggcgg 1560
ctgaacagcg cgccagcgcg gcggaaaccc gcgctgaagc cgcagagcgt caggcacagg 1620
cgcttgccgc gcaacaaaaa gcgcagccgc cggttcagcc tgtcgccgcg caacctgcgc 1680
cgcagcccgc cacgcaaacg gcggataaca gcgggtttga attccacggc tacgcccgct 1740
cgggcctgct gatgaacgat tccgccgcga aaacgcaggg cggcccgtcc ttcacgccag 1800
cgggtgaaac cggcggtcac gtcgggcgtc tcggcaatga gccggacact taccttgaaa 1860
tgaacctaga gcacaaacag acgctcgcga acggcgccac cacgcgcttt aaagtgatgg 1920
tcgctgacgg tcagcgcagc tataacgact ggacggcctc caccagcgat ctcaacgtgc 1980
gccaggcgtt taccgaactc ggccacctgc cgaccttcat cggcgcgttt aaagatgcca 2040
ccgtctgggc cggtaaacgc ttcgatcgtg ataacttcga tatccactgg attgactccg 2100
acgtggtgtt cctcgccggt acgggtgcgg gtatctacga catgcgctgg agcgataacg 2160
cccgcagtaa cttctcgctg tatggccgca ccttcggcga tatcgaaaac agcgaaaaca 2220
ccgcccagaa ctatatcctt acgcttaata actacgtcgg gccggtacag ctgatggtga 2280
gcgggatgcg cgccaaagat aacgaagacc gcgtggatat cgagggtaac cgcgtgaaaa 2340
aagacgcggc ggaagatggc gtgcatgcgc tgctcggcct gcataacgac agcttctacg 2400
gtctgagcga cggctcctcg aaaaccgcac tgctgtatgg acatggcctg ggcgcggaag 2460
tgaaatccat cggctccgat ggcgcgctgc tgccgcaggc cgatacctgg cgtctcgcga 2520
cctacggcat gacaccgctc ggcggcggct ggcatatcgc accggcggtg ctggcgcaga 2580
gcagtaaaga tcgctacgtc aaaggcgaca gctaccagtg ggcgaccgcc aacctgcgcc 2640
tcattcagga gattaaccag aactttgagc tgcagtatga gggcagctat cagtacatgg 2700
atctgcgccc gaaaggttac aacgaccgca acgcggtcag cggcaacttc tataagctga 2760

-continued

```
cctttgcgcc gacgctgaaa gcgggcgacg tgggcgaatt cctcaagcgt cctgaactgc   2820
gcctgttcgc cacctggatg gactgggatc atcgcctgga taactacgcc agcaatgatg   2880
cctttggcag caccggcttt accgccggcg gtgaatggaa cttcggcgta cagatggaaa   2940
cctggttctg agctcgaatt ggggcgtttt ctgtgaggct gactagcgcg tggcagctca   3000
aaatctctac attctgcaca ttcagaccca tggtctgctg cgagggcaga acttggaact   3060
ggggcgagat gccgacaccg gcgggcagac caagtacgtc ttagaactgg ctcaagccca   3120
agctaaatcc ccacaagtcc aacaagtcga catcatcacc cgccaaatca ccgacccccg   3180
cgtcagtgtt ggttacagtc aggcgatcga accctttgcg cccaaaggtc ggattgtccg   3240
tttgcctttt ggccccaaac gctacctccg taaagagctg ctttggcccc atctctacac   3300
ctttgcggat gcaattctcc aatatctggc tcagcaaaag cgcaccccga cttggattca   3360
ggcccactat gctgatgctg gccaagtggg atcactgctg agtcgctggt tgaatgtacc   3420
gctaattttc acagggcatt ctctggggcg gatcaagcta aaaaagctgt tggagcaaga   3480
ctggccgctt gaggaaattg aagcgcaatt caatattcaa cagcgaattg atgcggagga   3540
gatgacgctc actcatgctg actggattgt cgccagcact cagcaggaag tggaggagca   3600
ataccgcgtt tacgatcgct acaacccaga gcgcaagctt gtcattccac cgggtgtcga   3660
taccgatcgc ttcaggtttc agcccttggg cgatcgcggt gttgttctcc aacaggaact   3720
gagccgcttt ctgcgcgacc cagaaaaacc tcaaattctc tgcctctgtc gccccgcacc   3780
tcgcaaaaat gtaccggcgc tggtgcgagc ctttggcgaa catccttggc tgcgcaaaaa   3840
agccaacctt gtcttagtac tgggcagccg ccaagacatc aaccagatgg atcgcggcag   3900
tcggcaggtg ttccaagaga ttttccatct ggtcgatcgc tacgacctct acggcagcgt   3960
cgcctatccc aaacagcatc aggctgatga tgtgccggag ttctatcgcc tagcggctca   4020
ttccggcggg gtattcgtca atccggcgct gaccgaacct tttggtttga caattttgga   4080
ggcaggaagc tgcggcgtgc cggtggtggc aacccatgat ggcggccccc aggaaattct   4140
caaacactgt gatttcggca ctttagttga tgtcagccga cccgctaata tcgcgactgc   4200
actcgccacc ctgctgagcg atcgcgatct ttggcagtgc tatcaccgca atggcattga   4260
aaaagttccc gcccattaca gctgggatca acatgtcaat accctgtttg agcgcatgga   4320
aacggtggct ttgcctcgtc gtcgtgctgt cagtttcgta cggagtcgca aacgcttgat   4380
tgatgccaaa cgccttgtcg ttagtgacat cgacaacaca ctgttgggcg atcgtcaagg   4440
actcgagaat ttaatgacct atctcgatca gtatcgcgat cattttgcct ttggaattgc   4500
cacggggcgt cgcctagact ctgcccaaga agtcttgaaa gagtggggcg ttccttcgcc   4560
aaacttctgg gtgacttccg tcggcagcga gattcactat ggcaccgatg ctgaaccgga   4620
tatcagctgg gaaaagcata tcaatcgcaa ctggaatcct cagcgaattc gggcagtaat   4680
ggcacaacta ccctttcttg aactgcagcc ggaagaggat caaacaccct tcaaagtcag   4740
cttctttgtc cgcgatcgcc acgagactgt gctgcgagaa gtacggcaac atcttcgccg   4800
ccatcgcctg cggctgaagt caatctattc ccatcaggag tttcttgaca ttctgccgct   4860
agctgcctcg aaaggggatg cgattcgcca cctctcactc cgctggcgga ttcctcttga   4920
gaacattttg gtggcaggcg attctggtaa cgatgaggaa atgctcaagg gccataatct   4980
cggcgttgta gttggcaatt actcaccgga attggagcca ctgcgcagct acgagcgcgt   5040
ctattttgct gagggccact atgctaatgg cattctggaa gccttaaaac actatcgctt   5100
ttttgaggcg atcgcttaac cttttcagaa tgagacgttg atcggcacgt aagcgtgaga   5160
```

-continued cgttgatcgg cacgtaagag gttccaactt tcaccataat gaaataagat cactaccggg 5220
cgtatttttt gagttatcga gattttcagg agctaaggaa gctaaaatgg agaaaaaaat 5280
cactggatat accaccgttg atatatccca atggcatcgt aaagaacatt ttgaggcatt 5340
tcagtcagtt gctcaatgta cctataacca gaccgttcag ctggatatta cggccttttt 5400
aaagaccgta aagaaaaata agcacaagtt ttatccggcc tttattcaca ttcttgcccg 5460
cctgatgaat gctcatccgg aattccgtat ggcaatgaaa gacggtgagc tggtgatatg 5520
ggatagtgtt cacccttgtt acaccgtttt ccatgagcaa actgaaacgt tttcatcgct 5580
ctggagtgaa taccacgacg atttccggca gtttctacac atatattcgc aagatgtggc 5640
gtgttacggt gaaaacctgg cctatttccc taaagggttt attgagaata tgtttttcgt 5700
ctcagccaat ccctgggtga gtttcaccag ttttgattta aacgtggcca atatggacaa 5760
cttcttcgcc cccgttttca ccatgggcaa atattatacg caaggcgaca aggtgctgat 5820
gccgctggcg attcaggttc atcatgccgt ttgtgatggc ttccatgtcg gcagaatgct 5880
taatgaatta caacagtact gcgatgagtg gcagggcggg gcgtaatttt tttaaggcag 5940
ttattggtgc ccttaaacgc ctggttgcta cgcctgaata agtgataata agcggatgaa 6000
tggcagaaat tcgatgataa gctgtcaaac acaaccacca tcaaacagga ttttcgcctg 6060
ctggggcaaa ccagcgtgga ccgcttgctg caactctctc agggccaggc ggtgaagggc 6120
aatcagctgt tgcccgtctc actggtgaaa agaaaaacca ccctggcgcc caatacgcaa 6180
accgcctctc cccgcgcgtt ggccgattca ttaatgcagc tggcacgaca ggtttcccga 6240
ctggaaagcg ggcagtgagc gcaacgcaat taatgtaagt tagcgcgaat tgcaagctgg 6300
ccgacgcgct gggctacgtc ttgctggcgt tcgggagcag aagagcatac atctggaagc 6360
aaagccagga aagcggccta tggagctgtg cggcagcgct cagtaggcaa tttttcaaaa 6420
tattgttaag ccttttctga gcatggtatt tttcatggta ttaccaatta gcaggaaaat 6480
aagccattga atataaaaga taaaaatgtc ttgtttacaa tagagtgggg ggggtcagcc 6540
tgccgccttg ggccgggtga tgtcgtactt gcccgccgcg aactcggtta ccgtccagcc 6600
cagcgcgacc agctccggca acgcctcgcg cacccgcttg cggcgcttgc gcatggtcga 6660
accactggcc tctgacggcc agacatagcc gcacaaggta tctatggaag ccttgccggt 6720
tttgccgggg tcgatccagc cacacagccg ctggtgcagc aggcgggcgg tttcgctgtc 6780
cagcgcccgc acctcgtcca tgctgatgcg cacatgctgg ccgccaccca tgacggcctg 6840
cgcgatcaag ggttcagggg ccacgtacag gcgcccgtcc gcctcgtcgc tggcgtactc 6900
cgacagcagc cgaaacccct gccgcttgcg gccattctgg gcgatgatgg ataccttcca 6960
aaggcgctcg atgcagtcct gtatgtgctt gagcgcccca ccactatcga cctctgcccc 7020
gatttccttt gccagcgccc gatagctacc tttgaccaca tggcattcag cggtgacggc 7080
ctcccacttg ggttccagga acagccggag ctgccgtccg ccttcggtct tgggttccgg 7140
gccaagcact aggccattag gcccagccat ggccaccagc ccttgcagga tgcgcagatc 7200
atcagcgccc agcggctccg ggccgctgaa ctcgatccgc ttgccgtcgc cgtagtcata 7260
cgtcacgtcc agcttgctgc gcttgcgctc gccccgcttg agggcacgga acaggccggg 7320
ggccagacag tgcgccgggt cgtgccggac gtggctgagg ctgtgcttgt tcttaggctt 7380
caccacgggg cacccccttg ctcttgcgct gcctctccag cacggcgggc ttgagcaccc 7440
cgccgtcatg ccgcctgaac caccgatcag cgaacggtgc gccatagttg gccttgctca 7500

-continued

```
caccgaagcg gacgaagaac cggcgctggt cgtcgtccac accccattcc tcggcctcgg   7560
cgctggtcat gctcgacagg taggactgcc agcggatgtt atcgaccagt accgagctgc   7620
cccggctggc ctgctgctgg tcgcctgcgc ccatcatggc cgcgcccttg ctggcatggt   7680
gcaggaacac gatagagcac ccggtatcgg cggcgatggc ctccatgcga ccgatgacct   7740
gggccatggg gccgctggcg ttttcttcct cgatgtggaa ccggcgcagc gtgtccagca   7800
ccatcaggcg gcggccctcg gcggcgcgct tgaggccgtc gaaccactcc ggggccatga   7860
tgttgggcag gctgccgatc agcggctgga tcagcaggcc gtcagccacg gcttgccgtt   7920
cctcggcgct gaggtgcgcc ccaagggcgt gcaggcggtg atgaatggcg gtgggcgggt   7980
cttcggcggg caggtagatc accgggccgg tgggcagttc gcccacctcc agcagatccg   8040
gcccgcctgc aatctgtgcg gccagttgca gggccagcat ggatttaccg gcaccaccgg   8100
gcgacaccag cgccccgacc gtaccggcca ccatgttggg caaaacgtag tccagcggtg   8160
gcggcgctgc tgcgaacgcc tccagaatat tgataggctt atgggtagcc attgattgcc   8220
tcctttgcag gcagttggtg gttaggcgct ggcggggtca ctacccccgc cctgcgccgc   8280
tctgagttct tccaggcact cgcgcagcgc ctcgtattcg tcgtcggtca gccagaactt   8340
gcgctgacgc atccctttgg ccttcatgcg ctcggcatat cgcgcttggc gtacagcgtc   8400
agggctggcc agcaggtcgc cggtctgctt gtccttttgg tctttcatat cagtcaccga   8460
gaaacttgcc ggggccgaaa ggcttgtctt cgcggaacaa ggacaaggtg cagccgtcaa   8520
ggttaaggct ggccatatca gcgactgaaa agcggccagc ctcggccttg tttgacgtat   8580
aaccaaagcc accgggcaac caatagccct tgtcactttt gatcaggtag accgaccctg   8640
aagcgctttt ttcgtattcc ataaaacccc cttctgtgcg tgagtactca tagtataaca   8700
ggcgtgagta ccaacgcaag cactacatgc tgaaatctgg cccgcccctg tccatgcctc   8760
gctggcgggg tgccggtgcc cgtgccagct cggcccgcgc aagctggacg ctgggcagac   8820
ccatgacctt gctgacggtg cgctcgatgt aatccgcttc gtggccgggc ttgcgctctg   8880
ccagcgctgg gctggcctcg gccatggcct tgccgatttc ctcggcactg cggccccggc   8940
tggccagctt ctgcgcggcg ataaagtcgc acttgctgag gtcatgaccg aagcgcttga   9000
ccagcccggc catctcgctg cggtactcgt ccagcgccgt gcgccggtgg cggctaagct   9060
gccgctcggg cagttcgagg ctggccagcc tgcgggcctt ctcctgctgc cgctgggcct   9120
gctcgatctg ctggccagcc tgctgcacca gcgccgggcc agcggtggcg gtcttgccct   9180
tggattcacg cagcagcacc cacggctgat aaccggcgcg ggtggtgtgc ttgtccttgc   9240
ggttggtgaa gcccgccaag cggccatagt ggcggctgtc ggcgctggcc gggtcggcgt   9300
cgtactcgct ggccagcgtc cgggcaatct gcccccgaag ttcaccgcct gcggcgtcgg   9360
ccaccttgac ccatgcctga tagttcttcg ggctggtttc cactaccagg gcaggctccc   9420
ggccctcggc tttcatgtca tccaggtcaa actcgctgag gtcgtccacc agcaccagac   9480
catgccgctc ctgctcggcg ggcctgatat acacgtcatt gccctgggca ttcatccgct   9540
tgagccatgg cgtgttctgg agcacttcgg cggctgacca ttcccggttc atcatctggc   9600
cggtgggtgc gtccctgacg ccgatatcga agcgctcaca gcccatggcc ttgagctgtc   9660
ggcctatggc ctgcaaagtc ctgtcgttct tcatcgggcc accaagcgca gccagatcga   9720
gccgtcctcg gttgtcagtg gcgtcaggtc gagcaagagc aacgatgcga tcagcagcac   9780
caccgtaggc atcatggaag ccagcatcac ggttagccat agcttccagt gccacccccg   9840
cgacgcgctc cgggcgctct gcgcggcgct gctcacctcg gcggctacct cccgcaactc   9900
```

```
tttggccagc tccacccatg ccgcccctgt ctggcgctgg gctttcagcc actccgccgc   9960
ctgcgcctcg ctggcctgct tggtctggct catgacctgc cgggcttcgt cggccagtgt  10020
cgccatgctc tgggccagcg gttcgatctg ctccgctaac tcgttgatgc ctctggattt  10080
cttcactctg tcgattgcgt tcatggtcta ttgcctcccg gtattcctgt aagtcgatga  10140
tctgggcgtt ggcggtgtcg atgttcaggg ccacgtctgc ccggtcggtg cggatgcccc  10200
ggccttccat ctccaccacg ttcggcccca ggtgaacacc gggcaggcgc tcgatgccct  10260
gcgcctcaag tgttctgtgg tcaatgcggg cgtcgtggcc agcccgctct aatgcccggt  10320
tggcatggtc ggcccatgcc tcgcgggtct gctcaagcca tgccttgggc ttgagcgctt  10380
cggtcttctg tgccccgccc ttctccgggg tcttgccgtt gtaccgcttg aaccactgag  10440
cggcgggccg ctcgatgccg tcattgatcc gctcggagat catcaggtgg cagtgcgggt  10500
tctcgccgcc accggcatgg atggccagcg tatacggcag gcgctcggca ccggtcaggt  10560
gctgggcgaa ctcggacgcc agcgccttct gctggtcgag ggtcagctcg accggcaggg  10620
caaattcgac ctccttgaac agccgcccat tggcgcgttc atacaggtcg gcagcatccc  10680
agtagtcggc gggccgctcg acgaactccg gcatgtgccc ggattcggcg tgcaagactt  10740
catccatgtc gcgggcatac ttgccttcgc gctggatgta gtcggccttg gccctggccg  10800
attggccgcc cgacctgctg ccggttttcg ccgtaaggtg ataaatcgcc atgctgcctc  10860
gctgttgctt ttgcttttcg gctccatgca atggccctcg gagagcgcac cgcccgaagg  10920
gtggccgtta ggccagtttc tcgaagagaa accggtaagt gcgccctccc ctacaaagta  10980
gggtcgggat tgccgccgct gtgcctccat gatagcctac gagacagcac attaacaatg  11040
gggtgtcaag atggttaagg ggagcaacaa ggcggcggat cggctggcca agctcgaaga  11100
acaacgagcg cgaatcaatg ccgaaattca gcgggagcgg gcaagggaac agcagcaaga  11160
gcgcaagaac gaaacaaggc gcaaggtgct ggtgggggcc atgattttgg ccaaggtgaa  11220
cagcagcgag tggccggagg atcggctcat ggcggcaatg gatgcgtacc ttgaacgcga  11280
ccacgaccgc gccttgttcg gtctgccgcc acgccagaag gatgagccgg gctgaatgat  11340
cgaccgagac aggccctgcg gggctgcaca cgcgccccca cccttcgggt agggggaaag  11400
gccgctaaag cggctaaaag cgctccagcg tatttctgcg gggtttggtg tggggtttag  11460
cgggctttgc ccgcctttcc ccctgccgcg cagcggtggg gcggtgtgta gcctagcgca  11520
gcgaatagac cagctatccg gcctctggcc gggcatattg ggcaagggca gcagcgcccc  11580
acaagggcgc tgataaccgc gcctagtgga ttattcttag ataatcatgg atggattttt  11640
ccaacacccc gccagccccc gcccctgctg ggtttgcagg tttgggggcg tgacagttat  11700
tgcaggggtt cgtgacagtt attgcagggg ggcgtgacag ttattgcagg ggttcgtgac  11760
agttagtacg ggagtgacgg gcactggctg gcaatgtcta gcaacggcag gcatttcggc  11820
tgagggtaaa agaactttcc gctaagcgat agactgtatg taaacacagt attgcaagga  11880
cgcggaacat gcctcatgtg gcggccagga cggccagccg ggatcgggat actggtcgtt  11940
accagagcca ccgacccgag caaacccttc tctatcagat cgttgacgag tattacccgg  12000
cattcgctgc gcttatggca gagcagggaa aggaattgcc gggctatgtg caacgggaat  12060
ttgaagaatt tctccaatgc gggcggctgg agcatggctt tctacgggtt cgctgcgagt  12120
cttgccacgc cgagcacctg gtcgctttca gaaatcaatc taaagtatat atgagtaaac  12180
ttggtctgac agttaccaat gcttaatcag tgaggcacct atctcagcga tctgtctatt  12240
```

```
tcgttcatcc atagttgcct gactccccgt cgtgtagata actacgatac gggagggctt  12300

accatctggc cccagtgctg caatgatacc gcgagaccca cgctcaccgg ctccagattt  12360

atcagcaata aaccagccag ccggaagggc cgagcgcaga agtggtcctg caactttatc  12420

cgcctccatc cagtctatta attgttgccg ggaagctaga gtaagtagtt cgccagttaa  12480

tagtttgcgc aacgttgttg ccattgctac aggcatcgtg gtgtcacgct cgtcgtttgg  12540

tatggcttca ttcagctccg gttcccaacg atcaaggcga gttacatgat cccccatgtt  12600

gtgcaaaaaa gcggttagct ccttcggtcc tccgatcgtt gtcagaagta agttggccgc  12660

agtgttatca ctcatggtta tggcagcact gcataattct cttactgtca tgccatccgt  12720

aagatgcttt tctgtgactg gtgagtactc aaccaagtca ttctgagaat agtgtatgcg  12780

gcgaccgagt tgctcttgcc cggcgtcaac acgggataat accgcgccac atagcagaac  12840

tttaaaagtg ctcatcattg gaaaacgttc ttcggggcga aaactctcaa ggatcttacc  12900

gctgttgaga tccagttcga tgtaacccac tcgtgcaccc aactgatctt cagcatcttt  12960

tactttcacc agcgtttctg ggtgagcaaa aacaggaagg caaaatgccg caaaaaaggg  13020

aataagggcg acacggaaat gttgaatact catactcttc ctttttcaat attattgaag  13080

catttatcag ggttattgtc tcatgagcgg atacatattt gaatgtattt agaaaaataa  13140

acaaaagagt ttgtagaaac gcaaaaaggc catccgtcag gatggccttc tgcttaattt  13200

gatgcctggc agtttatggc gggcgtcctg cccgccaccc tccgggccgt tgcttcgcaa  13260

cgttcaaatc cgctcccggc ggatttgtcc tactcaggag agcgttcacc gacaaacaac  13320

agataaaacg aa                                                      13332


<210> SEQ ID NO 92
<211> LENGTH: 21
<212> TYPE: DNA
<213> ORGANISM: Artificial Sequence
<220> FEATURE:
<223> OTHER INFORMATION: PCR primer

<400> SEQUENCE: 92

gcagtaactt ctcgctgtat g                                               21


<210> SEQ ID NO 93
<211> LENGTH: 23
<212> TYPE: DNA
<213> ORGANISM: Artificial Sequence
<220> FEATURE:
<223> OTHER INFORMATION: PCR primer

<400> SEQUENCE: 93

gtgttttcgc tgttttcgat atc                                             23


<210> SEQ ID NO 94
<211> LENGTH: 1518
<212> TYPE: DNA
<213> ORGANISM: Enterobacter sakazakii

<400> SEQUENCE: 94

atgattaaaa aaagtacgct tgcccttacc cttggcttaa tggccggtac tcccgccgcc     60

tttgccgaca gcaatatgtc cagcattgag gcgcgtctcg ccgcgctgga acaacgtctt    120

caggcggctg aacagcgcgc cagcgcggcg gaaacccgcg ctgaagccgc agagcgtcag    180

gcacaggcgc ttgccgcgca acaaaaagcg cagccgccgg ttcagcctgt cgccgcgcaa    240

cctgcgccgc agcccgccac gcaaacggcg gataacagcg ggtttgaatt ccacggctac    300
```

```
gcccgctcgg gcctgctgat gaacgattcc gccgcgaaaa cgcagggcgg cccgtccttc    360

acgccagcgg gtgaaaccgg cggtcacgtc gggcgtctcg gcaatgagcc ggacacttac    420

cttgaaatga acctagagca caaacagacg ctcgcgaacg gcgccaccac gcgctttaaa    480

gtgatggtcg ctgacggtca gcgcagctat aacgactgga cggcctccac cagcgatctc    540

aacgtgcgcc aggcgtttac cgaactcggc cacctgccga ccttcatcgg cgcgtttaaa    600

gatgccaccg tctgggccgg taaacgcttc gatcgtgata acttcgatat ccactggatt    660

gactccgacg tggtgttcct cgccggtacg ggtgcgggta tctacgacat gcgctggagc    720

gataacgccc gcagtaactt ctcgctgtat ggccgcacct tcggcgatat cgaaaacagc    780

gaaaacaccg cccagaacta tatccttacg cttaataact acgtcgggcc ggtacagctg    840

atggtgagcg ggatgcgcgc caaagataac gaagaccgcg tggatatcga gggtaaccgc    900

gtgaaaaaag acgcggcgga agatggcgtg catgcgctgc tcggcctgca taacgacagc    960

ttctacggtc tgagcgacgg ctcctcgaaa accgcactgc tgtatggaca tggcctgggc   1020

gcggaagtga aatccatcgg ctccgatggc gcgctgctgc cgcaggccga tacctggcgt   1080

ctcgcgacct acggcatgac accgctcggc ggcggctggc atatcgcacc ggcggtgctg   1140

gcgcagagca gtaaagatcg ctacgtcaaa ggcgacagct accagtgggc gaccgccaac   1200

ctgcgcctca ttcaggagat taaccagaac tttgagctgc agtatgaggg cagctatcag   1260

tacatggatc tgcgcccgaa aggttacaac gaccgcaacg cggtcagcgg caacttctat   1320

aagctgacct ttgcgccgac gctgaaagcg ggcgacgtgg gcgaattcct caagcgtcct   1380

gaactgcgcc tgttcgccac ctggatggac tgggatcatc gcctggataa ctacgccagc   1440

aatgatgcct ttggcagcac cggctttacc gccggcggtg aatggaactt cggcgtacag   1500

atggaaacct ggttctga                                                 1518


<210> SEQ ID NO 95
<211> LENGTH: 505
<212> TYPE: PRT
<213> ORGANISM: Enterobacter sakazakii

<400> SEQUENCE: 95

Met Ile Lys Lys Ser Thr Leu Ala Leu Thr Leu Gly Leu Met Ala Gly
1               5                   10                  15

Thr Pro Ala Ala Phe Ala Asp Ser Asn Met Ser Ser Ile Glu Ala Arg
            20                  25                  30

Leu Ala Ala Leu Glu Gln Arg Leu Gln Ala Ala Glu Gln Arg Ala Ser
        35                  40                  45

Ala Ala Glu Thr Arg Ala Glu Ala Ala Glu Arg Gln Ala Gln Ala Leu
    50                  55                  60

Ala Ala Gln Gln Lys Ala Gln Pro Pro Val Gln Pro Val Ala Ala Gln
65                  70                  75                  80

Pro Ala Pro Gln Pro Ala Thr Gln Thr Ala Asp Asn Ser Gly Phe Glu
                85                  90                  95

Phe His Gly Tyr Ala Arg Ser Gly Leu Leu Met Asn Asp Ser Ala Ala
            100                 105                 110

Lys Thr Gln Gly Gly Pro Ser Phe Thr Pro Ala Gly Glu Thr Gly Gly
        115                 120                 125

His Val Gly Arg Leu Gly Asn Glu Pro Asp Thr Tyr Leu Glu Met Asn
    130                 135                 140

Leu Glu His Lys Gln Thr Leu Ala Asn Gly Ala Thr Thr Arg Phe Lys
```

```
145                 150                 155                 160

Val Met Val Ala Asp Gly Gln Arg Ser Tyr Asn Asp Trp Thr Ala Ser
                165                 170                 175

Thr Ser Asp Leu Asn Val Arg Gln Ala Phe Thr Glu Leu Gly His Leu
            180                 185                 190

Pro Thr Phe Ile Gly Ala Phe Lys Asp Ala Thr Val Trp Ala Gly Lys
        195                 200                 205

Arg Phe Asp Arg Asp Asn Phe Asp Ile His Trp Ile Asp Ser Asp Val
    210                 215                 220

Val Phe Leu Ala Gly Thr Gly Ala Gly Ile Tyr Asp Met Arg Trp Ser
225                 230                 235                 240

Asp Asn Ala Arg Ser Asn Phe Ser Leu Tyr Gly Arg Thr Phe Gly Asp
                245                 250                 255

Ile Glu Asn Ser Glu Asn Thr Ala Gln Asn Tyr Ile Leu Thr Leu Asn
            260                 265                 270

Asn Tyr Val Gly Pro Val Gln Leu Met Val Ser Gly Met Arg Ala Lys
        275                 280                 285

Asp Asn Glu Asp Arg Val Asp Ile Glu Gly Asn Arg Val Lys Lys Asp
    290                 295                 300

Ala Ala Glu Asp Gly Val His Ala Leu Leu Gly Leu His Asn Asp Ser
305                 310                 315                 320

Phe Tyr Gly Leu Ser Asp Gly Ser Ser Lys Thr Ala Leu Leu Tyr Gly
                325                 330                 335

His Gly Leu Gly Ala Glu Val Lys Ser Ile Gly Ser Asp Gly Ala Leu
            340                 345                 350

Leu Pro Gln Ala Asp Thr Trp Arg Leu Ala Thr Tyr Gly Met Thr Pro
        355                 360                 365

Leu Gly Gly Gly Trp His Ile Ala Pro Ala Val Leu Ala Gln Ser Ser
    370                 375                 380

Lys Asp Arg Tyr Val Lys Gly Asp Ser Tyr Gln Trp Ala Thr Ala Asn
385                 390                 395                 400

Leu Arg Leu Ile Gln Glu Ile Asn Gln Asn Phe Glu Leu Gln Tyr Glu
                405                 410                 415

Gly Ser Tyr Gln Tyr Met Asp Leu Arg Pro Lys Gly Tyr Asn Asp Arg
            420                 425                 430

Asn Ala Val Ser Gly Asn Phe Tyr Lys Leu Thr Phe Ala Pro Thr Leu
        435                 440                 445

Lys Ala Gly Asp Val Gly Glu Phe Leu Lys Arg Pro Glu Leu Arg Leu
    450                 455                 460

Phe Ala Thr Trp Met Asp Trp Asp His Arg Leu Asp Asn Tyr Ala Ser
465                 470                 475                 480

Asn Asp Ala Phe Gly Ser Thr Gly Phe Thr Ala Gly Gly Glu Trp Asn
                485                 490                 495

Phe Gly Val Gln Met Glu Thr Trp Phe
            500                 505
```

<210> SEQ ID NO 96
<211> LENGTH: 30
<212> TYPE: DNA
<213> ORGANISM: Artificial Sequence
<220> FEATURE:
<223> OTHER INFORMATION: PCR primer

<400> SEQUENCE: 96
ccacaatgga ctgccagccg tcaaaggatg 30

<210> SEQ ID NO 97
<211> LENGTH: 30
<212> TYPE: DNA
<213> ORGANISM: Artificial Sequence
<220> FEATURE:
<223> OTHER INFORMATION: PCR primer

<400> SEQUENCE: 97
gcccaactgg tcacggacat cgtcgataac 30

<210> SEQ ID NO 98
<211> LENGTH: 29
<212> TYPE: DNA
<213> ORGANISM: Artificial Sequence
<220> FEATURE:
<223> OTHER INFORMATION: PCR primer

<400> SEQUENCE: 98
tgcaatggct ccaggaagcc cgatcgatg 29

<210> SEQ ID NO 99
<211> LENGTH: 30
<212> TYPE: DNA
<213> ORGANISM: Artificial Sequence
<220> FEATURE:
<223> OTHER INFORMATION: PCR primer

<400> SEQUENCE: 99
ggcagcatta cggctcagac cttggtcatg 30

<210> SEQ ID NO 100
<211> LENGTH: 1246
<212> TYPE: DNA
<213> ORGANISM: Synechocystis PCC6803

<400> SEQUENCE: 100
ccacaatgga ctgccagccg tcaaaggatg gttgtttgct cataatgctt gcctgtctgt 60
cgttgaactt gggggaaatc cctgcccaaa gtatggcaga aaacctttcc cttcccaatg 120
ccccaacttc cggtaacccg atctgagcta cagtggagtt ccgcggtgaa ttgttaccga 180
cggtgagacc acgtcctaac ttttagccca tttttcggtt ccccaacggc caagattaac 240
aaaattaaat tttagatatt aacttttaag ttttcccatg gcttctcaat tacgtgttta 300
tgtgccggag catcctctaa ttaagcattg gttgggggta gctagggatg aaaacacgcc 360
gccggttttg tttaaaactg ccatggggga attgggacgt tggttgacct atgaggccgc 420
tcgttattgg ttgccgacgg tggatacgga agtgaaaact cccctggcga tcgccaaggc 480
cagtcttatt gacccccaaa cgccctttgt cattgtgccc attttgcggg cggggttggc 540
tctggtggaa ggggcccagg ggttgttgcc cctggcaaaa atttaccatc tgggtttagt 600
gcgcaatgaa actaccctgg aacctagtct gtatctgaac aagttgccgg agcggtttgc 660
ccccggtacc catcttttgt tgctagatcc catgttggct acgggtaata ccatcatggc 720
tgctttggat ttgctgatgg cccgggacat tgatgccaat ttaatccgtt tggtctccgt 780
ggtggccgcc cccactgccc tgcaaaaatt aagtaatgcc catcccaatt tgaccatcta 840
caccgccatg attgacgaac aactcaatga ccggggttac attgtgcccg gcctagggga 900
tgcaggcgat cgttgctttg gtacttgata acaccattaa actagtgatc aaataattac 960
aaattcaccc ccaaacgtta acaacaggag taaagtcatg gctcaaaaag ataacttcgc 1020
cggaggattt ttattaggta cggtcattgg tggcgtagtg gggggaattt tgggttctgt 1080
cctggccaat cgagctgcta cccaaagccc cgaccgggaa aaattagaca ctgagggggt 1140
aggaaatctc gatagtgagg aaaatattga gttggctcgc cgtcgcctgg aagacaaaat 1200
tgcccaactt aatttggtta tcgacgatgt ccgtgaccag ttgggc 1246

<210> SEQ ID NO 101
<211> LENGTH: 1281
<212> TYPE: DNA
<213> ORGANISM: Synechococcus PCC7942

<400> SEQUENCE: 101
tgcaatggct ccaggaagcc cgatcgatgg gatttcaagt cgctttagat gattttggga 60
cgggttattc cagccttggt tacctcaagc gtttgcccat caatgctctc aaaattgatc 120
gcagctttat tcgcgatctg ccgcacgacc atgacgatca agcgatcgtg caggcgattg 180
ttgcaatggc caaggtcttg aaacttcgca cgatcgcaga aggcgtagaa cgcctcgagc 240
aagccgcctt cttagaagcg attggttgtg atgctgtgca agggttcttc tatggcccac 300
cactgcccga agcagaagcg cttgccttcc tgcaccgttc cgcttcccct ggggtctgaa 360
cgttaaaatc aggagctgtc ttctgctgat tggcatggct cctcaactgc gtatcttcgt 420
gccgccccat cccttaattc ggcactggct gggcattgcc cgcgatcgcc agacgccgac 480
gcctctgttt cgcaccgcga tcgcagagct gggccgctgg ctcgcctatg aggctgtgcg 540
ggaatggcta ccaacgattc cagcggcggt gcaaactcct cttgcagaaa ccccagcgga 600
gttcgtcgat ttttcgcaac ccttggcgat cgtgccgatt ctgcgcgcag gtctgggttt 660
agtggagtct gtccaacagg ttttgccgac tgcccgcatt tttcacgtgg gtctcaagcg 720
ggatgaagtc agtcttgaac cgcgctgcta cctcaatcac ctgccagagc aacttgaagt 780
gaacagtcgc gttctggttc tcgacccgat gctggcgaca ggtggctcgc tgctctatac 840
ccttgatttg ctgcgcgatc gcggtgtctc tgctgagcaa gtgcgggtgc tttcaattgt 900
ggctgccccg ccagcgctac aaaaactcag tcaagcctac ccggcgttga cgatttacag 960
cgccatcatt gatgagcagc tgaacgacaa aggctttatc gtgccggggc tgggggatgc 1020
tggcgatcgc ctgtttggta ctccttgatc tgctgactga attcgctagg cttcagcgtt 1080
gagcaaagcc tgaacggcct gccgaatgaa gctttcatcc tgcggatttt ggctggggtt 1140
gcccgcgcgg tgaccccaga tcgagggaat tgggcaatag tgcgccttag gaatcaactg 1200
cgcttcggcc tcacaatcct ctggggtgaa gtagagatct gttgtcgagg gcatgaccaa 1260
ggtctgagcc gtaatgctgc c 1281

<210> SEQ ID NO 102
<211> LENGTH: 9385
<212> TYPE: DNA
<213> ORGANISM: Artificial Sequence
<220> FEATURE:
<223> OTHER INFORMATION: plasmid pLybAL3f containing Synechocystis upp gene

<400> SEQUENCE: 102
gcggccgcaa ggggttcgcg tcagcgggtg ttggcgggtg tcggggctgg cttaactatg 60
cggcatcaga gcagattgta ctgagagtgc accatatgcg gtgtgaaata ccgcacagat 120
gcgtaaggag aaaataccgc atcaggcgcc attcgccatt cagctgcgca actgttggga 180
agggcgatcg gtgcgggcct cttcgctatt acgccagctg gcgaaagggg gatgtgctgc 240

-continued

```
aaggcgatta agttgggtaa cgccagggtt ttcccagtca cgacgttgta aaacgacggc    300
cagtgaattg taatacgact cactataggg cgaattcgag ctcggtaccc ggggatccca    360
cgcccaactg gtcacggaca tcgtcgataa ccaaattaag ttgggcaatt ttgtcttcca    420
ggcgacggcg agccaactca atattttcct cactatcgag atttcctacc ccctcagtgt    480
ctaatttttc ccggtcgggg ctttgggtag cagctcgatt ggccaggaca gaacccaaaa    540
ttccccccac tacgccacca atgaccgtac ctaataaaaa tcctccggcg aagttatctt    600
tttgagccat gactttactc ctgttgttaa cgtttggggg tgaatttgta attatttgat    660
cactagttta atggtgttat caagtaccaa agcaacgatc gcctgcatcc cctaggccgg    720
gcacaatgta accccggtca ttgagttgtt cgtcaatcat ggcggtgtag atggtcaaat    780
tgggatgggc attacttaat ttttgcaggg cagtgggggc ggccaccacg gagaccaaac    840
ggattaaatt ggcatcaatg tcccgggcca tcagcaaatc caaagcagcc atgatggtat    900
tacccgtagc caacatggga tctagcaaca aaagatgggt accgggggca aaccgctccg    960
gcaacttgtt cagatacaga ctaggttcca gggtagtttc attgcgcact aaacccagat   1020
ggtaaatttt tgccaggggc aacaacccct gggccccttc caccagagcc aaccccgccc   1080
gcaaaatggg cacaatgaca aagggcgttt gggggtcaat aagactggcc ttggcgatcg   1140
ccaggggagt tttcacttcc gtatccaccg tcggcaacca ataacgagcg gcctcatagg   1200
tcaaccaacg tcccaattcc cccatggcag ttttaaacaa aaccggcggc gtgttttcat   1260
ccctagctac ccccaaccaa tgcttaatta gaggatgctc cggcacataa acacgtaatt   1320
gagaagccat gggaaaactt aaaagttaat atctaaaatt taattttgtt aatcttggcc   1380
gttggggaac cgaaaaatgg gctaaaagtt aggacgtggt ctcaccgtcg gtaacaattc   1440
accgcggaac tccactgtag ctcagatcgg gttaccggaa gttggggcat tgggaaggga   1500
aaggttttct gccatacttt gggcagggat ttcccccaag ttcaacgaca gacaggcaag   1560
cattatgagc aaacaaccat cctttgacgg ctggcagtcc attgtgggtg ggatcctcta   1620
gagtcgacct gcaggcatgc aagcttgagt attctatagt ctcacctaaa tagcttggcg   1680
taatcatggt catagctgtt tcctgtgtga aattgttatc cgctcacaat tccacacaac   1740
atacgagccg gaagcataaa gtgtaaagcc tggggtgcct aatgagtgag ctaactcaca   1800
ttaattgcgt tgcgctcact gcccgctttc cagtcgggaa acctgtcgtg ccagctgcat   1860
taatgaatcg gccaacgcga acccccttgcg gccgcccggg ccgtcgacca attctcatgt   1920
ttgacagctt atcatcgaat ttctgccatt catccgctta ttatcactta ttcaggcgta   1980
gcaaccaggc gtttaagggc accaataact gccttaaaaa aattacgccc cgccctgcca   2040
ctcatcgcag tactgttgta attcattaag cattctgccg acatggaagc catcacaaac   2100
ggcatgatga acctgaatcg ccagcggcat cagcaccttg tcgccttgcg tataatattt   2160
gcccatggtg aaaacggggg cgaagaagtt gtccatattg gccacgttta aatcaaaact   2220
ggtgaaactc acccagggat tggctgagac gaaaaacata ttctcaataa accctttagg   2280
gaaataggcc aggttttcac cgtaacacgc cacatcttgc gaatatatgt gtagaaactg   2340
ccggaaatcg tcgtggtatt cactccagag cgatgaaaac gtttcagttt gctcatggaa   2400
aacggtgtaa caagggtgaa cactatccca tatcaccagc tcaccgtctt tcattgccat   2460
acgaaattcc ggatgagcat tcatcaggcg ggcaagaatg tgaataaagg ccggataaaa   2520
cttgtgctta tttttcttta cggtctttaa aaaggccgta atatccagct gaacggtctg   2580
gttataggta cattgagcaa ctgactgaaa tgcctcaaaa tgttctttac gatgccattg   2640
```

-continued

```
ggatatatca acggtggtat atccagtgat ttttttctcc attttagctt ccttagctcc   2700

tgaaaatctc gataactcaa aaaatacgcc cggtagtgat cttatttcat tatggtgaaa   2760

gttggaacct cttacgtgcc gatcaacgtc tcattttcgc caaaagttgg cccagggctt   2820

cccggtatca acagggacac caggatttat ttattctgcg aagtgatctt ccgtcacagg   2880

tatttattcg cgataagctc atggagcggc gtaaccgtcg cacaggaagg acagagaaag   2940

cgcggatctg ggaagtgacg gacagaacgg tcaggacctg gattggggag gcggttgccg   3000

ccgctgctgc tgacggtgtg acgttctctg ttccggtcac accacatacg ttccgccatt   3060

cctatgcgat gcacatgctg tatgccggta taccgctgaa agttctgcaa agcctgatgg   3120

gacataagtc catcagttca acggaagtct acacgaaggt ttttgcgctg gatgtggctg   3180

cccggcaccg ggtgcagttt gcgatgccgg agtctgatgc ggttgcgatg ctgaaacaat   3240

tatcctgaga ataaatgcct tggcctttat atggaaatgt ggaactgagt ggatatgctg   3300

tttttgtctg ttaaacagag aagctggctg ttatccactg agaagcgaac gaaacagtcg   3360

ggaaaatctc ccattatcgt agagatccgc attattaatc tcaggagcct gtgtagcgtt   3420

tataggaagt agtgttctgt catgatgcct gcaagcggta acgaaaacga tttgaatatg   3480

ccttcaggaa caatagaaat cttcgtgcgg tgttacgttg aagtggagcg gattatgtca   3540

gcaatggaca gaacaaccta atgaacacag aaccatgatg tggtctgtcc ttttacagcc   3600

agtagtgctc gccgcagtcg agcgacaggg cgaagccctc ggctggttgc cctcgccgct   3660

gggctggcgg ccgtctatgg ccctgcaaac gcgccagaaa cgccgtcgaa gccgtgtgcg   3720

agacaccgcg gccggccgcc ggcgttgtgg atacctcgcg gaaaacttgg ccctcactga   3780

cagatgaggg gcggacgttg acacttgagg ggccgactca cccggcgcgg cgttgacaga   3840

tgaggggcag gctcgatttc ggccggcgac gtggagctgg ccagcctcgc aaatcggcga   3900

aaacgcctga ttttacgcga gtttcccaca gatgatgtgg acaagcctgg ggataagtgc   3960

cctgcggtat tgacacttga ggggcgcgac tactgacaga tgaggggcgc gatccttgac   4020

acttgagggg cagagtgctg acagatgagg ggcgcaccta ttgacatttg aggggctgtc   4080

cacaggcaga aaatccagca tttgcaaggg tttccgcccg tttttcggcc accgctaacc   4140

tgtcttttaa cctgctttta aaccaatatt tataaacctt gtttttaacc agggctgcgc   4200

cctgtgcgcg tgaccgcgca cgccgaaggg gggtgccccc ccttctcgaa ccctcccggt   4260

cgagtgagcg aggaagcacc agggaacagc acttatatat tctgcttaca cacgatgcct   4320

gaaaaaactt cccttggggt tatccactta tccacgggga tatttttata attatttttt   4380

ttatagtttt tagatcttct tttttagagc gccttgtagg cctttatcca tgctggttct   4440

agagaaggtg ttgtgacaaa ttgccctttc agtgtgacaa atcaccctca aatgacagtc   4500

ctgtctgtga caaattgccc ttaaccctgt gacaaattgc cctcagaaga agctgttttt   4560

tcacaaagtt atccctgctt attgactctt ttttatttag tgtgacaatc taaaaacttg   4620

tcacacttca catggatctg tcatggcgga aacagcggtt atcaatcaca agaaacgtaa   4680

aaatagcccg cgaatcgtcc agtcaaacga cctcactgag gcggcatata gtctctcccg   4740

ggatcaaaaa cgtatgctgt atctgttcgt tgaccagatc agaaaatctg atggcaccct   4800

acaggaacat gacggtatct gcgagatcca tgttgctaaa tatgctgaaa tattcggatt   4860

gacctctgcg gaagccagta aggatatacg gcaggcattg aagagtttcg cggggaagga   4920

agtggttttt tatcgccctg aagaggatgc cggcgatgaa aaaggctatg aatcttttcc   4980
```

-continued

```
ttggtttatc aaacgtgcgc acagtccatc cagagggctt tacagtgtac atatcaaccc   5040
atatctcatt cccttcttta tcgggttaca gaaccggttt acgcagtttc ggcttagtga   5100
aacaaaagaa atcaccaatc cgtatgccat gcgtttatac gaatccctgt gtcagtatcg   5160
taagccggat ggctcaggca tcgtctctct gaaaatcgac tggatcatag agcgttacca   5220
gctgcctcaa agttaccagc gtatgcctga cttccgccgc cgcttcctgc aggtctgtgt   5280
taatgagatc aacagcagaa ctccaatgcg cctctcatac attgagaaaa agaaaggccg   5340
ccagacgact catatcgtat tttccttccg cgatatcact tccatgacga caggatagtc   5400
tgagggttat ctgtcacaga tttgagggtg gttcgtcaca tttgttctga cctactgagg   5460
gtaatttgtc acagttttgc tgtttccttc agcctgcatg gattttctca tactttttga   5520
actgtaattt ttaaggaagc caaatttgag ggcagtttgt cacagttgat ttccttctct   5580
ttcccttcgt catgtgacct gatatcgggg gttagttcgt catcattgat gagggttgat   5640
tatcacagtt tattactctg aattggctat ccgcgtgtgt acctctacct ggagtttttc   5700
ccacggtgga tatttcttct tgcgctgagc gtaagagcta tctgacagaa cagttcttct   5760
ttgcttcctc gccagttcgc tcgctatgct cggttacacg gctgcggcga gcgctagtga   5820
taataagtga ctgaggtatg tgctcttctt atctcctttt gtagtgttgc tcttatttta   5880
aacaactttg cggtttttg atgactttgc gattttgttg ttgctttgca gtaaattgca   5940
agatttaata aaaaaacgca aagcaatgat taaaggatgt tcagaatgaa actcatggaa   6000
acacttaacc agtgcataaa cgctggtcat gaaatgacga aggctatcgc cattgcacag   6060
tttaatgatg acagcccgga agcgaggaaa ataacccggc gctggagaat aggtgaagca   6120
gcggatttag ttggggtttc ttctcaggct atcagagatg ccgagaaagc agggcgacta   6180
ccgcacccgg atatggaaat tcgaggacgg gttgagcaac gtgttggtta tacaattgaa   6240
caaattaatc atatgcgtga tgtgtttggt acgcgattgc gacgtgctga agacgtattt   6300
ccaccggtga tcggggttgc tgcccataaa ggtggcgttt acaaaacctc agtttctgtt   6360
catcttgctc aggatctggc tctgaagggg ctacgtgttt tgctcgtgga aggtaacgac   6420
ccccagggaa cagcctcaat gtatcacgga tgggtaccag atcttcatat tcatgcagaa   6480
gacactctcc tgcctttcta tcttggggaa aaggacgatg tcacttatgc aataaagccc   6540
acttgctggc cggggcttga cattattcct tcctgtctgg ctctgcaccg tattgaaact   6600
gagttaatgg gcaaatttga tgaaggtaaa ctgcccaccg atccacacct gatgctccga   6660
ctggccattg aaactgttgc tcatgactat gatgtcatag ttattgacag cgcgcctaac   6720
ctgggtatcg gcacgattaa tgtcgtatgt gctgctgatg tgctgattgt tcccacgcct   6780
gctgagttgt ttgactacac ctccgcactg cagtttttcg atatgcttcg tgatctgctc   6840
aagaacgttg atcttaaagg gttcgagcct gatgtacgta ttttgcttac caaatacagc   6900
aatagtaatg gctctcagtc cccgtggatg gaggagcaaa ttcgggatgc ctggggaagc   6960
atggttctaa aaaatgttgt acgtgaaacg gatgaagttg gtaaaggtca gatccggatg   7020
agaactgttt ttgaacaggc cattgatcaa cgctcttcaa ctggtgcctg gagaaatgct   7080
ctttctattt gggaacctgt ctgcaatgaa attttcgatc gtctgattaa accacgctgg   7140
gagattagat aatgaagcgt gcgcctgtta ttccaaaaca tacgctcaat actcaaccgg   7200
ttgaagatac ttcgttatcg acaccagctg ccccgatggt ggattcgtta attgcgcgcg   7260
taggagtaat ggctcgcggt aatgccatta ctttgcctgt atgtggtcgg gatgtgaagt   7320
ttactcttga agtgctccgg ggtgatagtg ttgagaagac ctctcgggta tggtcaggta   7380
```

-continued

```
atgaacgtga ccaggagctg cttactgagg acgcactgga tgatctcatc ccttcttttc   7440
tactgactgg tcaacagaca ccggcgttcg gtcgaagagt atctggtgtc atagaaattg   7500
ccgatgggag tcgccgtcgt aaagctgctg cacttaccga aagtgattat cgtgttctgg   7560
ttggcgagct ggatgatgag cagatggctg cattatccag attgggtaac gattatcgcc   7620
caacaagtgc ttatgaacgt ggtcagcgtt atgcaagccg attgcagaat gaatttgctg   7680
gaaatatttc tgcgctggct gatgcggaaa atatttcacg taagattatt acccgctgta   7740
tcaacaccgc caaattgcct aaatcagttg ttgctctttt ttctcacccc ggtgaactat   7800
ctgcccggtc aggtgatgca cttcaaaaag cctttacaga taaagaggaa ttacttaagc   7860
agcaggcatc taaccttcat gagcagaaaa aagctggggt gatatttgaa gctgaagaag   7920
ttatcactct tttaacttct gtgcttaaaa cgtcatctgc atcaagaact agtttaagct   7980
cacgacatca gtttgctcct ggagcgacag tattgtataa gggcgataaa atggtgctta   8040
acctggacag gtctcgtgtt ccaactgagt gtatagagaa aattgaggcc attcttaagg   8100
aacttgaaaa gccagcaccc tgatgcgacc acgttttagt ctacgtttat ctgtctttac   8160
ttaatgtcct ttgttacagg ccagaaagca taactggcct gaatattctc tctgggccca   8220
ctgttccact tgtatcgtcg gtctgataat cagactggga ccacggtccc actcgtatcg   8280
tcggtctgat tattagtctg ggaccacggt cccactcgta tcgtcggtct gattattagt   8340
ctgggaccac ggtcccactc gtatcgtcgg tctgataatc agactgggac cacggtccca   8400
ctcgtatcgt cggtctgatt attagtctgg gaccatggtc ccactcgtat cgtcggtctg   8460
attattagtc tgggaccacg gtcccactcg tatcgtcggt ctgattatta gtctggaacc   8520
acggtcccac tcgtatcgtc ggtctgatta ttagtctggg accacggtcc cactcgtatc   8580
gtcggtctga ttattagtct gggaccacga tcccactcgt gttgtcggtc tgattatcgg   8640
tctgggacca cggtcccact tgtattgtcg atcagactat cagcgtgaga ctacgattcc   8700
atcaatgcct gtcaagggca agtattgaca tgtcgtcgta acctgtagaa cggagtaacc   8760
tcggtgtgcg gttgtatgcc tgctgtggat tgctgctgtg tcctgcttat ccacaacatt   8820
ttgcgcacgg ttatgtggac aaaatacctg gttacccagg ccgtgccggc acgttaaccg   8880
ggctgcatcc gatgcaagtg tgtcgctgtc gacgagctcg cgagctcgga catgaggttg   8940
ccccgtattc agtgtcgctg atttgtattg tctgaagttg tttttacgtt aagttgatgc   9000
agatcaatta atacgatacc tgcgtcataa ttgattattt gacgtggttt gatggcctcc   9060
acgcacgttg tgatatgtag atgataatca ttatcacttt acgggtcctt tccggtgatc   9120
cgacaggtta cggggcggcg acctcgcggg ttttcgctat ttatgaaaat tttccggttt   9180
aaggcgtttc cgttcttctt cgtcataact taatgttttt atttaaaata ccctctgaaa   9240
agaaaggaaa cgacaggtgc tgaaagcgag ctttttggcc tctgtcgttt cctttctctg   9300
tttttgtccg tggaatgaac aatggaagtc cgagctcatc gctaataact tcgtatagca   9360
tacattatac gaagttatat tcgat                                         9385
```

<210> SEQ ID NO 103
<211> LENGTH: 9420
<212> TYPE: DNA
<213> ORGANISM: Artificial Sequence
<220> FEATURE:
<223> OTHER INFORMATION: plasmid pLybAL5f containing Synechococcus upp gene

<400> SEQUENCE: 103

-continued

```
gcggccgcaa ggggttcgcg tcagcgggtg ttggcgggtg tcggggctgg cttaactatg     60
cggcatcaga gcagattgta ctgagagtgc accatatgcg gtgtgaaata ccgcacagat    120
gcgtaaggag aaaataccgc atcaggcgcc attcgccatt cagctgcgca actgttggga    180
agggcgatcg gtgcgggcct cttcgctatt acgccagctg gcgaaagggg gatgtgctgc    240
aaggcgatta agttgggtaa cgccagggtt ttcccagtca cgacgttgta aaacgacggc    300
cagtgaattg taatacgact cactataggg cgaattcgag ctcggtaccc ggggatccca    360
cggcagcatt acggctcaga ccttggtcat gccctcgaca acagatctct acttcacccc    420
agaggattgt gaggccgaag cgcagttgat tcctaaggcg cactattgcc caattccctc    480
gatctggggt caccgcgcgg gcaaccccag ccaaaatccg caggatgaaa gcttcattcg    540
gcaggccgtt caggctttgc tcaacgctga agcctagcga attcagtcag cagatcaagg    600
agtaccaaac aggcgatcgc cagcatcccc cagccccggc acgataaagc ctttgtcgtt    660
cagctgctca tcaatgatgg cgctgtaaat cgtcaacgcc gggtaggctt gactgagttt    720
ttgtagcgct ggcggggcag ccacaattga aagcacccgc acttgctcag cagagacacc    780
gcgatcgcgc agcaaatcaa gggtatagag cagcgagcca cctgtcgcca gcatcgggtc    840
gagaaccaga acgcgactgt tcacttcaag ttgctctggc aggtgattga ggtagcagcg    900
cggttcaaga ctgacttcat cccgcttgag acccacgtga aaaatgcggg cagtcggcaa    960
aacctgttgg acagactcca ctaaacccag acctgcgcgc agaatcggca cgatcgccaa   1020
gggttgcgaa aaatcgacga actccgctgg ggtttctgca agaggagttt gcaccgccgc   1080
tggaatcgtt ggtagccatt cccgcacagc ctcataggcg agccagcggc ccagctctgc   1140
gatcgcggtg cgaaacagag gcgtcggcgt ctggcgatcg cgggcaatgc ccagccagtg   1200
ccgaattaag ggatggggcg gcacgaagat acgcagttga ggagccatgc caatcagcag   1260
aagacagctc ctgattttaa cgttcagacc ccaggggaag cggaacggtg caggaaggca   1320
agcgcttctg cttcgggcag tggtgggcca tagaagaacc cttgcacagc atcacaacca   1380
atcgcttcta agaaggcggc ttgctcgagg cgttctacgc cttctgcgat cgtgcgaagt   1440
ttcaagacct tggccattgc aacaatcgcc tgcacgatcg cttgatcgtc atggtcgtgc   1500
ggcagatcgc gaataaagct gcgatcaatt ttgagagcat tgatgggcaa acgcttgagg   1560
taaccaaggc tggaataacc cgtcccaaaa tcatctaaag cgacttgaaa tcccatcgat   1620
cgggcttcct ggagccattg cagtgggatc ctctagagtc gacctgcagg catgcaagct   1680
tgagtattct atagtctcac ctaaatagct tggcgtaatc atggtcatag ctgtttcctg   1740
tgtgaaattg ttatccgctc acaattccac acaacatacg agccggaagc ataaagtgta   1800
aagcctgggg tgcctaatga gtgagctaac tcacattaat tgcgttgcgc tcactgcccg   1860
ctttccagtc gggaaacctg tcgtgccagc tgcattaatg aatcggccaa cgcgaacccc   1920
ttgcggccgc ccgggccgtc gaccaattct catgtttgac agcttatcat cgaatttctg   1980
ccattcatcc gcttattatc acttattcag gcgtagcaac caggcgttta agggcaccaa   2040
taactgcctt aaaaaaatta cgccccgccc tgccactcat cgcagtactg ttgtaattca   2100
ttaagcattc tgccgacatg gaagccatca caaacggcat gatgaacctg aatcgccagc   2160
ggcatcagca ccttgtcgcc ttgcgtataa tatttgccca tggtgaaaac gggggcgaag   2220
aagttgtcca tattggccac gtttaaatca aaactggtga aactcaccca gggattggct   2280
gagacgaaaa acatattctc aataaaccct ttagggaaat aggccaggtt ttcaccgtaa   2340
```

-continued

```
cacgccacat cttgcgaata tatgtgtaga aactgccgga aatcgtcgtg gtattcactc   2400
cagagcgatg aaaacgtttc agtttgctca tggaaaacgg tgtaacaagg gtgaacacta   2460
tcccatatca ccagctcacc gtctttcatt gccatacgaa attccggatg agcattcatc   2520
aggcgggcaa gaatgtgaat aaaggccgga taaaacttgt gcttattttt ctttacggtc   2580
tttaaaaagg ccgtaatatc cagctgaacg gtctggttat aggtacattg agcaactgac   2640
tgaaatgcct caaaatgttc tttacgatgc cattgggata tatcaacggt ggtatatcca   2700
gtgatttttt tctccatttt agcttcctta gctcctgaaa atctcgataa ctcaaaaaat   2760
acgcccggta gtgatcttat ttcattatgg tgaaagttgg aacctcttac gtgccgatca   2820
acgtctcatt ttcgccaaaa gttggcccag ggcttcccgg tatcaacagg gacaccagga   2880
tttatttatt ctgcgaagtg atcttccgtc acaggtattt attcgcgata agctcatgga   2940
gcggcgtaac cgtcgcacag gaaggacaga gaaagcgcgg atctgggaag tgacggacag   3000
aacggtcagg acctggattg gggaggcggt tgccgccgct gctgctgacg gtgtgacgtt   3060
ctctgttccg gtcacaccac atacgttccg ccattcctat gcgatgcaca tgctgtatgc   3120
cggtataccg ctgaaagttc tgcaaagcct gatgggacat aagtccatca gttcaacgga   3180
agtctacacg aaggtttttg cgctggatgt ggctgcccgg caccgggtgc agtttgcgat   3240
gccggagtct gatgcggttg cgatgctgaa acaattatcc tgagaataaa tgccttggcc   3300
tttatatgga aatgtggaac tgagtggata tgctgttttt gtctgttaaa cagagaagct   3360
ggctgttatc cactgagaag cgaacgaaac agtcgggaaa atctcccatt atcgtagaga   3420
tccgcattat taatctcagg agcctgtgta gcgtttatag gaagtagtgt tctgtcatga   3480
tgcctgcaag cggtaacgaa aacgatttga atatgccttc aggaacaata gaaatcttcg   3540
tgcggtgtta cgttgaagtg gagcggatta tgtcagcaat ggacagaaca acctaatgaa   3600
cacagaacca tgatgtggtc tgtcctttta cagccagtag tgctcgccgc agtcgagcga   3660
cagggcgaag ccctcggctg gttgccctcg ccgctgggct ggcggccgtc tatggccctg   3720
caaacgcgcc agaaacgccg tcgaagccgt gtgcgagaca ccgcggccgg ccgccggcgt   3780
tgtggatacc tcgcggaaaa cttggccctc actgacagat gaggggcgga cgttgacact   3840
tgaggggccg actcacccgg cgcggcgttg acagatgagg ggcaggctcg atttcggccg   3900
gcgacgtgga gctggccagc ctcgcaaatc ggcgaaaacg cctgatttta cgcgagtttc   3960
ccacagatga tgtggacaag cctggggata agtgccctgc ggtattgaca cttgaggggc   4020
gcgactactg acagatgagg ggcgcgatcc ttgacacttg aggggcagag tgctgacaga   4080
tgaggggcgc acctattgac atttgagggg ctgtccacag gcagaaaatc cagcatttgc   4140
aagggtttcc gcccgttttt cggccaccgc taacctgtct tttaacctgc ttttaaacca   4200
atatttataa accttgtttt taaccagggc tgcgccctgt gcgcgtgacc gcgcacgccg   4260
aaggggggtg cccccccttc tcgaaccctc ccggtcgagt gagcgaggaa gcaccaggga   4320
acagcactta tatattctgc ttacacacga tgcctgaaaa aacttccctt ggggttatcc   4380
acttatccac ggggatattt ttataattat ttttttata gtttttagat cttcttttt   4440
agagcgcctt gtaggccttt atccatgctg gttctagaga aggtgttgtg acaaattgcc   4500
ctttcagtgt gacaaatcac cctcaaatga cagtcctgtc tgtgacaaat tgcccttaac   4560
cctgtgacaa attgccctca gaagaagctg ttttttcaca aagttatccc tgcttattga   4620
ctcttttta tttagtgtga caatctaaaa acttgtcaca cttcacatgg atctgtcatg   4680
gcggaaacag cggttatcaa tcacaagaaa cgtaaaaata gcccgcgaat cgtccagtca   4740
```

aacgacctca ctgaggcggc atatagtctc tcccgggatc aaaaacgtat gctgtatctg 4800
ttcgttgacc agatcagaaa atctgatggc accctacagg aacatgacgg tatctgcgag 4860
atccatgttg ctaaatatgc tgaaatattc ggattgacct ctgcggaagc cagtaaggat 4920
atacggcagg cattgaagag tttcgcgggg aaggaagtgg ttttttatcg ccctgaagag 4980
gatgccggcg atgaaaaagg ctatgaatct tttccttggt ttatcaaacg tgcgcacagt 5040
ccatccagag ggctttacag tgtacatatc aacccatatc tcattccctt ctttatcggg 5100
ttacagaacc ggtttacgca gtttcggctt agtgaaacaa aagaaatcac caatccgtat 5160
gccatgcgtt tatacgaatc cctgtgtcag tatcgtaagc cggatggctc aggcatcgtc 5220
tctctgaaaa tcgactggat catagagcgt taccagctgc ctcaaagtta ccagcgtatg 5280
cctgacttcc gccgccgctt cctgcaggtc tgtgttaatg agatcaacag cagaactcca 5340
atgcgcctct catacattga gaaaaagaaa ggccgccaga cgactcatat cgtatttttcc 5400
ttccgcgata tcacttccat gacgacagga tagtctgagg gttatctgtc acagatttga 5460
gggtggttcg tcacatttgt tctgacctac tgagggtaat ttgtcacagt tttgctgttt 5520
ccttcagcct gcatggattt tctcatactt tttgaactgt aatttttaag gaagccaaat 5580
ttgagggcag tttgtcacag ttgatttcct tctctttccc ttcgtcatgt gacctgatat 5640
cgggggttag ttcgtcatca ttgatgaggg ttgattatca cagtttatta ctctgaattg 5700
gctatccgcg tgtgtacctc tacctggagt ttttcccacg gtggatattt cttcttgcgc 5760
tgagcgtaag agctatctga cagaacagtt cttctttgct tcctcgccag ttcgctcgct 5820
atgctcggtt acacggctgc ggcgagcgct agtgataata agtgactgag gtatgtgctc 5880
ttcttatctc cttttgtagt gttgctctta ttttaaacaa ctttgcggtt ttttgatgac 5940
tttgcgattt tgttgttgct ttgcagtaaa ttgcaagatt taataaaaaa acgcaaagca 6000
atgattaaag gatgttcaga atgaaactca tggaaacact taaccagtgc ataaacgctg 6060
gtcatgaaat gacgaaggct atcgccattg cacagtttaa tgatgacagc ccggaagcga 6120
ggaaaataac ccggcgctgg agaataggtg aagcagcgga tttagttggg gtttcttctc 6180
aggctatcag agatgccgag aaagcagggc gactaccgca cccggatatg gaaattcgag 6240
gacgggttga gcaacgtgtt ggttatacaa ttgaacaaat taatcatatg cgtgatgtgt 6300
ttggtacgcg attgcgacgt gctgaagacg tatttccacc ggtgatcggg gttgctgccc 6360
ataaaggtgg cgtttacaaa acctcagttt ctgttcatct tgctcaggat ctggctctga 6420
aggggctacg tgttttgctc gtggaaggta acgacccccca gggaacagcc tcaatgtatc 6480
acggatgggt accagatctt catattcatg cagaagacac tctcctgcct ttctatcttg 6540
gggaaaagga cgatgtcact tatgcaataa agcccacttg ctggccgggg cttgacatta 6600
ttccttcctg tctggctctg caccgtattg aaactgagtt aatgggcaaa tttgatgaag 6660
gtaaactgcc caccgatcca cacctgatgc tccgactggc cattgaaact gttgctcatg 6720
actatgatgt catagttatt gacagcgcgc ctaacctggg tatcggcacg attaatgtcg 6780
tatgtgctgc tgatgtgctg attgttccca cgcctgctga gttgtttgac tacacctccg 6840
cactgcagtt tttcgatatg cttcgtgatc tgctcaagaa cgttgatctt aaagggttcg 6900
agcctgatgt acgtattttg cttaccaaat acagcaatag taatggctct cagtccccgt 6960
ggatggagga gcaaattcgg gatgcctggg gaagcatggt tctaaaaaat gttgtacgtg 7020
aaacggatga agttggtaaa ggtcagatcc ggatgagaac tgtttttgaa caggccattg 7080

-continued

```
atcaacgctc ttcaactggt gcctggagaa atgctctttc tatttgggaa cctgtctgca   7140
atgaaatttt cgatcgtctg attaaaccac gctgggagat tagataatga agcgtgcgcc   7200
tgttattcca aaacatacgc tcaatactca accggttgaa gatacttcgt tatcgacacc   7260
agctgccccg atggtggatt cgttaattgc gcgcgtagga gtaatggctc gcggtaatgc   7320
cattactttg cctgtatgtg gtcgggatgt gaagtttact cttgaagtgc tccggggtga   7380
tagtgttgag aagacctctc gggtatggtc aggtaatgaa cgtgaccagg agctgcttac   7440
tgaggacgca ctggatgatc tcatcccttc ttttctactg actggtcaac agacaccggc   7500
gttcggtcga agagtatctg gtgtcataga aattgccgat gggagtcgcc gtcgtaaagc   7560
tgctgcactt accgaaagtg attatcgtgt tctggttggc gagctggatg atgagcagat   7620
ggctgcatta tccagattgg gtaacgatta tcgcccaaca agtgcttatg aacgtggtca   7680
gcgttatgca agccgattgc agaatgaatt tgctggaaat atttctgcgc tggctgatgc   7740
ggaaaatatt tcacgtaaga ttattacccg ctgtatcaac accgccaaat tgcctaaatc   7800
agttgttgct cttttttctc accccggtga actatctgcc cggtcaggtg atgcacttca   7860
aaaagccttt acagataaag aggaattact taagcagcag gcatctaacc ttcatgagca   7920
gaaaaaagct ggggtgatat ttgaagctga agaagttatc actcttttaa cttctgtgct   7980
taaaacgtca tctgcatcaa gaactagttt aagctcacga catcagtttg ctcctggagc   8040
gacagtattg tataagggcg ataaaatggt gcttaacctg gacaggtctc gtgttccaac   8100
tgagtgtata gagaaaattg aggccattct taaggaactt gaaaagccag caccctgatg   8160
cgaccacgtt ttagtctacg tttatctgtc tttacttaat gtcctttgtt acaggccaga   8220
aagcataact ggcctgaata ttctctctgg gcccactgtt ccacttgtat cgtcggtctg   8280
ataatcagac tgggaccacg gtcccactcg tatcgtcggt ctgattatta gtctgggacc   8340
acggtcccac tcgtatcgtc ggtctgatta ttagtctggg accacggtcc cactcgtatc   8400
gtcggtctga taatcagact gggaccacgg tcccactcgt atcgtcggtc tgattattag   8460
tctgggacca tggtcccact cgtatcgtcg gtctgattat tagtctggga ccacggtccc   8520
actcgtatcg tcggtctgat tattagtctg gaaccacggt cccactcgta tcgtcggtct   8580
gattattagt ctgggaccac ggtcccactc gtatcgtcgg tctgattatt agtctgggac   8640
cacgatccca ctcgtgttgt cggtctgatt atcggtctgg gaccacggtc ccacttgtat   8700
tgtcgatcag actatcagcg tgagactacg attccatcaa tgcctgtcaa gggcaagtat   8760
tgacatgtcg tcgtaacctg tagaacggag taacctcggt gtgcggttgt atgcctgctg   8820
tggattgctg ctgtgtcctg cttatccaca acattttgcg cacggttatg tggacaaaat   8880
acctggttac ccaggccgtg ccggcacgtt aaccgggctg catccgatgc aagtgtgtcg   8940
ctgtcgacga gctcgcgagc tcggacatga ggttgccccg tattcagtgt cgctgatttg   9000
tattgtctga agttgttttt acgttaagtt gatgcagatc aattaatacg atacctgcgt   9060
cataattgat tatttgacgt ggtttgatgg cctccacgca cgttgtgata tgtagatgat   9120
aatcattatc actttacggg tcctttccgg tgatccgaca ggttacgggg cggcgacctc   9180
gcgggttttc gctatttatg aaaattttcc ggtttaaggc gtttccgttc ttcttcgtca   9240
taacttaatg tttttattta aaataccctc tgaaaagaaa ggaaacgaca ggtgctgaaa   9300
gcgagctttt tggcctctgt cgtttccttt ctctgttttt gtccgtggaa tgaacaatgg   9360
aagtccgagc tcatcgctaa taacttcgta tagcatacat tatacgaagt tatattcgat   9420
```

<210> SEQ ID NO 104
<211> LENGTH: 22
<212> TYPE: DNA
<213> ORGANISM: Artificial Sequence
<220> FEATURE:
<223> OTHER INFORMATION: PCR primer

<400> SEQUENCE: 104
gtaatacgac tcactatagg gc 22

<210> SEQ ID NO 105
<211> LENGTH: 24
<212> TYPE: DNA
<213> ORGANISM: Artificial Sequence
<220> FEATURE:
<223> OTHER INFORMATION: PCR primer

<400> SEQUENCE: 105
cacacaggaa acagctatga ccat 24

<210> SEQ ID NO 106
<211> LENGTH: 5641
<212> TYPE: DNA
<213> ORGANISM: Artificial Sequence
<220> FEATURE:
<223> OTHER INFORMATION: plasmid pLybAL4f containing Synechocystis upp gene

<400> SEQUENCE: 106
tgcaccatat gcggtgtgaa ataccgcaca gatgcgtaag gagaaaatac cgcatcaggc 60
gccattcgcc attcagctgc gcaactgttg ggaagggcga tcggtgcggg cctcttcgct 120
attacgccag ctggcgaaag ggggatgtgc tgcaaggcga ttaagttggg taacgccagg 180
gttttcccag tcacgacgtt gtaaaacgac ggccagtgaa ttgtaatacg actcactata 240
gggcgaattc gagctcggta cccggggatc ccacgcccaa ctggtcacgg acatcgtcga 300
taaccaaatt aagttgggca attttgtctt ccaggcgacg gcgagccaac tcaatatttt 360
cctcactatc gagatttcct accccctcag tgtctaattt ttcccggtcg gggctttggg 420
tagcagctcg attggccagg acagaaccca aaattccccc cactacgcca ccaatgaccg 480
tacctaataa aaatcctccg gcgaagttat ctttttgagc catgacttta ctcctgttgt 540
taacgtttgg gggtgaattt gtaattattt gatcactagt ttaatggtgt tatcaagtac 600
caaagcaacg atcgcctgca tcccctaggc cgggcacaat gtaaccccgg tcattgagtt 660
gttcgtcaat catggcggtg tagatggtca aattgggatg ggcattactt aatttttgca 720
gggcagtggg ggcggccacc acggagacca aacggattaa attggcatca atgtcccggg 780
ccatcagcaa atccaaagca gccatgatgg tattacccgt agccaacatg ggatctagca 840
acaaaagatg ggtaccgggg gcaaaccgct ccggcaactt gttcagatac agactaggtt 900
ccagggtagt ttcattgcgc actaaaccca gatggtaaat tttgccaggg ggcaacaacc 960
cctgggcccc ttccaccaga gccaaccccg cccgcaaaat gggcacaatg acaaagggcg 1020
tttgggggtc aataagactg gccttggcga tcgccagggg agttttcact tccgtatcca 1080
ccgtcggcaa ccaataacga gcggcctcat aggtcaacca acgtcccaat tcccccatgg 1140
cagttttaaa caaaaccggc ggcgtgtttt catccctagc tacccccaac caatgcttaa 1200
ttagaggatg ctccggcaca taaacacgta attgagaagc catgggaaaa cttaaaagtt 1260
aatatctaaa atttaatttt gttaatcttg gccgttgggg aaccgaaaaa tgggctaaaa 1320
gttaggacgt ggtctcaccg tcggtaacaa ttcaccgcgg aactccactg tagctcagat 1380

-continued

```
cgggttaccg gaagttgggg cattgggaag ggaaaggttt tctgccatac tttgggcagg   1440
gatttccccc aagttcaacg acagacaggc aagcattatg agcaaacaac catcctttga   1500
cggctggcag tccattgtgg gtgggatcct ctagagtcga cctgcaggca tgcaagcttg   1560
agtattctat agtctcacct aaatagcttg gcgtaatcat ggtcatagct gtttcctgtg   1620
tgaaattgtt atccgctcac aattccacac aacatacgag ccggaagcat aaagtgtaaa   1680
gcctggggtg cctaatgagt gagctaactc acattaattg cgttgcgctc actgcccgct   1740
ttccagtcgg gaaacctgtc gtgccagctg cattaatgaa tcggccaacg cgaacccctt   1800
gcggccgccc gggccgtcga ccaattctca tgtttgacag cttatcatcg aatttctgcc   1860
attcatccgc ttattatcac ttattcaggc gtagcaacca ggcgtttaag ggcaccaata   1920
actgccttaa aaaaattacg ccccgccctg ccactcatcg cagtactgtt gtaattcatt   1980
aagcattctg ccgacatgga agccatcaca aacggcatga tgaacctgaa tcgccagcgg   2040
catcagcacc ttgtcgcctt gcgtataata tttgcccatg gtgaaaacgg gggcgaagaa   2100
gttgtccata ttggccacgt ttaaatcaaa actggtgaaa ctcacccagg gattggctga   2160
gacgaaaaac atattctcaa taaacccttt agggaaatag gccaggtttt caccgtaaca   2220
cgccacatct tgcgaatata tgtgtagaaa ctgccggaaa tcgtcgtggt attcactcca   2280
gagcgatgaa aacgtttcag tttgctcatg gaaaacggtg taacaagggt gaacactatc   2340
ccatatcacc agctcaccgt ctttcattgc catacgaaat tccggatgag cattcatcag   2400
gcgggcaaga atgtgaataa aggccggata aaacttgtgc ttatttttct ttacggtctt   2460
taaaaaggcc gtaatatcca gctgaacggt ctggttatag gtacattgag caactgactg   2520
aaatgcctca aaatgttctt tacgatgcca ttgggatata tcaacggtgg tatatccagt   2580
gatttttttc tccattttag cttccttagc tcctgaaaat ctcgataact caaaaaatac   2640
gcccggtagt gatcttattt cattatggtg aaagttggaa cctcttacgt gccgatcaac   2700
gtctcatttt cgccaaaagt tggcccaggg cttcccggta tcaacaggga caccaggatt   2760
tatttattct gcgaagtgat cttccgtcac aggtatttat tcgcgataag ctcatggagc   2820
ggcgtaaccg tcgcacagga aggacagaga aagcgcggat ctgggaagtg acggacagaa   2880
cggtcaggac ctggattggg gaggcggttg ccgccgctgc tgctgacggt gtgacgttct   2940
ctgttccggt cacaccacat acgttccgcc attcctatgc gatgcacatg ctgtatgccg   3000
gtataccgct gaaagttctg caaagcctga tgggacataa gtccatcagt tcaacggaag   3060
tctacacgaa ggtttttgcg ctggatgtgg ctgcccggca ccgggtgcag tttgcgatgc   3120
cggagtctga tgcggttgcg atgctgaaac aattatcctg agaataaatg ccttggcctt   3180
tatatggaaa tgtggaactg agtggatatg ctgtttttgt ctgttaaaca gagaagctgg   3240
ctgttatcca ctgagaagcg aacgaaacag tcgggaaaat ctcccattat cgtagagatc   3300
cgcattatta atctcaggag cctgtgtagc gtttatagga agtagtgttc tgtcatgatg   3360
cctgcaagcg gtaacgaaaa cgatttgaat atgccttcag gaacaataga aatcttcgtg   3420
cggtgttacg ttgaagtgga gcggattatg tcagcaatgg acagaacaac ctaatgaaca   3480
cagaaccatg atgtggtctg tccttttaca gccagtagtg ctcgccgcag tcgagcgaca   3540
gggcgaagcc ctcggctggt tgccctcgcc gctgggctgg cggccgtcta tggccctgca   3600
aacgcgccag aaacgccgtc gaagccgtgt gcgagacacc gcggccggcc gccggcgttg   3660
tggatacctc gcggaaaact tggccctcac tgacagatga ggggcggacg ttgacacttg   3720
```

```
aggggccgac tcacccggcg cggcgttgac agatgagggg caggctcgat ttcggccggc   3780

gacgtggagc tggccagcct cgcaaatcgg cgaaaacgcc tgattttacg cgagtttccc   3840

acagatgatg tggacaagcc tggggataag tgccctgcgg tattgacact tgagggggcgc  3900

gactactgac agatgagggg cgcgatcctt gacacttgag ggcagagtg ctgacagatg    3960

aggggcgcac ctattgacat ttgaggggct gtccacaggc agaaaatcca gcatttgcaa   4020

gggtttccgc ccgtttttcg gccaccgcta acctgtcttt taacctgctt ttaaaccaat   4080

atttataaac cttgttttta accagggctg cgccctgtgc gcgtgaccgc gcacgccgaa   4140

ggggggtgcc ccccttctc gaaccctccc ggtcgagtga gcgaggaagc accagggaac    4200

agcacttata tattctgctt acacacgatg cctgaaaaaa cttcccttgg ggttatccac   4260

ttatccacgg ggatattttt ataattattt tttttatagt ttttagatct tcttttttag   4320

agcgccttgt aggcctttat ccatgctggt tctagagaag gtgttgtgac aaattgccct   4380

ttcagtgtga caaatcaccc tcaaatgaca gtcctgtctg tgacaaattg cccttaaccc   4440

tgtgacaaat tgccctcaga agaagctgtt ttttcacaaa gttatccctg cttattgact   4500

ctttttattt tagtgtgaca atctaaaaac ttgtcacact tcacatggat ctgtcatggc   4560

ggaaacagcg gttatcaatc acaagaaacg taaaaatagc ccgcgaatcg tccagtcaaa   4620

cgacctcact gaggcggcat atagtctctc ccgggatcaa aaacgtatgc tgtatctgtt   4680

cgttgaccag atcagaaaat ctgatggcac cctacaggaa catgacggta tctgcgagat   4740

ccatgttgct aaatatgctg aaatattcgg attgacctct gcggaagcca gtaaggatat   4800

acggcaggca ttgaagagtt tcgcggggaa ggaagtggtt ttttatcgcc ctgaagagga   4860

tgccggcgat gaaaaaggct atgaatcttt tccttggttt atcaaacgtg cgcacagtcc   4920

atccagaggg ctttacagtg tacatatcaa cccatatctc attcccttct ttatcgggtt   4980

acagaaccgg tttacgcagt ttcggcttag tgaaacaaaa gaaatcacca atccgtatgc   5040

catgcgttta tacgaatccc tgtgtcagta tcgtaagccg gatggctcag gcatcgtctc   5100

tctgaaaatc gactggatca tagagcgtta ccagctgcct caaagttacc agcgtatgcc   5160

tgacttccgc cgccgcttcc tgcaggtctg tgttaatgag atcaacagca gaactccaat   5220

gcgcctctca tacattgaga aaaagaaagg ccgccagacg actcatatcg tattttcctt   5280

ccgcgatatc acttccatga cgacaggata gtctgagggt tatctgtcac agatttgagg   5340

gtggttcgtc acatttgttc tgacctactg agggtaattt gtcacagttt tgctgtttcc   5400

ttcagcctgc atggattttc tcatactttt tgaactgtaa tttttaagga agccaaattt   5460

gagggcagtt tgtcacagtt gatttccttc tctttccctt cgtcatgtga cctgatatcg   5520

ggggttagtt cgtcatcatt gatgagggtt gattatcaca gtttattact ctgaattggc   5580

tatccgcgtg tgtacctcta cctggagttt ttcccacggt ggatatttct tcttgcgctg   5640

a                                                                   5641
```

```
<210> SEQ ID NO 107
<211> LENGTH: 5218
<212> TYPE: DNA
<213> ORGANISM: Artificial Sequence
<220> FEATURE:
<223> OTHER INFORMATION: plasmid pLybAL9f containing partially deleted
      Synechocystis upp gene

<400> SEQUENCE: 107

tgcaccatat gcggtgtgaa ataccgcaca gatgcgtaag gagaaaatac cgcatcaggc     60
```

-continued

```
gccattcgcc attcagctgc gcaactgttg ggaagggcga tcggtgcggg cctcttcgct    120
attacgccag ctggcgaaag ggggatgtgc tgcaaggcga ttaagttggg taacgccagg    180
gttttcccag tcacgacgtt gtaaaacgac ggccagtgaa ttgtaatacg actcactata    240
gggcgaattc gagctcggta cccggggatc ccacgcccaa ctggtcacgg acatcgtcga    300
taaccaaatt aagttgggca attttgtctt ccaggcgacg gcgagccaac tcaatatttt    360
cctcactatc gagatttcct accccctcag tgtctaattt ttcccggtcg ggctttggg    420
tagcagctcg attggccagg acagaaccca aaattccccc cactacgcca ccaatgaccg    480
tacctaataa aaatcctccg gcgaagttat ctttttgagc catgacttta ctcctgttgt    540
taacgtttgg gggtgaattt gtaattattt gatcactagt ttaatggtgt tatcaagtac    600
caaagcaacg atcgcctgca tcccctagcg ccaggggagt tttcacttcc gtatccaccg    660
tcggcaacca ataacgagcg gcctcatagg tcaaccaacg tcccaattcc cccatggcag    720
ttttaaacaa aaccggcggc gtgttttcat ccctagctac ccccaaccaa tgcttaatta    780
gaggatgctc cggcacataa acacgtaatt gagaagccat gggaaaactt aaaagttaat    840
atctaaaatt taattttgtt aatcttggcc gttggggaac cgaaaaatgg gctaaaagtt    900
aggacgtggt ctcaccgtcg gtaacaattc accgcggaac tccactgtag ctcagatcgg    960
gttaccggaa gttggggcat tgggaaggga aaggttttct gccatacttt gggcagggat   1020
ttcccccaag ttcaacgaca gacaggcaag cattatgagc aaacaaccat cctttgacgg   1080
ctggcagtcc attgtgggtg ggatcctcta gagtcgacct gcaggcatgc aagcttgagt   1140
attctatagt ctcacctaaa tagcttggcg taatcatggt catagctgtt tcctgtgtga   1200
aattgttatc cgctcacaat tccacacaac atacgagccg gaagcataaa gtgtaaagcc   1260
tggggtgcct aatgagtgag ctaactcaca ttaattgcgt tgcgctcact gcccgctttc   1320
cagtcgggaa acctgtcgtg ccagctgcat taatgaatcg gccaacgcga accccttgcg   1380
gccgcccggg ccgtcgacca attctcatgt ttgacagctt atcatcgaat ttctgccatt   1440
catccgctta ttatcactta ttcaggcgta gcaaccaggc gtttaagggc accaataact   1500
gccttaaaaa aattacgccc cgccctgcca ctcatcgcag tactgttgta attcattaag   1560
cattctgccg acatggaagc catcacaaac ggcatgatga acctgaatcg ccagcggcat   1620
cagcaccttg tcgccttgcg tataatattt gcccatggtg aaaacggggg cgaagaagtt   1680
gtccatattg gccacgttta aatcaaaact ggtgaaactc acccagggat tggctgagac   1740
gaaaaacata ttctcaataa accctttagg gaaataggcc aggttttcac cgtaacacgc   1800
cacatcttgc gaatatatgt gtagaaactg ccggaaatcg tcgtggtatt cactccagag   1860
cgatgaaaac gtttcagttt gctcatggaa aacggtgtaa caagggtgaa cactatccca   1920
tatcaccagc tcaccgtctt tcattgccat acgaaattcc ggatgagcat tcatcaggcg   1980
ggcaagaatg tgaataaagg ccggataaaa cttgtgctta tttttcttta cggtctttaa   2040
aaaggccgta atatccagct gaacggtctg gttataggta cattgagcaa ctgactgaaa   2100
tgcctcaaaa tgttctttac gatgccattg ggatatatca acggtggtat atccagtgat   2160
ttttttctcc attttagctt ccttagctcc tgaaaatctc gataactcaa aaaatacgcc   2220
cggtagtgat cttatttcat tatggtgaaa gttggaacct cttacgtgcc gatcaacgtc   2280
tcattttcgc caaaagttgg cccagggctt cccggtatca acagggacac caggatttat   2340
ttattctgcg aagtgatctt ccgtcacagg tatttattcg cgataagctc atggagcggc   2400
gtaaccgtcg cacaggaagg acagagaaag cgcggatctg ggaagtgacg gacagaacgg   2460
```

```
tcaggacctg gattggggag gcggttgccg ccgctgctgc tgacggtgtg acgttctctg   2520
ttccggtcac accacatacg ttccgccatt cctatgcgat gcacatgctg tatgccggta   2580
taccgctgaa agttctgcaa agcctgatgg gacataagtc catcagttca acggaagtct   2640
acacgaaggt ttttgcgctg gatgtggctg cccggcaccg ggtgcagttt gcgatgccgg   2700
agtctgatgc ggttgcgatg ctgaaacaat tatcctgaga ataaatgcct tggcctttat   2760
atggaaatgt ggaactgagt ggatatgctg tttttgtctg ttaaacagag aagctggctg   2820
ttatccactg agaagcgaac gaaacagtcg ggaaaatctc ccattatcgt agagatccgc   2880
attattaatc tcaggagcct gtgtagcgtt tataggaagt agtgttctgt catgatgcct   2940
gcaagcggta acgaaaacga tttgaatatg ccttcaggaa caatagaaat cttcgtgcgg   3000
tgttacgttg aagtggagcg gattatgtca gcaatggaca gaacaaccta atgaacacag   3060
aaccatgatg tggtctgtcc ttttacagcc agtagtgctc gccgcagtcg agcgacaggg   3120
cgaagccctc ggctggttgc cctcgccgct gggctggcgg ccgtctatgg ccctgcaaac   3180
gcgccagaaa cgccgtcgaa gccgtgtgcg agacaccgcg gccggccgcc ggcgttgtgg   3240
atacctcgcg gaaaacttgg ccctcactga cagatgaggg gcggacgttg acacttgagg   3300
ggccgactca cccggcgcgg cgttgacaga tgaggggcag gctcgatttc ggccggcgac   3360
gtggagctgg ccagcctcgc aaatcggcga aaacgcctga ttttacgcga gtttcccaca   3420
gatgatgtgg acaagcctgg ggataagtgc cctgcggtat tgacacttga ggggcgcgac   3480
tactgacaga tgaggggcgc gatccttgac acttgagggg cagagtgctg acagatgagg   3540
ggcgcaccta ttgacatttg aggggctgtc cacaggcaga aaatccagca tttgcaaggg   3600
tttccgcccg tttttcggcc accgctaacc tgtcttttaa cctgctttta aaccaatatt   3660
tataaacctt gtttttaacc agggctgcgc cctgtgcgcg tgaccgcgca cgccgaaggg   3720
gggtgccccc ccttctcgaa ccctcccggt cgagtgagcg aggaagcacc agggaacagc   3780
acttatatat tctgcttaca cacgatgcct gaaaaaactt cccttggggt tatccactta   3840
tccacgggga tatttttata attatttttt ttatagtttt tagatcttct tttttagagc   3900
gccttgtagg cctttatcca tgctggttct agagaaggtg ttgtgacaaa ttgccctttc   3960
agtgtgacaa atcaccctca aatgacagtc ctgtctgtga caaattgccc ttaaccctgt   4020
gacaaattgc cctcagaaga agctgttttt tcacaaagtt atccctgctt attgactctt   4080
ttttatttag tgtgacaatc taaaaacttg tcacacttca catggatctg tcatggcgga   4140
aacagcggtt atcaatcaca agaaacgtaa aaatagcccg cgaatcgtcc agtcaaacga   4200
cctcactgag gcggcatata gtctctcccg ggatcaaaaa cgtatgctgt atctgttcgt   4260
tgaccagatc agaaaatctg atggcaccct acaggaacat gacggtatct gcgagatcca   4320
tgttgctaaa tatgctgaaa tattcggatt gacctctgcg gaagccagta aggatatacg   4380
gcaggcattg aagagtttcg cggggaagga agtggttttt tatcgccctg aagaggatgc   4440
cggcgatgaa aaaggctatg aatcttttcc ttggtttatc aaacgtgcgc acagtccatc   4500
cagagggctt tacagtgtac atatcaaccc atatctcatt cccttcttta tcgggttaca   4560
gaaccggttt acgcagtttc ggcttagtga aacaaaagaa atcaccaatc cgtatgccat   4620
gcgtttatac gaatccctgt gtcagtatcg taagccggat ggctcaggca tcgtctctct   4680
gaaaatcgac tggatcatag agcgttacca gctgcctcaa agttaccagc gtatgcctga   4740
cttccgccgc cgcttcctgc aggtctgtgt taatgagatc aacagcagaa ctccaatgcg   4800
```

cctctcatac attgagaaaa agaaaggccg ccagacgact catatcgtat tttccttccg 4860
cgatatcact tccatgacga caggatagtc tgagggttat ctgtcacaga tttgagggtg 4920
gttcgtcaca tttgttctga cctactgagg gtaatttgtc acagttttgc tgtttccttc 4980
agcctgcatg gattttctca tactttttga actgtaattt ttaaggaagc caaatttgag 5040
ggcagtttgt cacagttgat ttccttctct ttcccttcgt catgtgacct gatatcgggg 5100
gttagttcgt catcattgat gagggttgat tatcacagtt tattactctg aattggctat 5160
ccgcgtgtgt acctctacct ggagtttttc ccacggtgga tatttcttct tgcgctga 5218

<210> SEQ ID NO 108
<211> LENGTH: 880
<212> TYPE: DNA
<213> ORGANISM: Artificial Sequence
<220> FEATURE:
<223> OTHER INFORMATION: sequence of partially deleted Synechocystis upp

<400> SEQUENCE: 108
gagctcggta cccggggatc ccacgcccaa ctggtcacgg acatcgtcga taaccaaatt 60
aagttgggca attttgtctt ccaggcgacg gcgagccaac tcaatatttt cctcactatc 120
gagatttcct accccctcag tgtctaattt ttcccggtcg gggctttggg tagcagctcg 180
attggccagg acagaaccca aaattccccc cactacgcca ccaatgaccg tacctaataa 240
aaatcctccg gcgaagttat ctttttgagc catgacttta ctcctgttgt taacgtttgg 300
gggtgaattt gtaattattt gatcactagt ttaatggtgt tatcaagtac caaagcaacg 360
atcgcctgca tcccctagcg ccaggggagt tttcacttcc gtatccaccg tcggcaacca 420
ataacgagcg gcctcatagg tcaaccaacg tcccaattcc cccatggcag ttttaaacaa 480
aaccggcggc gtgttttcat ccctagctac ccccaaccaa tgcttaatta gaggatgctc 540
cggcacataa acacgtaatt gagaagccat gggaaaactt aaaagttaat atctaaaatt 600
taattttgtt aatcttggcc gttggggaac cgaaaaatgg gctaaaagtt aggacgtggt 660
ctcaccgtcg gtaacaattc accgcggaac tccactgtag ctcagatcgg gttaccggaa 720
gttggggcat tgggaaggga aaggttttct gccatacttt gggcagggat ttcccccaag 780
ttcaacgaca gacaggcaag cattatgagc aaacaaccat cctttgacgg ctggcagtcc 840
attgtgggtg ggatcctcta gagtcgacct gcaggcatgc 880

<210> SEQ ID NO 109
<211> LENGTH: 5800
<212> TYPE: DNA
<213> ORGANISM: Artificial Sequence
<220> FEATURE:
<223> OTHER INFORMATION: plasmid pLybAL6fb containing Synechococcus upp
gene

<400> SEQUENCE: 109
tgcaccatat gcggtgtgaa ataccgcaca gatgcgtaag gagaaaatac cgcatcaggc 60
gccattcgcc attcagctgc gcaactgttg ggaagggcga tcggtgcggg cctcttcgct 120
attacgccag ctggcgaaag ggggatgtgc tgcaaggcga ttaagttggg taacgccagg 180
gttttcccag tcacgacgtt gtaaaacgac ggccagtgaa ttgtaatacg actcactata 240
gggcgaattc gagctcggta cccggggatc ccacggcagc attacggctc agaccttggt 300
catgccctcg acaacagatc tctacttcac cccagaggat tgtgaggccg aagcgcagtt 360
gattcctaag gcgcactatt gcccaattcc ctcgatctgg ggtcaccgcg cgggcaaccc 420

```
cagccaaaat ccgcaggatg aaagcttcat tcggcaggcc gttcaggctt tgctcaacgc    480
tgaagcctag cgaattcagt cagcagatca aggagtacca aacaggcgat cgccagcatc    540
ccccagcccc ggcacgataa agcctttgtc gttcagctgc tcatcaatga tggcgctgta    600
aatcgtcaac gccgggtagg cttgactgag tttttgtagc gctggcgggg cagccacaat    660
tgaaagcacc cgcacttgct cagcagagac accgcgatcg cgcagcaaat caagggtata    720
gagcagcgag ccacctgtcg ccagcatcgg gtcgagaacc agaacgcgac tgttcacttc    780
aagttgctct ggcaggtgat tgaggtagca gcgcggttca agactgactt catcccgctt    840
gagacccacg tgaaaaatgc gggcagtcgg caaaacctgt tggacagact ccactaaacc    900
cagacctgcg cgcagaatcg gcacgatcgc caagggttgc gaaaaatcga cgaactccgc    960
tggggtttct gcaagaggag tttgcaccgc cgctggaatc gttggtagcc attcccgcac   1020
agcctcatag gcgagccagc ggcccagctc tgcgatcgcg gtgcgaaaca gaggcgtcgg   1080
cgtctggcga tcgcgggcaa tgcccagcca gtgccgaatt aagggatggg gcggcacgaa   1140
gatacgcagt tgaggagcca tgccaatcag cagaagacag ctcctgattt taacgttcag   1200
accccagggg aagcggaacg gtgcaggaag gcaagcgctt ctgcttcggg cagtggtggg   1260
ccatagaaga accettgcac agcatcacaa ccaatcgctt ctaagaaggc ggcttgctcg   1320
aggcgttcta cgccttctgc gatcgtgcga agtttcaaga ccttggccat tgcaacaatc   1380
gcctgcacga tcgcttgatc gtcatggtcg tgcggcagat cgcgaataaa gctgcgatca   1440
attttgagag cattgatggg caaacgcttg aggtaaccaa ggctggaata acccgtccca   1500
aaatcatcta aagcgacttg aaatcccatc gatcgggctt cctggagcca ttgcagtggg   1560
atcctctaga gtcgacctgc aggcatgcaa gcttgagtat tctatagtct cacctaaata   1620
gcttggcgta atcatggtca tagctgtttc ctgtgtgaaa ttgttatccg ctcacaattc   1680
cacacaacat acgagccgga agcataaagt gtaaagcctg gggtgcctaa tgagtgagct   1740
aactcacatt aattgcgttg cgctcactgc ccgctttcca gtcgggaaac ctgtcgtgcc   1800
agctgcatta atgaatcggc caacgcgaac cccttgcggc cgcccgggcc gtcgaccaat   1860
tctcatgttt gacagcttat catcgaattt ctgccattca tccgcttatt atcacttatt   1920
caggcgtagc aaccaggcgt ttaagggcac caataactgc cttaaaaaaa ttacgccccg   1980
ccctgccact catcgcagta ctgttgtaat tcattaagca ttctgccgac atggaagcca   2040
tcacaaacgg catgatgaac ctgaatcgcc agcggcatca gcaccttgtc gccttgcgta   2100
taatatttgc ccatggtgaa aacgggggcg aagaagttgt ccatattggc cacgtttaaa   2160
tcaaaactgg tgaaactcac ccagggattg gctgagacga aaaacatatt ctcaataaac   2220
cctttaggga aataggccag gttttcaccg taacacgcca catcttgcga atatatgtgt   2280
agaaactgcc ggaaatcgtc gtggtattca ctccagagcg atgaaaacgt ttcagtttgc   2340
tcatggaaaa cggtgtaaca agggtgaaca ctatcccata tcaccagctc accgtctttc   2400
attgccatac gaaattccgg atgagcattc atcaggcggg caagaatgtg aataaaggcc   2460
ggataaaact tgtgcttatt tttctttacg gtctttaaaa aggccgtaat atccagctga   2520
acggtctggt tataggtaca ttgagcaact gactgaaatg cctcaaaatg ttctttacga   2580
tgccattggg atatatcaac ggtggtatat ccagtgattt ttttctccat tttagcttcc   2640
ttagctcctg aaaatctcga taactcaaaa aatacgcccg gtagtgatct tatttcatta   2700
tggtgaaagt tggaacctct tacgtgccga tcaacgtctc attttcgcca aaagttggcc   2760
cagggcttcc cggtatcaac agggacacca ggatttattt attctgcgaa gtgatcttcc   2820
```

-continued

```
gtcacaggta tttattcgcg ataagctcat ggagcggcgt aaccgtcgca caggaaggac   2880
agagaaagcg cggatctggg aagtgacgga cagaacggtc aggacctgga ttggggaggc   2940
ggttgccgcc gctgctgctg acggtgtgac gttctctgtt ccggtcacac cacatacgtt   3000
ccgccattcc tatgcgatgc acatgctgta tgccggtata ccgctgaaag ttctgcaaag   3060
cctgatggga cataagtcca tcagttcaac ggaagtctac acgaaggttt ttgcgctgga   3120
tgtggctgcc cggcaccggg tgcagtttgc gatgccggag tctgatgcgg ttgcgatgct   3180
gaaacaatta tcctgagaat aaatgccttg gcctttatat ggaaatgtgg aactgagtgg   3240
atatgctgtt tttgtctgtt aaacagagaa gctggctgtt atccactgag aagcgaacga   3300
aacagtcggg aaaatctccc attatcgtag agatccgcat tattaatctc aggagcctgt   3360
gtagcgttta taggaagtag tgttctgtca tgatgcctgc aagcggtaac gaaaacgatt   3420
tgaatatgcc ttcaggaaca atagaaatct tcgtgcggtg ttacgttgaa gtggagcgga   3480
ttatgtcagc aatggacaga acaacctaat gaacacagaa ccatgatgtg gtctgtcctt   3540
ttacagccag tagtgctcgc cgcagtcgag cgacagggcg aagccctcgg ctggttgccc   3600
tcgccgctgg gctggcggcc gtctatggcc ctgcaaacgc gccagaaacg ccgtcgaagc   3660
cgtgtgcgag acaccgcggc cggccgccgg cgttgtggat acctcgcgga aaacttggcc   3720
ctcactgaca gatgaggggc ggacgttgac acttgagggg ccgactcacc cggcgcggcg   3780
ttgacagatg aggggcaggc tcgatttcgg ccggcgacgt ggagctggcc agcctcgcaa   3840
atcggcgaaa acgcctgatt ttacgcgagt ttcccacaga tgatgtggac aagcctgggg   3900
ataagtgccc tgcggtattg acacttgagg ggcgcgacta ctgacagatg aggggcgcga   3960
tccttgacac ttgaggggca gagtgctgac agatgagggg cgcacctatt gacatttgag   4020
gggctgtcca caggcagaaa atccagcatt tgcaagggtt tccgcccgtt tttcggccac   4080
cgctaacctg tcttttaacc tgcttttaaa ccaatattta taaaccttgt ttttaaccag   4140
ggctgcgccc tgtgcgcgtg accgcgcacg ccgaaggggg gtgccccccc ttctcgaacc   4200
ctcccggtcg agtgagcgag gaagcaccag ggaacagcac ttatatattc tgcttacaca   4260
cgatgcctga aaaaacttcc cttggggtta tccacttatc cacggggata tttttataat   4320
tattttttt atagttttta gatcttcttt tttagagcgc cttgtaggcc tttatccatg   4380
ctggttctag agaaggtgtt gtgacaaatt gccctttcag tgtgacaaat caccctcaaa   4440
tgacagtcct gtctgtgaca aattgccctt aaccctgtga caaattgccc tcagaagaag   4500
ctgtttttc acaaagttat ccctgcttat tgactctttt ttatttagtg tgacaatcta   4560
aaaacttgtc acacttcaca tggatctgtc atggcggaaa cagcggttat caatcacaag   4620
aaacgtaaaa atagcccgcg aatcgtccag tcaaacgacc tcactgaggc ggcatatagt   4680
ctctcccggg atcaaaaacg tatgctgtat ctgttcgttg accagatcag aaaatctgat   4740
ggcaccctac aggaacatga cggtatctgc gagatccatg ttgctaaata tgctgaaata   4800
ttcggattga cctctgcgga agccagtaag gatatacggc aggcattgaa gagtttcgcg   4860
gggaaggaag tggtttttta tcgccctgaa gaggatgccg gcgatgaaaa aggctatgaa   4920
tcttttcctt ggtttatcaa acgtgcgcac agtccatcca gagggcttta cagtgtacat   4980
atcaacccat atctcattcc cttctttatc gggttacaga accggtttac gcagtttcgg   5040
cttagtgaaa caaaagaaat caccaatccg tatgccatgc gtttatacga atccctgtgt   5100
cagtatcgta agccggatgg ctcaggcatc gtctctctga aaatcgactg gatcatagag   5160
```

cgttaccagc tgcctcaaag ttaccagcgt atgcctgact tccgccgccg cttcctgcag 5220
gtctgtgtta atgagatcaa cagcagaact ccaatgcgcc tctcatacat tgagaaaaag 5280
aaaggccgcc agacgactca tatcgtattt tccttccgcg atatcacttc catgacgaca 5340
ggatagtctg agggttatct gtcacagatt tgagggtggt tcgtcacatt tgttctgacc 5400
tactgagggt aatttgtcac agttttgctg tttccttcag cctgcatgga ttttctcata 5460
ctttttgaac tgtaattttt aaggaagcca aatttgaggg cagtttgtca cagttgattt 5520
ccttctcttt cccttcgtca tgtgacctga tatcgggggt tagttcgtca tcattgatga 5580
gggttgatta tcacagttta ttactctgaa ttggctatcc gcgtgtgtac ctctacctgg 5640
agtttttccc acggtggata tttcttcttg cgctgagcgt aagagctatc tgacagaaca 5700
gttcttcttt gcttcctcgc cagttcgctc gctatgctcg gttacacggc tgcggcgagc 5760
gctagtgata ataagtgact gaggtatgtg ctcttcttat 5800

<210> SEQ ID NO 110
<211> LENGTH: 5731
<212> TYPE: DNA
<213> ORGANISM: Artificial Sequence
<220> FEATURE:
<223> OTHER INFORMATION: plasmid pLybAL10fb containing partially deleted
Synechococcus upp gene

<400> SEQUENCE: 110
tgcaccatat gcggtgtgaa ataccgcaca gatgcgtaag gagaaaatac cgcatcaggc 60
gccattcgcc attcagctgc gcaactgttg ggaagggcga tcggtgcggg cctcttcgct 120
attacgccag ctggcgaaag ggggatgtgc tgcaaggcga ttaagttggg taacgccagg 180
gttttcccag tcacgacgtt gtaaaacgac ggccagtgaa ttgtaatacg actcactata 240
gggcgaattc gagctcggta cccggggatc ccacggcagc attacggctc agaccttggt 300
catgccctcg acaacagatc tctacttcac cccagaggat tgtgaggccg aagcgcagtt 360
gattcctaag gcgcactatt gcccaattcc ctcgatctgg ggtcaccgcg cgggcaaccc 420
cagccaaaat ccgcaggatg aaagcttcat tcggcaggcc gttcaggctt tgctcaacgc 480
tgaagcctag cgaattcagt cagcagatca aggagtacca aacaggcgat cgccagcatc 540
ccccagcccc ggcacgataa agcctttgtc gttcagctgc tcatcaatga tggcgctgta 600
aatcgtcaac gccgggtagg cttgactgag tttttgtagc gctggcgggg cagccacaat 660
tgaaagcacc cgcacttgct cagcagagac accgcgatcg cgcagcaaat caagggtata 720
gagcagcgag ccacctgtcg ccagcatcgg gtcgagaacc agaacgcgac tgttcacttc 780
aagttgctct ggcaggtgat tgaggtagca gcgcggttca agactgactt catcccgctc 840
gcgcagaatc ggcacgatcg ccaagggttg cgaaaaatcg acgaactccg ctggggtttc 900
tgcaagagga gtttgcaccg ccgctggaat cgttggtagc cattcccgca cagcctcata 960
ggcgagccag cggcccagct ctgcgatcgc ggtgcgaaac agaggcgtcg gcgtctggcg 1020
atcgcgggca atgcccagcc agtgccgaat taagggatgg ggcggcacga agatacgcag 1080
ttgaggagcc atgccaatca gcagaagaca gctcctgatt ttaacgttca gaccccaggg 1140
gaagcggaac ggtgcaggaa ggcaagcgct tctgcttcgg gcagtggtgg gccatagaag 1200
aacccttgca cagcatcaca accaatcgct tctaagaagg cggcttgctc gaggcgttct 1260
acgccttctg cgatcgtgcg aagtttcaag accttggcca ttgcaacaat cgcctgcacg 1320
atcgcttgat cgtcatggtc gtgcggcaga tcgcgaataa agctgcgatc aattttgaga 1380

-continued

```
gcattgatgg gcaaacgctt gaggtaacca aggctggaat aacccgtccc aaaatcatct   1440
aaagcgactt gaaatcccat cgatcgggct tcctggagcc attgcagtgg gatcctctag   1500
agtcgacctg caggcatgca agcttgagta ttctatagtc tcacctaaat agcttggcgt   1560
aatcatggtc atagctgttt cctgtgtgaa attgttatcc gctcacaatt ccacacaaca   1620
tacgagccgg aagcataaag tgtaaagcct ggggtgccta atgagtgagc taactcacat   1680
taattgcgtt gcgctcactg cccgctttcc agtcgggaaa cctgtcgtgc cagctgcatt   1740
aatgaatcgg ccaacgcgaa ccccttgcgg ccgcccgggc cgtcgaccaa ttctcatgtt   1800
tgacagctta tcatcgaatt tctgccattc atccgcttat tatcacttat tcaggcgtag   1860
caaccaggcg tttaagggca ccaataactg ccttaaaaaa attacgcccc gccctgccac   1920
tcatcgcagt actgttgtaa ttcattaagc attctgccga catggaagcc atcacaaacg   1980
gcatgatgaa cctgaatcgc cagcggcatc agcaccttgt cgccttgcgt ataatatttg   2040
cccatggtga aaacgggggc gaagaagttg tccatattgg ccacgtttaa atcaaaactg   2100
gtgaaactca cccagggatt ggctgagacg aaaaacatat tctcaataaa ccctttaggg   2160
aaataggcca ggttttcacc gtaacacgcc acatcttgcg aatatatgtg tagaaactgc   2220
cggaaatcgt cgtggtattc actccagagc gatgaaaacg tttcagtttg ctcatggaaa   2280
acggtgtaac aagggtgaac actatcccat atcaccagct caccgtcttt cattgccata   2340
cgaaattccg gatgagcatt catcaggcgg gcaagaatgt gaataaaggc cggataaaac   2400
ttgtgcttat ttttctttac ggtctttaaa aaggccgtaa tatccagctg aacggtctgg   2460
ttataggtac attgagcaac tgactgaaat gcctcaaaat gttctttacg atgccattgg   2520
gatatatcaa cggtggtata tccagtgatt tttttctcca ttttagcttc cttagctcct   2580
gaaaatctcg ataactcaaa aaatacgccc ggtagtgatc ttatttcatt atggtgaaag   2640
ttggaacctc ttacgtgccg atcaacgtct cattttcgcc aaaagttggc ccagggcttc   2700
ccggtatcaa cagggacacc aggatttatt tattctgcga agtgatcttc cgtcacaggt   2760
atttattcgc gataagctca tggagcggcg taaccgtcgc acaggaagga cagagaaagc   2820
gcggatctgg gaagtgacgg acagaacggt caggacctgg attggggagg cggttgccgc   2880
cgctgctgct gacggtgtga cgttctctgt tccggtcaca ccacatacgt tccgccattc   2940
ctatgcgatg cacatgctgt atgccggtat accgctgaaa gttctgcaaa gcctgatggg   3000
acataagtcc atcagttcaa cggaagtcta cacgaaggtt tttgcgctgg atgtggctgc   3060
ccggcaccgg gtgcagtttg cgatgccgga gtctgatgcg gttgcgatgc tgaaacaatt   3120
atcctgagaa taaatgcctt ggcctttata tggaaatgtg gaactgagtg gatatgctgt   3180
ttttgtctgt taaacagaga agctggctgt tatccactga gaagcgaacg aaacagtcgg   3240
gaaaatctcc cattatcgta gagatccgca ttattaatct caggagcctg tgtagcgttt   3300
ataggaagta gtgttctgtc atgatgcctg caagcggtaa cgaaaacgat ttgaatatgc   3360
cttcaggaac aatagaaatc ttcgtgcggt gttacgttga agtggagcgg attatgtcag   3420
caatggacag aacaacctaa tgaacacaga accatgatgt ggtctgtcct tttacagcca   3480
gtagtgctcg ccgcagtcga gcgacagggc gaagccctcg gctggttgcc ctcgccgctg   3540
ggctggcggc cgtctatggc cctgcaaacg cgccagaaac gccgtcgaag ccgtgtgcga   3600
gacaccgcgg ccggccgccg gcgttgtgga tacctcgcgg aaaacttggc cctcactgac   3660
agatgagggg cggacgttga cacttgaggg gccgactcac ccggcgcggc gttgacagat   3720
gaggggcagg ctcgatttcg gccggcgacg tggagctggc cagcctcgca aatcggcgaa   3780
```

```
aacgcctgat tttacgcgag tttcccacag atgatgtgga caagcctggg gataagtgcc   3840

ctgcggtatt gacacttgag ggcgcgact actgacagat gaggggcgcg atccttgaca   3900

cttgaggggc agagtgctga cagatgaggg gcgcacctat tgacatttga ggggctgtcc   3960

acaggcagaa aatccagcat ttgcaagggt ttccgcccgt ttttcggcca ccgctaacct   4020

gtcttttaac ctgcttttaa accaatattt ataaaccttg tttttaacca gggctgcgcc   4080

ctgtgcgcgt gaccgcgcac gccgaagggg ggtgcccccc cttctcgaac cctcccggtc   4140

gagtgagcga ggaagcacca gggaacagca cttatatatt ctgcttacac acgatgcctg   4200

aaaaaacttc ccttggggtt atccacttat ccacggggat atttttataa ttattttttt   4260

tatagttttt agatcttctt ttttagagcg ccttgtaggc ctttatccat gctggttcta   4320

gagaaggtgt tgtgacaaat tgccctttca gtgtgacaaa tcaccctcaa atgacagtcc   4380

tgtctgtgac aaattgccct taaccctgtg acaaattgcc ctcagaagaa gctgtttttt   4440

cacaaagtta tccctgctta ttgactcttt tttatttagt gtgacaatct aaaaacttgt   4500

cacacttcac atggatctgt catggcggaa acagcggtta tcaatcacaa gaaacgtaaa   4560

aatagcccgc gaatcgtcca gtcaaacgac ctcactgagg cggcatatag tctctcccgg   4620

gatcaaaaac gtatgctgta tctgttcgtt gaccagatca gaaaatctga tggcacccta   4680

caggaacatg acggtatctg cgagatccat gttgctaaat atgctgaaat attcggattg   4740

acctctgcgg aagccagtaa ggatatacgg caggcattga agagtttcgc ggggaaggaa   4800

gtggtttttt atcgccctga agaggatgcc ggcgatgaaa aaggctatga atcttttcct   4860

tggtttatca aacgtgcgca cagtccatcc agagggcttt acagtgtaca tatcaaccca   4920

tatctcattc ccttctttat cgggttacag aaccggttta cgcagtttcg gcttagtgaa   4980

acaaaagaaa tcaccaatcc gtatgccatg cgtttatacg aatccctgtg tcagtatcgt   5040

aagccggatg gctcaggcat cgtctctctg aaaatcgact ggatcataga gcgttaccag   5100

ctgcctcaaa gttaccagcg tatgcctgac ttccgccgcc gcttcctgca ggtctgtgtt   5160

aatgagatca acagcagaac tccaatgcgc ctctcataca ttgagaaaaa gaaaggccgc   5220

cagacgactc atatcgtatt ttccttccgc gatatcactt ccatgacgac aggatagtct   5280

gagggttatc tgtcacagat ttgagggtgg ttcgtcacat ttgttctgac ctactgaggg   5340

taatttgtca cagttttgct gtttccttca gcctgcatgg attttctcat actttttgaa   5400

ctgtaatttt taaggaagcc aaatttgagg gcagtttgtc acagttgatt tccttctctt   5460

tcccttcgtc atgtgacctg atatcggggg ttagttcgtc atcattgatg agggttgatt   5520

atcacagttt attactctga attggctatc cgcgtgtgta cctctacctg gagtttttcc   5580

cacggtggat atttcttctt gcgctgagcg taagagctat ctgacagaac agttcttctt   5640

tgcttcctcg ccagttcgct cgctatgctc ggttacacgg ctgcggcgag cgctagtgat   5700

aataagtgac tgaggtatgt gctcttctta t                                  5731
```

<210> SEQ ID NO 111
<211> LENGTH: 651
<212> TYPE: DNA
<213> ORGANISM: Synechocystis PCC6803

<400> SEQUENCE: 111

```
atggcttctc aattacgtgt ttatgtgccg gagcatcctc taattaagca ttggttgggg     60

gtagctaggg atgaaaacac gccgccggtt ttgtttaaaa ctgccatggg ggaattggga    120
```

```
cgttggttga cctatgaggc cgctcgttat tggttgccga cggtggatac ggaagtgaaa    180

actcccctgg cgatcgccaa ggccagtctt attgaccccc aaacgccctt tgtcattgtg    240

cccattttgc gggcggggtt ggctctggtg gaaggggccc aggggttgtt gcccctggca    300

aaaatttacc atctgggttt agtgcgcaat gaaactaccc tggaacctag tctgtatctg    360

aacaagttgc cggagcggtt tgcccccggt acccatcttt tgttgctaga tcccatgttg    420

gctacgggta ataccatcat ggctgctttg gatttgctga tggcccggga cattgatgcc    480

aatttaatcc gtttggtctc cgtggtggcc gcccccactg ccctgcaaaa attaagtaat    540

gcccatccca atttgaccat ctacaccgcc atgattgacg aacaactcaa tgaccggggt    600

tacattgtgc ccggcctagg ggatgcaggc gatcgttgct ttggtacttg a             651
```

<210> SEQ ID NO 112
<211> LENGTH: 216
<212> TYPE: PRT
<213> ORGANISM: Synechocystis PCC6803

<400> SEQUENCE: 112

```
Met Ala Ser Gln Leu Arg Val Tyr Val Pro Glu His Pro Leu Ile Lys
1               5                   10                  15

His Trp Leu Gly Val Ala Arg Asp Glu Asn Thr Pro Pro Val Leu Phe
            20                  25                  30

Lys Thr Ala Met Gly Glu Leu Gly Arg Trp Leu Thr Tyr Glu Ala Ala
        35                  40                  45

Arg Tyr Trp Leu Pro Thr Val Asp Thr Glu Val Lys Thr Pro Leu Ala
    50                  55                  60

Ile Ala Lys Ala Ser Leu Ile Asp Pro Gln Thr Pro Phe Val Ile Val
65                  70                  75                  80

Pro Ile Leu Arg Ala Gly Leu Ala Leu Val Glu Gly Ala Gln Gly Leu
                85                  90                  95

Leu Pro Leu Ala Lys Ile Tyr His Leu Gly Leu Val Arg Asn Glu Thr
            100                 105                 110

Thr Leu Glu Pro Ser Leu Tyr Leu Asn Lys Leu Pro Glu Arg Phe Ala
        115                 120                 125

Pro Gly Thr His Leu Leu Leu Leu Asp Pro Met Leu Ala Thr Gly Asn
    130                 135                 140

Thr Ile Met Ala Ala Leu Asp Leu Leu Met Ala Arg Asp Ile Asp Ala
145                 150                 155                 160

Asn Leu Ile Arg Leu Val Ser Val Val Ala Ala Pro Thr Ala Leu Gln
                165                 170                 175

Lys Leu Ser Asn Ala His Pro Asn Leu Thr Ile Tyr Thr Ala Met Ile
            180                 185                 190

Asp Glu Gln Leu Asn Asp Arg Gly Tyr Ile Val Pro Gly Leu Gly Asp
        195                 200                 205

Ala Gly Asp Arg Cys Phe Gly Thr
    210                 215
```

<210> SEQ ID NO 113
<211> LENGTH: 654
<212> TYPE: DNA
<213> ORGANISM: Synechococcus PCC7942

<400> SEQUENCE: 113

```
atggctcctc aactgcgtat cttcgtgccg ccccatccct taattcggca ctggctgggc     60

attgcccgcg atcgccagac gccgacgcct ctgtttcgca ccgcgatcgc agagctgggc    120
```

```
cgctggctcg cctatgaggc tgtgcgggaa tggctaccaa cgattccagc ggcggtgcaa    180

actcctcttg cagaaacccc agcggagttc gtcgattttt cgcaaccctt ggcgatcgtg    240

ccgattctgc gcgcaggtct gggtttagtg gagtctgtcc aacaggtttt gccgactgcc    300

cgcatttttc acgtgggtct caagcgggat gaagtcagtc ttgaaccgcg ctgctacctc    360

aatcacctgc cagagcaact tgaagtgaac agtcgcgttc tggttctcga cccgatgctg    420

gcgacaggtg gctcgctgct ctataccctt gatttgctgc gcgatcgcgg tgtctctgct    480

gagcaagtgc gggtgctttc aattgtggct gccccgccag cgctacaaaa actcagtcaa    540

gcctacccgg cgttgacgat ttacagcgcc atcattgatg agcagctgaa cgacaaaggc    600

tttatcgtgc cggggctggg ggatgctggc gatcgcctgt ttggtactcc ttga          654
```

<210> SEQ ID NO 114
<211> LENGTH: 217
<212> TYPE: PRT
<213> ORGANISM: Synechococcus PCC7942

<400> SEQUENCE: 114

```
Met Ala Pro Gln Leu Arg Ile Phe Val Pro Pro His Pro Leu Ile Arg
1               5                   10                  15

His Trp Leu Gly Ile Ala Arg Asp Arg Gln Thr Pro Thr Pro Leu Phe
            20                  25                  30

Arg Thr Ala Ile Ala Glu Leu Gly Arg Trp Leu Ala Tyr Glu Ala Val
        35                  40                  45

Arg Glu Trp Leu Pro Thr Ile Pro Ala Ala Val Gln Thr Pro Leu Ala
    50                  55                  60

Glu Thr Pro Ala Glu Phe Val Asp Phe Ser Gln Pro Leu Ala Ile Val
65                  70                  75                  80

Pro Ile Leu Arg Ala Gly Leu Gly Leu Val Glu Ser Val Gln Gln Val
                85                  90                  95

Leu Pro Thr Ala Arg Ile Phe His Val Gly Leu Lys Arg Asp Glu Val
            100                 105                 110

Ser Leu Glu Pro Arg Cys Tyr Leu Asn His Leu Pro Glu Gln Leu Glu
        115                 120                 125

Val Asn Ser Arg Val Leu Val Leu Asp Pro Met Leu Ala Thr Gly Gly
    130                 135                 140

Ser Leu Leu Tyr Thr Leu Asp Leu Leu Arg Asp Arg Gly Val Ser Ala
145                 150                 155                 160

Glu Gln Val Arg Val Leu Ser Ile Val Ala Ala Pro Pro Ala Leu Gln
                165                 170                 175

Lys Leu Ser Gln Ala Tyr Pro Ala Leu Thr Ile Tyr Ser Ala Ile Ile
            180                 185                 190

Asp Glu Gln Leu Asn Asp Lys Gly Phe Ile Val Pro Gly Leu Gly Asp
        195                 200                 205

Ala Gly Asp Arg Leu Phe Gly Thr Pro
    210                 215
```

<210> SEQ ID NO 115
<211> LENGTH: 2184
<212> TYPE: DNA
<213> ORGANISM: Artificial Sequence
<220> FEATURE:
<223> OTHER INFORMATION: PCR product
<220> FEATURE:
<221> NAME/KEY: misc_feature
<222> LOCATION: (7)..(12)

-continued

<223> OTHER INFORMATION: AflI restriction site
<220> FEATURE:
<221> NAME/KEY: misc_feature
<222> LOCATION: (2173)..(2178)
<223> OTHER INFORMATION: NheI restriction site

<400> SEQUENCE: 115
ttgcatctta agaaggagga tccatatgat cttgatggaa cgctggcgga aatcaaaccg 60
catcccgatc aggtcgtcgt gcctgacaat attctgcaag gactacagct actggcaacc 120
gcaagtgatg gtgcattggc attgatatca gggcgctcaa tggtggagct tgacgcactg 180
gcaaaacctt atcgcttccc gttagcgggc gtgcatgggg cggagcgccg tgacatcaat 240
ggtaaaacac atatcgttca tctgccggat gcgattgcgc gtgatattag cgtgcaactg 300
catacagtca tcgctcagta tcccggcgcg gagctggagg cgaaagggat ggcttttgcg 360
ctgcattatc gtcaggctcc gcagcatgaa gacgcattaa tgacattagc gcaacgtatt 420
actcagatct ggccacaaat ggcgttacag cagggaaagt gtgttgtcga gatcaaaccg 480
agaggtacca gtaaaggtga ggcaattgca gcttttatgc aggaagctcc ctttatcggg 540
cgaacgcccg tatttctggg cgatgattta accgatgaat ctggcttcgc agtcgttaac 600
cgactgggcg gaatgtcagt aaaaattggc acaggtgcaa ctcaggcatc atggcgactg 660
gcgggtgtgc cggatgtctg gagctggctt gaaatgataa ccaccgcatt acaacaaaaa 720
agagaaaata acaggagtga tgactatgag tcgtttagtc gtagtatcta accggattgc 780
accaccagac gagcacgccg ccagtgccgg tggccttgcc gttggcatac tgggggcact 840
gaaagccgca ggcggactgt ggtttggctg gagtggtgaa acagggaatg aggatcagcc 900
gctaaaaaag gtgaaaaaag gtaacattac gtgggcctct tttaacctca gcgaacagga 960
ccttgacgaa tactacaacc aattctccaa tgccgttctc tggcccgctt ttcattatcg 1020
gctcgatctg gtgcaatttc agcgtcctgc ctgggacggc tatctacgcg taaatgcgtt 1080
gctggcagat aaattactgc cgctgttgca agacgatgac attatctgga tccacgatta 1140
tcacctgttg ccatttgcgc atgaattacg caaacgggga gtgaataatc gcattggttt 1200
ctttctgcat attcctttcc cgacaccgga aatcttcaac gcgctgccga catatgacac 1260
cttgcttgaa cagctttgtg attatgattt gctgggtttc cagacagaaa acgatcgtct 1320
ggcgttcctg gattgtcttt ctaacctgac ccgcgtcacg acacgtagcg caaaaagcca 1380
tacagcctgg ggcaaagcat ttcgaacaga agtctacccg atcggcattg aaccgaaaga 1440
aatagccaaa caggctgccg ggccactgcc gccaaaactg gcgcaactta aagcggaact 1500
gaaaaacgta caaaatatct tttctgtcga acggctggat tattccaaag gtttgccaga 1560
gcgttttctc gcctatgaag cgttgctgga aaaatatccg cagcatcatg gtaaaattcg 1620
ttatacccag attgcaccaa cgtcgcgtgg tgatgtgcaa gcctatcagg atattcgtca 1680
tcagctcgaa aatgaagctg gacgaattaa tggtaaatac gggcaattag gctggacgcc 1740
gctttattat ttgaatcagc attttgaccg taaattactg atgaaaatat tccgctactc 1800
tgacgtgggc ttagtgacgc cactgcgtga cgggatgaac ctggtagcaa aagagtatgt 1860
tgctgctcag gacccagcca atccgggcgt tcttgttctt tcgcaatttg cgggagcggc 1920
aaacgagtta acgtcggcgt taattgttaa cccctacgat cgtgacgaag ttgcagctgc 1980
gctggatcgt gcattgacta tgtcgctggc ggaacgtatt tcccgtcatg cagaaatgct 2040
ggacgttatc gtgaaaaacg atattaacca ctggcaggag tgcttcatta gcgacctaaa 2100
gcagatagtt ccgcgaagcg cggaaagcca gcagcgcgat aaagttgcta cctttccaaa 2160
gcttgcgtag gagctagcaa tctc 2184

<210> SEQ ID NO 116
<211> LENGTH: 46
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: AflI restriction site

<400> SEQUENCE: 116
ttgcatctta agaaggagga tccatatgat cttgatggaa cgctgg 46

<210> SEQ ID NO 117
<211> LENGTH: 28
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: NheI restriction site

<400> SEQUENCE: 117
gagattgcta gctcctacgc aagctttg 28

<210> SEQ ID NO 118
<211> LENGTH: 12051
<212> TYPE: DNA
<213> ORGANISM: Artificial Sequence
<220> FEATURE:
<223> OTHER INFORMATION: plasmid pLybAL23 containing otsBA operon

<400> SEQUENCE: 118
aggcccagtc tttcgactga gcctttcgtt ttatttgatg cctggcagtt ccctactctc 60
gcatggggag accccacact accatcggcg ctacggcgtt tcacttctga gttcggcatg 120
gggtcaggtg ggaccaccgc gctactgccg ccaggcaaat tctgttttat cagaccgctt 180
ctgcgttctg atttaatctg tatcaggctg aaaatcttct ctcatccgcc aaaacagcca 240
agcttgcatg cctgcaggtc gactctagat ggctacgagg gcagacagta agtggattta 300
ccataatccc ttaattgtac gcaccgctaa aacgcgttca gcgcgatcac ggcagcagac 360
aggtaaaaat ggcaacaaac caccctaaaa actgcgcgat cgcgcctgat aaattttaac 420
cgtatgaata cctatgcaac cagagggtac aggccacatt acccccactt aatccactga 480
agctgccatt tttcatggtt tcaccatccc agcgaagggc catgcatgca tcgaaattaa 540
tacgacgaaa ttaatacgac tcactatagg gcaattgtta tcagctatgc gccgaccaga 600
acaccttgcc gatcagccaa acgtctcttc aggccactga ctagcgataa ctttccccac 660
aacggaacaa ctctcactgc atgggatcat tgggtactgt gggtttagtg gttgtaaaaa 720
cacctgaccg ctatccctga tcagtttctt gaaggtaaac tcatcacccc caagtctggc 780
tatgcagaaa tcacctggct caacagcctg ctcagggtca acgagaatta acattccgtc 840
aggaaagctt ggcttggagc ctgttggtgc ggtcatggaa ttaccttcaa cctcaagcca 900
gaatgcagaa tcactggctt tcttggttgt gcttacccat ctctccgcat cacctttggt 960
aaaggttcta agcttaggtg agaacatccc tgcctgaaca tgagaaaaaa cagggtactc 1020

-continued

```
atactcactt ctaagtgacg gctgcatact aaccgcttca tacatctcgt agatttctct   1080
ggcgattgaa gggctaaatt cttcaacgct aactttgaga atttttgtaa gcaatgcggc   1140
gttataagca tttaatgcat tgatgccatt aaataaagca ccaacgcctg actgccccat   1200
ccccatcttg tctgcgacag attcctggga taagccaagt tcatttttct tttttcata    1260
aattgcttta aggcgacgtg cgtcctcaag ctgctcttgt gttaatggtt tctttttgt    1320
gctcatacgt taaatctatc accgcaaggg ataaatatct aacaccgtgc gtgttgacta   1380
ttttacctct ggcggtgata atggttgcat cttaagaagg aggatccata tgatcttgat   1440
ggaacgctgg cggaaatcaa accgcatccc gatcaggtcg tcgtgcctga caatattctg   1500
caaggactac agctactggc aaccgcaagt gatggtgcat tggcattgat atcagggcgc   1560
tcaatggtgg agcttgacgc actggcaaaa ccttatcgct tcccgttagc gggcgtgcat   1620
ggggcggagc gccgtgacat caatggtaaa acacatatcg ttcatctgcc ggatgcgatt   1680
gcgcgtgata ttagcgtgca actgcataca gtcatcgctc agtatcccgg cgcggagctg   1740
gaggcgaaag ggatggcttt tgcgctgcat tatcgtcagg ctccgcagca tgaagacgca   1800
ttaatgacat tagcgcaacg tattactcag atctggccac aaatggcgtt acagcaggga   1860
aagtgtgttg tcgagatcaa accgagaggt accagtaaag gtgaggcaat tgcagctttt   1920
atgcaggaag ctccctttat cgggcgaacg cccgtatttc tgggcgatga tttaaccgat   1980
gaatctggct tcgcagtcgt taaccgactg ggcggaatgt cagtaaaaat tggcacaggt   2040
gcaactcagg catcatggcg actggcgggt gtgccggatg tctggagctg gcttgaaatg   2100
ataaccaccg cattacaaca aaaaagagaa aataacagga gtgatgacta tgagtcgttt   2160
agtcgtagta tctaaccgga ttgcaccacc agacgagcac gccgccagtg ccggtggcct   2220
tgccgttggc atactggggg cactgaaagc cgcaggcgga ctgtggtttg gctggagtgg   2280
tgaaacaggg aatgaggatc agccgctaaa aaaggtgaaa aaaggtaaca ttacgtgggc   2340
ctcttttaac ctcagcgaac aggaccttga cgaatactac aaccaattct ccaatgccgt   2400
tctctggccc gcttttcatt atcggctcga tctggtgcaa tttcagcgtc ctgcctggga   2460
cggctatcta cgcgtaaatg cgttgctggc agataaatta ctgccgctgt tgcaagacga   2520
tgacattatc tggatccacg attatcacct gttgccattt gcgcatgaat tacgcaaacg   2580
gggagtgaat aatcgcattg gtttctttct gcatattcct ttcccgacac cggaaatctt   2640
caacgcgctg ccgacatatg acaccttgct tgaacagctt tgtgattatg atttgctggg   2700
tttccagaca gaaaacgatc gtctggcgtt cctggattgt ctttctaacc tgacccgcgt   2760
cacgacacgt agcgcaaaaa gccatacagc ctggggcaaa gcatttcgaa cagaagtcta   2820
cccgatcggc attgaaccga aagaaatagc caaacaggct gccgggccac tgccgccaaa   2880
actggcgcaa cttaaagcgg aactgaaaaa cgtacaaaat atcttttctg tcgaacggct   2940
ggattattcc aaaggtttgc cagagcgttt tctcgcctat gaagcgttgc tggaaaaata   3000
tccgcagcat catggtaaaa ttcgttatac ccagattgca ccaacgtcgc gtggtgatgt   3060
gcaagcctat caggatattc gtcatcagct cgaaaatgaa gctggacgaa ttaatggtaa   3120
atacgggcaa ttaggctgga cgccgcttta ttatttgaat cagcattttg accgtaaatt   3180
actgatgaaa atattccgct actctgacgt gggcttagtg acgccactgc gtgacgggat   3240
gaacctggta gcaaaagagt atgttgctgc tcaggaccca gccaatccgg gcgttcttgt   3300
tctttcgcaa tttgcgggag cggcaaacga gttaacgtcg gcgttaattg ttaaccccta   3360
cgatcgtgac gaagttgcag ctgcgctgga tcgtgcattg actatgtcgc tggcggaacg   3420
```

-continued

```
tatttcccgt catgcagaaa tgctggacgt tatcgtgaaa aacgatatta accactggca   3480
ggagtgcttc attagcgacc taaagcagat agttccgcga agcgcggaaa gccagcagcg   3540
cgataaagtt gctacctttc caaagcttgc gtaggagcta gctgcctcga aaggggatgc   3600
gattcgccac ctctcactcc gctggcggat tcctcttgag aacattttgg tggcaggcga   3660
ttctggtaac gatgaggaaa tgctcaaggg ccataatctc ggcgttgtag ttggcaatta   3720
ctcaccggaa ttggagccac tgcgcagcta cgagcgcgtc tattttgctg agggccacta   3780
tgctaatggc attctggaag ccttaaaaca ctatcgcttt tttgaggcga tcgcttaacc   3840
ttttcagaat gagacgttga tcggcacgta agcgtgagac gttgatcggc acgtaagagg   3900
ttccaacttt caccataatg aaataagatc actaccgggc gtattttttg agttatcgag   3960
attttcagga gctaaggaag ctaaaatgga gaaaaaaatc actggatata ccaccgttga   4020
tatatcccaa tggcatcgta aagaacattt tgaggcattt cagtcagttg ctcaatgtac   4080
ctataaccag accgttcagc tggatattac ggccttttta aagaccgtaa agaaaaataa   4140
gcacaagttt tatccggcct ttattcacat tcttgcccgc ctgatgaatg ctcatccgga   4200
attccgtatg gcaatgaaag acggtgagct ggtgatatgg gatagtgttc acccttgtta   4260
caccgttttc catgagcaaa ctgaaacgtt ttcatcgctc tggagtgaat accacgacga   4320
tttccggcag tttctacaca tatattcgca agatgtggcg tgttacggtg aaaacctggc   4380
ctatttccct aaagggttta ttgagaatat gtttttcgtc tcagccaatc cctgggtgag   4440
tttcaccagt tttgatttaa acgtggccaa tatggacaac ttcttcgccc ccgttttcac   4500
catgggcaaa tattatacgc aaggcgacaa ggtgctgatg ccgctggcga ttcaggttca   4560
tcatgccgtt tgtgatggct tccatgtcgg cagaatgctt aatgaattac aacagtactg   4620
cgatgagtgg cagggcgggg cgtaattttt ttaaggcagt tattggtgcc cttaaacgcc   4680
tggttgctac gcctgaataa gtgataataa gcggatgaat ggcagaaatt cgatgataag   4740
ctgtcaaaca caaccaccat caaacaggat tttcgcctgc tggggcaaac cagcgtggac   4800
cgcttgctgc aactctctca gggccaggcg gtgaagggca atcagctgtt gcccgtctca   4860
ctggtgaaaa gaaaaaccac cctggcgccc aatacgcaaa ccgcctctcc ccgcgcgttg   4920
gccgattcat taatgcagct ggcacgacag gtttcccgac tggaaagcgg gcagtgagcg   4980
caacgcaatt aatgtaagtt agcgcgaatt gcaagctggc cgacgcgctg ggctacgtct   5040
tgctggcgtt cgggagcaga agagcataca tctggaagca aagccaggaa agcggcctat   5100
ggagctgtgc ggcagcgctc agtaggcaat tttttcaaaat attgttaagc cttttctgag   5160
catggtattt ttcatggtat taccaattag caggaaaata agccattgaa tataaaagat   5220
aaaaatgtct tgtttacaat agagtggggg gggtcagcct gccgccttgg gccgggtgat   5280
gtcgtacttg cccgccgcga actcggttac cgtccagccc agcgcgacca gctccggcaa   5340
cgcctcgcgc acccgcttgc ggcgcttgcg catggtcgaa ccactggcct ctgacggcca   5400
gacatagccg cacaaggtat ctatggaagc cttgccggtt ttgccggggt cgatccagcc   5460
acacagccgc tggtgcagca ggcgggcggt ttcgctgtcc agcgcccgca cctcgtccat   5520
gctgatgcgc acatgctggc cgccacccat gacggcctgc gcgatcaagg ggttcagggc   5580
cacgtacagg cgcccgtccg cctcgtcgct ggcgtactcc gacagcagcc gaaacccctg   5640
ccgcttgcgg ccattctggg cgatgatgga taccttccaa aggcgctcga tgcagtcctg   5700
tatgtgcttg agcgccccac cactatcgac ctctgccccg atttcctttg ccagcgcccg   5760
```

-continued

```
atagctacct ttgaccacat ggcattcagc ggtgacggcc tcccacttgg gttccaggaa   5820
cagccggagc tgccgtccgc cttcggtctt gggttccggg ccaagcacta ggccattagg   5880
cccagccatg gccaccagcc cttgcaggat gcgcagatca tcagcgccca gcggctccgg   5940
gccgctgaac tcgatccgct tgccgtcgcc gtagtcatac gtcacgtcca gcttgctgcg   6000
cttgcgctcg ccccgcttga gggcacggaa caggccgggg gccagacagt gcgccgggtc   6060
gtgccggacg tggctgaggc tgtgcttgtt cttaggcttc accacggggc accccccttgc   6120
tcttgcgctg cctctccagc acggcgggct tgagcacccc gccgtcatgc cgcctgaacc   6180
accgatcagc gaacggtgcg ccatagttgg ccttgctcac accgaagcgg acgaagaacc   6240
ggcgctggtc gtcgtccaca ccccattcct cggcctcggc gctggtcatg ctcgacaggt   6300
aggactgcca gcggatgtta tcgaccagta ccgagctgcc ccggctggcc tgctgctggt   6360
cgcctgcgcc catcatggcc gcgcccttgc tggcatggtg caggaacacg atagagcacc   6420
cggtatcggc ggcgatggcc tccatgcgac cgatgacctg ggccatgggg ccgctggcgt   6480
tttcttcctc gatgtggaac cggcgcagcg tgtccagcac catcaggcgg cggccctcgg   6540
cggcgcgctt gaggccgtcg aaccactccg gggccatgat gttgggcagg ctgccgatca   6600
gcggctggat cagcaggccg tcagccacgg cttgccgttc ctcggcgctg aggtgcgccc   6660
caagggcgtg caggcggtga tgaatggcgg tgggcgggtc ttcggcgggc aggtagatca   6720
ccgggccggt gggcagttcg cccacctcca gcagatccgg cccgcctgca atctgtgcgg   6780
ccagttgcag ggccagcatg gatttaccgg caccaccggg cgacaccagc gccccgaccg   6840
taccggccac catgttgggc aaaacgtagt ccagcggtgg cggcgctgct gcgaacgcct   6900
ccagaatatt gataggctta tgggtagcca ttgattgcct cctttgcagg cagttggtgg   6960
ttaggcgctg gcggggtcac tacccccgcc ctgcgccgct ctgagttctt ccaggcactc   7020
gcgcagcgcc tcgtattcgt cgtcggtcag ccagaacttg cgctgacgca tccctttggc   7080
cttcatgcgc tcggcatatc gcgcttggcg tacagcgtca gggctggcca gcaggtcgcc   7140
ggtctgcttg tccttttggt ctttcatatc agtcaccgag aaacttgccg gggccgaaag   7200
gcttgtcttc gcggaacaag gacaaggtgc agccgtcaag gttaaggctg gccatatcag   7260
cgactgaaaa gcggccagcc tcggccttgt ttgacgtata accaaagcca ccgggcaacc   7320
aatagccctt gtcacttttg atcaggtaga ccgaccctga agcgcttttt tcgtattcca   7380
taaaaccccc ttctgtgcgt gagtactcat agtataacag gcgtgagtac caacgcaagc   7440
actacatgct gaaatctggc ccgcccctgt ccatgcctcg ctggcggggt gccggtgccc   7500
gtgccagctc ggcccgcgca agctggacgc tgggcagacc catgaccttg ctgacggtgc   7560
gctcgatgta atccgcttcg tggccgggct tgcgctctgc cagcgctggg ctggcctcgg   7620
ccatggcctt gccgatttcc tcggcactgc ggccccggct ggccagcttc tgcgcggcga   7680
taaagtcgca cttgctgagg tcatgaccga agcgcttgac cagcccggcc atctcgctgc   7740
ggtactcgtc cagcgccgtg cgccggtggc ggctaagctg ccgctcgggc agttcgaggc   7800
tggccagcct gcgggccttc tcctgctgcc gctgggcctg ctcgatctgc tggccagcct   7860
gctgcaccag cgccgggcca gcggtggcgg tcttgccctt ggattcacgc agcagcaccc   7920
acggctgata accggcgcgg gtggtgtgct tgtccttgcg gttggtgaag cccgccaagc   7980
ggccatagtg gcggctgtcg gcgctggccg ggtcggcgtc gtactcgctg gccagcgtcc   8040
gggcaatctg cccccgaagt tcaccgcctg cggcgtcggc caccttgacc catgcctgat   8100
agttcttcgg gctggtttcc actaccaggg caggctcccg gccctcggct ttcatgtcat   8160
```

ccaggtcaaa ctcgctgagg tcgtccacca gcaccagacc atgccgctcc tgctcggcgg 8220
gcctgatata cacgtcattg ccctgggcat tcatccgctt gagccatggc gtgttctgga 8280
gcacttcggc ggctgaccat tcccggttca tcatctggcc ggtgggtgcg tccctgacgc 8340
cgatatcgaa gcgctcacag cccatggcct tgagctgtcg gcctatggcc tgcaaagtcc 8400
tgtcgttctt catcgggcca ccaagcgcag ccagatcgag ccgtcctcgg ttgtcagtgg 8460
cgtcaggtcg agcaagagca acgatgcgat cagcagcacc accgtaggca tcatggaagc 8520
cagcatcacg gttagccata gcttccagtg ccaccccgc gacgcgctcc gggcgctctg 8580
cgcggcgctg ctcacctcgg cggctacctc ccgcaactct ttggccagct ccacccatgc 8640
cgcccctgtc tggcgctggg ctttcagcca ctccgccgcc tgcgcctcgc tggcctgctt 8700
ggtctggctc atgacctgcc gggcttcgtc ggccagtgtc gccatgctct gggccagcgg 8760
ttcgatctgc tccgctaact cgttgatgcc tctggatttc ttcactctgt cgattgcgtt 8820
catggtctat tgcctcccgg tattcctgta agtcgatgat ctgggcgttg gcggtgtcga 8880
tgttcagggc cacgtctgcc cggtcggtgc ggatgccccg gccttccatc tccaccacgt 8940
tcggccccag gtgaacaccg ggcaggcgct cgatgccctg cgcctcaagt gttctgtggt 9000
caatgcgggc gtcgtggcca gcccgctcta atgcccggtt ggcatggtcg gcccatgcct 9060
cgcgggtctg ctcaagccat gccttgggct tgagcgcttc ggtcttctgt gccccgccct 9120
tctccggggt cttgccgttg taccgcttga accactgagc ggcgggccgc tcgatgccgt 9180
cattgatccg ctcggagatc atcaggtggc agtgcgggtt ctcgccgcca ccggcatgga 9240
tggccagcgt atacggcagg cgctcggcac cggtcaggtg ctgggcgaac tcggacgcca 9300
gcgccttctg ctggtcgagg gtcagctcga ccggcagggc aaattcgacc tccttgaaca 9360
gccgcccatt ggcgcgttca tacaggtcgg cagcatccca gtagtcggcg ggccgctcga 9420
cgaactccgg catgtgcccg gattcggcgt gcaagacttc atccatgtcg cgggcatact 9480
tgccttcgcg ctggatgtag tcggccttgg ccctggccga ttggccgccc gacctgctgc 9540
cggttttcgc cgtaaggtga taaatcgcca tgctgcctcg ctgttgcttt tgcttttcgg 9600
ctccatgcaa tggccctcgg agagcgcacc gcccgaaggg tggccgttag gccagtttct 9660
cgaagagaaa ccggtaagtg cgccctcccc tacaaagtag ggtcgggatt gccgccgctg 9720
tgcctccatg atagcctacg agacagcaca ttaacaatgg ggtgtcaaga tggttaaggg 9780
gagcaacaag gcggcggatc ggctggccaa gctcgaagaa caacgagcgc gaatcaatgc 9840
cgaaattcag cgggagcggg caagggaaca gcagcaagag cgcaagaacg aaacaaggcg 9900
caaggtgctg gtgggggcca tgattttggc caaggtgaac agcagcgagt ggccggagga 9960
tcggctcatg gcggcaatgg atgcgtacct tgaacgcgac cacgaccgcg ccttgttcgg 10020
tctgccgcca cgccagaagg atgagccggg ctgaatgatc gaccgagaca ggccctgcgg 10080
ggctgcacac gcgcccccac ccttcgggta gggggaaagg ccgctaaagc ggctaaaagc 10140
gctccagcgt atttctgcgg ggtttggtgt ggggtttagc gggctttgcc cgcctttccc 10200
cctgccgcgc agcggtgggg cggtgtgtag cctagcgcag cgaatagacc agctatccgg 10260
cctctggccg ggcatattgg gcaagggcag cagcgcccca caagggcgct gataaccgcg 10320
cctagtggat tattcttaga taatcatgga tggatttttc caacaccccg ccagcccccg 10380
cccctgctgg gtttgcaggt ttgggggcgt gacagttatt gcaggggttc gtgacagtta 10440
ttgcaggggg gcgtgacagt tattgcaggg gttcgtgaca gttagtacgg gagtgacggg 10500
cactggctgg caatgtctag caacggcagg catttcggct gagggtaaaa gaactttccg 10560
ctaagcgata gactgtatgt aaacacagta ttgcaaggac gcggaacatg cctcatgtgg 10620
cggccaggac ggccagccgg gatcgggata ctggtcgtta ccagagccac cgacccgagc 10680
aaacccttct ctatcagatc gttgacgagt attacccggc attcgctgcg cttatggcag 10740
agcagggaaa ggaattgccg ggctatgtgc aacgggaatt tgaagaattt ctccaatgcg 10800
ggcggctgga gcatggcttt ctacgggttc gctgcgagtc ttgccacgcc gagcacctgg 10860
tcgctttcag aaatcaatct aaagtatata tgagtaaact tggtctgaca gttaccaatg 10920
cttaatcagt gaggcaccta tctcagcgat ctgtctattt cgttcatcca tagttgcctg 10980
actccccgtc gtgtagataa ctacgatacg ggagggctta ccatctggcc ccagtgctgc 11040
aatgataccg cgagacccac gctcaccggc tccagattta tcagcaataa accagccagc 11100
cggaagggcc gagcgcagaa gtggtcctgc aactttatcc gcctccatcc agtctattaa 11160
ttgttgccgg gaagctagag taagtagttc gccagttaat agtttgcgca acgttgttgc 11220
cattgctaca ggcatcgtgg tgtcacgctc gtcgtttggt atggcttcat tcagctccgg 11280
ttcccaacga tcaaggcgag ttacatgatc ccccatgttg tgcaaaaaag cggttagctc 11340
cttcggtcct ccgatcgttg tcagaagtaa gttggccgca gtgttatcac tcatggttat 11400
ggcagcactg cataattctc ttactgtcat gccatccgta agatgctttt ctgtgactgg 11460
tgagtactca accaagtcat tctgagaata gtgtatgcgg cgaccgagtt gctcttgccc 11520
ggcgtcaaca cgggataata ccgcgccaca tagcagaact ttaaaagtgc tcatcattgg 11580
aaaacgttct tcggggcgaa aactctcaag gatcttaccg ctgttgagat ccagttcgat 11640
gtaacccact cgtgcaccca actgatcttc agcatctttt actttcacca gcgtttctgg 11700
gtgagcaaaa acaggaaggc aaaatgccgc aaaaaaggga ataagggcga cacggaaatg 11760
ttgaatactc atactcttcc tttttcaata ttattgaagc atttatcagg gttattgtct 11820
catgagcgga tacatatttg aatgtattta gaaaaataaa caaaagagtt tgtagaaacg 11880
caaaaaggcc atccgtcagg atggccttct gcttaatttg atgcctggca gtttatggcg 11940
ggcgtcctgc ccgccaccct ccgggccgtt gcttcgcaac gttcaaatcc gctcccggcg 12000
gatttgtcct actcaggaga gcgttcaccg acaaacaaca gataaaacga a 12051

<210> SEQ ID NO 119
<211> LENGTH: 23
<212> TYPE: DNA
<213> ORGANISM: Artificial Sequence
<220> FEATURE:
<223> OTHER INFORMATION: PCR primer

<400> SEQUENCE: 119
ttcattatcg gctcgatctg gtg 23

<210> SEQ ID NO 120
<211> LENGTH: 25
<212> TYPE: DNA
<213> ORGANISM: Artificial Sequence
<220> FEATURE:
<223> OTHER INFORMATION: PCR primer

<400> SEQUENCE: 120
caacaggtga taatcgtgga tccag 25

<210> SEQ ID NO 121
<211> LENGTH: 11348

<212> TYPE: DNA
<213> ORGANISM: Artificial Sequence
<220> FEATURE:
<223> OTHER INFORMATION: plasmid pLybAL28 containing otsBA operon

<400> SEQUENCE: 121
aggcccagtc tttcgactga gcctttcgtt ttatttgatg cctggcagtt ccctactctc 60
gcatggggag accccacact accatcggcg ctacggcgtt tcacttctga gttcggcatg 120
gggtcaggtg ggaccaccgc gctactgccg ccaggcaaat tctgttttat cagaccgctt 180
ctgcgttctg atttaatctg tatcaggctg aaaatcttct ctcatccgcc aaaacagcca 240
agcttgcatg ccgttattga tggaatggga agaagcaatg gtcacaataa actggaggtt 300
atgggtatgt tttttagccc taatgctcca atcgccttga ttgtatcgaa tgatgcagtc 360
tctaaaattg tatccgtaaa agacctctgc accgccgacg ggtctggatt atgggcaata 420
atcacagtcg agccagacta cccctggagg taaactccgg ggctggagcc ataaagatta 480
ggaattcatt aagaaatgta acaatcgacg ttctagatca taccacgccc ccactgtccg 540
gcagggtgaa cagaggagac tttcccctgt tacagtgtca gtgacaaaac aactttttgg 600
catcggtgca ggtggtgagc catggcggcc cagatcattg aaattctttc cccggaggaa 660
atccgacgta cccttacccg tctggcttcc caggtaattt aggtaccgtt aagaaggagg 720
atccatatga tcttgatgga acgctggcgg aaatcaaacc gcatcccgat caggtcgtcg 780
tgcctgacaa tattctgcaa ggactacagc tactggcaac cgcaagtgat ggtgcattgg 840
cattgatatc agggcgctca atggtggagc ttgacgcact ggcaaaacct tatcgcttcc 900
cgttagcggg cgtgcatggg gcggagcgcc gtgacatcaa tggtaaaaca catatcgttc 960
atctgccgga tgcgattgcg cgtgatatta gcgtgcaact gcatacagtc atcgctcagt 1020
atcccggcgc ggagctggag gcgaaaggga tggcttttgc gctgcattat cgtcaggctc 1080
cgcagcatga agacgcatta atgacattag cgcaacgtat tactcagatc tggccacaaa 1140
tggcgttaca gcagggaaag tgtgttgtcg agatcaaacc gagaggtacc agtaaaggtg 1200
aggcaattgc agcttttatg caggaagctc cctttatcgg gcgaacgccc gtatttctgg 1260
gcgatgattt aaccgatgaa tctggcttcg cagtcgttaa ccgactgggc ggaatgtcag 1320
taaaaattgg cacaggtgca actcaggcat catggcgact ggcgggtgtg ccggatgtct 1380
ggagctggct tgaaatgata accaccgcat tacaacaaaa aagagaaaat aacaggagtg 1440
atgactatga gtcgtttagt cgtagtatct aaccggattg caccaccaga cgagcacgcc 1500
gccagtgccg gtggccttgc cgttggcata ctgggggcac tgaaagccgc aggcggactg 1560
tggtttggct ggagtggtga aacagggaat gaggatcagc cgctaaaaaa ggtgaaaaaa 1620
ggtaacatta cgtgggcctc ttttaacctc agcgaacagg accttgacga atactacaac 1680
caattctcca atgccgttct ctggcccgct tttcattatc ggctcgatct ggtgcaattt 1740
cagcgtcctg cctgggacgg ctatctacgc gtaaatgcgt tgctggcaga taaattactg 1800
ccgctgttgc aagacgatga cattatctgg atccacgatt atcacctgtt gccatttgcg 1860
catgaattac gcaaacgggg agtgaataat cgcattggtt tctttctgca tattcctttc 1920
ccgacaccgg aaatcttcaa cgcgctgccg acatatgaca ccttgcttga acagctttgt 1980
gattatgatt tgctgggttt ccagacagaa aacgatcgtc tggcgttcct ggattgtctt 2040
tctaacctga cccgcgtcac gacacgtagc gcaaaaagcc atacagcctg ggcaaagca 2100 tttcgaacag aagtctaccc gatcggcatt gaaccgaaag aaatagccaa acaggctgcc 2160

-continued

```
gggccactgc cgccaaaact ggcgcaactt aaagcggaac tgaaaaacgt acaaaatatc   2220
ttttctgtcg aacggctgga ttattccaaa ggtttgccag agcgttttct cgcctatgaa   2280
gcgttgctgg aaaaatatcc gcagcatcat ggtaaaattc gttataccca gattgcacca   2340
acgtcgcgtg gtgatgtgca agcctatcag gatattcgtc atcagctcga aaatgaagct   2400
ggacgaatta atggtaaata cgggcaatta ggctggacgc cgctttatta tttgaatcag   2460
cattttgacc gtaaattact gatgaaaata ttccgctact ctgacgtggg cttagtgacg   2520
ccactgcgtg acgggatgaa cctggtagca aaagagtatg ttgctgctca ggacccagcc   2580
aatccgggcg ttcttgttct ttcgcaattt gcgggagcgg caaacgagtt aacgtcggcg   2640
ttaattgtta acccctacga tcgtgacgaa gttgcagctg cgctggatcg tgcattgact   2700
atgtcgctgg cggaacgtat ttcccgtcat gcagaaatgc tggacgttat cgtgaaaaac   2760
gatattaacc actggcagga gtgcttcatt agcgacctaa agcagatagt tccgcgaagc   2820
gcggaaagcc agcagcgcga taaagttgct acctttccaa agcttgcgta ggagctagct   2880
gcctcgaaag ggatgcgat tcgccacctc tcactccgct ggcggattcc tcttgagaac   2940
attttggtgg caggcgattc tggtaacgat gaggaaatgc tcaagggcca taatctcggc   3000
gttgtagttg gcaattactc accggaattg gagccactgc gcagctacga gcgcgtctat   3060
tttgctgagg gccactatgc taatggcatt ctggaagcct taaaacacta tcgctttttt   3120
gaggcgatcg cttaaccttt tcagaatgag acgttgatcg gcacgtaagc gtgagacgtt   3180
gatcggcacg taagaggttc caactttcac cataatgaaa taagatcact accgggcgta   3240
tttttttgagt tatcgagatt ttcaggagct aaggaagcta aaatggagaa aaaaatcact   3300
ggatatacca ccgttgatat atcccaatgg catcgtaaag aacattttga ggcatttcag   3360
tcagttgctc aatgtaccta taaccagacc gttcagctgg atattacggc ctttttaaag   3420
accgtaaaga aaaataagca caagttttat ccggccttta ttcacattct tgcccgcctg   3480
atgaatgctc atccggaatt ccgtatggca atgaaagacg gtgagctggt gatatgggat   3540
agtgttcacc cttgttacac cgttttccat gagcaaactg aaacgttttc atcgctctgg   3600
agtgaatacc acgacgattt ccggcagttt ctacacatat attcgcaaga tgtggcgtgt   3660
tacggtgaaa acctggccta tttccctaaa gggtttattg agaatatgtt tttcgtctca   3720
gccaatccct gggtgagttt caccagtttt gatttaaacg tggccaatat ggacaacttc   3780
ttcgcccccg ttttcaccat gggcaaatat tatacgcaag gcgacaaggt gctgatgccg   3840
ctggcgattc aggttcatca tgccgtttgt gatggcttcc atgtcggcag aatgcttaat   3900
gaattacaac agtactgcga tgagtggcag ggcggggcgt aattttttta aggcagttat   3960
tggtgccctt aaacgcctgg ttgctacgcc tgaataagtg ataataagcg gatgaatggc   4020
agaaattcga tgataagctg tcaaacacaa ccaccatcaa acaggatttt cgcctgctgg   4080
ggcaaaccag cgtggaccgc ttgctgcaac tctctcaggg ccaggcggtg aagggcaatc   4140
agctgttgcc cgtctcactg gtgaaaagaa aaaccaccct ggcgcccaat acgcaaaccg   4200
cctctccccg cgcgttggcc gattcattaa tgcagctggc acgacaggtt tcccgactgg   4260
aaagcgggca gtgagcgcaa cgcaattaat gtaagttagc gcgaattgca agctggccga   4320
cgcgctgggc tacgtcttgc tggcgttcgg gagcagaaga gcatacatct ggaagcaaag   4380
ccaggaaagc ggcctatgga gctgtgcggc agcgctcagt aggcaatttt tcaaaatatt   4440
gttaagcctt ttctgagcat ggtatttttc atggtattac caattagcag gaaaataagc   4500
cattgaatat aaaagataaa aatgtcttgt ttacaataga gtgggggggg tcagcctgcc   4560
```

gccttgggcc gggtgatgtc gtacttgccc gccgcgaact cggttaccgt ccagcccagc 4620
gcgaccagct ccggcaacgc ctcgcgcacc cgcttgcggc gcttgcgcat ggtcgaacca 4680
ctggcctctg acggccagac atagccgcac aaggtatcta tggaagcctt gccggttttg 4740
ccggggtcga tccagccaca cagccgctgg tgcagcaggc gggcggtttc gctgtccagc 4800
gcccgcacct cgtccatgct gatgcgcaca tgctggccgc cacccatgac ggcctgcgcg 4860
atcaaggggt tcagggccac gtacaggcgc ccgtccgcct cgtcgctggc gtactccgac 4920
agcagccgaa acccctgccg cttgcggcca ttctgggcga tgatggatac cttccaaagg 4980
cgctcgatgc agtcctgtat gtgcttgagc gccccaccac tatcgacctc tgccccgatt 5040
tcctttgcca gcgcccgata gctacctttg accacatggc attcagcggt gacggcctcc 5100
cacttgggtt ccaggaacag ccggagctgc cgtccgcctt cggtcttggg ttccgggcca 5160
agcactaggc cattaggccc agccatggcc accagccctt gcaggatgcg cagatcatca 5220
gcgcccagcg gctccgggcc gctgaactcg atccgcttgc cgtcgccgta gtcatacgtc 5280
acgtccagct tgctgcgctt gcgctcgccc cgcttgaggg cacggaacag gccgggggcc 5340
agacagtgcg ccgggtcgtg ccggacgtgg ctgaggctgt gcttgttctt aggcttcacc 5400
acggggcacc cccttgctct tgcgctgcct ctccagcacg gcgggcttga gcaccccgcc 5460
gtcatgccgc ctgaaccacc gatcagcgaa cggtgcgcca tagttggcct tgctcacacc 5520
gaagcggacg aagaaccggc gctggtcgtc gtccacaccc cattcctcgg cctcggcgct 5580
ggtcatgctc gacaggtagg actgccagcg gatgttatcg accagtaccg agctgccccg 5640
gctggcctgc tgctggtcgc ctgcgcccat catggccgcg cccttgctgg catggtgcag 5700
gaacacgata gagcacccgg tatcggcggc gatggcctcc atgcgaccga tgacctgggc 5760
catggggccg ctggcgtttt cttcctcgat gtggaaccgg cgcagcgtgt ccagcaccat 5820
caggcggcgg ccctcggcgg cgcgcttgag gccgtcgaac cactccgggg ccatgatgtt 5880
gggcaggctg ccgatcagcg gctggatcag caggccgtca gccacggctt gccgttcctc 5940
ggcgctgagg tgcgccccaa gggcgtgcag gcggtgatga atggcggtgg gcgggtcttc 6000
ggcgggcagg tagatcaccg ggccggtggg cagttcgccc acctccagca gatccggccc 6060
gcctgcaatc tgtgcggcca gttgcagggc cagcatggat ttaccggcac caccgggcga 6120
caccagcgcc ccgaccgtac cggccaccat gttgggcaaa acgtagtcca gcggtggcgg 6180
cgctgctgcg aacgcctcca gaatattgat aggcttatgg gtagccattg attgcctcct 6240
ttgcaggcag ttggtggtta ggcgctggcg gggtcactac ccccgccctg cgccgctctg 6300
agttcttcca ggcactcgcg cagcgcctcg tattcgtcgt cggtcagcca gaacttgcgc 6360
tgacgcatcc ctttggcctt catgcgctcg gcatatcgcg cttggcgtac agcgtcaggg 6420
ctggccagca ggtcgccggt ctgcttgtcc ttttggtctt tcatatcagt caccgagaaa 6480
cttgccgggg ccgaaaggct tgtcttcgcg gaacaaggac aaggtgcagc cgtcaaggtt 6540
aaggctggcc atatcagcga ctgaaaagcg gccagcctcg gccttgtttg acgtataacc 6600
aaagccaccg ggcaaccaat agcccttgtc acttttgatc aggtagaccg accctgaagc 6660
gctttttttcg tattccataa aaccccccttc tgtgcgtgag tactcatagt ataacaggcg 6720
tgagtaccaa cgcaagcact acatgctgaa atctggcccg cccctgtcca tgcctcgctg 6780
gcggggtgcc ggtgcccgtg ccagctcggc ccgcgcaagc tggacgctgg gcagacccat 6840
gaccttgctg acggtgcgct cgatgtaatc cgcttcgtgg ccgggcttgc gctctgccag 6900

-continued

```
cgctgggctg gcctcggcca tggccttgcc gatttcctcg gcactgcggc cccggctggc   6960
cagcttctgc gcggcgataa agtcgcactt gctgaggtca tgaccgaagc gcttgaccag   7020
cccggccatc tcgctgcggt actcgtccag cgccgtgcgc cggtggcggc taagctgccg   7080
ctcgggcagt tcgaggctgg ccagcctgcg ggccttctcc tgctgccgct gggcctgctc   7140
gatctgctgg ccagcctgct gcaccagcgc cgggccagcg gtggcggtct tgcccttgga   7200
ttcacgcagc agcacccacg gctgataacc ggcgcgggtg gtgtgcttgt ccttgcggtt   7260
ggtgaagccc gccaagcggc catagtggcg gctgtcggcg ctggccgggt cggcgtcgta   7320
ctcgctggcc agcgtccggg caatctgccc ccgaagttca ccgcctgcgg cgtcggccac   7380
cttgacccat gcctgatagt tcttcgggct ggtttccact accagggcag gctcccggcc   7440
ctcggctttc atgtcatcca ggtcaaactc gctgaggtcg tccaccagca ccagaccatg   7500
ccgctcctgc tcggcgggcc tgatatacac gtcattgccc tgggcattca tccgcttgag   7560
ccatggcgtg ttctggagca cttcggcggc tgaccattcc cggttcatca tctggccggt   7620
gggtgcgtcc ctgacgccga tatcgaagcg ctcacagccc atggccttga gctgtcggcc   7680
tatggcctgc aaagtcctgt cgttcttcat cgggccacca agcgcagcca gatcgagccg   7740
tcctcggttg tcagtggcgt caggtcgagc aagagcaacg atgcgatcag cagcaccacc   7800
gtaggcatca tggaagccag catcacggtt agccatagct tccagtgcca cccccgcgac   7860
gcgctccggg cgctctgcgc ggcgctgctc acctcggcgg ctacctcccg caactctttg   7920
gccagctcca cccatgccgc ccctgtctgg cgctgggctt tcagccactc cgccgcctgc   7980
gcctcgctgg cctgcttggt ctggctcatg acctgccggg cttcgtcggc cagtgtcgcc   8040
atgctctggg ccagcggttc gatctgctcc gctaactcgt tgatgcctct ggatttcttc   8100
actctgtcga ttgcgttcat ggtctattgc ctcccggtat tcctgtaagt cgatgatctg   8160
ggcgttggcg gtgtcgatgt tcagggccac gtctgcccgg tcggtgcgga tgccccggcc   8220
ttccatctcc accacgttcg gccccaggtg aacaccgggc aggcgctcga tgccctgcgc   8280
ctcaagtgtt ctgtggtcaa tgcgggcgtc gtggccagcc cgctctaatg cccggttggc   8340
atggtcggcc catgcctcgc gggtctgctc aagccatgcc ttgggcttga gcgcttcggt   8400
cttctgtgcc ccgcccttct ccggggtctt gccgttgtac cgcttgaacc actgagcggc   8460
gggccgctcg atgccgtcat tgatccgctc ggagatcatc aggtggcagt gcgggttctc   8520
gccgccaccg gcatggatgg ccagcgtata cggcaggcgc tcggcaccgg tcaggtgctg   8580
ggcgaactcg gacgccagcg ccttctgctg gtcgagggtc agctcgaccg gcagggcaaa   8640
ttcgacctcc ttgaacagcc gcccattggc gcgttcatac aggtcggcag catcccagta   8700
gtcggcgggc cgctcgacga actccggcat gtgcccggat tcggcgtgca agacttcatc   8760
catgtcgcgg gcatacttgc cttcgcgctg gatgtagtcg gccttggccc tggccgattg   8820
gccgcccgac ctgctgccgg ttttcgccgt aaggtgataa atcgccatgc tgcctcgctg   8880
ttgcttttgc ttttcggctc catgcaatgg ccctcggaga gcgcaccgcc cgaagggtgg   8940
ccgttaggcc agtttctcga agagaaaccg gtaagtgcgc cctcccctac aaagtagggt   9000
cgggattgcc gccgctgtgc ctccatgata gcctacgaga cagcacatta acaatggggt   9060
gtcaagatgg ttaaggggag caacaaggcg gcggatcggc tggccaagct cgaagaacaa   9120
cgagcgcgaa tcaatgccga aattcagcgg gagcgggcaa gggaacagca gcaagagcgc   9180
aagaacgaaa caaggcgcaa ggtgctggtg ggggccatga ttttggccaa ggtgaacagc   9240
agcgagtggc cggaggatcg gctcatggcg gcaatggatg cgtaccttga acgcgaccac   9300
```

```
gaccgcgcct tgttcggtct gccgccacgc cagaaggatg agccgggctg aatgatcgac    9360
cgagacaggc cctgcggggc tgcacacgcg cccccaccct tcgggtaggg ggaaaggccg    9420
ctaaagcggc taaaagcgct ccagcgtatt tctgcggggt ttggtgtggg gtttagcggg    9480
ctttgcccgc ctttcccct gccgcgcagc ggtggggcgg tgtgtagcct agcgcagcga     9540
atagaccagc tatccggcct ctggccgggc atattgggca agggcagcag cgccccacaa    9600
gggcgctgat aaccgcgcct agtggattat tcttagataa tcatggatgg atttttccaa    9660
caccccgcca gcccccgccc ctgctgggtt tgcaggtttg ggggcgtgac agttattgca    9720
ggggttcgtg acagttattg caggggggcg tgacagttat tgcaggggtt cgtgacagtt    9780
agtacgggag tgacgggcac tggctggcaa tgtctagcaa cggcaggcat ttcggctgag    9840
ggtaaaagaa ctttccgcta agcgatagac tgtatgtaaa cacagtattg caaggacgcg    9900
gaacatgcct catgtggcgg ccaggacggc cagccgggat cgggatactg gtcgttacca    9960
gagccaccga cccgagcaaa cccttctcta tcagatcgtt gacgagtatt acccggcatt   10020
cgctgcgctt atggcagagc agggaaagga attgccgggc tatgtgcaac gggaatttga   10080
agaatttctc caatgcgggc ggctggagca tggctttcta cggttcgct gcgagtcttg    10140
ccacgccgag cacctggtcg ctttcagaaa tcaatctaaa gtatatatga gtaaacttgg   10200
tctgacagtt accaatgctt aatcagtgag gcacctatct cagcgatctg tctatttcgt   10260
tcatccatag ttgcctgact ccccgtcgtg tagataacta cgatacggga gggcttacca   10320
tctggcccca gtgctgcaat gataccgcga gacccacgct caccggctcc agatttatca   10380
gcaataaacc agccagccgg aagggccgag cgcagaagtg gtcctgcaac tttatccgcc   10440
tccatccagt ctattaattg ttgccgggaa gctagagtaa gtagttcgcc agttaatagt   10500
ttgcgcaacg ttgttgccat tgctacaggc atcgtggtgt cacgctcgtc gtttggtatg   10560
gcttcattca gctccggttc ccaacgatca aggcgagtta catgatcccc catgttgtgc   10620
aaaaaagcgg ttagctcctt cggtcctccg atcgttgtca gaagtaagtt ggccgcagtg   10680
ttatcactca tggttatggc agcactgcat aattctctta ctgtcatgcc atccgtaaga   10740
tgcttttctg tgactggtga gtactcaacc aagtcattct gagaatagtg tatgcggcga   10800
ccgagttgct cttgcccggc gtcaacacgg gataataccg cgccacatag cagaacttta   10860
aaagtgctca tcattggaaa acgttcttcg gggcgaaaac tctcaaggat cttaccgctg   10920
ttgagatcca gttcgatgta acccactcgt gcacccaact gatcttcagc atcttttact   10980
ttcaccagcg tttctgggtg agcaaaaaca ggaaggcaaa atgccgcaaa aaagggaata   11040
agggcgacac ggaaatgttg aatactcata ctcttccttt ttcaatatta ttgaagcatt   11100
tatcagggtt attgtctcat gagcggatac atatttgaat gtatttagaa aaataaacaa   11160
aagagtttgt agaaacgcaa aaaggccatc cgtcaggatg gccttctgct taatttgatg   11220
cctggcagtt tatggcgggc gtcctgcccg ccaccctccg ggccgttgct tcgcaacgtt   11280
caaatccgct cccggcggat ttgtcctact caggagagcg ttcaccgaca aacaacagat   11340
aaaacgaa                                                            11348
```

<210> SEQ ID NO 122
<211> LENGTH: 11527
<212> TYPE: DNA
<213> ORGANISM: Artificial Sequence
<220> FEATURE:
<223> OTHER INFORMATION: plasmid pLybAL29 containing otsBA operon

<400> SEQUENCE: 122
aggcccagtc tttcgactga gcctttcgtt ttatttgatg cctggcagtt ccctactctc 60
gcatggggag accccacact accatcggcg ctacggcgtt tcacttctga gttcggcatg 120
gggtcaggtg ggaccaccgc gctactgccg ccaggcaaat tctgttttat cagaccgctt 180
ctgcgttctg atttaatctg tatcaggctg aaaatcttct ctcatccgcc aaaacagcca 240
agcttgcatg ccgagcctga tgtgtgacac ctaagatcac tccagttctc tttggaaact 300
ggctgatgag tgaagacacc atctttggca agatcatccg gcgcgagatt ccagcagaca 360
ttgtttatga agatgatctc tgtctggctt ttcgagatgt ggcaccccaa gcgccggttc 420
acattctggt gattcccaag caaccaattg ccaacctttt ggaagcgaca gcagaacatc 480
aagcgctgct gggtcatttg ttgctgactg taaaggcgat cgcggcccaa gaaggactca 540
ccgagggcta ccgcaccgtg attaacacgg gccctgcggg tgggcaaacc gtttaccacc 600
tgcatattca cttactgggc gggcgatcgc tggcttggcc gcccggctga gaaaagtctg 660
aaagttcttt acaaaactca atctgcttgt tagattttac tcacgaggct attaagtctc 720
gtaaatagtt caactaagga ctcatcgcaa aatgacgact gcattgcagc ggcgcgagag 780
cgccagcctg tggcagcagt tctgcgagtg ggtaaccagc accgacaacc gcctctatgt 840
gggttggttc ggcgtgctga tgatccccac tctgctgacc ggtaccgtta agaaggagga 900
tccatatgat cttgatggaa cgctggcgga aatcaaaccg catcccgatc aggtcgtcgt 960
gcctgacaat attctgcaag gactacagct actggcaacc gcaagtgatg gtgcattggc 1020
attgatatca gggcgctcaa tggtggagct tgacgcactg gcaaaacctt atcgcttccc 1080
gttagcgggc gtgcatgggg cggagcgccg tgacatcaat ggtaaaacac atatcgttca 1140
tctgccggat gcgattgcgc gtgatattag cgtgcaactg catacagtca tcgctcagta 1200
tcccggcgcg gagctggagg cgaaagggat ggcttttgcg ctgcattatc gtcaggctcc 1260
gcagcatgaa gacgcattaa tgacattagc gcaacgtatt actcagatct ggccacaaat 1320
ggcgttacag cagggaaagt gtgttgtcga gatcaaaccg agaggtacca gtaaaggtga 1380
ggcaattgca gcttttatgc aggaagctcc ctttatcggg cgaacgcccg tatttctggg 1440
cgatgattta accgatgaat ctggcttcgc agtcgttaac cgactgggcg gaatgtcagt 1500
aaaaattggc acaggtgcaa ctcaggcatc atggcgactg gcgggtgtgc cggatgtctg 1560
gagctggctt gaaatgataa ccaccgcatt acaacaaaaa agagaaaata acaggagtga 1620
tgactatgag tcgtttagtc gtagtatcta accggattgc accaccagac gagcacgccg 1680
ccagtgccgg tggccttgcc gttggcatac tgggggcact gaaagccgca ggcggactgt 1740
ggtttggctg gagtggtgaa acagggaatg aggatcagcc gctaaaaaag gtgaaaaaag 1800
gtaacattac gtgggcctct tttaacctca gcgaacagga ccttgacgaa tactacaacc 1860
aattctccaa tgccgttctc tggcccgctt ttcattatcg gctcgatctg gtgcaatttc 1920
agcgtcctgc ctgggacggc tatctacgcg taaatgcgtt gctggcagat aaattactgc 1980
cgctgttgca agacgatgac attatctgga tccacgatta tcacctgttg ccatttgcgc 2040
atgaattacg caaacgggga gtgaataatc gcattggttt ctttctgcat attcctttcc 2100
cgacaccgga aatcttcaac gcgctgccga catatgacac cttgcttgaa cagctttgtg 2160
attatgattt gctgggtttc cagacagaaa acgatcgtct ggcgttcctg gattgtcttt 2220
ctaacctgac ccgcgtcacg acacgtagcg caaaaagcca tacagcctgg ggcaaagcat 2280
ttcgaacaga agtctacccg atcggcattg aaccgaaaga aatagccaaa caggctgccg 2340

-continued

```
ggccactgcc gccaaaactg gcgcaactta aagcggaact gaaaaacgta caaaatatct   2400
tttctgtcga acggctggat tattccaaag gtttgccaga gcgttttctc gcctatgaag   2460
cgttgctgga aaaatatccg cagcatcatg gtaaaattcg ttatacccag attgcaccaa   2520
cgtcgcgtgg tgatgtgcaa gcctatcagg atattcgtca tcagctcgaa aatgaagctg   2580
gacgaattaa tggtaaatac gggcaattag gctggacgcc gctttattat ttgaatcagc   2640
attttgaccg taaattactg atgaaaatat tccgctactc tgacgtgggc ttagtgacgc   2700
cactgcgtga cgggatgaac ctggtagcaa aagagtatgt tgctgctcag gacccagcca   2760
atccgggcgt tcttgttctt tcgcaatttg cgggagcggc aaacgagtta acgtcggcgt   2820
taattgttaa cccctacgat cgtgacgaag ttgcagctgc gctggatcgt gcattgacta   2880
tgtcgctggc ggaacgtatt tcccgtcatg cagaaatgct ggacgttatc gtgaaaaacg   2940
atattaacca ctggcaggag tgcttcatta gcgacctaaa gcagatagtt ccgcgaagcg   3000
cggaaagcca gcagcgcgat aaagttgcta cctttccaaa gcttgcgtag gagctagctg   3060
cctcgaaagg ggatgcgatt cgccacctct cactccgctg gcggattcct cttgagaaca   3120
ttttggtggc aggcgattct ggtaacgatg aggaaatgct caagggccat aatctcggcg   3180
ttgtagttgg caattactca ccggaattgg agccactgcg cagctacgag cgcgtctatt   3240
ttgctgaggg ccactatgct aatggcattc tggaagcctt aaaacactat cgcttttttg   3300
aggcgatcgc ttaacctttt cagaatgaga cgttgatcgg cacgtaagcg tgagacgttg   3360
atcggcacgt aagaggttcc aactttcacc ataatgaaat aagatcacta ccgggcgtat   3420
tttttgagtt atcgagattt tcaggagcta aggaagctaa aatggagaaa aaaatcactg   3480
gatataccac cgttgatata tcccaatggc atcgtaaaga acattttgag gcatttcagt   3540
cagttgctca atgtacctat aaccagaccg ttcagctgga tattacggcc tttttaaaga   3600
ccgtaaagaa aaataagcac aagttttatc cggcctttat tcacattctt gcccgcctga   3660
tgaatgctca tccggaattc cgtatggcaa tgaaagacgg tgagctggtg atatgggata   3720
gtgttcaccc ttgttacacc gttttccatg agcaaactga aacgttttca tcgctctgga   3780
gtgaatacca cgacgatttc cggcagtttc tacacatata ttcgcaagat gtggcgtgtt   3840
acggtgaaaa cctggcctat ttccctaaag ggtttattga gaatatgttt ttcgtctcag   3900
ccaatccctg ggtgagtttc accagttttg atttaaacgt ggccaatatg gacaacttct   3960
tcgcccccgt tttcaccatg ggcaaatatt atacgcaagg cgacaaggtg ctgatgccgc   4020
tggcgattca ggttcatcat gccgtttgtg atggcttcca tgtcggcaga atgcttaatg   4080
aattacaaca gtactgcgat gagtggcagg gcggggcgta atttttttaa ggcagttatt   4140
ggtgccctta aacgcctggt tgctacgcct gaataagtga taataagcgg atgaatggca   4200
gaaattcgat gataagctgt caaacacaac caccatcaaa caggattttc gcctgctggg   4260
gcaaaccagc gtggaccgct tgctgcaact ctctcagggc caggcggtga agggcaatca   4320
gctgttgccc gtctcactgg tgaaaagaaa aaccaccctg gcgcccaata cgcaaaccgc   4380
ctctccccgc gcgttggccg attcattaat gcagctggca cgacaggttt cccgactgga   4440
aagcgggcag tgagcgcaac gcaattaatg taagttagcg cgaattgcaa gctggccgac   4500
gcgctgggct acgtcttgct ggcgttcggg agcagaagag catacatctg gaagcaaagc   4560
caggaaagcg gcctatggag ctgtgcggca gcgctcagta ggcaattttt caaaatattg   4620
ttaagccttt tctgagcatg gtatttttca tggtattacc aattagcagg aaaataagcc   4680
```

-continued

```
attgaatata aaagataaaa atgtcttgtt tacaatagag tggggggggt cagcctgccg   4740
ccttgggccg ggtgatgtcg tacttgcccg ccgcgaactc ggttaccgtc cagcccagcg   4800
cgaccagctc cggcaacgcc tcgcgcaccc gcttgcggcg cttgcgcatg gtcgaaccac   4860
tggcctctga cggccagaca tagccgcaca aggtatctat ggaagccttg ccggttttgc   4920
cggggtcgat ccagccacac agccgctggt gcagcaggcg ggcggtttcg ctgtccagcg   4980
cccgcacctc gtccatgctg atgcgcacat gctggccgcc acccatgacg gcctgcgcga   5040
tcaaggggtt cagggccacg tacaggcgcc cgtccgcctc gtcgctggcg tactccgaca   5100
gcagccgaaa cccctgccgc ttgcggccat tctgggcgat gatggatacc ttccaaaggc   5160
gctcgatgca gtcctgtatg tgcttgagcg ccccaccact atcgacctct gccccgattt   5220
cctttgccag cgcccgatag ctacctttga ccacatggca ttcagcggtg acggcctccc   5280
acttgggttc caggaacagc cggagctgcc gtccgccttc ggtcttgggt tccgggccaa   5340
gcactaggcc attaggccca gccatggcca ccagcccttg caggatgcgc agatcatcag   5400
cgcccagcgg ctccgggccg ctgaactcga tccgcttgcc gtcgccgtag tcatacgtca   5460
cgtccagctt gctgcgcttg cgctcgcccc gcttgagggc acggaacagg ccgggggcca   5520
gacagtgcgc cgggtcgtgc cggacgtggc tgaggctgtg cttgttctta ggcttcacca   5580
cggggcaccc ccttgctctt gcgctgcctc tccagcacgg cgggcttgag caccccgccg   5640
tcatgccgcc tgaaccaccg atcagcgaac ggtgcgccat agttggcctt gctcacaccg   5700
aagcggacga agaaccggcg ctggtcgtcg tccacacccc attcctcggc ctcggcgctg   5760
gtcatgctcg acaggtagga ctgccagcgg atgttatcga ccagtaccga gctgccccgg   5820
ctggcctgct gctggtcgcc tgcgcccatc atggccgcgc ccttgctggc atggtgcagg   5880
aacacgatag agcacccggt atcggcggcg atggcctcca tgcgaccgat gacctgggcc   5940
atggggccgc tggcgttttc ttcctcgatg tggaaccggc gcagcgtgtc cagcaccatc   6000
aggcggcggc cctcggcggc gcgcttgagg ccgtcgaacc actccggggc catgatgttg   6060
ggcaggctgc cgatcagcgg ctggatcagc aggccgtcag ccacggcttg ccgttcctcg   6120
gcgctgaggt gcgccccaag ggcgtgcagg cggtgatgaa tggcggtggg cgggtcttcg   6180
gcgggcaggt agatcaccgg gccggtgggc agttcgccca cctccagcag atccggcccg   6240
cctgcaatct gtgcggccag ttgcagggcc agcatggatt taccggcacc accgggcgac   6300
accagcgccc cgaccgtacc ggccaccatg ttgggcaaaa cgtagtccag cggtggcggc   6360
gctgctgcga acgcctccag aatattgata ggcttatggg tagccattga ttgcctcctt   6420
tgcaggcagt tggtggttag gcgctggcgg ggtcactacc cccgccctgc gccgctctga   6480
gttcttccag gcactcgcgc agcgcctcgt attcgtcgtc ggtcagccag aacttgcgct   6540
gacgcatccc tttggccttc atgcgctcgg catatcgcgc ttggcgtaca gcgtcagggc   6600
tggccagcag gtcgccggtc tgcttgtcct tttggtcttt catatcagtc accgagaaac   6660
ttgccggggc cgaaaggctt gtcttcgcgg aacaaggaca aggtgcagcc gtcaaggtta   6720
aggctggcca tatcagcgac tgaaaagcgg ccagcctcgg ccttgtttga cgtataacca   6780
aagccaccgg gcaaccaata gcccttgtca cttttgatca ggtagaccga ccctgaagcg   6840
ctttttttcgt attccataaa accccccttct gtgcgtgagt actcatagta taacaggcgt   6900
gagtaccaac gcaagcacta catgctgaaa tctggcccgc ccctgtccat gcctcgctgg   6960
cggggtgccg gtgcccgtgc cagctcggcc cgcgcaagct ggacgctggg cagacccatg   7020
accttgctga cggtgcgctc gatgtaatcc gcttcgtggc cgggcttgcg ctctgccagc   7080
```

```
gctgggctgg cctcggccat ggccttgccg atttcctcgg cactgcggcc ccggctggcc   7140
agcttctgcg cggcgataaa gtcgcacttg ctgaggtcat gaccgaagcg cttgaccagc   7200
ccggccatct cgctgcggta ctcgtccagc gccgtgcgcc ggtggcggct aagctgccgc   7260
tcgggcagtt cgaggctggc cagcctgcgg gccttctcct gctgccgctg ggcctgctcg   7320
atctgctggc cagcctgctg caccagcgcc gggccagcgg tggcggtctt gcccttggat   7380
tcacgcagca gcacccacgg ctgataaccg gcgcgggtgg tgtgcttgtc cttgcggttg   7440
gtgaagcccg ccaagcggcc atagtggcgg ctgtcggcgc tggccgggtc ggcgtcgtac   7500
tcgctggcca gcgtccgggc aatctgcccc cgaagttcac cgcctgcggc gtcggccacc   7560
ttgacccatg cctgatagtt cttcgggctg gtttccacta ccagggcagg ctcccggccc   7620
tcggctttca tgtcatccag gtcaaactcg ctgaggtcgt ccaccagcac cagaccatgc   7680
cgctcctgct cggcgggcct gatatacacg tcattgccct gggcattcat ccgcttgagc   7740
catggcgtgt tctggagcac ttcggcggct gaccattccc ggttcatcat ctggccggtg   7800
ggtgcgtccc tgacgccgat atcgaagcgc tcacagccca tggccttgag ctgtcggcct   7860
atggcctgca aagtcctgtc gttcttcatc gggccaccaa gcgcagccag atcgagccgt   7920
cctcggttgt cagtggcgtc aggtcgagca agagcaacga tgcgatcagc agcaccaccg   7980
taggcatcat ggaagccagc atcacggtta gccatagctt ccagtgccac cccgcgacg    8040
cgctccgggc gctctgcgcg gcgctgctca cctcggcggc tacctcccgc aactctttgg   8100
ccagctccac ccatgccgcc cctgtctggc gctgggcttt cagccactcc gccgcctgcg   8160
cctcgctggc ctgcttggtc tggctcatga cctgccgggc ttcgtcggcc agtgtcgcca   8220
tgctctgggc cagcggttcg atctgctccg ctaactcgtt gatgcctctg gatttcttca   8280
ctctgtcgat tgcgttcatg gtctattgcc tcccggtatt cctgtaagtc gatgatctgg   8340
gcgttggcgg tgtcgatgtt cagggccacg tctgcccggt cggtgcggat gccccggcct   8400
tccatctcca ccacgttcgg ccccaggtga acaccgggca ggcgctcgat gccctgcgcc   8460
tcaagtgttc tgtggtcaat gcgggcgtcg tggccagccc gctctaatgc ccggttggca   8520
tggtcggccc atgcctcgcg ggtctgctca agccatgcct tgggcttgag cgcttcggtc   8580
ttctgtgccc cgcccttctc cggggtcttg ccgttgtacc gcttgaacca ctgagcggcg   8640
ggccgctcga tgccgtcatt gatccgctcg gagatcatca ggtggcagtg cgggttctcg   8700
ccgccaccgg catggatggc cagcgtatac ggcaggcgct cggcaccggt caggtgctgg   8760
gcgaactcgg acgccagcgc cttctgctgg tcgagggtca gctcgaccgg cagggcaaat   8820
tcgacctcct tgaacagccg cccattggcg cgttcataca ggtcggcagc atcccagtag   8880
tcggcgggcc gctcgacgaa ctccggcatg tgcccggatt cggcgtgcaa gacttcatcc   8940
atgtcgcggg catacttgcc ttcgcgctgg atgtagtcgg ccttggccct ggccgattgg   9000
ccgcccgacc tgctgccggt tttcgccgta aggtgataaa tcgccatgct gcctcgctgt   9060
tgcttttgct tttcggctcc atgcaatggc cctcggagag cgcaccgccc gaagggtggc   9120
cgttaggcca gtttctcgaa gagaaaccgg taagtgcgcc ctcccctaca aagtagggtc   9180
gggattgccg ccgctgtgcc tccatgatag cctacgagac agcacattaa caatggggtg   9240
tcaagatggt taaggggagc aacaaggcgg cggatcggct ggccaagctc gaagaacaac   9300
gagcgcgaat caatgccgaa attcagcggg agcgggcaag ggaacagcag caagagcgca   9360
agaacgaaac aaggcgcaag gtgctggtgg gggccatgat tttggccaag gtgaacagca   9420
```

-continued gcgagtggcc ggaggatcgg ctcatggcgg caatggatgc gtaccttgaa cgcgaccacg 9480
accgcgcctt gttcggtctg ccgccacgcc agaaggatga gccgggctga atgatcgacc 9540
gagacaggcc ctgcggggct gcacacgcgc cccccaccctt cgggtagggg gaaaggccgc 9600
taaagcggct aaaagcgctc cagcgtattt ctgcggggtt tggtgtgggg tttagcgggc 9660
tttgcccgcc tttcccccctg ccgcgcagcg gtggggcggt gtgtagccta gcgcagcgaa 9720
tagaccagct atccggcctc tggccgggca tattgggcaa gggcagcagc gccccacaag 9780
ggcgctgata accgcgccta gtggattatt cttagataat catggatgga tttttccaac 9840
accccgccag cccccgcccc tgctgggttt gcaggtttgg gggcgtgaca gttattgcag 9900
gggttcgtga cagttattgc aggggggcgt gacagttatt gcaggggttc gtgacagtta 9960
gtacgggagt gacgggcact ggctggcaat gtctagcaac ggcaggcatt tcggctgagg 10020
gtaaaagaac tttccgctaa gcgatagact gtatgtaaac acagtattgc aaggacgcgg 10080
aacatgcctc atgtggcggc caggacggcc agccgggatc gggatactgg tcgttaccag 10140
agccaccgac ccgagcaaac ccttctctat cagatcgttg acgagtatta cccggcattc 10200
gctgcgctta tggcagagca gggaaaggaa ttgccgggct atgtgcaacg ggaatttgaa 10260
gaatttctcc aatgcgggcg gctggagcat ggctttctac gggttcgctg cgagtcttgc 10320
cacgccgagc acctggtcgc tttcagaaat caatctaaag tatatatgag taaacttggt 10380
ctgacagtta ccaatgctta atcagtgagg cacctatctc agcgatctgt ctatttcgtt 10440
catccatagt tgcctgactc cccgtcgtgt agataactac gatacgggag ggcttaccat 10500
ctggccccag tgctgcaatg ataccgcgag acccacgctc accggctcca gatttatcag 10560
caataaacca gccagccgga agggccgagc gcagaagtgg tcctgcaact ttatccgcct 10620
ccatccagtc tattaattgt tgccgggaag ctagagtaag tagttcgcca gttaatagtt 10680
tgcgcaacgt tgttgccatt gctacaggca tcgtggtgtc acgctcgtcg tttggtatgg 10740
cttcattcag ctccggttcc caacgatcaa ggcgagttac atgatccccc atgttgtgca 10800
aaaaagcggt tagctccttc ggtcctccga tcgttgtcag aagtaagttg gccgcagtgt 10860
tatcactcat ggttatggca gcactgcata attctcttac tgtcatgcca tccgtaagat 10920
gcttttctgt gactggtgag tactcaacca agtcattctg agaatagtgt atgcggcgac 10980
cgagttgctc ttgcccggcg tcaacacggg ataataccgc gccacatagc agaactttaa 11040
aagtgctcat cattggaaaa cgttcttcgg ggcgaaaact ctcaaggatc ttaccgctgt 11100
tgagatccag ttcgatgtaa cccactcgtg cacccaactg atcttcagca tcttttactt 11160
tcaccagcgt ttctgggtga gcaaaaacag gaaggcaaaa tgccgcaaaa aagggaataa 11220
gggcgacacg gaaatgttga atactcatac tcttcctttt tcaatattat tgaagcattt 11280
atcagggtta ttgtctcatg agcggataca tatttgaatg tatttagaaa aataaacaaa 11340
agagtttgta gaaacgcaaa aaggccatcc gtcaggatgg ccttctgctt aatttgatgc 11400
ctggcagttt atggcgggcg tcctgcccgc caccctccgg gccgttgctt cgcaacgttc 11460
aaatccgctc ccggcggatt tgtcctactc aggagagcgt tcaccgacaa acaacagata 11520
aaacgaa 11527

<210> SEQ ID NO 123
<211> LENGTH: 11769
<212> TYPE: DNA
<213> ORGANISM: Artificial Sequence
<220> FEATURE:
<223> OTHER INFORMATION: plasmid pLybAL30 containing otsBA operon

<400> SEQUENCE: 123
aggcccagtc tttcgactga gcctttcgtt ttatttgatg cctggcagtt ccctactctc 60
gcatggggag accccacact accatcggcg ctacggcgtt tcacttctga gttcggcatg 120
gggtcaggtg ggaccaccgc gctactgccg ccaggcaaat tctgttttat cagaccgctt 180
ctgcgttctg atttaatctg tatcaggctg aaaatcttct ctcatccgcc aaaacagcca 240
agcttgcatg caccagtaaa cataaatctc cccggcgacg caaaaaacgg gtgaccatca 300
agccggtgcg cttcggcatt tttctgcttt gcctagcagg cattgtgggg ggggcaactg 360
ccctaattat caatcgtact ggcgatcccc taggtgggtt gctagaagac cccctagatg 420
ttttcctgga ccaaccttca gaatttatcc ccgatgaagc cacgagccgg aatttgattc 480
tcagtcaacc caacttcaat cagcaagtgg gtcagatggt agtacaaggc tggcttgata 540
gtaaaaagtt agcctttggc caaaactacg atgtcggggc attgcagagt gttttagccc 600
ccaatctcct tgcccaacaa cggggtcggg cccaacggga tcaagcccaa aaggtctatc 660
accaatacga acacaagttg cagattttag cctatcaagt taacccccaa gaccccaacc 720
gagccaccgt tactgcccgg gtagaagaaa ttagccagcc ctttacccta ggtaatcaac 780
agcagaaggg ctccgccacc aaagatgact tgactgtgcg ctatcagcta gtacgacacc 840
aaggggtttg gaaaattgac caaatacaag tggtaaatgg cccccgttag tgcgtggcgt 900
taactcccct tttgaccaat ggcatacggc tagatgcccc cataggtacg gaaacctgca 960
cttccgagaa ctaagcccct accgtcacta taagagtgtg aacgtgtcgg ccccaggcaa 1020
tggattggaa ccatggcttt tcggcccatc gttgtgtctt atattcttac ttgttaacgg 1080
gagttaatta aaattatggg aaaagttgtt gggattgacc tcggtaccgt taagaaggag 1140
gatccatatg atcttgatgg aacgctggcg gaaatcaaac cgcatcccga tcaggtcgtc 1200
gtgcctgaca atattctgca aggactacag ctactggcaa ccgcaagtga tggtgcattg 1260
gcattgatat cagggcgctc aatggtggag cttgacgcac tggcaaaacc ttatcgcttc 1320
ccgttagcgg gcgtgcatgg ggcggagcgc cgtgacatca atggtaaaac acatatcgtt 1380
catctgccgg atgcgattgc gcgtgatatt agcgtgcaac tgcatacagt catcgctcag 1440
tatcccggcg cggagctgga ggcgaaaggg atggcttttg cgctgcatta tcgtcaggct 1500
ccgcagcatg aagacgcatt aatgacatta gcgcaacgta ttactcagat ctggccacaa 1560
atggcgttac agcagggaaa gtgtgttgtc gagatcaaac cgagaggtac cagtaaaggt 1620
gaggcaattg cagcttttat gcaggaagct ccctttatcg ggcgaacgcc cgtatttctg 1680
ggcgatgatt taaccgatga atctggcttc gcagtcgtta accgactggg cggaatgtca 1740
gtaaaaattg gcacaggtgc aactcaggca tcatggcgac tggcgggtgt gccggatgtc 1800
tggagctggc ttgaaatgat aaccaccgca ttacaacaaa aaagagaaaa taacaggagt 1860
gatgactatg agtcgtttag tcgtagtatc taaccggatt gcaccaccag acgagcacgc 1920
cgccagtgcc ggtggccttg ccgttggcat actgggggca ctgaaagccg caggcggact 1980
gtggtttggc tggagtggtg aaacagggaa tgaggatcag ccgctaaaaa aggtgaaaaa 2040
aggtaacatt acgtgggcct cttttaacct cagcgaacag gaccttgacg aatactacaa 2100
ccaattctcc aatgccgttc tctggcccgc ttttcattat cggctcgatc tggtgcaatt 2160
tcagcgtcct gcctgggacg gctatctacg cgtaaatgcg ttgctggcag ataaattact 2220
gccgctgttg caagacgatg acattatctg gatccacgat tatcacctgt tgccatttgc 2280

-continued

```
gcatgaatta cgcaaacggg gagtgaataa tcgcattggt ttctttctgc atattccttt   2340
cccgacaccg gaaatcttca acgcgctgcc gacatatgac accttgcttg aacagctttg   2400
tgattatgat ttgctgggtt tccagacaga aaacgatcgt ctggcgttcc tggattgtct   2460
ttctaacctg acccgcgtca cgacacgtag cgcaaaaagc catacagcct ggggcaaagc   2520
atttcgaaca gaagtctacc cgatcggcat tgaaccgaaa gaaatagcca aacaggctgc   2580
cgggccactg ccgccaaaac tggcgcaact taaagcggaa ctgaaaaacg tacaaaatat   2640
cttttctgtc gaacggctgg attattccaa aggtttgcca gagcgttttc tcgcctatga   2700
agcgttgctg gaaaaatatc cgcagcatca tggtaaaatt cgttataccc agattgcacc   2760
aacgtcgcgt ggtgatgtgc aagcctatca ggatattcgt catcagctcg aaaatgaagc   2820
tggacgaatt aatggtaaat acgggcaatt aggctggacg ccgctttatt atttgaatca   2880
gcattttgac cgtaaattac tgatgaaaat attccgctac tctgacgtgg gcttagtgac   2940
gccactgcgt gacgggatga acctggtagc aaaagagtat gttgctgctc aggacccagc   3000
caatccgggc gttcttgttc tttcgcaatt tgcgggagcg gcaaacgagt taacgtcggc   3060
gttaattgtt aacccctacg atcgtgacga agttgcagct gcgctggatc gtgcattgac   3120
tatgtcgctg gcggaacgta tttcccgtca tgcagaaatg ctggacgtta tcgtgaaaaa   3180
cgatattaac cactggcagg agtgcttcat tagcgaccta aagcagatag ttccgcgaag   3240
cgcggaaagc cagcagcgcg ataaagttgc tacctttcca aagcttgcgt aggagctagc   3300
tgcctcgaaa ggggatgcga ttcgccacct ctcactccgc tggcggattc ctcttgagaa   3360
cattttggtg gcaggcgatt ctggtaacga tgaggaaatg ctcaagggcc ataatctcgg   3420
cgttgtagtt ggcaattact caccggaatt ggagccactg cgcagctacg agcgcgtcta   3480
ttttgctgag ggccactatg ctaatggcat tctggaagcc ttaaaacact atcgcttttt   3540
tgaggcgatc gcttaacctt ttcagaatga gacgttgatc ggcacgtaag cgtgagacgt   3600
tgatcggcac gtaagaggtt ccaactttca ccataatgaa ataagatcac taccgggcgt   3660
atttttttgag ttatcgagat tttcaggagc taaggaagct aaaatggaga aaaaaatcac   3720
tggatatacc accgttgata tatcccaatg gcatcgtaaa gaacattttg aggcatttca   3780
gtcagttgct caatgtacct ataaccagac cgttcagctg gatattacgg cctttttaaa   3840
gaccgtaaag aaaaataagc acaagtttta tccggccttt attcacattc ttgcccgcct   3900
gatgaatgct catccggaat tccgtatggc aatgaaagac ggtgagctgg tgatatggga   3960
tagtgttcac ccttgttaca ccgttttcca tgagcaaact gaaacgtttt catcgctctg   4020
gagtgaatac cacgacgatt tccggcagtt tctacacata tattcgcaag atgtggcgtg   4080
ttacggtgaa aacctggcct atttccctaa agggtttatt gagaatatgt ttttcgtctc   4140
agccaatccc tgggtgagtt tcaccagttt tgatttaaac gtggccaata tggacaactt   4200
cttcgccccc gttttcacca tgggcaaata ttatacgcaa ggcgacaagg tgctgatgcc   4260
gctggcgatt caggttcatc atgccgtttg tgatggcttc catgtcggca gaatgcttaa   4320
tgaattacaa cagtactgcg atgagtggca gggcggggcg taattttttt aaggcagtta   4380
ttggtgccct taaacgcctg gttgctacgc ctgaataagt gataataagc ggatgaatgg   4440
cagaaattcg atgataagct gtcaaacaca accaccatca aacaggattt tcgcctgctg   4500
gggcaaacca gcgtggaccg cttgctgcaa ctctctcagg gccaggcggt gaagggcaat   4560
cagctgttgc ccgtctcact ggtgaaaaga aaaaccaccc tggcgcccaa tacgcaaacc   4620
gcctctcccc gcgcgttggc cgattcatta atgcagctgg cacgacaggt ttcccgactg   4680
```

gaaagcgggc agtgagcgca acgcaattaa tgtaagttag cgcgaattgc aagctggccg 4740
acgcgctggg ctacgtcttg ctggcgttcg ggagcagaag agcatacatc tggaagcaaa 4800
gccaggaaag cggcctatgg agctgtgcgg cagcgctcag taggcaattt ttcaaaatat 4860
tgttaagcct tttctgagca tggtattttt catggtatta ccaattagca ggaaaataag 4920
ccattgaata taaaagataa aaatgtcttg tttacaatag agtggggggg gtcagcctgc 4980
cgccttgggc cgggtgatgt cgtacttgcc cgccgcgaac tcggttaccg tccagcccag 5040
cgcgaccagc tccggcaacg cctcgcgcac ccgcttgcgg cgcttgcgca tggtcgaacc 5100
actggcctct gacggccaga catagccgca caaggtatct atggaagcct tgccggtttt 5160
gccggggtcg atccagccac acagccgctg gtgcagcagg cgggcggttt cgctgtccag 5220
cgcccgcacc tcgtccatgc tgatgcgcac atgctggccg ccacccatga cggcctgcgc 5280
gatcaagggg ttcagggcca cgtacaggcg cccgtccgcc tcgtcgctgg cgtactccga 5340
cagcagccga aacccctgcc gcttgcggcc attctgggcg atgatggata ccttccaaag 5400
gcgctcgatg cagtcctgta tgtgcttgag cgccccacca ctatcgacct ctgccccgat 5460
ttcctttgcc agcgcccgat agctaccttt gaccacatgg cattcagcgg tgacggcctc 5520
ccacttgggt tccaggaaca gccggagctg ccgtccgcct tcggtcttgg gttccgggcc 5580
aagcactagg ccattaggcc cagccatggc caccagccct tgcaggatgc gcagatcatc 5640
agcgcccagc ggctccgggc cgctgaactc gatccgcttg ccgtcgccgt agtcatacgt 5700
cacgtccagc ttgctgcgct tgcgctcgcc ccgcttgagg gcacggaaca ggccgggggc 5760
cagacagtgc gccgggtcgt gccggacgtg gctgaggctg tgcttgttct taggcttcac 5820
cacggggcac cccccttgctc ttgcgctgcc tctccagcac ggcgggcttg agcaccccgc 5880
cgtcatgccg cctgaaccac cgatcagcga acggtgcgcc atagttggcc ttgctcacac 5940
cgaagcggac gaagaaccgg cgctggtcgt cgtccacacc ccattcctcg gcctcggcgc 6000
tggtcatgct cgacaggtag gactgccagc ggatgttatc gaccagtacc gagctgcccc 6060
ggctggcctg ctgctggtcg cctgcgccca tcatggccgc gcccttgctg gcatggtgca 6120
ggaacacgat agagcacccg gtatcggcgg cgatggcctc catgcgaccg atgacctggg 6180
ccatggggcc gctggcgttt tcttcctcga tgtggaaccg gcgcagcgtg tccagcacca 6240
tcaggcggcg gccctcggcg gcgcgcttga ggccgtcgaa ccactccggg gccatgatgt 6300
tgggcaggct gccgatcagc ggctggatca gcaggccgtc agccacggct tgccgttcct 6360
cggcgctgag gtgcgcccca agggcgtgca ggcggtgatg aatggcggtg ggcgggtctt 6420
cggcgggcag gtagatcacc gggccggtgg gcagttcgcc cacctccagc agatccggcc 6480
cgcctgcaat ctgtgcggcc agttgcaggg ccagcatgga tttaccggca ccaccgggcg 6540
acaccagcgc cccgaccgta ccggccacca tgttgggcaa aacgtagtcc agcggtggcg 6600
gcgctgctgc gaacgcctcc agaatattga taggcttatg ggtagccatt gattgcctcc 6660
tttgcaggca gttggtggtt aggcgctggc ggggtcacta cccccgccct gcgccgctct 6720
gagttcttcc aggcactcgc gcagcgcctc gtattcgtcg tcggtcagcc agaacttgcg 6780
ctgacgcatc cctttggcct tcatgcgctc ggcatatcgc gcttggcgta cagcgtcagg 6840
gctggccagc aggtcgccgg tctgcttgtc cttttggtct ttcatatcag tcaccgagaa 6900
acttgccggg gccgaaaggc ttgtcttcgc ggaacaagga caaggtgcag ccgtcaaggt 6960
taaggctggc catatcagcg actgaaaagc ggccagcctc ggccttgttt gacgtataac 7020

-continued

```
caaagccacc gggcaaccaa tagcccttgt cacttttgat caggtagacc gaccctgaag   7080
cgcttttttc gtattccata aaaccccctt ctgtgcgtga gtactcatag tataacaggc   7140
gtgagtacca acgcaagcac tacatgctga aatctggccc gcccctgtcc atgcctcgct   7200
ggcggggtgc cggtgcccgt gccagctcgg cccgcgcaag ctggacgctg ggcagaccca   7260
tgaccttgct gacggtgcgc tcgatgtaat ccgcttcgtg gccgggcttg cgctctgcca   7320
gcgctgggct ggcctcggcc atggccttgc cgatttcctc ggcactgcgg ccccggctgg   7380
ccagcttctg cgcggcgata aagtcgcact tgctgaggtc atgaccgaag cgcttgacca   7440
gcccggccat ctcgctgcgg tactcgtcca gcgccgtgcg ccggtggcgg ctaagctgcc   7500
gctcgggcag ttcgaggctg gccagcctgc gggccttctc ctgctgccgc tgggcctgct   7560
cgatctgctg gccagcctgc tgcaccagcg ccgggccagc ggtggcggtc ttgcccttgg   7620
attcacgcag cagcacccac ggctgataac cggcgcgggt ggtgtgcttg tccttgcggt   7680
tggtgaagcc cgccaagcgg ccatagtggc ggctgtcggc gctggccggg tcggcgtcgt   7740
actcgctggc cagcgtccgg gcaatctgcc cccgaagttc accgcctgcg gcgtcggcca   7800
ccttgaccca tgcctgatag ttcttcgggc tggtttccac taccagggca ggctcccggc   7860
cctcggcttt catgtcatcc aggtcaaact cgctgaggtc gtccaccagc accagaccat   7920
gccgctcctg ctcggcgggc ctgatataca cgtcattgcc ctgggcattc atccgcttga   7980
gccatggcgt gttctggagc acttcggcgg ctgaccattc ccggttcatc atctggccgg   8040
tgggtgcgtc cctgacgccg atatcgaagc gctcacagcc catggccttg agctgtcggc   8100
ctatggcctg caaagtcctg tcgttcttca tcgggccacc aagcgcagcc agatcgagcc   8160
gtcctcggtt gtcagtggcg tcaggtcgag caagagcaac gatgcgatca gcagcaccac   8220
cgtaggcatc atggaagcca gcatcacggt tagccatagc ttccagtgcc acccccgcga   8280
cgcgctccgg gcgctctgcg cggcgctgct cacctcggcg gctacctccc gcaactcttt   8340
ggccagctcc acccatgccg cccctgtctg gcgctgggct ttcagccact ccgccgcctg   8400
cgcctcgctg gcctgcttgg tctggctcat gacctgccgg gcttcgtcgg ccagtgtcgc   8460
catgctctgg gccagcggtt cgatctgctc cgctaactcg ttgatgcctc tggatttctt   8520
cactctgtcg attgcgttca tggtctattg cctcccggta ttcctgtaag tcgatgatct   8580
gggcgttggc ggtgtcgatg ttcagggcca cgtctgcccg gtcggtgcgg atgccccggc   8640
cttccatctc caccacgttc ggccccaggt gaacaccggg caggcgctcg atgccctgcg   8700
cctcaagtgt tctgtggtca atgcgggcgt cgtggccagc ccgctctaat gcccggttgg   8760
catggtcggc ccatgcctcg cgggtctgct caagccatgc cttgggcttg agcgcttcgg   8820
tcttctgtgc cccgcccttc tccggggtct tgccgttgta ccgcttgaac cactgagcgg   8880
cgggccgctc gatgccgtca ttgatccgct cggagatcat caggtggcag tgcgggttct   8940
cgccgccacc ggcatggatg gccagcgtat acggcaggcg ctcggcaccg gtcaggtgct   9000
gggcgaactc ggacgccagc gccttctgct ggtcgagggt cagctcgacc ggcagggcaa   9060
attcgacctc cttgaacagc cgcccattgg cgcgttcata caggtcggca gcatcccagt   9120
agtcggcggg ccgctcgacg aactccggca tgtgcccgga ttcggcgtgc aagacttcat   9180
ccatgtcgcg ggcatacttg ccttcgcgct ggatgtagtc ggccttggcc ctggccgatt   9240
ggccgcccga cctgctgccg gttttcgccg taaggtgata aatcgccatg ctgcctcgct   9300
gttgcttttg cttttcggct ccatgcaatg gccctcggag agcgcaccgc ccgaagggtg   9360
gccgttaggc cagtttctcg aagagaaacc ggtaagtgcg ccctccccta caaagtaggg   9420
```

-continued

```
tcgggattgc cgccgctgtg cctccatgat agcctacgag acagcacatt aacaatgggg   9480
tgtcaagatg gttaagggga gcaacaaggc ggcggatcgg ctggccaagc tcgaagaaca   9540
acgagcgcga atcaatgccg aaattcagcg ggagcgggca agggaacagc agcaagagcg   9600
caagaacgaa acaaggcgca aggtgctggt gggggccatg attttggcca aggtgaacag   9660
cagcgagtgg ccggaggatc ggctcatggc ggcaatggat gcgtaccttg aacgcgacca   9720
cgaccgcgcc ttgttcggtc tgccgccacg ccagaaggat gagccgggct gaatgatcga   9780
ccgagacagg ccctgcgggg ctgcacacgc gcccccaccc ttcgggtagg gggaaaggcc   9840
gctaaagcgg ctaaaagcgc tccagcgtat ttctgcgggg tttggtgtgg ggtttagcgg   9900
gctttgcccg cctttccccc tgccgcgcag cggtggggcg gtgtgtagcc tagcgcagcg   9960
aatagaccag ctatccggcc tctggccggg catattgggc aagggcagca gcgccccaca  10020
agggcgctga taaccgcgcc tagtggatta ttcttagata atcatggatg gatttttcca  10080
acaccccgcc agcccccgcc cctgctgggt ttgcaggttt gggggcgtga cagttattgc  10140
aggggttcgt gacagttatt gcaggggggc gtgacagtta ttgcaggggt tcgtgacagt  10200
tagtacggga gtgacgggca ctggctggca atgtctagca acggcaggca tttcggctga  10260
gggtaaaaga actttccgct aagcgataga ctgtatgtaa acacagtatt gcaaggacgc  10320
ggaacatgcc tcatgtggcg gccaggacgg ccagccggga tcgggatact ggtcgttacc  10380
agagccaccg acccgagcaa acccttctct atcagatcgt tgacgagtat tacccggcat  10440
tcgctgcgct tatggcagag cagggaaagg aattgccggg ctatgtgcaa cgggaatttg  10500
aagaatttct ccaatgcggg cggctggagc atggctttct acgggttcgc tgcgagtctt  10560
gccacgccga gcacctggtc gctttcagaa atcaatctaa agtatatatg agtaaacttg  10620
gtctgacagt taccaatgct taatcagtga ggcacctatc tcagcgatct gtctatttcg  10680
ttcatccata gttgcctgac tccccgtcgt gtagataact acgatacggg agggcttacc  10740
atctggcccc agtgctgcaa tgataccgcg agacccacgc tcaccggctc cagatttatc  10800
agcaataaac cagccagccg gaagggccga gcgcagaagt ggtcctgcaa ctttatccgc  10860
ctccatccag tctattaatt gttgccggga agctagagta agtagttcgc cagttaatag  10920
tttgcgcaac gttgttgcca ttgctacagg catcgtggtg tcacgctcgt cgtttggtat  10980
ggcttcattc agctccggtt cccaacgatc aaggcgagtt acatgatccc ccatgttgtg  11040
caaaaaagcg gttagctcct tcggtcctcc gatcgttgtc agaagtaagt tggccgcagt  11100
gttatcactc atggttatgg cagcactgca taattctctt actgtcatgc catccgtaag  11160
atgcttttct gtgactggtg agtactcaac caagtcattc tgagaatagt gtatgcggcg  11220
accgagttgc tcttgcccgg cgtcaacacg ggataatacc gcgccacata gcagaacttt  11280
aaaagtgctc atcattggaa aacgttcttc ggggcgaaaa ctctcaagga tcttaccgct  11340
gttgagatcc agttcgatgt aacccactcg tgcacccaac tgatcttcag catcttttac  11400
tttcaccagc gtttctgggt gagcaaaaac aggaaggcaa aatgccgcaa aaaagggaat  11460
aagggcgaca cggaaatgtt gaatactcat actcttcctt tttcaatatt attgaagcat  11520
ttatcagggt tattgtctca tgagcggata catatttgaa tgtatttaga aaaataaaca  11580
aaagagtttg tagaaacgca aaaaggccat ccgtcaggat ggccttctgc ttaatttgat  11640
gcctggcagt ttatggcggg cgtcctgccc gccaccctcc gggccgttgc ttcgcaacgt  11700
tcaaatccgc tcccggcgga tttgtcctac tcaggagagc gttcaccgac aaacaacaga  11760
```

taaaacgaa 11769

<210> SEQ ID NO 124
<211> LENGTH: 11477
<212> TYPE: DNA
<213> ORGANISM: Artificial Sequence
<220> FEATURE:
<223> OTHER INFORMATION: plasmid pLybAL31 containing otsBA operon

<400> SEQUENCE: 124
aggcccagtc tttcgactga gcctttcgtt ttatttgatg cctggcagtt ccctactctc 60
gcatggggag accccacact accatcggcg ctacggcgtt tcacttctga gttcggcatg 120
gggtcaggtg ggaccaccgc gctactgccg ccaggcaaat tctgttttat cagaccgctt 180
ctgcgttctg atttaatctg tatcaggctg aaaatcttct ctcatccgcc aaaacagcca 240
agcttgcatg caaagctcac taactgggcg ggattttccg ggtccggttg ctgacggtaa 300
tagtcgtcta aaagtttggc cacatccaaa aggctgtcgg cggggggatg ctggccggcg 360
aggggattaa ttctgcttgt catatacaaa aattgtaaaa aatggagggc ggcgatcagg 420
ggcttagaca cccaaatcct agccaaaaag ggttaactag ccaagggcta tccatgggca 480
aagagataaa agaaaaagtc tccaaatccc tggtcataga gaaaaaattg ccaaagttac 540
cccaggccat acacggccca gcgccaagat ggggagcaca aattcaaact ttgtaaacag 600
gccggaagct atccggccaa ggagcactca gattgtgtta acgttcaggg gagttgctta 660
acacaatttt ccaattaata gtattaatat tttcttaact tgcaccgtac catggtgaga 720
aagcctatct gagcccttat ttgattaacc ttcgactgat tattgatccc ctgtgcagtc 780
tcccctctcc ctctgtcttt ttgctcccga acacgttgcc catagactca ggtaccgtta 840
agaaggagga tccatatgat cttgatggaa cgctggcgga aatcaaaccg catcccgatc 900
aggtcgtcgt gcctgacaat attctgcaag gactacagct actggcaacc gcaagtgatg 960
gtgcattggc attgatatca gggcgctcaa tggtggagct tgacgcactg gcaaaacctt 1020
atcgcttccc gttagcgggc gtgcatgggg cggagcgccg tgacatcaat ggtaaaacac 1080
atatcgttca tctgccggat gcgattgcgc gtgatattag cgtgcaactg catacagtca 1140
tcgctcagta tcccggcgcg gagctggagg cgaaagggat ggcttttgcg ctgcattatc 1200
gtcaggctcc gcagcatgaa gacgcattaa tgacattagc gcaacgtatt actcagatct 1260
ggccacaaat ggcgttacag cagggaaagt gtgttgtcga gatcaaaccg agaggtacca 1320
gtaaaggtga ggcaattgca gcttttatgc aggaagctcc ctttatcggg cgaacgcccg 1380
tatttctggg cgatgattta accgatgaat ctggcttcgc agtcgttaac cgactgggcg 1440
gaatgtcagt aaaaattggc acaggtgcaa ctcaggcatc atggcgactg gcgggtgtgc 1500
cggatgtctg gagctggctt gaaatgataa ccaccgcatt acaacaaaaa agagaaaata 1560
acaggagtga tgactatgag tcgtttagtc gtagtatcta accggattgc accaccagac 1620
gagcacgccg ccagtgccgg tggccttgcc gttggcatac tgggggcact gaaagccgca 1680
ggcggactgt ggtttggctg gagtggtgaa acagggaatg aggatcagcc gctaaaaaag 1740
gtgaaaaaag gtaacattac gtgggcctct tttaacctca gcgaacagga ccttgacgaa 1800
tactacaacc aattctccaa tgccgttctc tggcccgctt ttcattatcg gctcgatctg 1860
gtgcaatttc agcgtcctgc ctgggacggc tatctacgcg taaatgcgtt gctggcagat 1920
aaattactgc cgctgttgca agacgatgac attatctgga tccacgatta tcacctgttg 1980
ccatttgcgc atgaattacg caaacgggga gtgaataatc gcattggttt ctttctgcat 2040

-continued

```
attcctttcc cgacaccgga aatcttcaac gcgctgccga catatgacac cttgcttgaa   2100
cagctttgtg attatgattt gctgggtttc cagacagaaa acgatcgtct ggcgttcctg   2160
gattgtcttt ctaacctgac ccgcgtcacg acacgtagcg caaaaagcca tacagcctgg   2220
ggcaaagcat ttcgaacaga agtctacccg atcggcattg aaccgaaaga aatagccaaa   2280
caggctgccg ggccactgcc gccaaaactg gcgcaactta aagcggaact gaaaaacgta   2340
caaaatatct tttctgtcga acggctggat tattccaaag gtttgccaga gcgttttctc   2400
gcctatgaag cgttgctgga aaaatatccg cagcatcatg gtaaaattcg ttatacccag   2460
attgcaccaa cgtcgcgtgg tgatgtgcaa gcctatcagg atattcgtca tcagctcgaa   2520
aatgaagctg gacgaattaa tggtaaatac gggcaattag gctggacgcc gctttattat   2580
ttgaatcagc attttgaccg taaattactg atgaaaatat tccgctactc tgacgtgggc   2640
ttagtgacgc cactgcgtga cgggatgaac ctggtagcaa aagagtatgt tgctgctcag   2700
gacccagcca atccgggcgt tcttgttctt tcgcaatttg cgggagcggc aaacgagtta   2760
acgtcggcgt taattgttaa cccctacgat cgtgacgaag ttgcagctgc gctggatcgt   2820
gcattgacta tgtcgctggc ggaacgtatt tcccgtcatg cagaaatgct ggacgttatc   2880
gtgaaaaacg atattaacca ctggcaggag tgcttcatta gcgacctaaa gcagatagtt   2940
ccgcgaagcg cggaaagcca gcagcgcgat aaagttgcta cctttccaaa gcttgcgtag   3000
gagctagctg cctcgaaagg ggatgcgatt cgccacctct cactccgctg gcggattcct   3060
cttgagaaca ttttggtggc aggcgattct ggtaacgatg aggaaatgct caagggccat   3120
aatctcggcg ttgtagttgg caattactca ccggaattgg agccactgcg cagctacgag   3180
cgcgtctatt ttgctgaggg ccactatgct aatggcattc tggaagcctt aaaacactat   3240
cgctttttttg aggcgatcgc ttaacctttt cagaatgaga cgttgatcgg cacgtaagcg   3300
tgagacgttg atcggcacgt aagaggttcc aactttcacc ataatgaaat aagatcacta   3360
ccgggcgtat tttttgagtt atcgagattt tcaggagcta aggaagctaa aatggagaaa   3420
aaaatcactg gatataccac cgttgatata tcccaatggc atcgtaaaga acattttgag   3480
gcatttcagt cagttgctca atgtacctat aaccagaccg ttcagctgga tattacggcc   3540
tttttaaaga ccgtaaagaa aaataagcac aagttttatc cggcctttat tcacattctt   3600
gcccgcctga tgaatgctca tccggaattc cgtatggcaa tgaaagacgg tgagctggtg   3660
atatgggata gtgttcaccc ttgttacacc gttttccatg agcaaactga aacgttttca   3720
tcgctctgga gtgaatacca cgacgatttc cggcagtttc tacacatata ttcgcaagat   3780
gtggcgtgtt acggtgaaaa cctggcctat ttccctaaag ggtttattga gaatatgttt   3840
ttcgtctcag ccaatccctg ggtgagtttc accagttttg atttaaacgt ggccaatatg   3900
gacaacttct tcgcccccgt tttcaccatg ggcaaatatt atacgcaagg cgacaaggtg   3960
ctgatgccgc tggcgattca ggttcatcat gccgtttgtg atggcttcca tgtcggcaga   4020
atgcttaatg aattacaaca gtactgcgat gagtggcagg gcggggcgta atttttttaa   4080
ggcagttatt ggtgccctta aacgcctggt tgctacgcct gaataagtga taataagcgg   4140
atgaatggca gaaattcgat gataagctgt caaacacaac caccatcaaa caggattttc   4200
gcctgctggg gcaaaccagc gtggaccgct tgctgcaact ctctcagggc caggcggtga   4260
agggcaatca gctgttgccc gtctcactgg tgaaaagaaa aaccaccctg gcgcccaata   4320
cgcaaaccgc ctctccccgc gcgttggccg attcattaat gcagctggca cgacaggttt   4380
```

```
cccgactgga aagcgggcag tgagcgcaac gcaattaatg taagttagcg cgaattgcaa   4440
gctggccgac gcgctgggct acgtcttgct ggcgttcggg agcagaagag catacatctg   4500
gaagcaaagc caggaaagcg gcctatggag ctgtgcggca gcgctcagta ggcaattttt   4560
caaaatattg ttaagccttt tctgagcatg gtatttttca tggtattacc aattagcagg   4620
aaaataagcc attgaatata aaagataaaa atgtcttgtt tacaatagag tggggggggt   4680
cagcctgccg ccttgggccg ggtgatgtcg tacttgcccg ccgcgaactc ggttaccgtc   4740
cagcccagcg cgaccagctc cggcaacgcc tcgcgcaccc gcttgcggcg cttgcgcatg   4800
gtcgaaccac tggcctctga cggccagaca tagccgcaca aggtatctat ggaagccttg   4860
ccggttttgc cggggtcgat ccagccacac agccgctggt gcagcaggcg ggcggtttcg   4920
ctgtccagcg cccgcacctc gtccatgctg atgcgcacat gctggccgcc acccatgacg   4980
gcctgcgcga tcaaggggtt cagggccacg tacaggcgcc cgtccgcctc gtcgctggcg   5040
tactccgaca gcagccgaaa cccctgccgc ttgcggccat tctgggcgat gatggatacc   5100
ttccaaaggc gctcgatgca gtcctgtatg tgcttgagcg ccccaccact atcgacctct   5160
gccccgattt cctttgccag cgcccgatag ctacctttga ccacatggca ttcagcggtg   5220
acggcctccc acttgggttc caggaacagc cggagctgcc gtccgccttc ggtcttgggt   5280
tccgggccaa gcactaggcc attaggccca gccatggcca ccagcccttg caggatgcgc   5340
agatcatcag cgcccagcgg ctccgggccg ctgaactcga tccgcttgcc gtcgccgtag   5400
tcatacgtca cgtccagctt gctgcgcttg cgctcgcccc gcttgagggc acggaacagg   5460
ccgggggcca gacagtgcgc cgggtcgtgc cggacgtggc tgaggctgtg cttgttctta   5520
ggcttcacca cggggcaccc ccttgctctt gcgctgcctc tccagcacgg cgggcttgag   5580
caccccgccg tcatgccgcc tgaaccaccg atcagcgaac ggtgcgccat agttggcctt   5640
gctcacaccg aagcggacga agaaccggcg ctggtcgtcg tccacacccc attcctcggc   5700
ctcggcgctg gtcatgctcg acaggtagga ctgccagcgg atgttatcga ccagtaccga   5760
gctgccccgg ctggcctgct gctggtcgcc tgcgcccatc atggccgcgc ccttgctggc   5820
atggtgcagg aacacgatag agcacccggt atcggcggcg atggcctcca tgcgaccgat   5880
gacctgggcc atggggccgc tggcgttttc ttcctcgatg tggaaccggc gcagcgtgtc   5940
cagcaccatc aggcggcggc cctcggcggc gcgcttgagg ccgtcgaacc actccggggc   6000
catgatgttg ggcaggctgc cgatcagcgg ctggatcagc aggccgtcag ccacggcttg   6060
ccgttcctcg gcgctgaggt gcgccccaag ggcgtgcagg cggtgatgaa tggcggtggg   6120
cgggtcttcg gcgggcaggt agatcaccgg gccggtgggc agttcgccca cctccagcag   6180
atccggcccg cctgcaatct gtgcggccag ttgcagggcc agcatggatt taccggcacc   6240
accgggcgac accagcgccc cgaccgtacc ggccaccatg ttgggcaaaa cgtagtccag   6300
cggtggcggc gctgctgcga acgcctccag aatattgata ggcttatggg tagccattga   6360
ttgcctcctt tgcaggcagt tggtggttag gcgctggcgg ggtcactacc cccgccctgc   6420
gccgctctga gttcttccag gcactcgcgc agcgcctcgt attcgtcgtc ggtcagccag   6480
aacttgcgct gacgcatccc tttggccttc atgcgctcgg catatcgcgc ttggcgtaca   6540
gcgtcagggc tggccagcag gtcgccggtc tgcttgtcct tttggtcttt catatcagtc   6600
accgagaaac ttgccggggc cgaaaggctt gtcttcgcgg aacaaggaca aggtgcagcc   6660
gtcaaggtta aggctggcca tatcagcgac tgaaaagcgg ccagcctcgg ccttgtttga   6720
cgtataacca aagccaccgg gcaaccaata gcccttgtca cttttgatca ggtagaccga   6780
```

```
ccctgaagcg ctttttcgt attccataaa accccccttct gtgcgtgagt actcatagta   6840
taacaggcgt gagtaccaac gcaagcacta catgctgaaa tctggcccgc ccctgtccat   6900
gcctcgctgg cggggtgccg gtgcccgtgc cagctcggcc cgcgcaagct ggacgctggg   6960
cagacccatg accttgctga cggtgcgctc gatgtaatcc gcttcgtggc cgggcttgcg   7020
ctctgccagc gctgggctgg cctcggccat ggccttgccg atttcctcgg cactgcggcc   7080
ccggctggcc agcttctgcg cggcgataaa gtcgcacttg ctgaggtcat gaccgaagcg   7140
cttgaccagc ccggccatct cgctgcggta ctcgtccagc gccgtgcgcc ggtggcggct   7200
aagctgccgc tcgggcagtt cgaggctggc cagcctgcgg gccttctcct gctgccgctg   7260
ggcctgctcg atctgctggc cagcctgctg caccagcgcc gggccagcgg tggcggtctt   7320
gcccttggat tcacgcagca gcacccacgg ctgataaccg gcgcgggtgg tgtgcttgtc   7380
cttgcggttg gtgaagcccg ccaagcggcc atagtggcgg ctgtcggcgc tggccgggtc   7440
ggcgtcgtac tcgctggcca gcgtccgggc aatctgcccc cgaagttcac cgcctgcggc   7500
gtcggccacc ttgacccatg cctgatagtt cttcgggctg gtttccacta ccagggcagg   7560
ctcccggccc tcggctttca tgtcatccag gtcaaactcg ctgaggtcgt ccaccagcac   7620
cagaccatgc cgctcctgct cggcgggcct gatatacacg tcattgccct gggcattcat   7680
ccgcttgagc catggcgtgt tctggagcac ttcggcggct gaccattccc ggttcatcat   7740
ctggccggtg ggtgcgtccc tgacgccgat atcgaagcgc tcacagccca tggccttgag   7800
ctgtcggcct atggcctgca aagtcctgtc gttcttcatc gggccaccaa gcgcagccag   7860
atcgagccgt cctcggttgt cagtggcgtc aggtcgagca agagcaacga tgcgatcagc   7920
agcaccaccg taggcatcat ggaagccagc atcacggtta gccatagctt ccagtgccac   7980
ccccgcgacg cgctccgggc gctctgcgcg gcgctgctca cctcggcggc tacctcccgc   8040
aactctttgg ccagctccac ccatgccgcc cctgtctggc gctgggcttt cagccactcc   8100
gccgcctgcg cctcgctggc ctgcttggtc tggctcatga cctgccgggc ttcgtcggcc   8160
agtgtcgcca tgctctgggc cagcggttcg atctgctccg ctaactcgtt gatgcctctg   8220
gatttcttca ctctgtcgat tgcgttcatg gtctattgcc tcccggtatt cctgtaagtc   8280
gatgatctgg gcgttggcgg tgtcgatgtt cagggccacg tctgcccggt cggtgcggat   8340
gccccggcct tccatctcca ccacgttcgg ccccaggtga acaccgggca ggcgctcgat   8400
gccctgcgcc tcaagtgttc tgtggtcaat gcgggcgtcg tggccagccc gctctaatgc   8460
ccggttggca tggtcggccc atgcctcgcg ggtctgctca agccatgcct tgggcttgag   8520
cgcttcggtc ttctgtgccc cgcccttctc cggggtcttg ccgttgtacc gcttgaacca   8580
ctgagcggcg ggccgctcga tgccgtcatt gatccgctcg gagatcatca ggtggcagtg   8640
cgggttctcg ccgccaccgg catggatggc cagcgtatac ggcaggcgct cggcaccggt   8700
caggtgctgg gcgaactcgg acgccagcgc cttctgctgg tcgagggtca gctcgaccgg   8760
cagggcaaat tcgacctcct tgaacagccg cccattggcg cgttcataca ggtcggcagc   8820
atcccagtag tcggcgggcc gctcgacgaa ctccggcatg tgcccggatt cggcgtgcaa   8880
gacttcatcc atgtcgcggg catacttgcc ttcgcgctgg atgtagtcgg ccttggccct   8940
ggccgattgg ccgcccgacc tgctgccggt tttcgccgta aggtgataaa tcgccatgct   9000
gcctcgctgt tgcttttgct tttcggctcc atgcaatggc cctcggagag cgcaccgccc   9060
gaagggtggc cgttaggcca gtttctcgaa gagaaaccgg taagtgcgcc ctcccctaca   9120
```

-continued aagtagggtc gggattgccg ccgctgtgcc tccatgatag cctacgagac agcacattaa 9180
caatggggtg tcaagatggt taaggggagc aacaaggcgg cggatcggct ggccaagctc 9240
gaagaacaac gagcgcgaat caatgccgaa attcagcggg agcgggcaag ggaacagcag 9300
caagagcgca agaacgaaac aaggcgcaag gtgctggtgg gggccatgat tttggccaag 9360
gtgaacagca gcgagtggcc ggaggatcgg ctcatggcgg caatggatgc gtaccttgaa 9420
cgcgaccacg accgcgcctt gttcggtctg ccgccacgcc agaaggatga gccgggctga 9480
atgatcgacc gagacaggcc ctgcggggct gcacacgcgc ccccaccctt cgggtagggg 9540
gaaaggccgc taaagcggct aaaagcgctc cagcgtattt ctgcggggtt tggtgtgggg 9600
tttagcgggc tttgcccgcc tttccccctg ccgcgcagcg gtggggcggt gtgtagccta 9660
gcgcagcgaa tagaccagct atccggcctc tggccgggca tattgggcaa gggcagcagc 9720
gccccacaag ggcgctgata accgcgccta gtggattatt cttagataat catggatgga 9780
tttttccaac accccgccag cccccgcccc tgctgggttt gcaggtttgg gggcgtgaca 9840
gttattgcag ggg ttcgtga cagttattgc aggggggcgt gacagttatt gcaggggttc 9900
gtgacagtta gtacgggagt gacgggcact ggctggcaat gtctagcaac ggcaggcatt 9960
tcggctgagg gtaaaagaac tttccgctaa gcgatagact gtatgtaaac acagtattgc 10020
aaggacgcgg aacatgcctc atgtggcggc caggacggcc agccgggatc gggatactgg 10080
tcgttaccag agccaccgac ccgagcaaac ccttctctat cagatcgttg acgagtatta 10140
cccggcattc gctgcgctta tggcagagca gggaaaggaa ttgccgggct atgtgcaacg 10200
ggaatttgaa gaatttctcc aatgcgggcg gctggagcat ggctttctac gggttcgctg 10260
cgagtcttgc cacgccgagc acctggtcgc tttcagaaat caatctaaag tatatatgag 10320
taaacttggt ctgacagtta ccaatgctta atcagtgagg cacctatctc agcgatctgt 10380
ctatttcgtt catccatagt tgcctgactc cccgtcgtgt agataactac gatacgggag 10440
ggcttaccat ctggccccag tgctgcaatg ataccgcgag acccacgctc accggctcca 10500
gatttatcag caataaacca gccagccgga agggccgagc gcagaagtgg tcctgcaact 10560
ttatccgcct ccatccagtc tattaattgt tgccgggaag ctagagtaag tagttcgcca 10620
gttaatagtt tgcgcaacgt tgttgccatt gctacaggca tcgtggtgtc acgctcgtcg 10680
tttggtatgg cttcattcag ctccggttcc caacgatcaa ggcgagttac atgatccccc 10740
atgttgtgca aaaaagcggt tagctccttc ggtcctccga tcgttgtcag aagtaagttg 10800
gccgcagtgt tatcactcat ggttatggca gcactgcata attctcttac tgtcatgcca 10860
tccgtaagat gcttttctgt gactggtgag tactcaacca agtcattctg agaatagtgt 10920
atgcggcgac cgagttgctc ttgcccggcg tcaacacggg ataataccgc gccacatagc 10980
agaactttaa aagtgctcat cattggaaaa cgttcttcgg ggcgaaaact ctcaaggatc 11040
ttaccgctgt tgagatccag ttcgatgtaa cccactcgtg cacccaactg atcttcagca 11100
tcttttactt tcaccagcgt ttctgggtga gcaaaaacag gaaggcaaaa tgccgcaaaa 11160
aagggaataa gggcgacacg gaaatgttga atactcatac tcttcctttt tcaatattat 11220
tgaagcattt atcagggtta ttgtctcatg agcggataca tatttgaatg tatttagaaa 11280
aataaacaaa agagtttgta gaaacgcaaa aaggccatcc gtcaggatgg ccttctgctt 11340
aatttgatgc ctggcagttt atggcgggcg tcctgcccgc caccctccgg gccgttgctt 11400
cgcaacgttc aaatccgctc ccggcggatt tgtcctactc aggagagcgt tcaccgacaa 11460
acaacagata aaacgaa 11477

<210> SEQ ID NO 125
<211> LENGTH: 11258
<212> TYPE: DNA
<213> ORGANISM: Artificial Sequence
<220> FEATURE:
<223> OTHER INFORMATION: plasmid pLybAL36 containing otsBA operon

<400> SEQUENCE: 125

```
aggcccagtc tttcgactga gcctttcgtt ttatttgatg cctggcagtt ccctactctc     60
gcatggggag accccacact accatcggcg ctacggcgtt tcacttctga gttcggcatg    120
gggtcaggtg ggaccaccgc gctactgccg ccaggcaaat tctgttttat cagaccgctt    180
ctgcgttctg atttaatctg tatcaggctg aaaatcttct ctcatccgcc aaaacagcca    240
agcttgcatg caggaaaaca agctcagaat gctgcgggga gaagggcaac tccccaccag    300
ccccaaattt ttgctggcga taaatatttt tcggtttaat tgttcacaaa gctttttgaa    360
tttgagttta tagaaattta ttggctggta atgctttttt gccccccctgc aggacttcat    420
tgatccttgc ctataccatc aatatcattg gtcaataatg atgatgattg actaaaacat    480
gtttaacaaa atttaacgca tatgctaaat gcgtaaactg catatgcctt ggctgagtgt    540
aatttacgtt acaaatttta acgaaacggg aaccctatat tgatctctac tgttatctgg    600
cttgaagcgt tggtaccgtt aagaaggagg atccatatga tcttgatgga acgctggcgg    660
aaatcaaacc gcatcccgat caggtcgtcg tgcctgacaa tattctgcaa ggactacagc    720
tactggcaac cgcaagtgat ggtgcattgg cattgatatc agggcgctca atggtggagc    780
ttgacgcact ggcaaaacct tatcgcttcc cgttagcggg cgtgcatggg gcggagcgcc    840
gtgacatcaa tggtaaaaca catatcgttc atctgccgga tgcgattgcg cgtgatatta    900
gcgtgcaact gcatacagtc atcgctcagt atcccggcgc ggagctggag gcgaaaggga    960
tggcttttgc gctgcattat cgtcaggctc cgcagcatga agacgcatta atgacattag   1020
cgcaacgtat tactcagatc tggccacaaa tggcgttaca gcagggaaag tgtgttgtcg   1080
agatcaaacc gagaggtacc agtaaaggtg aggcaattgc agcttttatg caggaagctc   1140
cctttatcgg gcgaacgccc gtatttctgg gcgatgattt aaccgatgaa tctggcttcg   1200
cagtcgttaa ccgactgggc ggaatgtcag taaaaattgg cacaggtgca actcaggcat   1260
catggcgact ggcgggtgtg ccggatgtct ggagctggct tgaaatgata accaccgcat   1320
tacaacaaaa aagagaaaat aacaggagtg atgactatga gtcgtttagt cgtagtatct   1380
aaccggattg caccaccaga cgagcacgcc gccagtgccg gtggccttgc cgttggcata   1440
ctgggggcac tgaaagccgc aggcggactg tggtttggct ggagtggtga aacagggaat   1500
gaggatcagc cgctaaaaaa ggtgaaaaaa ggtaacatta cgtgggcctc ttttaacctc   1560
agcgaacagg accttgacga atactacaac caattctcca atgccgttct ctggcccgct   1620
tttcattatc ggctcgatct ggtgcaattt cagcgtcctg cctgggacgg ctatctacgc   1680
gtaaatgcgt tgctggcaga taaattactg ccgctgttgc aagacgatga cattatctgg   1740
atccacgatt atcacctgtt gccatttgcg catgaattac gcaaacgggg agtgaataat   1800
cgcattggtt tctttctgca tattcctttc ccgacaccgg aaatcttcaa cgcgctgccg   1860
acatatgaca ccttgcttga acagctttgt gattatgatt tgctgggttt ccagacagaa   1920
aacgatcgtc tggcgttcct ggattgtctt tctaacctga cccgcgtcac gacacgtagc   1980
gcaaaaagcc atacagcctg ggcaaagca tttcgaacag aagtctaccc gatcggcatt   2040
```

-continued gaaccgaaag aaatagccaa acaggctgcc gggccactgc cgccaaaact ggcgcaactt 2100
aaagcggaac tgaaaaacgt acaaaatatc ttttctgtcg aacggctgga ttattccaaa 2160
ggtttgccag agcgtttttct cgcctatgaa gcgttgctgg aaaaatatcc gcagcatcat 2220
ggtaaaattc gttataccca gattgcacca acgtcgcgtg gtgatgtgca agcctatcag 2280
gatattcgtc atcagctcga aaatgaagct ggacgaatta atggtaaata cgggcaatta 2340
ggctggacgc cgctttatta tttgaatcag cattttgacc gtaaattact gatgaaaata 2400
ttccgctact ctgacgtggg cttagtgacg ccactgcgtg acgggatgaa cctggtagca 2460
aaagagtatg ttgctgctca ggacccagcc aatccgggcg ttcttgttct ttcgcaattt 2520
gcgggagcgg caaacgagtt aacgtcggcg ttaattgtta acccctacga tcgtgacgaa 2580
gttgcagctg cgctggatcg tgcattgact atgtcgctgg cggaacgtat ttcccgtcat 2640
gcagaaatgc tggacgttat cgtgaaaaac gatattaacc actggcagga gtgcttcatt 2700
agcgacctaa agcagatagt tccgcgaagc gcggaaagcc agcagcgcga taaagttgct 2760
acctttccaa agcttgcgta ggagctagct gcctcgaaag ggatgcgat tcgccacctc 2820 tcactccgct ggcggattcc tcttgagaac attttggtgg caggcgattc tggtaacgat 2880
gaggaaatgc tcaagggcca taatctcggc gttgtagttg gcaattactc accggaattg 2940
gagccactgc gcagctacga gcgcgtctat tttgctgagg gccactatgc taatggcatt 3000
ctggaagcct taaaacacta tcgctttttt gaggcgatcg cttaaccttt tcagaatgag 3060
acgttgatcg gcacgtaagc gtgagacgtt gatcggcacg taagaggttc caactttcac 3120
cataatgaaa taagatcact accgggcgta ttttttgagt tatcgagatt ttcaggagct 3180
aaggaagcta aaatggagaa aaaaatcact ggatatacca ccgttgatat atcccaatgg 3240
catcgtaaag aacattttga ggcatttcag tcagttgctc aatgtaccta taaccagacc 3300
gttcagctgg atattacggc ctttttaaag accgtaaaga aaaataagca caagttttat 3360
ccggccttta ttcacattct tgcccgcctg atgaatgctc atccggaatt ccgtatggca 3420
atgaaagacg gtgagctggt gatatgggat agtgttcacc cttgttacac cgttttccat 3480
gagcaaactg aaacgttttc atcgctctgg agtgaatacc acgacgattt ccggcagttt 3540
ctacacatat attcgcaaga tgtggcgtgt tacggtgaaa acctggccta tttccctaaa 3600
gggtttattg agaatatgtt tttcgtctca gccaatccct gggtgagttt caccagtttt 3660
gatttaaacg tggccaatat ggacaacttc ttcgcccccg ttttcaccat gggcaaatat 3720
tatacgcaag gcgacaaggt gctgatgccg ctggcgattc aggttcatca tgccgtttgt 3780
gatggcttcc atgtcggcag aatgcttaat gaattacaac agtactgcga tgagtggcag 3840
ggcggggcgt aattttttta aggcagttat tggtgccctt aaacgcctgg ttgctacgcc 3900
tgaataagtg ataataagcg gatgaatggc agaaattcga tgataagctg tcaaacacaa 3960
ccaccatcaa acaggatttt cgcctgctgg ggcaaaccag cgtggaccgc ttgctgcaac 4020
tctctcaggg ccaggcggtg aagggcaatc agctgttgcc cgtctcactg gtgaaaagaa 4080
aaaccaccct ggcgcccaat acgcaaaccg cctctccccg cgcgttggcc gattcattaa 4140
tgcagctggc acgacaggtt tcccgactgg aaagcgggca gtgagcgcaa cgcaattaat 4200
gtaagttagc gcgaattgca agctggccga cgcgctgggc tacgtcttgc tggcgttcgg 4260
gagcagaaga gcatacatct ggaagcaaag ccaggaaagc ggcctatgga gctgtgcggc 4320
agcgctcagt aggcaatttt tcaaaatatt gttaagcctt ttctgagcat ggtatttttc 4380
atggtattac caattagcag gaaaataagc cattgaatat aaaagataaa aatgtcttgt 4440

```
ttacaataga gtgggggggg tcagcctgcc gccttgggcc gggtgatgtc gtacttgccc   4500
gccgcgaact cggttaccgt ccagcccagc gcgaccagct ccggcaacgc ctcgcgcacc   4560
cgcttgcggc gcttgcgcat ggtcgaacca ctggcctctg acggccagac atagccgcac   4620
aaggtatcta tggaagcctt gccggttttg ccggggtcga tccagccaca cagccgctgg   4680
tgcagcaggc gggcggtttc gctgtccagc gcccgcacct cgtccatgct gatgcgcaca   4740
tgctggccgc cacccatgac ggcctgcgcg atcaaggggt tcagggccac gtacaggcgc   4800
ccgtccgcct cgtcgctggc gtactccgac agcagccgaa acccctgccg cttgcggcca   4860
ttctgggcga tgatggatac cttccaaagg cgctcgatgc agtcctgtat gtgcttgagc   4920
gccccaccac tatcgacctc tgccccgatt tcctttgcca gcgcccgata gctacctttg   4980
accacatggc attcagcggt gacggcctcc cacttgggtt ccaggaacag ccggagctgc   5040
cgtccgcctt cggtcttggg ttccgggcca agcactaggc cattaggccc agccatggcc   5100
accagccctt gcaggatgcg cagatcatca gcgcccagcg gctccgggcc gctgaactcg   5160
atccgcttgc cgtcgccgta gtcatacgtc acgtccagct tgctgcgctt gcgctcgccc   5220
cgcttgaggg cacggaacag gccgggggcc agacagtgcg ccgggtcgtg ccggacgtgg   5280
ctgaggctgt gcttgttctt aggcttcacc acggggcacc cccttgctct tgcgctgcct   5340
ctccagcacg gcgggcttga gcaccccgcc gtcatgccgc ctgaaccacc gatcagcgaa   5400
cggtgcgcca tagttggcct tgctcacacc gaagcggacg aagaaccggc gctggtcgtc   5460
gtccacaccc cattcctcgg cctcggcgct ggtcatgctc gacaggtagg actgccagcg   5520
gatgttatcg accagtaccg agctgccccg gctggcctgc tgctggtcgc ctgcgcccat   5580
catggccgcg cccttgctgg catggtgcag gaacacgata gagcacccgg tatcggcggc   5640
gatggcctcc atgcgaccga tgacctgggc catggggccg ctggcgtttt cttcctcgat   5700
gtggaaccgg cgcagcgtgt ccagcaccat caggcggcgg ccctcggcgg cgcgcttgag   5760
gccgtcgaac cactccgggg ccatgatgtt gggcaggctg ccgatcagcg gctggatcag   5820
caggccgtca gccacggctt gccgttcctc ggcgctgagg tgcgccccaa gggcgtgcag   5880
gcggtgatga atggcggtgg gcgggtcttc ggcgggcagg tagatcaccg ggccggtggg   5940
cagttcgccc acctccagca gatccggccc gcctgcaatc tgtgcggcca gttgcagggc   6000
cagcatggat ttaccggcac caccgggcga caccagcgcc ccgaccgtac cggccaccat   6060
gttgggcaaa acgtagtcca gcggtggcgg cgctgctgcg aacgcctcca gaatattgat   6120
aggcttatgg gtagccattg attgcctcct ttgcaggcag ttggtggtta ggcgctggcg   6180
gggtcactac ccccgccctg cgccgctctg agttcttcca ggcactcgcg cagcgcctcg   6240
tattcgtcgt cggtcagcca gaacttgcgc tgacgcatcc ctttggcctt catgcgctcg   6300
gcatatcgcg cttggcgtac agcgtcaggg ctggccagca ggtcgccggt ctgcttgtcc   6360
ttttggtctt tcatatcagt caccgagaaa cttgccgggg ccgaaaggct tgtcttcgcg   6420
gaacaaggac aaggtgcagc cgtcaaggtt aaggctggcc atatcagcga ctgaaaagcg   6480
gccagcctcg gccttgtttg acgtataacc aaagccaccg ggcaaccaat agcccttgtc   6540
acttttgatc aggtagaccg accctgaagc gcttttttcg tattccataa aacccccttc   6600
tgtgcgtgag tactcatagt ataacaggcg tgagtaccaa cgcaagcact acatgctgaa   6660
atctggcccg cccctgtcca tgcctcgctg gcggggtgcc ggtgcccgtg ccagctcggc   6720
ccgcgcaagc tggacgctgg gcagacccat gaccttgctg acggtgcgct cgatgtaatc   6780
```

-continued cgcttcgtgg ccgggcttgc gctctgccag cgctgggctg gcctcggcca tggccttgcc 6840
gatttcctcg gcactgcggc cccggctggc cagcttctgc gcggcgataa agtcgcactt 6900
gctgaggtca tgaccgaagc gcttgaccag cccggccatc tcgctgcggt actcgtccag 6960
cgccgtgcgc cggtggcggc taagctgccg ctcgggcagt tcgaggctgg ccagcctgcg 7020
ggccttctcc tgctgccgct gggcctgctc gatctgctgg ccagcctgct gcaccagcgc 7080
cgggccagcg gtggcggtct tgcccttgga ttcacgcagc agcacccacg gctgataacc 7140
ggcgcgggtg gtgtgcttgt ccttgcggtt ggtgaagccc gccaagcggc catagtggcg 7200
gctgtcggcg ctggccgggt cggcgtcgta ctcgctggcc agcgtccggg caatctgccc 7260
ccgaagttca ccgcctgcgg cgtcggccac cttgacccat gcctgatagt tcttcgggct 7320
ggtttccact accagggcag gctcccggcc ctcggctttc atgtcatcca ggtcaaactc 7380
gctgaggtcg tccaccagca ccagaccatg ccgctcctgc tcggcgggcc tgatatacac 7440
gtcattgccc tgggcattca tccgcttgag ccatggcgtg ttctggagca cttcggcggc 7500
tgaccattcc cggttcatca tctggccggt gggtgcgtcc ctgacgccga tatcgaagcg 7560
ctcacagccc atggccttga gctgtcggcc tatggcctgc aaagtcctgt cgttcttcat 7620
cgggccacca agcgcagcca gatcgagccg tcctcggttg tcagtggcgt caggtcgagc 7680
aagagcaacg atgcgatcag cagcaccacc gtaggcatca tggaagccag catcacggtt 7740
agccatagct tccagtgcca cccccgcgac gcgctccggg cgctctgcgc ggcgctgctc 7800
acctcggcgg ctacctcccg caactctttg gccagctcca cccatgccgc ccctgtctgg 7860
cgctgggctt tcagccactc cgccgcctgc gcctcgctgg cctgcttggt ctggctcatg 7920
acctgccggg cttcgtcggc cagtgtcgcc atgctctggg ccagcggttc gatctgctcc 7980
gctaactcgt tgatgcctct ggatttcttc actctgtcga ttgcgttcat ggtctattgc 8040
ctcccggtat tcctgtaagt cgatgatctg ggcgttggcg gtgtcgatgt tcagggccac 8100
gtctgcccgg tcggtgcgga tgccccggcc ttccatctcc accacgttcg gccccaggtg 8160
aacaccgggc aggcgctcga tgccctgcgc ctcaagtgtt ctgtggtcaa tgcgggcgtc 8220
gtggccagcc cgctctaatg cccggttggc atggtcggcc catgcctcgc gggtctgctc 8280
aagccatgcc ttgggcttga gcgcttcggt cttctgtgcc ccgcccttct ccggggtctt 8340
gccgttgtac cgcttgaacc actgagcggc gggccgctcg atgccgtcat tgatccgctc 8400
ggagatcatc aggtggcagt gcgggttctc gccgccaccg gcatggatgg ccagcgtata 8460
cggcaggcgc tcggcaccgg tcaggtgctg ggcgaactcg gacgccagcg ccttctgctg 8520
gtcgagggtc agctcgaccg gcagggcaaa ttcgacctcc ttgaacagcc gcccattggc 8580
gcgttcatac aggtcggcag catcccagta gtcggcgggc cgctcgacga actccggcat 8640
gtgcccggat tcggcgtgca agacttcatc catgtcgcgg gcatacttgc cttcgcgctg 8700
gatgtagtcg gccttggccc tggccgattg gccgcccgac ctgctgccgg ttttcgccgt 8760
aaggtgataa atcgccatgc tgcctcgctg ttgcttttgc ttttcggctc catgcaatgg 8820
ccctcggaga gcgcaccgcc cgaagggtgg ccgttaggcc agtttctcga agagaaaccg 8880
gtaagtgcgc cctcccctac aaagtagggt cgggattgcc gccgctgtgc ctccatgata 8940
gcctacgaga cagcacatta acaatggggt gtcaagatgg ttaaggggag caacaaggcg 9000
gcggatcggc tggccaagct cgaagaacaa cgagcgcgaa tcaatgccga aattcagcgg 9060
gagcgggcaa gggaacagca gcaagagcgc aagaacgaaa caaggcgcaa ggtgctggtg 9120
ggggccatga ttttggccaa ggtgaacagc agcgagtggc cggaggatcg gctcatggcg 9180
gcaatggatg cgtaccttga acgcgaccac gaccgcgcct tgttcggtct gccgccacgc 9240
cagaaggatg agccgggctg aatgatcgac cgagacaggc cctgcggggc tgcacacgcg 9300
cccccaccct tcgggtaggg ggaaaggccg ctaaagcggc taaaagcgct ccagcgtatt 9360
tctgcggggt ttggtgtggg gtttagcggg ctttgcccgc ctttcccct gccgcgcagc 9420 ggtggggcgg tgtgtagcct agcgcagcga atagaccagc tatccggcct ctggccgggc 9480
atattgggca agggcagcag cgccccacaa gggcgctgat aaccgcgcct agtggattat 9540
tcttagataa tcatggatgg atttttccaa caccccgcca gcccccgccc ctgctgggtt 9600
tgcaggtttg ggggcgtgac agttattgca ggggttcgtg acagttattg caggggggcg 9660
tgacagttat tgcaggggtt cgtgacagtt agtacgggag tgacgggcac tggctggcaa 9720
tgtctagcaa cggcaggcat ttcggctgag ggtaaaagaa ctttccgcta agcgatagac 9780
tgtatgtaaa cacagtattg caaggacgcg gaacatgcct catgtggcgg ccaggacggc 9840
cagccgggat cgggatactg gtcgttacca gagccaccga cccgagcaaa cccttctcta 9900
tcagatcgtt gacgagtatt acccggcatt cgctgcgctt atggcagagc agggaaagga 9960
attgccgggc tatgtgcaac gggaatttga agaatttctc caatgcgggc ggctggagca 10020
tggctttcta cgggttcgct gcgagtcttg ccacgccgag cacctggtcg ctttcagaaa 10080
tcaatctaaa gtatatatga gtaaacttgg tctgacagtt accaatgctt aatcagtgag 10140
gcacctatct cagcgatctg tctatttcgt tcatccatag ttgcctgact ccccgtcgtg 10200
tagataacta cgatacggga gggcttacca tctggcccca gtgctgcaat gataccgcga 10260
gacccacgct caccggctcc agatttatca gcaataaacc agccagccgg aagggccgag 10320
cgcagaagtg gtcctgcaac tttatccgcc tccatccagt ctattaattg ttgccgggaa 10380
gctagagtaa gtagttcgcc agttaatagt ttgcgcaacg ttgttgccat tgctacaggc 10440
atcgtggtgt cacgctcgtc gtttggtatg gcttcattca gctccggttc ccaacgatca 10500
aggcgagtta catgatcccc catgttgtgc aaaaaagcgg ttagctcctt cggtcctccg 10560
atcgttgtca gaagtaagtt ggccgcagtg ttatcactca tggttatggc agcactgcat 10620
aattctctta ctgtcatgcc atccgtaaga tgcttttctg tgactggtga gtactcaacc 10680
aagtcattct gagaatagtg tatgcggcga ccgagttgct cttgcccggc gtcaacacgg 10740
gataataccg cgccacatag cagaacttta aaagtgctca tcattggaaa acgttcttcg 10800
gggcgaaaac tctcaaggat cttaccgctg ttgagatcca gttcgatgta acccactcgt 10860
gcacccaact gatcttcagc atcttttact ttcaccagcg tttctgggtg agcaaaaaca 10920
ggaaggcaaa atgccgcaaa aaagggaata agggcgacac ggaaatgttg aatactcata 10980
ctcttccttt ttcaatatta ttgaagcatt tatcagggtt attgtctcat gagcggatac 11040
atatttgaat gtatttagaa aaataaacaa aagagtttgt agaaacgcaa aaaggccatc 11100
cgtcaggatg gccttctgct taatttgatg cctggcagtt tatggcgggc gtcctgcccg 11160
ccaccctccg ggccgttgct tcgcaacgtt caaatccgct cccggcggat ttgtcctact 11220
caggagagcg ttcaccgaca aacaacagat aaaacgaa 11258

<210> SEQ ID NO 126
<211> LENGTH: 11453
<212> TYPE: DNA
<213> ORGANISM: Artificial Sequence
<220> FEATURE:
<223> OTHER INFORMATION: plasmid pLybAL37 containing otsBA operon

<400> SEQUENCE: 126
aggcccagtc tttcgactga gcctttcgtt ttatttgatg cctggcagtt ccctactctc 60
gcatggggag accccacact accatcggcg ctacggcgtt tcacttctga gttcggcatg 120
gggtcaggtg ggaccaccgc gctactgccg ccaggcaaat tctgttttat cagaccgctt 180
ctgcgttctg atttaatctg tatcaggctg aaaatcttct ctcatccgcc aaaacagcca 240
agcttgcatg cataaatttc tgttttgacc aaaccatccc gacataactc ggtcagggct 300
tgcaaaacag cggggatgcg atcgtgctgc cagagactgc aaaggtgagc caataaccac 360
tgcgtctgcc agtcatcagg tatcgcttgg cagcgctgca acccagcttc gaggacgcga 420
acatcaactg ttttggccag ttgctgaacc tgtcgccaac aatgttcaaa atcaccgctt 480
ggccagccgt cactctctgc aaacgctgca tcagtcatgt gcaatcaata caggttaaaa 540
accatgctaa tggctccacc taagcgggct tcagagtcaa ggcttgtagc aattgctact 600
aaaaactgcg atcgctgctg aaatgagctg gaattctgtc cctctcagct caaaaagtat 660
caatgattac ttaatgtttg ttctgcgcaa acttcttgca gaacatgcat gatttacaaa 720
aagttgtagt ttctgttacc aattgcgaat cgagaactgc ctaatctgcc gagtatgcaa 780
gctgctttgt aggcagatga atccatggta ccgttaagaa ggaggatcca tatgatcttg 840
atggaacgct ggcggaaatc aaaccgcatc ccgatcaggt cgtcgtgcct gacaatattc 900
tgcaaggact acagctactg gcaaccgcaa gtgatggtgc attggcattg atatcagggc 960
gctcaatggt ggagcttgac gcactggcaa aaccttatcg cttcccgtta gcgggcgtgc 1020
atggggcgga gcgccgtgac atcaatggta aaacacatat cgttcatctg ccggatgcga 1080
ttgcgcgtga tattagcgtg caactgcata cagtcatcgc tcagtatccc ggcgcggagc 1140
tggaggcgaa agggatggct tttgcgctgc attatcgtca ggctccgcag catgaagacg 1200
cattaatgac attagcgcaa cgtattactc agatctggcc acaaatggcg ttacagcagg 1260
gaaagtgtgt tgtcgagatc aaaccgagag gtaccagtaa aggtgaggca attgcagctt 1320
ttatgcagga agctcccttt atcgggcgaa cgcccgtatt tctgggcgat gatttaaccg 1380
atgaatctgg cttcgcagtc gttaaccgac tgggcggaat gtcagtaaaa attggcacag 1440
gtgcaactca ggcatcatgg cgactggcgg gtgtgccgga tgtctggagc tggcttgaaa 1500
tgataaccac cgcattacaa caaaaaagag aaaataacag gagtgatgac tatgagtcgt 1560
ttagtcgtag tatctaaccg gattgcacca ccagacgagc acgccgccag tgccggtggc 1620
cttgccgttg gcatactggg ggcactgaaa gccgcaggcg gactgtggtt tggctggagt 1680
ggtgaaacag ggaatgagga tcagccgcta aaaaaggtga aaaaaggtaa cattacgtgg 1740
gcctctttta acctcagcga acaggacctt gacgaatact acaaccaatt ctccaatgcc 1800
gttctctggc ccgcttttca ttatcggctc gatctggtgc aatttcagcg tcctgcctgg 1860
gacggctatc tacgcgtaaa tgcgttgctg gcagataaat tactgccgct gttgcaagac 1920
gatgacatta tctggatcca cgattatcac ctgttgccat ttgcgcatga attacgcaaa 1980
cggggagtga ataatcgcat tggtttcttt ctgcatattc ctttcccgac accggaaatc 2040
ttcaacgcgc tgccgacata tgacaccttg cttgaacagc tttgtgatta tgatttgctg 2100
ggtttccaga cagaaaacga tcgtctggcg ttcctggatt gtctttctaa cctgacccgc 2160
gtcacgacac gtagcgcaaa aagccataca gcctggggca aagcatttcg aacagaagtc 2220
tacccgatcg gcattgaacc gaaagaaata gccaaacagg ctgccgggcc actgccgcca 2280
aaactggcgc aacttaaagc ggaactgaaa aacgtacaaa atatcttttc tgtcgaacgg 2340

-continued

```
ctggattatt ccaaaggttt gccagagcgt tttctcgcct atgaagcgtt gctggaaaaa   2400
tatccgcagc atcatggtaa aattcgttat acccagattg caccaacgtc gcgtggtgat   2460
gtgcaagcct atcaggatat tcgtcatcag ctcgaaaatg aagctggacg aattaatggt   2520
aaatacgggc aattaggctg gacgccgctt tattatttga atcagcattt tgaccgtaaa   2580
ttactgatga aatattccg ctactctgac gtgggcttag tgacgccact gcgtgacggg    2640
atgaacctgg tagcaaaaga gtatgttgct gctcaggacc cagccaatcc gggcgttctt   2700
gttctttcgc aatttgcggg agcggcaaac gagttaacgt cggcgttaat tgttaacccc   2760
tacgatcgtg acgaagttgc agctgcgctg gatcgtgcat tgactatgtc gctggcggaa   2820
cgtatttccc gtcatgcaga aatgctggac gttatcgtga aaaacgatat taaccactgg   2880
caggagtgct tcattagcga cctaaagcag atagttccgc gaagcgcgga aagccagcag   2940
cgcgataaag ttgctacctt tccaaagctt gcgtaggagc tagctgcctc gaaaggggat   3000
gcgattcgcc acctctcact ccgctggcgg attcctcttg agaacatttt ggtggcaggc   3060
gattctggta acgatgagga aatgctcaag ggccataatc tcggcgttgt agttggcaat   3120
tactcaccgg aattggagcc actgcgcagc tacgagcgcg tctattttgc tgagggccac   3180
tatgctaatg gcattctgga agccttaaaa cactatcgct tttttgaggc gatcgcttaa   3240
ccttttcaga atgagacgtt gatcggcacg taagcgtgag acgttgatcg gcacgtaaga   3300
ggttccaact ttcaccataa tgaaataaga tcactaccgg gcgtattttt tgagttatcg   3360
agattttcag gagctaagga agctaaaatg gagaaaaaaa tcactggata taccaccgtt   3420
gatatatccc aatggcatcg taaagaacat tttgaggcat ttcagtcagt tgctcaatgt   3480
acctataacc agaccgttca gctggatatt acggcctttt taaagaccgt aaagaaaaat   3540
aagcacaagt tttatccggc ctttattcac attcttgccc gcctgatgaa tgctcatccg   3600
gaattccgta tggcaatgaa agacggtgag ctggtgatat gggatagtgt tcacccttgt   3660
tacaccgttt tccatgagca aactgaaacg ttttcatcgc tctggagtga ataccacgac   3720
gatttccggc agtttctaca catatattcg caagatgtgg cgtgttacgg tgaaaacctg   3780
gcctatttcc ctaaagggtt tattgagaat atgtttttcg tctcagccaa tccctgggtg   3840
agtttcacca gttttgattt aaacgtggcc aatatggaca acttcttcgc ccccgttttc   3900
accatgggca aatattatac gcaaggcgac aaggtgctga tgccgctggc gattcaggtt   3960
catcatgccg tttgtgatgg cttccatgtc ggcagaatgc ttaatgaatt acaacagtac   4020
tgcgatgagt ggcagggcgg ggcgtaattt ttttaaggca gttattggtg cccttaaacg   4080
cctggttgct acgcctgaat aagtgataat aagcggatga atggcagaaa ttcgatgata   4140
agctgtcaaa cacaaccacc atcaaacagg attttcgcct gctggggcaa accagcgtgg   4200
accgcttgct gcaactctct cagggccagg cggtgaaggg caatcagctg ttgcccgtct   4260
cactggtgaa aagaaaaacc accctggcgc ccaatacgca aaccgcctct ccccgcgcgt   4320
tggccgattc attaatgcag ctggcacgac aggtttcccg actggaaagc gggcagtgag   4380
cgcaacgcaa ttaatgtaag ttagcgcgaa ttgcaagctg gccgacgcgc tgggctacgt   4440
cttgctggcg ttcgggagca gaagagcata catctggaag caaagccagg aaagcggcct   4500
atggagctgt gcggcagcgc tcagtaggca atttttcaaa atattgttaa gccttttctg   4560
agcatggtat ttttcatggt attaccaatt agcaggaaaa taagccattg aatataaaag   4620
ataaaaatgt cttgtttaca atagagtggg gggggtcagc ctgccgcctt gggccgggtg   4680
```

-continued

```
atgtcgtact tgcccgccgc gaactcggtt accgtccagc ccagcgcgac cagctccggc   4740
aacgcctcgc gcacccgctt gcggcgcttg cgcatggtcg aaccactggc ctctgacggc   4800
cagacatagc cgcacaaggt atctatggaa gccttgccgg ttttgccggg gtcgatccag   4860
ccacacagcc gctggtgcag caggcgggcg gtttcgctgt ccagcgcccg cacctcgtcc   4920
atgctgatgc gcacatgctg gccgccaccc atgacggcct gcgcgatcaa ggggttcagg   4980
gccacgtaca ggcgcccgtc cgcctcgtcg ctggcgtact ccgacagcag ccgaaacccc   5040
tgccgcttgc ggccattctg ggcgatgatg gataccttcc aaaggcgctc gatgcagtcc   5100
tgtatgtgct tgagcgcccc accactatcg acctctgccc cgatttcctt tgccagcgcc   5160
cgatagctac ctttgaccac atggcattca gcggtgacgg cctcccactt gggttccagg   5220
aacagccgga gctgccgtcc gccttcggtc ttgggttccg ggccaagcac taggccatta   5280
ggcccagcca tggccaccag cccttgcagg atgcgcagat catcagcgcc cagcggctcc   5340
gggccgctga actcgatccg cttgccgtcg ccgtagtcat acgtcacgtc cagcttgctg   5400
cgcttgcgct cgccccgctt gagggcacgg aacaggccgg gggccagaca gtgcgccggg   5460
tcgtgccgga cgtggctgag gctgtgcttg ttcttaggct tcaccacggg gcaccccctt   5520
gctcttgcgc tgcctctcca gcacggcggg cttgagcacc ccgccgtcat gccgcctgaa   5580
ccaccgatca gcgaacggtg cgccatagtt ggccttgctc acaccgaagc ggacgaagaa   5640
ccggcgctgg tcgtcgtcca caccccattc ctcggcctcg gcgctggtca tgctcgacag   5700
gtaggactgc cagcggatgt tatcgaccag taccgagctg ccccggctgg cctgctgctg   5760
gtcgcctgcg cccatcatgg ccgcgccctt gctggcatgg tgcaggaaca cgatagagca   5820
cccggtatcg gcggcgatgg cctccatgcg accgatgacc tgggccatgg ggccgctggc   5880
gttttcttcc tcgatgtgga accggcgcag cgtgtccagc accatcaggc ggcggccctc   5940
ggcggcgcgc ttgaggccgt cgaaccactc cggggccatg atgttgggca ggctgccgat   6000
cagcggctgg atcagcaggc cgtcagccac ggcttgccgt tcctcggcgc tgaggtgcgc   6060
cccaagggcg tgcaggcggt gatgaatggc ggtgggcggg tcttcggcgg gcaggtagat   6120
caccgggccg gtgggcagtt cgcccacctc cagcagatcc ggcccgcctg caatctgtgc   6180
ggccagttgc agggccagca tggatttacc ggcaccaccg ggcgacacca gcgccccgac   6240
cgtaccggcc accatgttgg gcaaaacgta gtccagcggt ggcggcgctg ctgcgaacgc   6300
ctccagaata ttgataggct tatgggtagc cattgattgc ctcctttgca ggcagttggt   6360
ggttaggcgc tggcggggtc actacccccg ccctgcgccg ctctgagttc ttccaggcac   6420
tcgcgcagcg cctcgtattc gtcgtcggtc agccagaact tgcgctgacg catccctttg   6480
gccttcatgc gctcggcata tcgcgcttgg cgtacagcgt cagggctggc cagcaggtcg   6540
ccggtctgct tgtccttttg gtctttcata tcagtcaccg agaaacttgc cggggccgaa   6600
aggcttgtct tcgcggaaca aggacaaggt gcagccgtca aggttaaggc tggccatatc   6660
agcgactgaa aagcggccag cctcggcctt gtttgacgta taaccaaagc caccgggcaa   6720
ccaatagccc ttgtcacttt tgatcaggta gaccgaccct gaagcgcttt tttcgtattc   6780
cataaaaccc ccttctgtgc gtgagtactc atagtataac aggcgtgagt accaacgcaa   6840
gcactacatg ctgaaatctg gcccgcccct gtccatgcct cgctggcggg gtgccggtgc   6900
ccgtgccagc tcggcccgcg caagctggac gctgggcaga cccatgacct tgctgacggt   6960
gcgctcgatg taatccgctt cgtggccggg cttgcgctct gccagcgctg ggctggcctc   7020
ggccatggcc ttgccgattt cctcggcact gcggccccgg ctggccagct tctgcgcggc   7080
```

gataaagtcg cacttgctga ggtcatgacc gaagcgcttg accagcccgg ccatctcgct 7140
gcggtactcg tccagcgccg tgcgccggtg gcggctaagc tgccgctcgg gcagttcgag 7200
gctggccagc ctgcgggcct tctcctgctg ccgctgggcc tgctcgatct gctggccagc 7260
ctgctgcacc agcgccgggc cagcggtggc ggtcttgccc ttggattcac gcagcagcac 7320
ccacggctga taaccggcgc gggtggtgtg cttgtccttg cggttggtga agcccgccaa 7380
gcggccatag tggcggctgt cggcgctggc cgggtcggcg tcgtactcgc tggccagcgt 7440
ccgggcaatc tgcccccgaa gttcaccgcc tgcggcgtcg gccaccttga cccatgcctg 7500
atagttcttc gggctggttt ccactaccag ggcaggctcc cggccctcgg ctttcatgtc 7560
atccaggtca aactcgctga ggtcgtccac cagcaccaga ccatgccgct cctgctcggc 7620
gggcctgata tacacgtcat tgccctgggc attcatccgc ttgagccatg gcgtgttctg 7680
gagcacttcg gcggctgacc attcccggtt catcatctgg ccggtgggtg cgtccctgac 7740
gccgatatcg aagcgctcac agcccatggc cttgagctgt cggcctatgg cctgcaaagt 7800
cctgtcgttc ttcatcgggc caccaagcgc agccagatcg agccgtcctc ggttgtcagt 7860
ggcgtcaggt cgagcaagag caacgatgcg atcagcagca ccaccgtagg catcatggaa 7920
gccagcatca cggttagcca tagcttccag tgccaccccc gcgacgcgct ccgggcgctc 7980
tgcgcggcgc tgctcacctc ggcggctacc tcccgcaact ctttggccag ctccacccat 8040
gccgcccctg tctggcgctg ggctttcagc cactccgccg cctgcgcctc gctggcctgc 8100
ttggtctggc tcatgacctg ccgggcttcg tcggccagtg tcgccatgct ctgggccagc 8160
ggttcgatct gctccgctaa ctcgttgatg cctctggatt tcttcactct gtcgattgcg 8220
ttcatggtct attgcctccc ggtattcctg taagtcgatg atctgggcgt tggcggtgtc 8280
gatgttcagg gccacgtctg cccggtcggt gcggatgccc cggccttcca tctccaccac 8340
gttcggcccc aggtgaacac cgggcaggcg ctcgatgccc tgcgcctcaa gtgttctgtg 8400
gtcaatgcgg gcgtcgtggc cagcccgctc taatgcccgg ttggcatggt cggcccatgc 8460
ctcgcgggtc tgctcaagcc atgccttggg cttgagcgct tcggtcttct gtgccccgcc 8520
cttctccggg gtcttgccgt tgtaccgctt gaaccactga gcggcgggcc gctcgatgcc 8580
gtcattgatc cgctcggaga tcatcaggtg gcagtgcggg ttctcgccgc caccggcatg 8640
gatggccagc gtatacggca ggcgctcggc accggtcagg tgctgggcga actcggacgc 8700
cagcgccttc tgctggtcga gggtcagctc gaccggcagg gcaaattcga cctccttgaa 8760
cagccgccca ttggcgcgtt catacaggtc ggcagcatcc cagtagtcgg cgggccgctc 8820
gacgaactcc ggcatgtgcc cggattcggc gtgcaagact tcatccatgt cgcgggcata 8880
cttgccttcg cgctggatgt agtcggcctt ggccctggcc gattggccgc ccgacctgct 8940
gccggttttc gccgtaaggt gataaatcgc catgctgcct cgctgttgct tttgcttttc 9000
ggctccatgc aatggccctc ggagagcgca ccgcccgaag ggtggccgtt aggccagttt 9060
ctcgaagaga aaccggtaag tgcgccctcc cctacaaagt agggtcggga ttgccgccgc 9120
tgtgcctcca tgatagccta cgagacagca cattaacaat ggggtgtcaa gatggttaag 9180
gggagcaaca aggcggcgga tcggctggcc aagctcgaag aacaacgagc gcgaatcaat 9240
gccgaaattc agcgggagcg ggcaagggaa cagcagcaag agcgcaagaa cgaaacaagg 9300
cgcaaggtgc tggtgggggc catgattttg gccaaggtga acagcagcga gtggccggag 9360
gatcggctca tggcggcaat ggatgcgtac cttgaacgcg accacgaccg cgccttgttc 9420

-continued

```
ggtctgccgc cacgccagaa ggatgagccg ggctgaatga tcgaccgaga caggccctgc   9480
ggggctgcac acgcgccccc acccttcggg tagggggaaa ggccgctaaa gcggctaaaa   9540
gcgctccagc gtatttctgc ggggtttggt gtggggttta gcgggctttg cccgcctttc   9600
cccctgccgc gcagcggtgg ggcggtgtgt agcctagcgc agcgaataga ccagctatcc   9660
ggcctctggc cgggcatatt gggcaagggc agcagcgccc cacaagggcg ctgataaccg   9720
cgcctagtgg attattctta gataatcatg gatggatttt tccaacaccc cgccagcccc   9780
cgcccctgct gggtttgcag gtttgggggc gtgacagtta ttgcaggggt tcgtgacagt   9840
tattgcaggg gggcgtgaca gttattgcag ggggttcgtga cagttagtac gggagtgacg   9900
ggcactggct ggcaatgtct agcaacggca ggcatttcgg ctgagggtaa aagaactttc   9960
cgctaagcga tagactgtat gtaaacacag tattgcaagg acgcggaaca tgcctcatgt  10020
ggcggccagg acggccagcc gggatcggga tactggtcgt taccagagcc accgacccga  10080
gcaaaccctt ctctatcaga tcgttgacga gtattacccg gcattcgctg cgcttatggc  10140
agagcaggga aaggaattgc cgggctatgt gcaacgggaa tttgaagaat ttctccaatg  10200
cgggcggctg gagcatggct ttctacgggt tcgctgcgag tcttgccacg ccgagcacct  10260
ggtcgctttc agaaatcaat ctaaagtata tatgagtaaa cttggtctga cagttaccaa  10320
tgcttaatca gtgaggcacc tatctcagcg atctgtctat ttcgttcatc catagttgcc  10380
tgactccccg tcgtgtagat aactacgata cgggagggct taccatctgg ccccagtgct  10440
gcaatgatac cgcgagaccc acgctcaccg gctccagatt tatcagcaat aaaccagcca  10500
gccggaaggg ccgagcgcag aagtggtcct gcaactttat ccgcctccat ccagtctatt  10560
aattgttgcc gggaagctag agtaagtagt tcgccagtta atagtttgcg caacgttgtt  10620
gccattgcta caggcatcgt ggtgtcacgc tcgtcgtttg gtatggcttc attcagctcc  10680
ggttcccaac gatcaaggcg agttacatga tcccccatgt tgtgcaaaaa agcggttagc  10740
tccttcggtc ctccgatcgt tgtcagaagt aagttggccg cagtgttatc actcatggtt  10800
atggcagcac tgcataattc tcttactgtc atgccatccg taagatgctt ttctgtgact  10860
ggtgagtact caaccaagtc attctgagaa tagtgtatgc ggcgaccgag ttgctcttgc  10920
ccggcgtcaa cacgggataa taccgcgcca catagcagaa ctttaaaagt gctcatcatt  10980
ggaaaacgtt cttcggggcg aaaactctca aggatcttac cgctgttgag atccagttcg  11040
atgtaaccca ctcgtgcacc caactgatct tcagcatctt ttactttcac cagcgtttct  11100
gggtgagcaa aaacaggaag gcaaaatgcc gcaaaaaagg gaataagggc gacacggaaa  11160
tgttgaatac tcatactctt cctttttcaa tattattgaa gcatttatca gggttattgt  11220
ctcatgagcg gatacatatt tgaatgtatt tagaaaaata aacaaaagag tttgtagaaa  11280
cgcaaaaagg ccatccgtca ggatggcctt ctgcttaatt tgatgcctgg cagtttatgg  11340
cgggcgtcct gcccgccacc ctccgggccg ttgcttcgca acgttcaaat ccgctcccgg  11400
cggatttgtc ctactcagga gagcgttcac cgacaaacaa cagataaaac gaa         11453
```

<210> SEQ ID NO 127
<211> LENGTH: 1754
<212> TYPE: DNA
<213> ORGANISM: Artificial Sequence
<220> FEATURE:
<223> OTHER INFORMATION: PCR product
<220> FEATURE:
<221> NAME/KEY: misc_feature
<222> LOCATION: (7)..(12)
<223> OTHER INFORMATION: AflII restriction site
<220> FEATURE:
<221> NAME/KEY: misc_feature
<222> LOCATION: (1743)..(1748)
<223> OTHER INFORMATION: XbaI restriction site

<400> SEQUENCE: 127

```
tattcgctta agccaaagga gaatgattga tgaaatcccc cgcaccttct cgcccgcaaa     60

aaatggcgtt aattccagcc tgtatctttt tgtgtttcgc tgcgctatcg gtgcaggcag    120

aagaaacacc ggtaacacca cagccgcctg atattttatt agggccgctg tttaatgatg    180

tgcaaaacgc caaacttttt ccggaccaaa aaacctttgc cgatgccgtg ccgaacagcg    240

atccgctgat gatccttgct gattatcgga tgcagcaaaa ccagagcgga tttgatctgc    300

gccatttcgt taacgtcaat ttcaccctgc cgaaagaagg cgagaaatat gttccgccag    360

aggggcagtc actgcgcgaa catattgacg gactttggcc ggtattaacg cgttctaccg    420

aaaacaccga aaaatgggat tctctgttac cgctgccgga accttatgtc gtgccgggcg    480

gacgctttcg cgaggtatat tactgggaca gttacttcac catgttagga cttgccgaaa    540

gcggtcactg ggataaagtc gcggatatgg tggccaattt tgctcatgaa atagacactt    600

acggtcatat tcccaacggc aaccgcagtt actatttaag ccgctcgcaa ccgcccttct    660

ttgccctgat ggtagagtta ctggcgcagc atgaaggcga tgccgcgttg aagcaatacc    720

tgccgcaaat gcaaaaagaa tatgcttact ggatggacgg tgttgaaaac ctgcaagccg    780

gacaacagga aaaacgcgtt gtcaaacttc aggatggtac ccttctcaac cgctactggg    840

acgatcgcga tacgccacga ccagagtcat gggtggaaga tattgccacc gccaaaagca    900

atccgaatcg acctgccact gaaatttacc gcgacctgcg ctctgccgct gcgtctggct    960

gggatttcag ctcgcgctgg atggacaacc cgcagcagtt aaatacctta cgcaccacca   1020

gcatcgtacc ggtcgatctg aacagcctga tgtttaaaat ggaaaaaatc ctcgcccgcg   1080

ccagcaaagc tgccggagat aacgcgatgg caaaccagta cgaaacgctg gcaaatgccc   1140

gtcaaaaagg gatcgaaaaa tacctgtgga acgatcaaca aggctggtat gccgattacg   1200

acctgaaaag tcataaagtg cgcaatcagt taaccgcggc cgccctgttc ccgctgtacg   1260

tcaatgcggc agcgaaagat cgcgccaaca aaatggcgac ggcgacgaaa acacatctgc   1320

tgcaacccgg cggcctgaac accacgtcgg tgaaaagtgg gcaacaatgg gatgcgccaa   1380

atggctgggc accgttacag tgggtcgcga cagaaggatt acaaaactac gggcaaaaag   1440

aggtggcgat ggacattagc tggcacttcc tgaccaatgt tcagcacacc tatgaccggg   1500

agaaaaagct ggtggaaaaa tatgatgtca gcaccaccgg aacgggggc ggcggtggcg    1560

aatatccatt acaggatggc tttggctgga ccaatggcgt gacgctgaaa atgctggatt   1620

tgatctgccc gaaagagcaa ccgtgtgaca atgttccggc gacgcgtccg accgttaagt   1680

cagcaacgac gcaaccctca accaaagagg cacaacccac accttaacca gcgcttactc   1740

cgtctagatc attc                                                     1754
```

<210> SEQ ID NO 128
<211> LENGTH: 29
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: AflII restriction site

<400> SEQUENCE: 128
tattcgctta agccaaagga gaatgattg 29

<210> SEQ ID NO 129
<211> LENGTH: 27
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: XbaI restriction site

<400> SEQUENCE: 129
gaatgatcta gacggagtaa gcgctgg 27

<210> SEQ ID NO 130
<211> LENGTH: 6282
<212> TYPE: DNA
<213> ORGANISM: Artificial Sequence
<220> FEATURE:
<223> OTHER INFORMATION: plasmid pLybAL24 containing treA

<400> SEQUENCE: 130
tagtcatgcc ccgcgcccac cggaaggagc tgactgggtt gaaggctctc aagggcatcg 60
gtcgataaat attctgaaat gagctgttga caattaatca tcgaactagt taacttttac 120
gcaagttctt aagccaaagg agaatgattg atgaaatccc ccgcaccttc tcgcccgcaa 180
aaaatggcgt taattccagc ctgtatcttt ttgtgtttcg ctgcgctatc ggtgcaggca 240
gaagaaacac cggtaacacc acagccgcct gatattttat tagggccgct gtttaatgat 300
gtgcaaaacg ccaaactttt tccggaccaa aaaacctttg ccgatgccgt gccgaacagc 360
gatccgctga tgatccttgc tgattatcgg atgcagcaaa accagagcgg atttgatctg 420
cgccatttcg ttaacgtcaa tttcaccctg ccgaaagaag gcgagaaata tgttccgcca 480
gaggggcagt cactgcgcga acatattgac ggactttggc cggtattaac gcgttctacc 540
gaaaacaccg aaaaatggga ttctctgtta ccgctgccgg aaccttatgt cgtgccgggc 600
ggacgctttc gcgaggtata ttactgggac agttacttca ccatgttagg acttgccgaa 660
agcggtcact gggataaagt cgcggatatg gtggccaatt ttgctcatga aatagacact 720
tacggtcata ttcccaacgg caaccgcagt tactatttaa gccgctcgca accgcccttc 780
tttgccctga tggtagagtt actggcgcag catgaaggcg atgccgcgtt gaagcaatac 840
ctgccgcaaa tgcaaaaaga atatgcttac tggatggacg gtgttgaaaa cctgcaagcc 900
ggacaacagg aaaaacgcgt tgtcaaactt caggatggta cccttctcaa ccgctactgg 960
gacgatcgcg atacgccacg accagagtca tgggtggaag atattgccac cgccaaaagc 1020
aatccgaatc gacctgccac tgaaatttac cgcgacctgc gctctgccgc tgcgtctggc 1080
tgggatttca gctcgcgctg gatggacaac ccgcagcagt taaatacctt acgcaccacc 1140
agcatcgtac cggtcgatct gaacagcctg atgtttaaaa tggaaaaaat cctcgcccgc 1200
gccagcaaag ctgccggaga taacgcgatg gcaaaccagt acgaaacgct ggcaaatgcc 1260
cgtcaaaaag ggatcgaaaa atacctgtgg aacgatcaac aaggctggta tgccgattac 1320
gacctgaaaa gtcataaagt gcgcaatcag ttaaccgcgg ccgccctgtt cccgctgtac 1380
gtcaatgcgg cagcgaaaga tcgcgccaac aaaatggcga cggcgacgaa aacacatctg 1440
ctgcaacccg gcggcctgaa caccacgtcg gtgaaaagtg ggcaacaatg ggatgcgcca 1500

-continued aatggctggg caccgttaca gtgggtcgcg acagaaggat tacaaaacta cgggcaaaaa 1560
gaggtggcga tggacattag ctggcacttc ctgaccaatg ttcagcacac ctatgaccgg 1620
gagaaaaagc tggtggaaaa atatgatgtc agcaccaccg gaacgggggg cggcggtggc 1680
gaatatccat tacaggatgg ctttggctgg accaatggcg tgacgctgaa aatgctggat 1740
ttgatctgcc cgaaagagca accgtgtgac aatgttccgg cgacgcgtcc gaccgttaag 1800
tcagcaacga cgcaaccctc aaccaaagag gcacaaccca caccttaacc agcgcttact 1860
ccgtctagac atcaccatca ccatcattaa ttaagtttgt gtttaaactg caggcatgca 1920
agcttctgtt ttggcggatg agagaagatt ttcagcctga tacagattaa atcagaacgc 1980
agaagcggtc tgataaaaca gaatttgcct ggcggcagta gcgcggtggt cccacctgac 2040
cccatgccga actcagaagt gaaacgccgt agcgccgatg gtagtgtggg gtctccccat 2100
gcgagagtag ggaactgcca ggcatcaaat aaaacgaaag gctcagtcga aagactgggc 2160
ctttcgtttt atctgttgtt tgtcggtgaa cgctctcctg agtaggacaa atccgccggg 2220
agcggatttg aacgttgcga agcaacggcc cggagggtgg cgggcaggac gcccgccata 2280
aactgccagg catcaaatta agcagaaggc catcctgacg gatggccttt ttgcgtttct 2340
acaaactctt ttgtttattt ttctaaatac attcaaatat gtatccgctc atgaaaaaaa 2400
atccttacgt ttcgctaagg atgtcagcgt aatgctctgc cagtgttaca accaattaac 2460
caattctgat tagaaaaact catcgagcat caaatgaaac tgcaatttat tcatatcagg 2520
attatcaata ccatattttt gaaaaagccg tttctgtaat gaaggagaaa actcaccgag 2580
gcagttccat aggatggcaa gatcctggta tcggtctgcg attccgactc gtccaacatc 2640
aatacaacct attaatttcc cctcgtcaaa aataaggtta tcaagtgaga aatcaccatg 2700
agtgacgact gaatccggtg agaatggcaa aagcttatgc atttctttcc agacttgttc 2760
aacaggccag ccattacgct cgtcatcaaa atcactcgca tcaaccaaac cgttattcat 2820
tcgtgattgc gcctgagcga gacgaaatac gcgatcgctg ttaaaaggac aattacaaac 2880
aggaatcgaa tgcaaccggc gcaggaacac tgccagcgca tcaacaatat tttcacctga 2940
atcaggatat tcttctaata cctggaatgc tgttttcccg gggatcgcag tggtgagtaa 3000
ccatgcatca tcaggagtac ggataaaatg cttgatggtc ggaagaggca taaattccgt 3060
cagccagttt agtctgacca tctcatctgt aacatcattg gcaacgctac ctttgccatg 3120
tttcagaaac aactctggcg catcgggctt cccatacaat cgatagattg tcgcacctga 3180
ttgcccgaca ttatcgcgag cccatttata cccatataaa tcagcatcca tgttggaatt 3240
taatcgcggc ctcgagcaag acgtttcccg ttgaatatgg ctcataacac cccttgtatt 3300
actgtttatg taagcagaca gttttattgt tcatgaccaa aatcccttaa cgtgagtttt 3360
cgttccactg agcgtcagac cccgtagaaa agatcaaagg atcttcttga gatccttttt 3420
ttctgcgcgt aatctgctgc ttgcaaacaa aaaaaccacc gctaccagcg gtggtttgtt 3480
tgccggatca agagctacca actctttttc cgaaggtaac tggcttcagc agagcgcaga 3540
taccaaatac tgtccttcta gtgtagccgt agttaggcca ccacttcaag aactctgtag 3600
caccgcctac atacctcgct ctgctaatcc tgttaccagt ggctgctgcc agtggcgata 3660
agtcgtgtct taccgggttg gactcaagac gatagttacc ggataaggcg cagcggtcgg 3720
gctgaacggg gggttcgtgc acacagccca gcttggagcg aacgacctac accgaactga 3780
gatacctaca gcgtgagcta tgagaaagcg ccacgcttcc cgaagggaga aaggcggaca 3840
ggtatccggt aagcggcagg gtcggaacag gagagcgcac gagggagctt ccagggggaa 3900
acgcctggta tctttatagt cctgtcgggt ttcgccacct ctgacttgag cgtcgatttt 3960
tgtgatgctc gtcagggggg cggagcctat ggaaaaacgc cagcaacgcg gcctttttac 4020
ggttcctggc cttttgctgg ccttttgctc acatgttctt tcctgcgtta tcccctgatt 4080
ctgtggataa ccgtattacc gcctttgagt gagctgatac cgctcgccgc agccgaacga 4140
ccgagcgcag cgagtcagtg agcgaggaag cggaagagcg cctgatgcgg tattttctcc 4200
ttacgcatct gtgcggtatt tcacaccgca tatatggtgc actctcagta caatctgctc 4260
tgatgccgca tagttaagcc agtatacact ccgctatcgc tacgtgactg ggtcatggct 4320
gcgccccgac acccgccaac acccgctgac gcgccctgac gggcttgtct gctcccggca 4380
tccgcttaca gacaagctgt gaccgtctcc gggagctgca tgtgtcagag gttttcaccg 4440
tcatcaccga aacgcgcgag gcagctgcgg taaagctcat cagcgtggtc gtgaagcgat 4500
tcacagatgt ctgcctgttc atccgcgtcc agctcgttga gtttctccag aagcgttaat 4560
gtctggcttc tgataaagcg ggccatgtta agggcggttt tttcctgttt ggtcacttga 4620
tgcctccgtg taagggggaa tttctgttca tgggggtaat gataccgatg aaacgagaga 4680
ggatgctcac gatacgggtt actgatgatg aacatgcccg gttactggaa cgttgtgagg 4740
gtaaacaact ggcggtatgg atgcggcggg accagagaaa aatcactcag ggtcaatgcc 4800
agcgcttcgt taatacagat gtaggtgttc cacagggtag ccagcagcat cctgcgatgc 4860
agatccggaa cataatggtg cagggcgctg acttccgcgt ttccagactt tacgaaacac 4920
ggaaaccgaa gaccattcat gttgttgctc aggtcgcaga cgttttgcag cagcagtcgc 4980
ttcacgttcg ctcgcgtatc ggtgattcat tctgctaacc agtaaggcaa ccccgccagc 5040
ctagccgggt cctcaacgac aggagcacga tcatgcgcac ccgtggccag gacccaacgc 5100
tgcccgagat gcgccgcgtg cggctgctgg agatggcgga cgcgatggat atgttctgcc 5160
aagggttggt ttgcgcattc acagttctcc gcaagaattg attggctcca attcttggag 5220
tggtgaatcc gttagcgagg tgccgccggc ttccattcag gtcgaggtgg cccggctcca 5280
tgcaccgcga cgcaacgcgg ggaggcagac aaggtatagg gcggcgccta caatccatgc 5340
caacccgttc catgtgctcg ccgaggcggc ataaatcgcc gtgacgatca gcggtccagt 5400
gatcgaagtt aggctggtaa gagccgcgag cgatccttga agctgtccct gatggtcgtc 5460
atctacctgc ctggacagca tggcctgcaa cgcgggcatc ccgatgccgc cggaagcgag 5520
aagaatcata atggggaagg ccatccagcc tcgcgtcgcg aacgccagca agacgtagcc 5580
cagcgcgtcg gccgccatgc cggcgataat ggcctgcttc tcgccgaaac gtttggtggc 5640
gggaccagtg acgaaggctt gagcgagggc gtgcaagatt ccgaataccg caagcgacag 5700
gccgatcatc gtcgcgctcc agcgaaagcg gtcctcgccg aaaatgaccc agagcgctgc 5760
cggcacctgt cctacgagtt gcatgataaa gaagacagtc ataagtgcgg cgacgatagt 5820
catgccccgc gcccaccgga aggagctgac tgggttgaag gctctcaagg gcatcggtcg 5880
acgctctccc ttatgcgact cctgcattag gaagcagccc agtagtaggt tgaggccgtt 5940
gagcaccgcc gccgcaagga atggtgcatg ctcgatggct acgagggcag acagtaagtg 6000
gatttaccat aatcccttaa ttgtacgcac cgctaaaacg cgttcagcgc gatcacggca 6060
gcagacaggt aaaaatggca acaaaccacc ctaaaaactg cgcgatcgcg cctgataaat 6120
tttaaccgta tgaataccta tgcaaccaga gggtacaggc cacattaccc ccacttaatc 6180
cactgaagct gccatttttc atggtttcac catcccagcg aagggccatg catgcatcga 6240
aattaatacg acgaaattaa tacgactcac tatagggcaa tt 6282

<210> SEQ ID NO 131
<211> LENGTH: 27
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (9)..(14)
<223> OTHER INFORMATION: AflII restriction site

<400> SEQUENCE: 131
cgcaagttct taagccaaag gagaatg 27

<210> SEQ ID NO 132
<211> LENGTH: 26
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(12)
<223> OTHER INFORMATION: XbaI restriction site

<400> SEQUENCE: 132
aagcgctcta gaaggtgtgg gttgtg 26

<210> SEQ ID NO 133
<211> LENGTH: 6264
<212> TYPE: DNA
<213> ORGANISM: Artificial Sequence
<220> FEATURE:
<223> OTHER INFORMATION: plasmid pLybAL33 containing 6-His tagged treA

<400> SEQUENCE: 133
tagtcatgcc ccgcgcccac cggaaggagc tgactgggtt gaaggctctc aagggcatcg 60
gtcgataaat attctgaaat gagctgttga caattaatca tcgaactagt taacttttac 120
gcaagttctt aagccaaagg agaatgattg atgaaatccc ccgcaccttc tcgcccgcaa 180
aaaatggcgt taattccagc ctgtatcttt ttgtgtttcg ctgcgctatc ggtgcaggca 240
gaagaaacac cggtaacacc acagccgcct gatattttat tagggccgct gtttaatgat 300
gtgcaaaacg ccaaactttt tccggaccaa aaaacctttg ccgatgccgt gccgaacagc 360
gatccgctga tgatccttgc tgattatcgg atgcagcaaa accagagcgg atttgatctg 420
cgccatttcg ttaacgtcaa tttcaccctg ccgaaagaag gcgagaaata tgttccgcca 480
gaggggcagt cactgcgcga acatattgac ggactttggc cggtattaac gcgttctacc 540
gaaaacaccg aaaaatggga ttctctgtta ccgctgccgg aaccttatgt cgtgccgggc 600
ggacgctttc gcgaggtata ttactgggac agttacttca ccatgttagg acttgccgaa 660
agcggtcact gggataaagt cgcggatatg gtggccaatt ttgctcatga aatagacact 720
tacggtcata ttcccaacgg caaccgcagt tactatttaa gccgctcgca accgcccttc 780
tttgccctga tggtagagtt actggcgcag catgaaggcg atgccgcgtt gaagcaatac 840
ctgccgcaaa tgcaaaaaga atatgcttac tggatggacg gtgttgaaaa cctgcaagcc 900
ggacaacagg aaaaacgcgt tgtcaaactt caggatggta cccttctcaa ccgctactgg 960
gacgatcgcg atacgccacg accagagtca tgggtggaag atattgccac cgccaaaagc 1020
aatccgaatc gacctgccac tgaaatttac cgcgacctgc gctctgccgc tgcgtctggc 1080
tgggatttca gctcgcgctg gatggacaac ccgcagcagt taaatacctt acgcaccacc 1140
agcatcgtac cggtcgatct gaacagcctg atgtttaaaa tggaaaaaat cctcgcccgc 1200
gccagcaaag ctgccggaga taacgcgatg gcaaaccagt acgaaacgct ggcaaatgcc 1260
cgtcaaaaag ggatcgaaaa atacctgtgg aacgatcaac aaggctggta tgccgattac 1320
gacctgaaaa gtcataaagt gcgcaatcag ttaaccgcgg ccgccctgtt cccgctgtac 1380
gtcaatgcgg cagcgaaaga tcgcgccaac aaaatggcga cggcgacgaa aacacatctg 1440
ctgcaacccg gcggcctgaa caccacgtcg gtgaaaagtg ggcaacaatg ggatgcgcca 1500
aatggctggg caccgttaca gtgggtcgcg acagaaggat tacaaaacta cgggcaaaaa 1560
gaggtggcga tggacattag ctggcacttc ctgaccaatg ttcagcacac ctatgaccgg 1620
gagaaaaagc tggtggaaaa atatgatgtc agcaccaccg gaacgggggg cggcggtggc 1680
gaatatccat tacaggatgg ctttggctgg accaatggcg tgacgctgaa aatgctggat 1740
ttgatctgcc cgaaagagca accgtgtgac aatgttccgg cgacgcgtcc gaccgttaag 1800
tcagcaacga cgcaaccctc aaccaaagag gcacaaccca caccttctag acatcaccat 1860
caccatcatt aattaagttt gtgtttaaac tgcaggcatg caagcttctg ttttggcgga 1920
tgagagaaga ttttcagcct gatacagatt aaatcagaac gcagaagcgg tctgataaaa 1980
cagaatttgc ctggcggcag tagcgcggtg gtcccacctg accccatgcc gaactcagaa 2040
gtgaaacgcc gtagcgccga tggtagtgtg gggtctcccc atgcgagagt agggaactgc 2100
caggcatcaa ataaaacgaa aggctcagtc gaaagactgg gcctttcgtt ttatctgttg 2160
tttgtcggtg aacgctctcc tgagtaggac aaatccgccg ggagcggatt tgaacgttgc 2220
gaagcaacgg cccggagggt ggcgggcagg acgcccgcca taaactgcca ggcatcaaat 2280
taagcagaag gccatcctga cggatggcct ttttgcgttt ctacaaactc ttttgtttat 2340
ttttctaaat acattcaaat atgtatccgc tcatgaaaaa aaatccttac gtttcgctaa 2400
ggatgtcagc gtaatgctct gccagtgtta caaccaatta accaattctg attagaaaaa 2460
ctcatcgagc atcaaatgaa actgcaattt attcatatca ggattatcaa taccatattt 2520
ttgaaaaagc cgtttctgta atgaaggaga aaactcaccg aggcagttcc ataggatggc 2580
aagatcctgg tatcggtctg cgattccgac tcgtccaaca tcaatacaac ctattaattt 2640
cccctcgtca aaaataaggt tatcaagtga gaaatcacca tgagtgacga ctgaatccgg 2700
tgagaatggc aaaagcttat gcatttcttt ccagacttgt tcaacaggcc agccattacg 2760
ctcgtcatca aaatcactcg catcaaccaa accgttattc attcgtgatt gcgcctgagc 2820
gagacgaaat acgcgatcgc tgttaaaagg acaattacaa acaggaatcg aatgcaaccg 2880
gcgcaggaac actgccagcg catcaacaat attttcacct gaatcaggat attcttctaa 2940
tacctggaat gctgttttcc cggggatcgc agtggtgagt aaccatgcat catcaggagt 3000
acggataaaa tgcttgatgg tcggaagagg cataaattcc gtcagccagt ttagtctgac 3060
catctcatct gtaacatcat tggcaacgct acctttgcca tgtttcagaa acaactctgg 3120
cgcatcgggc ttcccataca atcgatagat tgtcgcacct gattgcccga cattatcgcg 3180
agcccattta tacccatata aatcagcatc catgttggaa tttaatcgcg gcctcgagca 3240
agacgtttcc cgttgaatat ggctcataac accccttgta ttactgttta tgtaagcaga 3300
cagttttatt gttcatgacc aaaatccctt aacgtgagtt ttcgttccac tgagcgtcag 3360
accccgtaga aaagatcaaa ggatcttctt gagatccttt ttttctgcgc gtaatctgct 3420

```
gcttgcaaac aaaaaaacca ccgctaccag cggtggtttg tttgccggat caagagctac   3480
caactctttt tccgaaggta actggcttca gcagagcgca gataccaaat actgtccttc   3540
tagtgtagcc gtagttaggc caccacttca agaactctgt agcaccgcct acatacctcg   3600
ctctgctaat cctgttacca gtggctgctg ccagtggcga taagtcgtgt cttaccgggt   3660
tggactcaag acgatagtta ccggataagg cgcagcggtc gggctgaacg gggggttcgt   3720
gcacacagcc cagcttggag cgaacgacct acaccgaact gagataccta cagcgtgagc   3780
tatgagaaag cgccacgctt cccgaaggga gaaaggcgga caggtatccg gtaagcggca   3840
gggtcggaac aggagagcgc acgagggagc ttccaggggg aaacgcctgg tatctttata   3900
gtcctgtcgg gtttcgccac ctctgacttg agcgtcgatt tttgtgatgc tcgtcagggg   3960
ggcggagcct atggaaaaac gccagcaacg cggccttttt acggttcctg gccttttgct   4020
ggccttttgc tcacatgttc tttcctgcgt tatcccctga ttctgtggat aaccgtatta   4080
ccgcctttga gtgagctgat accgctcgcc gcagccgaac gaccgagcgc agcgagtcag   4140
tgagcgagga agcggaagag cgcctgatgc ggtattttct ccttacgcat ctgtgcggta   4200
tttcacaccg catatatggt gcactctcag tacaatctgc tctgatgccg catagttaag   4260
ccagtataca ctccgctatc gctacgtgac tgggtcatgg ctgcgccccg acacccgcca   4320
acacccgctg acgcgccctg acgggcttgt ctgctcccgg catccgctta cagacaagct   4380
gtgaccgtct ccgggagctg catgtgtcag aggttttcac cgtcatcacc gaaacgcgcg   4440
aggcagctgc ggtaaagctc atcagcgtgg tcgtgaagcg attcacagat gtctgcctgt   4500
tcatccgcgt ccagctcgtt gagtttctcc agaagcgtta atgtctggct tctgataaag   4560
cgggccatgt taagggcggt tttttcctgt ttggtcactt gatgcctccg tgtaaggggg   4620
aatttctgtt catgggggta atgataccga tgaaacgaga gaggatgctc acgatacggg   4680
ttactgatga tgaacatgcc cggttactgg aacgttgtga gggtaaacaa ctggcggtat   4740
ggatgcggcg ggaccagaga aaaatcactc agggtcaatg ccagcgcttc gttaatacag   4800
atgtaggtgt tccacagggt agccagcagc atcctgcgat gcagatccgg aacataatgg   4860
tgcagggcgc tgacttccgc gtttccagac tttacgaaac acggaaaccg aagaccattc   4920
atgttgttgc tcaggtcgca gacgttttgc agcagcagtc gcttcacgtt cgctcgcgta   4980
tcggtgattc attctgctaa ccagtaaggc aaccccgcca gcctagccgg gtcctcaacg   5040
acaggagcac gatcatgcgc acccgtggcc aggacccaac gctgcccgag atgcgccgcg   5100
tgcggctgct ggagatggcg gacgcgatgg atatgttctg ccaagggttg gtttgcgcat   5160
tcacagttct ccgcaagaat tgattggctc caattcttgg agtggtgaat ccgttagcga   5220
ggtgccgccg gcttccattc aggtcgaggt ggcccggctc catgcaccgc gacgcaacgc   5280
ggggaggcag acaaggtata gggcggcgcc tacaatccat gccaacccgt tccatgtgct   5340
cgccgaggcg gcataaatcg ccgtgacgat cagcggtcca gtgatcgaag ttaggctggt   5400
aagagccgcg agcgatcctt gaagctgtcc ctgatggtcg tcatctacct gcctggacag   5460
catggcctgc aacgcgggca tcccgatgcc gccggaagcg agaagaatca taatggggaa   5520
ggccatccag cctcgcgtcg cgaacgccag caagacgtag cccagcgcgt cggccgccat   5580
gccggcgata atggcctgct tctcgccgaa acgtttggtg gcgggaccag tgacgaaggc   5640
ttgagcgagg gcgtgcaaga ttccgaatac cgcaagcgac aggccgatca tcgtcgcgct   5700
ccagcgaaag cggtcctcgc cgaaaatgac ccagagcgct gccggcacct gtcctacgag   5760
```

ttgcatgata aagaagacag tcataagtgc ggcgacgata gtcatgcccc gcgcccaccg 5820
gaaggagctg actgggttga aggctctcaa gggcatcggt cgacgctctc ccttatgcga 5880
ctcctgcatt aggaagcagc ccagtagtag gttgaggccg ttgagcaccg ccgccgcaag 5940
gaatggtgca tgctcgatgg ctacgagggc agacagtaag tggatttacc ataatccctt 6000
aattgtacgc accgctaaaa cgcgttcagc gcgatcacgg cagcagacag gtaaaaatgg 6060
caacaaacca ccctaaaaac tgcgcgatcg cgcctgataa attttaaccg tatgaatacc 6120
tatgcaacca gagggtacag gccacattac ccccacttaa tccactgaag ctgccatttt 6180
tcatggtttc accatcccag cgaagggcca tgcatgcatc gaaattaata cgacgaaatt 6240
aatacgactc actatagggc aatt 6264

<210> SEQ ID NO 134
<211> LENGTH: 1698
<212> TYPE: DNA
<213> ORGANISM: Escherichia coli

<400> SEQUENCE: 134
atgaaatccc ccgcaccttc tcgcccgcaa aaaatggcgt taattccagc ctgtatcttt 60
ttgtgtttcg ctgcgctatc ggtgcaggca gaagaaacac cggtaacacc acagccgcct 120
gatattttat tagggccgct gtttaatgat gtgcaaaacg ccaaactttt tccggaccaa 180
aaaacctttg ccgatgccgt gccgaacagc gatccgctga tgatccttgc tgattatcgg 240
atgcagcaaa accagagcgg atttgatctg cgccatttcg ttaacgtcaa tttcaccctg 300
ccgaaagaag gcgagaaata tgttccgcca gaggggcagt cactgcgcga acatattgac 360
ggactttggc cggtattaac gcgttctacc gaaaacaccg aaaaatggga ttctctgtta 420
ccgctgccgg aaccttatgt cgtgccgggc ggacgctttc gcgaggtata ttactgggac 480
agttacttca ccatgttagg acttgccgaa agcggtcact gggataaagt cgcggatatg 540
gtggccaatt ttgctcatga aatagacact tacggtcata ttcccaacgg caaccgcagt 600
tactatttaa gccgctcgca accgcccttc tttgccctga tggtagagtt actggcgcag 660
catgaaggcg atgccgcgtt gaagcaatac ctgccgcaaa tgcaaaaaga atatgcttac 720
tggatggacg gtgttgaaaa cctgcaagcc ggacaacagg aaaaacgcgt tgtcaaactt 780
caggatggta cccttctcaa ccgctactgg gacgatcgcg atacgccacg accagagtca 840
tgggtggaag atattgccac cgccaaaagc aatccgaatc gacctgccac tgaaatttac 900
cgcgacctgc gctctgccgc tgcgtctggc tgggatttca gctcgcgctg gatggacaac 960
ccgcagcagt taaatacctt acgcaccacc agcatcgtac cggtcgatct gaacagcctg 1020
atgtttaaaa tggaaaaaat cctcgcccgc gccagcaaag ctgccggaga taacgcgatg 1080
gcaaaccagt acgaaacgct ggcaaatgcc cgtcaaaaag ggatcgaaaa atacctgtgg 1140
aacgatcaac aaggctggta tgccgattac gacctgaaaa gtcataaagt gcgcaatcag 1200
ttaaccgcgg ccgccctgtt cccgctgtac gtcaatgcgg cagcgaaaga tcgcgccaac 1260
aaaatggcga cggcgacgaa aacacatctg ctgcaacccg gcggcctgaa caccacgtcg 1320
gtgaaaagtg ggcaacaatg ggatgcgcca aatggctggg caccgttaca gtgggtcgcg 1380
acagaaggat tacaaaacta cgggcaaaaa gaggtggcga tggacattag ctggcacttc 1440
ctgaccaatg ttcagcacac ctatgaccgg gagaaaaagc tggtggaaaa atatgatgtc 1500
agcaccaccg gaacgggggg cggcggtggc gaatatccat tacaggatgg ctttggctgg 1560
accaatggcg tgacgctgaa aatgctggat ttgatctgcc cgaaagagca accgtgtgac 1620
aatgttccgg cgacgcgtcc gaccgttaag tcagcaacga cgcaaccctc aaccaaagag 1680
gcacaaccca caccttaa 1698

<210> SEQ ID NO 135
<211> LENGTH: 565
<212> TYPE: PRT
<213> ORGANISM: Escherichia coli

<400> SEQUENCE: 135

Met Lys Ser Pro Ala Pro Ser Arg Pro Gln Lys Met Ala Leu Ile Pro
1 5 10 15

Ala Cys Ile Phe Leu Cys Phe Ala Ala Leu Ser Val Gln Ala Glu Glu
20 25 30

Thr Pro Val Thr Pro Gln Pro Pro Asp Ile Leu Leu Gly Pro Leu Phe
35 40 45

Asn Asp Val Gln Asn Ala Lys Leu Phe Pro Asp Gln Lys Thr Phe Ala
50 55 60

Asp Ala Val Pro Asn Ser Asp Pro Leu Met Ile Leu Ala Asp Tyr Arg
65 70 75 80

Met Gln Gln Asn Gln Ser Gly Phe Asp Leu Arg His Phe Val Asn Val
85 90 95

Asn Phe Thr Leu Pro Lys Glu Gly Glu Lys Tyr Val Pro Pro Glu Gly
100 105 110

Gln Ser Leu Arg Glu His Ile Asp Gly Leu Trp Pro Val Leu Thr Arg
115 120 125

Ser Thr Glu Asn Thr Glu Lys Trp Asp Ser Leu Leu Pro Leu Pro Glu
130 135 140

Pro Tyr Val Val Pro Gly Gly Arg Phe Arg Glu Val Tyr Tyr Trp Asp
145 150 155 160

Ser Tyr Phe Thr Met Leu Gly Leu Ala Glu Ser Gly His Trp Asp Lys
165 170 175

Val Ala Asp Met Val Ala Asn Phe Ala His Glu Ile Asp Thr Tyr Gly
180 185 190

His Ile Pro Asn Gly Asn Arg Ser Tyr Tyr Leu Ser Arg Ser Gln Pro
195 200 205

Pro Phe Phe Ala Leu Met Val Glu Leu Leu Ala Gln His Glu Gly Asp
210 215 220

Ala Ala Leu Lys Gln Tyr Leu Pro Gln Met Gln Lys Glu Tyr Ala Tyr
225 230 235 240

Trp Met Asp Gly Val Glu Asn Leu Gln Ala Gly Gln Gln Glu Lys Arg
245 250 255

Val Val Lys Leu Gln Asp Gly Thr Leu Leu Asn Arg Tyr Trp Asp Asp
260 265 270

Arg Asp Thr Pro Arg Pro Glu Ser Trp Val Glu Asp Ile Ala Thr Ala
275 280 285

Lys Ser Asn Pro Asn Arg Pro Ala Thr Glu Ile Tyr Arg Asp Leu Arg
290 295 300

Ser Ala Ala Ala Ser Gly Trp Asp Phe Ser Ser Arg Trp Met Asp Asn
305 310 315 320

Pro Gln Gln Leu Asn Thr Leu Arg Thr Thr Ser Ile Val Pro Val Asp
325 330 335

Leu Asn Ser Leu Met Phe Lys Met Glu Lys Ile Leu Ala Arg Ala Ser
340 345 350

```
Lys Ala Ala Gly Asp Asn Ala Met Ala Asn Gln Tyr Glu Thr Leu Ala
        355                 360                 365

Asn Ala Arg Gln Lys Gly Ile Glu Lys Tyr Leu Trp Asn Asp Gln Gln
    370                 375                 380

Gly Trp Tyr Ala Asp Tyr Asp Leu Lys Ser His Lys Val Arg Asn Gln
385                 390                 395                 400

Leu Thr Ala Ala Ala Leu Phe Pro Leu Tyr Val Asn Ala Ala Ala Lys
                405                 410                 415

Asp Arg Ala Asn Lys Met Ala Thr Ala Thr Lys Thr His Leu Leu Gln
            420                 425                 430

Pro Gly Gly Leu Asn Thr Thr Ser Val Lys Ser Gly Gln Gln Trp Asp
        435                 440                 445

Ala Pro Asn Gly Trp Ala Pro Leu Gln Trp Val Ala Thr Glu Gly Leu
    450                 455                 460

Gln Asn Tyr Gly Gln Lys Glu Val Ala Met Asp Ile Ser Trp His Phe
465                 470                 475                 480

Leu Thr Asn Val Gln His Thr Tyr Asp Arg Glu Lys Lys Leu Val Glu
                485                 490                 495

Lys Tyr Asp Val Ser Thr Thr Gly Thr Gly Gly Gly Gly Gly Glu Tyr
            500                 505                 510

Pro Leu Gln Asp Gly Phe Gly Trp Thr Asn Gly Val Thr Leu Lys Met
        515                 520                 525

Leu Asp Leu Ile Cys Pro Lys Glu Gln Pro Cys Asp Asn Val Pro Ala
    530                 535                 540

Thr Arg Pro Thr Val Lys Ser Ala Thr Thr Gln Pro Ser Thr Lys Glu
545                 550                 555                 560

Ala Gln Pro Thr Pro
                565


<210> SEQ ID NO 136
<211> LENGTH: 1738
<212> TYPE: DNA
<213> ORGANISM: Artificial Sequence
<220> FEATURE:
<223> OTHER INFORMATION: PCR product
<220> FEATURE:
<221> NAME/KEY: misc_feature
<222> LOCATION: (9)..(14)
<223> OTHER INFORMATION: AflII restriction site
<220> FEATURE:
<221> NAME/KEY: misc_feature
<222> LOCATION: (1727)..(1732)
<223> OTHER INFORMATION: XbaI restriction site

<400> SEQUENCE: 136

cgcaagttct taagccaaag gagaatgatt gatgaaatcc cccgcacctt ctcgcccgca      60

aaaaatggcg ttaattccag cctgtatctt tttgtgtttc gctgcgctat cggtgcaggc     120

agaagaaaca ccggtaacac cacagccgcc tgatatttta ttagggccgc tgtttaatga     180

tgtgcaaaac gccaaacttt ttccggacca aaaaaccttt gccgatgccg tgccgaacag     240

cgatccgctg atgatccttg ctgattatcg gatgcagcaa aaccagagcg gatttgatct     300

gcgccatttc gttaacgtca atttcaccct gccgaaagaa ggcgagaaat atgttccgcc     360

agaggggcag tcactgcgcg aacatattga cggactttgg ccggtattaa cgcgttctac     420

cgaaaacacc gaaaaatggg attctctgtt accgctgccg gaaccttatg tcgtgccggg     480

cggacgcttt cgcgaggtat attactggga cagttacttc accatgttag gacttgccga     540

aagcggtcac tgggataaag tcgcggatat ggtggccaat tttgctcatg aaatagacac     600
```

```
ttacggtcat attcccaacg gcaaccgcag ttactattta agccgctcgc aaccgccctt    660

ctttgccctg atggtagagt tactggcgca gcatgaaggc gatgccgcgt tgaagcaata    720

cctgccgcaa atgcaaaaag aatatgctta ctggatggac ggtgttgaaa acctgcaagc    780

cggacaacag gaaaaacgcg ttgtcaaact tcaggatggt acccttctca accgctactg    840

ggacgatcgc gatacgccac gaccagagtc atgggtggaa gatattgcca ccgccaaaag    900

caatccgaat cgacctgcca ctgaaattta ccgcgacctg cgctctgccg ctgcgtctgg    960

ctgggatttc agctcgcgct ggatggacaa cccgcagcag ttaaatacct tacgcaccac   1020

cagcatcgta ccggtcgatc tgaacagcct gatgtttaaa atggaaaaaa tcctcgcccg   1080

cgccagcaaa gctgccggag ataacgcgat ggcaaaccag tacgaaacgc tggcaaatgc   1140

ccgtcaaaaa gggatcgaaa aatacctgtg gaacgatcaa caaggctggt atgccgatta   1200

cgacctgaaa agtcataaag tgcgcaatca gttaaccgcg gccgccctgt tcccgctgta   1260

cgtcaatgcg gcagcgaaag atcgcgccaa caaaatggcg acggcgacga aaacacatct   1320

gctgcaaccc ggcggcctga acaccacgtc ggtgaaaagt gggcaacaat gggatgcgcc   1380

aaatggctgg gcaccgttac agtgggtcgc gacagaagga ttacaaaact acgggcaaaa   1440

agaggtggcg atggacatta gctggcactt cctgaccaat gttcagcaca cctatgaccg   1500

ggagaaaaag ctggtggaaa aatatgatgt cagcaccacc ggaacggggg gcggcggtgg   1560

cgaatatcca ttacaggatg gctttggctg gaccaatggc gtgacgctga aaatgctgga   1620

tttgatctgc ccgaaagagc aaccgtgtga caatgttccg gcgacgcgtc cgaccgttaa   1680

gtcagcaacg acgcaaccct caaccaaaga ggcacaaccc acaccttcta gagcgctt     1738
```

```
<210> SEQ ID NO 137
<211> LENGTH: 573
<212> TYPE: PRT
<213> ORGANISM: Artificial Sequence
<220> FEATURE:
<223> OTHER INFORMATION: treA with 6-His tag

<400> SEQUENCE: 137

Met Lys Ser Pro Ala Pro Ser Arg Pro Gln Lys Met Ala Leu Ile Pro
1               5                   10                  15

Ala Cys Ile Phe Leu Cys Phe Ala Ala Leu Ser Val Gln Ala Glu Glu
            20                  25                  30

Thr Pro Val Thr Pro Gln Pro Pro Asp Ile Leu Leu Gly Pro Leu Phe
        35                  40                  45

Asn Asp Val Gln Asn Ala Lys Leu Phe Pro Asp Gln Lys Thr Phe Ala
    50                  55                  60

Asp Ala Val Pro Asn Ser Asp Pro Leu Met Ile Leu Ala Asp Tyr Arg
65                  70                  75                  80

Met Gln Gln Asn Gln Ser Gly Phe Asp Leu Arg His Phe Val Asn Val
                85                  90                  95

Asn Phe Thr Leu Pro Lys Glu Gly Glu Lys Tyr Val Pro Pro Glu Gly
            100                 105                 110

Gln Ser Leu Arg Glu His Ile Asp Gly Leu Trp Pro Val Leu Thr Arg
        115                 120                 125

Ser Thr Glu Asn Thr Glu Lys Trp Asp Ser Leu Leu Pro Leu Pro Glu
    130                 135                 140

Pro Tyr Val Val Pro Gly Gly Arg Phe Arg Glu Val Tyr Tyr Trp Asp
145                 150                 155                 160
```

-continued

```
Ser Tyr Phe Thr Met Leu Gly Leu Ala Glu Ser Gly His Trp Asp Lys
                165                 170                 175

Val Ala Asp Met Val Ala Asn Phe Ala His Glu Ile Asp Thr Tyr Gly
            180                 185                 190

His Ile Pro Asn Gly Asn Arg Ser Tyr Tyr Leu Ser Arg Ser Gln Pro
        195                 200                 205

Pro Phe Phe Ala Leu Met Val Glu Leu Leu Ala Gln His Glu Gly Asp
    210                 215                 220

Ala Ala Leu Lys Gln Tyr Leu Pro Gln Met Gln Lys Glu Tyr Ala Tyr
225                 230                 235                 240

Trp Met Asp Gly Val Glu Asn Leu Gln Ala Gly Gln Gln Glu Lys Arg
                245                 250                 255

Val Val Lys Leu Gln Asp Gly Thr Leu Leu Asn Arg Tyr Trp Asp Asp
            260                 265                 270

Arg Asp Thr Pro Arg Pro Glu Ser Trp Val Glu Asp Ile Ala Thr Ala
        275                 280                 285

Lys Ser Asn Pro Asn Arg Pro Ala Thr Glu Ile Tyr Arg Asp Leu Arg
    290                 295                 300

Ser Ala Ala Ala Ser Gly Trp Asp Phe Ser Ser Arg Trp Met Asp Asn
305                 310                 315                 320

Pro Gln Gln Leu Asn Thr Leu Arg Thr Thr Ser Ile Val Pro Val Asp
                325                 330                 335

Leu Asn Ser Leu Met Phe Lys Met Glu Lys Ile Leu Ala Arg Ala Ser
            340                 345                 350

Lys Ala Ala Gly Asp Asn Ala Met Ala Asn Gln Tyr Glu Thr Leu Ala
        355                 360                 365

Asn Ala Arg Gln Lys Gly Ile Glu Lys Tyr Leu Trp Asn Asp Gln Gln
    370                 375                 380

Gly Trp Tyr Ala Asp Tyr Asp Leu Lys Ser His Lys Val Arg Asn Gln
385                 390                 395                 400

Leu Thr Ala Ala Ala Leu Phe Pro Leu Tyr Val Asn Ala Ala Ala Lys
                405                 410                 415

Asp Arg Ala Asn Lys Met Ala Thr Ala Thr Lys Thr His Leu Leu Gln
            420                 425                 430

Pro Gly Gly Leu Asn Thr Thr Ser Val Lys Ser Gly Gln Gln Trp Asp
        435                 440                 445

Ala Pro Asn Gly Trp Ala Pro Leu Gln Trp Val Ala Thr Glu Gly Leu
    450                 455                 460

Gln Asn Tyr Gly Gln Lys Glu Val Ala Met Asp Ile Ser Trp His Phe
465                 470                 475                 480

Leu Thr Asn Val Gln His Thr Tyr Asp Arg Glu Lys Lys Leu Val Glu
                485                 490                 495

Lys Tyr Asp Val Ser Thr Thr Gly Thr Gly Gly Gly Gly Gly Glu Tyr
            500                 505                 510

Pro Leu Gln Asp Gly Phe Gly Trp Thr Asn Gly Val Thr Leu Lys Met
        515                 520                 525

Leu Asp Leu Ile Cys Pro Lys Glu Gln Pro Cys Asp Asn Val Pro Ala
    530                 535                 540

Thr Arg Pro Thr Val Lys Ser Ala Thr Thr Gln Pro Ser Thr Lys Glu
545                 550                 555                 560

Ala Gln Pro Thr Pro Ser Arg His His His His His His
                565                 570
```

-continued

```
<210> SEQ ID NO 138
<211> LENGTH: 1269
<212> TYPE: DNA
<213> ORGANISM: Artificial Sequence
<220> FEATURE:
<223> OTHER INFORMATION: sequence of partially deleted Synechococcus upp

<400> SEQUENCE: 138

gagctcggta cccggggatc ccacggcagc attacggctc agaccttggt catgccctcg     60

acaacagatc tctacttcac cccagaggat tgtgaggccg aagcgcagtt gattcctaag    120

gcgcactatt gcccaattcc ctcgatctgg ggtcaccgcg cgggcaaccc cagccaaaat    180

ccgcaggatg aaagcttcat tcggcaggcc gttcaggctt tgctcaacgc tgaagcctag    240

cgaattcagt cagcagatca aggagtacca aacaggcgat cgccagcatc ccccagcccc    300

ggcacgataa agcctttgtc gttcagctgc tcatcaatga tggcgctgta aatcgtcaac    360

gccgggtagg cttgactgag tttttgtagc gctggcgggg cagccacaat tgaaagcacc    420

cgcacttgct cagcagagac accgcgatcg cgcagcaaat caagggtata gagcagcgag    480

ccacctgtcg ccagcatcgg gtcgagaacc agaacgcgac tgttcacttc aagttgctct    540

ggcaggtgat tgaggtagca gcgcggttca agactgactt catcccgctc gcgcagaatc    600

ggcacgatcg ccaagggttg cgaaaaatcg acgaactccg ctggggtttc tgcaagagga    660

gtttgcaccg ccgctggaat cgttggtagc cattcccgca cagcctcata ggcgagccag    720

cggcccagct ctgcgatcgc ggtgcgaaac agaggcgtcg gcgtctggcg atcgcgggca    780

atgcccagcc agtgccgaat taagggatgg ggcggcacga agatacgcag ttgaggagcc    840

atgccaatca gcagaagaca gctcctgatt ttaacgttca gaccccaggg gaagcggaac    900

ggtgcaggaa ggcaagcgct tctgcttcgg gcagtggtgg gccatagaag aacccttgca    960

cagcatcaca accaatcgct tctaagaagg cggcttgctc gaggcgttct acgccttctg   1020

cgatcgtgcg aagtttcaag accttggcca ttgcaacaat cgcctgcacg atcgcttgat   1080

cgtcatggtc gtgcggcaga tcgcgaataa agctgcgatc aattttgaga gcattgatgg   1140

gcaaacgctt gaggtaacca aggctggaat aacccgtccc aaaatcatct aaagcgactt   1200

gaaatcccat cgatcgggct tcctggagcc attgcagtgg gatcctctag agtcgacctg   1260

caggcatgc                                                           1269
```